US012121590B2

(12) United States Patent
Howard

(10) Patent No.: US 12,121,590 B2
(45) Date of Patent: *Oct. 22, 2024

(54) PYRROLOBENZODIAZEPINES AND CONJUGATES THEREOF

(71) Applicant: MEDIMMUNE LIMITED, Cambridge (GB)

(72) Inventor: Philip Wilson Howard, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,681

(22) Filed: Jun. 6, 2023

(65) Prior Publication Data

US 2024/0075159 A1 Mar. 7, 2024

Related U.S. Application Data

(63) Continuation of application No. 17/223,712, filed on Apr. 6, 2021, now Pat. No. 11,701,430, which is a continuation of application No. 16/837,336, filed on Apr. 1, 2020, now Pat. No. 10,994,023, which is a continuation of application No. 16/412,138, filed on May 14, 2019, now Pat. No. 10,646,584, which is a continuation of application No. 15/847,308, filed on Dec. 19, 2017, now Pat. No. 10,335,497, which is a continuation of application No. 14/051,743, filed on Oct. 11, 2013, now Pat. No. 9,889,207.

(60) Provisional application No. 61/712,928, filed on Oct. 12, 2012.

(51) Int. Cl.

| | |
|---|---|
| ***C07D 487/04*** | (2006.01) |
| ***A61K 45/06*** | (2006.01) |
| ***A61K 47/65*** | (2017.01) |
| ***A61K 47/68*** | (2017.01) |
| ***A61P 35/00*** | (2006.01) |
| ***C07D 519/00*** | (2006.01) |

(52) U.S. Cl.

CPC .......... *A61K 47/6855* (2017.08); *A61K 45/06* (2013.01); *A61K 47/65* (2017.08); *A61K 47/68035* (2023.08); *C07D 487/04* (2013.01); *C07D 519/00* (2013.01); *Y02P 20/582* (2015.11)

(58) Field of Classification Search

CPC .. C07D 487/04; A61K 47/6855; A61K 47/65; A61K 47/6803; A61P 35/00

See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

United States Office Action for U.S. Appl. No. 10/598,518 dated Mar. 13, 2009 (7 pages).

(Continued)

*Primary Examiner* — Bruck Kifle

(74) *Attorney, Agent, or Firm* — Casimir Jones SC; Lisa Mueller

(57) ABSTRACT

A compound which is either A:

A

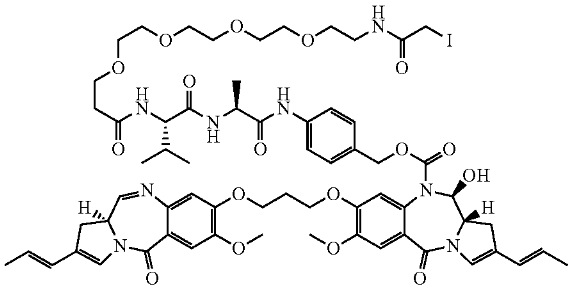

or B:

B

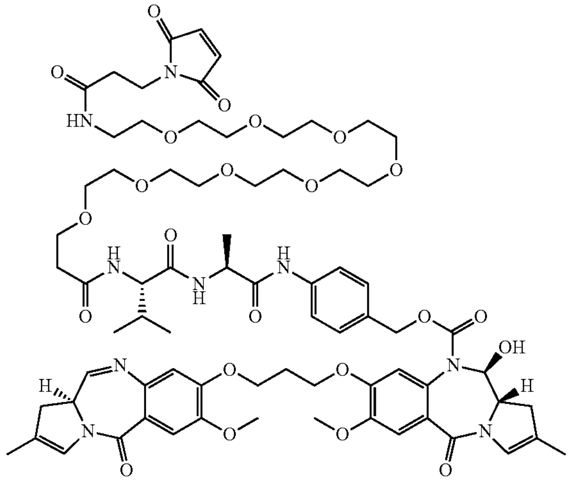

and salts and solvates thereof, as well as their conjugates with a cell-binding agent.

16 Claims, 1 Drawing Sheet

Specification includes a Sequence Listing.

(56) References Cited

U.S. PATENT DOCUMENTS 4,239,683 A 12/1980 Takanabe et al.
4,309,437 A 1/1982 Ueda et al.
4,353,827 A 10/1982 Hunkeler et al.
4,382,032 A 5/1983 Hunkeler et al.
4,386,028 A 5/1983 Hunkeler et al.
4,405,516 A 9/1983 Hunkeler et al.
4,405,517 A 9/1983 Hunkeler et al.
4,407,752 A 10/1983 Hunkeler et al.
4,427,587 A 1/1984 Kaneko et al.
4,427,588 A 1/1984 Kaneko et al.
4,701,325 A 10/1987 Ueda et al.
4,816,567 A 3/1989 Cabilly et al.
4,923,984 A 5/1990 Matsumura et al.
5,362,852 A 11/1994 Geoghegan
5,418,241 A 5/1995 Jegham et al.
5,440,021 A 8/1995 Chuntharapai et al.
5,583,024 A 12/1996 McElroy et al.
5,621,002 A 4/1997 Bosslet et al.
5,644,033 A 7/1997 Seon
5,674,713 A 10/1997 McElroy et al.
5,700,670 A 12/1997 Yamagishi et al.
5,773,223 A 6/1998 Shyamala et al.
5,792,616 A 8/1998 Persico et al.
5,854,399 A 12/1998 Salomon et al.
5,869,445 A 2/1999 Cheever et al.
5,976,551 A 11/1999 Mottez et al.
6,011,146 A 1/2000 Mottez et al.
6,153,408 A 11/2000 Abastado et al.
6,214,345 B1 4/2001 Firestone et al.
6,218,519 B1 4/2001 Kenten et al.
6,268,488 B1 7/2001 Barbas, III et al.
6,362,331 B1 3/2002 Kamal et al.
6,518,404 B1 2/2003 Li et al.
6,534,482 B1 3/2003 Fikes et al.
6,555,339 B1 4/2003 Liaw et al.
6,562,806 B1 5/2003 Thurston et al.
6,602,677 B1 8/2003 Wood et al.
6,608,192 B1 8/2003 Thurston et al.
6,660,742 B2 12/2003 Lee
6,660,856 B2 12/2003 Wang
6,677,435 B2 1/2004 Barbas, III et al.
6,747,144 B1 6/2004 Thurston et al.
6,759,509 B1 7/2004 King et al.
6,835,807 B1 12/2004 Sasaki et al.
6,884,799 B2 4/2005 Kamal et al.
6,909,006 B1 6/2005 Thurston et al.
7,049,311 B1 5/2006 Thurston et al.
7,067,511 B2 6/2006 Thurston et al.
7,223,837 B2 5/2007 De Groot et al.
7,244,724 B2 7/2007 Liu et al.
7,265,105 B2 9/2007 Thurston et al.
7,375,078 B2 5/2008 Feng
7,407,951 B2 8/2008 Thurston et al.
7,429,658 B2 9/2008 Howard et al.
7,511,032 B2 3/2009 Liu et al.
7,521,541 B2 4/2009 Eigenbrot et al.
7,528,126 B2 5/2009 Howard et al.
7,557,099 B2 7/2009 Howard et al.
7,612,062 B2 11/2009 Gregson et al.
7,704,924 B2 4/2010 Thurston et al.
7,723,485 B2 5/2010 Junutula et al.
7,741,319 B2 6/2010 Howard et al.
8,034,808 B2 11/2011 Delavault et al.
8,163,736 B2 4/2012 Gauzy et al.
8,321,774 B2 11/2012 Barthel et al.
8,487,092 B2 7/2013 Howard et al.
8,501,934 B2 8/2013 Howard et al.
8,592,576 B2 11/2013 Howard et al.
8,633,185 B2 1/2014 Howard et al.
8,637,664 B2 1/2014 Howard et al.
8,697,688 B2 4/2014 Howard et al.
8,829,184 B2 9/2014 Howard et al.
8,940,733 B2 1/2015 Howard et al.
9,102,704 B2 8/2015 Howard
9,242,013 B2 1/2016 Howard et al.
9,321,774 B2 4/2016 Howard et al.
9,376,440 B2 6/2016 Howard et al.
9,387,259 B2 7/2016 Jeffrey et al.
9,388,187 B2 7/2016 Howard et al.
9,399,073 B2 7/2016 Howard et al.
9,399,641 B2 7/2016 Howard et al.
9,415,117 B2 8/2016 Howard
9,464,141 B2 10/2016 Asundi et al.
9,526,798 B2 12/2016 Jeffrey et al.
9,562,049 B2 2/2017 Howard
9,592,240 B2 3/2017 Howard et al.
9,624,227 B2 4/2017 Howard et al.
9,649,390 B2 5/2017 Howard et al.
9,707,301 B2 7/2017 Jeffrey et al.
9,713,647 B2 7/2017 Jeffrey et al.
9,732,084 B2 8/2017 Howard et al.
9,745,303 B2 8/2017 Howard et al.
9,889,207 B2 2/2018 Howard
9,956,298 B2 5/2018 Howard et al.
2001/0055751 A1 12/2001 Reiter et al.
2002/0034749 A1 3/2002 Billing-Medel et al.
2002/0042366 A1 4/2002 Thompson et al.
2002/0150573 A1 10/2002 Nussenzweig
2002/0193567 A1 12/2002 Jacobs et al.
2003/0060612 A1 3/2003 Goddard et al.
2003/0062401 A1 4/2003 Hasz et al.
2003/0064397 A1 4/2003 Spancake et al.
2003/0065143 A1 4/2003 Eaton et al.
2003/0091580 A1 5/2003 Mitcham et al.
2003/0096743 A1 5/2003 Senter et al.
2003/0096961 A1 5/2003 Baker et al.
2003/0105292 A1 6/2003 Liaw et al.
2003/0109676 A1 6/2003 Li et al.
2003/0118592 A1 6/2003 Ledbetter et al.
2003/0119121 A1 6/2003 Baker et al.
2003/0119122 A1 6/2003 Baker et al.
2003/0119125 A1 6/2003 Baker et al.
2003/0119126 A1 6/2003 Baker et al.
2003/0119128 A1 6/2003 Baker et al.
2003/0119129 A1 6/2003 Baker et al.
2003/0119130 A1 6/2003 Baker et al.
2003/0119131 A1 6/2003 Baker et al.
2003/0124140 A1 7/2003 Bangur et al.
2003/0124579 A1 7/2003 Mack et al.
2003/0129192 A1 7/2003 Chenault et al.
2003/0130189 A1 7/2003 Senter et al.
2003/0134790 A1 7/2003 Langenfeld
2003/0143557 A1 7/2003 Penner
2003/0157089 A1 8/2003 Xu et al.
2003/0165504 A1 9/2003 Retter et al.
2003/0185830 A1 10/2003 Xu et al.
2003/0186372 A1 10/2003 Baker et al.
2003/0186373 A1 10/2003 Baker et al.
2003/0194704 A1 10/2003 Penn et al.
2003/0195196 A1 10/2003 Thurston et al.
2003/0206918 A1 11/2003 Fanger et al.
2003/0219806 A1 11/2003 Glucksmann et al.
2003/0224411 A1 12/2003 Stanton et al.
2003/0224454 A1 12/2003 Ryseck et al.
2003/0228319 A1 12/2003 Frantz et al.
2003/0232056 A1 12/2003 Fanger et al.
2003/0232350 A1 12/2003 Afar et al.
2004/0001827 A1 1/2004 Dennis
2004/0005320 A1 1/2004 Thompson et al.
2004/0005538 A1 1/2004 Chen et al.
2004/0005563 A1 1/2004 Mack et al.
2004/0005598 A1 1/2004 Devaux et al.
2004/0018194 A1 1/2004 Francisco et al.
2004/0018553 A1 1/2004 Billing-Medel et al.
2004/0022727 A1 2/2004 Stanton et al.
2004/0044179 A1 3/2004 Baker et al.
2004/0044180 A1 3/2004 Baker et al.
2004/0052793 A1 3/2004 Carter et al.
2004/0101874 A1 5/2004 Ghosh et al.
2004/0101899 A1 5/2004 Dillon et al.
2004/0121940 A1 6/2004 De Groot et al.
2004/0138269 A1 7/2004 Sun et al.
2004/0197325 A1 10/2004 Law et al.
2004/0198722 A1 10/2004 Thurston et al.

(56) References Cited

U.S. PATENT DOCUMENTS

| | | | |
|---|---|---|---|
| 2004/0249130 | A1 | 12/2004 | Stanton et al. |
| 2005/0271615 | A1 | 12/2005 | Shabat et al. |
| 2006/0116422 | A1 | 6/2006 | De Groot et al. |
| 2007/0072846 | A1 | 3/2007 | Vishnuvajjala et al. |
| 2007/0154906 | A1 | 7/2007 | Martin et al. |
| 2007/0185336 | A1 | 8/2007 | Rossen et al. |
| 2007/0191349 | A1 | 8/2007 | Howard et al. |
| 2007/0232592 | A1 | 10/2007 | Delavault et al. |
| 2007/0249591 | A1 | 10/2007 | Howard et al. |
| 2008/0090812 | A1 | 4/2008 | Pepper et al. |
| 2008/0092940 | A1 | 4/2008 | Nakajima |
| 2008/0112961 | A1 | 5/2008 | Stavenhagen et al. |
| 2008/0206239 | A1 | 8/2008 | Jones et al. |
| 2008/0213289 | A1 | 9/2008 | Francisco et al. |
| 2008/0214525 | A1 | 9/2008 | Howard et al. |
| 2009/0036431 | A1 | 2/2009 | Gauzy et al. |
| 2009/0148942 | A1 | 6/2009 | McDonagh et al. |
| 2009/0149449 | A1 | 6/2009 | Liu et al. |
| 2009/0274713 | A1 | 11/2009 | Chari et al. |
| 2009/0304710 | A1 | 12/2009 | Park et al. |
| 2010/0028346 | A1 | 2/2010 | Lutz et al. |
| 2010/0047257 | A1 | 2/2010 | Blanc et al. |
| 2010/0113425 | A1 | 5/2010 | Howard et al. |
| 2010/0203007 | A1 | 8/2010 | Li et al. |
| 2010/0316656 | A1 | 12/2010 | Bouchard et al. |
| 2011/0039969 | A1 | 2/2011 | Muratoglu et al. |
| 2011/0091372 | A1 | 4/2011 | Ghayur et al. |
| 2011/0160192 | A1 | 6/2011 | Howard et al. |
| 2011/0195021 | A1 | 8/2011 | Deckert et al. |
| 2011/0195022 | A1 | 8/2011 | Deckert et al. |
| 2011/0196148 | A1 | 8/2011 | Howard et al. |
| 2011/0201803 | A1 | 8/2011 | Howard et al. |
| 2011/0256157 | A1 | 10/2011 | Howard et al. |
| 2012/0233172 | A1 | 9/2012 | Skillcorn et al. |
| 2012/0238731 | A1 | 9/2012 | Fishkin et al. |
| 2013/0028917 | A1 | 1/2013 | Howard et al. |
| 2013/0028919 | A1 | 1/2013 | Howard et al. |
| 2013/0137659 | A1 | 5/2013 | Commercon et al. |
| 2013/0244171 | A1 | 9/2013 | Yamasaki et al. |
| 2013/0266595 | A1 | 10/2013 | Flygare et al. |
| 2013/0266596 | A1 | 10/2013 | Li et al. |
| 2013/0302359 | A1 | 11/2013 | Li et al. |
| 2013/0304357 | A1 | 11/2013 | Koci et al. |
| 2014/0030279 | A1 | 1/2014 | Polakis et al. |
| 2014/0030280 | A1 | 1/2014 | Polakis |
| 2014/0066435 | A1 | 3/2014 | Howard et al. |
| 2014/0088089 | A1 | 3/2014 | Chari |
| 2014/0120118 | A1 | 5/2014 | Howard |
| 2014/0127239 | A1 | 5/2014 | Howard |
| 2014/0155590 | A1 | 6/2014 | Commercon et al. |
| 2014/0234346 | A1 | 8/2014 | Howard |
| 2014/0274907 | A1 | 9/2014 | Howard et al. |
| 2014/0275522 | A1 | 9/2014 | Howard et al. |
| 2014/0286970 | A1 | 9/2014 | Jeffrey et al. |
| 2014/0294868 | A1 | 10/2014 | Howard et al. |
| 2014/0302066 | A1 | 10/2014 | Jeffrey et al. |
| 2015/0111880 | A1 | 4/2015 | Howard et al. |
| 2015/0126495 | A1 | 5/2015 | Howard et al. |
| 2015/0133435 | A1 | 5/2015 | Howard et al. |
| 2015/0158869 | A1 | 6/2015 | Howard |
| 2015/0183883 | A1 | 7/2015 | Asundi |
| 2015/0265722 | A1 | 9/2015 | Van Berkel |
| 2015/0273077 | A1 | 10/2015 | Van Berkel |
| 2015/0273078 | A1 | 10/2015 | Van Berkel |
| 2015/0274737 | A1 | 10/2015 | Howard et al. |
| 2015/0283258 | A1 | 10/2015 | Van Berkel |
| 2015/0283262 | A1 | 10/2015 | Van Berkel |
| 2015/0283263 | A1 | 10/2015 | Van Berkel |
| 2015/0297746 | A1 | 10/2015 | Van Berkel |
| 2015/0315196 | A1 | 11/2015 | Howard et al. |
| 2015/0344482 | A1 | 12/2015 | Howard et al. |
| 2016/0015828 | A1 | 1/2016 | Torgor |
| 2016/0031887 | A1 | 2/2016 | Howard et al. |
| 2016/0075787 | A1 | 3/2016 | Zheng et al. |
| 2016/0144052 | A1 | 5/2016 | Howard et al. |
| 2016/0074527 | A1 | 7/2016 | Flygare et al. |
| 2016/0250344 | A1 | 9/2016 | Howard et al. |
| 2016/0250345 | A1 | 9/2016 | Howard et al. |
| 2016/0250346 | A1 | 9/2016 | Howard et al. |
| 2016/0256561 | A1 | 9/2016 | Howard et al. |
| 2016/0263242 | A1 | 9/2016 | Howard et al. |
| 2016/0310611 | A1 | 10/2016 | Flygare et al. |
| 2017/0239365 | A1 | 8/2017 | Howard et al. |
| 2017/0290924 | A1 | 10/2017 | Jeffrey et al. |
| 2017/0298137 | A1 | 10/2017 | Jeffrey et al. |
| 2017/0340752 | A1 | 11/2017 | Howard |
| 2018/0125997 | A1 | 5/2018 | Howard et al. |
| 2018/0134717 | A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |

(56) References Cited

FOREIGN PATENT DOCUMENTS

| | | |
|---|---|---|
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006111759 | 10/2006 |
| WO | WO 2007039752 | 4/2007 |

(56) References Cited

FOREIGN PATENT DOCUMENTS

| | | |
|---|---|---|
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015159076 | 10/2015 |
| WO | WO 2016037644 | 3/2016 |
| WO | WO 2016040868 | 3/2016 |
| WO | WO 2016044560 | 3/2016 |

OTHER PUBLICATIONS

United States Patent Office Action for U.S. Appl. No. 13/124,232 dated Jun. 20, 2012 (13 pages).

Alley, M.C. et al., ""SJG-136 (NSC 694501), a novel rationally designed DNA minor groove interstrand cross-linking agent with potent and broad spectrum antitumor activity. Part 2: Efficacy evaluations,"" Cancer Res. (2004) 64:6700-6706.

Adair, J.R. et al., "Antibody-drug conjugates—a perfect synergy," Exp. Opin. Biol. Ther. (2012), pp. 1-16.

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird, R.E. et al., "ABCB1 genetic polymorphism influences the pharmacology of the new pyrrolobenzodiazepine derivative SJG-136," Pharmacogenomics Journal (2008) 8(4):289-296.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al., "Parallel synthesis of a novel C2-aryl pyrrolo[2,1- c][1,4]benzodiazepine (PBD) library," J. Comb. Chem. (2007) 9:437-445.

Arai H., et al., ""Molecular cloning of human endothelin receptors and their expression in vascular endothelial cells and smooth muscle cells,"" Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

Attie T., et al., "Mutation of the endothelin-receptor B gene in Waardenburg-Hirschsprung disease," Hum. Mol. Genet. 4, 2407-2409, 1995.

Auricchio A., et al., "Endothelin-B receptor mutations in patients with isolated Hirschsprung disease from a non-inbred population," Hum. Mol. Genet. 5:351-354, 1996.

(56) References Cited

OTHER PUBLICATIONS

Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Blanc et al., "SAR3419: an anti-CD19-Maytansinoid Immunoconjugate for the treatment of B-cell malignancies," Clin Cancer Res., 2011, 17(20):6448-58.
Blumberg H., et al., ""Interleukin 20: Discovery, Receptor Identification, and Role in Epidermal Function,"" Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(1B):463-70.
Brinster et al., ""Introits increase transcriptional efficiency in transgenic mice,"" (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.
Calcutt, M.W., ""Determination of chemically reduced pyrrolobenzodiazepine SJG-136 in human plasma by HPLC-MS/MS: application to an anticancer phase I dose escalation study,"" J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., ""Plasmin-Activated Prodrugs for Cancer Chemotherapy. 2. Synthesis and Biological Activity of Peptidyl Derivatives of Doxorubicin,"" (1983) J. Med. Chem. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., ""A novel approach to the synthesis of cytotoxic C2-C3 unsaturated pyrrolo[2,1- c][1,4]benzodiazepines (PBDs) with conjugated acrylyl C2-substituents,"" Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., ""Structure of the extracellular region of HER2 alone and in complex with the Herceptin Fab,"" Nature 421, 756-760, 2003.
Ciccodicola, A , et al., ""Molecular characterization of a gene of the 'EGF family' expressed in undifferentiated human NTERA2 teratocarcinoma cells,"" EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI), a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
Collins, "Generation and initial analysis of more than 15,000 full-length human and mouse eDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey E. Quinn JE, Buhler R, et al., "LuCap35: a new model of prostate cancer progression to androgen independence." The Prostate 2003;55:239-46.
Courtney, S. M. et al., "A new convenient procedure for the synthesis of pyrrolo[2,1-c][1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.

(56) References Cited

OTHER PUBLICATIONS

Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use of ATP bioluminescence as a measure of cell proliferation and cytotoxicity," (1993) J. Immunol. Meth. 160:81-88.
Dall'Acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2- d][1,4]benzodiazepin-6-one," J. Heterocyclic. Chem. (1980) 17:701-703.
Davis et al., "Identification of a family of Fe receptor homo logs with preferential B cell expression," (2001) Proc. Natl. Acad. Sci. USA 98(17):9772-9777.
De Groot et al., ""Cascade-Release Dendrimers"" Liberate All End Groups upon a Single Triggering Event in the Dendritic Core, (2003) Angew. Chern. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chern. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Dennis et al., (2002) "Albumin Binding as a General Strategy for Improving the Pharmacokinetics of Proteins" J Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.
Dubowchik et al, "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Foloppe, M.P et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.

(56) References Cited

OTHER PUBLICATIONS

Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al."Automation of solid-phase peptide synthesis" in Macromolecular Sequencing and Synthesis, Alan R. Liss, Inc., 1988, pp. 199-218.
Genbank accession No. 11038674 (2013).
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NM006424 (2013).
Genbank accession No. NP _001194 (2013).
Genbank accession No. NP _001774.10 (2013).
Genbank accession No. NP _003203 (2013).
Genbank accession No. NP 002111.1 (2013).
Genbank accession No. NP_001707.1 (2013).
Genbank accession No. NP_001773.1 (2013).
Genbank accession No. NP_002552.2 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol 273:73-80.
Glynne-Jones et al., "TENB2, a Proteoglycan Identified in Prostate Cancer That is Associated With Disease Progression and Androgen Independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 23-200.
Greene, T.W. et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1- c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant staphylococcus aureus," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.

(56) References Cited

OTHER PUBLICATIONS

Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).
Hartley J A: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-linksDNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (Ig-alpha/mb-1) gene," (1994) Immunogenetics 40(4):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chern. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
International Preliminary Report on Patentability for Application No. PCT/US2011/032632 dated Jul. 27, 2012 (6 pages).
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2014/054958 dated Jul. 2, 2014 (13 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report for Application No. PCT/US2011/032632 dated Jul. 27, 2011 (5 pages).
International Written Opinion for Application No. PCT/US2011/032632 dated Jul. 27, 2011 (4 pages).
Itoh et al., "Sibanomicin, a new pyrrolo(1,4)benzodiazepine antitumor antibiotic produced by a *micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., ""Tamoxifen: a most unlikely pioneering medicine, "" Nature Reviews: Drug Discovery (2003) 2:205-213.
Junutula, et al., "Site-specific conjugation of a cytotoxic drug to an antibody improves the therapeutic index," 2008b Nature Biotech., 26(8):925-932.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22): 3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.

(56) References Cited

OTHER PUBLICATIONS

Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anti-cancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., ""A Novel Peptide Delivery System Involving Peptidase Activated Prodrugs as Antimicrobial Agents. Synthesis and Biological Activity of Peptidyl Derivatives of 5 Fluorouracil,"" (1984) J. Med. Chern. 27:1447-1451.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin.6," (1999) Brit. Jour. Cancer 79(5-6):707-717.
Lambert J., "Drug-conjugated monoclonal antibodies for the treatment of cancer," (2005) Current Opin. In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X Atp receptor subunit from brain and immune system," (1997) FEBS Lett. 418(1-2):195-199.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Levenson et al., "MCF-7: The First Hormone-responsive Breast Cancer Cell Line," (1997) Cancer Res. 57(15):3071-3078.
Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mastroberardino et al., "Amino-acid transport by heterodimers of 4F2hc/CD98 and members of a permease family," Nature 395 (6699):288-291 (1998).
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS Is Associated With MD-1 and Transmits an Activation Signal in Human B Cells," (1998) Blood 92:2815-2822.

(56) References Cited

OTHER PUBLICATIONS

Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and sequence analysis of a cDNA encoding human non-selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combinding high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," the Journal of Biological Chemistry, vol. 278, No. 33, Issue of Aug. 15, pp. 30813-30820, 2003.
O'Neil, Chemical Abstract No. 171573p, "The synthesis of Functionalized Pyrrolo- [2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular cloning of a non-isopeptide-selective human endothelin receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "Dppe: A Convenient Replacement for Triphenylphosphine in the Staudinger and Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
PCT/US2012/059864 International Search Report and Written Opinion dated Dec. 21, 2012 (7 pages).
Pepper, C., "Fludarabine-mediated suppression of the excision repair enzyme ERCC1 contributes to the cytotoxic synergy with the DNA minor groove crosslinking agent SJG-136 (Nsc 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al., "Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.

(56) References Cited

OTHER PUBLICATIONS

Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10): 895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, p. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c- erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, THE DOBeta Gene is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody—Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Tawaragi Y., et al., "Primary structure of nonspecific crossreacting antigen (NCA), a member of carcinoembryonic antigen (CEA) gene family, deduced from cdna sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson U.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).

(56) References Cited

OTHER PUBLICATIONS

Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis—Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
United States Office Action for U.S. Appl. No. 10/598,518 dated Sep. 28, 2009 (6 pages).
United States Patent Office Action for U.S. Appl. No. 13/087,575 dated Feb. 1, 2013 (16 pages).
United States Patent Office Final Rejection for U.S. Appl. No. 13/087,575 dated Aug. 12, 2013 (16 pages).
United States Patent Office Notice of Allowance for U.S. Appl. No. 13/124,232 dated Mar. 6, 2013 (5 pages).
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a human protein homologous to the mouse Lyb-2 B cell differentiation antigen and sequence of the corresponding cDNA," (1990) J. Immunol. 144(12):4870-4877.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for C3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody—drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomeraseI, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).

(56) References Cited

OTHER PUBLICATIONS

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Yu et al., "Human mb-1 gene: complete edna sequence and its expression in B cells bearing membrane Ig of various isotypes," (1992) J. Immunol. 148(2) 633-637.

Zammarchi et al., "Pre-Clinical Development of Adct-402, a Novel Pyrrolobenzodiazepine (PBD)—Based Antibody Drug Conjugate (ADC) Targeting CD19-Expressing B-Cell Malignancies," Blood, 2015, 126:1564, Abstract.

PYRROLOBENZODIAZEPINES AND CONJUGATES THEREOF

CROSS-REFERENCE TO RELATED APPLICATIONS

This application is a continuation of copending U.S. application Ser. No. 17/223,712, filed Apr. 6, 2021, which is a continuation of U.S. application Ser. No. 16/837,336, filed on Apr. 1, 2020, which issued as U.S. Pat. No. 10,994,023 on May 4, 2021, which is a continuation of U.S. application Ser. No. 16/412,138, filed on May 14, 2019, which issued as U.S. Pat. No. 10,646,584 on May 12, 2020, which is a continuation of U.S. application Ser. No. 15/847,308, filed on Dec. 19, 2017, which issued as U.S. Pat. No. 10,335,497 on Jul. 2, 2019, which is a continuation of U.S. application Ser. No. 14/051,743, filed on Oct. 11, 2013, which issued as U.S. Pat. No. 9,889,207 on Feb. 13, 2018, which claims the benefit of U.S. Provisional Application No. 61/712,928, filed on Oct. 11, 2012, the entire contents of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 550,222 Byte XML file named "36197-307-ST26.xml," created on Jun. 6, 2023.

The present invention relates to pyrrolobenzodiazepines (PBDs), in particular pyrrolobenzodiazepines having a labile N10 protecting group, in the form of a linker to a cell binding agent.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.,* 87, 5793-5795 (1965); Leimgruber, et al., *J. Am. Chem. Soc.,* 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, *D. and Thurston, D. E., Chem. Rev.* 2011 111 (4), 2815-2864). Family members include abbeymycin (Hochlowski, et al., *J. Antibiotics,* 40, 145-148 (1987)), chicamycin (Konishi, et al., *J. Antibiotics,* 37, 200-206 (1984)), DC-81 (Japanese Patent 58-180 487; Thurston, et al., *Chem. Brit.,* 26, 767-772 (1990); Bose, et al., *Tetrahedron,* 48, 751-758 (1992)), mazethramycin (Kuminoto, et al., *J. Antibiotics,* 33, 665-667 (1980)), neothramycins A and B (Takeuchi, et al., *J. Antibiotics,* 29, 93-96 (1976)), porothramycin (Tsunakawa, et al., *J. Antibiotics,* 41, 1366-1373 (1988)), prothracarcin (Shimizu, et al, *J. Antibiotics,* 29, 2492-2503 (1982); *Langley and Thurston, J. Org. Chem.,* 52, 91-97 (1987)), sibanomicin (DC-102) (Hara, et al., *J. Antibiotics,* 41, 702-704 (1988); Itoh, et al., *J. Antibiotics,* 41, 1281-1284 (1988)), sibiromycin (Leber, et al., *J. Am. Chem. Soc.,* 110, 2992-2993 (1988)) and tomamycin (Arima, et al., *J. Antibiotics,* 25, 437-444 (1972)). PBDs are of the general structure:

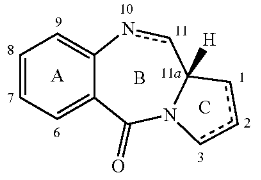

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III.* Springer-Verlag, New York, pp. 3-11 (1975); Hurley and Needham-VanDevanter, *Acc. Chem. Res.,* 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

SG2000

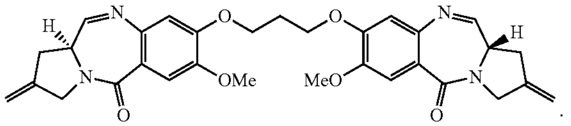

WO 2007/085930 describes the preparation of dimer PBD compounds having linker groups for connection to a cell binding agent, such as an antibody. The linker is present in the bridge linking the monomer PBD units of the dimer.

The present inventors have described dimer PBD compounds having linker groups for connection to a cell binding agent, such as an antibody, in WO 2011/130598. The linker in these compounds is attached to one of the available N10 positions, and are generally cleaved by action of an enzyme on the linker group.

Antibody-Drug Conjugates

Antibody therapy has been established for the targeted treatment of patients with cancer, immunological and angiogenic disorders (Carter, P. (2006) *Nature Reviews Immunology* 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6): 3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b *Nature Biotech.*, 26(8):925-932; Dornan et al (2009) *Blood* 114(13):2721-2729; U.S. Pat. Nos. 7,521,541; 7,723,485; WO2009/052249; McDonagh (2006) *Protein Eng. Design & Sel.* 19(7): 299-307; Doronina et al (2006) *Bioconj. Chem.* 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

The present inventors have developed particular PBD dimers with linking groups for the formation of PBD conjugates with cell binding agents, and in particular PBD antibody conjugates.

SUMMARY OF THE INVENTION

In a first aspect, the present invention provides compound A:

A

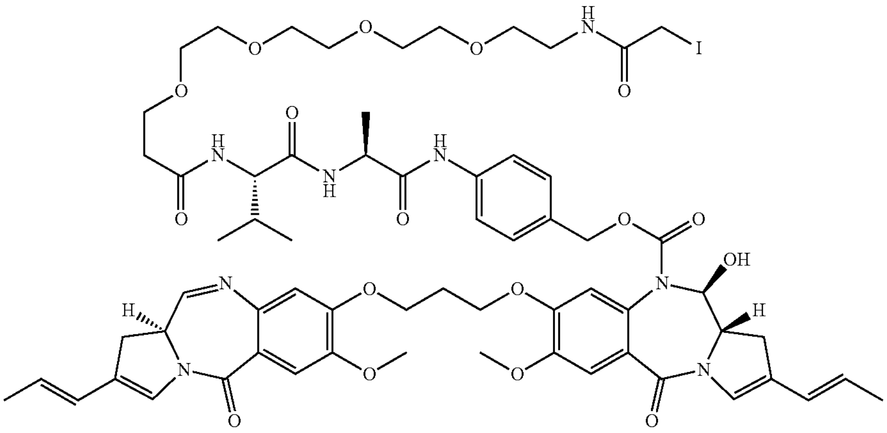

and salts of solvates thereof.

WO 2011/130598 discloses compound 80:

80

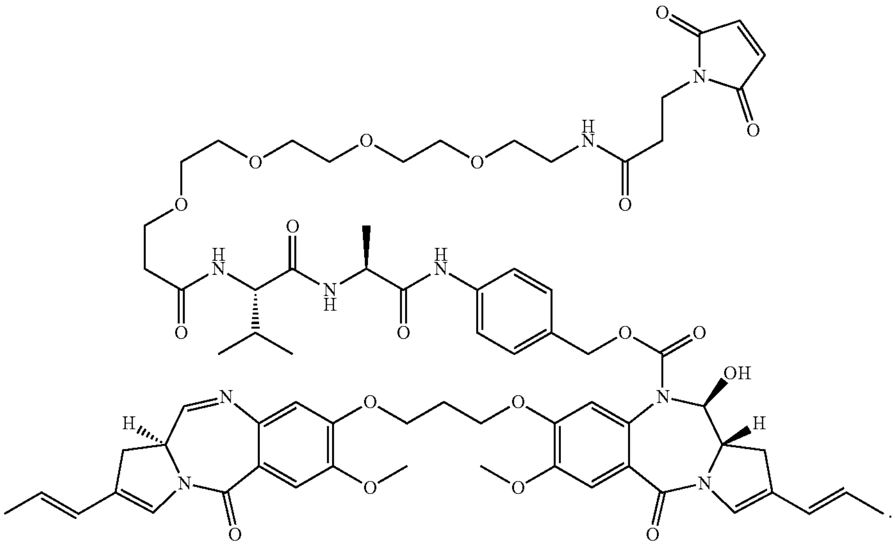
.

Compound A differs from this by comprising an iodoacetamide group for linking to the cell binding agent. This group may offer advantages over compound 80 with regards to its stability when bound to a cell binding agent (see below). The malemide group in compound 80 can undergo a retro-Michael reaction, becoming unconjugated from the cell binding agent, and thus vulnerable to scavenging by other thiol containing biological molecules, such as albumin and glutathione. Such unconjugation cannot occur with compound A. Also, the iodoacetamide group may avoid other unwanted side reactions.

In a second aspect, the present invention provides compound B:

B

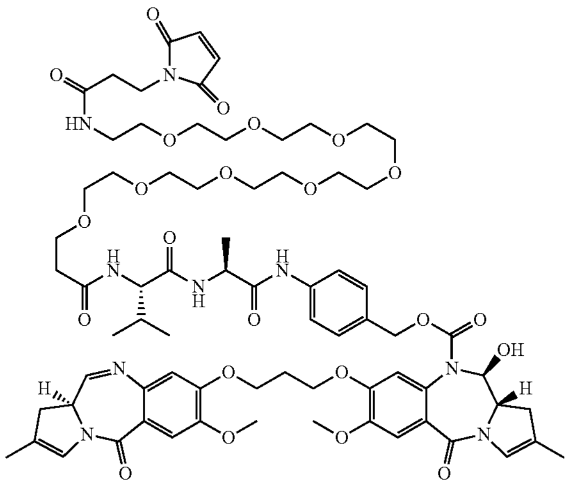

and salts and solvates thereof.

Compound B differs from previously disclosed PBD dimers with a drug linker having a C2-3 endo-double bond, by having a smaller, less lipophilic C2 substituent, e.g. 4F-phenyl, propylene. As such, the conjugates of compound B (see below) are less likely to aggregate once synthesised. Such aggregation of conjugates can be measured by Size exclusion chromatography (SEC).

Both compound A and B have two $sp^2$ centres in each C-ring, which may allow for stronger binding in the minor groove of DNA, than for compounds with only one $sp^2$ centre in each C-ring.

A third aspect of the present invention provides a conjugate of formula ConjA:

ConjA

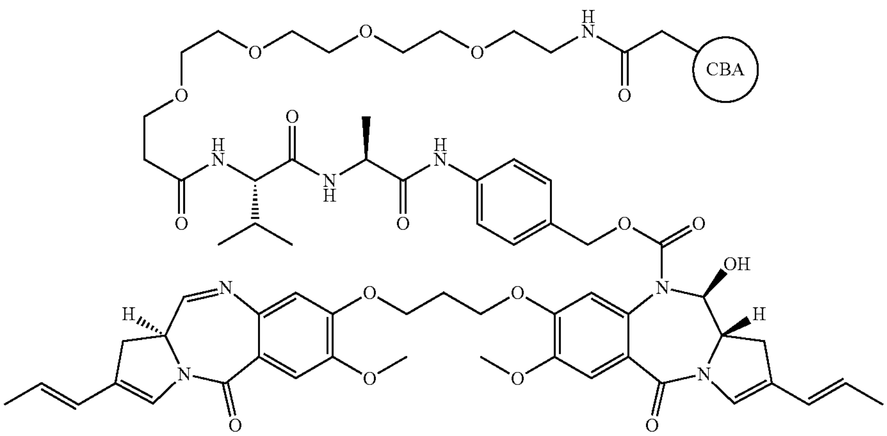

-continued or ConjB:

ConjB

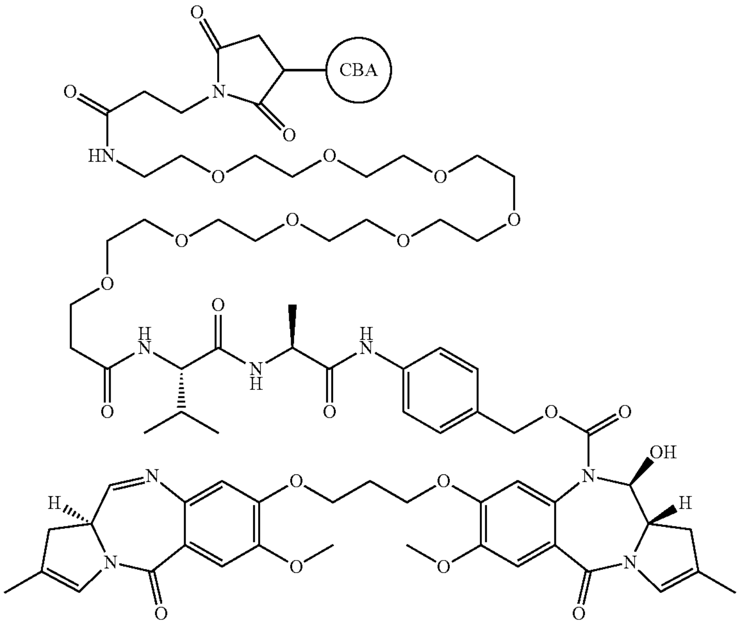

where CBA represents a cell binding agent. The link to the moiety shown is via a free S (active thiol) on the cell binding agent.

DETAILED DESCRIPTION OF THE INVENTION

Figure 1:
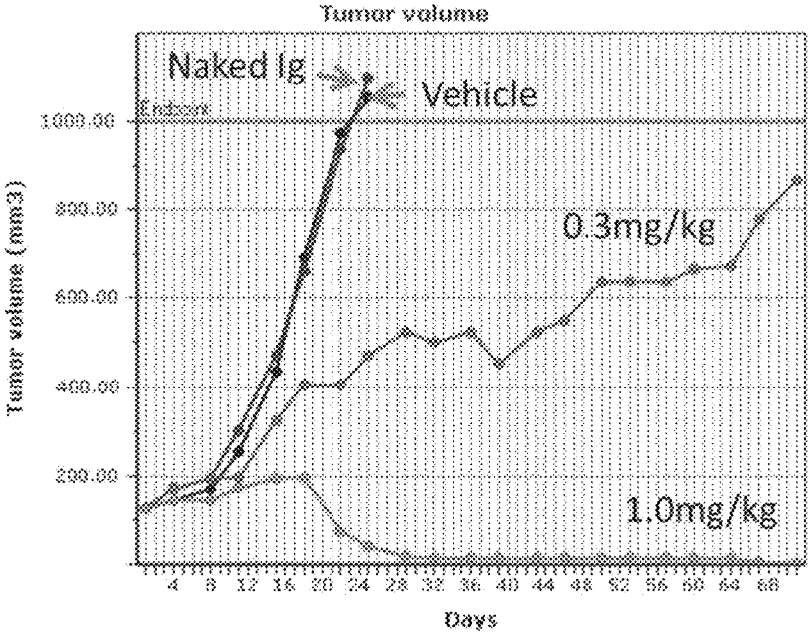
FIG. 1 shows the effect on mean tumour volume in groups of 10 miced dosed with ADC1A at 0.3 or 1.0 mg/kg compared to vehicle or naked kg controls.

The present invention provides a PBD dimer with a linker connected through the N10 position on one of the PBD moieties suitable for forming a PBD dimer conjugated via the linker to a cell binding agent.

The present invention is suitable for use in providing a PBD compound to a preferred site in a subject. The conjugate allows the release of an active PBD compound that does not retain any part of the linker. There is no stub present that could affect the reactivity of the PBD compound. Thus ConjA would release the compound RelA:

RelA

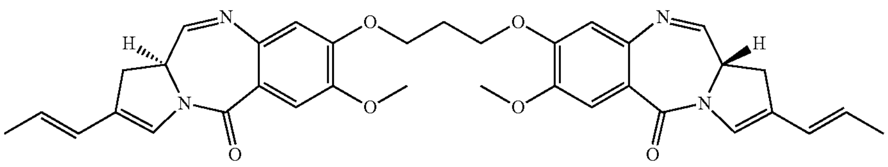

and ConjB would release the compound RelB:

RelB

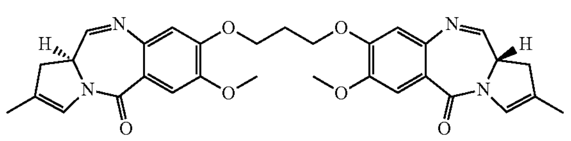

A further aspect of the present invention is the compound RelB, and salts and solvates thereof.

The specified link between the PBD dimer and the cell binding agent, e.g. antibody, in the present invention is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA or RelB is achieved at the desired activation site of the conjugates of formulae ConjA or ConjB by the action of an enzyme, such as cathepsin, on the linking group, and in particular on the valine-alanine dipeptide moiety.

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', $F(ab')_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) *Nature*, 352:624-628; Marks et al (1991) *J. Mol. Biol.*, 222:581-597 or from transgenic mice carrying a fully human immunoglobulin system (Lonberg (2008) *Curr. Opinion* 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity.

Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Graftinq

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VHxVL combination. The method is described in *Nature Biotechnology* (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at www.wehi.edu.au). Alternatively, MHC class II-binding motifs may be identified using computational threading methods such as those devised by Altuvia et al. (*J. Mol. Biol.* 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:

(a) determining the conformational structure of the variable region of the non-human (e.g. rodent) antibody (or fragment thereof) by constructing a three-dimensional model of the non-human antibody variable region;

(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;

(c) defining for the non-human antibody to be humanized, a set of heavy and light chain surface exposed amino acid residues using the set of framework positions generated in step (b);

(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;

(e) substituting, in the amino acid sequence of the non-human antibody to be humanized, the set of heavy and light chain surface exposed amino acid residues defined in step (c) with the set of heavy and light chain surface exposed amino acid residues identified in step (d);

(f) constructing a three-dimensional model of the variable region of the non-human antibody resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and (h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in Methods 36, 43-60 (2005).

Examples of cell binding agents include those agents described for use in WO 2007/085930, which is incorporated herein.

Tumour-associate antigens and cognate antibodies for use in embodiments of the present invention are listed below.

Tumor-Associated Antigens and Cognate Antibodies (1) BMPR1B (Bone Morphogenetic Protein Receptor-Type IB)

Nucleotide

Genbank accession no. NM_001203

Genbank version no. NM_001203.2 GI: 169790809

Genbank record update date: Sep. 23, 2012 02:06 PM

Polypeptide

Genbank accession no. NP_001194

Genbank version no. NP_001194.1 GI: 4502431

Genbank record update date: Sep. 23, 2012 02:06 PM

Cross-References ten Dijke, P., et al *Science* 264 (5155): 101-104 (1994), *Oncogene* 14 10 (11):1377-1382 (1997)); WO2004/063362 (Claim 2); WO2003/042661 (Claim 12); US2003/134790-A1 (Page 38-39); WO2002/102235 (Claim 13; Page 296); WO2003/055443 (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377 (Page 349-350); WO2002/30268 (Claim 27; Page 376); 15 WO2001/48204 (Example; FIG. 4); NP_001194 bone morphogenetic protein receptor, type IB/pid=NP_001194.1; MIM: 603248; AY065994

(2) E16 (LAT1, SLC7A5)

Nucleotide

Genbank accession no. NM_003486

Genbank version no. NM_003486.5 GI: 71979931

Genbank record update date: Jun. 27, 2012 12:06 PM

Polypeptide

Genbank accession no. NP_003477

Genbank version no. NP_003477.4 GI: 71979932

Genbank record update date: Jun. 27, 2012 12:06 PM

Cross References
*Biochem. Biophys. Res.*
*Commun.* 255 (2), 283-288 (1999), *Nature* 395 (6699):288-291 (1998), Gaugitsch, H. W., et 20 al (1992) *J. Biol. Chem.* 267 (16):11267-11273); WO2004/048938 (Example 2); WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10; Page 293); WO2002/64798 (Claim 33; Page 93-95); WO2000/14228 (Claim 5; Page 133-136); US2003/224454 (FIG. 3); 25 WO2003/025138 (Claim 12; Page 150); NP_003477 solute carrier family 7 (cationic amino
acid transporter, y+system), member 5/pid=NP_003477.3—*Homo sapiens;*
MIM: 600182; NM_015923.

Figure 2:
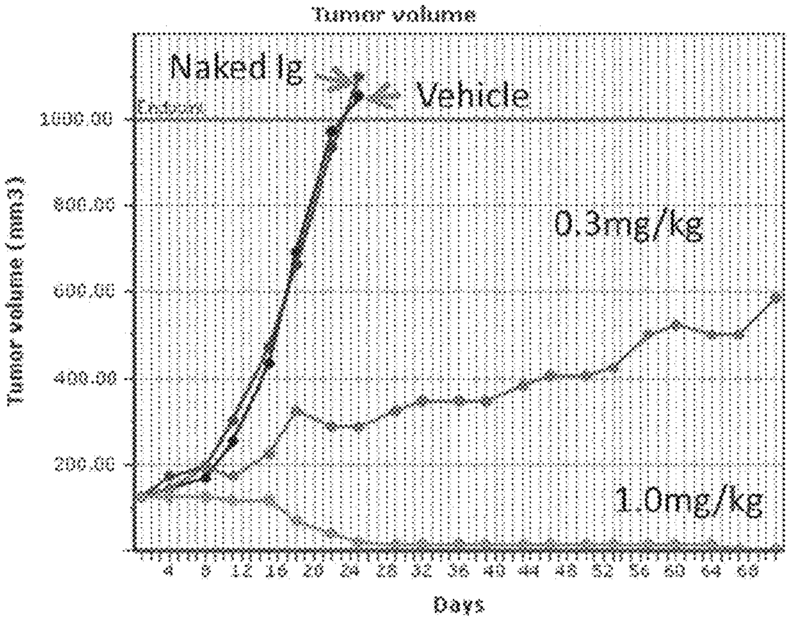
FIG. 2 shows the effect on mean tumour volume in groups of 10 miced dosed with ADC1B at 0.3 or 1.0 mg/kg (green) compared to vehicle or naked Ig controls.

(3) STEAP1 (Six Transmembrane Epithelial Antigen of Prostate)
Nucleotide
Genbank accession no. NM_012449
Genbank version no. NM_012449.2 GI: 22027487
Genbank record update date: Sep. 9, 2012 02:57 PM
Polypeptide
Genbank accession no. NP_036581
Genbank version no. NP_036581.1 GI: 9558759
Genbank record update date: Sep. 9, 2012 02:57 PM
Cross References
*Cancer Res.* 61 (15), 5857-5860 (2001), Hubert, R. S., et al (1999) *Proc. Natl. Acad. Sci. U.S.A.* 96 (25):14523-14528); WO2004/065577 (Claim 6); WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2); WO2002/89747 (Example 5; Page 618-619); WO2003/022995 (Example 9; FIG. 13A, 35 Example 53; Page 173, Example 2; FIG. 2A); six transmembrane epithelial antigen of the prostate; MIM: 604415.

(4) 0772P (CA125, MUC16)
Nucleotide
Genbank accession no. AF361486
Genbank version no. AF361486.3 GI: 34501466
Genbank record update date: Mar. 11, 2010 07:56 AM
Polypeptide
Genbank accession no. AAK74120
Genbank version no. AAK74120.3 GI: 34501467
Genbank record update date: Mar. 11, 2010 07:56 AM
Cross References
*J. Biol. Chem.* 276 (29):27371-27375 (2001)); WO2004/045553 (Claim 14); WO2002/92836 (Claim 6; FIG. 12); WO2002/83866 (Claim 15; Page 116-121); US2003/124140 (Example 16); GI: 34501467;

(5) MPF (MPF, MSLN, SMR, Megakaryocyte Potentiating Factor, Mesothelin)
Nucleotide
Genbank accession no. NM_005823
Genbank version no. NM_005823.5 GI: 293651528
Genbank record update date: Sep. 2, 2012 01:47 PM
Polypeptide
Genbank accession no. NP_005814
Genbank version no. NP_005814.2 GI: 53988378
Genbank record update date: Sep. 2, 2012 01:47 PM
Cross References
Yamaguchi, N., et al *Biol. Chem.* 269 (2), 805-808 (1994), *Proc. Natl. Acad. Sci. U.S.A.* 96 (20):11531-11536 (1999), *Proc. Natl. Acad. Sci. U.S.A.* 93 10 (1):136-140 (1996), *J. Biol. Chem.* 270 (37):21984-21990 (1995)); WO2003/101283 (Claim 14); (WO2002/102235 (Claim 13; Page 287-288); WO2002/101075 (Claim 4; Page 308-309); WO2002/71928 (Page 320-321); WO94/10312 (Page 52-57); IM: 601051.

(6) Napi3b (NAPI-3B, NPTIIb, SLC34A2, Solute Carrier Family 34 (Sodium Phosphate), Member 2, Type II Sodium-Dependent Phosphate Transporter 3b)
Nucleotide
Genbank accession no. NM_006424
Genbank version no. NM_006424.2 GI: 110611905
Genbank record update date: Jul. 22, 2012 03:39 PM
Polypeptide
Genbank accession no. NP_006415
Genbank version no. NP_006415.2 GI: 110611906
Genbank record update date: Jul. 22, 2012 03:39 PM
Cross References
*J. Biol. Chem.* 277 (22):19665-19672 (2002), *Genomics* 62 (2):281-284 (1999), Feild, J. A., et al (1999) *Biochem. Biophys. Res. Commun.* 258 (3):578-582); WO2004/022778 (Claim 2); EP1394274 (Example 11); WO2002/102235 (Claim 13; Page 20 326); EP0875569 (Claim 1; Page 17-19); WO2001/57188 (Claim 20; Page 329); WO2004/032842 (Example IV); WO2001/75177 (Claim 24; Page 139-140); MIM: 604217.

(7) Sema 5b (FLJ10372, KIAA1445, Mm.42015, SEMASB, SEMAG, Semaphorin 5b Hlog, 25 Sema Domain, Seven Thrombospondin Repeats (Type 1 and Type 1-Like), Transmembrane Domain™ and Short Cytoplasmic Domain, (Semaphorin) 5B)
Nucleotide
Genbank accession no. AB040878
Genbank version no. AB040878.1 GI: 7959148
Genbank record update date: Aug. 2, 2006 05:40 PM
Polypeptide
Genbank accession no. BAA95969
Genbank version no. BAA95969.1 GI: 7959149
Genbank record update date: Aug. 2, 2006 05:40 PM
Cross References
Nagase T., et al (2000) *DNA Res.* 7 (2):143-150); WO2004/000997 (Claim 1); WO2003/003984 (Claim 1); WO2002/06339 (Claim 1; Page 50); WO2001/88133 (Claim 1; Page 41-43, 48-58); WO2003/054152 (Claim 20); WO2003/101400 (Claim 11); Accession: 30 Q9P283; Genew; HGNC: 10737

(8) PSCA hIg (2700050C12Rik, C530008016Rik, RIKEN cDNA 2700050C12, RIKEN cDNA 2700050C12 Gene)
Nucleotide
Genbank accession no. AY358628
Genbank version no. AY358628.1 GI: 37182377
Genbank record update date: Dec. 1, 2009 04:15 AM
Polypeptide
Genbank accession no. AAQ88991
Genbank version no. AAQ88991.1 GI: 37182378
Genbank record update date: Dec. 1, 2009 04:15 AM
Cross References
Ross et al (2002) *Cancer Res.* 62:2546-2553; US2003/129192 (Claim 2); US2004/044180 (Claim 12); US2004/044179 35 (Claim 11); US2003/096961 (Claim 11); US2003/232056 (Example 5); WO2003/105758 16 (Claim 12); US2003/206918 (Example 5); EP1347046 (Claim 1); WO2003/025148 (Claim 20); GI: 37182378.

(9) ETBR (Endothelin Type B Receptor)
Nucleotide
Genbank accession no. AY275463
Genbank version no. AY275463.1 GI: 30526094

Genbank record update date: Mar. 11, 2010 02:26 AM
Polypeptide
Genbank accession no. AAP32295
Genbank version no. AAP32295.1 GI: 30526095
Genbank record update date: Mar. 11, 2010 02:26 AM
Cross References
Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997;
Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-15 2409, 1995; Auricchio A., et al *Hum. Mol. Genet.* 5:351-354, 1996; Amiel J., et al *Hum. Mol.*
Genet. 5, 355-357, 1996; Hofstra R. M. W., et al *Nat. Genet.* 12, 445-447, 1996; Svensson P. J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004/045516 (Claim 1); WO2004/048938 (Example 2); WO2004/040000 (Claim 151); WO2003/087768 (Claim 1); 20 WO2003/016475 (Claim 1); WO2003/016475 (Claim 1); WO2002/61087 (FIG. 1); WO2003/016494 (FIG. 6); WO2003/025138 (Claim 12; Page 144); WO2001/98351 (Claim 1; Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004.
(10) MSG783 (RNF124, Hypothetical Protein FLJ20315)
Nucleotide
Genbank accession no. NM_017763
Genbank version no. NM_017763.4 GI: 167830482
Genbank record update date: Jul. 22, 2012 12:34 AM
Polypeptide
Genbank accession no. NP_060233
Genbank version no. NP_060233.3 GI: 56711322
Genbank record update date: Jul. 22, 2012 12:34 AM
Cross References
WO2003/104275 (Claim 1); WO2004/046342 (Example 2); WO2003/042661 (Claim 12); WO2003/083074 (Claim 14; Page 61); WO2003/018621 (Claim 1); WO2003/024392 (Claim 2; FIG. 93); WO2001/66689 (Example 6); LocusID: 54894.
(11) STEAP2 (HGNC_8639, IPCA-1, PCANAP1, STAMP1, STEAP2, STMP, Prostate Cancer Associated Gene 1, Prostate Cancer Associated Protein 1, Six Transmembrane Epithelial Antigen of Prostate 2, Six Transmembrane Prostate Protein)
Nucleotide
Genbank accession no. AF455138
Genbank version no. AF455138.1 GI: 22655487
Genbank record update date: Mar. 11, 2010 01:54 AM
Polypeptide
Genbank accession no. AAN04080
Genbank version no. AAN04080.1 GI: 22655488
Genbank record update date: Mar. 11, 2010 01:54 AM
Cross References
Lab. Invest. 82 (11):1573-1582 (2002)); WO2003/087306; US2003/064397 (Claim 1; FIG. 1); WO2002/72596 (Claim 13; Page 54-55); WO2001/72962 (Claim 1; FIG. 4B); 35 WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); GI: 22655488.
(12) TrpM4 (BR22450, FLJ20041, TRPM4, TRPM4B, Transient Receptor Potential Cation 5 Channel, Subfamily M, Member 4)
Nucleotide
Genbank accession no. NM_017636
Genbank version no. NM_017636.3 GI: 304766649
Genbank record update date: Jun. 29, 2012 11:27 AM
Polypeptide
Genbank accession no. NP_060106
Genbank version no. NP_060106.2 GI: 21314671
Genbank record update date: Jun. 29, 2012 11:27 AM
Cross References
Xu, X. Z., et al *Proc. Natl. Acad. Sci. U.S.A.* 98 (19):10692-10697 (2001), *Cell* 109 (3):397-407 (2002), *J. Biol. Chem.* 278 (33):30813-30820 (2003)); US2003/143557 (Claim 4); WO2000/40614 (Claim 14; Page 100-103); WO2002/10382 (Claim 1; FIG. 9A); WO2003/042661 (Claim 12); WO2002/30268 (Claim 27; Page 391); US2003/219806 (Claim 4); WO2001/62794 (Claim 10 14; FIG. 1A-D); MIM: 606936.
(13) CRIPTO (CR, CR1, CRGF, CRIPTO, TDGF1, Teratocarcinoma-Derived Growth Factor)
Nucleotide
Genbank accession no. NM_003212
Genbank version no. NM_003212.3 GI: 292494881
Genbank record update date: Sep. 23, 2012 02:27 PM
Polypeptide
Genbank accession no. NP_003203
Genbank version no. NP 003203.1 GI: 4507425
Genbank record update date: Sep. 23, 2012 02:27 PM
Cross References
Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO2002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); MIM: 187395.
(14) CD21 (CR2 (Complement Receptor 2) or C3DR (C3d/Epstein Barr Virus Receptor) or Hs.73792)
Nucleotide
Genbank accession no M26004
Genbank version no. M26004.1 GI: 181939
Genbank record update date: Jun. 23, 2010 08:47 AM
Polypeptide
Genbank accession no. AAA35786
Genbank version no. AAA35786.1 GI: 181940
Genbank record update date: Jun. 23, 2010 08:47 AM
Cross References
Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/

005538 (Example 1); WO2003/062401 (Claim 9); WO2004/045520 (Example 4); WO91/02536 (FIGS. 9.1-9.9); WO2004/020595 (Claim 1); Accession: P20023; Q13866; Q14212; EMBL; M26004; AAA35786.1.

(15) CD79b (CD79B, CD79p, IGb (Immunoglobulin-Associated Beta), B29)

Nucleotide

Genbank accession no NM_000626

Genbank version no. NM_000626.2 GI: 90193589

Genbank record update date: Jun. 26, 2012 01:53 PM

Polypeptide

Genbank accession no. NP_000617

Genbank version no. NP_000617.1 GI: 11038674

Genbank record update date: Jun. 26, 2012 01:53 PM

Cross References

*Proc. Natl. Acad. Sci. U.S.A.* (2003) 100 (7):4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003/062401 (claim 9); WO2002/78524 (Example 2); US2002/150573 (claim 35 5, page 15); U.S. Pat. No. 5,644,033; WO2003/048202 (claim 1, pages 306 and 309); WO 99/58658, U.S. Pat. No. 6,534,482 (claim 13, FIG. 17A/B); WO2000/55351 (claim 11, pages 1145-1146); MIM: 147245

(16) FcRH2 (IFGP4, IRTA4, SPAP1A (SH2 Domain Containing Phosphatase Anchor Protein 5 1a), SPAP1B, SPAP1C)

Nucleotide

Genbank accession no NM_030764

Genbank version no. NM_030764.3 GI: 227430280

Genbank record update date: Jun. 30, 2012 12:30 AM

Polypeptide

Genbank accession no. NP_110391

Genbank version no. NP_110391.2 GI: 19923629

Genbank record update date: Jun. 30, 2012 12:30 AM

Cross References

AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004/016225 (Claim 2); WO2003/077836; WO2001/38490 (Claim 5; FIG. 18D-1-18D-2); WO2003/097803 (Claim 12);

10 WO2003/089624 (Claim 25): MIM: 606509.

(17) HER2 (ErbB2)

Nucleotide

Genbank accession no M11730

Genbank version no. M11730.1 GI: 183986

Genbank record update date: Jun. 23, 2010 08:47 AM

Polypeptide

Genbank accession no. AAA75493

Genbank version no. AAA75493.1 GI: 306840

Genbank record update date: Jun. 23, 2010 08:47 AM

Cross References

Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swiercz J. M., et al *J. Cell Biol.* 165, 869-15 880, 2004; Kuhns J. J., et al *J. Biol. Chem.* 274, 36422-36427, 1999; Cho H.-S., et al *Nature* 421, 756-760, 2003; Ehsani A., et al (1993) *Genomics* 15, 426-429; WO2004/048938 (Example 2); WO2004/027049 (FIG. 11); WO2004/009622; WO2003/081210;

WO2003/089904 (Claim 9); WO2003/016475 (Claim 1); US2003/118592; WO2003/008537 (Claim 1); WO2003/055439 (Claim 29; FIG. 1A-B); WO2003/025228 (Claim 37; FIG. 5C); 20 WO2002/22636 (Example 13; Page 95-107); WO2002/12341 (Claim 68; FIG. 7); WO2002/13847 (Page 71-74); WO2002/14503 (Page 114-117); WO2001/53463 (Claim 2; Page 41-46); WO2001/41787 (Page 15); WO2000/44899 (Claim 52; FIG. 7); WO2000/20579 (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 25 (Example 3; FIG. 4); Accession: P04626; EMBL; M11767; AAA35808.1. EMBL; M11761; AAA35808.1

Antibodies

Abbott: US20110177095

For example, an antibody comprising CDRs having overall at least 80% sequence identity to CDRs having amino acid sequences of SEQ ID NO:3 (CDR-H1), SEQ ID NO:4 (CDR-H2), SEQ ID NO:5 (CDR-H3), SEQ ID NO:104 and/or SEQ ID NO:6 (CDR-L1), SEQ ID NO:7 (CDR-L2), and SEQ ID NO:8 (CDR-L3), wherein the anti-HER2 antibody or anti-HER2 binding fragment has reduced immunogenicity as compared to an antibody having a VH of SEQ ID NO:1 and a VL of SEQ ID NO:2.

Biogen: US20100119511

For example, ATCC accession numbers: PTA-10355, PTA-10356, PTA-10357, PTA-10358

For example, a purified antibody molecule that binds to HER2 comprising a all six CDR's from an antibody selected from the group consisting of BIIB71F10 (SEQ ID NOs:11, 13), BIIB69A09 (SEQ ID NOs:15, 17); BIIB67F10 (SEQ ID NOs:19, 21); BIIB67F11 (SEQ ID NOs:23, 25), BIIB66A12 (SEQ ID NOs:27, 29), BIIB66C01 (SEQ ID NOs:31, 33), BIIB65C10 (SEQ ID NOs:35, 37), BIIB65H09 (SEQ ID NOs:39, 41) and BIIB65B03 (SEQ ID NOs:43, 45), or CDRs which are identical or which have no more than two alterations from said CDRs.

Herceptin (Genentech)—U.S. Pat. No. 6,054,297; ATCC accession no. CRL-10463 (Genentech)

Pertuzumab (Genentech)

US20110117097 for example, see SEQ IDs No. 15&16, SEQ IDs No. 17&18, SEQ IDs No. 23&24 & ATCC accession numbers HB-12215, HB-12216, CRL 10463, HB-12697.

US20090285837

US20090202546 for example, ATCC accession numbers: HB-12215, HB-12216, CRL 10463, HB-12698.

US20060088523 for example, ATCC accession numbers: HB-12215, HB-12216 for example, an antibody comprising the variable light and variable heavy amino acid sequences in SEQ ID Nos. 3 and 4, respectively.

for example, an antibody comprising a light chain amino acid sequence selected from SEQ ID No. 15 and 23, and a heavy chain amino acid sequence selected from SEQ ID No. 16 and 24

US20060018899 for example, ATCC accession numbers: (7C2) HB-12215, (7F3) HB-12216, (4D5) CRL-10463, (2C4) HB-12697.

for example, an antibody comprising the amino acid sequence in SEQ ID No. 23, or a deamidated and/or oxidized variant thereof.

US2011/0159014 for example, an antibody having a light chain variable domain comprising the hypervariable regions of SEQ ID NO: 1".

For example, an antibody having a heavy chain variable domain comprising the hypervariable regions of SEQ ID NO: 2.

US20090187007

Glycotope: TrasGEX antibody http://www.glycotope.com/pipeline

For example, see International Joint Cancer Institute and Changhai Hospital Cancer Cent: HMTI-Fc Ab—Gao J., et al *BMB Rep.* 2009 Oct. 31; 42(10):636-41.

Symphogen: US20110217305

Union Stem Cell & Gene Engineering, China—Liu H Q., et al *Xi Bao Yu Fen Zi Mian YiXue Za Zhi.* 2010 May; 26(5):456-8.

(18) NCA (CEACAM6)

Nucleotide

Genbank accession no M18728

Genbank version no. M18728.1 GI: 189084

Genbank record update date: Jun. 23, 2010 08:48 AM

Polypeptide

Genbank accession no. AAA59907

Genbank version no. AAA59907.1 GI: 189085

Genbank record update date: Jun. 23, 2010 08:48 AM

Cross References

Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4); WO2004/031238; WO2003/042661 (Claim 12); WO2002/78524 (Example 2); WO2002/86443 (Claim 27; Page 427); WO2002/60317 (Claim 2); Accession: P40199; 014920; EMBL; M29541; AAA59915.1.

EMBL; M18728.

(19) MDP (DPEP1)

Nucleotide

Genbank accession no BC017023

Genbank version no. BC017023.1 GI: 16877538

Genbank record update date: Mar. 6, 2012 01:00 PM

Polypeptide

Genbank accession no. AAH17023

Genbank version no. AAH17023.1 GI: 16877539

Genbank record update date: Mar. 6, 2012 01:00 PM

Cross References

*Proc. Natl. Acad. Sci. U.S.A.* 99 (26):16899-16903 (2002)); WO2003/016475 (Claim 1); WO2002/64798 (Claim 33; Page 85-87); JP05003790 (FIG. 6-8); WO99/46284 (FIG. 9); MIM: 179780.

(20) IL20R-alpha (IL20Ra, ZCYTOR7)

Nucleotide

Genbank accession no AF184971

Genbank version no. AF184971.1 GI: 6013324

Genbank record update date: Mar. 10, 2010 10:00 PM

Polypeptide

Genbank accession no. AAF01320

Genbank version no. AAF01320.1 GI: 6013325

Genbank record update date: Mar. 10, 2010 10:00 PM

Cross References

Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) 10 *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (Claim 2; Page 63); WO2002/22153 (Page 45-47); US2002/042366 (Page 20-21); WO2001/46261 (Page 57-59); WO2001/46232 (Page 63-65); WO98/37193 (Claim 1; Page 55-59); Accession: Q9UHF4; Q6UWA9; Q96SH8; EMBL; AF184971; AAF01320.1.

(21) Brevican (BCAN, BEHAB)

Nucleotide

Genbank accession no AF229053

Genbank version no. AF229053.1 GI: 10798902

Genbank record update date: Mar. 11, 2010 12:58 AM

Polypeptide

Genbank accession no. AAG23135

Genbank version no. AAG23135.1 GI: 10798903

Genbank record update date: Mar. 11, 2010 12:58 AM

Cross References

Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (Claim 11); US2003/186373 (Claim 11); US2003/119131 (Claim 1; FIG. 52); US2003/119122 (Claim 1; 20 FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)

(22) EphB2R (DRT, ERK, Hek5, EPHT3, Tyro5)

Nucleotide

Genbank accession no NM_004442

Genbank version no. NM_004442.6 GI: 111118979

Genbank record update date: Sep. 8, 2012 04:43 PM

Polypeptide

Genbank accession no. NP_004433

Genbank version no. NP_004433.2 GI: 21396504

Genbank record update date: Sep. 8, 2012 04:43 PM

Cross References

Chan, J. and Watt, V. M., *Oncogene* 6 (6), 1057-1061 (1991) *Oncogene* 10 (5):897-905 (1995), *Annu. Rev. Neurosci.* 21:309-345 (1998), *Int. Rev. Cytol.* 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); MIM: 600997.

(23) ASLG659 (B7h)

Nucleotide

Genbank accession no. AX092328

Genbank version no. AX092328.1 GI: 13444478

Genbank record update date: Jan. 26, 2011 07:37 AM

Cross References

US2004/0101899 (Claim 2); WO2003104399 (Claim 11); WO2004000221 (FIG. 3); US2003/165504 (Claim 1); US2003/124140 (Example 2); US2003/065143 (FIG. 60); WO2002/102235 (Claim 13; Page 299); US2003/091580 (Example 2); WO2002/10187 (Claim 6; FIG. 10); WO2001/94641 (Claim 12; FIG. 7b); WO2002/02624 (Claim 13; FIG. 1A-1B); US2002/034749 (Claim 54; Page 45-46); WO2002/06317 (Example 2; Page 320-321, Claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (Claim 12); WO2003/004989 (Claim 1); WO2002/71928 (Page 233-234, 452-453); WO 01/16318.

(24) PSCA (Prostate Stem Cell Antigen Precursor)

Nucleotide

Genbank accession no AJ297436

Genbank version no. AJ297436.1 GI: 9367211

Genbank record update date: Feb. 1, 2011 11:25 AM

Polypeptide

Genbank accession no. CAB97347

Genbank version no. CAB97347.1 GI: 9367212

Genbank record update date: Feb. 1, 2011 11:25 AM

Cross References

Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (Claim 17); WO2003/008537 (Claim 1); WO2002/81646 (Claim 1; Page 164); WO2003/003906 (Claim 10; Page 288); WO2001/40309 (Example 1; FIG. 17); US2001/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: 043653; EMBL; AF043498; AAC39607.1

(25) GEDA

Nucleotide

Genbank accession no AY260763

Genbank version no. AY260763.1 GI: 30102448

Genbank record update date: Mar. 11, 2010 02:24 AM

Polypeptide

Genbank accession no. AAP14954

Genbank version no. AAP14954.1 GI: 30102449

Genbank record update date: Mar. 11, 2010 02:24 AM

Cross References

AP14954 lipoma HMGIC fusion-partnerlike protein/pid=AAP14954.1—*Homo sapiens* (human); WO2003/054152 (Claim 20); WO2003/000842 (Claim 1); WO2003/023013 (Example 3, Claim 20); US2003/194704 (Claim 45); GI: 30102449; (26) BAFF-R (B cell-activating factor receptor, BLyS receptor 3, BR3)

Nucleotide

Genbank accession no AF116456

Genbank version no. AF116456.1 GI: 4585274

Genbank record update date: Mar. 10, 2010 09:44 PM

Polypeptide

Genbank accession no. AAD25356

Genbank version no. AAD25356.1 GI: 4585275

Genbank record update date: Mar. 10, 2010 09:44 PM

Cross References

BAFF receptor/pid=NP_443177.1—*Homo sapiens*: Thompson, J. S., et al *Science* 293 (5537), 2108-2111 (2001); WO2004/058309; WO2004/011611; WO2003/045422 (Example; Page 32-33); WO2003/014294 (Claim 35; FIG. 6B); WO2003/035846 (Claim 70; Page 615-616); WO2002/94852 (Col 136-137); WO2002/38766 25 (Claim 3; Page 133); WO2002/24909 (Example 3; FIG. 3); MIM: 606269; NP_443177.1; NM_052945_1; AF132600 (27) CD22 (B-cell receptor CD22-B isoform, BL-CAM, Lyb-8, Lyb8, SIGLEC-2, FLJ22814)

Nucleotide

Genbank accession no AK026467

Genbank version no. AK026467.1 GI: 10439337

Genbank record update date: Sep. 11, 2006 11:24 PM

Polypeptide

Genbank accession no. BAB15489

Genbank version no. BAB15489.1 GI: 10439338

Genbank record update date: Sep. 11, 2006 11:24 PM

Cross References

Wilson et al (1991) *J. Exp. Med.* 173:137-146; 30 WO2003/072036 (Claim 1; FIG. 1); IM: 107266; NP_001762.1; NM_001771_1.

(27a) CD22 (CD22 Molecule)

Nucleotide

Genbank accession no X52785

Genbank version no. X52785.1 GI: 29778

Genbank record update date: Feb. 2, 2011 10:09 AM

Polypeptide

Genbank accession no. CAA36988

Genbank version no. CAA36988.1 GI: 29779

Genbank record update date: Feb. 2, 2011 10:09 AM

Cross References

Stamenkovic I. et al., *Nature* 345 (6270), 74-77 (1990)??

Other information

Official Symbol: CD22

Other Aliases: SIGLEC-2, SIGLEC2

Other Designations: B-cell receptor CD22; B-lymphocyte cell adhesion molecule; BL-CAM; CD22 antigen; T-cell surface antigen Leu-14; sialic acid binding Ig-like lectin 2; sialic acid-binding Ig-like lectin 2

Antibodies

G5/44 (Inotuzumab): DiJoseph J F., et al *Cancer Immunol Immunother.* 2005 January; 54(1):11-24.

Epratuzumab-Goldenberg D M., et al *Expert RevAnticancer Ther.* 6(10): 1341-53, 2006.

(28) CD79a (CD79A, CD79alpha), Immunoglobulin-Associated Alpha, a B Cell-Specific Protein that Covalently Interacts with Ig Beta (CD79B) and Forms a Complex on the Surface with Ig M 35 Molecules, Transduces a Signal Involved in B-Cell Differentiation), pI: 4.84, MW: 25028 TM: 2

[P] Gene Chromosome: 19q13.2).

Nucleotide

Genbank accession no NM_001783

Genbank version no. NM_001783.3 GI: 90193587

Genbank record update date: Jun. 26, 2012 01:48 PM

Polypeptide

Genbank accession no. NP_001774

Genbank version no. NP_001774.1 GI: 4502685

Genbank record update date: Jun. 26, 2012 01:48 PM

Cross References

WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295; Preud'homme et al (1992) *Clin. Exp.* 5 *Immunol.* 90(1):141-146; Yu et al (1992) *J. Immunol.* 148(2) 633-637; Sakaguchi et al (1988)

*EMBO J.* 7(11):3457-3464

(29) CXCR5 (Burkitt's Lymphoma Receptor 1, a G Protein-Coupled Receptor that is Activated by the CXCL13 Chemokine, Functions in Lymphocyte Migration and Humoral Defense, Plays a 10 Role in HIV-2 Infection and Perhaps Development of AIDS, Lymphoma, Myeloma, and Leukemia); 372 aa, pI: 8.54 MW: 41959 TM: 7 [P] Gene Chromosome: 11q23.3, Nucleotide Genbank accession no NM_001716

Genbank version no. NM_001716.4 GI: 342307092

Genbank record update date: Sep. 30, 2012 01:49 PM

Polypeptide

Genbank accession no. NP_001707

Genbank version no. NP_001707.1 GI: 4502415

Genbank record update date: Sep. 30, 2012 01:49 PM

Cross References

WO2004/040000; WO2004/015426; US2003/105292 (Example 2); U.S. Pat. No. 6,555,339 (Example 2); WO2002/61087 (FIG. 1); WO2001/57188 (Claim 20, page 269); WO2001/72830 (pages 12-13); WO2000/22129 (Example 1, pages 152-153, 15 Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta Subunit of MHC Class II Molecule (La Antigen) that Binds Peptides and 20 Presents them to CD4+T Lymphocytes); 273 aa, pI: 6.56, MW: 30820.TM: 1 [P] Gene Chromosome: 6p21.3)

Nucleotide

Genbank accession no NM_002120

Genbank version no. NM_002120.3 GI: 118402587

Genbank record update date: Sep. 8, 2012 04:46 PM

Polypeptide

Genbank accession no. NP 002111

Genbank version no. NP_002111.1 GI: 4504403

Genbank record update date: Sep. 8, 2012 04:46 PM

Cross References

Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci USA* 99:16899-16903; Servenius et al (1987) *J. Biol. Chem.* 262:8759-8766; Beck et al (1996) *J. Mol. Biol.* 25 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic Receptor P2X Ligand-Gated Ion Channel 5, an Ion Channel Gated by Extracellular ATP, May be Involved in Synaptic Transmission and Neurogenesis, Deficiency May Contribute to the Pathophysiology of Idiopathic Detrusor Instability); 422 Aa), pI: 7.63, MW: 47206 TM: 1 [P] Gene Chromosome: 17p13.3).

Nucleotide

Genbank accession no NM_002561

Genbank version no. NM_002561.3 GI: 325197202

Genbank record update date: Jun. 27, 2012 12:41 AM

Polypeptide

Genbank accession no. NP_002552

Genbank version no. NP_002552.2 GI: 28416933

Genbank record update date: Jun. 27, 2012 12:41 AM

Cross References

Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-Cell Differentiation Antigen CD72, Lyb-2); 359 aa, pI: 8.66, MW: 40225, TM: 1 5 [P] Gene Chromosome: 9p13.3).

Nucleotide

Genbank accession no NM_001782

Genbank version no. NM001782.2 GI: 194018444

Genbank record update date: Jun. 26, 2012 01:43 PM

Polypeptide

Genbank accession no. NP_001773

Genbank version no. NP_001773.1 GI: 4502683

Genbank record update date: Jun. 26, 2012 01:43 PM

Cross References

WO2004042346 (claim 65); WO2003/026493 (pages 51-52, 57-58); WO2000/75655 (pages 105-106); Von Hoegen et al (1990) *J. Immunol.* 144(12):4870-4877; Strausberg et al (2002) *Proc. Natl. Acad. Sci USA* 99:16899-16903.

(33) LY64 (Lymphocyte Antigen 64 (RP105), Type I Membrane Protein of the Leucine Rich Repeat (LRR) Family, Regulates B-Cell Activation and Apoptosis, Loss of Function is Associated with Increased Disease Activity in Patients with Systemic Lupus Erythematosis); 661 aa, pI: 6.20, MW: 74147 TM: 1 [P] Gene Chromosome: 5q12).

Nucleotide

Genbank accession no NM_005582

Genbank version no. NM_005582.2 GI: 167555126

Genbank record update date: Sep. 2, 2012 01:50 PM

Polypeptide

Genbank accession no. NP_005573

Genbank version no. NP_005573.2 GI: 167555127

Genbank record update date: Sep. 2, 2012 01:50 PM

Cross References

US2002/193567; WO97/07198 (claim 11, pages 39-42); Miura et al (1996) 15 Genomics 38(3):299-304; Miura et al (1998) *Blood* 92:2815-2822; WO2003/083047; WO97/44452 (claim 8, pages 57-61); WO2000/12130 (pages 24-26).

(34) FcRH1 (Fc Receptor-Like Protein 1, a Putative Receptor for the Immunoglobulin Fc Domain that Contains C2 Type Ig-Like and ITAM Domains, May have a Role in B-Lymphocyte 20 Differentiation); 429 aa, pI: 5.28, MW: 46925 TM: 1 [P] Gene Chromosome: 1q21-1q22)

Nucleotide

Genbank accession no NM052938

Genbank version no. NM_052938.4 GI: 226958543

Genbank record update date: Sep. 2, 2012 01:43 PM

Polypeptide

Genbank accession no. NP_443170

Genbank version no. NP_443170.1 GI: 16418419

Genbank record update date: Sep. 2, 2012 01:43 PM

Cross References

WO2003/077836; WO2001/38490 (claim 6, FIG. 18E-1-18-E-2); Davis et al (2001) *Proc. Natl. Acad. Sci USA* 98(17):9772-9777; WO2003/089624 (claim 8); EP1347046 (claim 1); WO2003/089624 (claim 7).

(35) IRTA2 (Immunoglobulin Superfamily Receptor Translocation Associated 2, a Putative Immunoreceptor with Possible Roles in B Cell Development and Lymphomagenesis; Deregulation of the Gene by Translocation Occurs in Some B Cell Malignancies); 977 aa, pI: 6.88, MW: 106468, TM: 1 [P] Gene Chromosome: 1q21)

Nucleotide

Genbank accession no AF343662

Genbank version no. AF343662.1 GI: 13591709

Genbank record update date: Mar. 11, 2010 01:16 AM

Polypeptide

Genbank accession no. AAK31325

Genbank version no. AAK31325.1 GI: 13591710

Genbank record update date: Mar. 11, 2010 01:16 AM

Cross References

AF343663, AF343664, AF343665, AF369794, AF397453, AK090423, AK090475, AL834187, AY358085; Mouse: AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18-2).

(36) TENB2 (TMEFF2, Tomoregulin, TPEF, HPP1, TR, Putative Transmembrane 35 Proteoglycan, Related to the EGF/Heregulin Family of Growth Factors and Follistatin); 374 aa)

Nucleotide

Genbank accession no AF179274

Genbank version no. AF179274.2 GI: 12280939

Genbank record update date: Mar. 11, 2010 01:05 AM

Polypeptide

Genbank accession no. AAD55776

Genbank version no. AAD55776.2 GI: 12280940

Genbank record update date: Mar. 11, 2010 01:05 AM

Cross References

NCBI Accession: AAD55776, AAF91397, AAG49451, NCBI RefSeq: NP_057276; NCBI Gene: 23671; OMIM: 605734; SwissProt Q9UIK5; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; 5 US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer*. October 15; 94(2):178-84.

(37) PSMA—FOLH1 (Folate Hydrolase (Prostate-Specific Membrane Antigen) 1)

Nucleotide

Genbank accession no M99487

Genbank version no. M99487.1 GI: 190663

Genbank record update date: Jun. 23, 2010 08:48 AM

Polypeptide

Genbank accession no. AAA60209

Genbank version no. AAA60209.1 GI: 190664

Genbank record update date: Jun. 23, 2010 08:48 AM

Cross References

Israeli R. S., et al *Cancer Res.* 53 (2), 227-230 (1993)

Other Information

Official Symbol: FOLH1

Other Aliases: GIG27, FGCP, FOLH, GCP2, GCPII, NAALAD1, NAALAdase, PSM, PSMA, mGCP Other Designations: N-acetylated alpha-linked acidic dipeptidase 1; N-acetylated-alpha-linked acidic dipeptidase I; NAALADase I; cell growth-inhibiting gene 27 protein; folylpoly-gamma-glutamate carboxypeptidase; glutamate carboxylase II; glutamate carboxypeptidase 2; glutamate carboxypeptidase II; membrane glutamate carboxypeptidase; prostate specific membrane antigen variant F; pteroylpoly-gamma-glutamate carboxypeptidase Antibodies U.S. Pat. No. 7,666,425:

Antibodies produces by Hybridomas having the following ATCC references: ATCC accession No. HB-12101, ATCC accession No. HB-12109, ATCC accession No. HB-12127 and ATCC accession No. HB-12126.

Proscan: a monoclonal antibody selected from the group consisting of 8H12, 3E11, 17G1, 29B4, 30C1 and 20F2 (U.S. Pat. No. 7,811,564; Moffett S., et al Hybridoma (Larchmt). 2007 December; 26(6):363-72).

Cytogen: monoclonal antibodies 7E11-C5 (ATCC accession No. HB 10494) and 9H10-A4 (ATCC accession No. HB11430)—U.S. Pat. No. 5,763,202

GlycoMimetics: NUH2—ATCC accession No. HB 9762 (U.S. Pat. No. 7,135,301)

Human Genome Science: HPRAJ70—ATCC accession No. 97131 (U.S. Pat. No. 6,824,993); Amino acid sequence encoded by the cDNA clone (HPRAJ70) deposited as American Type Culture Collection ("ATCC") Deposit No. 97131

Medarex: Anti-PSMA antibodies that lack fucosyl residues—U.S. Pat. No. 7,875,278

Mouse anti-PSMA antibodies include the 3F5.4G6, 3D7.1.1, 4E10-1.14, 3E11, 4D8, 3E6, 3C9, 2C7, 1G3, 3C4, 3C6, 4D4, 1G9, 5C8B9, 3G6, 4C8B9, and monoclonal antibodies. Hybridomas secreting 3F5.4G6, 3D7.1.1, 4E10-1.14, 3E11, 4D8, 3E6, 3C9, 2C7, 1G3, 3C4, 3C6, 4D4, 1G9, 5C8B9, 3G6 or 4C8B9 have been publicly deposited and are described in U.S. Pat. No. 6,159,508. Relevant hybridomas have been publicly deposited and are described in U.S. Pat. No. 6,107,090. Moreover, humanized anti-PSMA antibodies, including a humanized version of J591, are described in further detail in PCT Publication WO 02/098897.

Other mouse anti-human PSMA antibodies have been described in the art, such as mAb 107-1A4 (Wang, S. et al. (2001) *Int. J. Cancer* 92:871-876) and mAb 2C9 (Kato, K. et al. (2003) *Int. J. Urol.* 10:439-444).

Examples of human anti-PSMA monoclonal antibodies include the 4A3, 7F12, 8C12, 8A11, 16F9, 2A10, 2C6, 2F5 and 1C3 antibodies, isolated and structurally characterized as originally described in PCT Publications WO 01/09192 and WO 03/064606 and in U.S. Provisional Application Ser. No. 60/654,125, entitled "Human Monoclonal Antibodies to Prostate Specific Membrane Antigen (PSMA)", filed on Feb. 18, 2005. The V.sub.H amino acid sequences of 4A3, 7F12, 8C12, 8A11, 16F9, 2A10, 2C6, 2F5 and 1C3 are shown in SEQ ID NOs: 1-9, respectively. The V.sub.L amino acid sequences of 4A3, 7F12, 8C12, 8A11, 16F9, 2A10, 2C6, 2F5 and 1C3 are shown in SEQ ID NOs: 10-18, respectively.

Other human anti-PSMA antibodies include the antibodies disclosed in PCT Publication WO 03/034903 and US Application No. 2004/0033229.

NW Biotherapeutics: A hybridoma cell line selected from the group consisting of 3F5.4G6 having ATCC accession number HB12060, 3D7-1.I. having ATCC accession number HB12309, 4E10-1.14 having ATCC accession number HB12310, 3E11 (ATCC HB12488), 4D8 (ATCC HB12487), 3E6 (ATCC HB12486), 3C9 (ATCC HB12484), 2C7 (ATCC HB12490), 1G3 (ATCC HB12489), 3C4 (ATCC HB12494), 3C6 (ATCC HB12491), 4D4 (ATCC HB12493), 1G9 (ATCC HB12495), 5C8B9 (ATCC HB12492) and 3G6 (ATCC HB12485)—see U.S. Pat. No. 6,150,508

PSMA Development Company/Progenics/Cytogen—Seattle Genetics: mAb 3.9, produced by the hybridoma deposited under ATCC Accession No. PTA-3258 or mAb 10.3, produced by the hybridoma deposited under ATCC Accession No. PTA-3347—U.S. Pat. No. 7,850,971

PSMA Development Company—Compositions of PSMA antibodies (US 20080286284, Table 1)

This application is a divisional of U.S. patent application Ser. No. 10/395,894, filed on Mar. 21, 2003 (U.S. Pat. No. 7,850,971)

University Hospital Freiburg, Germany—mAbs 3/A12, 3/E7, and 3/F11 (Wolf P., et al *Prostate.* 2010 Apr. 1; 70(5):562-9).

(38) SST (Somatostatin Receptor; Note that there are 5 Subtypes)

(38.1) SSTR2 (Somatostatin Receptor 2)

Nucleotide

Genbank accession no NM_001050

Genbank version no. NM_001050.2 GI: 44890054

Genbank record update date: Aug. 19, 2012 01:37 PM

Polypeptide

Genbank accession no. NP_001041

Genbank version no. NP_001041.1 GI: 4557859

Genbank record update date: Aug. 19, 2012 01:37 PM

Cross References

Yamada Y., et al *Proc. Natl. Acad. Sci. U.S.A.* 89 (1), 251-255 (1992); Susini C., et al *Ann Oncol.* 2006 December; 17(12):1733-42

Other Information

Official Symbol: SSTR2

Other Designations: SRIF-1; SS2R; somatostatin receptor type 2

(38.2) SSTR5 (Somatostatin Receptor 5)

Nucleotide

Genbank accession no D16827

Genbank version no. D16827.1 GI: 487683

Genbank record update date: Aug. 1, 2006 12:45 PM

Polypeptide

Genbank accession no. BAA04107

Genbank version no. BAA04107.1 GI: 487684

Genbank record update date: Aug. 1, 2006 12:45 PM

Cross References

Yamada, Y., et al *Biochem. Biophys. Res. Commun.* 195 (2), 844-852 (1993)

Other Information

Official Symbol: SSTR5

Other Aliases: SS-5-R

Other Designations: Somatostatin receptor subtype 5; somatostatin receptor type 5

(38.3) SSTR1

(38.4) SSTR3

(38.5) SSTR4

AvB6—Both Subunits (39+40)

(39) ITGAV (Integrin, alpha V;

Nucleotide

Genbank accession no M14648 J02826 M18365

Genbank version no. M14648.1 GI: 340306

Genbank record update date: Jun. 23, 2010 08:56 AM

Polypeptide

Genbank accession no. AAA36808

Genbank version no. AAA36808.1 GI: 340307

Genbank record update date: Jun. 23, 2010 08:56 AM

Cross References

Suzuki S., et al *Proc. Natd. Acad. Sci. U.S.A.* 83 (22), 8614-8618 (1986)

Other Information

Official Symbol: ITGAV

Other Aliases: CD51, MSK8, VNRA, VTNR

Other Designations: antigen identified by monoclonal antibody L230; integrin alpha-V; integrin alphaVbeta3; integrin, alpha V (vitronectin receptor, alpha polypeptide, antigen CD51); vitronectin receptor subunit alpha

(40) ITGB6 (Integrin, Beta 6)

Nucleotide

Genbank accession no NM_000888

Genbank version no. NM_000888.3 GI: 9966771

Genbank record update date: Jun. 27, 2012 12:46 AM

Polypeptide

Genbank accession no. NP_000879

Genbank version no. NP_000879.2 GI: 9625002

Genbank record update date: Jun. 27, 2012 12:46 AM

Cross References

Sheppard D. J., et al *Biol. Chem.* 265 (20), 11502-11507 (1990)

Other Information

Official Symbol: ITGB6

Other Designations: integrin beta-6

Antibodies

Biogen: U.S. Pat. No. 7,943,742—Hybridoma clones 6.3G9 and 6.8G6 were deposited with the ATCC, accession numbers ATCC PTA-3649 and -3645, respectively.

Biogen: U.S. Pat. No. 7,465,449—In some embodiments, the antibody comprises the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5.

Centocor (J&J): U.S. Pat. Nos. 7,550,142; 7,163,681

For example in U.S. Pat. No. 7,550,142—an antibody having human heavy chain and human light chain variable regions comprising the amino acid sequences shown in SEQ ID NO: 7 and SEQ ID NO: 8.

Seattle Genetics: 15H3 (Ryan M C., et al *Cancer Res* Apr. 15, 2012; 72(8 Supplement): 4630)

(41) CEACAM5 (Carcinoembryonic Antigen-Related Cell Adhesion Molecule 5)

Nucleotide

Genbank accession no M17303

Genbank version no. M17303.1 GI: 178676

Genbank record update date: Jun. 23, 2010 08:47 AM

Polypeptide

Genbank accession no. AAB59513

Genbank version no. AAB59513.1 GI: 178677

Genbank record update date: Jun. 23, 2010 08:47 AM

Cross References

Beauchemin N., et al *Mol. Cell. Biol.* 7 (9), 3221-3230 (1987)

Other Information

Official Symbol: CEACAM5

Other Aliases: CD66e, CEA

Other Designations: meconium antigen 100

Antibodies

AstraZeneca-MedImmune: US 20100330103; US20080057063; US20020142359 for example an antibody having complementarity determining regions (CDRs) with the following sequences: heavy chain; CDR1—DNYMH, CDR2—WIDPENGDTE YAPKFRG, CDR3—LIYAGYLAMD Y; and light chain CDR1—SASSSVTYMH, CDR2—STSNLAS, CDR3—QQRSTYPLT.

Hybridoma 806.077 deposited as European Collection of Cell Cultures (ECACC) deposit no. 96022936.

Research Corporation Technologies, Inc.: U.S. Pat. No. 5,047,507

Bayer Corporation: U.S. Pat. No. 6,013,772

BioAlliance: U.S. Pat. Nos. 7,982,017; 7,674,605

U.S. Pat. No. 7,674,605 an antibody comprising the heavy chain variable region sequence from the amino acid sequence of SEQ ID NO: 1, and the light chain variable region sequence from the amino acid sequence of SEQ ID NO:2.

an antibody comprising the heavy chain variable region sequence from the amino acid sequence of SEQ ID NO:5, and the light chain variable region sequence from the amino acid sequence of SEQ ID NO:6.

Celltech Therapeutics Limited: U.S. Pat. No. 5,877,293

The Dow Chemical Company: U.S. Pat. Nos. 5,472,693; 6,417,337; 6,333,405

U.S. Pat. No. 5,472,693—for example, ATCC No. CRL-11215

U.S. Pat. No. 6,417,337—for example, ATCC CRL-12208

U.S. Pat. No. 6,333,405—for example, ATCC CRL-12208

Immunomedics, Inc: U.S. Pat. Nos. 7,534,431; 7,230,084; 7,300,644; 6,730,300;

US20110189085 an antibody having CDRs of the light chain variable region comprise: CDR1 comprises KASQDVGTSVA (SEQ ID NO: 20); CDR2 comprises WTSTRHT (SEQ ID NO: 21); and CDR3 comprises QQYSLYRS (SEQ ID NO: 22);

and the CDRs of the heavy chain variable region of said anti-CEA antibody comprise: CDR1 comprises TYWMS (SEQ ID NO: 23); CDR2 comprises EIHPDSSTINYAPSLKD (SEQ ID NO: 24); and CDR3 comprises LYFGFPWFAY (SEQ ID NO: 25).

US20100221175; US20090092598; US20070202044; US20110064653; US20090185974; US20080069775.

(42) MET (Met Proto-Oncogene; Hepatocyte Growth Factor Receptor)

Nucleotide

Genbank accession no M35073

Genbank version no. M35073.1 GI: 187553

Genbank record update date: Mar. 6, 2012 11:12 AM

Polypeptide

Genbank accession no. AAA59589

Genbank version no. AAA59589.1 GI: 553531

Genbank record update date: Mar. 6, 2012 11:12 AM

Cross References

Dean M., et al *Nature* 318 (6044), 385-388 (1985)

Other Information

Official Symbol: MET

Other Aliases: AUTS9, HGFR, RCCP2, c-Met

Other Designations: HGF receptor; HGF/SF receptor; SF receptor; hepatocyte growth factor receptor; met proto-oncogene tyrosine kinase; proto-oncogene c-Met; scatter factor receptor; tyrosine-protein kinase Met Antibodies Abgenix/Pfizer: US20100040629 for example, the antibody produced by hybridoma 13.3.2 having American Type Culture Collection (ATCC) accession number PTA-5026; the antibody produced by hybridoma 9.1.2 having ATCC accession number PTA-5027; the antibody produced by hybridoma 8.70.2 having ATCC accession number PTA-5028; or the antibody produced by hybridoma 6.90.3 having ATCC accession number PTA-5029.

Amgen/Pfizer: US20050054019 for example, an antibody comprising a heavy chain having the amino acid sequences set forth in SEQ ID NO: 2 where X2 is glutamate and X4 is serine and a light chain having the amino acid sequence set forth in SEQ ID NO: 4 where X8 is alanine, without the signal sequences; an antibody comprising a heavy chain having the amino acid sequences set forth in SEQ ID NO: 6 and a light chain having the amino acid sequence set forth in SEQ ID NO: 8, without the signal sequences; an antibody comprising a heavy chain having the amino acid sequences set forth in SEQ ID NO: 10 and a light chain having the amino acid sequence set forth in SEQ ID NO: 12, without the signal sequences; or an antibody comprising a heavy chain having the amino acid sequences set forth in SEQ ID NO: 14 and a light chain having the amino acid sequence set forth in SEQ ID NO: 16, without the signal sequences.

Agouron Pharmaceuticals (Now Pfizer): US20060035907

Eli Lilly: US20100129369

Genentech: U.S. Pat. No. 5,686,292; US20100028337; US20100016241; US20070129301; US20070098707; US20070092520, US20060270594; US20060134104; US20060035278; US20050233960; US20050037431

U.S. Pat. No. 5,686,292—for example, ATCC HB-11894 and ATCC HB-11895 US 20100016241—for example, ATCC HB-11894 (hybridoma 1A3.3.13) or HB-11895 (hybridoma 5D5.11.6)

National Defense Medical Center, Taiwan: Lu R M., et al *Biomaterials.* 2011 April; 32(12):3265-74.

Novartis: US20090175860 for example, an antibody comprising the sequences of CDR1, CDR2 and CDR3 of heavy chain 4687, wherein the sequences of CDR1, CDR2, and CDR3 of heavy chain 4687 are residues 26-35, 50-65, and 98-102, respectively, of SEQ ID NO: 58; and the sequences of CDR1, CDR2, and CDR3 of light chain 5097, wherein the sequences of CDR1, CDR2, and CDR3 of light chain 5097 are residues 24-39, 55-61, and 94-100 of SEQ ID NO: 37.

Pharmacia Corporation: US20040166544

Pierre Fabre: US20110239316, US20110097262, US20100115639

Sumsung: US 20110129481—for example a monoclonal antibody produced from a hybridoma cell having accession number KCLRF-BP-00219 or accession number of KCLRF-BP-00223.

Samsung: US 20110104176—for example an antibody produced by a hybridoma cell having Accession Number: KCLRF-BP-00220.

University of Turin Medical School: DN-30 Pacchiana G., et al *J Biol Chem.* 2010 Nov. 12; 285(46):36149-57

Van Andel Research Institute: Jiao Y., et al *Mol Biotechnol.* 2005 September; 31(1):41-54.

(43) MUC1 (Mucin 1, Cell Surface Associated)

Nucleotide

Genbank accession no J05581

Genbank version no. J05581.1 GI: 188869

Genbank record update date: Jun. 23, 2010 08:48 AM

Polypeptide

Genbank accession no. AAA59876

Genbank version no. AAA59876.1 GI: 188870

Genbank record update date: Jun. 23, 2010 08:48 AM

Cross References

Gendler S. J., et al *J. Biol. Chem.* 265 (25), 15286-15293 (1990)

Other Information

Official Symbol: MUC1

Other Aliases: RP11-263K19.2, CD227, EMA, H23AG, KL-6, MAM6, MUC-1, MUC-1/SEC, MUC-1/X, MUC1/ZD, PEM, PEMT, PUM Other Designations: DF3 antigen; H23 antigen; breast carcinoma-associated antigen DF3; carcinoma-associated mucin; episialin; krebs von den Lungen-6; mucin 1, transmembrane; mucin-1; peanut-reactive urinary mucin; polymorphic epithelial mucin; tumor associated epithelial mucin; tumor-associated epithelial membrane antigen; tumor-associated mucin Antibodies AltaRex—Quest Pharma Tech: U.S. Pat. No. 6,716,966—for example an Alt-1 antibody produced by the hybridoma ATCC No PTA-975.

AltaRex—Quest Pharma Tech: U.S. Pat. No. 7,147,850

CRT: 5E5—Sørensen AL., et al Glycobiologyvol. 16 no. 2 pp. 96-107, 2006; HMFG2—Burchell J., et al *Cancer Res.,* 47, 5476-5482 (1987)

Glycotope GT-MAB: GT-MAB 2.5-GEX (Website: http://www.glycotope.com/pipeline/pankomab-gex)

Immunogen: U.S. Pat. No. 7,202,346 for example, antibody MJ-170: hybridoma cell line MJ-170 ATCC accession no. PTA-5286Monoclonal antibody MJ-171: hybridoma cell line MJ-171 ATCC accession no. PTA-5287; monoclonal antibody MJ-172: hybridoma cell line MJ-172 ATCC accession no. PTA-5288; or monoclonal antibody MJ-173: hybridoma cell line MJ-173 ATCC accession no. PTA-5302

Immunomedics: U.S. Pat. No. 6,653,104

Ramot Tel Aviv Uni: U.S. Pat. No. 7,897,351

Regents Uni. CA: U.S. Pat. No. 7,183,388; US20040005647; US20030077676.

Roche GlycArt: U.S. Pat. No. 8,021,856

Russian National Cancer Research Center: Imuteran—Ivanov P K., et al *Biotechnol J.* 2007 July; 2(7):863-70

Technische Univ Braunschweig: (11B6, HT186-B7, HT186-D11, HT186-G2, HT200-3A-C1, HT220-M-D1, HT220-M-G8)—Thie H., et al *PLoS One.* 2011 Jan. 14; 6(1):e15921

(44) CA9 (Carbonic Anhydrase IX)

Nucleotide

Genbank accession no. X66839

Genbank version no. X66839.1 GI: 1000701

Genbank record update date: Feb. 2, 2011 10:15 AM

Polypeptide

Genbank accession no. CAA47315

Genbank version no. CAA47315.1 GI: 1000702

Genbank record update date: Feb. 2, 2011 10:15 AM

Cross References

Pastorek J., et al *Oncogene* 9 (10), 2877-2888 (1994)

Other Information

Official Symbol: CA9

Other Aliases: CAIX, MN

Other Designations: CA-IX; P54/58N; RCC-associated antigen G250; RCC-associated protein G250; carbonate dehydratase IX; carbonic anhydrase 9; carbonic dehydratase; membrane antigen MN; pMW1; renal cell carcinoma-associated antigen G250

Antibodies

Abgenix/Amgen: US20040018198

Affibody: Anti-CAIX Affibody molecules (http://www.affibody.com/en/Product-Portfolio/Pipeline/)

Bayer: U.S. Pat. No. 7,462,696

Bayer/Morphosys: 3ee9 mAb—Petrul H M., et al *Mol Cancer Ther.* 2012 February; 11(2):340-9

Harvard Medical School: Antibodies G10, G36, G37, G39, G45, G57, G106, G119, G6, G27, G40 and G125. Xu C., et al *PLoS One.* 2010 Mar. 10; 5(3):e9625

Institute of Virology, Slovak Academy of Sciences (Bayer)—U.S. Pat. No. 5,955,075 for example, M75—ATCC Accession No. HB 11128 or MN12—ATCC Accession No. HB 11647

Institute of Virology, Slovak Academy of Sciences: U.S. Pat. No. 7,816,493 for example the M75 monoclonal antibody that is secreted from the hybridoma VU-M75, which was deposited at the American Type Culture Collection under ATCC No. HB 11128; or the V/10 monoclonal antibody secreted from the hybridoma V/10-VU, which was deposited at the International Depository Authority of the Belgian Coordinated Collection of Microorganisms (BCCM) at the Laboratorium voor Moleculaire Bioloqie-Plasmidencollectie (LMBP) at the Universeit Gent in Gent, Belgium, under Accession No. LMBP 6009CB.

Institute of Virology, Slovak Academy of Sciences US20080177046; US20080176310; US20080176258; US20050031623

Novartis: US20090252738

Wilex: U.S. Pat. No. 7,691,375—for example the antibody produced by the hybridoma cell line DSM ASC 2526.

Wilex: US20110123537; Rencarex: Kennett R H., et al *Curr Opin Mol Ther.* 2003 February; 5(1):70-5

Xencor: US20090162382

(45) EGFRvIII (Epidermal Growth Factor Receptor (EGFR), Transcript Variant 3,

Nucleotide

Genbank accession no. NM_201283

Genbank version no. NM_201283.1 GI: 41327733

Genbank record update date: Sep. 30, 2012 01:47 PM

Polypeptide

Genbank accession no. NP_958440

Genbank version no. NP_958440.1 GI: 41327734

Genbank record update date: Sep. 30, 2012 01:47 PM

Cross-References

Batra S K., et al *Cell Growth Differ* 1995; 6:1251-1259.

Antibodies:

U.S. Pat. Nos. 7,628,986 and 7,736,644 (Amgen)

For example, a heavy chain variable region amino acid sequence selected from the group consisting of SEQ ID NO: 142 and variants & a light chain variable region amino acid sequence selected from the group consisting of: SEQ ID NO: 144 and variants.

US20100111979 (Amgen)

For example, an antibody comprising a heavy chain amino acid sequence comprising:

CDR1 consisting of a sequence selected from the group consisting of the amino acid sequences for the CDR1 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17);

CDR2 consisting of a sequence selected from the group consisting of the amino acid sequences for the CDR2 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17); and CDR3 consisting of a sequence selected from the group consisting of the amino acid sequences for the CDR3 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

US20090240038 (Amgen)

For example, an antibody having at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.

US20090175887 (Amgen)

For example, an antibody having a heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

US20090156790 (Amgen)

For example, antibody having heavy chain polypeptide and a light chain polypeptide, wherein at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.

US20090155282, US20050059087 and US20050053608 (Amgen)

For example, an antibody heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).

MR1-1 (U.S. Pat. No. 7,129,332; Duke)

For example, a variant antibody having the sequence of SEQ ID NO. 18 with the substitutions S98P-T99Y in the CDR3 VH, and F92W in CDR3 VL.

L8A4, H10, Y10 (Wikstrand C J., et al *Cancer Res.* 1995 Jul. 15; 55(14):3140-8; Duke)

US20090311803 (Harvard University)

For example, SEQ ID NO:9 for antibody heavy chain variable region, and SEQ ID NO: 3 for light chain variable region amino acid sequences US20070274991 (EMD72000, also known as matuzumab; Harvard University)

For example, SEQ ID NOs: 3 & 9 for light chain and heavy chain respectively

U.S. Pat. No. 6,129,915 (Schering)

For example, SEQ. ID NOs: 1, 2, 3, 4, 5 and 6.

mAb CH12—Wang H., et al *FASEB J.* 2012 January; 26(1):73-80 (Shanghai Cancer Institute).

RAbDMvIII—Gupta P., et al *BMC Biotechnol.* 2010 Oct. 7; 10:72 (Stanford University Medical Center).

mAb Ua30—Ohman L., et al *Tumour Biol.* 2002 March-April; 23(2):61-9 (Uppsala University).

Han D G., et al *Nan Fang Yi Ke Da Xue Xue Bao.* 2010 January; 30(1):25-9 (Xi'an Jiaotong University).

(46) CD33 (CD33 Molecule)

Nucleotide

Genbank accession no. M_23197

Genbank version no. NM_23197.1 GI: 180097

Genbank record update date: Jun. 23, 2010 08:47 AM

Polypeptide

Genbank accession no. AAA51948

Genbank version no. AAA51948.1 GI: 188098

Genbank record update date: Jun. 23, 2010 08:47 AM

Cross-References

Simmons D., et al *J. Immunol.* 141 (8), 2797-2800 (1988)

Other Information

Official Symbol: CD33

Other Aliases: SIGLEC-3, SIGLEC3, p67

Other Designations: CD33 antigen (gp67); gp67; myeloid cell surface antigen CD33; sialic acid binding Ig-like lectin 3; sialic acid-binding Ig-like lectin Antibodies H195 (Lintuzumab)—Raza A., et al *Leuk Lymphoma.* 2009 August; 50(8):1336-44; U.S. Pat. No. 6,759,045 (Seattle Genetics/lmmunomedics)

mAb OKT9: Sutherland, D. R. et al. *Proc Natl Acad Sci USA* 78(7): 4515-4519 1981, Schneider, C., et al *J Biol Chem* 257, 8516-8522 (1982)

mAb E6: Hoogenboom, H. R., et al *J Immunol* 144, 3211-3217 (1990)

U.S. Pat. No. 6,590,088 (Human Genome Sciences)

For example, SEQ ID NOs: 1 and 2 and ATCC accession no. 97521

U.S. Pat. No. 7,557,189 (Immunogen)

For example, an antibody or fragment thereof comprising a heavy chain variable region which comprises three CDRs having the amino acid sequences of SEQ ID NOs:1-3 and a light chain variable region comprising three CDRs having the amino acid sequences of SEQ ID NOs:4-6.

(47) CD19 (CD19 Molecule)

Nucleotide

Genbank accession no. NM_001178098

Genbank version no. NM_001178098.1 GI: 296010920

Genbank record update date: Sep. 10, 2012 12:43 AM

Polypeptide

Genbank accession no. NP_001171569

Genbank version no. NP_001171569.1 GI: 296010921

Genbank record update date: Sep. 10, 2012 12:43 AM

Cross-References

Tedder T F., et al *J. Immunol.* 143 (2): 712-7 (1989)

Other Information

Official Symbol: CD19

Other Aliases: B4, CVID3

Other Designations: B-lymphocyte antigen CD19; B-lymphocyte surface antigen B4; T-cell surface antigen Leu-12; differentiation antigen CD19

Antibodies

Immunogen: HuB4—Al-Katib A M., et al *Clin Cancer Res.* 2009 Jun. 15; 15(12):4038-45.

4G7: Kügler M., et al *Protein Eng Des Sel.* 2009 March; 22(3):135-47

For example, sequences in FIG. 3 of Knappik, A. et al. *J Mol Biol* 2000 February; 296(1):57-86

AstraZeneca/MedImmune: MEDI-551—Herbst R., et al *J Pharmacol Exp Ther.* 2010 October; 335(1):213-22

Glenmark Pharmaceuticals: GBR-401—Hou S., et al *Mol Cancer Ther November* 2011 10 (Meeting Abstract Supplement) C164

U.S. Pat. No. 7,109,304 (Immunomedics)

For example, an antibody comprising the sequence of hA19Vk (SEQ ID NO:7) and the sequence of hA19VH (SEQ ID NO:10)

U.S. Pat. No. 7,902,338 (Immunomedics)

For example, an antibody or antigen-binding fragment thereof that comprises the light chain complementarity determining region CDR sequences CDR1 of SEQ ID NO: 16 (KASQSVDYDGDSYLN); CDR2 of SEQ ID NO: 17 (DASNLVS); and CDR3 of SEQ ID NO: 18 (QQSTEDPWT) and the heavy chain CDR sequences CDR1 of SEQ ID NO: 19 (SYWMN); CDR2 of SEQ ID NO: 20 (QIWPGDGDTNYNGKFKG) and CDR3 of SEQ ID NO: 21 (RETTTVGRYYYAMDY) and also comprises human antibody framework (FR) and constant region sequences with one or more framework region amino acid residues substituted from the corresponding framework region sequences of the parent murine antibody, and wherein said substituted FR residues comprise the substitution of serine for phenylalanine at Kabat residue 91 of the heavy chain variable region.

Medarex: MDX-1342—Cardarelli P M., et al *Cancer Immunol Immunother.* 2010 February; 59(2):257-65.

MorphoSys/Xencor: MOR-208/XmAb-5574—Zalevsky J., et al *Blood.* 2009 Apr. 16; 113(16):3735-43

U.S. Pat. No. 7,968,687 (Seattle Genetics)

An antibody or antigen-binding fragment comprising a heavy chain variable domain comprising the amino acid sequence of SEQ ID NO:9 and a light chain variable domain comprising the amino acid sequence of SEQ ID NO: 24.

4G7 chim—Lang P., et al *Blood.* 2004 May 15; 103(10): 3982-5 (University of Tübingen)

For example, FIG. 6 and SEQ ID No: 80 of US20120082664

Zhejiang University School of Medicine: 2E8—Zhang J., et al *J Drug Target.* 2010 November; 18(9):675-8

(48) IL2RA (Interleukin 2 Receptor, Alpha); *NCBI Reference Sequence*: NM_0004172);

Nucleotide

Genbank accession no. NM_000417

Genbank version no. NM_000417.2 GI: 269973860

Genbank record update date: Sep. 9, 2012 04:59 PM

Polypeptide

Genbank accession no. NP_000408

Genbank version no. NP_000408.1 GI: 4557667

Genbank record update date: Sep. 9, 2012 04:59 PM

Cross-References

Kuziel W. A., et al *J. Invest. Dermatol.* 94 (6 SUPPL), 27S-32S (1990)

Other Information

Official Symbol: IL2RA

Other Aliases: RP11-536K7.1, CD25, IDDM10, IL2R, TCGFR

Other Designations: FIL-2 receptor subunit alpha; IL-2-RA; IL-2R subunit alpha; IL2-RA; TAC antigen; interleukin-2 receptor subunit alpha; p55

Antibodies

U.S. Pat. No. 6,383,487 (Novartis/UCL: Baxilisimab [Simulect])

U.S. Pat. No. 6,521,230 (Novartis/UCL: Baxilisimab [Simulect])

For example, an antibody having an antigen binding site comprises at least one domain which comprises CDR1 having the amino acid sequence in SEQ. ID. NO: 7, CDR2 having the amino acid sequence in SEQ. ID. NO: 8, and CDR3 having the amino acid sequence in SEQ. ID. NO: 9; or said CDR1, CDR2 and CDR3 taken in sequence as a whole comprise an amino acid sequence which is at least 90% identical to SEQ. ID. NOs: 7, 8 and 9 taken in sequence as a whole.

Daclizumab—Rech A J., et al *Ann N Y Acad Sci.* 2009 September; 1174:99-106 (Roche)

(49) AXL (AXL Receptor Tyrosine Kinase)

Nucleotide

Genbank accession no. M76125

Genbank version no. M76125.1 GI: 292869

Genbank record update date: Jun. 23, 2010 08:53 AM

Polypeptide

Genbank accession no. AAA61243

Genbank version no. AAA61243.1 GI: 29870

Genbank record update date: Jun. 23, 2010 08:53 AM

Cross-References

O'Bryan J. P., et al *Mol. Cell. Biol.* 11 (10), 5016-5031 (1991); Bergsagel P. L., et al *J. Immunol.* 148 (2), 590-596 (1992)

Other Information

Official Symbol: AXL

Other Aliases: JTK11, UFO

Other Designations: AXL oncogene; AXL transforming sequence/gene; oncogene AXL; tyrosine-protein kinase receptor UFO Antibodies YW327.6S2—Ye X., et al *Oncogene.* 2010 Sep. 23; 29(38):5254-64. (Genentech)

BergenBio: BGB324 (http://www.bergenbio.com/BGB324)

(50) CD30—TNFRSF8 (Tumor Necrosis Factor Receptor Superfamily, Member 8)

Nucleotide

Genbank accession no. M83554

Genbank version no. M83554.1 GI: 180095

Genbank record update date: Jun. 23, 2010 08:53 AM

Polypeptide

Genbank accession no. AAA51947

Genbank version no. AAA51947.1 GI: 180096

Genbank record update date: Jun. 23, 2010 08:53 AM

Cross-References

Durkop H., et al *Cell* 68 (3), 421-427 (1992)

Other Information

Official Symbol: TNFRSF8

Other Aliases: CD30, D1S166E, Ki-1

Other Designations: CD30L receptor; Ki-1 antigen; cytokine receptor CD30; lymphocyte activation antigen CD30; tumor necrosis factor receptor superfamily member 8

(51) BCMA (B-Cell Maturation Antigen)—TNFRSF17 (Tumor Necrosis Factor Receptor Superfamily, Member 17)

Nucleotide

Genbank accession no. Z29574

Genbank version no. Z29574.1 GI: 471244

Genbank record update date: Feb. 2, 2011 10:40 AM

Polypeptide

Genbank accession no. CAA82690

Genbank version no. CAA82690.1 GI: 471245

Genbank record update date: Feb. 2, 2011 10:40 AM

Cross-References

Laabi Y., et al *Nucleic Acids Res.* 22 (7), 1147-1154 (1994)

Other Information

Official Symbol: TNFRSF17

Other Aliases: BCM, BCMA, CD269

Other Designations: B cell maturation antigen; B-cell maturation factor; B-cell maturation protein; tumor necrosis factor receptor superfamily member 17

(52) CT Ags—CTA (Cancer Testis Antigens)

Cross-References

Fratta E., et al. *Mol Oncol.* 2011 April; 5(2):164-82; Lim S H., at al *Am J Blood Res.* 2012; 2(1):29-35.

(53) CD174 (Lewis Y)—FUT3 (Fucosyltransferase 3 (Galactoside 3(4)-L-fucosyltransferase, Lewis Blood Group)

Nucleotide

Genbank accession no. NM000149

Genbank version no. NM000149.3 GI: 148277008

Genbank record update date: Jun. 26, 2012 04:49 PM

Polypeptide

Genbank accession no. NP_000140

Genbank version no. NP_000140.1 GI: 4503809

Genbank record update date: Jun. 26, 2012 04:49 PM

Cross-References

Kukowska-Latallo, J. F., et al *Genes Dev.* 4 (8), 1288-1303 (1990)

Other Information

Official Symbol: FUT3

Other Aliases: CD174, FT3B, FucT-III, LE, Les

Other Designations: Lewis FT; alpha-(1,3/1,4)-fucosyltransferase; blood group Lewis alpha-4-fucosyltransferase; fucosyltransferase III; galactoside 3(4)-L-fucosyltransferase

(54) CLEC14A (C-Type Lectin Domain Family 14, Member a; Genbank Accession No. NM175060)

Nucleotide

Genbank accession no. NM175060

Genbank version no. NM175060.2 GI: 371123930

Genbank record update date: Apr. 1, 2012 03:34 PM

Polypeptide

Genbank accession no. NP_778230

Genbank version no. NP_778230.1 GI: 28269707

Genbank record update date: Apr. 1, 2012 03:34 PM

Other Information

Official Symbol: CLEC14A

Other Aliases: UNQ236/PRO269, C14orf27, CEG1, EGFR-5

Other Designations: C-type lectin domain family 14 member A; CIECT and EGF-like domain containing protein; epidermal growth factor receptor 5

(55) GRP78—HSPA5 (Heat Shock 70 kDa Protein 5 (Glucose-Regulated Protein, 78 kDa)

Nucleotide

Genbank accession no. NM005347

Genbank version no. NM005347.4 GI: 305855105

Genbank record update date: Sep. 30, 2012 01:42 PM

Polypeptide

Genbank accession no. NP_005338

Genbank version no. NP_005338.1 GI: 16507237

Genbank record update date: Sep. 30, 2012 01:42 PM

Cross-References

Ting J., et al *DNA*7 (4), 275-286 (1988)

Other Information

Official Symbol: HSPA5

Other Aliases: BIP, GRP78, MIF2

Other Designations: 78 kDa glucose-regulated protein; endoplasmic reticulum lumenal Ca(2+)-binding protein grp78; immunoglobulin heavy chain-binding protein

(56) Cd70 (Cd70 Molecule) L08096

Nucleotide

Genbank accession no. L08096

Genbank version no. L08096.1 GI: 307127

Genbank record update date: Jun. 23, 2012 08:54 AM

Polypeptide

Genbank accession no. AAA36175

Genbank version no. AAA36175.1 GI: 307128

Genbank record update date: Jun. 23, 2012 08:54 AM

Cross-References

Goodwin R. G., et al *Cell* 73 (3), 447-456 (1993)

Other Information

Official Symbol: CD70

Other Aliases: CD27L, CD27LG, TNFSF7

Other Designations: CD27 ligand; CD27-L; CD70 antigen; Ki-24 antigen; surface antigen CD70; tumor necrosis factor (ligand) superfamily, member 7; tumor necrosis factor ligand superfamily member 7

Antibodies

MDX-1411 against CD70 (Medarex)

hi F6 (Oflazoglu, E., et al, *Clin Cancer Res.* 2008 Oct. 1; 14(19):6171-80; Seattle Genetics)

For example, see US20060083736 SEQ ID NOs: 1, 2, 11 and 12 and FIG. 1.

(57) Stem Cell Specific Antigens. For Example:

5T4 (see entry (63) below)

CD25 (see entry (48) above)

CD32

Polypeptide

Genbank accession no. ABK42161

Genbank version no. ABK42161.1 GI: 117616286

Genbank record update date: Jul. 25, 2007 03:00 PM

LGR5/GPR49

Nucleotide

Genbank accession no. NM_003667

Genbank version no. NM_003667.2 GI: 24475886

Genbank record update date: Jul. 22, 2012 03:38 PM

Polypeptide

Genbank accession no. NP_003658

Genbank version no. NP_003658.1 GI: 4504379

Genbank record update date: Jul. 22, 2012 03:38 PM

Prominin/CD133

Nucleotide

Genbank accession no. NM_006017

Genbank version no. NM006017.2 GI: 224994187

Genbank record update date: Sep. 30, 2012 01:47 PM

Polypeptide

Genbank accession no. NP_006008

Genbank version no. NP_006008.1 GI: 5174387

Genbank record update date: Sep. 30, 2012 01:47 PM

(58) ASG-5

Cross-References (Smith L. M., et.al *AACR* 2010 *Annual Meeting* (abstract #2590); Gudas J. M., et.al. *AACR* 2010 *Annual Meeting* (abstract #4393)

Antibodies

Anti-AGS-5 Antibody: M6.131 (Smith, L. M., et.al *AACR* 2010 *Annual Meeting* (abstract #2590)

(59) ENPP3 (Ectonucleotide Pyrophosphatase/Phosphodiesterase 3)

Nucleotide

Genbank accession no. AF005632

Genbank version no. AF005632.2 GI: 4432589

Genbank record update date: Mar. 10, 2010 09:41 PM

Polypeptide

Genbank accession no. AAC51813

Genbank version no. AAC51813.1 GI: 2465540

Genbank record update date: Mar. 10, 2010 09:41 PM

Cross-References

Jin-Hua P., et al *Genomics* 45 (2), 412-415 (1997)

Other Information

Official Symbol: ENPP3

Other Aliases: RP5-988G15.3, B10, CD203c, NPP3, PDIBETA, PDNP3

Other Designations: E-NPP 3; dJ1005H11.3 (phosphodiesterase I/nucleotide pyrophosphatase 3); dJ914N13.3 (phosphodiesterase I/nucleotide pyrophosphatase 3);

ectonucleotide pyrophosphatase/phosphodiesterase family member 3; gp130RB13-6; phosphodiesterase I beta; phosphodiesterase I/nucleotide pyrophosphatase 3; phosphodiesterase-I beta

(60) PRR4 (Proline Rich 4 (Lacrimal))
Nucleotide
Genbank accession no. NM_007244
Genbank version no. NM_007244.2 GI: 154448885
Genbank record update date: Jun. 28, 2012 12:39 PM
Polypeptide
Genbank accession no. NP_009175
Genbank version no. NP_009175.2 GI: 154448886
Genbank record update date: Jun. 28, 2012 12:39 PM
Cross-References
Dickinson D. P., et al *Invest. Ophthalmol. Vis. Sci.* 36 (10), 2020-2031 (1995)
Other Information
Official Symbol: PRR4
Other Aliases: LPRP, PROL4
Other Designations: lacrimal proline-rich protein; nasopharyngeal carcinoma-associated proline-rich protein 4; proline-rich polypeptide 4; proline-rich protein 4

(61) GCC—GUCY2C (Guanylate Cyclase 2C (Heat Stable Enterotoxin Receptor)
Nucleotide
Genbank accession no. NM_004963
Genbank version no. NM_004963.3 GI: 222080082
Genbank record update date: Sep. 2, 2012 01:50 PM
Polypeptide
Genbank accession no. NP_004954
Genbank version no. NP_004954.2 GI: 222080083
Genbank record update date: Sep. 2, 2012 01:50 PM
Cross-References
De Sauvage F. J., et al *J. Biol. Chem.* 266 (27), 17912-17918 (1991); Singh S., et al *Biochem. Biophys. Res. Commun.* 179 (3), 1455-1463 (1991)
Other Information
Official Symbol: GUCY2C
Other Aliases: DIAR6, GUC2C, MUCIL, STAR
Other Designations: GC-C; STA receptor; guanylyl cyclase C; hSTAR; heat-stable enterotoxin receptor; intestinal guanylate cyclase

(62) Liv-1—SLC39A6 (Solute Carrier Family 39 (Zinc Transporter), Member 6)
Nucleotide
Genbank accession no. U41060
Genbank version no. U41060.2 GI: 12711792
Genbank record update date: Nov. 30, 2009 04:35 PM
Polypeptide
Genbank accession no. AAA96258
Genbank version no. AAA96258.2 GI: 12711793
Genbank record update date: Nov. 30, 2009 04:35 PM
Cross-References
Taylor K M., et al *Biochim Biophys Acta.* 2003 Apr. 1; 1611(1-2):16-30
Other Information
Official Symbol: SLC39A6
Other Aliases: LIV-1
Other Designations: LIV-1 protein, estrogen regulated; ZIP-6; estrogen-regulated protein LIV-1; solute carrier family 39 (metal ion transporter), member 6; solute carrier family 39 member 6; zinc transporter ZIP6; zrt- and lrt-like protein 6

(63) 5T4, Trophoblast Glycoprotein, TPBG—TPBG (Trophoblast Glycoprotein)
Nucleotide
Genbank accession no. AJ012159
Genbank version no. AJ012159.1 GI: 3805946
Genbank record update date: Feb. 1, 2011 10:27 AM
Polypeptide
Genbank accession no. CAA09930
Genbank version no. CAA09930.1 GI: 3805947
Genbank record update date: Feb. 1, 2011 10:27 AM
Cross-References
King K. W., et al *Biochim. Biophys. Acta* 1445 (3), 257-270 (1999)
Other Information
Official Symbol: TPBG
Other Aliases: 5T4, 5T4AG, M6P1
Other Designations: 5T4 oncofetal antigen; 5T4 oncofetal trophoblast glycoprotein; 5T4 oncotrophoblast glycoprotein

(64) CD56—NCMA1 (Neural Cell Adhesion Molecule 1)
Nucleotide
Genbank accession no. NM_000615
Genbank version no. NM_000615.6 GI: 336285433
Genbank record update date: Sep. 23, 2012 02:32 PM
Polypeptide
Genbank accession no. NP_000606
Genbank version no. NP_000606.3 GI: 94420689
Genbank record update date: Sep. 23, 2012 02:32 PM
Cross-References
Dickson, G., et al, *Cell* 50 (7), 1119-1130 (1987)
Other information
Official Symbol: NCAM1
Other Aliases: CD56, MSK39, NCAM
Other Designations: antigen recognized by monoclonal antibody 5.1H11; neural cell adhesion molecule, NCAM
Antibodies
Immunogen: HuN901 (Smith S V., et al *Curr Opin Mol Ther.* 2005 August; 7(4):394-401) For example, see humanized from murine N901 antibody. See FIGS. 1b and 1e of Roguska, M. A., et al. *Proc Natl Acad Sci* USA February 1994; 91:969-973.

(65) CanAg (Tumor Associated Antigen CA242)
Cross-References
Haglund C., et al *Br J Cancer* 60:845-851, 1989; Baeckstrom D., et al *J Biol Chem* 266:21537-21547, 1991
Antibodies
huC242 (Tolcher A W et al., *J Clin Oncol.* 2003 Jan. 15; 21(2):211-22; Immunogen)
For example, see US20080138898A1 SEQ ID NO: 1 and 2

(66) FOLR1 (Folate Receptor 1)
Nucleotide
Genbank accession no. J05013
Genbank version no. J05013.1 GI: 182417
Genbank record update date: Jun. 23, 2010 08:47 AM
Polypeptide
Genbank accession no. AAA35823
Genbank version no. AAA35823.1 GI: 182418
Genbank record update date: Jun. 23, 2010 08:47 AM
Cross-References
Elwood P. C., et al *J. Biol. Chem.* 264 (25), 14893-14901 (1989)
Other Information
Official Symbol: FOLR1
Other Aliases: FBP, FOLR Other Designations: FR-alpha; KB cells FBP; adult folate-binding protein; folate binding protein; folate receptor alpha; folate receptor, adult; ovarian tumor-associated antigen MOv18
Antibodies
M9346A—Whiteman K R., et al *Cancer Res* Apr. 15, 2012; 72(8 Supplement): 4628 (Immunogen)
(67) GPNMB (Glycoprotein (Transmembrane) nmb)
Nucleotide
Genbank accession no. X76534
Genbank version no. X76534.1 GI: 666042
Genbank record update date: Feb. 2, 2011 10:10 AM
Polypeptide
Genbank accession no. CAA54044
Genbank version no. CAA54044.1 GI: 666043
Genbank record update date: Feb. 2, 2011 10:10 AM
Cross-References
Weterman M. A., et al *Int. J. Cancer* 60 (1), 73-81 (1995)
Other Information
Official Symbol: GPNMB
Other Aliases: UNQ1725/PRO9925, HGFIN, NMB
Other Designations: glycoprotein NMB; glycoprotein nmb-like protein; osteoactivin; transmembrane glycoprotein HGFIN; transmembrane glycoprotein NMB
Antibodies
Celldex Therapeutics: CR011 (Tse K F., et al *Clin Cancer Res.* 2006 Feb. 15; 12(4):1373-82)
For example, see EP1827492B1 SEQ ID NO: 22, 24, 26, 31, 33 and 35
(68) TIM-1—HAVCR1 (Hepatitis a Virus Cellular Receptor 1)
Nucleotide
Genbank accession no. AF043724
Genbank version no. AF043724.1 GI: 2827453
Genbank record update date: Mar. 10, 2010 06:24 PM
Polypeptide
Genbank accession no. AAC39862
Genbank version no. AAC39862.1 GI: 2827454
Genbank record update date: Mar. 10, 2010 06:24 PM
Cross-References
Feigelstock D., et al *J. Virol.* 72 (8), 6621-6628 (1998)
Other Information
Official Symbol: HAVCRi
Other Aliases: HAVCR, HAVCR-1, KIM-1, KIM1, TIM, TIM-1, TIM1, TIMD-1, TIMD1
Other Designations: T cell immunoglobin domain and mucin domain protein 1; T-cell membrane protein 1; kidney injury molecule 1
(69) RG-1/Prostate Tumor Target Mindin—Mindin/RG-1
Cross-References
Parry R., et al *Cancer Res.* 2005 Sep. 15; 65(18):8397-405
(70) B7-H4—VTCN1 (V-set domain containing T cell activation inhibitor 1
Nucleotide
Genbank accession no. BX648021
Genbank version no. BX648021.1 GI: 34367180
Genbank record update date: Feb. 2, 2011 08:40 AM
Cross-References
Sica G L., et al *Immunity.* 2003 June; 18(6):849-61
Other Information
Official Symbol: VTCN1
Other Aliases: RP11-229A19.4, B7-H4, B7H4, B7S1, B7X, B7h.5, PRO1291, VCTN1
Other Designations: B7 family member, H4; B7 superfamily member 1; T cell costimulatory molecule B7x; T-cell costimulatory molecule B7x; V-set domain-containing T-cell activation inhibitor 1; immune costimulatory protein B7-H4
(71) PTK7 (PTK7 Protein Tyrosine Kinase 7)
Nucleotide
Genbank accession no. AF447176
Genbank version no. AF447176.1 GI: 17432420
Genbank record update date: Nov. 28, 2008 01:51 PM
Polypeptide
Genbank accession no. AAL39062
Genbank version no. AAL39062.1 GI: 17432421
Genbank record update date: Nov. 28, 2008 01:51 PM
Cross-References
Park S. K., et al *J. Biochem.* 119 (2), 235-239 (1996)
Other Information
Official Symbol: PTK7
Other Aliases: CCK-4, CCK4
Other Designations: colon carcinoma kinase 4; inactive tyrosine-protein kinase 7; pseudo tyrosine kinase receptor 7; tyrosine-protein kinase-like 7
(72) CD37 (CD37 Molecule)
Nucleotide
Genbank accession no. NM_001040031
Genbank version no. NM_001040031.1 GI: 91807109
Genbank record update date: Jul. 29, 2012 02:08 PM
Polypeptide
Genbank accession no. NP_001035120
Genbank version no. NP_001035120.1 GI: 91807110
Genbank record update date: Jul. 29, 2012 02:08 PM
Cross-References
Schwartz-Albiez R., et al *J. Immunol.* 140 (3), 905-914 (1988)
Other Information
Official Symbol: CD37
Other Aliases: GP52-40, TSPAN26
Other Designations: CD37 antigen; cell differentiation antigen 37; leukocyte antigen CD37; leukocyte surface antigen CD37; tetraspanin-26; tspan-26
Antibodies
Boehringer Ingelheim: mAb 37.1 (Heider K H., et al *Blood.* 2011 Oct. 13; 118(15):4159-68)
Trubion: CD37-SMIP (G28-1 scFv-Ig) ((Zhao X., et al *Blood.* 2007; 110: 2569-2577)
For example, see US20110171208A1 SEQ ID NO: 253
Immunogen: K7153A (Deckert J., et al *Cancer Res* Apr. 15, 2012; 72(8 Supplement): 4625)
(73) CD138—SDC1 (syndecan 1)
Nucleotide
Genbank accession no. AJ551176
Genbank version no. AJ551176.1 GI: 29243141
Genbank record update date: Feb. 1, 2011 12:09 PM
Polypeptide
Genbank accession no. CAD80245
Genbank version no. CAD80245.1 GI: 29243142
Genbank record update date: Feb. 1, 2011 12:09 PM
Cross-References
O'Connell F P., et al *Am J Clin Pathol.* 2004 February; 121(2):254-63
Other Information
Official Symbol: SDC1
Other Aliases: CD138, SDC, SYND1, syndecan
Other Designations: CD138 antigen; heparan sulfate proteoglycan fibroblast growth factor receptor; syndecan proteoglycan 1; syndecan-1

Antibodies

Biotest: chimerized MAb (nBT062)—(Jagannath S., et al Poster ASH #3060, 2010; WIPO Patent Application WO/2010/128087)

For example, see US20090232810 SEQ ID NO: 1 and 2

Immunogen: B-B4 (Tassone P., et al *Blood* 104_3688-3696)

For example, see US20090175863A1 SEQ ID NO: 1 and 2

(74) CD74 (CD74 Molecule, Major Histocompatibility Complex, Class II Invariant Chain)

Nucleotide

Genbank accession no. NM_004355

Genbank version no. NM_004355.1 GI: 343403784

Genbank record update date: Sep. 23, 2012 02:30 PM

Polypeptide

Genbank accession no. NP_004346

Genbank version no. NP_004346.1 GI: 10835071

Genbank record update date: Sep. 23, 2012 02:30 PM

Cross-References

Kudo, J., et al *Nucleic Acids Res.* 13 (24), 8827-8841 (1985)

Other Information

Official Symbol: CD74

Other Aliases: DHLAG, HLADG, II, Ia-GAMMA

Other Designations: CD74 antigen (invariant polypeptide of major histocompatibility complex, class II antigen-associated); HLA class II histocompatibility antigen gamma chain; HLA-DR antigens-associated invariant chain; HLA-DR-gamma; Ia-associated invariant chain; MHC HLA-DR gamma chain; gamma chain of class II antigens; p33

Antibodies

Immunomedics: hLL1 (Milatuzumab)—Berkova Z., et al *Expert Opin Investig Drugs.* 2010 January; 19(1):141-9)

For example, see US20040115193 SEQ ID NOs: 19, 20, 21, 22, 23 and 24

Genmab: HuMax-CD74 (see website)

(75) Claudins—CLs (Claudins)

Cross-References

Offner S., et al *Cancer Immunol Immunother.* 2005 May; 54(5):431-45, Suzuki H., et al *Ann N Y Acad Sci.* 2012 July; 1258:65-70)

In humans, 24 members of the family have been described—see literature reference.

(76) EGFR (Epidermal Growth Factor Receptor)

Nucleotide

Genbank accession no. NM_005228

Genbank version no. NM_005228.3 GI: 41927737

Genbank record update date: Sep. 30, 2012 01:47 PM

Polypeptide

Genbank accession no. NP_005219

Genbank version no. NP_005219.2 GI: 29725609

Genbank record update date: Sep. 30, 2012 01:47 PM

Cross-References

Dhomen N S., et al *Crit Rev Oncog.* 2012; 17(1):31-50

Other Information

Official Symbol: EGFR

Other Aliases: ERBB, ERBB1, HER1, PIG61, mENA

Other Designations: avian erythroblastic leukemia viral (v-erb-b) oncogene homolog; cell growth inhibiting protein 40; cell proliferation-inducing protein 61; proto-oncogene c-ErbB-1; receptor tyrosine-protein kinase erbB-1

Antibodies

BMS: Cetuximab (Erbitux)—Broadbridge V T., et al *Expert Rev Anticancer Ther.* 2012 May; 12(5):555-65.

For example, see U.S. Pat. No. 6,217,866—ATTC deposit No. 9764.

Amgen: Panitumumab (Vectibix)—Argiles G., et al *Future Oncol.* 2012 April; 8(4):373-89

For example, see U.S. Pat. No. 6,235,883 SEQ ID NOs: 23-38.

Genmab: Zalutumumab—Rivera F., et al *Expert Opin Biol Ther.* 2009 May; 9(5):667-74.

YM Biosciences: Nimotuzumab—Ramakrishnan M S., et al MAbs. 2009 January-February; 1(1):41-8.

For example, see U.S. Pat. No. 5,891,996 SEQ ID NOs: 27-34.

(77) Her3 (ErbB3)—ERBB3 (v-Erb-b2 Erythroblastic Leukemia Viral Oncogene Homolog 3 (Avian))

Nucleotide

Genbank accession no. M34309

Genbank version no. M34309.1 GI: 183990

Genbank record update date: Jun. 23, 2010 08:47 PM

Polypeptide

Genbank accession no. AAA35979

Genbank version no. AAA35979.1 GI: 306841

Genbank record update date: Jun. 23, 2010 08:47 PM

Cross-References

Plowman, G. D., et al., *Proc. Natl. Acad. Sci. U.S.A.* 87 (13), 4905-4909 (1990)

Other Information

Official Symbol: ERBB3

Other Aliases: ErbB-3, HER3, LCCS2, MDA-BF-1, c-erbB-3, c-erbB3, erbB3-S, p180-ErbB3, p45-sErbB3, p85-sErbB3

Other Designations: proto-oncogene-like protein c-ErbB-3; receptor tyrosine-protein kinase erbB-3; tyrosine kinase-type cell surface receptor HER3

Antibodies

Merimack Pharma: MM-121 (Schoeberl B., et al *Cancer Res.* 2010 Mar. 15; 70(6):2485-2494)

For example, see US2011028129 SEQ ID NOs: 1, 2, 3, 4, 5, 6, 7 and 8.

(78) RON—MST1R (Macrophage Stimulating 1 Receptor (c-Met-Related Tyrosine Kinase))

Nucleotide

Genbank accession no. X70040

Genbank version no. X70040.1 GI: 36109

Genbank record update date: Feb. 2, 2011 10:17 PM

Polypeptide

Genbank accession no. CCA49634

Genbank version no. CCA49634.1 GI: 36110

Genbank record update date: Feb. 2, 2011 10:17 PM

Cross-References

Ronsin C., et al *Oncogene* 8 (5), 1195-1202 (1993)

Other Information

Official Symbol: MST1R

Other Aliases: CD136, CDw136, PTK8, RON

Other Designations: MSP receptor; MST1R variant RON30; MST1R variant RON62; PTK8 protein tyrosine kinase 8; RON variant E2E3; c-met-related tyrosine kinase; macrophage-stimulating protein receptor; p185-Ron; soluble RON variant 1; soluble RON variant 2; soluble RON variant 3; soluble RONvariant 4

(79) EPHA2 (EPH Receptor A2)

Nucleotide

Genbank accession no. BC037166

Genbank version no. BC037166.2 GI: 33879863

Genbank record update date: Mar. 6, 2012 01:59 PM

Polypeptide
Genbank accession no. AAH37166
Genbank version no. AAH37166.1 GI: 22713539
Genbank record update date: Mar. 6, 2012 01:59 PM
Cross-References
Strausberg R. L., et al *Proc. Natl. Acad. Sci. U.S.A.* 99 (26), 16899-16903 (2002)
Other Information
Official Symbol: EPHA2
Other Aliases: ARCC2, CTPA, CTPP1, ECK
Other Designations: ephrin type-A receptor 2; epithelial cell receptor protein tyrosine kinase; soluble EPHA2 variant 1; tyrosine-protein kinase receptor ECK
Antibodies
Medimmune: 101 (Lee J W., et al *Clin Cancer Res.* 2010 May 1; 16(9):2562-2570)
For example, see US20090304721A1 FIGS. 7 and 8.
(80) CD20—MS4A1 (Membrane-Spanning 4-Domains, Subfamily a, Member 1)
Nucleotide
Genbank accession no. M27394
Genbank version no. M27394.1 GI: 179307
Genbank record update date: Nov. 30, 2009 11:16 AM
Polypeptide
Genbank accession no. AAA35581
Genbank version no. AAA35581.1 GI: 179308
Genbank record update date: Nov. 30, 2009 11:16 AM
Cross-References
Tedder T. F., et al *Proc. Natl. Acad. Sci. U.S.A.* 85 (1), 208-212 (1988)
Other Information
Official Symbol: MS4A1
Other Aliases: B1, Bp35, CD20, CVID5, LEU-16, MS4A2, S7
Other Designations: B-lymphocyte antigen CD20; B-lymphocyte cell-surface antigen B1; CD20 antigen; CD20 receptor; leukocyte surface antigen Leu-16
Antibodies
Genentech/Roche: Rituximab—Abdulla N E., et al *BioDrugs.* 2012 Apr. 1; 26(2):71-82.
For example, see U.S. Pat. No. 5,736,137, ATCC deposit No. HB-69119.
GSK/Genmab: Ofatumumab—Nightingale G., et al *Ann Pharmacother.* 2011 October; 45(10):1248-55.
For example, see US20090169550A1 SEQ ID NOs: 2, 4 and 5.
Immunomedics: Veltuzumab—Goldenberg D M., et al *Leuk Lymphoma.* 2010 May; 51(5):747-55.
For example, see U.S. Pat. No. 7,919,273B2 SEQ ID NOs: 1, 2, 3, 4, 5 and 6.
(81) Tenascin C—TNC (Tenascin C)
Nucleotide
Genbank accession no. NM002160
Genbank version no. NM_002160.3 GI: 340745336
Genbank record update date: Sep. 23, 2012 02:33 PM
Polypeptide
Genbank accession no. NP_002151
Genbank version no. NP_002151.2 GI: 153946395
Genbank record update date: Sep. 23, 2012 02:33 PM
Cross-References
Nies D. E., et al *J. Biol. Chem.* 266 (5), 2818-2823 (1991); Siri A., et al *Nucleic Acids Res.* 19 (3), 525-531 (1991)
Other Information
Official Symbol: TNC
Other Aliases: 150-225, GMEM, GP, HXB, JI, TN, TN-C
Other Designations: GP 150-225; cytotactin; glioma-associated-extracellular matrix antigen; hexabrachion (tenascin); myotendinous antigen; neuronectin; tenascin; tenascin-C isoform 14/AD1/16
Antibodies
Philogen: G11 (von Lukowicz T., et al *J Nucl Med.* 2007 April; 48(4):582-7) and F16 (Pedretti M., et al *Lung Cancer.* 2009 April; 64(1):28-33)
For example, see U.S. Pat. No. 7,968,685 SEQ ID NOs: 29, 35, 45 and 47.
(82) FAP (Fibroblast Activation Protein, Alpha)
Nucleotide
Genbank accession no. U09278
Genbank version no. U09278.1 GI: 1888315
Genbank record update date: Jun. 23, 2010 09:22 AM
Polypeptide
Genbank accession no. AAB49652
Genbank version no. AAB49652.1 GI: 1888316
Genbank record update date: Jun. 23, 2010 09:22 AM
Cross-References
Scanlan, M. J., et al *Proc. Natl. Acad. Sci. U.S.A.* 91 (12), 5657-5661 (1994)
Other Information
Official Symbol: FAP
Other Aliases: DPPIV, FAPA
Other Designations: 170 kDa melanoma membrane-bound gelatinase; integral membrane serine protease; seprase
(83) DKK-1 (Dickkopf 1 Homolog (*Xenopus laevis*)
Nucleotide
Genbank accession no. NM_012242
Genbank version no. NM_012242.2 GI: 61676924
Genbank record update date: Sep. 30, 2012 01:48 PM
Polypeptide
Genbank accession no. NP_036374
Genbank version no. NP_036374.1 GI: 7110719
Genbank record update date: Sep. 30, 2012 01:48 PM
Cross-References
Fedi P. et al *J. Biol. Chem.* 274 (27), 19465-19472 (1999)
Other Information
Official Symbol: DKK1
Other Aliases: UNQ492/PRO1008, DKK-1, SK
Other Designations: dickkopf related protein-1; dickkopf-1 like; dickkopf-like protein 1; dickkopf-related protein 1; hDkk-1
Antibodies
Novartis: BHQ880 (Fulciniti M., et al *Blood.* 2009 Jul. 9; 114(2):371-379) For example, see US20120052070A1 SEQ ID NOs: 100 and 108.
(84) CD52 (CD52 Molecule)
Nucleotide
Genbank accession no. NM_001803
Genbank version no. NM_001803.2 GI: 68342029
Genbank record update date: Sep. 30, 2012 01:48 PM
Polypeptide
Genbank accession no. NP_001794
Genbank version no. NP_001794.2 GI: 68342030
Genbank record update date: Sep. 30, 2012 01:48 PM
Cross-References
Xia M. Q., et al *Eur. J. Immunol.* 21 (7), 1677-1684 (1991)
Other Information
Official Symbol: CD52
Other Aliases: CDW52
Other Designations: CAMPATH-1 antigen; CD52 antigen (CAMPATH-1 antigen); CDW52 antigen (CAMPATH-1 antigen); cambridge pathology 1 antigen; epididymal secretory protein E5; he5; human epididymis-specific protein 5

Antibodies

Alemtuzumab (Campath)—Skoetz N., et al *Cochrane Database Syst Rev.* 2012 Feb. 15; 2:CD008078.

For example, see Drugbank Acc. No. DB00087 (BIOD00109, BTD00109)

(85) CS1—SLAMF7 (SLAM Family Member 7)

Nucleotide

Genbank accession no. NM_021181

Genbank version no. NM_021181.3 GI: 1993571

Genbank record update date: Jun. 29, 2012 11:24 AM

Polypeptide

Genbank accession no. NP_067004

Genbank version no. NP_067004.3 GI: 19923572

Genbank record update date: Jun. 29, 2012 11:24 AM

Cross-References

Boles K. S., et al *Immunogenetics* 52 (3-4), 302-307 (2001)

Other Information

Official Symbol: SLAMF7

Other Aliases: UNQ576/PRO1138, 19A, CD319, CRACC, CS1

Other Designations: 19A24 protein; CD2 subset 1; CD2-like receptor activating cytotoxic cells; CD2-like receptor-activating cytotoxic cells; membrane protein FOAP-12; novel LY9 (lymphocyte antigen 9) like protein; protein 19A Antibodies BMS: elotuzumab/HuLuc63 (Benson D M., et al *J Clin Oncol.* 2012 Jun. 1; 30(16):2013-2015) For example, see US20110206701 SEQ ID NOs: 9, 10, 11, 12, 13, 14, 15 and 16.

(86) Endoglin—ENG (Endoglin)

Nucleotide

Genbank accession no. AF035753

Genbank version no. AF035753.1 GI: 3452260

Genbank record update date: Mar. 10, 2010 06:36 PM

Polypeptide

Genbank accession no. AAC32802

Genbank version no. AAC32802.1 GI: 3452261

Genbank record update date: Mar. 10, 2010 06:36 PM

Cross-References

Rius C., et al *Blood* 92 (12), 4677-4690 (1998)

Official Symbol: ENG

Other Information

Other Aliases: RP11-228B15.2, CD105, END, HHT1, ORW, ORW1

Other Designations: CD105 antigen

(87) Annexin A1—ANXA1 (Annexin A1)

Nucleotide

Genbank accession no. X05908

Genbank version no. X05908.1 GI: 34387

Genbank record update date: Feb. 2, 2011 10:02 AM

Polypeptide

Genbank accession no. CCA29338

Genbank version no. CCA29338.1 GI: 34388

Genbank record update date: Feb. 2, 2011 10:02 AM

Cross-References

Wallner B. P., et al *Nature* 320 (6057), 77-81 (1986)

Other Information

Official Symbol: ANXA1

Other Aliases: RP11-71A24.1, ANX1, LPC1

Other Designations: annexin I (lipocortin I); annexin-1; calpactin 11; calpactin-2; chromobindin-9; lipocortin I; p35; phospholipase A2 inhibitory protein (88) V-CAM (CD106)—VCAM1 (Vascular cell adhesion molecule 1)

Nucleotide

Genbank accession no. M60335

Genbank version no. M60335.1 GI: 340193

Genbank record update date: Jun. 23, 2010 08:56 AM

Polypeptide

Genbank accession no. AAA61269

Genbank version no. AAA61269.1 GI: 340194

Genbank record update date: Jun. 23, 2010 08:56 AM

Cross-References

Hession C., et al *J. Biol. Chem.* 266 (11), 6682-6685 (1991)

Other Information Official Symbol VCAM1

Other Aliases: CD106, INCAM-100

Other Designations: CD106 antigen; vascular cell adhesion protein 1

```
Antibody Sequences
Anti-Integrin αvβ6
RHAB6.2
QVQLVQSGSELKKPGASVKISCKASGFAFTDSYMHWVRQAPGQGLEWMGW

IDPENGDTEYAPKFQGRFVFSLDTSVSTAYLQISSLKAEDTAVYYCTRGT

PTAVPNLRGDLQVLAQKVAGPYPFDYWGQGTLVTVSS

RHCB6.2
QVQLVQSGAEVKKPGASVKVSCKASGYTFIDSYMHWVRQAPGQRLEWMGW

IDPENGDTEYAPKFQGRVTITTDTSASTAYMELSSLRSEDTAVYYCARGT

PTAVPNLRGDLQVLAQKVAGPYPFDYWGQGTLVTVSS

RHF
QVQLVQSGAEVKKPGASVKVSCKASGFNFIDSYMHWVRQAPGQRLEWMGW

IDPENGDTEYAPKFQGRVTFTTDTSASTAYMELSSLRSEDTAVYYCNEGT

PTGPYYFDYWGQGTLVTVSS

RHFB6
QVQLVQSGAEVKKPGASVKVSCKASGFNFIDSYMHWVRQAPGQRLEWMGW

IDPENGDTEYAPKFQGRVTFTTDTSASTAYMELSSLRSEDTAVYYCNEGT

PTAVPNLRGDLQVLAQKVAGPYYFDYWGQGTLVTVSS

RHAY100bP
QVQLVQSGSELKKPGASVKISCKASGFAFTDSYMHWVRQAPGQGLEWMGW

IDPENGDTEYAPKFQGRFVFSLDTSVSTAYLQISSLKAEDTAVYYCTRGT

PTGPYPFDYWGQGTLVTVSS

RKF
ENVLTQSPGTLSLSPGERATLSCSASSSVSYMHWFQQKPGQAPRLLIYST

SNLASGIPDRFSGSGSGTDFTLTISRLEPEDFAVYYCQQRSSYPLTFGGG

TKVEIK

RKFL36L50
ENVLTQSPGTLSLSPGERATLSCSASSSVSYMHWLQQKPGQAPRLLIYLT

SNLASGIPDRFSGSGSGTDFTLTISRLEPEDFAVYYCQQRSSYPLTFGGG

TKVEIK

RKC
EIVLTQSPGTLSLSPGERATLSCSASSSVSYMHWFQQKPGQAPRLLIYST

SNLASGIPDRFSGSGSGTDFTLTISRLEPEDFAVYYCQQRSSYPLTFGGG

TKVEIK
```

Anti-CD33
CD33 Hum195 VH
QVQLVQSGAEVKKPGSSVKVSCKASGYTFTDYNMHWVRQAPGQGLEWIGY

IYPYNGGTGYNQKFKSKATITADESTNTAYMELSSLRSEDTAVYYCARGR

PAMDYWGQGTLVTVSS

CD33 Hum195 VK
DIQMTQSPSSLSASVGDRVTITCRASESVDNYGISFMNWFQQKPGKAPKL

LIYAASNQGSGVPSRFSGSGSGTDFTLTISSLQPDDFATYYCQQSKEVPW

TFGQGTKVEIK

Anti-CD19
CD19 B4 resurfaced VH
QVQLVQPGAEVVKPGASVKLSCKTSGYTFTSNWMHWVKQRPGQGLEWIGE

IDPSDSYTNYNQNFKGKAKLTVDKSTSTAYMEVSSLRSDDTAVYYCARGS

NPYYYAMDYWGQGTSVTVSS

CD19 B4 resurfaced VK
EIVLTQSPAIMSASPGERVTMTCSASSGVNYMHWYQQKPGTSPRRWIYDT

SKLASGVPARFSGSGSGTSYSLTISSMEPEDAATYYCHQRGSYTFGGGTK

LEIK

Anti-Her2
Herceptin VH chain
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

Herceptin VL chain
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK

Anti-CD25
Simulect VK (also known as Basiliximab)
QIVSTQSPAIMSASPGEKVTMTCSASSSRSYMQWYQQKPGTSPKRWIYDT

SKLASGVPARFSGSGSGTSYSLTISSMEAEDAATYYCHQRSSYTFGGGTK

LEIK

Simulect VH
QLQQSGTVLARPGASVKMSCKASGYSFTRYWMHWIKQRPGQGLEWIGAIY

PGNSDTSYNQKFEGKAKLTAVTSASTAYMELSSLTHEDSAVYYCSRDYGY

YFDFWGQGTTLTVSS

Anti-PSMA
Deimmunised VH '1
EVQLVQSGPEVKKPGATVKISCKTSGYTFTEYTIHWVKQAPGKGLEWIGN

INPNNGGTTYNQKFEDKATLTVDKSTDTAYMELSSLRSEDTAVYYCAAGW

NFDYWGQGTLLTVSS

Deimmunised VK '1
DIQMTQSPSSLSTSVGDRVTLTCKASQDVGTAVDWYQQKPGPSPKLLIYW

ASTRHTGIPSRFSGSGSGTDFTLTISSLQPEDFADYYCQQYNSYPLTFGP

GTKVDIK

Deimmunised VH1 '5
EVKLVESGGGLVQPGGSMKLSCVASGFTFSNYWMNWVRQAPGKGLEWVAE

IRSQSNNFATHYAESVKGRVTISRDDSKSIVYLQMNNLRAEDTGVYYCTR

RWNNFWGQGTTVTVSS

Deimmunised VH2 '5
EVKLVESGGGLVQPGGSLKLSCVASGFTFSNYWMNWVRQAPGKGLEWVAE

IRSQSNNFATHYAESVKGRVTISRDDSKSIVYLQMNNLRAEDTAVYYCTR

RWNNFWGQGTTVTVSS

Deimmunised VH3 '5
EVQLVESGGGLVQPGGSLKLSCVASGFTFSNYWMNWVRQAPGKGLEWVAE

IRSQSNNFATHYAESVKGRVTISRDDSKSIVYLQMNNLRAEDTAVYYCTR

RWNNFWGQGTTVTVSS

Deimmunised VH4 '5
EVQLVESGGGLVQPGGSLKLSCVASGFTFSNYWMNWVRQAPGKGLEWVAE

IRSQSNNFATHYAESVKGRFTISRDDSKSIVYLQMNNLRAEDTAVYYCTR

RWNNFWGQGTTVTVSS

Deimmunised VK1 '5
NIVMTQFPSSMSASVGDRVTITCKASENVGTYVSWYQQKPDQSPKMLIYG

ASNRFTGVPDRFTGSGSATDFTLTISSLQTEDLADYYCGQSYTFPYTFGQ

GTKLEMK

Deimmunised VK2 '5
NIVMTQFPSSMSASVGDRVTITCKASENVGTYVSWYQQKPDQSPKMLIYG

ASNRFTGVPDRFSGSGSGTDFTLTISSLQAEDLADYYCGQSYTFPYTFGQ

GTKLEIK

Deimmunised VK3 '5
NIQMTQFPSAMSASVGDRVTITCKASENVGTYVSWYQQKPDQSPKMLIYG

ASNRFTGVPDRFSGSGSGTDFTLTISSLQAEDLADYYCGQSYTFPYTFGQ

GTKLEIK

Deimmunised VK4 '5
NIQMTQFPSAMSASVGDRVTITCKASENVGTYVSWYQQKPDQSPKMLIYG

ASNRFTGVPDRFSGSGSGTDFTLTISSLQAEDEADYYCGQSYTFPYTFGQ

GTKLEIK

Deimmunised VK DI '5
NIVMTQFPKSMSASAGERMTLTCKASENVGTYVSWYQQKPTQSPKMLIYG

ASNRFTGVPDRFSGSGSGTDFILTISSVQAEDLVDYYCGQSYTFPYTFGG

GTKLEMK

Deimmunised VH DI '5
EVKLEESGGGLVQPGGSMKISCVASGFTFSNYWMNWVRQSPEKGLEWVAE

IRSQSNNFATHYAESVKGRVIISRDDSKSSVYLQMNSLRAEDTAVYYCTR

RWNNFWGQGTTVTVSS

Humanised RHA '5
EVQLVESGGGLVQPGGSLKLSCAASGFTFSNYWMNWVRQASGKGLEWVGE

IRSQSNNFATHYAESVKGRFTISRDDSKNTAYLQMNSLKTEDTAVYYCTR

RWNNFWGQGTTVTVSS

-continued

Humanised RHB '5
EVKLVESGGGLVQPGGSLKLSCAASGFTFSNYWMNWVRQASGKGLEWVAE

IRSQSNNFATHYAESVKGRVIISRDDSKNTVYLQMNSLRTEDTAVYYCTR

RWNNFWGQGTTVTVSS

Humanised RHC '5
EVQLVESGGGLVQPGGSLKLSCAASGFTFSNYWMNWVRQASGKGLEWVAE

IRSQSNNFATHYAESVKGRVIISRDDSKNTVYLQMNSLRTEDTAVYYCTR

RWNNFWGQGTTVTVSS

Humanised RHD '5
EVKLVESGGGLVQPGGSLKLSCAASGFTFSNYWMNWVRQASGKGLEWVGE

IRSQSNNFATHYAESVKGRVIISRDDSKNTVYLQMNSLRTEDTAVYYCTR

RWNNFWGQGTTVTVSS

Humanised RHE '5
EVKLVESGGGLVQPGGSLKLSCAASGFTFSNYWMNWVRQASGKGLEWVAE

IRSQSNNFATHYAESVKGRFTISRDDSKNTVYLQMNSLRTEDTAVYYCTR

RWNNFWGQGTTVTVSS

Humanised RHF '5
EVKLVESGGGLVQPGGSLKLSCAASGFTFSNYWMNWVRQASGKGLEWVAE

IRSQSNNFATHYAESVKGRVIISRDDSKNTAYLQMNSLRTEDTAVYYCTR

RWNNFWGQGTTVTVSS

Humanised RHG '5
EVKLVESGGGLVQPGGSLKLSCAASGFTFSNYWMNWVRQASGKGLEWVAE

IRSQSNNFATHYAESVKGRVIISRDDSKNTAYLQMNSLRTEDTAVYYCTR

RWNNFWGQGTTVTVSS

Humanised RKA '5
DIQMTQSPSSVSASVGDRVTITCKASENVGTYVSWYQQKPGTAPKLLIYG

ASNRFTGVPSRFSGSGSATDFTLTINNLQPEDFATYYCGQSYTFPYTFGQ

GTKVEIK

Humanised RKB '5
DIQMTQSPSSVSASVGDRVTITCKASENVGTYVSWYQQKPGTAPKLLIYG

ASNRFTGVPSRFSGSGSATDFTLTINNLQPEDFATYYCGQSYTFPYTFGQ

GTKVEIK

Humanised RKC '5
DIQMTQSPSSVSASVGDRVTITCKASENVGTYVSWYQQKPGTAPKMLIYG

ASNRFTGVPSRFSGSGSATDFTLTINNLQPEDFATYYCGQSYTFPYTFGQ

GTKVEIK

Humanised RKD '5
DIQMTQSPSSVSASVGDRVTITCKASENVGTYVSWYQQKPGTAPKMLIYG

ASNRFTGVPSRFSGSGSATDFTLTINNLQPEDFATYYCGQSYTFPYTFGQ

GTKVEIK

Humanised RKE '5
NIVMTQSPSSVSASVGDRVTITCKASENVGTYVSWYQQKPGTAPKLLIYG

ASNRFTGVPDRFTGSGSATDFILTINNLQPEDFATYYCGQSYTFPYTFGQ

GTKVEIK

-continued

Humanised RKF '5
NIVMTQSPSSVSASVGDRVTITCKASENVGTYVSWYQQKPGTAPKMLIYG

ASNRFTGVPSRFSGSGSATDFILTINNLQPEDFATYYCGQSYTFPYTFGQ

GTKVEIK

Humanised RKG '5
NIVMTQSPSSVSASVGDRVTITCKASENVGTYVSWYQQKPGTAPKMLIYG

ASNRFTGVPDRFTGSGSATDFTLTINNLQPEDFATYYCGQSYTFPYTFGQ

GTKVEIK

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol Chem.* 277:35035-35043; WO 01/45746). Antibodies of the invention include fusion proteins with ABP sequences taught by: (i) Dennis et al (2002) *J Biol Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Embodiments of the present invention include ConjA wherein the cell binding agent is selected from an antibody to any of the antigens discussed above.

Embodiments of the present invention include ConjB wherein the cell binding agent is selected from an antibody to any of the antigens discussed above.

Embodiments of the present invention include ConjA wherein the cell binding agent is selected from any of the antibodies discussed above.

Embodiments of the present invention include ConjB wherein the cell binding agent is selected from any of the antibodies discussed above.

The present invention may also relate to conjugates where the cell binding agent is selected from an antibody to any of the antigens discussed above and any of the antibodies discussed above linked to different drugs.

Drug Loading

The drug loading is the average number of PBD drugs per cell binding agent, e.g. antibody. Where the compounds of the invention are bound to cysteines, drug loading may range from 1 to 8 drugs (D) per cell binding agent, i.e. where 1, 2, 3, 4, 5, 6, 7, and 8 drug moieties are covalently attached to the cell binding agent. Compositions of conjugates include collections of cell binding agents, e.g. antibodies, conjugated with a range of drugs, from 1 to 8. Where the compounds of the invention are bound to lysines, drug loading may range from 1 to 80 drugs (D) per cell binding agent, although an upper limit of 40, 20, 10 or 8 may be preferred. Compositions of conjugates include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) *Clin. Cancer Res.* 10:7063-7070; Sanderson et al (2005) *Clin. Cancer Res.* 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b *Nature Biotech.,* 26(8):925-932; Dornan et al (2009) *Blood* 114(13): 2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine group per cell binding agent.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.,* 66, 1-19 (1977).

For example, if the compound is anionic, or has a functional group which may be anionic (e.g. —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^AOH$, where $R^A$ is $C_{1-4}$alkyl):

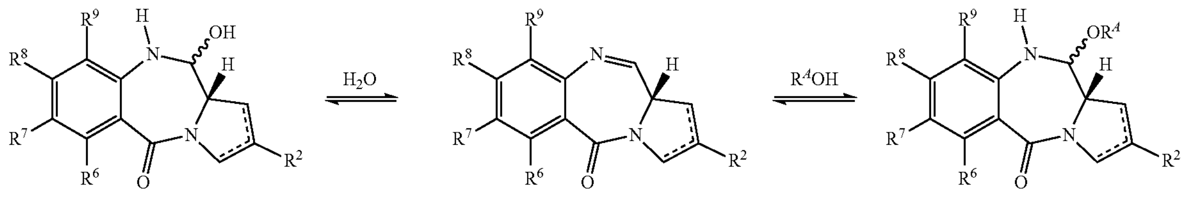

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or I meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, $-OCH_3$, is not to be construed as a reference to its structural isomer, a hydroxymethyl group, $-CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

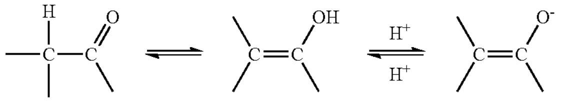

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^{1}$H, $^{2}$H (D), and $^{3}$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^{2}$H (deuterium, D), $^{3}$H (tritium), $^{11}$C $^{13}$C, $^{14}$C $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, WI), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 μl per well) into black 96 well plates. Plates of adherent cell lines are incubated overnight to allow adherence. Suspension cell cultures can be used on the day of seeding.

A stock solution (1 ml) of ADC (20 μg/ml) is made in the appropriate cell culture medium. Serial 10-fold dilutions of stock ADC are made in 15 ml centrifuge tubes by serially transferring 100 μl to 900 μl of cell culture medium.

Four replicate wells of each ADC dilution (100 μl) are dispensed in 96-well black plates, previously plated with cell suspension (100 μl), resulting in a final volume of 200 μl. Control wells receive cell culture medium (100 μl).

If the doubling time of the cell line is greater than 30 hours, ADC incubation is for 5 days, otherwise a four day incubation is done.

At the end of the incubation period, cell viability is assessed with the Alamar blue assay. AlamarBlue (Invitrogen) is dispensed over the whole plate (20 μl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

In Vivo Efficacy

The in vivo efficacy of antibody-drug conjugates (ADC) of the invention can be measured by tumor xenograft studies in mice. For example, the in vivo efficacy of an anti-HER2 ADC of the invention can be measured by a high expressing HER2 transgenic explant mouse model. An allograft is propagated from the Fo5 mmtv transgenic mouse which does not respond to, or responds poorly to, HERCEPTIN® therapy. Subjects are treated once with ADC at certain dose levels (mg/kg) and PBD drug exposure (μg/m$^2$); and placebo buffer control (Vehicle) and monitored over two weeks or more to measure the time to tumor doubling, log cell kill, and tumor shrinkage.

Use

The conjugates of the invention may be used to provide a PBD compound at a target location.

The target location is preferably a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound RelA or RelB. Thus, the conjugate may be used to selectively provide a compound RelA or RelB to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumour having $\alpha_v\beta_6$ integrin on the surface of the cell.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omegaI1 (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholinodoxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, New York, USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug conjugates Antibody drug conjugates, as well as conjugates with other cell binding agents, may be prepared by several routes, employing organic chemistry reactions, conditions, and reagents known to those skilled in the art, including reaction of a nucleophilic group of an antibody or cell binding agent with a drug-linker reagent. This method may be employed with a variety of antibodies and cell binding agents to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) *Anal. Biochem*. Vol 273:73-80; Soltec Ventures, Beverly, MA). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

In one embodiment, the patient is a population where each patient has a tumour having $\alpha_v\beta_6$ integrin on the surface of the cell.

EXAMPLES

General Experimental Methods for Examples 1 and 2

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4A molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B over 2.5 min. The composition was held for 0.5 min at 95% B, and then returned to 5% B in 0.1 minutes and held there for 0.9 min. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm

Example 1

(i) (S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone (9)

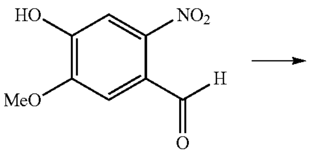

1

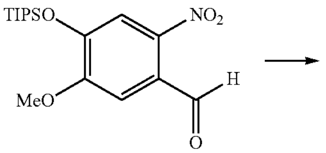

2

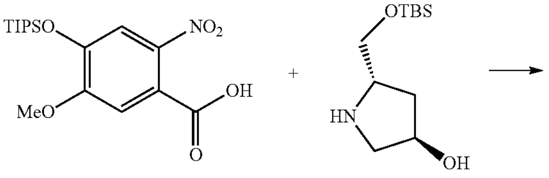

3

4

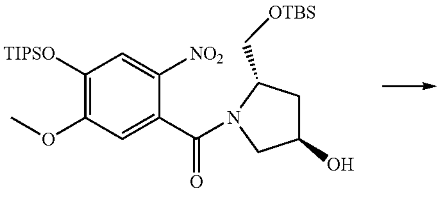

5

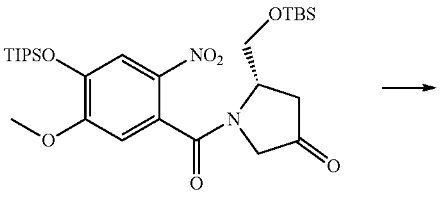

6

-continued

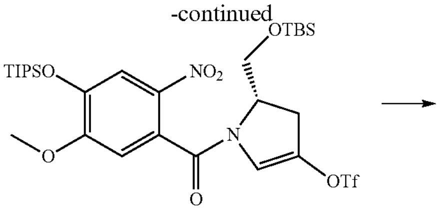

7

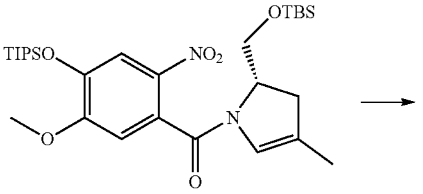

8

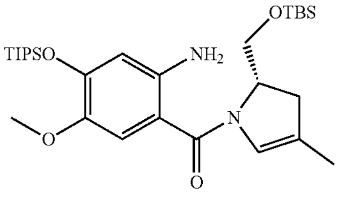

9

(a) 5-methoxy-2-nitro-4-((triisopropylsilyl)oxy)benzaldehyde (2)

Neat triisopropylsilylchloride (56.4 mL, 262 mmol) was added to a mixture of imidazole (48.7 g, 715.23 mmol) and 4-hydroxy-5-methoxy-2-nitrobenzaldehyde 1 (47 g, 238 mmol) (ground together). The mixture was heated until the phenol and imidazole melted and went into solution (100° C.). The reaction mixture was allowed to stir for 15 minutes and was then allowed to cool, whereupon a solid was observed to form at the bottom of the flask (imidazole chloride). The reaction mixture was diluted with 5% EtOAc/hexanes and loaded directly onto silica gel and the pad was eluted with 5% EtOAc/hexanes, followed by 10% EtOAc/hexanes (due to the low excess, very little unreacted TIPSCI was found in the product). The desired product was eluted with 5% ethyl acetate in hexane. Excess eluent was removed by rotary evaporation under reduced pressure, followed by drying under high vacuum to afford a crystalline light sensitive solid (74.4 g, 88%). Purity satisfactory by LC/MS (4.22 min (ES+) m/z (relative intensity) 353.88 ($[M+H]^+$, 100)); $^1H$ NMR (400 MHz, $CDCl_3$) δ 10.43 (s, 1H), 7.60 (s, 1H), 7.40 (s, 1H), 3.96 (s, 3H), 1.35-1.24 (m, 3H), 1.10 (m, 18H).

(b) 5-methoxy-2-nitro-4-((triisopropylsilyl)oxy)benzoic acid (3)

A solution of sodium chlorite (47.3 g, 523 mmol, 80% technical grade) and sodium dihydrogenphosphate monobasic (35.2 g, 293 mmol) ($NaH_2PO_4$) in water (800 mL) was added to a solution of compound 2 (74 g, 209 mmol) in tetrahydrofuran (500 mL) at room temperature. Hydrogen peroxide (60% w/w, 140 mL, 2.93 mol) was immediately added to the vigorously stirred biphasic mixture. The reaction mixture evolved gas (oxygen), the starting material dissolved and the temperature of the reaction mixture rose to 45° C. After 30 minutes LC/MS revealed that the reaction was complete. The reaction mixture was cooled in an ice bath and hydrochloric acid (1 M) was added to lower the pH to 3 (this step was found unnecessary in many instances, as the pH at the end of the reaction is already acidic; please check the pH before extraction). The reaction mixture was then extracted with ethyl acetate (1 L) and the organic phases washed with brine (2×100 mL) and dried over magnesium sulphate. The organic phase was filtered and excess solvent removed by rotary evaporation under reduced pressure to afford the product 3 in quantitative yield as a yellow solid. LC/MS (3.93 min (ES−) m/z (relative intensity) 367.74 ($[M-H]^-$, 100)); $^1$H NMR (400 MHz, $CDCl_3$) δ 7.36 (s, 1H), 7.24 (s, 1H), 3.93 (s, 3H), 1.34-1.22 (m, 3H), 1.10 (m, 18H).

(c) ((2S,4R)-2-(((tert-butyldimethylsilyl)oxy)methyl)-4-hydroxypyrrolidin-1-yl)(5-methoxy-2-nitro-4-((triisopropylsilyl)oxy)phenyl)methanone (5)

DCC (29.2 g, 141 mmol, 1.2 eq) was added to a solution of acid 3 (43.5 g, 117.8 mmol, 1 eq), and hydroxybenzotriazole hydrate (19.8 g, 129.6 mmol, 1.1 eq) in dichloromethane (200 mL) at 0° C. The cold bath was removed and the reaction was allowed to proceed for 30 mins at room temperature, at which time a solution of (2S,4R)-2-t-butyldimethylsilyloxymethyl-4-hydroxypyrrolidine 4 (30 g, 129.6 mmol, 1.1 eq) and triethylamine (24.66 mL, 176 mmol, 1.5 eq) in dichloromethane (100 mL) was added rapidly at −10° C. under argon (on large scale, the addition time could be shortened by cooling the reaction mixture even further. The reaction mixture was allowed to stir at room temperature for 40 minutes to 1 hour and monitored by LC/MS and TLC (EtOAc). The solids were removed by filtration over celite and the organic phase was washed with cold aqueous 0.1 M HCl until the pH was measured at 4 or 5. The organic phase was then washed with water, followed by saturated aqueous sodium bicarbonate and brine. The organic layer was dried over magnesium sulphate, filtered and excess solvent removed by rotary evaporation under reduced pressure. The residue was subjected to column flash chromatography (silica gel; gradient 40/60 ethyl acetate/hexane to 80/20 ethyl acetate/hexane). Excess solvent was removed by rotary evaporation under reduced pressure afforded the pure product 5, (45.5 g of pure product 66%, and 17 g of slightly impure product, 90% in total). LC/MS 4.43 min (ES+) m/z (relative intensity) 582.92 ($[M+H]^+$, 100); $^1$H NMR (400 MHz, $CDCl_3$) δ 7.66 (s, 1H), 6.74 (s, 1H), 4.54 (s, 1H), 4.40 (s, 1H), 4.13 (s, 1H), 3.86 (s, 3H), 3.77 (d, J=9.2 Hz, 1H), 3.36 (dd, J=11.3, 4.5 Hz, 1H), 3.14-3.02 (m, 1H), 2.38-2.28 (m, 1H), 2.10 (ddd, J=13.3, 8.4, 2.2 Hz, 1H), 1.36-1.19 (m, 3H), 1.15-1.05 (m, 18H), 0.91 (s, 9H), 0.17-0.05 (m, 6H), (presence of rotamers).

(d) (S)-5-(((tert-butyldimethylsilyl)oxy)methyl)-1-(5-methoxy-2-nitro-4-((triisopropylsilyl)oxy)benzoyl)pyrrolidin-3-one (6)

TCCA (8.82 g, 40 mmol, 0.7 eq) was added to a stirred solution of 5 (31.7 g, 54 mmol, 1 eq) and TEMPO (0.85 g, 5.4 mmol, 0.1 eq) in dry dichloromethane (250 mL) at 0° C. The reaction mixture was vigorously stirred for 20 minutes, at which point TLC (50/50 ethyl acetate/hexane) revealed complete consumption of the starting material. The reaction mixture was filtered through celite and the filtrate washed with aqueous saturated sodium bicarbonate (100 mL), sodium thiosulphate (9 g in 300 mL), brine (100 mL) and dried over magnesium sulphate. Rotary evaporation under reduced pressure afforded product 6 in quantitative yield. LC/MS 4.52 min (ES+) m/z (relative intensity) 581.08 ($[M+H]^+$, 100); $^1$H NMR (400 MHz, $CDCl_3$) δ 7.78-7.60 (m, 1H), 6.85-6.62 (m, 1H), 4.94 (dd, J=30.8, 7.8 Hz, 1H), 4.50-4.16 (m, 1H), 3.99-3.82 (m, 3H), 3.80-3.34 (m, 3H), 2.92-2.17 (m, 2H), 1.40-1.18 (m, 3H), 1.11 (t, J=6.2 Hz, 18H), 0.97-0.75 (m, 9H), 0.15-−0.06 (m, 6H), (presence of rotamers).

(e) (S)-5-(((tert-butyldimethylsilyl)oxy)methyl)-1-(5-methoxy-2-nitro-4-((triisopropylsilyl)oxy)benzoyl)-4,5-dihydro-1H-pyrrol-3-yl trifluoromethanesulfonate (7)

Triflic anhydride (27.7 mL, 46.4 g, 165 mmol, 3 eq) was injected (temperature controlled) to a vigorously stirred suspension of ketone 6 (31.9 g, 55 mmol, 1 eq) in dry dichloromethane (900 mL) in the presence of 2,6-lutidine (25.6 mL, 23.5 g, 220 mmol, 4 eq, dried over sieves) at −50° C. (acetone/dry ice bath). The reaction mixture was allowed to stir for 1.5 hours when LC/MS, following a mini work-up (water/dichloromethane), revealed the reaction to be complete. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel; 10/90 v/v ethyl acetate/hexane), removal of excess eluent afforded the product 7 (37.6 g, 96%) LC/MS, method 2, 4.32 min (ES+) m/z (relative intensity) 712.89 ($[M+H]^+$, 100); $^1$H NMR (400 MHz, $CDCl_3$) δ 7.71 (s, 1H), 6.75 (s, 1H), 6.05 (d, J=1.8 Hz, 1H), 4.78 (dd, J=9.8, 5.5 Hz, 1H), 4.15-3.75 (m, 5H), 3.17 (ddd, J=16.2, 10.4, 2.3 Hz, 1H), 2.99 (ddd, J=16.3, 4.0, 1.6 Hz, 1H), 1.45-1.19 (m, 3H), 1.15-1.08 (m, 18H), 1.05 (s, 6H), 0.95-0.87 (m, 9H), 0.15-0.08 (m, 6H).

(f) (S)-(2-(((tert-butyldimethylsilyl)oxy)methyl)-4-methyl-2,3-dihydro-1H-pyrrol-1-yl)(5-methoxy-2-nitro-4-((triisopropylsilyl)oxy)phenyl)methanone (8)

Triphenylarsine (1.71 g, 5.60 mmol, 0.4 eq) was added to a mixture of triflate 7 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(II) chloride (540 mg, 1.40 mmol, 0.1 eq) was added. The reaction was flushed with argon 3 more times before being warmed instantaneously to 110° C. (the drysyn heating block was previously warmed to 110° C. prior addition of the flask). After 10 mins the reaction was cooled to room temperature and filtered through a pad celite. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 8 (4.5 g, 55%). LC/MS, 4.27 min (ES+) m/z (relative intensity) 579.18 ($[M+H]^+$, 100); $^1$H NMR (400 MHz, $CDCl_3$) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(g) (S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone (9)

Zinc powder (28 g, 430 mmol, 37 eq) was added to a solution of compound 8 (6.7 g, 11.58 mmol) in 5% formic acid in ethanol v/v (70 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 9 (5.1 g, 80%). LC/MS, 4.23 min (ES+) m/z (relative intensity) 550.21 ($[M+H]^+$, 100); $^1H$ NMR (400 MHz, $CDCl_3$) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03--0.03 (m, J=6.2 Hz, 6H).

(ii) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate

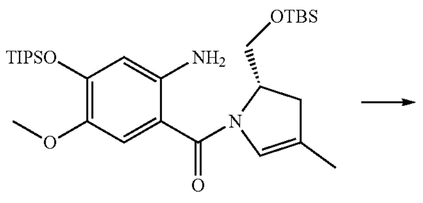

9

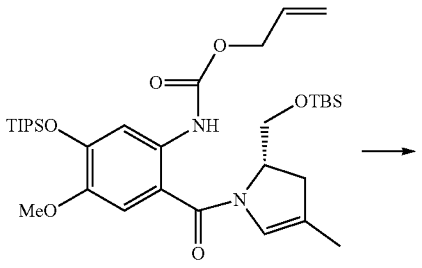

10

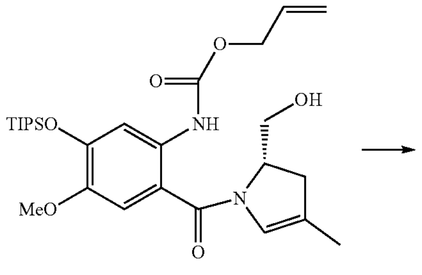

11

-continued

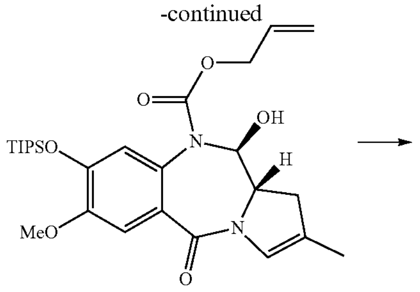

12

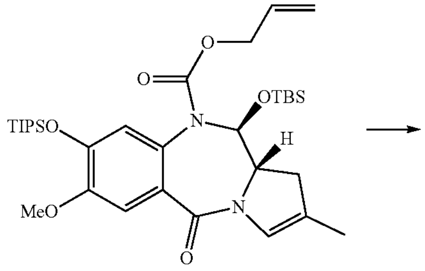

13

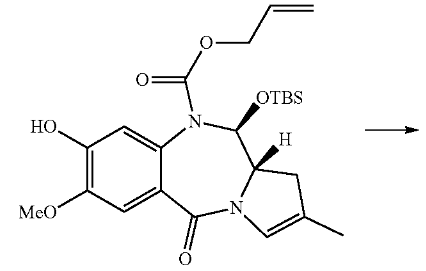

14

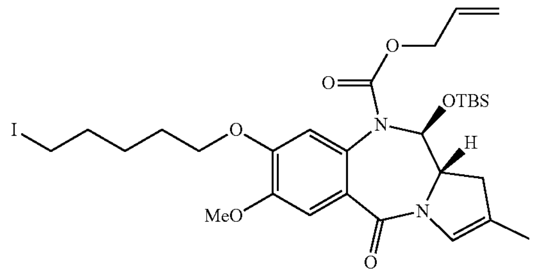

15

(a) (S)-allyl (2-(2-(((tert-butyldimethylsilyl)oxy)methyl)-4-methyl-2,3-dihydro-1H-pyrrole-1-carbonyl)-4-methoxy-5-((triisopropylsilyl)oxy)phenyl)carbamate (10)

Allyl chloroformate (0.30 mL, 3.00 mmol, 1.1 eq) was added to a solution of amine 9 (1.5 g, 2.73 mmol) in the presence of dry pyridine (0.48 mL, 6.00 mmol, 2.2 eq) in dry dichloromethane (20 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 10 which was used directly in the next reaction. LC/MS, 4.45 min (ES+) m/z (relative intensity) 632.91 ([M+H]$^+$, 100)

(b) (S)-allyl (2-(2-(hydroxymethyl)-4-methyl-2,3-dihydro-1H-pyrrole-1-carbonyl)-4-methoxy-5-((triisopropylsilyl)oxy)phenyl)carbamate (11)

The crude 10 was dissolved in a 7:1:1:2 mixture of acetic acid/methanol/tetrahydrofuran/water (28:4:4:8 mL) and allowed to stir at room temperature. After 3 hours, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel, 25% ethyl acetate in hexane). Pure fractions were collected and combined and excess eluent was removed by rotary evaporation under reduced pressure to afford the desired product 11 (1 g, 71%). LC/MS, 3.70 min (ES+) m/z (relative intensity) 519.13 ([M+H]$^+$, 95); $^1$H NMR (400 MHz, $CDCl_3$) δ 8.34 (s, 1H), 7.69 (s, 1H), 6.78 (s, 1H), 6.15 (s, 1H), 5.95 (ddt, J=17.2, 10.5, 5.7 Hz, 1H), 5.33 (dq, J=17.2, 1.5 Hz, 1H), 5.23 (ddd, J=10.4, 2.6, 1.3 Hz, 1H), 4.73 (tt, J=7.8, 4.8 Hz, 1H), 4.63 (dt, J=5.7, 1.4 Hz, 2H), 4.54 (s, 1H), 3.89-3.70 (m, 5H), 2.87 (dd, J=16.5, 10.5 Hz, 1H), 2.19 (dd, J=16.8, 4.6 Hz, 1H), 1.70 (d, J=1.3 Hz, 3H), 1.38-1.23 (m, 3H), 1.12 (s, 10H), 1.10 (s, 8H).

(c) (11S,11aS)-allyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (12)

Dimethyl sulphoxide (0.35 mL, 4.83 mmol, 2.5 eq) was added dropwise to a solution of oxalyl chloride (0.2 mL, 2.32 mmol, 1.2 eq) in dry dichloromethane (10 mL) at −78° C. (dry ice/acetone bath) under an atmosphere of argon. After 10 minutes a solution of 11 (1 g, 1.93 mmol) in dry dichloromethane (8 mL) was added slowly with the temperature still at −78° C. After 15 min triethylamine (1.35 mL, dried over 4A molecular sieves, 9.65 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 12 (658 mg, 66%). LC/MS, 3.52 min (ES+) m/z (relative intensity) 517.14 ([M+H]$^+$, 100); $^1$H NMR (400 MHz, $CDCl_3$) δ 7.20 (s, 1H), 6.75-6.63 (m, J=8.8, 4.0 Hz, 2H), 5.89-5.64 (m, J=9.6, 4.1 Hz, 2H), 5.23-5.03 (m, 2H), 4.68-4.38 (m, 2H), 3.84 (s, 3H), 3.83-3.77 (m, 1H), 3.40 (s, 1H), 3.05-2.83 (m, 1H), 2.59 (d, J=17.1 Hz, 1H), 1.78 (d, J=1.3 Hz, 3H), 1.33-1.16 (m, 3H), 1.09 (d, J=2.2 Hz, 9H), 1.07 (d, J=2.1 Hz, 9H).

(d) (11S,11aS)-allyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (13)

Tert-butyldimethylsilyltriflate (0.70 mL, 3.00 mmol, 3 eq) was added to a solution of compound 12 (520 mg, 1.00 mmol) and 2,6-lutidine (0.46 mL, 4.00 mmol, 4 eq) in dry dichloromethane (40 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 13 (540 mg, 85%). LC/MS, 4.42 min (ES+) m/z (relative intensity) 653.14 ([M+Na]$^+$, 100); $^1$H NMR (400 MHz, $CDCl_3$) δ 7.20 (s, 1H), 6.71-6.64 (m, J=5.5 Hz, 2H), 5.83 (d, J=9.0 Hz, 1H), 5.80-5.68 (m, J=5.9 Hz, 1H), 5.14-5.06 (m, 2H), 4.58 (dd, J=13.2, 5.2 Hz, 1H), 4.36 (dd, J=13.3, 5.5 Hz, 1H), 3.84 (s, 3H), 3.71 (td, J=10.1, 3.8 Hz, 1H), 2.91 (dd, J=16.9, 10.3 Hz, 1H), 2.36 (d, J=16.8 Hz, 1H), 1.75 (s, 3H), 1.31-1.16 (m, 3H), 1.12-1.01 (m, J=7.4, 2.1 Hz, 18H), 0.89-0.81 (m, 9H), 0.25 (s, 3H), 0.19 (s, 3H).

(e) (11S,11aS)-allyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (14)

Lithium acetate (87 mg, 0.85 mmol) was added to a solution of compound 13 (540 mg, 0.85 mmol) in wet dimethylformamide (6 mL, 50:1 DMF/water). After 4 hours, the reaction was complete and the reaction mixture was diluted with ethyl acetate (25 mL) and washed with aqueous citric acid solution (pH~3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 14 (400 mg, quantitative). LC/MS, (3.33 min (ES+) m/z (relative intensity) 475.26 ([M+H]$^+$, 100).

(f) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate (15)

Diiodopentane (0.63 mL, 4.21 mmol, 5 eq) and potassium carbonate (116 mg, 0.84 mmol, 1 eq) were added to a solution of phenol 14 (400 mg, 0.84 mmol) in acetone (4 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate). Pure fractions were collected and combined and excess eluent was removed to provide 15 in 90% yield. LC/MS, 3.90 min (ES+) m/z (relative intensity) 670.91 ([M]$^+$, 100). $^1$H NMR (400 MHz, $CDCl_3$) δ 7.23 (s, 1H), 6.69 (s, 1H), 6.60 (s, 1H), 5.87 (d, J=8.8 Hz, 1H), 5.83-5.68 (m, J=5.6 Hz, 1H), 5.15-5.01 (m, 2H), 4.67-4.58 (m, 1H), 4.45-4.35 (m, 1H), 4.04-3.93 (m, 2H), 3.91 (s, 3H), 3.73 (td, J=10.0, 3.8 Hz, 1H), 3.25-3.14 (m, J=8.5, 7.0 Hz, 2H), 2.92 (dd, J=16.8, 10.3

Hz, 1H), 2.38 (d, J=16.8 Hz, 1H), 1.95-1.81 (m, 4H), 1.77 (s, 3H), 1.64-1.49 (m, 2H), 0.88 (s, 9H), 0.25 (s, 3H), 0.23 (s, 3H).

(iii) (11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (20)

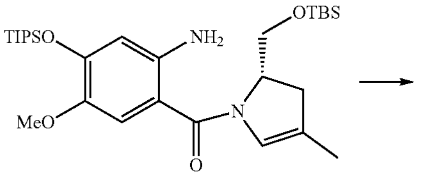

9

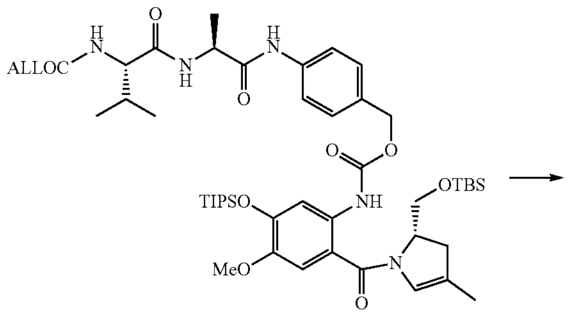

16

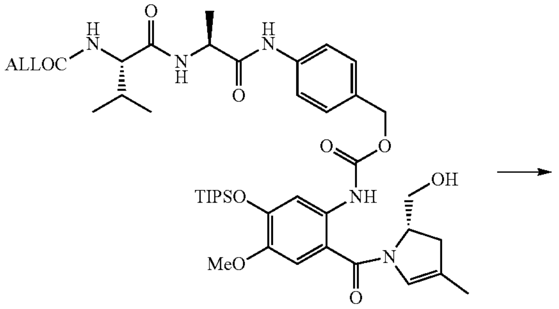

17

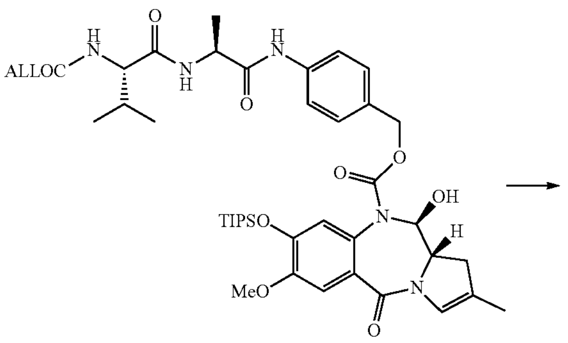

18

-continued

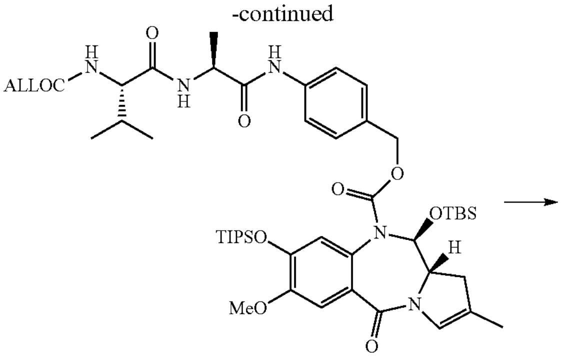

19

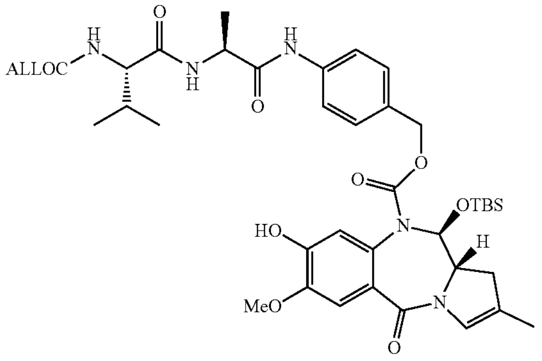

20

(a) Allyl 3-(2-(2-(4-((((2-((S)-2-(((tert-butyldimethylsilyl)oxy)methyl)-4-methyl-2, 3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate (16)

Triethylamine (2.23 mL, 18.04 mmol, 2.2 eq) was added to a stirred solution of the amine 9 (4 g, 8.20 mmol) and triphosgene (778 mg, 2.95 mmol, 0.36 eq) in dry tetrahydrofuran (40 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (4.12 g, 12.30 mmol, 1.5 eq) and triethylamine (1.52 mL, 12.30 mmol, 1.5 eq) in dry tetrahydrofuran (40 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 16 (3.9 g, 50%). LC/MS, 4.23 min (ES+) m/z (relative intensity) 952.36 ($[M+H]^+$, 100); $^1H$ NMR (400 MHz, $CDCl_3$) δ 8.62 (br s, 1H), 8.46 (s, 1H), 7.77 (br s, 1H), 7.53 (d, J=8.4 Hz, 2H), 7.32 (d, J=8.5 Hz, 2H), 6.76 (s, 1H), 6.57 (d, J=7.6 Hz, 1H), 6.17 (s, 1H), 6.03-5.83 (m, 1H), 5.26 (dd, J=33.8, 13.5 Hz, 3H), 5.10 (s, 2H), 4.70-4.60 (m, 2H), 4.58 (dd, J=5.7, 1.3 Hz, 2H), 4.06-3.99 (m, 1H), 3.92 (s, 1H), 3.82-3.71 (m, 1H), 3.75 (s, 3H), 2.79-2.64 (m, 1H), 2.54 (d, J=12.9 Hz, 1H), 2.16 (dq, J=13.5, 6.7 Hz, 1H), 1.67 (s, 3H), 1.46 (d, J=7.0 Hz, 3H), 1.35-1.24 (m, 3H), 1.12 (s, 9H), 1.10 (s, 9H), 0.97 (d, J=6.8 Hz, 3H), 0.94 (d, J=6.8 Hz, 3H), 0.87 (s, 9H), 0.07--0.02 (m, 6H).

(b) Allyl 3-(2-(2-(4-((((2-((S)-2-(hydroxymethyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl)propanamido)-4-methyl-2-oxopentanoate (17)

The TBS ether 16 (1.32 g, 1.38 mmol) was dissolved in a 7:1:1:2 mixture of acetic acid/methanol/tetrahydrofuran/water (14:2:2:4 mL) and allowed to stir at room temperature. After 3 hours no more starting material was observed by LC/MS. The reaction mixture was diluted with ethyl acetate (25 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol in dichloromethane). Pure fractions were collected and combined and excess eluent was removed by rotary evaporation under reduced pressure to afford the desired product 17 (920 mg, 80%). LC/MS, 3.60 min (ES+) m/z (relative intensity) 838.18 ($[M+H]^+$, 100). $^1$H NMR (400 MHz, $CDCl_3$) δ 8.55 (s, 1H), 8.35 (s, 1H), 7.68 (s, 1H), 7.52 (d, J=8.1 Hz, 2H), 7.31 (d, J=8.4 Hz, 2H), 6.77 (s, 1H), 6.71 (d, J=7.5 Hz, 1H), 6.13 (s, 1H), 5.97-5.82 (m, J=5.7 Hz, 1H), 5.41-5.15 (m, 3H), 5.10 (d, J=3.5 Hz, 2H), 4.76-4.42 (m, 5H), 4.03 (t, J=6.6 Hz, 1H), 3.77 (s, 5H), 2.84 (dd, J=16.7, 10.4 Hz, 1H), 2.26-2.08 (m, 2H), 1.68 (s, 3H), 1.44 (d, J=7.0 Hz, 3H), 1.30 (dt, J=14.7, 7.4 Hz, 3H), 1.12 (s, 9H), 1.10 (s, 9H), 0.96 (d, J=6.8 Hz, 3H), 0.93 (d, J=6.8 Hz, 3H).

(c) (11S,11aS)-4-(2-(1-((1-(allyloxy)-4-methyl-1,2-dioxopentan-3-yl)amino)-1-oxopropan-2-yl)hydrazinyl)benzyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (18)

Dimethyl sulphoxide (0.2 mL, 2.75 mmol, 2.5 eq) was added dropwise to a solution of oxalyl chloride (0.11 mL, 1.32 mmol, 1.2 eq) in dry dichloromethane (7 mL) at −78° C. (dry ice/acetone bath) under an atmosphere of argon. After 10 minutes a solution of 17 (920 mg, 1.10 mmol) in dry dichloromethane (5 mL) was added slowly with the temperature still at −78° C. After 15 min triethylamine (0.77 mL, dried over 4A molecular sieves, 5.50 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 2% methanol to 5% methanol in dichloromethane). Pure fractions were collected and combined and removal of excess eluent by rotary evaporation under reduced pressure afforded the product 18 (550 mg, 60%). LC/MS, 3.43 min (ES+) m/z (relative intensity) 836.01 ($[M]^+$, 100). $^1$H NMR (400 MHz, $CDCl_3$) δ 8.39 (s, 1H), 7.52-7.40 (m, 2H), 7.21-7.08 (m, J=11.5 Hz, 2H), 6.67 (s, 1H), 6.60-6.47 (m, J=7.4 Hz, 1H), 5.97-5.83 (m, 1H), 5.79-5.66 (m, 1H), 5.38-4.90 (m, 6H), 4.68-4.52 (m, J=18.4, 5.5 Hz, 4H), 4.04-3.94 (m, J=6.5 Hz, 1H), 3.87-3.76 (m, 5H), 3.00-2.88 (m, 1H), 2.66-2.49 (m, 2H), 2.21-2.08 (m, 2H), 1.76 (s, 3H), 1.45 (d, J=7.0 Hz, 3H), 1.09-0.98 (m, J=8.9 Hz, 18H), 0.96 (d, J=6.7 Hz, 3H), 0.93 (d, J=6.9 Hz, 3H).

(d) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (19)

Tert-butyldimethylsilyltriflate (0.38 mL, 1.62 mmol, 3 eq) was added to a solution of compound 18 (450 mg, 0.54 mmol) and 2,6-lutidine (0.25 mL, 2.16 mmol, 4 eq) in dry dichloromethane (5 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 19 (334 mg, 65%). LC/MS, 4.18 min (ES+) m/z (relative intensity) 950.50 ($[M]^+$, 100). $^1$H NMR (400 MHz, $CDCl_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(e) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (20)

Lithium acetate (50 mg, 0.49 mmol) was added to a solution of compound 19 (470 mg, 0.49 mmol) in wet dimethylformamide (4 mL, 50:1 DMF/water). After 4 hours, the reaction was complete and the reaction mixture was diluted with ethyl acetate and washed with citric acid (pH~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 25/75 v/v hexane/ethyl acetate). Pure fractions were collected and combined and excess eluent was removed by rotary evaporation under reduced pressure to give the product 20 (400 mg, quantitative). LC/MS, 3.32 min (ES+) m/z (relative intensity) 794.18 ($[M+H]^+$, 100). $^1$H NMR (400 MHz, $CDCl_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).
(iv) (11S,11aS)-4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (24)
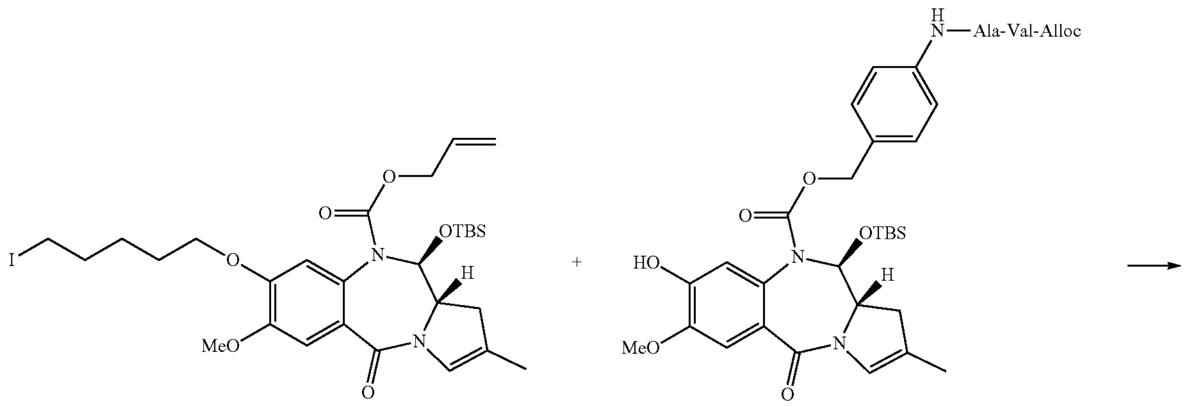
15 20
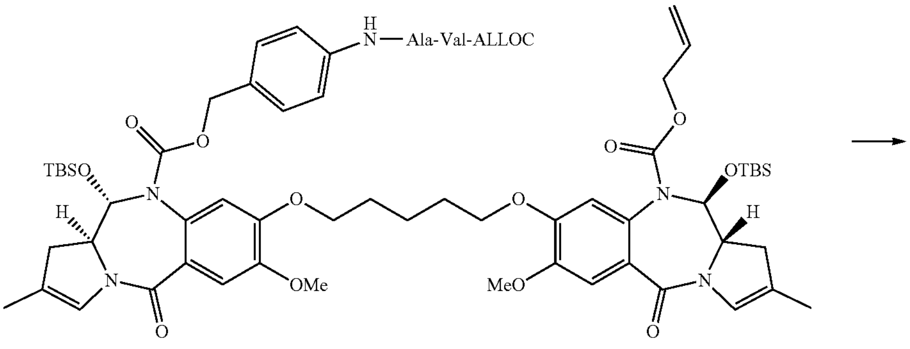
21
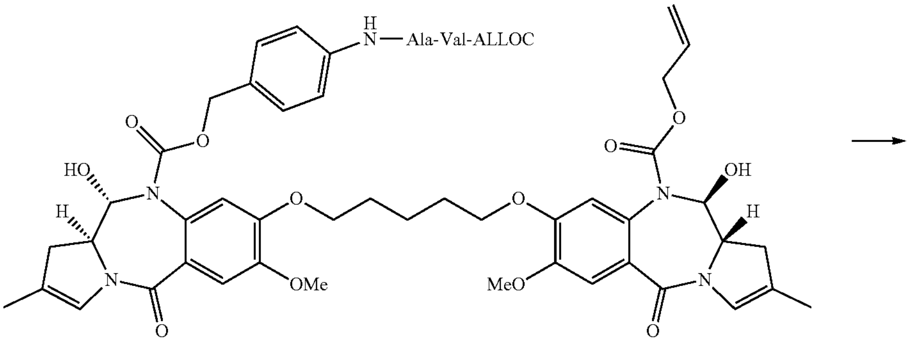
22

-continued

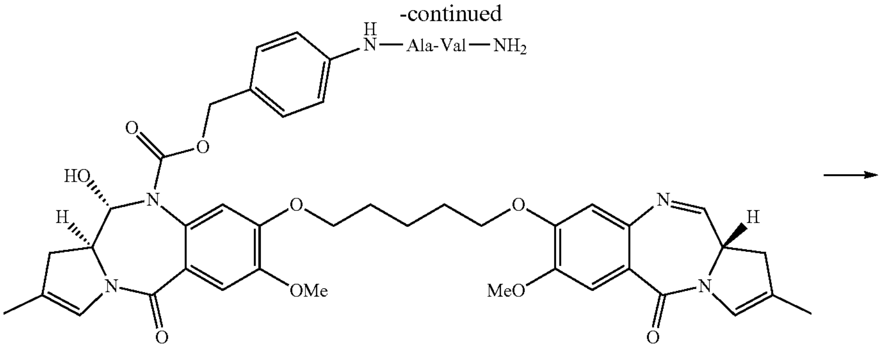

23

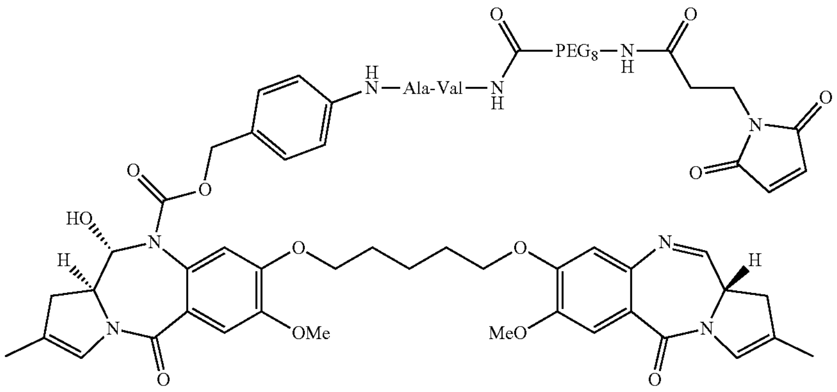

24

(a) (11S)-allyl 8-((5-(((11S)-10-(((4-(2-(1-((1-(allyloxy)-4-methyl-1,2-dioxopentan-3-yl)amino)-1-oxopropan-2-yl)hydrazinyl)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)pentyl)oxy)-11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate (21)

Potassium carbonate (70 mg, 0.504 mmol, 1 eq) was added to a solution of 15 (370 mg, 0.552 mmol, 1.2 eq) and phenol 20 (400 mg, 0.504 mmol) in dry acetone (25 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 21 (385 mg, 57%). LC/MS, 4.07 min (ES+) m/z (relative intensity) 1336.55 ($[M+H]^+$, 50).

(b) (11S)-allyl 8-((5-(((11S)-10-(((4-(2-(1-((1-(allyloxy)-4-methyl-1,2-dioxopentan-3-yl)amino)-1-oxopropan-2-yl)hydrazinyl)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)pentyl)oxy)-11-hydroxy-7-methoxy-2-methyl-5-oxo-11,11a-dihydro-1H-benzo[e]pyrrolo[1,2-a][1,4]diazepine-10(5H)-carboxylate (22)

Tetra-η-butylammonium fluoride (1M, 0.34 mL, 0.34 mmol, 2 eq) was added to a solution of 21 (230 mg, 0.172 mmol) in dry tetrahydrofuran (3 mL). The starting material was totally consumed after 10 minutes. The reaction mixture was diluted with ethyl acetate (30 mL) and washed sequentially with water and brine. The organic phase was dried over magnesium sulphate filtered and excess ethyl acetate removed by rotary evaporation under reduced pressure. The resulting residue 22 was used as a crude mixture for the next reaction. LC/MS, 2.87 min (ES+) m/z (relative intensity) 1108.11 ($[M+H]^+$, 100).

(c) (11S)-4-(2-(1-((1-amino-3-methyl-1-oxobutan-2-yl)amino)-1-oxopropan-2-yl)hydrazinyl)benzyl 11-hydroxy-7-methoxy-8-((5-((7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (23)

Tetrakis(triphenylphosphine)palladium(0) (12 mg, 0.01 mmol, 0.06 eq) was added to a solution of crude 22 (0.172 mmol) and pyrrolidine (36 μL, 0.43 mmol, 2.5 eq) in dry dichloromethane (10 mL). The reaction mixture was stirred 20 minutes and diluted with dichloromethane and washed sequentially with saturated aqueous ammonium chloride and brine. The organic phase was dried over magnesium sulphate filtered and excess dichloromethane removed by rotary evaporation under reduced pressure. The resulting residue 23 was used as a crude mixture for the next reaction. LC/MS, 2.38 min (ES+) m/z (relative intensity) 922.16 ($[M+H]^+$, 40).

(d) (11S,11aS)-4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (24)

1-ethyl-3-(3'-dimethylaminopropyl)carbodiimide (EDCI, 33 mg, 0.172 mmol) was added to a solution of crude 23 (0.172 mmol) and Mal-$(PEG)_8$-acid (100 mg, 0.172 mmol) in dry dichloromethane (10 mL). The reaction was stirred for 2 hours and the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was subjected to flash column chromatography (silica gel; 100% chloroform to 10% methanol in chloroform). Pure fractions were collected and combined and excess eluent was removed by rotary evaporation under reduced pressure to give 24 (B) (60 mg, 25% over 3 steps).

Example 2

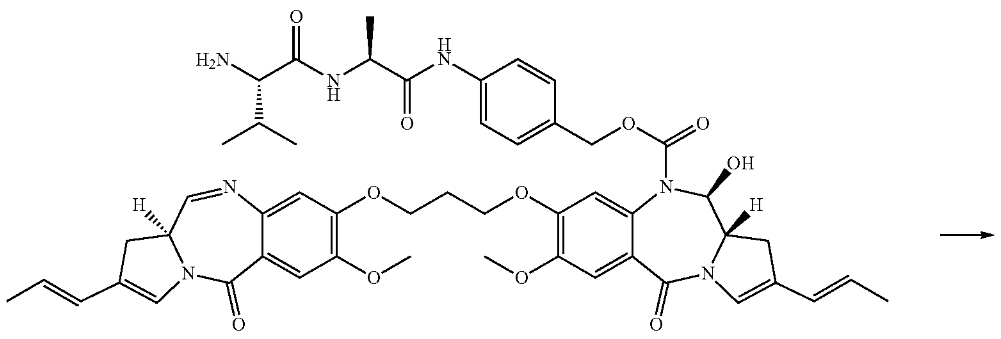

25

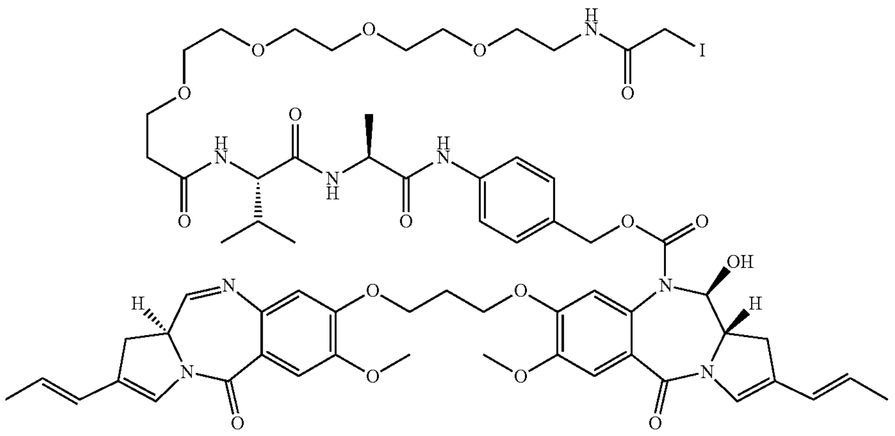

26

Compound 25 is compound 79 of WO 2011/130598

(11S)-4-(1-iodo-20-isopropyl-23-methyl-2,18,21-trioxo-6,9,12,15-tetraoxa-3,19,22-triazatetracosanamido)benzyl 11-hydroxy-7-methoxy-8-(3-((7-methoxy-5-oxo-2-((E)-prop-1-en-1-yl)-5,11a-dihydro-1H-benzo[e]pyrrolo[1,2-a][1,4]diazepin-8-yl)oxy)propoxy)-5-oxo-2-((E)-prop-1-en-1-yl)-11,11a-dihydro-1H-benzo[e]pyrrolo[1,2-a][1,4]diazepine-10(5H)-carboxylate (26)

N,N'-diisopropylcarbodiimide (DIC, 4.71 μL, 0.0304 mmol) was added to a solution of amine 25 (0.0276 mmol) and Iodo-$(PEG)_4$-acid (13.1 mg, 0.0304 mmol) in dry dichloromethane (0.8 mL). The reaction was stirred for 3 hours and the presence of starting material was no longer observed by LC/MS. The reaction mixture was directly loaded onto a thin-layer chromatography (TLC) plate and purified by prep-TLC (10% methanol in chloroform). Pure bands were scraped off the TLC plate, taken up in 10% methanol in chloroform, filtered and excess eluent removed by rotary evaporation under reduced pressure to give 26 (A) (20.9 mg, 56%). LC/MS, method 2, 3.08 min (ES+) m/z (relative intensity) 1361.16 ($[M+H]^+$, 100).

General Experimental Methods for Example 3

LCMS data were obtained using an Agilent 1200 series LC/MS with an Agilent 6110 quadrupole MS, with Electrospray ionisation. Mobile phase A—0.1% Acetic acid in water. Mobile Phase B—0.1% in acetonitrile. Flow rate of 1.00 ml/min. Gradient from 5% B rising up to 95% B over 3 minutes, remaining at 95% B for 1 minute and then back down to 5% B over 6 seconds. The total run time is 5 minutes. Column: Phenomenex Gemini-NX 3 μm C18, 30×2.00 mm. Chromatograms based on UV detection at 254 nm. Mass Spectra were achieved using the MS in positive mode. Proton NMR chemical shift values were measured on the delta scale at 400 MHz using a Bruker AV400. The following abbreviations have been used: s, singlet; d, doublet; t, triplet; q, quartet; m, multiplet; br, broad. Coupling constants are reported in Hz. Unless otherwise stated, column chromatography (by the flash procedure) were performed on Merck Kieselgel silica (Art. 9385). Mass spectroscopy (MS) data were collected using a Waters Micromass LCT instrument coupled to a Waters 2795 HPLC separations module. Thin Layer Chromatography (TLC) was performed on silica gel aluminium plates (Merck 60, $F_{254}$). All other chemicals and solvents were purchased from Sigma-Aldrich or Fisher Scientific and were used as supplied without further purification.

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm

Example 3

(i) Key Intermediates (a)

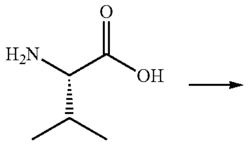

I1

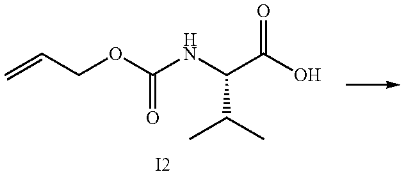

I2

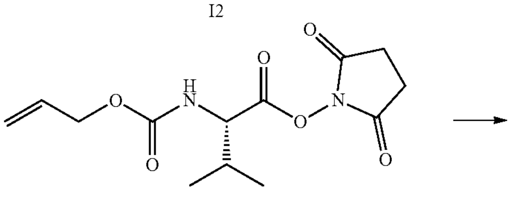

I3

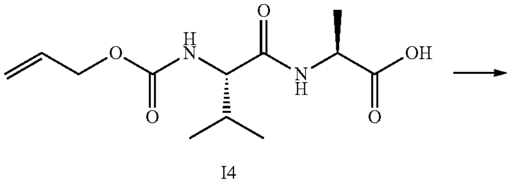

I4

-continued

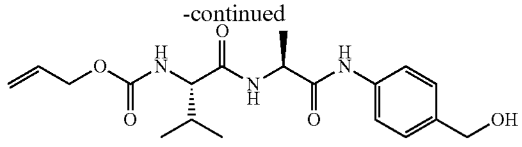

I5

(a-i) (S)-2-(allyloxycarbonylamino)-3-methylbutanoic acid (I2)

Allyl chloroformate (36.2 ml, 340.59 mmol, 1.2 eq) was added dropwise to a stirred solution of L-valine (11)(33.25 g, 283.82 mmol, 1.0 eq) and potassium carbonate (59.27 g, 425.74 mmol, 1.5 eq) in water (650 mL) and THF (650 mL). The reaction mixture was stirred at room temperature for 18 hours, then the solvent was concentrated under reduced pressure and the remaining solution extracted with diethyl ether (3×100 mL). The aqueous portion was acidified to pH 2 with conc. HCl and extracted with DCM (3×100 mL). The combined organics were washed with brine, dried over $MgSO_4$, filtered and concentrated under reduced pressure to afford the product as a colourless oil (57.1 g, assumed 100% yield). LC/MS (1.966 min (ES+)), m/z: 202.1 $[M+H]^+$. $^1H$ NMR (400 MHz, DMSO-$d_6$) δ 12.57 (br s, 1H), 7.43 (d, 1H, J=8.6 Hz), 5.96-5.86 (m, 1H), 5.30 (ddd, 1H, J=17.2, 3.4, 1.7 Hz), 5.18 (ddd, 1H, J=10.4, 2.9, 1.6 Hz), 4.48 (dt, 2H, J=5.3, 1.5 Hz), 3.85 (dd, 1H, J=8.6, 6.0 Hz), 2.03 (oct, 1H, J=6.6 Hz), 0.89 (d, 3H, J=6.4 Hz), 0.87 (d, 3H, J=6.5 Hz).

(a-ii) (S)-2,5-dioxopyrrolidin-1-yl 2-(allyloxycarbonylamino)-3-methylbutanoate (I3)

To a stirred solution of the protected acid 12 (60.6 g, 301.16 mmol, 1.0 eq) and N-hydroxysuccinimide (34.66 g, 301.16 mmol, 1.0 eq) in dry THE (800 mL) was added dicyclohexylcarbodiimide (62.14 g, 301.16 mmol, 1 eq). The reaction was stirred for 18 hours at room temperature. The reaction mixture was then filtered, the solid washed with THE and the combined filtrate was concentrated under reduced pressure. The residue was re-dissolved in DCM and left to stand at 0° C. for 30 minutes. The suspension was filtered and washed with cold DCM. Concentration of the filtrate under reduced pressure afforded the product as a viscous colourless oil (84.7 g, assumed 100% yield) which was used in the next step without further purification. LC/MS (2.194 min (ES+)), m/z: 321.0 $[M+Na]^+$. $^1H$ NMR (400 MHz, DMSO-$d_6$) δ 8.0 (d, 1H, J=8.3 Hz), 5.97-5.87 (m, 1H), 5.30 (ddd, 1H, J=17.2, 3.0, 1.7 Hz), 5.19 (ddd, 1H, J=10.4, 2.7, 1.4 Hz), 4.52 (dt, 2H, J=5.3, 1.4 Hz), 4.32 (dd, 1H, J=8.3, 6.6 Hz), 2.81 (m, 4H), 2.18 (oct, 1H, J=6.7 Hz), 1.00 (d, 6H, J=6.8 Hz), (a-iii) (S)-2-((S)-2-(allyloxycarbonylamino)-3-methylbutanamido)propanoic acid (I4)

A solution of succinimide ester I3 (12.99 g, 43.55 mmol, 1.0 eq) in THE (50 mL) was added to a solution of L-alanine (4.07 g, 45.73 mmol, 1.05 eq) and $NaHCO_3$ (4.02 g, 47.90 mmol, 1.1 eq) in THE (100 mL) and $H_2O$ (100 mL). The mixture was stirred at room temperature for 72 hours when the THF was removed under reduced pressure. The pH was adjusted to 3-4 with citric acid to precipitate a white gum. After extraction with ethyl acetate (6×150 mL), the combined organics were washed with $H_2O$ (200 mL), dried over $MgSO_4$, filtered and concentrated under reduced pressure. Trituration with diethyl ether afforded the product as a white powder which was collected by filtration and washed with diethyl ether (5.78 g, 49%). LC/MS (1.925 min (ES+)), m/z: 273.1 $[M+H]^+$. $^1H$ NMR (400 MHz, DMSO-$d_6$) δ 12.47 (br s, 1H), 8.17 (d, 1H, J=6.8 Hz), 7.16 (d, 1H, J=9.0 Hz), 5.95-5.85 (m, 1H), 5.29 (dd, 1H, J=17.2, 1.7 Hz), 5.17 (dd, 1H, J=10.4, 1.5 Hz), 4.46 (m, 2H), 4.18 (quin, 1H, J=7.2 Hz), 3.87 (dd, 1H, J=9.0, 7.1 Hz), 1.95 (oct, 1H, J=6.8 Hz), 1.26 (d, 3H, J=7.3 Hz), 0.88 (d, 3H, J=6.8 Hz), 0.83 (d, 3H, J=6.8 Hz).

(a-iv) Allyl (S)-1-((S)-1-(4-(hydroxymethyl)phenylamino)-1-oxopropan-2-ylamino)-3-methyl-1-oxobutan-2-ylcarbamate (I5)

EEDQ (5.51 g, 22.29 mmol, 1.05 eq) was added to a solution of p-aminobenzyl alcohol (2.74 g, 22.29 mmol, 1.05 eq) and acid 14 (5.78 g, 21.23 mmol, 1 eq) in dry THE (100 mL). and stirred at room temperature for 72 hours. The reaction mixture was then concentrated under reduced pressure and the resulting brown solid was triturated with diethyl ether and filtered with subsequent washing with an excess of diethyl ether to afford the product as an off-white solid (7.1 g, 88%). LC/MS (1.980 min (ES+)), m/z: 378.0 $[M+H]^+$. $^1H$ NMR (400 MHz, DMSO-$d_6$) δ 9.89 (br s, 1H), 8.13 (d, 1H, J=7.0 Hz), 7.52 (d, 2H, J=8.5 Hz), 7.26 (m, 1H), 7.23 (d, 2H, J=8.5 Hz), 5.91 (m, 1H), 5.30 (m, 1H), 5.17 (m, 1H), 4.46 (m, 2H), 5.09 (t, 1H, J=5.6 Hz), 4.48 (m, 2H), 4.42 (m, 3H), 3.89 (dd, 1H, J=8.6, 6.8 Hz), 1.97 (m, 1H), 1.30 (d, 3H, J=7.1 Hz), 0.88 (d, 3H, J=6.8 Hz), 0.83 (d, 3H, J=6.7 Hz).

(b)

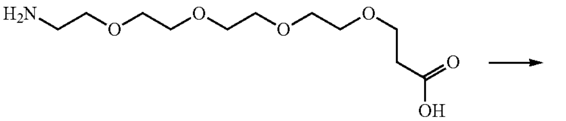

I6

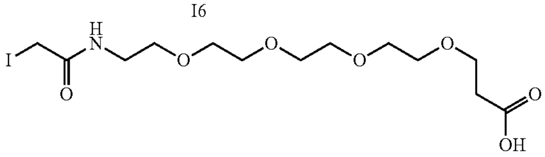

I7

1-iodo-2-oxo-6,9,12,15-tetraoxa-3-azaoctadecan-18-oic acid (I7)

A solution of iodoacetic anhydride (0.250 g, 0.706 mmol, 1.1 eq) in dry DCM (1 mL) was added to amino-$PEG_{(4)}$-acid 16 (0.170 g, 0.642 mmol, 1.0 eq) in DCM (1 mL). The mixture was stirred in the dark at room temperature overnight. The reaction mixture was washed with 0.1 M HCl, water, dried over $MgSO_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as an orange oil (0.118 g, 42%). LC/MS (1.623 min (ES+)), m/z: 433.98 $[M+H]^+$. $^1H$ NMR (400 MHz, $CDCl_3$) δ 8.069 (s, 1H), 7.22 (br s, 1H), 3.79 (t, 2H, J=5.8 Hz), 3.74 (s, 2H), 3.72-3.58 (m, 14H), 3.50-3.46 (m, 2H), 2.62 (t, 2H, J=5.8 Hz).

(ii) (11 S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (34)

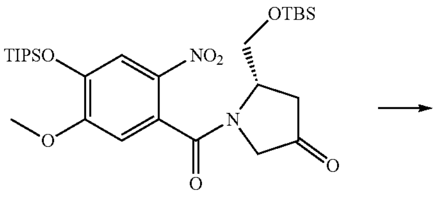

6

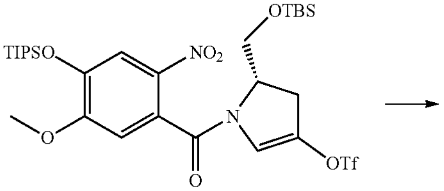

7

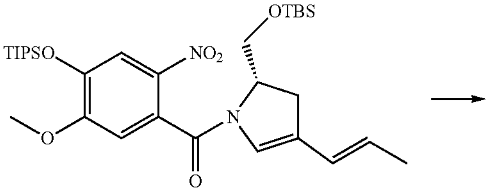

27

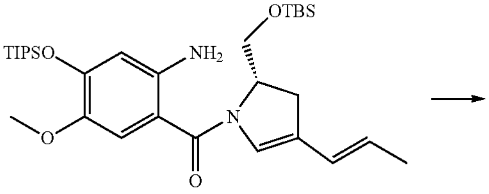

28

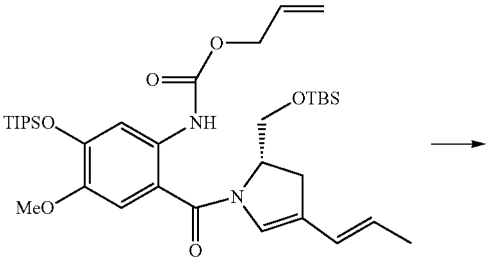

29

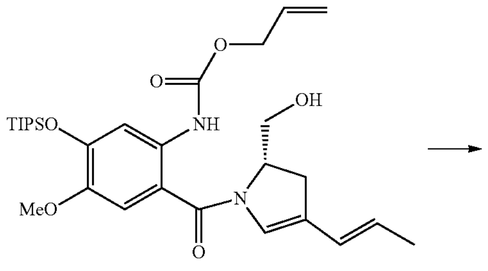

30

-continued

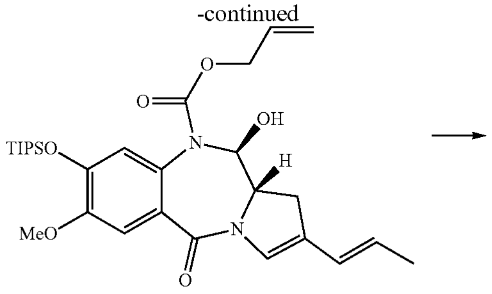

31

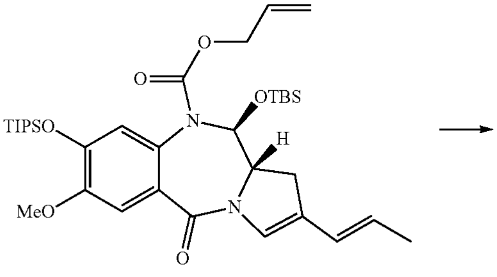

32

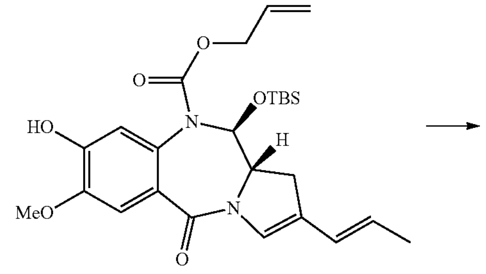

33

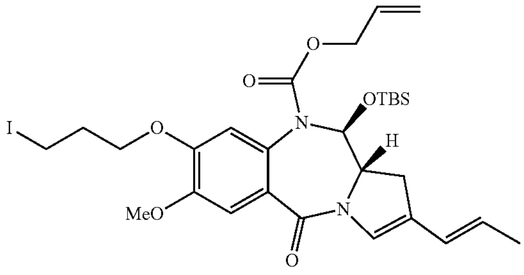

34

(a) (S)-5-((tert-butyldimethylsilyloxy)methyl)-1-(5-methoxy-2-nitro-4-(triisopropylsilyloxy)benzoyl)-4,5-dihydro-1H-pyrrol-3-yl trifluoromethanesulfonate (7)

Triflic anhydride (28.4 g, 100.0 mmol, 3.0 eq) was added dropwise, over 25 mins, to a vigorously stirred solution of the ketone 6 (19.5 g, 30.0 mmol, 1.0 eq) in DCM (550 mL) containing 2,6-lutidine (14.4 g, 130.0 mmol, 4.0 eq) at −50° C. The reaction mixture was stirred for 1.5 hours when LC/MS indicated complete reaction. The organic phase was washed successively with water (100 mL), saturated sodium bicarbonate (150 mL), brine (50 mL), and the organic phase was dried over $MgSO_4$, filtered and concentrated under reduced pressure. The residue was purified by flash chromatography (silica gel, 90/10 v/v n-hexane/EtOAc) to afford the product as a pale yellow oil (19.5 g, 82%). LC/MS (4.391 min (ES+)), m/z: 713.25 $[M+H]^+$. $^1$H NMR (400 MHz, $CDCl_3$) δ 7.68 (s, 1H), 6.72 (s, 1H), 6.02 (t, 1H, J=1.9 Hz), 4.75 (m, 1H), 4.05 (m, 2H), 3.87 (s, 3H), 3.15 (ddd, 1H, J=16.2, 10.3, 2.3 Hz), 2.96 (ddd, 1H, J=16.2, 4.0, 1.6 Hz), 1.28-1.21 (m, 3H), 1.07 (d, 18H, J=7.2 Hz), 0.88 (s, 9H), 0.09 (s, 3H), 0.08 (s, 3H).

(b) (S,E)-(2-((tert-butyldimethylsilyloxy)methyl)-4-(prop-1-enyl)-2,3-dihydro-1H-pyrrol-1-yl)(5-methoxy-2-nitro-4-(triisopropylsilyloxy)phenyl) methanone (27)

Tetrakis(triphenylphosphine)palladium(0) (0.41 g, 0.35 mmol, 0.03 eq) was added to a mixture of the triflate 7 (8.4 g, 11.8 mmol, 1.0 eq), E-1-propene-1-ylboronic acid (1.42 g, 16.5 mmol, 1.4 eq) and potassium phosphate (5.0 g, 23.6 mmol, 2.0 eq) in dry dioxane (60 mL) under a nitrogen atmosphere. The mixture was stirred at 25° C. for 120 mins when LC/MS indicated complete reaction. Ethyl acetate (120 mL) and water (120 mL) were added, the organic phase was removed, washed with brine (20 mL), dried over $MgSO_4$, filtered and concentrated under reduced pressure. The residue was purified by flash chromatography (silica gel, 95/5 v/v n-hexane/EtOAc to 90/10 v/v n-hexane/EtOAc) to afford the product as a yellow foam (4.96 g, 70%). LC/MS (4.477 min (ES+)), m/z: 605.0 $[M+H]^+$. $^1$H NMR (400 MHz, $CDCl_3$) δ 7.67 (s, 1H), 6.74 (s, 1H), 5.93 (d, 1H, J=15.4 Hz), 5.67 (s, 1H), 4.65 (m, 1H), 4.04 (m, 2H), 3.86 (s, 3H), 2.85 (m, 1H), 2.71 (m, 1H), 1.72 (dd, 3H, J=6.8, 1.0 Hz), 1.30-1.22 (m, 3H), 1.07 (d, 18H, J=7.2 Hz), 0.87 (s, 9H), 0.08 (s, 3H), 0.07 (s, 3H).

(c) (S,E)-(2-amino-5-methoxy-4-(triisopropylsilyloxy)phenyl)(2-((tert-butyldimethylsilyloxy)methyl)-4-(prop-1-enyl)-2,3-dihydro-1H-pyrrol-1-yl)methanone (28)

Zinc dust (22.0 g, 0.33 mol, 37 eq) was added, in portions over 20 mins, to a solution of the propenyl intermediate 27 (5.5 g, 9.1 mmol, 1.0 eq) in 5% v/v formic acid/ethanol (55 mL), using an ice bath to maintain the temperature between 25-30° C. After 30 mins, the reaction mixture was filtered through a short bed of Celite®. The Celite® was washed with ethyl acetate (65 mL) and the combined organics were washed successively with water (35 mL), saturated sodium bicarbonate (35 mL) and brine (10 mL). The organic phase was dried over $MgSO_4$, filtered and concentrated under reduced pressure. The residue was purified by flash chromatography (silica gel, 90/10 v/v n-hexane/EtOAc) to afford the product as a pale yellow oil (3.6 g, 69.0%). LC/MS (4.439 min (ES+)), m/z: 575.2 $[M+H]^+$. $^1$H NMR (400 MHz, $CDCl_3$) δ 6.75 (m, 1H), 6.40 (br s, 1H), 6.28 (m, 1H), 6.11 (d, 1H, J=15.4 Hz), 5.53 (m, 1H), 4.67 (m, 1H), 4.36 (m, 2H), 3.93 (br s, 1H), 3.84 (br s, 1H), 3.73 (s, 3H), 2.86 (dd, 1H, J=15.7, 10.4 Hz), 2.73 (dd, 1H, J=15.9, 4.5 Hz), 1.80 (dd, 3H, J=6.8, 1.3 Hz), 1.35-1.23 (m, 3H), 1.12 (d, 18H, J=7.3 Hz), 0.89 (s, 9H), 0.08 (s, 3H), 0.07 (s, 3H).

(d) (S,E)-allyl 2-(2-((tert-butyldimethylsilyloxy)methyl)-4-(prop-1-enyl)-2,3-dihydro-1H-pyrrole-1-carbonyl)-4-methoxy-5-(triisopropylsilyloxy)phenylcarbamate (29)

Allyl chloroformate (0.83 g, 6.88 mmol, 1.1 eq) was added to a solution of the amine 28 (3.6 g, 6.26 mmol, 1.0 eq) in dry DCM (80 mL) containing dry pyridine (1.09 g, 13.77 mmol, 2.2 eq) at −78° C. The dry ice was removed and the reaction mixture allowed to warm to room temperature. After stirring for a further 15 minutes, LC/MS indicated complete reaction. The organic phase was washed successively with 0.01N HCl (50 mL), saturated sodium bicarbonate (50 mL), brine (10 mL), dried over $MgSO_4$, filtered and concentrated under reduced pressure to leave a pale yellow oil which was used in the next step without further purification (4.12 g, assumed 100% yield). LC/MS (4.862 min (ES+)), m/z: 659.2 $[M+H]^+$.

(e) (S,E)-allyl 2-(2-(hydroxymethyl)-4-(prop-1-enyl)-2,3-dihydro-1H-pyrrole-1-carbonyl)-4-methoxy-5-(triisopropylsilyloxy)phenylcarbamate (30)

The crude intermediate 29 (assumed 100% yield, 4.12 g, 6.25 mmol, 1.0 eq) was dissolved in a mixture of acetic acid (70 mL), methanol (10 mL), THE (10 mL) and water (20 mL) and allowed to stir at room temperature. After 6 hours the reaction mixture was diluted with ethyl acetate (500 mL) and washed successively with water (2×500 mL), saturated sodium bicarbonate (300 mL) and brine (50 mL). The organic phase was dried over $MgSO_4$, filtered and concentrated under reduced pressure. The residue was purified by flash chromatography (silica gel, 1/99 v/v methanol/DCM to 5/95 v/v methanol/DCM) to afford the product as a yellow oil and a further 1 g of unreacted starting material was recovered. This material was subjected to the same reaction conditions as above, but was left stirring for 16 h. After work up and purification, additional product was isolated (2.7 g, 79%, 2 steps) LC/MS (3.742 min (ES+)), m/z: 545.2 $[M+H]^+$. $^1$H NMR (400 MHz, $CDCl_3$) δ 8.38 (m, 1H), 7.72 (m, 1H), 6.81 (s, 1H), 6.37 (m, 1H), 6.10 (d, 1H, J=15.8 Hz), 5.97 (m, 1H), 5.53 (m, 1H), 5.36 (ddd, 1H, J=17.2, 3.1, 1.5 Hz), 5.25 (ddd, 1H, J=10.4, 2.5, 1.3 Hz), 4.78 (m, 1H), 4.65 (dt, 2H, J=5.7, 1.3 Hz), 3.84 (m, 3H), 3.79 (s, 3H), 3.04 (dd, 1H, J=16.7, 10.5 Hz), 2.40 (dd, 1H, J=16.0, 4.5 Hz), 1.82 (dd, 3H, J=6.8, 1.0 Hz), 1.36-1.26 (m, 3H), 1.14 (d, 18H, J=7.3 Hz).

(f) (11S,11aS)-allyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (31)

Dry dimethyl sulfoxide (1.16 g, 14.87 mmol, 3.0 eq) was added dropwise to a solution of oxalyl chloride (0.94 g, 7.43 mmol, 1.5 eq) in DCM (25 mL) at −78° C. under an atmosphere of nitrogen. Maintaining the temperature at −78° C., after 10 mins a solution of the primary alcohol 30 (2.7 g, 4.96 mmol, 1.0 eq) in DCM (20 mL) was added dropwise. After a further 15 mins, dry triethylamine (2.5 g, 24.78 mmol, 5.0 eq) was added, and the reaction mixture allowed to warm to room temperature. The reaction mixture was washed successively with cold 0.1N HCl (50 mL), saturated sodium hydrogen carbonate (50 mL) and brine (10 mL) and the organic layer was dried over $MgSO_4$, filtered and concentrated under reduced pressure to afford the product as a yellow oil which was used in the next step without further purification (2.68 g, assumed 100% yield). LC/MS (3.548 min (ES+)), m/z: 543.2 $[M+H]^+$.

(g) (11S,11aS)-allyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (32)

Tert-butyldimethylsilyltrifluoromethane sulfonate (3.93 g, 14.87 mmol, 3.0 eq) was added to a solution of the carbinolamine 31 (assumed 100% yield, 2.68 g, 4.96 mmol, 1.0 eq) and 2,6-lutidine (2.12 g, 19.83 mmol, 4.0 eq) in dry DCM (40 mL) at 0° C. under an atmosphere of nitrogen. After 10 minutes, the reaction mixture was allowed to warm to room temperature and stirred for a further 60 minutes. The organic phase was washed successively with water (10 mL), saturated sodium bicarbonate (10 mL) and brine (5 mL), dried over $MgSO_4$, filtered and concentrated under reduced pressure. The residue was purified by flash chromatography (silica gel, chloroform to 2/98 v/v Methanol/chloroform) to afford the product as a yellow oil (2.0 g, 63%, 2 steps). LC/MS (4.748 min (ES+)), m/z: 657.2 $[M+H]^+$. $^1H$ NMR (400 MHz, $CDCl_3$) δ 7.19 (s, 1H), 6.86 (m, 1H), 6.66 (s, 1H), 6.22 (d, 1H, J=15.4 Hz), 5.81 (d, 1H, J=8.8 Hz), 5.78 (m, 1H), 5.48 (m, 1H), 5.11 (d, 1H, J=5.0 Hz), 5.08 (m, 1H), 4.58 (dd, 1H, J=13.4, 5.4 Hz), 4.35 (dd, 1H, J=13.2, 5.7 Hz), 3.83 (s, 3H), 3.76 (s, 1H), 3.00 (dd, 1H, J=15.6, 11.0 Hz), 2.53 (m, 1H), 1.81 (dd, 3H, J=6.8, 0.9 Hz), 1.30-1.18 (m, 3H), 1.08 (d, 9H, J=2.3 Hz), 1.06 (d, 9H, J=2.3 Hz), 0.86 (s, 9H), 0.25 (s, 3H), 0.18 (s, 3H).

(h) (11 S,11aS)-allyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (33)

Lithium acetate dihydrate (0.31 g, 3.04 mmol, 1.0 eq) was added to a solution of the diazepine 32 (2.0 g, 3.04 mmol, 1.0 eq) in wet DMF (20 mL) at 25° C. and stirred for 4 hours. The reaction mixture was diluted with ethyl acetate (200 mL) and washed successively with 0.1 M citric acid (50 mL, pH 3), water (50 mL) and brine (10 mL), dried over $MgSO_4$, filtered and concentrated under reduced pressure. The residue was purified by flash chromatography (silica gel, 50/50 v/v n-hexane/EtOAc to 25/75 v/v n-hexane/EtOAc) to afford the product as a pale yellow solid (0.68 g, 45%). LC/MS (3.352 min (ES+)), m/z: 501.1 $[M+H]^+$. $^1H$ NMR (400 MHz, $CDCl_3$) δ 7.02 (s, 1H), 6.66 (m, 1H), 6.53 (s, 1H), 6.03 (d, 1H, J=15.5 Hz), 5.80 (s, 1H), 5.63 (d, 1H, J=8.9 Hz), 5.55 (m, 1H), 5.29 (m, 1H), 4.87 (m, 2H), 4.39 (dd, 1H, J=13.5, 4.2 Hz), 4.20 (dd, 1H, J=13.2, 5.7 Hz), 3.73 (s, 3H), 3.59 (m, 1H), 2.81 (dd, 1H, J=16.1, 10.5 Hz), 2.35 (d, 1H, J=15.7 Hz), 1.61 (d, 3H, J=6.4 Hz), 0.67 (s, 9H), 0.05 (s, 3H), 0.00 (s, 3H).

(i) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (34)

Diiodopropane (0.295 g, 1.00 mmol, 5.0 eq) and potassium carbonate (0.028 g, 0.20 mmol, 1.0 eq) were added to a solution of the phenol 33 (0.100 g, 0.020 mmol, 1.0 eq) in dry acetone (5 mL). The reaction mixture was heated at 60° C. for 6 hours when LC/MS showed complete reaction. The reaction mixture was concentrated to dryness under reduced pressure and the residue was purified by flash chromatography (silica gel, 75/25 v/v n-hexane/EtOAc to 50/50 v/v n-hexane/EtOAc) to afford the product as a colourless oil (0.074 g, 56%). LC/MS (3.853 min (ES+)), m/z: 669.0 $[M+H]^+$. $^1H$ NMR (400 MHz, $CDCl_3$) δ 7.26 (s, 1H), 6.90 (s, 1H), 6.68 (s, 1H), 6.24 (d, 1H, J=15.3 Hz), 5.87 (d, 1H, J=8.9 Hz), 5.78 (m, 1H), 5.53 (m, 1H), 5.12 (m, 2H), 4.65 (m, 2H), 4.41 (m, 1H), 4.11 (m, 1H), 3.93 (s, 3H), 3.81 (m, 1H), 3.40 (t, 2H, J=6.7 Hz), 3.05 (dd, 1H, J=16.3, 10.1 Hz), 2.57 (m, 1H), 2.34 (m, 2H), 1.84 (d, 3H, J=6.6 Hz), 0.92 (s, 9H), 0.28 (s, 3H), 0.26 (s, 3H).

(iii) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (39)

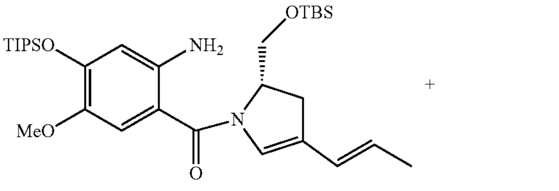

28

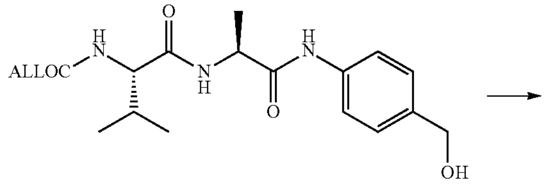

I5

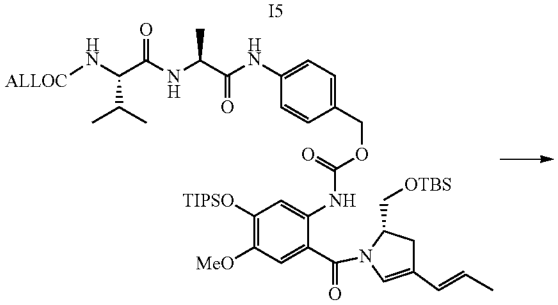

35

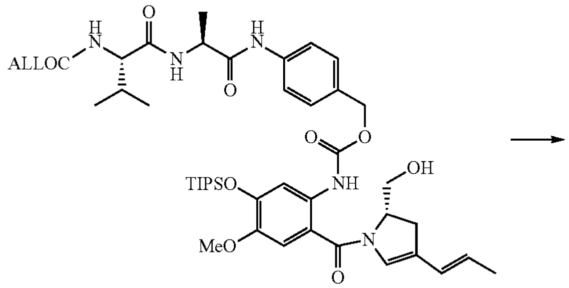

36

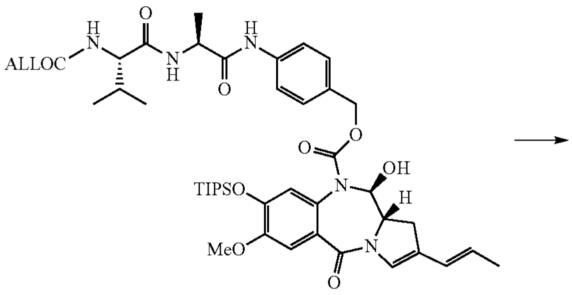

37

-continued

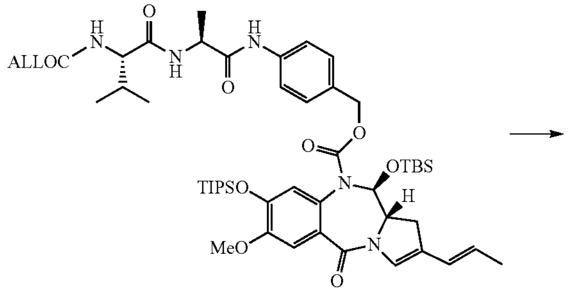

38

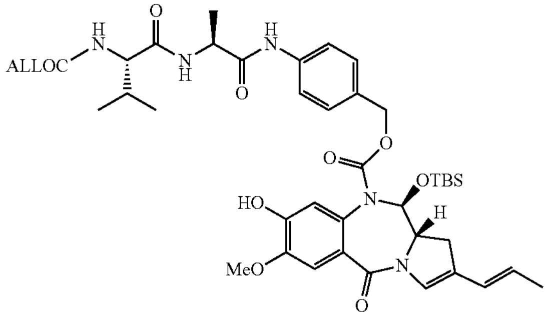

39

(a) Allyl ((S)-1-(((S)-1-((4-((((2-((S)-2-(((tert-butyldimethylsilyl)oxy)methyl)-4-((E)-prop-1-en-1-yl)-2,3-dihydro-1H-pyrrole-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl)carbamate (35)

Triethylamine (0.256 mL, 1.84 mmol, 2.2 eq) was added to a stirred solution of the amine 28 (0.480 g, 0.835 mmol, 1.0 eq) and triphosgene (0.089 g, 0.301 mmol, 0.36 eq) in dry THE (15 mL) at 5° C. (ice bath). The progress of the isocyanate reaction was monitored by periodically removing aliquots from the reaction mixture and quenching with methanol and performing LCMS analysis. Once the isocyanate reaction was complete a solution of Alloc-Val-Ala-PABOH 15 (0.473 g, 1.25 mmol, 1.5 eq) and triethylamine (0.174 mL, 1.25 mmol, 1.5 eq) in dry THE (10 mL) was rapidly added by injection to the freshly prepared isocyanate. The reaction was allowed to stir at 40° C. for 4 hours followed by stirring at room temperature overnight. The mixture was concentrated under reduced pressure, and purified by flash chromatography (silica gel, 20/80 v/v n-hexane/EtOAc to 50/50 v/v n-hexane/EtOAc, then 1/99 v/v DCM/MeOH to 5/95 v/v DCM/MeOH) to afford the product as a yellow solid (0.579 g, 71%). LC/MS (4.468 min (ES+)), m/z: 978.55 $[M+H]^+$. $^1H$ NMR (400 MHz, $CDCl_3$) δ 8.63 (br s, 1H), 8.42 (s, 1H), 7.78 (br s, 1H), 7.53 (d, 2H, J=8.1 Hz), 7.31 (d, 2H, J=8.6 Hz), 6.76 (s, 1H), 6.59 (d, 1H, J=7.6 Hz), 6.36 (br s, 1H), 6.04 (d, 1H, J=15.9 Hz), 5.90 (m, 1H), 5.55 (m, 1H), 5.33-5.21 (m, 3H), 5.10 (s, 2H), 4.66 (m, 2H), 4.57 (dd, 2H, J=5.6, 1.0 Hz), 3.98 (dd, 1H, J=7.3, 6.8 Hz), 3.90 (m, 1H), 3.81 (m, 1H), 3.78 (s, 3H), 2.82 (dd, 1H, J=15.4, 9.6 Hz), 2.72 (dd, 1H, J=15.9, 3.5 Hz), 2.17 (m, 1H), 1.78 (dd, 3H, J=6.5, 0.8 Hz), 1.46 (d, 3H, J=7.1 Hz), 1.29 (m, 3H), 1.11 (d, 18H, J=7.1 Hz), 0.97 (d, 3H, J=6.8 Hz), 0.92 (d, 3H, J=6.8 Hz), 0.83 (s, 9H), 0.04 (s, 3H), 0.01 (s, 3H).

(b) Allyl ((S)-1-(((S)-1-((4-((((2-((S)-2-(hydroxymethyl)-4-((E)-prop-1-en-1-yl)-2,3-dihydro-1H-pyrrole-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl)carbamate (36)

The silyl ether 35 (1.49 g, 1.52 mmol, 1.0 eq) was dissolved in a 7:1:1:2 mixture of acetic acid/methanol/tetrahydrofuran/water (14:2:2:4 mL) and allowed to stir at room temperature. After 2 hours the reaction was diluted with EtOAc (100 mL), washed sequentially with water, aq. sodium bicarbonate then brine. The organic phase was then dried over $MgSO_4$, filtered and concentrated under reduced pressure. The residue was purified by flash chromatography (silica gel, 100/0 then 99/1 to 92/8 v/v DCM/MeOH) to afford the product as an orange solid (1.2 g, 92%). LC/MS (3.649 min (ES+)), m/z: 865.44 $[M+H]^+$. $^1H$ NMR (400 MHz, $CDCl_3$) δ 8.44 (s, 1H), 8.35 (s, 1H), 7.69 (br s, 1H), 7.53 (d, 2H, J=8.7 Hz), 7.32 (d, 2H, J=8.3 Hz), 6.78 (s, 1H), 6.56 (m, 2H), 6.32 (br s, 1H), 6.05 (d, 1H, J=14.9 Hz), 5.90 (m, 1H), 5.56 (m, 1H), 5.30 (m, 2H), 5.22 (m, 1H), 5.10 (d, 2H, J=3.1 Hz), 4.73 (m, 1H), 4.64 (m, 1H), 4.57 (d, 2H, J=5.8 Hz), 4.01 (m, 1H), 3.79 (m, 2H), 3.76 (s, 3H), 2.98 (dd, 1H, J=16.3, 10.2 Hz), 2.38 (dd, 1H, J=16.6, 4.1 Hz), 2.16 (m, 1H), 1.78 (dd, 3H, J=6.8, 0.9 Hz), 1.46 (d, 3H, J=7.1 Hz), 1.29 (m, 3H), 1.11 (d, 18H, J=7.4 Hz), 0.97 (d, 3H, J=6.7 Hz), 0.92 (d, 3H, J=6.8 Hz).

(c) (11S,11aS)-4-((S)-2-((S)-2-(allyloxycarbonylamino)-3-methylbutanamido)propanamido)benzyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (37)

Dry dimethyl sulfoxide (0.180 g, 2.3 mmol, 3.0 eq) was added dropwise to a solution of oxalyl chloride (0.147 g, 1.1 mmol, 1.5 eq) in DCM (10 mL) at −78° C. under an atmosphere of nitrogen. Maintaining the temperature at −78° C., after 20 minutes, a solution of the primary alcohol 36 (0.666 g, 0.77 mmol, 1.0 eq) in DCM (10 mL) was added dropwise. After a further 15 minutes, dry triethylamine (0.390 g, 3.85 mmol, 5.0 eq) was added, and the reaction mixture allowed to warm to room temperature. The reaction mixture was washed successively with cold 0.1 N HCl (10 mL), saturated sodium hydrogen carbonate (10 mL) and brine (5 mL). The organic layer was then dried over $MgSO_4$, filtered and concentrated under reduced pressure. The residue was then purified by flash chromatography (silica gel, 50/50 v/v n-hexane/EtOAc to 25/75 v/v n-hexane/EtOAc) to afford the product as a white solid (0.356 g, 54%). LC/MS (3.487 min (ES+)), m/z: 862.2 $[M+H]^+$. $^1H$ NMR (400 MHz, $CDCl_3$) b 8.34 (br s, 1H), 7.47 (d, 2H, J=7.6 Hz), 7.17 (s, 1H), 7.14 (d, 2H, J=7.5 Hz), 6.86 (br s, 1H), 6.65 (br s, 1H), 6.42 (d, 1H, J=7.6 Hz), 6.22 (d, 1H, J=14.4 Hz), 5.80 (m, 1H), 5.40 (m, 1H), 5.53 (m, 1H), 5.32 (m, 1H), 5.21 (d, 2H, J=9.6 Hz), 5.06 (d, 1H, J=12.3 Hz), 4.90 (m, 1H), 4.58 (m, 3H), 3.98 (m, 1H), 3.84 (m, 1H), 3.81 (s, 3H), 3.50 (m, 1H), 3.05 (dd, 1H, J=16.0, 10.3 Hz), 2.76 (m, 1H), 2.15 (m, 1H), 1.80 (dd, 3H, J=6.7, 0.8 Hz), 1.44 (d, 3H, J=7.1 Hz), 1.16 (m, 3H), 1.01 (d, 18H, J=6.6 Hz), 0.96 (d, 3H, J=6.8 Hz), 0.92 (d, 3H, J=6.8 Hz).

(d) (11S,11aS)-4-((S)-2-((S)-2-(allyloxycarbonylamino)-3-methylbutanamido)propanamido)benzyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (38)

Tert-butyldimethylsilyltrifluoromethane sulfonate (0.46 g, 1.74 mmol, 3.0 eq) was added to a solution of secondary alcohol 37 (0.5 g, 0.58 mmol, 1.0 eq) and 2,6-lutidine (0.25 g, 2.32 mmol, 4.0 eq) in dry DCM (10 mL) at 0° C. under an atmosphere of nitrogen. After 10 minutes, the reaction mixture was allowed to warm to room temperature and stirred for a further 120 mins. The organic phase was then washed successively with water (10 mL), saturated sodium bicarbonate (10 mL) and brine (5 mL), dried over $MgSO_4$, filtered and concentrated under reduced pressure. The residue was purified by flash chromatography (silica gel, 50/50 v/v n-hexane/EtOAc) to afford the product as a white solid (0.320 g, 57%). LC/MS (4.415 min (ES+)), m/z: 976.52 $[M+H]^+$. $^1$H NMR (400 MHz, $CDCl_3$) δ 8.31 (br s, 1H), 7.48 (d, 2H, J=8.0 Hz), 7.21 (s, 1H), 7.14 (d, 2H, J=8.3 Hz), 6.89 (s, 1H), 6.65 (s, 1H), 6.38 (d, 1H, J=7.3 Hz), 6.25 (d, 1H, J=14.6 Hz), 5.93 (m, 1H), 5.85 (d, 1H, J=8.8 Hz), 5.50 (m, 1H), 5.34 (m, 1H), 5.24 (m, 2H), 5.15 (d, 1H, J=12.5 Hz), 4.86 (d, 1H, J=12.2 Hz), 4.62 (m, 3H), 4.01 (m, 1H), 3.86 (s, 3H), 3.78 (m, 1H), 3.04 (m, 1H), 2.56 (m, 1H), 2.20 (m, 1H), 1.84 (dd, 3H, J=6.6, 0.7 Hz), 1.48 (d, 3H, J=6.8 Hz), 1.20 (m, 3H), 1.05 (d, 9H, J=2.9 Hz), 1.03 (d, 9H, J=2.9 Hz), 0.99 (d, 3H, J=6.8 Hz), 0.95 (d, 3H, J=6.8 Hz), 0.88 (s, 9H), 0.27 (s, 3H), 0.14 (s, 3H).

(e) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (39)

Lithium acetate dihydrate (0.010 g, 0.10 mmol, 1.0 eq) was added to a solution of the silyl ether 38 (0.100 g, 0.10 mmol, 1.0 eq) in wet DMF (2 mL) at 25° C. for 3 hours. The reaction mixture was then diluted with ethyl acetate (20 mL) and washed successively with 0.1 M citric acid (20 mL, pH 3), water (20 mL) and brine (5 mL), dried over $MgSO_4$, filtered and concentrated under reduced pressure. The residue was purified by flash chromatography (silica gel, 5/95 v/v methanol/DCM) to afford the product as a pale yellow oil (0.070 g, 83%). LC/MS (3.362 min (ES+)), m/z: 820.2 $[M+H]^+$. $^1$H NMR (400 MHz, $CDCl_3$) δ 8.39 (s, 1H), 7.48 (d, 2H, J=8.2 Hz), 7.25 (s, 1H), 7.12 (d, 2H, J=8.1 Hz), 6.88 (s, 1H), 6.68 (s, 1H), 6.47 (d, 1H, J=7.6 Hz), 6.24 (d, 1H, J=15.2 Hz), 6.03 (s, 1H), 5.92 (m, 1H), 5.84 (d, 1H, J=8.9 Hz), 5.50 (m, 1H), 5.34 (m, 1H), 5.26 (m, 2H), 5.18 (d, 1H, J=12.3 Hz), 4.80 (d, 1H, J=12.4 Hz), 4.66-4.60 (m, 3H), 4.02 (m, 1H), 3.95 (s, 3H), 3.81 (m, 1H), 3.03 (m, 1H), 2.57 (m, 1H), 2.19 (m, 1H), 1.84 (dd, 3H, J=6.8, 0.8 Hz), 1.48 (d, 3H, J=7.1 Hz), 1.00 (d, 3H, J=6.8 Hz), 0.95 (d, 3H, J=6.8 Hz), 0.87 (s, 9H), 0.26 (s, 3H), 0.12 (s, 3H).

(iv) (11S,11aS)-4-((20S,23S)-1-iodo-20-isopropyl-23-methyl-2,18,21-trioxo-6,9,12,15-tetraoxa-3,19,22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (26, A)

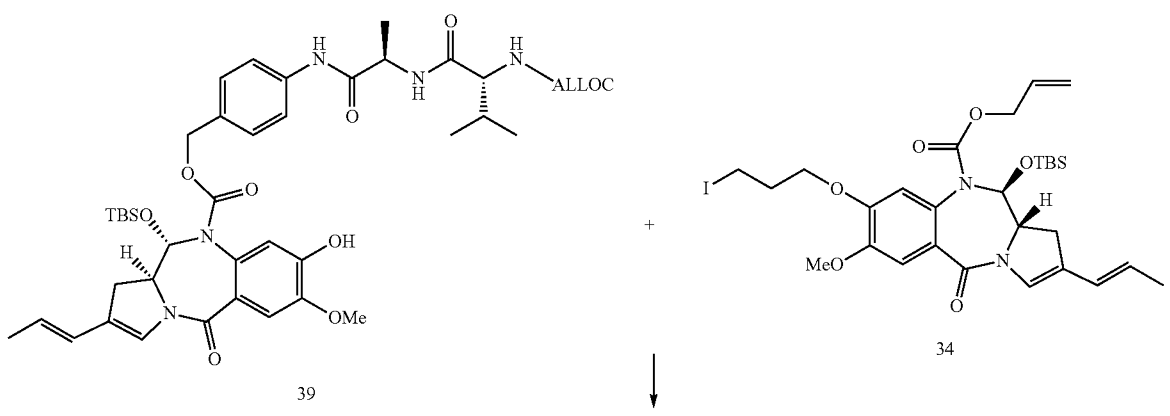

39 + 34

-continued
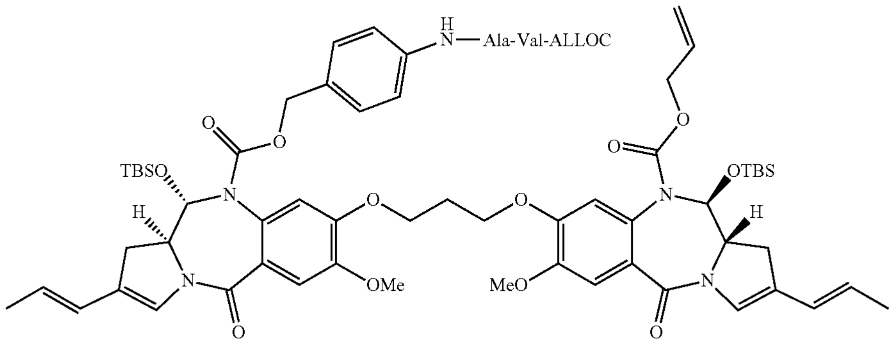
40
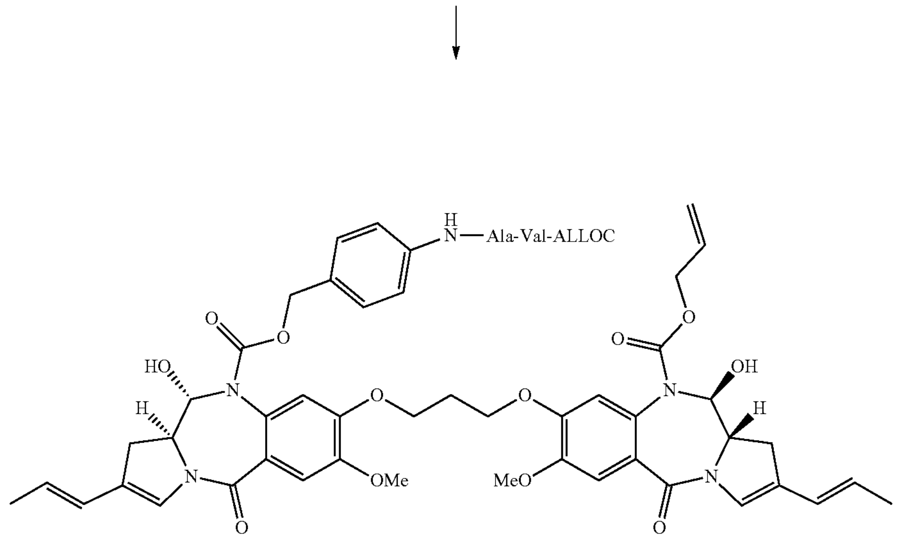
41
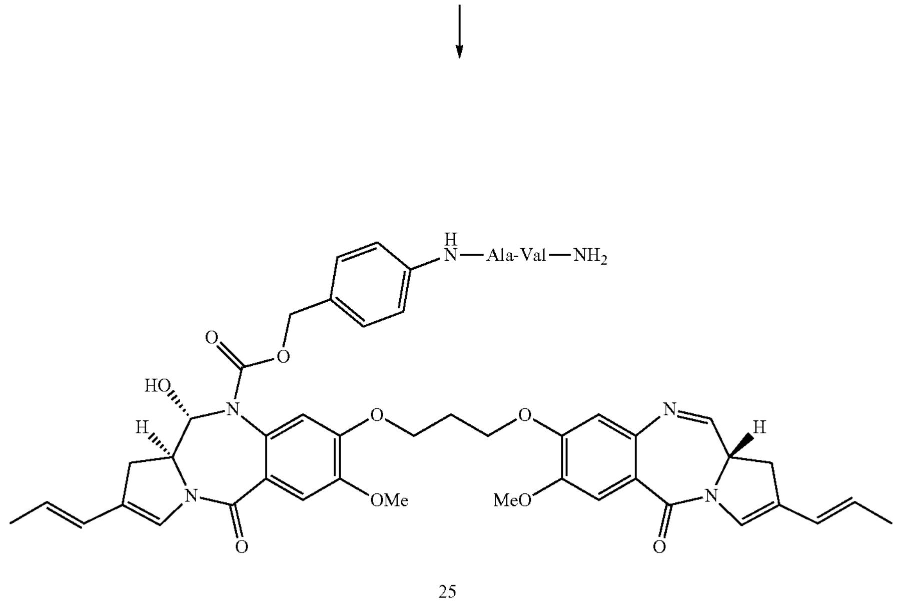
25

-continued

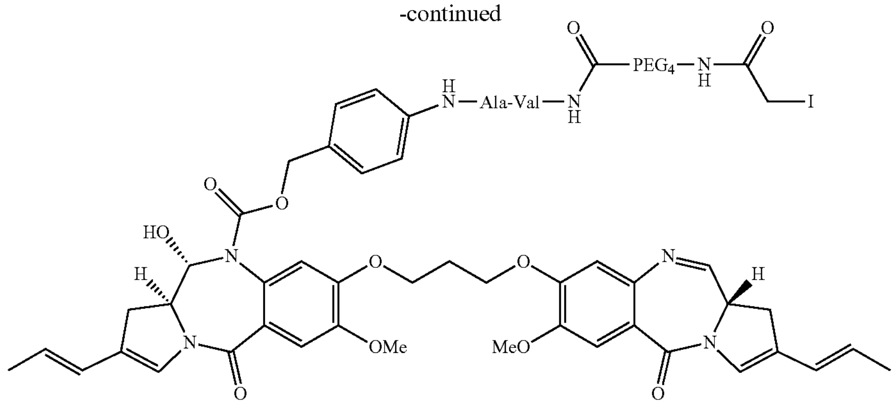

26

(a) (11S,11aS)-allyl 8-(3-((11S,11aS)-10-((4-((R)-2-((R)-2-(allyloxycarbonylamino)-3-methylbutanamido)propanamido)benzyloxy)carbonyl)-11-(tert-butyldimethylsilyloxy)-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-(tert-butyldimethylsilyloxy)-7-methoxy-5-oxo-2-((E)-prop-1-enyl)-11,11a-dihydro-1H-benzo[e]pyrrolo[1,2-a][1,4]diazepine-10(5H)-carboxylate (40)

Potassium carbonate (0.030 g, 0.21 mmol, 1.0 eq) was added to a solution of the phenol 39 (0.175 g, 0.21 mmol, 1.0 eq) and the iodo linker 34 (0.214 g, 0.32 mmol, 1.5 eq) in acetone (10 mL). The reaction mixture was heated under a nitrogen atmosphere at 75° C. in a sealed flask for 17 hours. The reaction mixture was concentrated to dryness under reduced pressure and purified by flash chromatography (silica gel, 2/98 v/v methanol/DCM to 5/95 v/v methanol/DCM) to afford the product as a pale yellow solid (0.100 g, 35%). LC/MS (4.293 min (ES+)), m/z: 1359.13 $[M]^+$.

(b) (11S,11aS)-allyl 8-(3-((11S,11aS)-10-((4-((R)-2-((R)-2-(allyloxycarbonylamino)-3-methylbutanamido)propanamido)benzyloxy)carbonyl)-11-hydroxy-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-hydroxy-7-methoxy-5-oxo-2-((E)-prop-1-enyl)-11,11a-dihydro-1H-benzo[e]pyrrolo[1,2-a][1,4]diazepine-10(5H)-carboxylate (41)

Tetra-n-butylammonium fluoride (1M, 0.22 mL, 0.22 mmol, 2.0 eq) was added to a solution of silyl ether 40 (0.150 g, 0.11 mmol, 1.0 eq) in dry THE (2 mL). The reaction mixture was stirred at room temperature for 20 minutes, after which LC/MS indicated complete reaction. The reaction mixture was diluted with ethyl acetate (10 mL) and washed sequentially with water (5 mL) and brine (5 mL). The organic phase was dried over $MgSO_4$, filtered and concentrated under reduced pressure to leave a yellow solid. Purification by flash chromatography (silica gel, 6/94 v/v methanol/DCM to 10/90 v/v methanol/DCM) afforded the product as a pale yellow solid (0.090 g, 73%). LC/MS (2.947 min (ES+)), m/z: 1154.0 $[M+Na]^+$. $^1H$ NMR (400 MHz, $CDCl_3$) δ 8.39 (br s, 1H), 7.39 (d, 2H, J=7.6 Hz), 7.18 (d, 2H, J=10.6 Hz), 7.10 (m, 3H), 6.86 (d, 2H, J=10.0 Hz), 6.74 (s, 1H), 6.55 (s, 1H), 6.22 (dd, 2H, J=15.3, 6.6 Hz), 5.85 (m, 2H), 5.74 (m, 3H), 5.52 (m, 2H), 5.22 (m, 1H), 5.00 (m, 2H), 4.57 (m, 6H), 4.41 (m, 2H), 4.09 (m, 4H), 3.85 (m, 11H), 3.06 (m, 2H), 2.76 (m, 2H), 2.20 (m, 2H), 2.08 (m, 1H), 1.79 (d, 6H, J=6.4 Hz), 1.40 (d, 3H, J=6.1 Hz), 0.90 (m, 6H).

(c) (11S,11aS)-4-((R)-2-((R)-2-amino-3-methylbutanamido)propanamido)benzyl 11-hydroxy-7-methoxy-8-(3-((S)-7-methoxy-5-oxo-2-((E)-prop-1-enyl)-5, 11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (25)

Tetrakis(triphenylphospene)palladium(0) (0.005 g, 0.005 mmol, 0.06 eq) was added to a solution of the bis-carbinolamine 41 (0.090 g, 0.08 mmol, 1.0 eq) and pyrrolidine (16 μL, 0.20 mmol, 2.5 eq) in dry DCM (5 mL). After 20 minutes, the reaction mixture was diluted with DCM (10 mL) and washed sequentially with saturated ammonium chloride (5 mL) and brine (5 mL), dried over $MgSO_4$, filtered and the solvent was removed under reduced pressure to leave the crude product as a pale yellow solid which was used in the next step without further purification (0.075 g, assumed 100% yield). LC/MS (2.060 min (ES+)), m/z: 947.2 $[M+H]^+$.

(d) (11S,11aS)-4-((20S,23S)-1-iodo-20-isopropyl-23-methyl-2,18,21-trioxo-6,9,12,15-tetraoxa-3,19,22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (26, A)

EDCI (0.015 g, 0.08 mmol, 1.0 eq) was added to a solution of amine 25 (assumed 100% yield 0.075 g, 0.08 mmol, 1.0 eq) and iodoacetamide-$PEG_4$-acid 17 (0.034 g, 0.08 mmol, 1.0 eq) in dry dichloromethane (5 mL) and the reaction was stirred in the dark. After 50 minutes, a further amount of iodoacetamide-$PEG_4$-acid 17 (0.007 g, 0.016 mmol, 0.2 eq) was added along with a further amount of EDCI (0.003 g, 0.016 mmol, 0.2 eq). After a total of 2.5 hours, the reaction mixture was diluted with dichloromethane (15 mL) and washed sequentially with water (10 mL) and brine (10 mL). The organic phase was dried over $MgSO_4$, filtered and concentrated under reduced pressure. The resulting residue was purified by flash chromatography (silica gel, Chloroform 100% to 90:10 v/v Chloroform: Methanol). Pure fractions were combined to afford the product (0.0254 g, 23%, 2 steps). The crude fractions were collected and purified by preparative TLC (silica gel, 90:10 v/v Chloroform:Methanol) to afford a second batch of product (0.0036 g, 3%, 2 steps). LC/MS (2.689 min (ES+)), m/z: 681.0 1/2$[M+2H]^+$.

Example 4: Activity of Released Compounds

K562 Assay

K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Compound RelB has an $IC_{50}$ of 0.425 nM in this assay.

Example 5

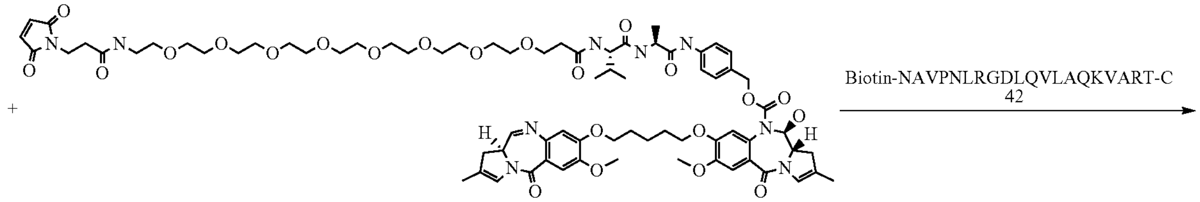

24

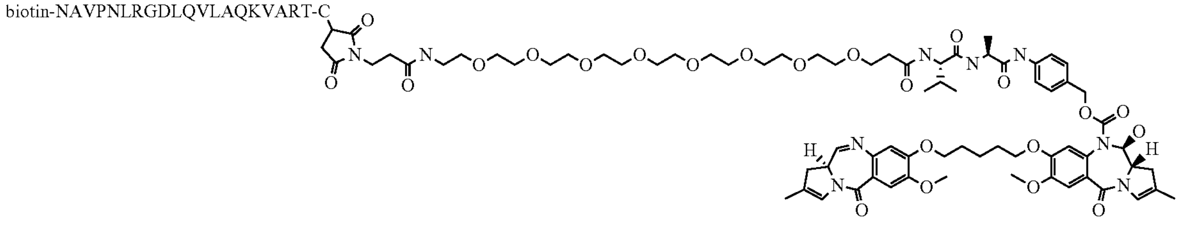

43

Biotin-A20FMDV-Cys-2 (43)

A solution of the peptide 42 (12.06 mg, 4.8 μmol, 1.0 eq) in 1/1 acetonitrile/water (1 mL) was added to a solution of 24 (12.06 mg, 4.8 μmol, 1.0 eq) in 1/1 acetonitrile/water (1 mL). The solution was stirred at room temperature for 24 hours. The acetonitrile/water was removed by lyophilisation to give a yellow foam. Purification by preparative HPLC followed by lyophilisation gave the product as a white foam (7.4 mg, 38%)

Preparative HPLC method: Reverse-phase ultra-high-performance liquid chromatography (UPLC) was carried out on Phenomenex Gemini NX 5μ C-18 columns of the following dimensions: 150×4.6 mm for analysis, and 150×21.20 mm for preparative work. All UPLC experiments were performed with gradient conditions: initial fixed composition 13% B to 75% B over 15 min, held for 2.0 min at 75% B, then 75% B to 13% B within 0.10 min held at 13% for 2.90 min. Total duration of gradient run was 20.00 min. Eluents used were solvent A ($H_2O$ with 0.1% Formic acid) and solvent B ($CH_3CN$ with 0.1% Formic acid). Flow rates used were 1.0 ml/min for analytical, and 20.0 ml/min for preparative HPLC. Detection was at 254 and 280 nm.

Analytical Data: LCMS 1.17 min (ES+) m/z (relative intensity) 1330 ($[M+2]^+/3$, 5%); 998 ($[M+3]^+/4$, 70); 798 ($[M+4]^+/5$, 100); 665 ($[M+5]^+/6$, 20).

Example 6: Formation of Conjugates

General Antibody Conjugation Procedure

Antibodies are diluted to 1-5 mg/mL in a reduction buffer (examples: phosphate buffered saline PBS, histidine buffer, sodium borate buffer, TRIS buffer). A freshly prepared solution of TCEP (tris(2-carboxyethyl)phosphine hydrochloride) is added to selectively reduce cysteine disulfide bridges. The amount of TCEP is proportional to the target level of reduction, within 1 to 4 molar equivalents per antibody, generating 2 to 8 reactive thiols. After reduction for several hours at 37° C., the mixture is cooled down to room temperature and excess drug-linker (A, B) added as a diluted DMSO solution (final DMSO content of up to 10% volume/volume of reaction mixture). The mixture is gently shaken at either 4° C. or room temperature for the appropriate time, generally 1-3 hours for compound B and 10-30 hours for compound A. Excess reactive thiols can be reacted with a 'thiol capping reagent' like N-ethyl maleimide (NEM) at the end of the conjugation. Antibody-drug conjugates are concentrated using centrifugal spin-filters with a molecular weight cut-off of 10 kDa or higher, then purified by tangential flow filtration (TFF) or Fast Protein Liquid Chromatography (FPLC). Corresponding antibody-drug conjugates can be determined by analysis by High-Performance Liquid Chromatography (HPLC) or Ultra-High-Performance Liquid Chromatography (UHPLC) to assess drug-per-antibody ratio (DAR) using reverse-phase chromatography (RP) or Hydrophobic-Interaction Chromatography (HIC), coupled with UV-Visible, Fluorescence or Mass-Spectrometer detection; aggregate level and monomer purity can be analysed by HPLC or UHPLC using size-exclusion chromatography coupled with UV-Visible, Fluorescence or Mass-Spectrometer detection. Final conjugate concentration is determined by a combination of spectroscopic (absorbance at 280, 214 and 330 nm) and biochemical assay (bicinchonic acid assay BCA; Smith, P. K., et al. (1985) *Anal. Biochem.* 150 (1): 76-85; using a known-concentration IgG antibody as reference). Antibody-drug conjugates are generally sterile filtered using 0.2 m filters under aseptic conditions, and stored at +4° C., −20° C. or −80° C.

Examples of particular conjugations are described below.

ADC1A

Antibody 1 (15 mg, 102 nanomoles) is diluted into 12.0 mL of a reduction buffer containing 10 mM sodium borate pH 8.4, 2.5 mM EDTA and a final antibody concentration of 1.25 mg/mL. A 10 mM solution of TCEP is added (2 molar equivalent/antibody, 204 nanomoles, 20 μL) and the reduction mixture is heated at 37° C. for two hour in an orbital incubator. After cooling down to room temperature, compound A is added as a DMSO solution (5 molar equivalent/antibody, 510 nanomoles, in 1.2 mL DMSO). The solution is mixed 18 hour at room temperature, then transferred into a 15 mL Amicon Ultracell 50 kDa MWCO spin filter, concentrated to ca. 2.0 mL and injected into a AKTA™FPLC using a GE Healthcare XK16/70 column packed with Superdex 200 PG, eluting with 1.5 mL/min of sterile-filtered Phosphate-buffered saline (PBS). Fractions corresponding to the desired ADC monomer peak are pooled, analysed and sterile-filtered. BCA assay gives a concentration of final ADC1A at 0.67 mg/mL in 12.5 mL, and the obtained mass is 8.4 mg (56% yield). HPLC analysis on a Waters Alliance system using a Agilent PLRP-S 1000 A 8 um 150×2.1 mm column eluting with a gradient of water and acetonitrile on a reduced sample of ADC1A at 280 nm shows a mixture of light and heavy chains attached to several molecules of A, consistent with a drug-per-antibody ratio (DAR) of 2.2 molecules of A per antibody. SEC analysis on an AKTA™FPLC using a GE Healthcare XK16/70 column packed with Superdex 200 PG, eluting with sterile-filtered Phosphate-buffered saline (PBS) on a sample of ADC1A at 280 nm shows a monomer purity of 95.3% with 4.7% aggregates.

ADC1B

Antibody 1 (15 mg, 102 nanomoles) is diluted into 12.0 mL of a reduction buffer containing 10 mM sodium borate pH 8.4, 2.5 mM EDTA and a final antibody concentration of 1.25 mg/mL. A 10 mM solution of TCEP is added (2 molar equivalent/antibody, 204 nanomoles, 20 μL) and the reduction mixture was heated at 37° C. for two hour in an orbital incubator. After cooling down to room temperature, Compound B is added as a DMSO solution (5 molar equivalent/antibody, 510 nanomoles, in 1.2 mL DMSO). The solution is mixed 5 hour at room temperature, then a second amount of Compound B is added as a DMSO solution (2 molar equivalent/antibody, 200 nanomoles, in 0.6 mL DMSO). The solution is mixed 15 hour at room temperature, then transferred into a 15 mL Amicon Ultracell 50 kDa MWCO spin filter, concentrated to ca. 2.0 mL and injected into an AKTA™FPLC using a GE Healthcare XK16/70 column packed with Superdex 200 PG, eluting with 1.5 mL/min of sterile-filtered Phosphate-buffered saline (PBS). Fractions corresponding to ADC1B monomer peak are pooled, analysed and sterile-filtered. BCA assay gives a concentration of final ADC1B at 1.02 mg/mL in 10.5 mL, and the obtained mass is 10.7 mg (71% yield). HPLC analysis on a Waters Alliance system using a Agilent PLRP-S 1000 A 8 um 150×2.1 mm column eluting with a gradient of water and acetonitrile on a reduced sample of ADC1B at 280 nm and 330 nm (drug-linker specific) shows a mixture of light and heavy chains attached to several molecules of B, consistent with a drug-per-antibody ratio (DAR) of 2.2 molecules of B per antibody. SEC analysis on a AKTA™FPLC using a GE Healthcare XK16/70 column packed with Superdex 200 PG, eluting with sterile-filtered Phosphate-buffered saline (PBS)

on a sample of ADC1B at 280 nm shows a monomer purity of 94.9% with 5.1% aggregates.

Example 7: In Vivo ADC Efficacy Studies

CB.17 SCID mice, aged 8-12 weeks, are injected with 1 $mm^3$ tumour fragments sub cutaneously in the flank. When tumours reach an average size of 100-150 $mm^3$, treatment is begun. Mice are weighed twice a week. Tumour size is measured twice a week. Animals are monitored individually. The endpoint of the experiment is a tumour volume of 1000 $mm^3$ or 60 days, whichever comes first. Responders can be followed longer.

Groups of 10 xenografted mice are injected i.v. with 0.2 ml of antibody drug conjugate (ADC), or naked antibody, in phosphate buffered saline (vehicle) or with 0.2 ml of vehicle alone. The concentration of ADC is adjusted to give, for example, 0.3 or 1.0 mg ADC/kg body weight in a single dose. Three identical doses may be given to each mouse at intervals of, for example, 1 week.

All documents and other references mentioned above are herein incorporated by reference.

ABBREVIATIONS

Ac acetyl
Acm acetamidomethyl
Alloc allyloxycarbonyl
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N-10 imine protecting group: 3-(2-methoxyethoxy)propanoate-Val-Ala-PAB
MC-OSu maleimidocaproyl-O—N-succinimide
Moc methoxycarbonyl
MP maleimidopropanamide
Mtr 4-methoxy-2,3,6-trimethtylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichlorethoxycarbonyl chloride
Trt trityl
Xan xanthyl

What is claimed is:

1. A method of treating cancer comprising administering to the patient a conjugate having the following formula:

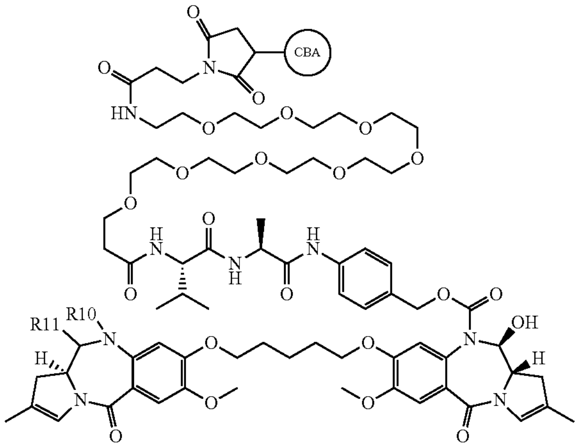

where $R^{10}$ and $R^{11}$ either (a) form a double bond between the carbon and nitrogen atoms to which they are bound; or (b) are H and $OR^A$ respectively, where RA is selected from H and C1-4 alkyl;

where CBA is a cell binding agent.

2. The method of claim 1, wherein the conjugate has the formula:

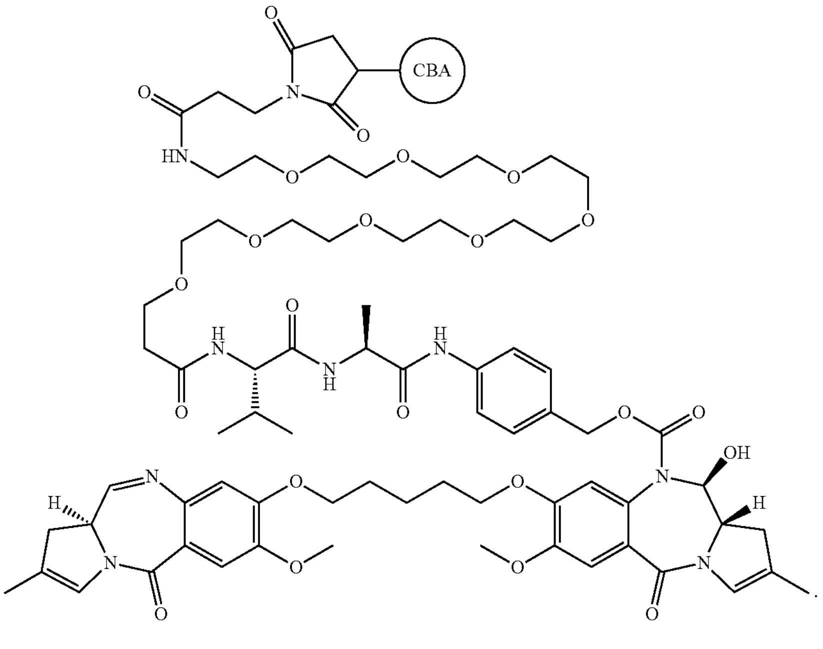

3. The method of claim 1, wherein CBA is a peptide.

4. The method of claim 3, wherein CBA is a linear or cyclic peptide comprising 4-30 contiguous amino acid residues.

5. The method of claim 4, wherein the linear or cyclic peptide comprises 6-20 contiguous amino acid residues.

6. The method of claim 1, wherein CBA is an antibody or an active fragment thereof.

7. The method of claim 6, wherein the antibody or antibody fragment is an antibody which binds to one or more tumor-associated antigens or cell-surface receptors selected from (1)-(88):

(1) BMPR1B;

(2) E16;

(3) STEAP1;

(4) 0772P;

(5) MPF;

(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA-FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30-TNFRSF8;
(51) BCMA-TNFRSF17;
(52) CT Ags-CTA;
(53) CD174 (Lewis Y)—FUT3;
(54) CLEC14A;
(55) GRP78-HSPA5;
(56) CD70;
(57) Stem Cell specific antigens;
(58) ASG-5;
(59) ENPP3;
(60) PRR4;
(61) GCC-GUCY2C;
(62) Liv-1-SLC39A6;
(63) 5T4;
(64) CD56-NCMA1;
(65) CanAg;
(66) FOLR1;
(67) GPNMB;
(68) TIM-1-HAVCR1;
(69) RG-1/Prostate tumor target Mindin-Mindin/RG-1;
(70) B7-H4-VTCN1;
(71) PTK7;
(72) CD37;
(73) CD138-SDC1;
(74) CD74;
(75) Claudins-CLs;
(76) EGFR;
(77) Her3;
(78) RON-MST1R;
(79) EPHA2;
(80) CD20-MS4A1;
(81) Tenascin C-TNC;
(82) FAP;
(83) DKK-1;
(84) CD52;
(85) CS1-SLAMF7;
(86) Endoglin-ENG;
(87) Annexin A1-ANXA1;
(88) V-CAM (CD106)-VCAM1.

8. The method of claim 1, wherein the cell binding agent is Biotin-A20DMDV-Cys-2.

9. The method of claim 1, wherein the cell binding agent has the sequence

```
                                         (SEQ ID NO: 15)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS.
```

10. The method of claim 1, wherein the cell binding agent has the sequence

```
                                         (SEQ ID NO: 16)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK.
```

11. The method of claim 2, wherein the patient is administered a chemotherapeutic agent, in combination with the conjugate.

12. The method of claim 2, wherein the cancer is carcinoma, lymphoma, blastoma, sarcoma, leukemia or lymphoid malignancies.

13. The method of claim 12, wherein the cancer is lymphoma.

14. The method of claim 12, wherein the cancer is squamous cell cancer, lung cancer, non-small cell lung cancer, adenocarcinoma of the lung, squamous carcinoma of the lung, cancer of the peritoneum, hepatocellular cancer, gastric cancer, stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma or head and neck cancer.

15. The method of claim 14, wherein the cancer is breast cancer.

16. A conjugate having the following formula:
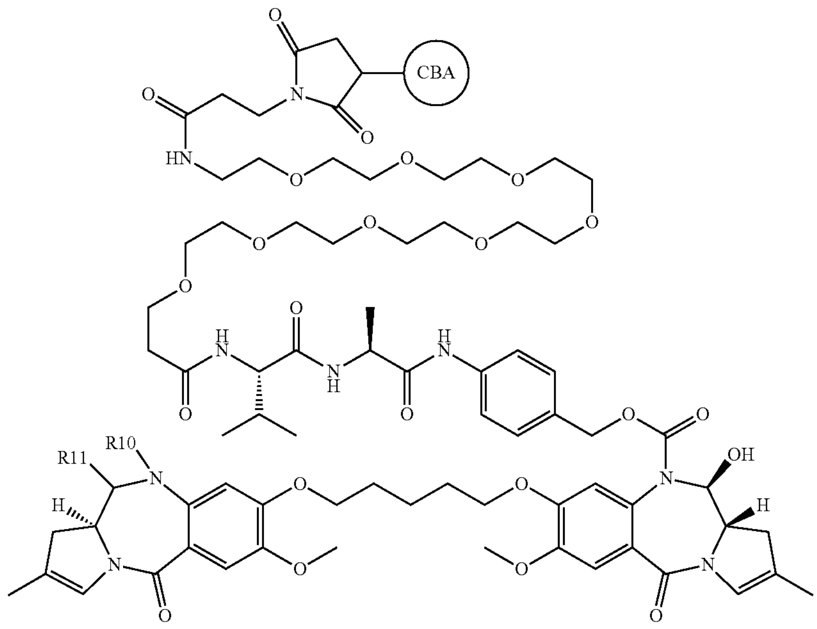
where $R^{10}$ and $R^{11}$ either
(a) form a double bond between the carbon and nitrogen atoms to which they are bound; or
(b) are H and $OR^A$ respectively, where $R^A$ is selected from H and C1-4 alkyl;
wherein CBA is a linear or cyclic peptide comprising 4-30 contiguous amino acid residues.
* * * * *

SEQUENCE LISTING

```
Sequence total quantity: 233
SEQ ID NO: 1          moltype = AA  length = 21
FEATURE               Location/Qualifiers
REGION                1..21
                      note = Synthetic sequence: A20FMDV-Cys polypeptide
source                1..21
                      mol_type = protein
                      organism = synthetic construct
SEQUENCE: 1
NAVPNLRGDL QVLAQKVART C                                            21

SEQ ID NO: 2          moltype = AA  length = 21
FEATURE               Location/Qualifiers
REGION                1..21
                      note = Synthetic sequence: A20FMDV-Cys polypeptide
VARIANT               4..18
                      note = Xaa is any amino acid residue
source                1..21
                      mol_type = protein
                      organism = synthetic construct
SEQUENCE: 2
NAVXXXXXXX XXXXXXXXRT C                                            21

SEQ ID NO: 3          moltype = AA  length = 137
FEATURE               Location/Qualifiers
REGION                1..137
                      note = Synthetic sequence: Anti-Integrin Alpha v Beta 6,
                       RHAB6.2
source                1..137
                      mol_type = protein
                      organism = synthetic construct
SEQUENCE: 3
QVQLVQSGSE LKKPGASVKI SCKASGFAFT DSYMHWVRQA PGQGLEWMGW IDPENGDTEY  60
APKFQGRFVF SLDTSVSTAY LQISSLKAED TAVYYCTRGT PTAVPNLRGD LQVLAQKVAG  120
PYPFDYWGQG TLVTVSS                                                 137

SEQ ID NO: 4          moltype = AA  length = 137
FEATURE               Location/Qualifiers
REGION                1..137
                      note = Synthetic sequence: Anti-Integrin Alpha v Beta 6,
                       RHCB6.2
source                1..137
```

-continued

```
                      mol_type = protein
                      organism = synthetic construct
SEQUENCE: 4
QVQLVQSGAE VKKPGASVKV SCKASGYTFI DSYMHWVRQA PGQRLEWMGW IDPENGDTEY  60
APKFQGRVTI TTDTSASTAY MELSSLRSED TAVYYCARGT PTAVPNLRGD LQVLAQKVAG  120
PYPFDYWGQG TLVTVSS                                                 137

SEQ ID NO: 5          moltype = AA  length = 120
FEATURE               Location/Qualifiers
REGION                1..120
                      note = Synthetic sequence: Anti-Integrin Alpha v Beta 6, RHF
source                1..120
                      mol_type = protein
                      organism = synthetic construct
SEQUENCE: 5
QVQLVQSGAE VKKPGASVKV SCKASGFNFI DSYMHWVRQA PGQRLEWMGW IDPENGDTEY  60
APKFQGRVTF TTDTSASTAY MELSSLRSED TAVYYCNEGT PTGPYYFDYW GQGTLVTVSS  120

SEQ ID NO: 6          moltype = AA  length = 137
FEATURE               Location/Qualifiers
REGION                1..137
                      note = Synthetic sequence: Anti-Integrin Alpha v Beta 6,
                       RHFB6
source                1..137
                      mol_type = protein
                      organism = synthetic construct
SEQUENCE: 6
QVQLVQSGAE VKKPGASVKV SCKASGFNFI DSYMHWVRQA PGQRLEWMGW IDPENGDTEY  60
APKFQGRVTF TTDTSASTAY MELSSLRSED TAVYYCNEGT PTAVPNLRGD LQVLAQKVAG  120
PYYFDYWGQG TLVTVSS                                                 137

SEQ ID NO: 7          moltype = AA  length = 120
FEATURE               Location/Qualifiers
REGION                1..120
                      note = Synthetic sequence: Anti-Integrin Alpha v Beta 6,
                       RHAY100bP
source                1..120
                      mol_type = protein
                      organism = synthetic construct
SEQUENCE: 7
QVQLVQSGSE LKKPGASVKI SCKASGFAFT DSYMHWVRQA PGQGLEWMGW IDPENGDTEY  60
APKFQGRFVF SLDTSVSTAY LQISSLKAED TAVYYCTRGT PTGPYPFDYW GQGTLVTVSS  120

SEQ ID NO: 8          moltype = AA  length = 106
FEATURE               Location/Qualifiers
REGION                1..106
                      note = Synthetic sequence: Anti-Integrin Alpha v Beta 6, RKF
source                1..106
                      mol_type = protein
                      organism = synthetic construct
SEQUENCE: 8
ENVLTQSPGT LSLSPGERAT LSCSASSSVS YMHWFQQKPG QAPRLLIYST SNLASGIPDR  60
FSGSGSGTDF TLTISRLEPE DFAVYYCQQR SSYPLTFGGG TKVEIK                 106

SEQ ID NO: 9          moltype = AA  length = 106
FEATURE               Location/Qualifiers
REGION                1..106
                      note = Synthetic sequence: Anti-Integrin Alpha v Beta 6,
                       RKFL36L50
source                1..106
                      mol_type = protein
                      organism = synthetic construct
SEQUENCE: 9
ENVLTQSPGT LSLSPGERAT LSCSASSSVS YMHWLQQKPG QAPRLLIYLT SNLASGIPDR  60
FSGSGSGTDF TLTISRLEPE DFAVYYCQQR SSYPLTFGGG TKVEIK                 106

SEQ ID NO: 10         moltype = AA  length = 106
FEATURE               Location/Qualifiers
REGION                1..106
                      note = Synthetic sequence: Anti-Integrin Alpha v Beta 6, RKC
source                1..106
                      mol_type = protein
                      organism = synthetic construct
SEQUENCE: 10
EIVLTQSPGT LSLSPGERAT LSCSASSSVS YMHWFQQKPG QAPRLLIYST SNLASGIPDR  60
FSGSGSGTDF TLTISRLEPE DFAVYYCQQR SSYPLTFGGG TKVEIK                 106

SEQ ID NO: 11         moltype = AA  length = 116
FEATURE               Location/Qualifiers
```

-continued

```
REGION                  1..116
                        note = Synthetic sequence: Anti-CD33, CD33 Hum195 VH
source                  1..116
                        mol_type = protein
                        organism = synthetic construct
SEQUENCE: 11
QVQLVQSGAE VKKPGSSVKV SCKASGYTFT DYNMHWVRQA PGQGLEWIGY IYPYNGGTGY  60
NQKFKSKATI TADESTNTAY MELSSLRSED TAVYYCARGR PAMDYWGQGT LVTVSS      116

SEQ ID NO: 12           moltype = AA  length = 111
FEATURE                 Location/Qualifiers
REGION                  1..111
                        note = Synthetic sequence: Anti-CD33, CD33 Hum195 VK
source                  1..111
                        mol_type = protein
                        organism = synthetic construct
SEQUENCE: 12
DIQMTQSPSS LSASVGDRVT ITCRASESVD NYGISFMNWF QQKPGKAPKL LIYAASNQGS  60
GVPSRFSGSG SGTDFTLTIS SLQPDDFATY YCQQSKEVPW TFGQGTKVEI K           111

SEQ ID NO: 13           moltype = AA  length = 120
FEATURE                 Location/Qualifiers
REGION                  1..120
                        note = Synthetic sequence: Anti-CD19, CD19 B4 resurfaced VH
source                  1..120
                        mol_type = protein
                        organism = synthetic construct
SEQUENCE: 13
QVQLVQPGAE VVKPGASVKL SCKTSGYTFT SNWMHWVKQR PGQGLEWIGE IDPSDSYTNY  60
NQNFKGKAKL TVDKSTSTAY MEVSSLRSDD TAVYYCARGS NPYYYAMDYW GQGTSVTVSS  120

SEQ ID NO: 14           moltype = AA  length = 104
FEATURE                 Location/Qualifiers
REGION                  1..104
                        note = Synthetic sequence: Anti-CD19, CD19 B4 resurfaced VK
source                  1..104
                        mol_type = protein
                        organism = synthetic construct
SEQUENCE: 14
EIVLTQSPAI MSASPGERVT MTCSASSGVN YMHWYQQKPG TSPRRWIYDT SKLASGVPAR  60
FSGSGSGTSY SLTISSMEPE DAATYYCHQR GSYTFGGGTK LEIK                  104

SEQ ID NO: 15           moltype = AA  length = 120
FEATURE                 Location/Qualifiers
REGION                  1..120
                        note = Synthetic sequence: Anti - Her2, Herceptin VH chain
source                  1..120
                        mol_type = protein
                        organism = synthetic construct
SEQUENCE: 15
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120

SEQ ID NO: 16           moltype = AA  length = 107
FEATURE                 Location/Qualifiers
REGION                  1..107
                        note = Synthetic sequence: Anti - Her2, Herceptin VL chain
source                  1..107
                        mol_type = protein
                        organism = synthetic construct
SEQUENCE: 16
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIK               107

SEQ ID NO: 17           moltype = AA  length = 104
FEATURE                 Location/Qualifiers
REGION                  1..104
                        note = Synthetic sequence: Anti-CD25, Simulect VK (also
                         known as Basiliximab)
source                  1..104
                        mol_type = protein
                        organism = synthetic construct
SEQUENCE: 17
QIVSTQSPAI MSASPGEKVT MTCSASSSRS YMQWYQQKPG TSPKRWIYDT SKLASGVPAR  60
FSGSGSGTSY SLTISSMEAE DAATYYCHQR SSYTFGGGTK LEIK                  104

SEQ ID NO: 18           moltype = AA  length = 115
FEATURE                 Location/Qualifiers
REGION                  1..115
```

```
                      note = Synthetic sequence: Anti-CD25, Simulect VH
source                1..115
                      mol_type = protein
                      organism = synthetic construct
SEQUENCE: 18
QLQQSGTVLA RPGASVKMSC KASGYSFTRY WMHWIKQRPG QGLEWIGAIY PGNSDTSYNQ  60
KFEGKAKLTA VTSASTAYME LSSLTHEDSA VYYCSRDYGY YFDFWGQGTT LTVSS       115

SEQ ID NO: 19         moltype = AA  length = 115
FEATURE               Location/Qualifiers
REGION                1..115
                      note = Synthetic sequence: Anti-PSMA, Deimmunised VH '1
source                1..115
                      mol_type = protein
                      organism = synthetic construct
SEQUENCE: 19
EVQLVQSGPE VKKPGATVKI SCKTSGYTFT EYTIHWVKQA PGKGLEWIGN INPNNGGTTY  60
NQKFEDKATL TVDKSTDTAY MELSSLRSED TAVYYCAAGW NFDYWGQGTL LTVSS       115

SEQ ID NO: 20         moltype = AA  length = 107
FEATURE               Location/Qualifiers
REGION                1..107
                      note = Synthetic sequence: Anti-PSMA, Deimmunised VK '1
source                1..107
                      mol_type = protein
                      organism = synthetic construct
SEQUENCE: 20
DIQMTQSPSS LSTSVGDRVT LTCKASQDVG TAVDWYQQKP GPSPKLLIYW ASTRHTGIPS  60
RFSGSGSGTD FTLTISSLQP EDFADYYCQQ YNSYPLTFGP GTKVDIK               107

SEQ ID NO: 21         moltype = AA  length = 116
FEATURE               Location/Qualifiers
REGION                1..116
                      note = Synthetic sequence: Anti-PSMA, Deimmunised VH1 '5
source                1..116
                      mol_type = protein
                      organism = synthetic construct
SEQUENCE: 21
EVKLVESGGG LVQPGGSMKL SCVASGFTFS NYWMNWVRQA PGKGLEWVAE IRSQSNNFAT  60
HYAESVKGRV TISRDDSKSI VYLQMNNLRA EDTGVYYCTR RWNNFWGQGT TVTVSS      116

SEQ ID NO: 22         moltype = AA  length = 116
FEATURE               Location/Qualifiers
REGION                1..116
                      note = Synthetic sequence: Anti-PSMA, Deimmunised VH2 '5
source                1..116
                      mol_type = protein
                      organism = synthetic construct
SEQUENCE: 22
EVKLVESGGG LVQPGGSLKL SCVASGFTFS NYWMNWVRQA PGKGLEWVAE IRSQSNNFAT  60
HYAESVKGRV TISRDDSKSI VYLQMNNLRA EDTAVYYCTR RWNNFWGQGT TVTVSS      116

SEQ ID NO: 23         moltype = AA  length = 116
FEATURE               Location/Qualifiers
REGION                1..116
                      note = Synthetic sequence: Anti-PSMA, Deimmunised VH3 '5
source                1..116
                      mol_type = protein
                      organism = synthetic construct
SEQUENCE: 23
EVQLVESGGG LVQPGGSLKL SCVASGFTFS NYWMNWVRQA PGKGLEWVAE IRSQSNNFAT  60
HYAESVKGRV TISRDDSKSI VYLQMNNLRA EDTAVYYCTR RWNNFWGQGT TVTVSS      116

SEQ ID NO: 24         moltype = AA  length = 116
FEATURE               Location/Qualifiers
REGION                1..116
                      note = Synthetic sequence: Anti-PSMA, Deimmunised VH4 '5
source                1..116
                      mol_type = protein
                      organism = synthetic construct
SEQUENCE: 24
EVQLVESGGG LVQPGGSLKL SCVASGFTFS NYWMNWVRQA PGKGLEWVAE IRSQSNNFAT  60
HYAESVKGRF TISRDDSKSI VYLQMNNLRA EDTAVYYCTR RWNNFWGQGT TVTVSS      116

SEQ ID NO: 25         moltype = AA  length = 107
FEATURE               Location/Qualifiers
REGION                1..107
                      note = Synthetic sequence: Anti-PSMA, Deimmunised VK1 '5
source                1..107
```

-continued

```
                        mol_type = protein
                        organism = synthetic construct
SEQUENCE: 25
NIVMTQFPSS MSASVGDRVT ITCKASENVG TYVSWYQQKP DQSPKMLIYG ASNRFTGVPD  60
RFTGSGSATD FTLTISSLQT EDLADYYCGQ SYTFPYTFGQ GTKLEMK                107

SEQ ID NO: 26           moltype = AA  length = 107
FEATURE                 Location/Qualifiers
REGION                  1..107
                        note = Synthetic sequence: Anti-PSMA, Deimmunised VK2 '5
source                  1..107
                        mol_type = protein
                        organism = synthetic construct
SEQUENCE: 26
NIVMTQFPSS MSASVGDRVT ITCKASENVG TYVSWYQQKP DQSPKMLIYG ASNRFTGVPD  60
RFSGSGSGTD FTLTISSLQA EDLADYYCGQ SYTFPYTFGQ GTKLEIK                107

SEQ ID NO: 27           moltype = AA  length = 107
FEATURE                 Location/Qualifiers
REGION                  1..107
                        note = Synthetic sequence: Anti-PSMA, Deimmunised VK3 '5
source                  1..107
                        mol_type = protein
                        organism = synthetic construct
SEQUENCE: 27
NIQMTQFPSA MSASVGDRVT ITCKASENVG TYVSWYQQKP DQSPKMLIYG ASNRFTGVPD  60
RFSGSGSGTD FTLTISSLQA EDLADYYCGQ SYTFPYTFGQ GTKLEIK                107

SEQ ID NO: 28           moltype = AA  length = 107
FEATURE                 Location/Qualifiers
REGION                  1..107
                        note = Synthetic sequence: Anti-PSMA, Deimmunised VK4 '5
source                  1..107
                        mol_type = protein
                        organism = synthetic construct
SEQUENCE: 28
NIQMTQFPSA MSASVGDRVT ITCKASENVG TYVSWYQQKP DQSPKMLIYG ASNRFTGVPD  60
RFSGSGSGTD FTLTISSLQA EDEADYYCGQ SYTFPYTFGQ GTKLEIK                107

SEQ ID NO: 29           moltype = AA  length = 107
FEATURE                 Location/Qualifiers
REGION                  1..107
                        note = Synthetic sequence: Anti-PSMA, Deimmunised VK DI '5
source                  1..107
                        mol_type = protein
                        organism = synthetic construct
SEQUENCE: 29
NIVMTQFPKS MSASAGERMT LTCKASENVG TYVSWYQQKP TQSPKMLIYG ASNRFTGVPD  60
RFSGSGSGTD FILTISSVQA EDLVDYYCGQ SYTFPYTFGG GTKLEMK                107

SEQ ID NO: 30           moltype = AA  length = 116
FEATURE                 Location/Qualifiers
REGION                  1..116
                        note = Synthetic sequence: Anti-PSMA, Deimmunised VH DI '5
source                  1..116
                        mol_type = protein
                        organism = synthetic construct
SEQUENCE: 30
EVKLEESGGG LVQPGGSMKI SCVASGFTFS NYWMNWVRQS PEKGLEWVAE IRSQSNNFAT  60
HYAESVKGRV IISRDDSKSS VYLQMNSLRA EDTAVYYCTR RWNNFWGQGT TVTVSS      116

SEQ ID NO: 31           moltype = AA  length = 116
FEATURE                 Location/Qualifiers
REGION                  1..116
                        note = Synthetic sequence: Anti-PSMA, Humanised RHA '5
source                  1..116
                        mol_type = protein
                        organism = synthetic construct
SEQUENCE: 31
EVQLVESGGG LVQPGGSLKL SCAASGFTFS NYWMNWVRQA SGKGLEWVGE IRSQSNNFAT  60
HYAESVKGRF TISRDDSKNT AYLQMNSLKT EDTAVYYCTR RWNNFWGQGT TVTVSS      116

SEQ ID NO: 32           moltype = AA  length = 116
FEATURE                 Location/Qualifiers
REGION                  1..116
                        note = Synthetic sequence: Anti-PSMA, Humanised RHB '5
source                  1..116
                        mol_type = protein
                        organism = synthetic construct
```

```
SEQUENCE: 32
EVKLVESGGG LVQPGGSLKL SCAASGFTFS NYWMNWVRQA SGKGLEWVAE IRSQSNNFAT  60
HYAESVKGRV IISRDDSKNT VYLQMNSLRT EDTAVYYCTR RWNNFWGQGT TVTVSS      116

SEQ ID NO: 33          moltype = AA  length = 116
FEATURE                Location/Qualifiers
REGION                 1..116
                       note = Synthetic sequence: Anti-PSMA, Humanised RHC '5
source                 1..116
                       mol_type = protein
                       organism = synthetic construct
SEQUENCE: 33
EVQLVESGGG LVQPGGSLKL SCAASGFTFS NYWMNWVRQA SGKGLEWVAE IRSQSNNFAT  60
HYAESVKGRV IISRDDSKNT VYLQMNSLRT EDTAVYYCTR RWNNFWGQGT TVTVSS      116

SEQ ID NO: 34          moltype = AA  length = 116
FEATURE                Location/Qualifiers
REGION                 1..116
                       note = Synthetic sequence: Anti-PSMA, Humanised RHD '5
source                 1..116
                       mol_type = protein
                       organism = synthetic construct
SEQUENCE: 34
EVKLVESGGG LVQPGGSLKL SCAASGFTFS NYWMNWVRQA SGKGLEWVGE IRSQSNNFAT  60
HYAESVKGRV IISRDDSKNT VYLQMNSLRT EDTAVYYCTR RWNNFWGQGT TVTVSS      116

SEQ ID NO: 35          moltype = AA  length = 116
FEATURE                Location/Qualifiers
REGION                 1..116
                       note = Synthetic sequence: Anti-PSMA, Humanised RHE '5
source                 1..116
                       mol_type = protein
                       organism = synthetic construct
SEQUENCE: 35
EVKLVESGGG LVQPGGSLKL SCAASGFTFS NYWMNWVRQA SGKGLEWVAE IRSQSNNFAT  60
HYAESVKGRF TISRDDSKNT VYLQMNSLRT EDTAVYYCTR RWNNFWGQGT TVTVSS      116

SEQ ID NO: 36          moltype = AA  length = 116
FEATURE                Location/Qualifiers
REGION                 1..116
                       note = Synthetic sequence: Anti-PSMA, Humanised RHF '5
source                 1..116
                       mol_type = protein
                       organism = synthetic construct
SEQUENCE: 36
EVKLVESGGG LVQPGGSLKL SCAASGFTFS NYWMNWVRQA SGKGLEWVAE IRSQSNNFAT  60
HYAESVKGRV IISRDDSKNT AYLQMNSLRT EDTAVYYCTR RWNNFWGQGT TVTVSS      116

SEQ ID NO: 37          moltype = AA  length = 116
FEATURE                Location/Qualifiers
REGION                 1..116
                       note = Synthetic sequence: Anti-PSMA, Humanised RHG '5
source                 1..116
                       mol_type = protein
                       organism = synthetic construct
SEQUENCE: 37
EVKLVESGGG LVQPGGSLKL SCAASGFTFS NYWMNWVRQA SGKGLEWVAE IRSQSNNFAT  60
HYAESVKGRV IISRDDSKNT AYLQMNSLRT EDTAVYYCTR RWNNFWGQGT TVTVSS      116

SEQ ID NO: 38          moltype = AA  length = 107
FEATURE                Location/Qualifiers
REGION                 1..107
                       note = Synthetic sequence: Anti-PSMA, Humanised RKA '5
source                 1..107
                       mol_type = protein
                       organism = synthetic construct
SEQUENCE: 38
DIQMTQSPSS VSASVGDRVT ITCKASENVG TYVSWYQQKP GTAPKLLIYG ASNRFTGVPS  60
RFSGSGSATD FTLTINNLQP EDFATYYCGQ SYTFPYTFGQ GTKVEIK                107

SEQ ID NO: 39          moltype = AA  length = 107
FEATURE                Location/Qualifiers
REGION                 1..107
                       note = Synthetic sequence: Anti-PSMA, Humanised RKB '5
source                 1..107
                       mol_type = protein
                       organism = synthetic construct
SEQUENCE: 39
DIQMTQSPSS VSASVGDRVT ITCKASENVG TYVSWYQQKP GTAPKLLIYG ASNRFTGVPS  60
```

```
RFSGSGSATD FTLTINNLQP EDFATYYCGQ SYTFPYTFGQ GTKVEIK                107

SEQ ID NO: 40           moltype = AA  length = 107
FEATURE                 Location/Qualifiers
REGION                  1..107
                        note = Synthetic sequence: Anti-PSMA, Humanised RKC '5
source                  1..107
                        mol_type = protein
                        organism = synthetic construct
SEQUENCE: 40
DIQMTQSPSS VSASVGDRVT ITCKASENVG TYVSWYQQKP GTAPKMLIYG ASNRFTGVPS  60
RFSGSGSATD FTLTINNLQP EDFATYYCGQ SYTFPYTFGQ GTKVEIK                107

SEQ ID NO: 41           moltype = AA  length = 107
FEATURE                 Location/Qualifiers
REGION                  1..107
                        note = Synthetic sequence: Anti-PSMA, Humanised RKD '5
source                  1..107
                        mol_type = protein
                        organism = synthetic construct
SEQUENCE: 41
DIQMTQSPSS VSASVGDRVT ITCKASENVG TYVSWYQQKP GTAPKMLIYG ASNRFTGVPS  60
RFSGSGSATD FTLTINNLQP EDFATYYCGQ SYTFPYTFGQ GTKVEIK                107

SEQ ID NO: 42           moltype = AA  length = 107
FEATURE                 Location/Qualifiers
REGION                  1..107
                        note = Synthetic sequence: Anti-PSMA, Humanised RKE '5
source                  1..107
                        mol_type = protein
                        organism = synthetic construct
SEQUENCE: 42
NIVMTQSPSS VSASVGDRVT ITCKASENVG TYVSWYQQKP GTAPKLLIYG ASNRFTGVPD  60
RFTGSGSATD FILTINNLQP EDFATYYCGQ SYTFPYTFGQ GTKVEIK                107

SEQ ID NO: 43           moltype = AA  length = 107
FEATURE                 Location/Qualifiers
REGION                  1..107
                        note = Synthetic sequence: Anti-PSMA, Humanised RKF '5
source                  1..107
                        mol_type = protein
                        organism = synthetic construct
SEQUENCE: 43
NIVMTQSPSS VSASVGDRVT ITCKASENVG TYVSWYQQKP GTAPKMLIYG ASNRFTGVPS  60
RFSGSGSATD FILTINNLQP EDFATYYCGQ SYTFPYTFGQ GTKVEIK                107

SEQ ID NO: 44           moltype = AA  length = 107
FEATURE                 Location/Qualifiers
REGION                  1..107
                        note = Synthetic sequence: Anti-PSMA, Humanised RKG '5
source                  1..107
                        mol_type = protein
                        organism = synthetic construct
SEQUENCE: 44
NIVMTQSPSS VSASVGDRVT ITCKASENVG TYVSWYQQKP GTAPKMLIYG ASNRFTGVPD  60
RFTGSGSATD FTLTINNLQP EDFATYYCGQ SYTFPYTFGQ GTKVEIK                107

SEQ ID NO: 45           moltype = DNA  length = 5560
FEATURE                 Location/Qualifiers
source                  1..5560
                        mol_type = other DNA
                        organism = synthetic construct
SEQUENCE: 45
cgcggggcgc ggagtcggcg gggcctcgcg ggacgccggg cagtgcggag accgcggcgc  60
tgaggacgcg ggagccggga gcgcagccgc ggggtggagt tcagcctact ctttcttaga  120
tgtgaaagga aaggaagatc atttcatgcc ttgttgataa aggttcagac ttctgctgat  180
tcataaccat ttggctctga gctatgacaa gagaggaaac aaaaagttaa acaagcaagc  240
ctgccataag tgagaagcaa acttccttga taacatgctt ttgcgaagtg caggaaaatt  300
aaatgtgggc accaagaaag aggatggtga gagtacagcc cccacccccc gtccaaaggt  360
cttgcgttgt aaatgccacc accattgtcc agaagactca gtcaacaata tttgcagcac  420
agacggatat tgtttcacga tgatagaaga ggatgactct gggttgcctg tggtcacttc  480
tggttgccta ggactagaag gctcagattt tcagtgtcgg gacactccca ttcctcatca  540
aagaagatca attgaatgct gcacagaaag gaacgaatgt aataaagacc tacaccctac  600
actgcctcca ttgaaaaaca gagattttgt tgatggacct atacaccaca gggctttact  660
tatatctgtg actgtctgta gtttgctctt ggtccttatc atattatttt gttacttccg  720
gtataaaaga caagaaacca gacctcgata cagcattggg ttagaacagg atgaaactta  780
cattcctcct ggagaatccc tgagagactt aattgagcag tctcagagct caggaagtgg  840
atcaggcctc cctctgctgg tccaaaggac tatagctaag cagattcaga tggtgaaaca  900
gattggaaaa ggtcgctatg gggaagtttg gatgggaaag tggcgtggcg aaaaggtagc  960
```

-continued

```
tgtgaaagtg ttcttcacca cagaggaagc cagctggttc agagagacag aaatatatca  1020
gacagtgttg atgaggcatg aaaacatttt gggtttcatt gctgcagata tcaaagggac  1080
agggtcctgg acccagttgt acctaatcac agactatcat gaaaatggtt cccttttatga  1140
ttatctgaag tccaccaccc tagacgctaa atcaatgctg aagttagcct actcttctgt  1200
cagtggctta tgtcatttac acacagaaat ctttagtact caaggcaaac cagcaattgc  1260
ccatcgagat ctgaaaagta aaaacattct ggtgaagaaa aatggaactt gctgtattgc  1320
tgacctgggc ctggctgtta aatttattag tgatacaaat gaagttgaca taccacctaa  1380
cactcgagtt ggcaccaaac gctatatgcc tccagaagtg ttggacgaga gcttgaacag  1440
aaatcacttc cagtcttaca tcatggctga catgtatagt tttggcctca tcctttggga  1500
ggttgctagg agatgtgtat caggaggtat agtggaagaa taccagcttc cttatcatga  1560
cctagtgccc agtgacccct cttatgagga catgagggag attgtgtgca tcaagaagtt  1620
acgcccctca ttcccaaacc ggtggagcag tgatgagtgt ctaaggcaga tgggaaaact  1680
catgacagaa tgctgggctc acaatcctgc atcaaggctg acagccctgc gggttaagaa  1740
aacacttgcc aaaatgtcag agtcccagga cattaaactc tgataggaga ggaaaagtaa  1800
gcatctctgc agaaagccaa caggtactct tctgtttgtg ggcagagcaa aagacatcaa  1860
ataagcatcc acagtacaag ccttgaacat cgtcctgctt cccagtgggt tcagacctca  1920
cctctcaggg agcgacctgg gcaaagacag agaagctccc agaaggagag attgatccat  1980
gtctgtttgt aggacggaga aaccgcttgg gtaacttgtt caagatatga tgcatgttgc  2040
tttctaagaa agccctgtat tttgtgattg ccttttttt tttttaagat gctttcattt  2100
tgccaaaata aaacagataa tgtggatggt ttaagggtta tagtattata gtttaaataa  2160
taacaacaaa attcttccca ggaactctgc tggaaggtaa attaaaatac ttgtttttcc  2220
attggtaaaa tattgttgca ctctgtgaac caaaagacag tctaagttgg aggacataga  2280
acggaactca tcttaaacat actccccacc ccgtcttggc ctcctcagac cactttggcc  2340
atccctgcat ttggggccgc tatggtaatg tgaatgcact gggtacaaac accgcctgtc  2400
taggaccaca tttggaattc ctgcaggtgg cctttgcag cttcaggcaa tatggaacaa  2460
atgaaggttt atgtgactct aatagaagta attgttgata ggtgttcttc agatccactt  2520
ctgtttctga ttgagttagg catctctttc atggtaaaac ccttttcatt aaacacaaag  2580
aaagcttttt tttttttttt tttttttttt tttttttaat gtgcagagga ttgacctgtg  2640
catgcttttg atctctcatt caaaggatca atattaaata aaattgtcat gagctgtgtt  2700
gaagacaggg tgctttcaaa tagaggtaat ttgctcttgt gttgtaagag gaacatgtca  2760
acaaagatag gaaatgaggg tgatcgtgca gatggcttgt atcttatata tgcaaaggag  2820
ccaatctcag aagcacaaag aaaaaagtgt gcatacctta ttttgtacag ataaagatga  2880
tgtctttttg ttattgtctg tctgttttgt atgtgtctga gataagggat agagaggaaa  2940
catccgtcag gctaatttaa ctacatttta ttttaaaaat agagaaacat aacctctaga  3000
tgggacagca gaggacagtt agtagaggcc acaaactgtt atgggctgct gtgttttgtt  3060
ctaaaatcaa tatggttgga gcatgtatat cttaggtgat catttcacat cttaggaatg  3120
cctactcatt ttattttatt ctagtgatgc tcaattcact atttaattta ttatattttc  3180
tcttctgtgg cacttataca aaatatctct tcacctactt agttctacag ggttttaact  3240
ttggagcaac atgaataaaa tcatcgagaa ggccaatatt gtttagcaac atgaatacaa  3300
tacagtttaa agttgtacac atcctgctca actttattca tatacatttc ctttctgtgg  3360
ttttcttttg cttcttagaa attctgttag tggttagtaa agaatttgaa agtactttct  3420
ccttgctgtt tttttttttt tttaagacat tcctcccaga atactccagg gggcagtgtt  3480
ttataacaca ttttccccac tgggtgattg aaggatggag gatttttgaa aatttgacag  3540
ctacatgaaa catgagaaaa cattttcctc acttctgaag tcggtttgca gctggtaact  3600
tgttcatcca gaaaacattc taaagcaatg agactttgtg agctgtgctt acagtttggg  3660
agaatcatga agattctttc tatattttgc atttacttcc cagtgcttca tagctgcatt  3720
ttgtttgtaa ctaagacaga agaatttcgt aatccttgaa attgaaaaaa aaaaaattgt  3780
gtttttaaag agtgaaaaca gttagaaaac aagtagaact gtaatcagaa cgctgcttca  3840
attgatatta aaaataacct caataataat gtaaaggttc ctttctcttg tgtcagttat  3900
attcttaggg atagcctaga aggaatatat ggttagaact aagtgtgact aatcatctga  3960
gccttgaaga gaaacttcag tgcctctaaa cagatcatct acaaaacaac aggtaaacat  4020
ttatgccagt taagtgggtc atgtttttgt ttcttgggtt tttcctaaat ttaagtgagg  4080
ttgggcttac cttgtagata aaattatgtt ttctttttgg taaatacttg aacgtggata  4140
acgtcaaatc agaatatttt gtgaggaggt gatgatttga aattaagcta gatttctagg  4200
gaggtgttgg ttccaatgaa ggatgggaag aaattaaaat agtcttcaaa cttcttcctt  4260
attatatttg gttgctttgg aaaagattgg tcctatcctc aatctaattt attcactatt  4320
aatattttaa aaacattcct gagatactta aaaagaccca cttagcgatt atagttgctc  4380
aatgaaacaa gaatttattt atgcatagat ttttctctgt atcttaccaa aatccacttt  4440
acttagataa cactaaattg ttcttaaaga ctactcattt cccaataatc ctttatgatt  4500
tcaaaatttc tagtggctca gaagtgaatt ttattttatt tgtctttcac ttgaataaat  4560
gagaacccag aaattaataa tgttgtttat tgcttactgt caggactatt tcaaagacta  4620
agaagagttt cttctaaccc ctccctctca aaggaatcct aaattattag ttgttagata  4680
agttttgtat gctaagatat tcaggtttat agtttatgta tgtgtgtata tatataaata  4740
tatatgtata tataaatatt atgttcagtt tggagtctgg cacaactcca ttatgtggat  4800
tagagagtaa gatattatgg atgataaagt actaaatgaa acataatatt tatttataaa  4860
agtgtgtaga ttgttaaatc acaaaaaagag tgctatgacc attatgtatg aggaaacagg  4920
cctttgacct cctggaaagc actgctcaaa agtcattagt gcccattttt gaattcccca  4980
aacagaaagc ttcttagaaa acatgctgag attttattta cagggaattc tttgacacat  5040
ttcaattggt gtgtagtcaa gtatagcaag tacttaataa tgactgaatt tcatgttcct  5100
acagtcatac atattcatta gaagttttat gttgttggtc tgatctgatt cttctttgtt  5160
tgtgggtgga acggcactga gagaagtata gtttttttaaa cttgaacatg ttcagtagtt  5220
acattgcctt agaaaaccca gacacatagc agtggaaatg aaagaaatgg catcagaagt  5280
gacttaattt agcaattgtg attcctcttg taaaacaaaa caaaaaaaca atgccatatt  5340
ttttggagaa aagttggcaa tatagggggtt tcgttgtctg tttcacaaga agactcattt  5400
gttcttttgg gggaaccagt gccttacaga ttttgtatat actgtaatta ttcaggacta  5460
gggaacaaac aattgtattg tatttgttac agattgtata tggctttgtt ttaacattcc  5520
cctaaataaa atggcttcat tctccccttg gaaaaaaaca                        5560
```

SEQ ID NO: 46          moltype = AA  length = 502

-continued

```
FEATURE                Location/Qualifiers
source                 1..502
                       mol_type = protein
                       organism = Homo sapiens
SEQUENCE: 46
MLLRSAGKLN VGTKKEDGES TAPTPRPKVL RCKCHHHCPE DSVNNICSTD GYCFTMIEED  60
DSGLPVVTSG CLGLEGSDFQ CRDTPIPHQR RSIECCTERN ECNKDLHPTL PPLKNRDFVD  120
GPIHHRALLI SVTVCSLLLV LIILFCYFRY KRQETRPRYS IGLEQDETYI PPGESLRDLI  180
EQSQSSGSGS GLPLLVQRTI AKQIQMVKQI GKGRYGEVWM GKWRGEKVAV KVFFTTEEAS  240
WFRETEIYQT VLMRHENILG FIAADIKGTG SWTQLYLITD YHENGSLYDY LKSTTLDAKS  300
MLKLAYSSVS GLCHLHTEIF STQGKPAIAH RDLKSKNILV KKNGTCCIAD LGLAVKFISD  360
TNEVDIPPNT RVGTKRYMPP EVLDESLNRN HFQSYIMADM YSFGLILWEV ARRCVSGGIV  420
EEYQLPYHDL VPSDPSYEDM REIVCIKKLR PSFPNRWSSD ECLRQMGKLM TECWAHNPAS  480
RLTALRVKKT LAKMSESQDI KL                                           502

SEQ ID NO: 47          moltype = DNA  length = 4543
FEATURE                Location/Qualifiers
source                 1..4543
                       mol_type = other DNA
                       organism = synthetic construct
SEQUENCE: 47
cggcgggcgg cgcgcacact gctcgctggg ccgcggctcc cgggtgtccc aggcccggcc  60
ggtgcgcaga gcatggcggg tgcgggcccg aagcggcgcg cgctagcggc gccggcggcc  120
gaggagaagg aagaggcgcg ggagaagatg ctggccgcca agagcgcgga cggctcggcg  180
ccggcaggcg agggcgaggg cgtgaccctg cagcggaaca tcacgctgct caacggcgtg  240
gccatcatcg tggggaccat tatcggctcg ggcatcttcg tgacgcccac gggcgtgctc  300
aaggaggcag gctcgccggg gctggcgctg gtggtgtggg ccgcgtgcgg cgtcttctcc  360
atcgtgggcg cgctctgcta cgcggagctc ggcaccacca tctccaaatc gggcggcgac  420
tacgcctaca tgctggaggt ctacggctcg ctgcccgcct tcctcaagct ctggatcgag  480
ctgctcatca tccggccttc atcgcagtac atcgtggccc tggtcttcgc cacctacctg  540
ctcaagccgc tcttccccac ctgcccggtg cccgaggagg cagccaagct cgtggcctgc  600
ctctgcgtgc tgctgctcac ggccgtgaac tgctacagcg tgaaggccgc cacccgggtc  660
caggatgcct ttgccgccgc caagctcctg gccctggccc tgatcatcct gctgggcttc  720
gtccagatcg ggaagggtga tgtgtccaat ctagatccca acttctcatt tgaaggcacc  780
aaactggatg tggggaacat tgtgctggca ttatacagcg gcctctttgc ctatggagga  840
tggaattact tgaatttcgt cacagaggaa atgatcaacc cctacagaaa cctgcccctg  900
gccatcatca tctccctgcc catcgtgacg ctggtgtacg tgctgaccaa cctggcctac  960
ttcaccaccc tgtccaccga gcagatgctg tcgtccgagg ccgtggccgt ggacttcggg  1020
aactatcacc tgggcgtcat gtcctggatc atccccgtct tcgtgggcct gtcctgcttc  1080
ggctccgtca atgggtccct gttcacatcc tccaggctct tcttcgtggg gtcccgggaa  1140
ggccacctgc cctccatcct ctccatgatc cacccacagc tcctcacccc cgtgccgtcc  1200
ctcgtgttca cgtgtgtgat gacgctgctc tacgccttct ccaaggacat cttctccgtc  1260
atcaacttct tcagcttctt caactggctc tgcgtggccc tggccatcat cggcatgatc  1320
tggctgcgcc acagaaagcc tgagcttgag cggcccatca aggtgaacct ggccctgcct  1380
gtgttcttca tcctggcctg cctcttcctg atcgccgtct ccttctggaa gacacccgtg  1440
gagtgtggca tcggcttcac catcatcctc agcgggctgc ccgtctactt cttcggggtc  1500
tggtggaaaa acaagcccaa gtggctcctc cagggcatct tctccacgac cgtcctgtgt  1560
cagaagctca tgcaggtggt cccccaggag acatagccag gaggccgagt ggctgccgga  1620
ggagcatgcg cagaggccag ttaaagtaga tcacctcctc gaacccactc cggttccccg  1680
caacccacag ctcagctgcc catcccagtc cctcgccgtc cctcccaggt cgggcagtgg  1740
aggctgctgt gaaaactctg gtacgaatct catccctcaa ctgagggcca gggacccagg  1800
tgtgcctgtg ctcctgccca ggagcagctt ttggtctcct tgggcccttt ttcccttccc  1860
tcctttgttt acttatatat atattttttt taaacttaaa ttttgggtca acttgacacc  1920
actaagatga ttttttaagg agctggggga aggcaggagc cttcctttct cctgccccaa  1980
gggcccagac cctgggcaaa cagagctact gagacttgga acctcattgc taccacagac  2040
ttgcactgaa gccggacagc tgcccagaca catgggcttg tgacattcgt gaaaaccaac  2100
cctgtgggct tatgtctctg ccttagggtt tgcagagtgg aaactcagcc gtagggtggc  2160
actgggaggg ggtgggggat ctgggcaagg tgggtgattc ctcccaggag gtgcttgagg  2220
ccccgatgga ctcctgacca taatcctagc cccgagacac catcctgagc cagggaacag  2280
ccccagggtt ggggggtgcc ggcatctccc ctagctcacc aggcctggcc tctgggcagt  2340
gtggcctctt ggctatttct gtgtccagtt ttggaggctg agttctggtt catgcagaca  2400
aagccctgtc cttcagtctt ctagaaacag agacaagaaa ggcagacaca ccgcggccag  2460
gcacccatgt gggcgcccac cctgggctcc acacagcagt gtcccctgcc ccagaggtcg  2520
cagctaccct cagcctccaa tgcattggcc tctgtaccgc ccggcagccc cttctggccg  2580
gtgctgggtt cccactcccg gcctaggcac ctcccogctc tccctgtcac gctcatgtcc  2640
tgtcctggtc ctgatgcccg ttgtctagga gacagagcca agcactgctc acgtctctgc  2700
cgcctgcgtt tggaggcccc tgggctctca cccagtcccc acccgcctgc agagagggaa  2760
ctagggcacc ccttgtttct gttgttcccg tgaatttttt tcgctatggg aggcagccga  2820
ggcctggcca atgcggccca ctttcctgag ctgtcgctgc ctccatggca gcagccaggg  2880
acccccagaa caagaagacc ccgcaggatc cctcctgagc tcggggggct ctgccttctc  2940
aggccccggg cttcccttct ccccagccag aggtggagcc aagtggtcca gcgtcactcc  3000
agtgctcagc tgtggctgga ggagctggcc tgtggcacag ccctgagtgt cccaagccgg  3060
gagccaacga agccggacac ggcttcactg accagcggct gctcaagccg caagctctca  3120
gcaagtgccc agtggagcct gccgccccg cctgggcacc gggacccccct caccatccag  3180
tgggcccgga gaaacctgat gaacagtttg gggactcagg accagatgtc cgtctctctt  3240
gcttgaggaa tgaagacctt tattcacccc tgccccgttg cttcccgctg cacatggaca  3300
gacttcacag cgtctgctca taggacctgc atccttcctg ggacgaatt ccactcgtcc  3360
aagggacagc ccacggtctg gaggccgagg accaccagca ggcaggtgga ctgactgtgt  3420
tgggcaagac ctcttccctc tgggcctgtt ctcttggctg caaataagga cagcagctgg  3480
```

-continued

```
tgccccacct gcctggtgca ttgctgtgtg aatccaggag gcagtggaca tcgtaggcag  3540
ccacggcccc gggtccagga gaagtgctcc ctggaggcac gcaccactgc ttcccactgg  3600
ggccggcggg gcccacgcac gacgtcagcc tcttaccttc ccgcctcggc taggggtcct  3660
cgggatgccg ttctgttcca acctcctgct ctgggacgtg gacatgcctc aaggatacag  3720
ggagccggcg gcctctcgac ggcacgcact tgcctgttgg ctgctgcggc tgtgggcgag  3780
catgggggct gccagcgtct gttgtggaaa gtagctgcta gtgaaatggc tggggccgct  3840
ggggtccgtc ttcacactgc gcaggtctct tctgggcgtc tgagctgggg tgggagctcc  3900
tccgcagaag gttggtgggg ggtccagtct gtgatccttg gtgctgtgtg ccccactcca  3960
gcctggggac cccacttcag aaggtagggg ccgtgtcccg cggtgctgac tgaggcctgc  4020
ttccccctcc ccctcctgct gtgctggaat tccacaggga ccagggccac cgcaggggac  4080
tgtctcagaa gacttgattt ttccgtccct ttttctccac actccactga caaacgtccc  4140
cagcggtttc cacttgtggg cttcaggtgt tttcaagcac aacccaccac aacaagcaag  4200
tgcattttca gtcgttgtgc tttttttgttt tgtgctaacg tcttactaat ttaaagatgc  4260
tgtcggcacc atgtttattt atttccagtg gtcatgctca gccttgctgc tctgcgtggc  4320
gcaggtgcca tgcctgctcc ctgtctgtgt cccagccacg cagggccatc cactgtgacg  4380
tcggccgacc aggctggaca ccctctgccg agtaatgacg tgtgtggctg ggaccttctt  4440
tattctgtgt taatggctaa cctgttacac tgggctgggt tgggtagggt gttctggctt  4500
ttttgtgggg tttttatttt taaagaaaca ctcaatcatc cta                   4543

SEQ ID NO: 48          moltype = AA  length = 507
FEATURE                Location/Qualifiers
source                 1..507
                       mol_type = protein
                       organism = Homo sapiens
SEQUENCE: 48
MAGAGPKRRA LAAPAAEEKE EAREKMLAAK SADGSAPAGE GEGVTLQRNI TLLNGVAIIV  60
GTIIGSGIFV TPTGVLKEAG SPGLALVVWA ACGVFSIVGA LCYAELGTTI SKSGGDYAYM  120
LEVYGSLPAF LKLWIELLII RPSSQYIVAL VFATYLLKPL FPTCPVPEEA AKLVACLCVL  180
LLTAVNCYSV KAATRVQDAF AAAKLLALAL IILLGFVQIG KGDVSNLDPN FSFEGTKLDV  240
GNIVLALYSG LFAYGGWNYL NFVTEEMINP YRNLPLAIII SLPIVTLVYV LTNLAYFTTL  300
STEQMLSSEA VAVDFGNYHL GVMSWIIPVF VGLSCFGSVN GSLFTSSRLF FVGSREGHLP  360
SILSMIHPQL LTPVPSLVFT CVMTLLYAFS KDIFSVINFF SFFNWLCVAL AIIGMIWLRH  420
RKPELERPIK VNLALPVFFI LACLFLIAVS FWKTPVECGI GFTIILSGLP VYFFGVWWKN  480
KPKWLLQGIF STTVLCQKLM QVVPQET                                      507

SEQ ID NO: 49          moltype = DNA  length = 1330
FEATURE                Location/Qualifiers
source                 1..1330
                       mol_type = other DNA
                       organism = synthetic construct
SEQUENCE: 49
gcggacgcgg ggcgccagca ggtggcgctg gacgcgcaac ggacaaggag gcggggcctg  60
cagctggctt ggaggctccg cgctctggag gctcaggcgc cgcgtggggc ccgcacctct  120
gggcagcagc ggcagccgag actcacggtc aagctaaggc gaagagtggg tggctgaagc  180
catactattt tatagaatta atggaaagca gaaaagacat cacaaaccaa gaagaacttt  240
ggaaaatgaa gcctaggaga aatttagaag aagacgatta tttgcataag gacacgggag  300
agaccagcat gctaaaaaga cctgtgcttt tgcatttgca ccaaacagcc catgctgatg  360
aatttgactg ccccttcagaa cttcagcaca cacaggaact ctttccacag tggcacttgc  420
caattaaaat agctgctatt atagcatctc tgacttttct ttacactctt ctgagggaag  480
taattcaccc tttagcaact tcccatcaac aatattttta taaaattcca atcctggtca  540
tcaacaaagt cttgccaatg gtttccatca ctctcttggc attggtttac ctgccaggtg  600
tgatagcagc aattgtccaa cttcataatg gaaccaagta taagaagttt ccacattggt  660
tggataagtg gatgttaaca agaaagcagt ttgggcttct cagtttcttt tttgctgtac  720
tgcatgcaat ttatagtctg tcttacccaa tgaggcgatc ctacagatac aagttgctaa  780
actgggcata tcaacaggtc caacaaaata aagaagatgc ctggattgag catgatgttt  840
ggagaatgga gatttatgtg tctctgggaa ttgtgggatt ggcaatactg gctctgttgg  900
ctgtgacatc tattccatct gtgagtgact ctttgacatg gagagaattt cactatattc  960
agagcaagct aggaattgtt tcccttctac tgggcacaat acacgcattg atttttgcct  1020
ggaataagtg gatagatata aaacaatttg tatggtatac acctccaact tttatgatag  1080
ctgttttcct tccaattgtt gtcctgatat ttaaaagcat actattcctg ccatgcttga  1140
ggaagaagat actgaagatt agacatggtt gggaagacgt caccaaaatt aacaaaactg  1200
agatatgttc ccagttgtag aattactgtt tacacacatt tttgttcaat attgatatat  1260
tttatcacca acatttcaag tttgtatttg ttaataaaat gattattcaa ggaaaaaaaa  1320
aaaaaaaaaa                                                         1330

SEQ ID NO: 50          moltype = AA  length = 339
FEATURE                Location/Qualifiers
source                 1..339
                       mol_type = protein
                       organism = Homo sapiens
SEQUENCE: 50
MESRKDITNQ EELWKMKPRR NLEEDDYLHK DTGETSMLKR PVLLHLHQTA HADEFDCPSE  60
LQHTQELFPQ WHLPIKIAAI IASLTFLYTL LREVIHPLAT SHQQYFYKIP ILVINKVLPM  120
VSITLLALVY LPGVIAAIVQ LHNGTKYKKF PHWLDKWMLT RKQFGLLSFF FAVLHAIYSL  180
SYPMRRSYRY KLLNWAYQQV QQNKEDAWIE HDVWRMEIYV SLGIVGLAIL ALLAVTSIPS  240
VSDSLTWREF HYIQSKLGIV SLLLGTIHAL IFAWNKWIDI KQFVWYTPPT FMIAVFLPIV  300
VLIFKSILFL PCLRKKILKI RHGWEDVTKI NKTEICSQL                         339

SEQ ID NO: 51          moltype = DNA  length = 21112
```

```
FEATURE                Location/Qualifiers
source                 1..21112
                       mol_type = other DNA
                       organism = synthetic construct
SEQUENCE: 51
cctgtgactt ctcttctcac ccctggcctg gtgataacca cagacaggat gggcataagc  60
agagaacctg gaaccagttc cacttcaaat ttgagcagca cctcccatga gagactgacc  120
actttggaag acactgtaga tacagaagcc atgcagcctt ccacacacac agcagtgacc  180
aacgtgagga cctccatttc tggacatgaa tcacaatctt ctgtcctatc tgactcagag  240
acacccaaag ccacatctcc aatgggtacc acctacacca tgggggaaac gagtgtttcc  300
atatccactt ctgacttctt tgagaccagc agaattcaga tagaaccaac atcctccctg  360
acttctggat tgagggagac cagcagctct gagaggatca gctcagccac agagggaagc  420
actgtccttt ctgaagtgcc cagtggtgct accactgagg tctccaggac agaagtgata  480
tcctctaggg gaacatccat gtcagggcct gatcagttca ccatatcacc agacatctct  540
actgaagcga tcaccaggct ttctacttcc cccattatga cagaatcagc agaaagtgcc  600
atcactattg agacaggttc tcctggggct acatcagagg gtaccctcac cttggacacc  660
tcaacaacaa ccttttggtc agggacccac tcaactgcat ctccaggatt ttcacactca  720
gagatgacca ctcttatgag tagaactcct ggagatgtgc catggccgag ccttccctct  780
gtggaagaag ccagctctgt ctcttcctca ctgtcttcac ctgccatgac ctcaacttct  840
tttttctcca cattaccaga gagcatctcc tcctctcctc atcctgtgac tgcacttctc  900
acccttggcc cagtgaagac cacagacatg ttgcgcacaa gctcagaacc tgaaaccagt  960
tcacctccaa atttgagcag cacctcagct gaaatattag ccacgtctga agtcaccaaa  1020
gatagagaga aaattcatcc ctcctcaaac acacctgtag tcaatgtagg gactgtgatt  1080
tataaacatc tatccccttc ctctgttttg gctgacttag tgacaacaaa acccacatct  1140
ccaatggcta ccacctccac tctggggaat acaagtgttt ccacatcaac tcctgccttc  1200
ccagaaacta tgatgacaca gccaacttcc tccctgactt ctggattaag ggagatcagt  1260
acctctcaag agaccagctc agcaacagag agaagtgctt ctctttctgg aatgcccact  1320
ggtgctacta ctaaggtctc cagaacagaa gccctctcct taggcagaac atccaccccca  1380
ggtcctgctc aatccacaat atcaccagaa atctccacgg aaaccatcac tagaatttct  1440
actcccctca ccacgacagg atcagcagaa atgaccatca cccccaaaac aggtcattct  1500
ggggcatcct cacaaggtac ctttaccttg gacacatcaa gcagagcctc ctggccagga  1560
actcactcag ctgcaactca cagatctcca cactcaggga tgaccactcc tatgagcaga  1620
ggtcctgagg atgtgtcatg gccaagccgc ccatcagtgg aaaaaactag ccctccatct  1680
tccctggtgt ctttatctgc agtaacctca ccttcgccac tttattccac accatctgag  1740
agtagccact cgtctcctct ccgggtgact tctcttttca cccctgtcat gatgaagacc  1800
acagacatgt tggacacaag cttggaacct gtgaccactt cacctcccag tatgaatatc  1860
acctcagatg agagtctggc cacttctaaa gccaccatgg agacagaggc aattcagctt  1920
tcagaaaaca cagctgtgac tcagatgggc accatcagtg ctagacaaga attctattcc  1980
tcttatccag gcctcccaga gccatccaaa gtgacatctc cagtggtcac ctcttccacc  2040
ataaaagaca ttgtttctac aaccatacct gcttcctctg agataacaag aattgagatg  2100
gagtcaacat ccaccctgac ccccacacca agggagacca gcacctccca ggagatccac  2160
tcagccacaa agccaagcac tgttccttac aaggcactca ctagtgccac gattgaggac  2220
tccatgacac aagtcatgtc ctctagcaga ggacctagcc ctgatcagtc cacaatgtca  2280
caagacatat ccactgaagt gatcaccagg ctctctacct cccccatcaa gacagaatct  2340
acagaaatga ccattaccac ccaaacaggt tctcctgggg ctacatcaag gggtaccctt  2400
accttggaca cttcaacaac ttttatgtca gggacccatt caactgcatc tcaaggattt  2460
tcacactcac agatgaccgc tcttatgagt agaactcctg gagaggtgcc atggctaagc  2520
catccctctg tggaagaagc cagctctgcc tctttctcac tgtcttcacc tgtcatgacc  2580
tcatcttctc ccgtttcttc cacattacca gacagcatcc actcttcttc gcttcctgtg  2640
acatcacttc tcacctcagg gctggtgaag accacagagc tgttgggcac aagctcagaa  2700
cctgaaacca gttcaccccc aaatttgagc agcacctcag ctgaaatact ggccaccact  2760
gaagtcacta cagatacaga gaaactggag atgaccaatg tggtaacctc aggttataca  2820
catgaatctc cttcctctgt cctagctgac tcagtgacaa caaaggccac atcttcaatg  2880
ggtatcacct accccacagg agatacaaat gttctcacat caacccctgc cttctctgac  2940
accagtagga ttcaaacaaa gtcaaagctc tcactgactc ctgggttgat ggagaccagc  3000
atctctgaag agaccagctc tgccacagaa aaaagcactg tcctttctag tgtgcccact  3060
ggtgctacta ctgaggtctc caggacagaa gccatctctt ctagcagaac atccatccca  3120
ggccctgctc aatccacaat gtcatcagac acctccatgg aaaccatcac tagaatttct  3180
acccccctca caaggaaaga atcaacagac atggccatca cccccaaaac aggtccttct  3240
ggggctacct cgcagggtac ctttaccttg gactcatcaa gcacagcctc ctggccagga  3300
actcactcag ctacaactca gagatttcca cggtcagtgg tgacaactcc tatgagcaga  3360
ggtcctgagg atgtgtcatg gccaagcccg ctgtctgtgg aaaaaaacag ccctccatct  3420
tccctggtat cttcatcttc agtaacctca ccttcgccac tttattccac accatctggg  3480
agtagccact cctctcctgt ccctgtcact tctcttttca cctctatcat gatgaaggcc  3540
acagacatgt tggatgcaag tttggaacct gagaccactt cagctcccaa tatgaatatc  3600
acctcagatg agagtctggc cgcttctaaa gccaccacgg agacagaggc aattcacgtt  3660
tttgaaaata cagcagcgtc ccatgtggaa accaccagtg ctacagagga actctattcc  3720
tcttccccag gcttctcaga gccaacaaaa gtgatatctc cagtggtcac ctcttcctct  3780
ataagagaca acatggtttc cacaacaatg cctggctcct ctggcattac aaggattgag  3840
atagagtcaa tgtcatctct gacccctgga ctgagggaga ccagaacctc ccaggacatc  3900
acctcatcca cagagacaag cactgtcctt tacaagatgc cctctggtgc cactcctgag  3960
gtctccagga cagaagttat gccctctagc agaacatcca ttcctggccc tgctcagtcc  4020
acaatgtcac tagacatctc cgatgaagtt gtcaccaggc tgtctacctc tcccatcatg  4080
acagaatctg cagaaataac catcaccacc caaacaggtt attctctggc tacatcccag  4140
gttacccttc ccttgggcac ctcaatgacc tttttgtcag ggacccactc aactatgtct  4200
caaggacttt cacactcaga gatgaccaat cttatgagca ggggtcctga aagtctgtca  4260
tggacgagcc ctcgctttgt ggaaacaact agatcttcct cttctctgac atcattacct  4320
ctcacgacct cactttctcc tgtgtcctcc acattactag acagtagccc ctcctctcct  4380
cttcctgtga cttcacttat cctcccaggc ctggtgaaga ctacagaagt gttggataca  4440
```

-continued

```
agctcagagc ctaaaaccag ttcatctcca aatttgagca gcacctcagt tgaaataccg  4500
gccacctctg aaatcatgac agatacagag aaaattcatc cttcctcaaa cacagcggtg  4560
gccaaagtga ggacctccag ttctgttcat gaatctcatt cctctgtcct agctgactca  4620
gaaacaacca taaccatacc ttcaatgggt atcacctccg ctgtggagga taccactgtt  4680
ttcacatcaa atcctgcctt ctctgagact aggaggattc cgacagagcc aacattctca  4740
ttgactcctg gattcaggga gactagcacc tctgaagaga ccacctcaat cacagaaaca  4800
agtgcagtcc tttttggagt gcccactagt gctactactg aagtctccat gacagaaata  4860
atgtcctcta atagaacaca catccctgac tctgatcagt ccacgatgtc tccagacatc  4920
atcactgaag tgatcaccag gctctcttcc tcatccatga tgtcagaatc aacacaaatg  4980
accatcacca cccaaaaaag ttctcctggg gctacagcac agagtactct taccttggcc  5040
acaacaacag ccccccttggc aaggacccac tcaactgttc ctcctagatt tttacactca  5100
gagatgacaa ctcttatgag taggagtcct gaaaatccat catggaagag ctctcccttt  5160
gtggaaaaaa ctagctcttc atcttctctg ttgtccttac ctgtcacgac ctcaccttct  5220
gtttcttcca cattaccgca gagtatccct tcctcctctt tttctgtgac ttcactcctc  5280
accccaggca tggtgaagac tacagacaca agcacagaac ctggaaccag tttatctcca  5340
aatctgagtg gcacctcagt tgaaatactg gctgcctctg aagtcaccac agatacagag  5400
aaaattcatc cttcttcaag catggcagtg accaatgtgg gaaccaccag ttctggacat  5460
gaactatatt cctctgtttc aatccactcg gagccatcca aggctacata cccagtgggt  5520
actccctctt ccatggctga aacctctatt tccacatcaa tgcctgctaa ttttgagacc  5580
acaggatttg aggctgagcc attttctcat ttgacttctg gacttaggaa gaccaacatg  5640
tccctggaca ccagctcagt cacaccaaca aatacacctt cttctcctgg gtccactcac  5700
cttttacaga gttccaagac tgatttcacc tcttctgcaa aaacatcatc cccagactgg  5760
cctccagcct cacagtatac tgaaattcca gtggacataa tcaccccctt taatgcttct  5820
ccatctatta cggagtccac tggataacc tccttcccag aatccaggtt tactatgtct  5880
gtaacagaaa gtactcatca tctgagtaca gatttgctgc cttcagctga gactatttcc  5940
actggcacag tgatgccttc tctatcagag gccatgactt catttgccac cactggagtt  6000
ccacgagcca tctcaggttc aggtagtcca ttctctagga cagagtcagg ccctggggat  6060
gctactctgt ccaccattgc agagagcctg ccttcatcca ctcctgtgcc attctcctct  6120
tcaaccttca ctaccactga ttcttcaacc atcccagccc tccatgagat aacttcctct  6180
tcagctaccc catatagagt ggacaccagt cttgggacag agagcagcac tactgaagga  6240
cgcttggtta tggtcagtac tttggacact tcaagccaac caggcaggac atcttcatca  6300
cccattttgg ataccagaat gacagagagc gttgagctgg gaacagtgac aagtgcttat  6360
caagttcctt cactctcaac acggttgaca agaactgatg gcattatgga acacatcaca  6420
aaaataccca atgaagcagc acacagaggt accataagac cagtcaaagg ccctcagaca  6480
tccacttcgc ctgccagtcc taaaggacta cacacaggag ggacaaaaag aatggagacc  6540
accaccacag ctctgaagac caccaccaca gctctgaaga ccacttccag agccaccttg  6600
accaccagtg tctatactcc cactttggga acactgactc ccctcaatgc atcaatgcaa  6660
atggccagca caatccccac agaaatgatg atcacaaccc catatgtttt ccctgatgtt  6720
ccagaaacga catcctcatt ggctaccagc ctgggagcag aaaccagcac agctcttccc  6780
aggacaaccc catctgtttt caatagagaa tcagagacca cagcctcact ggtctctcgt  6840
tctggggcag agagaagtcc ggttattcaa actctagatg tttcttctag tgagccagat  6900
acaacagctt catgggttat ccatcctgca gagaccatcc caactgtttc caagacaacc  6960
cccaattttt tccacagtga attagacact gtatcttcca cagccaccag tcatggggca  7020
gacgtcagct cagccattcc aacaaatatc tcacctagtg aactagatgc actgacccca  7080
ctggtcacta tttcggggac agatactagt acaacattcc caacactgac taagtcccca  7140
catgaaacag agacaagaac cacatggctc actcatcctg cagagaccag ctcaactatt  7200
cccagaacaa tccccaattt ttctcatcat gaatcagatg ccacaccttc aatagccacc  7260
agtcctgggg cagaaaccag ttcagctatt ccaattatga ctgtctcacc tggtgcagaa  7320
gatctggtga cctcacaggt cactagttct ggcacagaca gaaatatgac tattccaact  7380
ttgactcttt ctcctggtga accaaagacc atagcctcat tagtcaccca tcctgaagca  7440
cagacaagtt cggccattcc aacttcaact atctcgcctg ctgtatcacg gttggtgacc  7500
tcaatggtca ccagtttggc ggcaaagaca agtacaacta atcgagctct gacaaactcc  7560
cctggtgaac cagctacaac agtttcattg gtcacgcatt ctgcacagac cagcccaaca  7620
gttccctgga caacttccat ttttttccat agtaaatcag acaccacacc ttcaatgacc  7680
accagtcatg gggcagaatc cagttcagct gttccaactc caactgtttc aactgaggta  7740
ccaggagtag tgacccctttt ggtcaccagt tctagggcag tgatcagtac aactattcca  7800
attctgactc tttctcctgg tgaaccagag accacacctt caatggccac cagtcatggg  7860
gaagaagcca gttctgctat tccaactcca actgtttcac ctggggtacc aggagtggtg  7920
acctctctgg tcactagttc tagggcagtg actagtacaa ctattccaat tctgactttt  7980
tctcttggtg aaccagagac cacaccttca atggccacca gtcatgggac agaagctggc  8040
tcagctgttc caactgtttt acctgaggta ccaggaatgg tgacctctct ggttgctagt  8100
tctagggcag taaccagtac aactcttcca actctgactc tttctcctgg tgaaccagag  8160
accacacctt caatggccac cagtcatggg gcagaagcca gctcaactgt tccaactgtt  8220
tcacctgagg taccaggagt ggtgacctct ctggtcacta gttctagtgg agtaaacagt  8280
acaagtattc caactctgat tctttctcct ggtgaactag aaaccacacc ttcaatggcc  8340
accagtcatg gggcagaagc cagctcagct gttccaactc caactgtttc acctggggta  8400
tcaggagtgg tgacccctct ggtcactagt tccagggcag tgaccagtac aactattcca  8460
attctaactc tttcttctag tgagccagag accacacctt caatggccac cagtcatggg  8520
gtagaagcca gctcagctgt tctaactgtt tcacctgagg taccaggaat ggtgaccttt  8580
ctggtcacta gttctagagc agtaaccagt acaactattc caactctgac tatttcttct  8640
gatgaaccag agaccacaac ttcattggtc acccattctg aggcaaagat gatttcagcc  8700
attccaactt taggtgtctc ccctactgta caagggctgg tgacttcact ggtcactagt  8760
tctgggtcag agaccagtgc gttttcaaat ctaactgttg cctcaagtca accagagacc  8820
atagactcat gggtcgctca tcctgggaca gaagcaagtt ctgttgttcc aactttgact  8880
gtctccactg gtgagccgtt tacaaatatc tcattggtca cccatcctgc agagagtagc  8940
tcaactcttc ccaggacaac ctcaaggttt tcccacagtg aattagacac tatgccttct  9000
acagtcacca gtcctgaggc agaatccagc tcagccattt caacaactat ttcacctggt  9060
ataccaggtg tgctgacatc actggtcact agctctggga gagacatcag tgcaactttt  9120
ccaacagtgc ctgagtcccc acatgaatca gaggcaacag cctcatgggt tactcatcct  9180
```

-continued

```
gcagtcacca gcacaacagt tcccaggaca acccctaatt attctcatag tgaaccagac  9240
accacaccat caatagccac cagtcctggg gcagaagcca cttcagattt tccaacaata  9300
actgtctcac ctgatgtacc agatatggta acctcacagg tcactagttc tgggacagac  9360
accagtataa ctattccaac tctgactctt tcttctggtg agccagagac cacaacctca  9420
tttatcacct attctgagac acatacaagt tcagccattc caactctccc tgtctcccct  9480
gatgcatcaa agatgctgac ctcactggtc atcagttctg ggacagacag cactacaact  9540
ttcccaacac tgacggagac cccatatgaa ccagagacaa cagccataca gctcattcat  9600
cctgcagaga ccaacacaat ggttcccagg acaactccca agttttccca tagtaagtca  9660
gacaccacac tcccagtagc catcaccagt cctgggccag aagccagttc agctgtttca  9720
acgacaacta tctcacctga tatgtcagat ctggtgacct cactggtccc tagttctggg  9780
acagacacca gtacaacctt cccaacattg agtgagaccc catatgaacc agagactaca  9840
gccacgtggc tcactcatcc tgcagaaacc agcacaacgg tttctgggac aattcccaac  9900
ttttcccata ggggatcaga cactgcaccc tcaatggtca ccagtcctgg agtagacacg  9960
aggtcaggtg ttccaactac aaccatccca cccagtatac caggggtagt gacctcacag  10020
gtcactagtt ctgcaacaga cactagtaca gctattccaa ctttgactcc ttctcctggt  10080
gaaccagaga ccacagcctc atcagctacc catcctggga cacagactgg cttcactgtt  10140
ccaattcgga ctgttccctc tagtgagcca gatacaatgg cttcctgggt cactcatcct  10200
ccacagacca gcacacctgt ttccagaaca acctccagtt tttcccatag tagtccagat  10260
gccacacctg taatggccac cagtcctagg acagaagcca gttcagctgt actgacaaca  10320
atctcacctg gtgcaccaga gatggtgact tcacagatca ctagttctgg ggcagcaacc  10380
agtacaactg ttccaacttt gactcattct cctggtatgc cagagaccac agccttattg  10440
agcacccatc ccagaacaga gacaagtaaa acatttcctg cttcaactgt gtttcctcaa  10500
gtatcagaga ccacagcctc actcaccatt agacctggtg cagagactag cacagctctc  10560
ccaactcaga caacatcctc tctcttcacc ctacttgtaa ctggaaccag cagagttgat  10620
ctaagtccaa ctgcttcacc tggtgtttct gcaaaaacag ccccactttc cacccatcca  10680
gggacagaaa ccagcacaat gattccaact tcaactcttt cccttggttt actagagact  10740
acaggcttac tggccaccag ctcttcagca gagaccagca cgagtactct aactctgact  10800
gtttcccctg ctgtctctgg gctttccagt gcctctataa caactgataa gccccaaact  10860
gtgacctcct ggaacacaga aacctcacca tctgtaactt cagttggacc cccagaattt  10920
tccaggactg tcacaggcac cactatgacc ttgataccat cagagatgcc aacaccacct  10980
aaaaccagtc atggagaagg agtgagtcca accactatct tgagaactac aatggttgaa  11040
gccactaatt tagctaccac aggttccagt cccactgtgg ccaagacaac aaccaccttc  11100
aatacactgg ctggaagcct ctttactcct ctgaccacac ctgggatgtc caccttggcc  11160
tctgagagtg tgacctcaag aacaagttat aaccatcggt cctggatctc caccaccagc  11220
agttataacc gtcggtactg gacccctgcc accagcactc cagtgacttc tacattctcc  11280
ccagggattt ccacatcctc catccccagc tccacagcag ccacagtccc attcatggtg  11340
ccattcaccc tcaacttcac catcaccaac ctgcagtacg aggaggacat gcggcaccct  11400
ggttcaagga agttcaacgc cacagagaga gaactgcagg gtctgctcaa acccttgttc  11460
aggaatagca gtctggaata cctctattca ggctgcagac tagcctcact caggccagag  11520
aaggatagct cagccacggc agtggatgcc atctgcacac atcgccctga ccctgaagac  11580
ctcggactgg acagagagcg actgtactgg gagctgagca atctgacaaa tggcatccag  11640
gagctgggcc cttacaccct ggaccggaac agtctctatg tcaatggttt cacccatcga  11700
agctctatgc ccaccaccag cactcctggg acctccacag tggatgtggg aacctcaggg  11760
actccatcct ccagccccag ccccacgact gctggccctc tcctgatgcc gttcaccctc  11820
aacttcacca tcaccaacct gcagtacgag gaggacatgc gtcgcactgg ctccaggaag  11880
ttcaacacca tggagagtgt cctgcagggt ctgctcaagc cattgttcaa gaacaccagt  11940
gttggccctt tgtactctgg ctgcagattg accttgctca ggcccgagaa agatggggca  12000
gccactggag tggatgccat ctgcacccac cgccttgacc ccaaaagccc tggactcaac  12060
agggagcagc tgtactggga gctaagcaaa ctgaccaatg acattgaaga gctgggcccc  12120
tacaccctgg acaggaacag tctctatgtc aatggtttca cccatcagag ctctgtgtcc  12180
accaccagca ctcctgggac ctccacagtg gatctcagaa cctcagggac tccatcctcc  12240
ctctccagcc ccacaattat ggctgctggc cctctcctgg taccattcac cctcaacttc  12300
accatcacca acctgcagta tggggaggac atgggtcacc ctggctccag gaagttcaac  12360
accacagaga gggtcctgca gggtctgctt ggtcccatat tcaagaacac cagtgttggc  12420
cctctgtact ctggctgcag actgacctct ctcaggtccg agaaggatgg agcagccact  12480
ggagtggatg ccatctgcat ccatcatctt gaccccaaaa gccctggact caacagagag  12540
cggctgtact gggagctgag ccaactgacc aatggcatca aagagctggg cccctacacc  12600
ctggacagga acagtctcta tgtcaatggt ttcacccatc ggacctctgt gcccaccacc  12660
agcactcctg ggacctccac agtggacctt ggaacctcag ggactccatt ctccctccca  12720
agccccgcaa ctgctggccc tctcctggtg ctgttcaccc tcaacttcac catcaccaac  12780
ctgaagtatg aggaggacat gcatcgccct ggctccagga agttcaacac cactgagagg  12840
gtcctgcaga ccctggttgg tcctatgttc aagaacacca gtgttggcct tctgtactct  12900
ggctgcagac tgaccttgct caggtccgag aaggatggag cagccactgg agtggatgcc  12960
atctgcaccc accgtcttga ccccaaaagc cctggagtgg acagggagca gctatactgg  13020
gagctgagcc aactgaccaa tggcatcaaa gagctgggcc cctacaccct ggacaggaac  13080
agtctctatg tcaatggttt cacccattgg atccctgtgc ccaccagcag cacccctggg  13140
acctccacag tggaccttgg gtcagggact ccatcctccc tccccagccc cacaagtgct  13200
actgctggcc ctctcctggt gccgttcacc ctcaacttca ccatcaccaa cctgaagtac  13260
gaggaggaca tgcattgccc tggctccagg aagttcaaca ccacagagag agtcctgcag  13320
agtctgcttg gtcccatgtt caagaacacc agtgttggcc ctctgtactc tggctgcaga  13380
ctgaccttgc tcaggtccga gaaggatgga gcagccactg gagtggatgc catctgcacc  13440
caccgtcttg accccaaaag ccctggagtg gacagggagc agctatactg ggagctgagc  13500
cagctgacca atggcatcaa agagctgggt ccctacaccc tggacagaaa cagtctctat  13560
gtcaatggtt tcacccatca gacctctgcg cccaacacca gcactcctgg gacctccaca  13620
gtggaccttg ggacctcagg gactccatcc tccctcccca gccctacatc tgctggccct  13680
ctcctggtgc cattcaccct caacttcacc atcaccaacc tgcagtacga ggaggacatg  13740
catcacccag gctccaggaa gttcaacacc acggagcggg tcctgcaggg tctgcttggt  13800
cccatgttca agaacaccag tgtcggcctt ctgtactctg gctgcagact gaccttgctc  13860
aggcctgaga agaatggggc agccactgga atggatgcca tctgcagcca ccgtcttgac  13920
```

-continued

```
cccaaaagcc ctggactcaa cagagagcag ctgtactggg agctgagcca gctgacccat  13980
ggcatcaaag agctgggccc ctacaccctg gacaggaaca gtctctatgt caatggtttc  14040
acccatcgga gctctgtggc ccccaccagc actcctggga cctccacagt ggaccttggg  14100
acctcaggga ctccatcctc cctccccagc cccacaacag ctgttcctct cctggtgccg  14160
ttcaccctca actttaccat caccaatctg cagtatgggg aggacatgcg tcaccctggc  14220
tccaggaagt tcaacaccac agagagggtc ctgcagggtc tgcttggtcc cttgttcaag  14280
aactccagtg tcggccctct gtactctggc tgcagactga tctctctcag gtctgagaag  14340
gatggggcag ccactggagt ggatgccatc tgcacccacc accttaaccc tcaaagccct  14400
ggactggaca gggagcagct gtactggcag ctgagccaga tgaccaatgg catcaaagag  14460
ctgggcccct acaccctgga ccggaacagt ctctacgtca atggtttcac ccatcggagc  14520
tctgggctca ccaccagcac tccttggact tccacagttg accttggaac ctcagggact  14580
ccatcccccg tccccagccc cacaactgct ggccctctcc tggtgccatt caccctaaac  14640
ttcaccatca ccaacctgca gtatgaggag gacatgcatc gccctggatc taggaagttc  14700
aacgccacag agagggtcct gcagggtctg cttagtccca tattcaagaa ctccagtgtt  14760
ggccctctgt actctggctg cagactgacc tctctcaggc ccgagaagga tggggcagca  14820
actggaatgg atgctgtctg cctctaccac cctaatccca aaagacctgg gctggacaga  14880
gagcagctgt actgggagct aagccagctg acccacaaca tcactgagct gggcccctac  14940
agcctggaca gggacagtct ctatgtcaat ggtttcaccc atcagaactc tgtgcccacc  15000
accagtactc ctgggacctc cacagtgtac tgggcaacca ctgggactcc atcctccttc  15060
cccggccaca cagagcctgg ccctctcctg ataccattca ctttcaactt taccatcacc  15120
aacctgcatt atgaggaaaa catgcaacac cctggttcca ggaagttcaa caccacggag  15180
agggttctgc agggtctgct caagcccttg ttcaagaaca ccagtgttgg ccctctgtac  15240
tctggctgca gactgacctt gctcagacct gagaagcagg aggcagccac tggagtggac  15300
accatctgta cccaccgcgt tgatcccatc ggacctggac tggacagaga gcggctatac  15360
tgggagctga gccagctgac caacagcatc acagagctgg gaccctacac cctggatagg  15420
gacagtctct atgtcaatgg cttcaaccct tggagctctg tgccaaccac cagcactcct  15480
gggacctcca cagtgcacct ggcaacctct gggactccat cctccctgcc tggccacaca  15540
gcccctgtcc ctctcttgat accattcacc ctcaacttta ccatcaccaa cctgcattat  15600
gaagaaaaca tgcaacaccc tggttccagg aagttcaaca ccacggagag ggttctgcag  15660
ggtctgctca agcccttgtt caagagcacc agcgttggcc ctctgtactc tggctgcaga  15720
ctgaccttgc tcagacctga gaaacatggg gcagccactg gagtggacgc catctgcacc  15780
ctccgccttg atcccactgg tcctggactg gacagagagc ggctatactg ggagctgagc  15840
cagctgacca acagcgttac agagctgggc ccctacaccc tggacaggga cagtctctat  15900
gtcaatggct tcacccatcg gagctctgtg ccaaccacca gtattcctgg gacctctgca  15960
gtgcacctgg aaacctctgg gactccagcc tccctccctg gccacacagc cccaggccct  16020
ctcctggtgc cattcaccct caacttcact atcaccaacc tgcagtatga ggaggacatg  16080
cgtcaccctg gttccaggaa gttcaacacc acggagagag tcctgcaggg tctgctcaag  16140
cccttgttca agagcaccag tgttggccct ctgtactctg gctgcagact gaccttgctc  16200
aggcctgaaa aacgtggggc agccaccggc gtggacacca tctgcactca ccgccttgac  16260
cctctaaacc ctggactgga cagagagcag ctatactggg agctgagcaa actgacccgt  16320
ggcatcatcg agctgggccc ctacctcctg gacagaggca gtctctatgt caatggtttc  16380
acccatcgga actttgtgcc catcaccagc actcctggga cctccacagt acacctagga  16440
acctctgaaa ctccatcctc cctacctaga cccatagtgc ctggccctct cctggtgcca  16500
ttcaccctca acttcaccat caccaacttg cagtatgagg aggccatgcg acaccctggc  16560
tccaggaagt tcaataccac ggagagggtc ctacagggtc tgctcaggcc cttgttcaag  16620
aataccagta tcggccctct gtactccagc tgcagactga ccttgctcag gccagagaag  16680
gacaaggcag ccaccagagt ggatgccatc tgtacccacc accctgaccc tcaaagccct  16740
ggactgaaca gagagcagct gtactgggag ctgagccagc tgacccacgg catcactgag  16800
ctgggcccct acaccctgga cagggacagt ctctatgtcg atggtttcac tcattggagc  16860
cccataccaa ccaccagcac tcctgggacc tccatagtga acctgggaac ctctgggatc  16920
ccaccttccc tccctgaaac tacagccacc ggccctctcc tggtgccatt cacactcaac  16980
ttcaccatca ctaacctaca gtatgaggag aacatgggtc accctggctc caggaagttc  17040
aacatcacgg agagtgttct gcagggtctg ctcaagccct tgttcaagag caccagtgtt  17100
ggccctctgt attctggctg cagactgacc ttgctcaggc ctgagaagga cggagtagcc  17160
accagagtgg acgccatctg cacccaccgc cctgacccca aaatccctgg gctagacaga  17220
cagcagctat actgggagct gagccagctg acccacagca tcactgagct gggaccctac  17280
accctggata gggacagtct ctatgtcaat ggtttcaccc agcggagctc tgtgcccacc  17340
accagcactc ctgggacttt cacagtacag ccggaaacct ctgagactcc atcatccctc  17400
cctggcccca cagccactgg ccctgtcctg ctgccattca ccctcaattt taccatcatt  17460
aacctgcagt atgaggagga catgcatcgc cctggctcca ggaagttcaa caccacggag  17520
agggtccttc agggtctgct tatgcccttg ttcaagaaca ccagtgtcag ctctctgtac  17580
tctggttgca gactgacctt gctcaggcct gagaaggatg gggcagccac cagagtggat  17640
gctgtctgca cccatcgtcc tgaccccaaa agccctggac tggacagaga gcggctgtac  17700
tggaagctga gccagctgac ccacggcatc actgagctgg gcccctacac cctggacagg  17760
cacagtctct atgtcaatgg tttcacccat cagagctcta tgacgaccac cagaactcct  17820
gatacctcca caatgcacct ggcaacctcg agaactccag cctccctgtc tggacctacg  17880
accgccagcc ctctcctggt gctattcaca attaacttca ccatcactaa cctgcggtat  17940
gaggagaaca tgcatcaccc tggctctaga aagtttaaca ccacggagag agtccttcag  18000
ggtctgctca ggcctgtgtt caagaacacc agtgttggcc ctctgtactc tggctgcaga  18060
ctgaccttgc tcaggcccaa gaaggatggg gcagccacca aagtggatgc catctgcacc  18120
taccgccctg atcccaaaag ccctggactg gacagagagc agctatactg ggagctgagc  18180
cagctaaccc acagcatcac tgagctgggc ccctacaccc tggacaggga cagtctctat  18240
gtcaatggtt tcacacagcg gagctctgtg cccaccacta gcattcctgg gacccccaca  18300
gtggacctgg gaacatctgg gactccagtt tctaaacctg gtccctcggc tgccagccct  18360
ctcctggtgc tattcactct caacttcacc atcaccaacc tgcggtatga ggagaacatg  18420
cagcaccctg gctccaggaa gttcaacacc acggagaggg tccttcaggg cctgctcagg  18480
tccctgttca agagcaccag tgttggccct ctgtactctg gctgcagact gactttgctc  18540
aggcctgaaa aggatgggac agccactgga gtggatgcca tctgcaccca ccaccctgac  18600
cccaaaagcc ctaggctgga cagagagcag ctgtattggg agctgagcca gctgacccac  18660
```

-continued

```
aatatcactg agctgggccc ctatgccctg gacaacgaca gcctctttgt caatggtttc  18720
actcatcgga gctctgtgtc caccaccagc actcctggga cccccacagt gtatctggga  18780
gcatctaaga ctccagcctc gatatttggc ccttcagctg ccagccatct cctgatacta  18840
ttcaccctca acttcaccat cactaacctg cggtatgagg agaacatgtg gcctggctcc  18900
aggaagttca acactacaga gagggtcctt cagggcctgc taaggccctt gttcaagaac  18960
accagtgttg gccctctgta ctctggctgc aggctgacct tgctcaggcc agagaaagat  19020
ggggaagcca ccggagtgga tgccatctgc acccaccgcc ctgaccccac aggccctggg  19080
ctggacagag agcagctgta tttggagctg agccagctga cccacagcat cactgagctg  19140
ggcccctaca cactggacag ggacagtctc tatgtcaatg gtttcaccca tcggagctct  19200
gtacccacca ccagcaccgg ggtggtcagc gaggagccat tcacactgaa cttcaccatc  19260
aacaacctgc gctacatggc ggacatgggc caacccggct ccctcaagtt caacatcaca  19320
gacaacgtca tgcagcacct gctcagtcct ttgttccaga ggagcagcct gggtgcacgg  19380
tacacaggct gcagggtcat cgcactaagg tctgtgaaga acggtgctga gacacgggtg  19440
gacctcctct gcacctacct gcagcccctc agcggcccag gtctgcctat caagcaggtg  19500
ttccatgagc tgagccagca gacccatggc atcacccggc tgggccccta ctctctggac  19560
aaagacagcc tctaccttaa cggttacaat gaacctggtc cagatgagcc tcctacaact  19620
cccaagccag ccaccacatt cctgcctcct ctgtcagaag ccacaacagc catggggtac  19680
cacctgaaga ccctcacact caacttcacc atctccaatc tccagtattc accagatatg  19740
ggcaagggct cagctacatt caactccacc gagggggtcc ttcagcacct gctcagaccc  19800
ttgttccaga agagcagcat gggccccttc tacttgggtt gccaactgat ctccctcagg  19860
cctgagaagg atggggcagc cactggtgtg gacaccacct gcacctacca ccctgaccct  19920
gtgggccccg ggctggacat acagcagctt tactgggagc tgagtcagct gacccatggt  19980
gtcacccaac tgggcttcta tgtcctggac agggatagcc tcttcatcaa tggctatgca  20040
ccccagaatt tatcaatccg gggcgagtac cagataaatt tccacattgt caactggaac  20100
ctcagtaatc cagaccccac atcctcagag tacatcaccc tgctgaggga catccaggac  20160
aaggtcacca cactctacaa aggcagtcaa ctacatgaca cattccgctt ctgcctggtc  20220
accaacttga cgatggactc cgtgttggtc actgtcaagg cattgttctc ctccaatttg  20280
gaccccagcc tggtggagca agtctttcta gataagaccc tgaatgcctc attccattgg  20340
ctgggctcca cctaccagtt ggtggacatc catgtgacag aaatggagtc atcagtttat  20400
caaccaacaa gcagctccag cacccagcac ttctacctga atttcaccat caccaaccta  20460
ccatattccc aggacaaagc ccagccaggc accaccaatt accagaggaa caaaaggaat  20520
attgaggatg cgctcaacca actcttccga aacagcagca tcaagagtta tttttctgac  20580
tgtcaagttt caacattcag gtctgtcccc aacaggcacc acaccggggt ggactccctg  20640
tgtaacttct cgccactggc tcggagagta gacagagttg ccatctatga ggaatttctg  20700
cggatgaccc ggaatggtac ccagctgcag aacttcaccc tggacaggag cagtgtcctt  20760
gtggatgggt attctcccaa cagaaatgag cccttaactg ggaattctga ccttcccttc  20820
tgggctgtca tcctcatcgg cttggcagga ctcctgggac tcatcacatg cctgatctgc  20880
ggtgtcctgg tgaccacccg ccggcggaag aaggaaggag aatacaacgt ccagcaacag  20940
tgcccaggct actaccagtc acacctagac ctggaggatc tgcaatgact ggaacttgcc  21000
ggtgcctggg gtgcctttcc cccagccagg gtccaaagaa gcttggctgg ggcagaaata  21060
aaccatattg gtcggaaaaa aaaaaaaaaa aaaaaaaaaa aaaaaaaaaa aa          21112

SEQ ID NO: 52          moltype = AA  length = 6995
FEATURE                Location/Qualifiers
source                 1..6995
                       mol_type = protein
                       organism = Homo sapiens
SEQUENCE: 52
PVTSLLTPGL VITTDRMGIS REPGTSSTSN LSSTSHERLT TLEDTVDTEA MQPSTHTAVT  60
NVRTSISGHE SQSSVLSDSE TPKATSPMGT TYTMGETSVS ISTSDFFETS RIQIEPTSSL  120
TSGLRETSSS ERISSATEGS TVLSEVPSGA TTEVSRTEVI SSRGTSMSGP DQFTISPDIS  180
TEAITRLSTS PIMTESAESA ITIETGSPGA TSEGTLTLDT STTTFWSGTH STASPGFSHS  240
EMTTLMSRTP GDVPWPSLPS VEEASSVSSS LSSPAMTSTS FFSTLPESIS SSPHPVTALL  300
TLGPVKTTDM LRTSSEPETS SPPNLSSTSA EILATSEVTK DREKIHPSSN TPVVNVGTVI  360
YKHLSPSSVL ADLVTTKPTS PMATTSTLGN TSVSTSTPAF PETMMTQPTS SLTSGLREIS  420
TSQETSSATE RSASLSGMPT GATTKVSRTE ALSLGRTSTP GPAQSTISPE ISTETITRIS  480
TPLTTTGSAE MTITPKTGHS GASSQGTFTL DTSSRASWPG THSAATHRSP HSGMTTPMSR  540
GPEDVSWPSR PSVEKTSPPS SLVSLSAVTS PSPLYSTPSE SSHSSPLRVT SLFTPVMMKT  600
TDMLDTSLEP VTTSPPSMNI TSDESLATSK ATMETEAIQL SENTAVTQMG TISARQEFYS  660
SYPGLPEPSK VTSPVVTSST IKDIVSTTIP ASSEITRIEM ESTSTLTPTP RETSTSQEIH  720
SATKPSTVPY KALTSATIED SMTQVMSSSR GPSPDQSTMS QDISTEVITR LSTSPIKTES  780
TEMTITTQTG SPGATSRGTL TLDTSTTFMS GTHSTASQGF SHSQMTALMS RTPGEVPWLS  840
HPSVEEASSA SFSLSSPVMT SSSPVSSTLP DSIHSSSLPV TSLLTSGLVK TTELLGTSSE  900
PETSSPPNLS STSAEILATT EVTTDTEKLE MTNVVTSGYT HESPSSVLAD SVTTKATSSM  960
GITYPTGDTN VLTSTPAFSD TSRIQTKSKL SLTPGLMETS ISEETSSATE KSTVLSSVPT  1020
GATTEVSRTE AISSSRTSIP GPAQSTMSSD TSMETITRIS TPLTRKESTD MAITPKTGPS  1080
GATSQGTFTL DSSSTASWPG THSATTQRFP RSVVTTPMSR GPEDVSWPSP LSVEKNSPPS  1140
SLVSSSSVTS PSPLYSTPSG SSHSSPVPVT SLFTSIMMKA TDMLDASLEP ETTSAPNMNI  1200
TSDESLAASK ATTETEAIHV FENTAASHVE TTSATEELYS SSPGFSEPTK VISPVVTSSS  1260
IRDNMVSTTM PGSSGITRIE IESMSSLTPG LRETRTSQDI TSSTETSTVL YKMPSGATPE  1320
VSRTEVMPSS RTSIPGPAQS TMSLDISDEV VTRLSTSPIM TESAEITITT QTGYSLATSQ  1380
VTLPLGTSMT FLSGTHSTMS QGLSHSEMTN LMSRGPESLS WTSPRFVETT RSSSSLTSLP  1440
LTTSLSPVSS TLLDSSPSSP LPVTSLILPG LVKTTEVLDT SSEPKTSSSP NLSSTSVEIP  1500
ATSEIMTDTE KIHPSSNTAV AKVRTSSSVH ESHSSVLADS ETTITIPSMG ITSAVEDTTV  1560
FTSNPAFSET RRIPTEPTFS LTPGFRETST SEETTSITET SAVLFGVPTS ATTEVSMTEI  1620
MSSNRTHIPD SDQSTMSPDI ITEVITRLSS SSMMSESTQM TITTQKSSPG ATAQSTLTLA  1680
TTTAPLARTH STVPPRFLHS EMTTLMSRSP ENPSWKSSPF VEKTSSSSSL LSLPVTTSPS  1740
VSSTLPQSIP SSSFSVTSLL TPGMVKTTDT STEPGTSLSP NLSGTSVEIL AASEVTTDTE  1800
KIHPSSSMAV TNVGTTSSGH ELYSSVSIHS EPSKATYPVG TPSSMAETSI STSMPANFET  1860
```

-continued

```
TGFEAEPFSH LTSGLRKTNM SLDTSSVTPT NTPSSPGSTH LLQSSKTDFT SSAKTSSPDW  1920
PPASQYTEIP VDIITPFNAS PSITESTGIT SFPESRFTMS VTESTHHLST DLLPSAETIS  1980
TGTVMPSLSE AMTSFATTGV PRAISGSGSP FSRTESGPGD ATLSTIAESL PSSTPVPFSS  2040
STFTTTDSST IPALHEITSS SATPYRVDTS LGTESSTTEG RLVMVSTLDT SSQPGRTSSS  2100
PILDTRMTES VELGTVTSAY QVPSLSTRLT RTDGIMEHIT KIPNEAAHRG TIRPVKGPQT  2160
STSPASPKGL HTGGTKRMET TTTALKTTTT ALKTTSRATL TTSVYTPTLG TLTPLNASMQ  2220
MASTIPTEMM ITTPYVFPDV PETTSSLATS LGAETSTALP RTTPSVFNRE SETTASLVSR  2280
SGAERSPVIQ TLDVSSSEPD TTASWVIHPA ETIPTVSKTT PNFFHSELDT VSSTATSHGA  2340
DVSSAIPTNI SPSELDALTP LVTISGTDTS TTFPTLTKSP HETETRTTWL THPAETSSTI  2400
PRTIPNFSHH ESDATPSIAT SPGAETSSAI PIMTVSPGAE DLVTSQVTSS GTDRNMTIPT  2460
LTLSPGEPKT IASLVTHPEA QTSSAIPTST ISPAVSRLVT SMVTSLAAKT STTNRALTNS  2520
PGEPATTVSL VTHSAQTSPT VPWTTSIFFH SKSDTTPSMT TSHGAESSSA VPTPTVSTEV  2580
PGVVTPLVTS SRAVISTTIP ILTLSPGEPE TTPSMATSHG EEASSAIPTP TVSPGVPGVV  2640
TSLVTSSRAV TSTTIPILTF SLGEPETTPS MATSHGTEAG SAVPTVLPEV PGMVTSLVAS  2700
SRAVTSTTLP TLTLSPGEPE TTPSMATSHG AEASSTVPTV SPEVPGVVTS LVTSSSGVNS  2760
TSIPTLILSP GELETTPSMA TSHGAEASSA VPTPTVSPGV SGVVTPLVTS SRAVTSTTIP  2820
ILTLSSSEPE TTPSMATSHG VEASSAVLTV SPEVPGMVTF LVTSSRAVTS TTIPTLTISS  2880
DEPETTTSLV THSEAKMISA IPTLGVSPTV QGLVTSLVTS SGSETSAFSN LTVASSQPET  2940
IDSWVAHPGT EASSVVPTLT VSTGEPFTNI SLVTHPAESS STLPRTTSRF SHSELDTMPS  3000
TVTSPEAESS SAISTTISPG IPGVLTSLVT SSGRDISATF PTVPESPHES EATASWVTHP  3060
AVTSTTVPRT TPNYSHSEPD TTPSIATSPG AEATSDFPTI TVSPDVPDMV TSQVTSSGTD  3120
TSITIPTLTL SSGEPETTTS FITYSETHTS SAIPTLPVSP DASKMLTSLV ISSGTDSTTT  3180
FPTLTETPYE PETTAIQLIH PAETNTMVPR TTPKFSHSKS DTTLPVAITS PGPEASSAVS  3240
TTTISPDMSD LVTSLVPSSG TDTSTTFPTL SETPYEPETT ATWLTHPAET STTVSGTIPN  3300
FSHRGSDTAP SMVTSPGVDT RSGVPTTTIP PSIPGVVTSQ VTSSATDTST AIPTLTPSPG  3360
EPETTASSAT HPGTQTGFTV PIRTVPSSEP DTMASWVTHP PQTSTPVSRT TSSFSHSSPD  3420
ATPVMATSPR TEASSAVLTT ISPGAPEMVT SQITSSGAAT STTVPTLTHS PGMPETTALL  3480
STHPRTETSK TFPASTVFPQ VSETTASLTI RPGAETSTAL PTQTTSSLFT LLVTGTSRVD  3540
LSPTASPGVS AKTAPLSTHP GTETSTMIPT STLSLGLLET TGLLATSSSA ETSTSTLTLT  3600
VSPAVSGLSS ASITTDKPQT VTSWNTETSP SVTSVGPPEF SRTVTGTTMT LIPSEMPTPP  3660
KTSHGEGVSP TTILRTTMVE ATNLATTGSS PTVAKTTTTF NTLAGSLFTP LTTPGMSTLA  3720
SESVTSRTSY NHRSWISTTS SYNRRYWTPA TSTPVTSTFS PGISTSSIPS STAATVPFMV  3780
PFTLNFTITN LQYEEDMRHP GSRKFNATER ELQGLLKPLF RNSSLEYLYS GCRLASLRPE  3840
KDSSATAVDA ICTHRPDPED LGLDRERLYW ELSNLTNGIQ ELGPYTLDRN SLYVNGFTHR  3900
SSMPTTSTPG TSTVDVGTSG TPSSSPSPTT AGPLLMPFTL NFTITNLQYE EDMRRTGSRK  3960
FNTMESVLQG LLKPLFKNTS VGPLYSGCRL TLLRPEKDGA ATGVDAICTH RLDPKSPGLN  4020
REQLYWELSK LTNDIEELGP YTLDRNSLYV NGFTHQSSVS TTSTPGTSTV DLRTSGTPSS  4080
LSSPTIMAAG PLLVPFTLNF TITNLQYGED MGHPGSRKFN TTERVLQGLL GPIFKNTSVG  4140
PLYSGCRLTS LRSEKDGAAT GVDAICIHHL DPKSPGLNRE RLYWELSQLT NGIKELGPYT  4200
LDRNSLYVNG FTHRTSVPTT STPGTSTVDL GTSGTPFSLP SPATAGPLLV LFTLNFTITN  4260
LKYEEDMHRP GSRKFNTTER VLQTLVGPMF KNTSVGLLYS GCRLTLLRSE KDGAATGVDA  4320
ICTHRLDPKS PGVDREQLYW ELSQLTNGIK ELGPYTLDRN SLYVNGFTHW IPVPTSSTPG  4380
TSTVDLGSGT PSSLPSPTSA TAGPLLVPFT LNFTITNLKY EEDMHCPGSR KFNTTERVLQ  4440
SLLGPMFKNT SVGPLYSGCR LTLLRSEKDG AATGVDAICT HRLDPKSPGV DREQLYWELS  4500
QLTNGIKELG PYTLDRNSLY VNGFTHQTSA PNTSTPGTST VDLGTSGTPS SLPSPTSAGP  4560
LLVPFTLNFT ITNLQYEEDM HHPGSRKFNT TERVLQGLLG PMFKNTSVGL LYSGCRLTLL  4620
RPEKNGAATG MDAICSHRLD PKSPGLNREQ LYWELSQLTH GIKELGPYTL DRNSLYVNGF  4680
THRSSVAPTS TPGTSTVDLG TSGTPSSLPS PTTAVPLLVP FTLNFTITNL QYGEDMRHPG  4740
SRKFNTTERV LQGLLGPLFK NSSVGPLYSG CRLISLRSEK DGAATGVDAI CTHHLNPQSP  4800
GLDREQLYWQ LSQMTNGIKE LGPYTLDRNS LYVNGFTHRS SGLTTSTPWT STVDLGTSGT  4860
PSPVPSPTTA GPLLVPFTLN FTITNLQYEE DMHRPGSRKF NATERVLQGL LSPIFKNSSV  4920
GPLYSGCRLT SLRPEKDGAA TGMDAVCLYH PNPKRPGLDR EQLYWELSQL THNITELGPY  4980
SLDRDSLYVN GFTHQNSVPT TSTPGTSTVY WATTGTPSSF PGHTEPGPLL IPFTFNFTIT  5040
NLHYEENMQH PGSRKFNTTE RVLQGLLKPL FKNTSVGPLY SGCRLTLLRP EKQEAATGVD  5100
TICTHRVDPI GPGLDRERLY WELSQLTNSI TELGPYTLDR DSLYVNGFNP WSSVPTTSTP  5160
GTSTVHLATS GTPSSLPGHT APVPLLIPFT LNFTITNLHY EENMQHPGSR KFNTTERVLQ  5220
GLLKPLFKST SVGPLYSGCR LTLLRPEKHG AATGVDAICT LRLDPTGPGL DRERLYWELS  5280
QLTNSVTELG PYTLDRDSLY VNGFTHRSSV PTTSIPGTSA VHLETSGTPA SLPGHTAPGP  5340
LLVPFTLNFT ITNLQYEEDM RHPGSRKFNT TERVLQGLLK PLFKSTSVGP LYSGCRLTLL  5400
RPEKRGAATG VDTICTHRLD PLNPGLDREQ LYWELSKLTR GIIELGPYLL DRGSLYVNGF  5460
THRNFVPITS TPGTSTVHLG TSETPSSLPR PIVPGPLLVP FTLNFTITNL QYEEAMRHPG  5520
SRKFNTTERV LQGLLRPLFK NTSIGPLYSS CRLTLLRPEK DKAATRVDAI CTHHPDPQSP  5580
GLNREQLYWE LSQLTHGITE LGPYTLDRDS LYVDGFTHWS PIPTTSTPGT SIVNLGTSGI  5640
PPSLPETTAT GPLLVPFTLN FTITNLQYEE NMGHPGSRKF NITESVLQGL LKPLFKSTSV  5700
GPLYSGCRLT LLRPEKDGVA TRVDAICTHR PDPKIPGLDR QQLYWELSQL THSITELGPY  5760
TLDRDSLYVN GFTQRSSVPT TSTPGTFTVQ PETSETPSSL PGPTATGPVL LPFTLNFTII  5820
NLQYEEDMHR PGSRKFNTTE RVLQGLLMPL FKNTSVSSLY SGCRLTLLRP EKDGAATRVD  5880
AVCTHRPDPK SPGLDRERLY WKLSQLTHGI TELGPYTLDR HSLYVNGFTH QSSMTTTRTP  5940
DTSTMHLATS RTPASLSGPT TASPLLVLFT INFTITNLRY EENMHHPGSR KFNTTERVLQ  6000
GLLRPVFKNT SVGPLYSGCR LTLLRPKKDG AATKVDAICT YRPDPKSPGL DREQLYWELS  6060
QLTHSITELG PYTLDRDSLY VNGFTQRSSV PTTSIPGTPT VDLGTSGTPV SKPGPSAASP  6120
LLVLFTLNFT ITNLRYEENM QHPGSRKFNT TERVLQGLLR SLFKSTSVGP LYSGCRLTLL  6180
RPEKDGTATG VDAICTHHPD PKSPRLDREQ LYWELSQLTH NITELGPYAL DNDSLFVNGF  6240
THRSSVSTTS TPGTPTVYLG ASKTPASIFG PSAASHLLIL FTLNFTITNL RYEENMWPGS  6300
RKFNTTERVL QGLLRPLFKN TSVGPLYSGC RLTLLRPEKD GEATGVDAIC THRPDPTGPG  6360
LDREQLYLEL SQLTHSITEL GPYTLDRDSL YVNGFTHRSS VPTTSTGVVS EEPFTLNFTI  6420
NNLRYMADMG QPGSLKFNIT DNVMQHLLSP LFQRSSLGAR YTGCRVIALR SVKNGAETRV  6480
DLLCTYLQPL SGPGLPIKQV FHELSQQTHG ITRLGPYSLD KDSLYLNGYN EPGPDEPPTT  6540
PKPATTFLPP LSEATTAMGY HLKTLTLNFT ISNLQYSPDM GKGSATFNST EGVLQHLLRP  6600
```

-continued

```
LFQKSSMGPF YLGCQLISLR PEKDGAATGV DTTCTYHPDP VGPGLDIQQL YWELSQLTHG  6660
VTQLGFYVLD RDSLFINGYA PQNLSIRGEY QINFHIVNWN LSNPDPTSSE YITLLRDIQD  6720
KVTTLYKGSQ LHDTFRFCLV TNLTMDSVLV TVKALFSSNL DPSLVEQVFL DKTLNASFHW  6780
LGSTYQLVDI HVTEMESSVY QPTSSSSTQH FYLNFTITNL PYSQDKAQPG TTNYQRNKRN  6840
IEDALNQLFR NSSIKSYFSD CQVSTFRSVP NRHHTGVDSL CNFSPLARRV DRVAIYEEFL  6900
RMTRNGTQLQ NFTLDRSSVL VDGYSPNRNE PLTGNSDLPF WAVILIGLAG LLGLITCLIC  6960
GVLVTTRRRK KEGEYNVQQQ CPGYYQSHLD LEDLQ                            6995

SEQ ID NO: 53          moltype = DNA  length = 2187
FEATURE                Location/Qualifiers
source                 1..2187
                       mol_type = other DNA
                       organism = synthetic construct
SEQUENCE: 53
tgccaggctc tccaccccca cttcccaatt gaggaaaccg aggcagagga ggctcagcgc  60
cacgcactcc tctttctgcc tggccggcca ctcccgtctg ctgtgacgcg cggacagaga  120
gctaccggtg gacccacggt gcctccctcc ctgggatcta cacagaccat ggccttgcca  180
acggctcgac ccctgttggg gtcctgtggg acccccgccc tcggcagcct cctgttcctg  240
ctcttcagcc tcggatgggt gcagccctcg aggaccctgg ctggagagac agggcaggag  300
gctgcgcccc tggacggagt cctggccaac ccacctaaca tttccagcct ctcccctcgc  360
caactccttg gcttcccgtg tgcggaggtg tccggcctga gcacggagcg tgtccgggag  420
ctggctgtgg ccttggcaca gaagaatgtc aagctctcaa cagagcagct gcgctgtctg  480
gctcaccggc tctctgagcc ccccgaggac ctggacgccc tcccattgga cctgctgcta  540
ttcctcaacc cagatgcgtt ctcggggccc caggcctgca cccgtttctt ctcccgcatc  600
acgaaggcca atgtggacct gctcccgagg ggggctcccg agcgacagcg gctgctgcct  660
gcggctctgg cctgctgggg tgtgcggggg tctctgctga gcgaggctga tgtgcgggct  720
ctgggaggcc tggcttgcga cctgcctggg cgctttgtgg ccgagtcggc cgaagtgctg  780
ctaccccggc tggtgagctg cccgggaccc ctggaccagg accagcagga ggcagccagg  840
gcggctctgc agggcggggg accccctac ggcccccgt cgacatggtc tgtctccacg  900
atggacgctc tgcggggcct gctgcccgtg ctgggccagc ccatcatccg cagcatcccg  960
cagggcatcg tggccgcgtg gcggcaacgc tcctctcggg acccatcctg gcggcagcct  1020
gaacggacca tcctccggcc gcggttccgg cgggaagtgg agaagacagc ctgtccttca  1080
ggcaagaagg cccgcgagat agacgagagc ctcatcttct acaagaagtg ggagctggaa  1140
gcctgcgtgg atgcggccct gctggccacc cagatggacc gcgtgaacgc catcccttc  1200
acctacgagc agctggacgt cctaaagcat aaactggatg agctctaccc acaaggttac  1260
cccgagtctg tgatccagca cctgggctac ctcttcctca agatgagccc tgaggacatt  1320
cgcaagtgga atgtgacgtc cctggagacc ctgaaggctt tgcttgaagt caacaaaggg  1380
cacgaaatga gtcctcaggt ggccaccctg atcgaccgct ttgtgaaggg aaggggccag  1440
ctagacaaag acaccctaga caccctgacc gccttctacc ctgggtacct gtgctccctc  1500
agccccgagg agctgagctc cgtgcccccc agcagcatct gggcggtcag gccccaggac  1560
ctggacacgt gtgacccaag gcagctggac gtcctctatc ccaaggcccg ccttgctttc  1620
cagaacatga acgggtccga atacttcgtg aagatccagt ccttcctggg tggggccccc  1680
acggaggatt tgaaggcgct cagtcagcag aatgtgagca tggacttggc cacgttcatg  1740
aagctgcgga cggatgcggt gctgccgttg actgtggctg aggtgcagaa acttctggga  1800
ccccacgtgg agggcctgaa ggcggaggag cggcaccgcc cggtgcggga ctggatccta  1860
cggcagcggc aggacgacct ggacacgctg gggctggggc tacagggcgg catccccaac  1920
ggctacctgg tcctagacct cagcatgcaa gaggccctct cggggacgcc ctgcctccta  1980
ggacctggac ctgttctcac cgtcctggca ctgctcctag cctccaccct ggcctgaggg  2040
ccccactccc ttgctggccc cagccctgct ggggatcccc gcctggccag gagcaggcac  2100
gggtggtccc cgttccaccc caagagaact cgcgctcagt aaacgggaac atgccccctg  2160
cagacacgta aaaaaaaaaa aaaaaaa                                     2187

SEQ ID NO: 54          moltype = AA  length = 622
FEATURE                Location/Qualifiers
source                 1..622
                       mol_type = protein
                       organism = Homo sapiens
SEQUENCE: 54
MALPTARPLL GSCGTPALGS LLFLLFSLGW VQPSRTLAGE TGQEAAPLDG VLANPPNISS  60
LSPRQLLGFP CAEVSGLSTE RVRELAVALA QKNVKLSTEQ LRCLAHRLSE PPEDLDALPL  120
DLLLFLNPDA FSGPQACTRF FSRITKANVD LLPRGAPERQ RLLPAALACW GVRGSLLSEA  180
DVRALGGLAC DLPGRFVAES AEVLLPRLVS CPGPLDQDQQ EAARAALQGG GPPYGPPSTW  240
SVSTMDALRG LLPVLGQPII RSIPQGIVAA WRQRSSRDPS WRQPERTILR PRFRREVEKT  300
ACPSGKKARE IDESLIFYKK WELEACVDAA LLATQMDRVN AIPFTYEQLD VLKHKLDELY  360
PQGYPESVIQ HLGYLFLKMS PEDIRKWNVT SLETLKALLE VNKGHEMSPQ VATLIDRFVK  420
GRGQLDKDTL DTLTAFYPGY LCSLSPEELS SVPPSSIWAV RPQDLDTCDP RQLDVLYPKA  480
RLAFQNMNGS EYFVKIQSFL GGAPTEDLKA LSQQNVSMDL ATFMKLRTDA VLPLTVAEVQ  540
KLLGPHVEGL KAEERHRPVR DWILRQRQDD LDTLGLGLQG GIPNGYLVLD LSMQEALSGT  600
PCLLGPGPVL TVLALLLAST LA                                          622

SEQ ID NO: 55          moltype = DNA  length = 4167
FEATURE                Location/Qualifiers
source                 1..4167
                       mol_type = other DNA
                       organism = synthetic construct
SEQUENCE: 55
accttcgcca tatataccg gggcgctgcg ctccacctgg ccgccgcctc cagcccagca  60
cctgcggagg gagcgctgac catggctccc tggcctgaat tgggagatgc ccagcccaac  120
cccgataagt acctcgaagg ggccgcaggt cagcagccca ctgcccctga taaaagcaaa  180
```

-continued

```
gagaccaaca aaacagataa cactgaggca cctgtaacca agattgaact tctgccgtcc  240
tactccacgg ctacactgat agatgagccc actgaggtgg atgacccctg gaacctaccc  300
actcttcagg actcggggat caagtggtca gagagagaca ccaaagggaa gattctctgt  360
ttcttccaag ggattgggag attgatttta cttctcggat ttctctactt tttcgtgtgc  420
tccctggata ttcttagtag cgccttccag ctggttggag gaaaaatggc aggacagttc  480
ttcagcaaca gctctattat gtccaaccct ttgttggggc tggtgatcgg ggtgctggtg  540
accgtcttgg tgcagagctc cagcacctca acgtccatcg ttgtcagcat ggtgtcctct  600
tcattgctca ctgttcgggc tgccatcccc attatcatgg gggccaacat tggaacgtca  660
atcaccaaca ctattgttgc gctcatgcag gtgggagatc ggagtgagtt cagaagagct  720
tttgcaggag ccactgtcca tgacttcttc aactggctgt ccgtgttggt gctcttgccc  780
gtggaggtgg ccacccatta cctcgagatc ataacccagc ttatagtgga gagcttccac  840
ttcaagaatg gagaagatgc cccagatctt ctgaaagtca tcactaagcc cttcacaaag  900
ctcattgtcc agctggataa aaaagttatc agccaaattg caatgaacga tgaaaaagcg  960
aaaaacaaga gtcttgtcaa gatttggtgc aaaactttta ccaacaagac ccagattaac  1020
gtcactgttc cctcgactgc taactgcacc tccccttccc tctgttggac ggatggcatc  1080
caaaactgga ccatgaagaa tgtgacctac aaggagaaca tcgccaaatg ccagcatatc  1140
tttgtgaatt tccacctccc ggatcttgct gtgggcacca tcttgctcat actctccctg  1200
ctggtcctct gtggttgcct gatcatgatt gtcaagatcc tgggctctgt gctcaagggg  1260
caggtcgcca ctgtcatcaa gaagaccatc aacactgatt tccccttttcc ctttgcatgg  1320
ttgactggct acctggccat cctcgtcggg gcaggcatga ccttcatcgt acagagcagc  1380
tctgtgttca cgtcggcctt gaccccccctg attggaatcg gcgtgataac cattgagagg  1440
gcttatccac tcacgctggg ctccaacatc ggcaccacca ccaccgccat cctggccgcc  1500
ttagccagcc ctggcaatgc attgaggagt tcactccaga tcgccctgtg ccactttttc  1560
ttcaacatct ccggcatctt gctgtggtac ccgatcccgt tcactcgcct gcccatccgc  1620
atggccaagg ggctgggcaa catctctgcc aagtatcgct ggttcgccgt cttctacctg  1680
atcatcttct tcttcctgat cccgctgacg gtgtttggcc tctcgctggc cggctggcgg  1740
gtgctggttg gtgtcggggt tcccgtcgtc ttcatcatca tcctggtact gtgcctccga  1800
ctcctgcagt ctcgctgccc acgcgtcctg ccgaagaaac tccagaactg gaacttcctg  1860
ccgctgtgga tgcgctcgct gaagccctgg gatgccgtcg tctccaagtt caccggctgc  1920
ttccagatgc gctgctgctg ctgctgccgc gtgtgctgcc gcgcgtgctg cttgctgtgt  1980
ggctgcccca agtgctgccg ctgcagcaag tgctgcgagg acttggagga ggcgcaggag  2040
gggcaggatg tccctgtcaa ggctcctgag acctttgata acataaccat tagcagagag  2100
gctcagggtg aggtccctgc ctcggactca aagaccgaat gcacggcctt gtaggggacg  2160
ccccagattg tcagggatgg ggggatggtc cttgagtttt gcatgctctc ctccctccca  2220
cttctgcacc ctttcaccac ctcgaggaga tttgctcccc attagcgaat gaaattgatg  2280
cagtcctacc taactcgatt ccctttggct tggtggtagg cctgcagggc acttttattc  2340
caacccctgg tcactcagta atcttttact ccaggaaggc acaggatggt acctaaagag  2400
aattagagaa tgaacctggc gggacggatg tctaatcctg cgcctagctg ggttggtcag  2460
tagaacctat tttcagactc aaaaaccatc ttcagaaaga aaaggcccag ggaaggaatg  2520
tatgagaggc tctcccagat gaggaagtgt actctctatg actatcaagc tcaggcctct  2580
ccctttttttt aaaccaaagt ctggcaacca agagcagcag ctccatggcc tccttgcccc  2640
agatcagcct gggtcagggg acatagtgtc attgtttgga aactgcagac cacaaggtgt  2700
gggtctatcc cacttcctag tgctccccac attccccatc agggcttcct cacgtggaca  2760
ggtgtgctag tccaggcagt tcacttgcag tttccttgtc ctcatgcttc ggggatggga  2820
gccacgcctg aactagagtt caggctggat acatgtgctc acctgctgct cttgtcttcc  2880
taagagacag agagtggggc agatggagga gaagaaagtg aggaatgagt agcatagcat  2940
tctgccaaaa gggccccaga ttcttaattt agcaaactaa gaagcccaat tcaaaagcat  3000
tgtggctaaa gtctaacgct cctctcttgg tcagataaca aaagccctcc ctgttggatc  3060
ttttgaaata aaacgtgcaa gttatccagg ctcgtagcct gcatgctgcc accttgaatc  3120
ccagggagta tctgcacctg gaatagctct ccacccctct ctgcctcctt actttctgtg  3180
caagatgact tcctgggtta acttccttct ttccatccac ccacccactg gaatctcttt  3240
ccaaacattt ttccattttc ccacagatgg gctttgatta gctgtcctct ctccatgcct  3300
gcaaagctcc agatttttgg ggaaagctgt acccaactgg actgcccagt gaactgggat  3360
cattaagtac agtcgagcac acgtgtgtgc atgggtcaaa ggggtgtgtt ccttctcatc  3420
ctagatgcct tctctgtgcc ttccacagcc tcctgcctga ttacaccact gcccccgccc  3480
caccctcagc catcccaatt cttcctggcc agtgcgctcc agccttatct aggaaaggag  3540
gagtgggtgt agccgtgcag caagattggg gcctccccca tcccagcttc tccaccatcc  3600
cagcaagtca ggatatcaga cagtcctccc ctgaccctcc cccttgtaga tatcaattcc  3660
caaacagagc caaatactct atatctatag tcacagccct gtacagcatt tttcataagt  3720
tatatagtaa atggtctgca tgatttgtgc ttctagtgct ctcatttgga aatgaggcag  3780
gcttcttcta tgaaatgtaa agaaagaaac cactttgtat attttgtaat accacctctg  3840
tggccatgcc tgccccgccc actctgtata tatgtaagtt aaacccgggc aggggctgtg  3900
gccgtctttg tactctggtg atttttaaaa attgaatctt tgtacttgca ttgattgtat  3960
aataatttttg agaccaggtc tcgctgtgtt gctcaggctg gtctcaaact cctgagatca  4020
agcaatccgc ccacctcagc ctcccaaagt gctgagatca caggcgtgag ccaccaccag  4080
gcctgattgt aattttttttt ttttttttt tactggttat gggaagggag aaataaaatc  4140
atcaaaccca aaaaaaaaaa aaaaaaa                                     4167
```

```
SEQ ID NO: 56          moltype = AA  length = 690
FEATURE                Location/Qualifiers
source                 1..690
                       mol_type = protein
                       organism = Homo sapiens
SEQUENCE: 56
MAPWPELGDA QPNPDKYLEG AAGQQPTAPD KSKETNKTDN TEAPVTKIEL LPSYSTATLI  60
DEPTEVDDPW NLPTLQDSGI KWSERDTKGK ILCFFQGIGR LILLLGFLYF FVCSLDILSS  120
AFQLVGGKMA GQFFSNSSIM SNPLLGLVIG VLVTVLVQSS STSTSIVVSM VSSSLLTVRA  180
AIPIIMGANI GTSITNTIVA LMQVGDRSEF RRAFAGATVH DFFNWLSVLV LLPVEVATHY  240
LEIITQLIVE SFHFKNGEDA PDLLKVITKP FTKLIVQLDK KVISQIAMND EKAKNKSLVK  300
```

-continued

```
IWCKTFTNKT QINVTVPSTA NCTSPSLCWT DGIQNWTMKN VTYKENIAKC QHIFVNFHLP  360
DLAVGTILLI LSLLVLCGCL IMIVKILGSV LKGQVATVIK KTINTDFPFP FAWLTGYLAI  420
LVGAGMTFIV QSSSVFTSAL TPLIGIGVIT IERAYPLTLG SNIGTTTTAI LAALASPGNA  480
LRSSLQIALC HFFFNISGIL LWYPIPFTRL PIRMAKGLGN ISAKYRWFAV FYLIIFFFLI  540
PLTVFGLSLA GWRVLVGVGV PVVFIIILVL CLRLLQSRCP RVLPKKLQNW NFLPLWMRSL  600
KPWDAVVSKF TGCFQMRCCC CCRVCCRACC LLCGCPKCCR CSKCCEDLEE AQEGQDVPVK  660
APETFDNITI SREAQGEVPA SDSKTECTAL                                  690

SEQ ID NO: 57          moltype = DNA  length = 4559
FEATURE                Location/Qualifiers
source                 1..4559
                       mol_type = other DNA
                       organism = synthetic construct
SEQUENCE: 57
gcggccgccc cattcccaga ccggccgcca gcccatctgg ttagctcccg ccgctccgcg  60
ccgcccggga gtcgggagcc gcggggaacc gggcacctgc acccgcctct gggagtgagt  120
ggttccagct ggtgcctggc ctgtgtctct tggatgccct gtggcttcag tccgtctcct  180
gttgcccacc acctcgtccc tgggccgcct gataccccag cccaacagct aaggtgtgga  240
tggacagtag gggctggct tctctcactg gtcaggggtc ttctcccctg tctgcctccc  300
ggagctagga ctgcagaggg gcctatcatg gtgcttgcag gccccctggc tgtctcgctg  360
ttgctgccca gcctcacact gctggtgtcc cacctctcca gctcccagga tgtctccagt  420
gagcccagca gtgagcagca gctgtgcgcc cttagcaagc accccaccgt ggcctttgaa  480
gacctgcagc cgtgggtctc taacttcacc taccctggag cccgggattt ctcccagctg  540
gctttggacc cctccgggaa ccagctcatc gtgggagcca ggaactacct cttcagactc  600
agccttgcca atgtctctct tcttcaggcc acagagtggg cctccagtga ggacacgcgc  660
cgctcctgcc aaagcaaagg gaagactgag gaggagtgtc agaactacgt gcgagtcctg  720
atcgtcgccg gccggaaggt gttcatgtgt ggaaccaatg ccttttcccc catgtgcacc  780
agcagacagg tggggaacct cagccggact actgagaaga tcaatggtgt ggcccgctgc  840
ccctatgacc cacgccacaa ctccacagct gtcatctcct cccaggggga gctctatgca  900
gccacggtca tcgacttctc aggtcgggac cctgccatct accgcagcct gggcagtggg  960
ccaccgcttc gcactgccca atataactcc aagtggctta atgagccaaa cttcgtggca  1020
gcctatgata ttgggctgtt tgcatacttc ttcctgcggg agaacgcagt ggagcacgac  1080
tgtggacgca ccgtgtactc tcgcgtggcc cgcgtgtgca agaatgacgt gggggggcga  1140
ttcctgctgg aggacacatg gaccacattc atgaaggccc ggctcaactg ctcccgcccg  1200
ggcgaggtcc ccttctacta taacgagctg cagagtgcct tccacttgcc agagcaggac  1260
ctcatctatg gagttttcac aaccaacgta aacagcatcg cggcttctgc tgtctgcgcc  1320
ttcaacctca gtgctatctc ccaggctttc aatggcccat ttcgctacca ggagaacccc  1380
agggctgcct ggctccccat agccaacccc atccccaatt tccagtgtgg caccctgcct  1440
gagaccggtc ccaacgagaa cctgacggag cgcagcctgc aggacgcgca gcgcctcttc  1500
ctgatgagcg aggccgtgca gccggtgaca cccgagccct gtgtcaccca ggacagcgtg  1560
cgcttctcac acctcgtggt ggacctggtg caggctaaag acacgctcta ccatgtactc  1620
tacattggca ccgagtcggg caccatcctg aaggcgctgt ccacggcgag ccgcagcctc  1680
cacggctgct acctggagga gctgcacgtg ctgccccccg ggcgccgcga gcccctgcgc  1740
agcctgcgca tcctgcacag cgcccgcgcg ctcttcgtgg ggctgagaga cggcgtcctg  1800
cgggtcccac tggagaggtg cgccgcctac cgcagccagg gggcatgcct gggggcccgg  1860
gacccgtact gtggctggga cgggaagcag caacgttgca gcacactcga ggacagctcc  1920
aacatgagcc tctggaccca gaacatcacc gcctgtcctg tgcggaatgt gacacgggat  1980
gggggcttcg gcccatggtc accatggcaa ccatgtgagc acttggatgg ggacaactca  2040
ggctcttgcc tgtgtcgagc tcgatcctgt gattcccctc gaccccgctg tgggggcctt  2100
gactgcctgg ggccagccat ccacatcgcc aactgctcca ggaatggggc gtggaccccg  2160
tggtcatcgt gggcgctgtg cagcacgtcc tgtggcatcg gcttccaggt ccgccagcga  2220
agttgcagca accctgctcc ccgccacggg ggccgcatct gcgtgggcaa gagccgggag  2280
gaacggttct gtaatgagaa cacgccttgc ccggtgccca tcttctgggc ttcctggggc  2340
tcctggagca agtgcagcag caactgtgga gggggcatgc agtcgcggcg tcgggcctgc  2400
gagaacggca actcctgcct gggctgcggc gtggagttca agacgtgcaa ccccgagggc  2460
tgccccgaag tgcggcgcaa cacccccctgg acgccgtggc tgcccgtgaa cgtgacgcag  2520
ggcggggcac ggcaggagca gcggttccgc ttcacctgcc gcgcgcccct tgcagacccg  2580
cacggcctgc agttcggcag gagaaggacc gagacgagga cctgtcccgc ggacggctcc  2640
ggctcctgcg acaccgacgc cctggtggag gacctcctgc gcagcgggag cacctccccg  2700
cacacggtga gcgggggctg ggccgcctgg ggcccgtggt cgtcctgctc ccgggactgc  2760
gagctgggct tccgcgtccg caagagaacg tgcactaacc cggagccccg caacgggggc  2820
ctgccctgcg tgggcgatgc tgccgagtac caggactgca acccccaggc ttgcccagtt  2880
cggggtgctt ggtcctgctg gacctcatgg tctccatgct cagcttcctg tggtgggggt  2940
cactatcaac gcacccgttc ctgcaccagc cccgcaccct ccccaggtga ggacatctgt  3000
ctcgggctgc acacggagga ggcactatgt gccacacagg cctgcccaga aggctggtcg  3060
ccctggtctg agtggagtaa gtgcactgac gacggagccc agagccgaag ccggcactgt  3120
gaggagctcc tcccagggtc cagcgcctgt gctggaaaca gcagccagag ccgccccctgc  3180
ccctacagcg agattcccgt catcctgcca gcctccagca tggaggaggc caccggctgt  3240
gcagggttca atctcatcca cttggtggcc acgggcatct cctgcttctt gggctctggg  3300
ctcctgaccc tagcagtgta cctgtcttgc cagcactgcc agcgtcagtc ccaggagtcc  3360
acactggtcc atcctgccac ccccaaccat ttgcactaca agggcggagg caccccgaag  3420
aatgaaaagt acacacccat ggaattcaag accctgaaca agaataactt gatccctgat  3480
gacagagcca acttctaccc attgcagcag accaatgtgt acacgactac ttactaccca  3540
agcccccctga acaaacacag cttccggccc gaggcctcac ctggacaacg gtgcttcccc  3600
aacagctgat accgccgtcc tggggacttg ggcttcttgc cttcataagg cacagagcag  3660
atggagatgg gacagtggag ccagtttggt tttctccctc tgcactaggc caagaacttg  3720
ctgccttgcc tgtgggggggt cccatccggc ttcagagagc tctggctggc attgaccatg  3780
ggggaaaggg ctggtttcag gctgacatat ggccgcaggt ccagttcagc ccaggtctct  3840
catggttatc ttccaaccca ctgtcacgct gacactatgc tgccatgcct gggctgtgga  3900
```

-continued

```
cctactgggc atttgaggaa ctggagaatg gagatggcaa gagggcaggc ttttaagttt  3960
gggttggaga caacttcctg tggcccccac aagctgagtc tggccttctc cagctggccc  4020
caaaaaaggc ctttgctaca tcctgattat ctctgaaagt aatcaatcaa gtggctccag  4080
tagctctgga ttttctgcca gggctgggcc attgtggtgc tgccccagta tgacatggga  4140
ccaaggccag cgcaggttat ccacctctgc ctggaagtct atactctacc cagggcatcc  4200
ctctggtcag aggcagtgag tactgggaac tggaggctga cctgtgctta gaagtccttt  4260
aatctgggct ggtacaggcc tcagccttgc cctcaatgca cgaaaggtgg cccaggagag  4320
aggatcaatg ccacaggagg cagaagtctg gcctctgtgc ctctatggag actatcttcc  4380
agttgctgct caacagagtt gttggctgag acctgcttgg gagtctctgc tggcccttca  4440
tctgttcagg aacacacaca cacacacact cacacacgca cacacaatca caatttgcta  4500
cagcaacaaa aaagacattg ggctgtggca ttattaatta aagatgatat ccagtctcc   4559

SEQ ID NO: 58          moltype = AA  length = 1202
FEATURE                Location/Qualifiers
source                 1..1202
                       mol_type = protein
                       organism = Homo sapiens
SEQUENCE: 58
AAAPFPDRPP AHLVSSRRSA PPGSREPRGT GHLHPPLGVS GSSWCLACVS WMPCGFSPSP  60
VAHHLVPGPP DTPAQQLRCG WTVGGWLLSL VRGLLPCLPP GARTAEGPIM VLAGPLAVSL  120
LLPSLTLLVS HLSSSQDVSS EPSSEQQLCA LSKHPTVAFE DLQPWVSNFT YPGARDFSQL  180
ALDPSGNQLI VGARNYLFRL SLANVSLLQA TEWASSEDTR RSCQSKGKTE EECQNYVRVL  240
IVAGRKVFMC GTNAFSPMCT SRQVGNLSRT TEKINGVARC PYDPRHNSTA VISSQGELYA  300
ATVIDFSGRD PAIYRSLGSG PPLRTAQYNS KWLNEPNFVA AYDIGLFAYF FLRENAVEHD  360
CGRTVYSRVA RVCKNDVGGR FLLEDTWTTF MKARLNCSRP GEVPFYYNEL QSAFHLPEQD  420
LIYGVFTTNV NSIAASAVCA FNLSAISQAF NGPFRYQENP RAAWLPIANP IPNFQCGTLP  480
ETGPNENLTE RSLQDAQRLF LMSEAVQPVT PEPCVTQDSV RFSHLVVDLV QAKDTLYHVL  540
YIGTESGTIL KALSTASRSL HGCYLEELHV LPPGRREPLR SLRILHSARA LFVGLRDGVL  600
RVPLERCAAY RSQGACLGAR DPYCGWDGKQ QRCSTLEDSS NMSLWTQNIT ACPVRNVTRD  660
GGFGPWSPWQ PCEHLDGDNS GSCLCRARSC DSPRPRCGGL DCLGPAIHIA NCSRNGAWTP  720
WSSWALCSTS CGIGFQVRQR SCSNPAPRHG GRICVGKSRE ERFCNENTPC PVPIFWASWG  780
SWSKCSSNCG GGMQSRRRAC ENGNSCLGCG VEFKTCNPEG CPEVRRNTPW TPWLPVNVTQ  840
GGARQEQRFR FTCRAPLADP HGLQFGRRRT ETRTCPADGS GSCDTDALVE DLLRSGSTSP  900
HTVSGGWAAW GPWSSCSRDC ELGFRVRKRT CTNPEPRNGG LPCVGDAAEY QDCNPQACPV  960
RGAWSCWTSW SPCSASCGGG HYQRTRSCTS PAPSPGEDIC LGLHTEEALC ATQACPEGWS  1020
PWSEWSKCTD DGAQSRSRHC EELLPGSSAC AGNSSQSRPC PYSEIPVILP ASSMEEATGC  1080
AGFNLIHLVA TGISCFLGSG LLTLAVYLSC QHCQRQSQES TLVHPATPNH LHYKGGGTPK  1140
NEKYTPMEFK TLNKNNLIPD DRANFYPLQQ TNVYTTTYYP SPLNKHSFRP EASPGQRCFP  1200
NS                                                                1202

SEQ ID NO: 59          moltype = DNA  length = 1524
FEATURE                Location/Qualifiers
source                 1..1524
                       mol_type = other DNA
                       organism = synthetic construct
SEQUENCE: 59
gcggcagcag cgcgggcccc agcagcctcg gcagccacag ccgctgcagc cggggcagcc  60
tccgctgctg tcgcctcctc tgatgcgctt gccctctccc ggccccggga ctccgggaga  120
atgtgggtcc taggcatcgc ggcaactttt tgcggattgt tcttgcttcc aggctttgcg  180
ctgcaaatcc agtgctacca gtgtgaagaa ttccagctga acaacgactg ctcctccccc  240
gagttcattg tgaattgcac ggtgaacgtt caagacatgt gtcagaaaga agtgatggag  300
caaagtgccg ggatcatgta ccgcaagtcc tgtgcatcat cagcggcctg tctcatcgcc  360
tctgccgggt accagtcctt ctgctcccca gggaaactga actcagtttg catcagctgc  420
tgcaacaccc ctctttgtaa cgggccaagg cccaagaaaa ggggaagttc tgcctcggcc  480
ctcaggccag ggctccgcac caccatcctg ttcctcaaat tagccctctt ctcggcacac  540
tgctgaagct gaaggagatg ccaccccctc ctgcattgtt cttccagccc tcgcccccaa  600
ccccccacct ccctgagtga gtttcttctg ggtgtccttt tattctgggt agggagcggg  660
agtccgtgtt ctcttttgtt cctgtgcaaa taatgaaaga gctcggtaaa gcattctgaa  720
taaattcagc ctgactgaat ttcagtatgg tacttgaagg aaggaggtgg agtgaaagtt  780
cacccccatg tctgtgtaac cggagtcaag gccaggctgg cagagtcagt ccttagaagt  840
cactgaggtg ggcatctgcc ttttgtaaag cctccagtgt ccattccatc cctgatgggg  900
gcatagtttg agactgcaga gtgagagtga cgttttctta gggctggagg gccagttccc  960
actcaaggct ccctcgcttg acattcaaac ttcatgctcc tgaaaaccat tctctgcagc  1020
agaattggct ggtttcgcgc ctgagttggg ctctagtgac tcgagactca atgactggga  1080
cttagactgg ggctcggcct cgctctgaaa agtgcttaag aaaatcttct cagttctcct  1140
tgcagaggac tggcgccggg acgcgaagag caacgggcgc tgcacaaagc gggcgctgtc  1200
ggtggtggag tgcgcatgta cgcgcaggcg cttctcgtgg ttggcgtgct gcagcgacag  1260
gcggcagcac agcacctgca cgaacacccg ccgaaactgc tgcgaggaca ccgtgtacag  1320
gagcgggttg atgaccgagc tgaggtagaa aaacgtctcc gagaagggga ggaggatcat  1380
gtacgcccgg aagtaggacc tcgtccagtc gtgcttgggt ttggccgcag ccatgatcct  1440
ccgaatctgg ttgggcatcc agcatacggc caatgtcaca acaatcagcc ctgggcagac  1500
acgagcagga gggagagaca gaga                                        1524

SEQ ID NO: 60          moltype = AA  length = 141
FEATURE                Location/Qualifiers
source                 1..141
                       mol_type = protein
                       organism = Homo sapiens
SEQUENCE: 60
```

-continued

```
MWVLGIAATF CGLFLLPGFA LQIQCYQCEE FQLNNDCSSP EFIVNCTVNV QDMCQKEVME  60
QSAGIMYRKS CASSAACLIA SAGYQSFCSP GKLNSVCISC CNTPLCNGPR PKKRGSSASA  120
LRPGLRTTIL FLKLALFSAH C                                           141

SEQ ID NO: 61           moltype = DNA  length = 1329
FEATURE                 Location/Qualifiers
source                  1..1329
                        mol_type = other DNA
                        organism = synthetic construct
SEQUENCE: 61
atgcagccgc ctccaagtct gtgcggacgc gccctggttg cgctggttct tgcctgcggc  60
ctgtcgcgga tctggggaga ggagagaggc ttcccgcctg acagggccac tccgcttttg  120
caaaccgcag agataatgac gccacccact aagaccttat ggcccaaggg ttccaacgcc  180
agtctggcgc ggtcgttggc acctgcggag gtgcctaaag gagacaggac ggcaggatct  240
ccgccacgca ccatctcccc tcccccgtgc caaggaccca tcgagatcaa ggagactttc  300
aaatacatca acacggttgt gtcctgcctt gtgttcgtgc tggggatcat cgggaactcc  360
acacttctga gaattatcta caagaacaag tgcatgcgaa acggtcccaa tatcttgatc  420
gccagcttgg ctctgggaga cctgctgcac atcgtcattg acatccctat caatgtctac  480
aagctgctgg cagaggactg gccatttgga gctgagatgt gtaagctggt gcctttcata  540
cagaaagcct ccgtgggaat cactgtgctg agtctatgtg ctctgagtat tgacagatat  600
cgagctgttg cttcttggag tagaattaaa ggaattgggg ttccaaaatg gacagcagta  660
gaaattgttt tgatttgggt ggtctctgtg gttctggctg tccctgaagc cataggtttt  720
gatataatta cgatggacta caaaggaagt tatctgcgaa tctgcttgct tcatcccgtt  780
cagaagacag ctttcatgca gttttacaag acagcaaaag attggtggct attcagtttc  840
tatttctgct tgccattggc catcactgca ttttttata cactaatgac ctgtgaaatg  900
ttgagaaaga aaagtggcat gcagattgct ttaaatgatc acctaaagca gagacgggaa  960
gtggccaaaa ccgtcttttg cctggtcctt gtctttgccc tctgctggct tccccttcac  1020
ctcagcagga ttctgaagct cactctttat aatcagaatg atcccaatag atgtgaactt  1080
ttgagctttc tgttggtatt ggactatatt ggtatcaaca tggcttcact gaattcctgc  1140
attaacccaa ttgctctgta tttggtgagc aaaagattca aaaactgctt taagtcatgc  1200
ttatgctgct ggtgccagtc atttgaagaa aaacagtcct tggaggaaaa gcagtcgtgc  1260
ttaaagttca aagctaatga tcacggatat gacaacttcc gttccagtaa taaatacagc  1320
tcatcttga                                                          1329

SEQ ID NO: 62           moltype = AA  length = 442
FEATURE                 Location/Qualifiers
source                  1..442
                        mol_type = protein
                        organism = Homo sapiens
SEQUENCE: 62
MQPPPSLCGR ALVALVLACG LSRIWGEERG FPPDRATPLL QTAEIMTPPT KTLWPKGSNA  60
SLARSLAPAE VPKGDRTAGS PPRTISPPPC QGPIEIKETF KYINTVVSCL VFVLGIIGNS  120
TLLRIIYKNK CMRNGPNILI ASLALGDLLH IVIDIPINVY KLLAEDWPFG AEMCKLVPFI  180
QKASVGITVL SLCALSIDRY RAVASWSRIK GIGVPKWTAV EIVLIWVVSV VLAVPEAIGF  240
DIITMDYKGS YLRICLLHPV QKTAFMQFYK TAKDWWLFSF YFCLPLAITA FFYTLMTCEM  300
LRKKSGMQIA LNDHLKQRRE VAKTVFCLVL VFALCWLPLH LSRILKLTLY NQNDPNRCEL  360
LSFLLVLDYI GINMASLNSC INPIALYLVS KRFKNCFKSC LCCWCQSFEE KQSLEEKQSC  420
LKFKANDHGY DNFRSSNKYS SS                                          442

SEQ ID NO: 63           moltype = DNA  length = 4573
FEATURE                 Location/Qualifiers
source                  1..4573
                        mol_type = other DNA
                        organism = synthetic construct
SEQUENCE: 63
agaacaccaa ttacaaacca caggcttcct gctctaggga gttgatccag aattgtcttt  60
ctgaaaggaa gcactcggaa tccttccgaa ctttccaagt ccatccatga ttcagagata  120
ctgccttctc tctctctggg attttatgtg tttctgatag tgaattgttg atgtatttgc  180
tactttgctt cttttctctt tcaagacttg atcattttat atgctgtttg gagaaaaaaa  240
gaacttttgt tagcaaggag gtttcagaaa tgattttgga ttttctgtaa gtgtttaatt  300
tagttctagg ggacagcatc tctcatcccg gagtaaattt ctgcctttga cctgcatgga  360
ttattttttc aggctgcgga atttctcggc acctacctgt agtatggggc acttggtttg  420
gttgcagagt aagaaggtgg aagaatgagc tgtacttggt taagcagttg aaaccttttt  480
tgagcaggat ctgtaaaagc ataattgaat ttgtttcacc cccgtggatt ccagtgggcc  540
cgacagcgca acagtgcctg gcaacttgat gcatatggaa gagcaatgcc aagtgatctg  600
acataataca aattcacgaa gtgacattca atcacaagca aagttggaaa ttccaaagag  660
aagtggtgag atctttacta gtcacagtga agatgggaga aaatgacata cctgcagcag  720
atgtgggctg aaaatatcct cttctctgcc caatcaggaa tgctacctgt ttttgggaat  780
aaactttaga gaaaggaagg gccaaaacta cgacttggct ttctgaaacg gaagcataaa  840
tgttcttttc ctccatttgt ctggatctga gaacctgcat ttggtattag ctagtggaag  900
cagtatgtat ggttgaagtg cattgctgca gctggtagca tgagtggtgg ccaccagctg  960
cagctggctg ccctctggcc ctggctgctg atggctaccc tgcaggcagg ctttggacgc  1020
acaggactgg tactggcagc agcggtggag tctgaaagat cagcagaaca gaaagctatt  1080
atcagagtga tccccttgaa aatggacccc acaggaaaac tgaatctcac tttggaaggt  1140
gtgtttgctg gtgttgctga aataactcca gcagaaggaa aattaatgca gtcccacccg  1200
ctgtacctgt gcaatgccag tgatgacgac aatctggagc ctggattcat cagcatcgtc  1260
aagctggaga gtcctcgacg ggccccccgc ccctgcctgt cactggctag caaggctcgg  1320
atggcgggtg agcgaggagc cagtgctgtc ctctttgaca tcactgagga tcgagctgct  1380
gctgagcagc tgcagcagcc gctggggctg acctggccag tggtgttgat ctggggtaat  1440
```

-continued

```
gacgctgaga agctgatgga gtttgtgtac aagaaccaaa aggcccatgt gaggattgag  1500
ctgaaggagc ccccggcctg gccagattat gatgtgtgga tcctaatgac agtggtgggc  1560
accatctttg tgatcatcct ggcttcggtg ctgcgcatcc ggtgccgccc ccgccacagc  1620
aggccggatc cgcttcagca gagaacagcc tgggccatca gccagctggc caccaggagg  1680
taccaggcca gctgcaggca ggcccggggt gagtggccag actcagggag cagctgcagc  1740
tcagcccctg tgtgtgccat ctgtctggag gagttctctg aggggcagga gctacgggtc  1800
atttcctgcc tccatgagtt ccatcgtaac tgtgtggacc cctggttaca tcagcatcgg  1860
acttgccccc tctgcatgtt caacatcaca gagggagatt cattttccca gtccctggga  1920
ccctctcgat cttaccaaga accaggtcga agactccacc tcattcgcca gcatcccggc  1980
catgcccact accacctccc tgctgcctac ctgttgggcc cttcccggag tgcagtggct  2040
cggcccccac gacctggtcc cttcctgcca tcccaggagc caggcatggg ccctcggcat  2100
caccgcttcc ccagagctgc acatccccgg gctccaggag agcagcagcg cctggcagga  2160
gcccagcacc cctatgcaca aggctgggga ctgagccacc tccaatccac ctcacagcac  2220
cctgctgctt gcccagtgcc cctacgccgg gccaggcccc ctgacagcag tggatctgga  2280
gaaagctatt gcacagaacg cagtgggtac ctggcagatg ggccagccag tgactccagc  2340
tcagggccct gtcatggctc ttccagtgac tctgtggtca actgcacgga catcagccta  2400
cagggggtcc atggcagcag ttctactttc tgcagctccc taagcagtga ctttgacccc  2460
ctagtgtact gcagccctaa aggggatccc cagcgagtgg acatgcagcc tagtgtgacc  2520
tctcggcctc gttccttgga ctcggtggtg cccacagggg aaacccaggt ttccagccat  2580
gtccactacc accgccaccg gcaccaccac tacaaaaagc ggttccagtg gcatggcagg  2640
aagcctggcc cagaaaccgg agtcccccag tccaggcctc ctattcctcg gacacagccc  2700
cagccagagc caccttctcc tgatcagcaa gtcaccagat ccaactcagc agccccttcg  2760
gggcggctct ctaacccaca gtgccccagg gccctccctg agccagcccc tggcccagtt  2820
gacgcctcca gcatctgccc cagtaccagc agtctgttca acttgcaaaa atccagcctc  2880
tctgcccgac acccacagag gaaaaggcgg gggggtccct ccgagcccac ccctggctct  2940
cggccccagg atgcaactgt gcacccagct tgccagattt ttccccatta cacccccagt  3000
gtggcatatc cttggtcccc agaggcacac cccttgatct gtggacctcc aggcctggac  3060
aagaggctgc taccagaaac cccaggcccc tgttactcaa attcacagcc agtgtggttg  3120
tgcctgactc ctcgccagcc cctggaacca catccacctg gggaggggcc ttctgaatgg  3180
agttctgaca ccgcagaggg caggccatgc ccttatccgc actgccaggt gctgtcggcc  3240
cagcctggct cagaggagga actcgaggag ctgtgtgaac aggctgtgtg agatgttcag  3300
gcctagctcc aaccaagagt gtgctccaga tgtgtttggg ccctacctgg cacagagtcc  3360
tgctcctggg aaaggaaagg accacagcaa acaccattct ttttgccgta cttcctagaa  3420
gcactggaag aggactggtg atggtggagg gtgagagggt gccgtttcct gctccagctc  3480
cagaccttgt ctgcagaaaa catctgcagt gcagcaaatc catgtccagc caggcaacca  3540
gctgctgcct gtggcgtgtg tgggctggat cccttgaagg ctgagttttt gagggcagaa  3600
agctagctat gggtagccag gtgttacaaa ggtgctgctc cttctccaac ccctacttgg  3660
tttccctcac cccaagcctc atgttcatac cagccagtgg gttcagcaga acgcatgaca  3720
ccttatcacc tccctccttg ggtgagctct gaacaccagc tttggcccct ccacagtaag  3780
gctgctacat caggggcaac cctggctcta tcattttcct tttttgccaa aaggaccagt  3840
agcataggtg agccctgagc actaaaagga ggggtccctg aagctttccc actatagtgt  3900
ggagttctgt ccctgaggtg ggtacagcag ccttggttcc tctgggggtt gagaataaga  3960
atagtgggga gggaaaaact cctccttgaa gatttcctgt ctcagagtcc cagagaggta  4020
gaaaggagga atttctgctg gactttatct gggcagagga aggatggaat gaaggtagaa  4080
aaggcagaat tacagctgag cggggacaac aaagagttct tctctgggaa aagttttgtc  4140
ttagagcaag gatggaaaat ggggacaaca aaggaaaagc aaagtgtgac ccttgggttt  4200
ggacagccca gaggcccagc tccccagtat aagccataca ggccagggac ccacaggaga  4260
gtggattaga gcacaagtct ggcctcactg agtggacaag agctgatggg cctcatcagg  4320
gtgacattca ccccagggca gcctgaccac tcttggcccc tcaggcatta tcccatttgg  4380
aatgtgaatg tggtggcaaa gtgggcagag gaccccacct gggaaccttt ttccctcagt  4440
tagtggggag actagcacct aggtacccac atgggtattt atatctgaac cagacagacg  4500
cttgaatcag gcactatgtt aagaaatata tttatttgct aatatattta tccacaaaaa  4560
aaaaaaaaaa aaa                                                     4573

SEQ ID NO: 64          moltype = AA  length = 783
FEATURE                Location/Qualifiers
source                 1..783
                       mol_type = protein
                       organism = Homo sapiens
SEQUENCE: 64
MSGGHQLQLA ALWPWLLMAT LQAGFGRTGL VLAAAVESER SAEQKAIIRV IPLKMDPTGK  60
LNLTLEGVFA GVAEITPAEG KLMQSHPLYL CNASDDDNLE PGFISIVKLE SPRRAPRPCL  120
SLASKARMAG ERGASAVLFD ITEDRAAAEQ LQQPLGLTWP VVLIWGNDAE KLMEFVYKNQ  180
KAHVRIELKE PPAWPDYDVW ILMTVVGTIF VIILASVLRI RCRPRHSRPD PLQQRTAWAI  240
SQLATRRYQA SCRQARGEWP DSGSSCSSAP VCAICLEEFS EGQELRVISC LHEFHRNCVD  300
PWLHQHRTCP LCMFNITEGD SFSQSLGPSR SYQEPGRRLH LIRQHPGHAH YHLPAAYLLG  360
PSRSAVARPP RPGPFLPSQE PGMGPRHHRF PRAAHPRAPG EQQRLAGAQH PYAQGWGLSH  420
LQSTSQHPAA CPVPLRRARP PDSSGSGESY CTERSGYLAD GPASDSSSGP CHGSSSDSVV  480
NCTDISLQGV HGSSSTFCSS LSSDFDPLVY CSPKGDPQRV DMQPSVTSRP RSLDSVVPTG  540
ETQVSSHVHY HRHRHHHYKK RFQWHGRKPG PETGVPQSRP PIPRTQPQPE PPSPDQQVTR  600
SNSAAPSGRL SNPQCPRALP EPAPGPVDAS SICPSTSSLF NLQKSSLSAR HPQRKRRGGP  660
SEPTPGSRPQ DATVHPACQI FPHYTPSVAY PWSPEAHPLI CGPPGLDKRL LPETPGPCYS  720
NSQPVWLCLT PRQPLEPHPP GEGPSEWSSD TAEGRPCPYP HCQVLSAQPG SEEELEELCE  780
QAV                                                                783

SEQ ID NO: 65          moltype = DNA  length = 6857
FEATURE                Location/Qualifiers
source                 1..6857
                       mol_type = other DNA
```

-continued organism = synthetic construct
SEQUENCE: 65
gccccctccg agctccccga ctcctccccg cgctccacgg ctcttcccga ctccagtcag 60
cgttcctcgg gccctcggcg ccacaagctg tccgggcacg cagcccctag cggcgcgtcg 120
ctgccaagcc ggcctccgcg cgcctccctc cttccttctc ccctggctgt tcgcgatcca 180
gcttgggtag gcggggaagc agctggagtg cgaccgccac ggcagccacc ctgcaaccgc 240
cagtcggagg tgcagtccgt aggccctggc ccccgggtgg gcccttgggg agtcggcgcc 300
gctcccgagg agctgcaagg ctcgcccctg cccggcgtgg agggcgcggg gggcgcggag 360
gatattcttg gtgatcttgg aagtgtccgt atcatggaat caatctctat gatgggaagc 420
cctaagagcc ttagtgaaac tgttttacct aatggcataa atggtatcaa agatgcaagg 480
aaggtcactg taggtgtgat tggaagtgga gatttttgcca aatccttgac cattcgactt 540
attagatgcg gctatcatgt ggtcatagga agtagaaatc ctaagtttgc ttctgaattt 600
tttcctcatg tggtagatgt cactcatcat gaagatgctc tcacaaaaac aaatataata 660
tttgttgcta tacacagaga acattatacc tccctgtggg acctgagaca tctgcttgtg 720
ggtaaaatcc tgattgatgt gagcaataac atgaggataa accagtaccc agaatccaat 780
gctgaatatt tggcttcatt attcccagat tctttgattg tcaaaggatt taatgttgtc 840
tcagcttggg cacttcagtt aggacctaag gatgccagcc ggcaggttta tatatgcagc 900
aacaatattc aagcgcgaca acaggttatt gaacttgccc gccagttgaa tttcattccc 960
attgacttgg gatccttatc atcagccaga gagattgaaa atttacccct acgactcttt 1020
actctctgga gagggccagt ggtggtagct ataagcttgg ccacattttt tttcctttat 1080
tcctttgtca gagatgtgat tcatccatat gctagaaacc aacagagtga cttttacaaa 1140
attcctatag agattgtgaa taaaacctta cctatagttg ccattacttt gctctcccta 1200
gtatacctttg caggtcttct ggcagctgct tatcaacttt attacggcac caagtatagg 1260
agatttccac cttggttgga aacctggtta cagtgtagaa aacagcttgg attactaagt 1320
tttttcttcg ctatggtcca tgttgcctac agcctctgct taccgatgag aaggtcagag 1380
agatatttgt ttctcaacat ggcttatcag caggttcatg caaatattga aaactcttgg 1440
aatgaggaag aagtttggag aattgaaatg tatatctcct ttggcataat gagccttggc 1500
ttactttccc tcctggcagt cacttctatc ccttcagtga gcaatgcttt aaactggaga 1560
gaattcagtt ttattcagtc tacacttgga tatgtcgctc tgctcataag tactttccat 1620
gttttaattt atggatggaa acgagctttt gaggaagagt actacagatt ttatacacca 1680
ccaaactttg ttcttgctct tgttttgccc tcaattgtaa ttctgggtaa gattatttta 1740
ttccttccat gtataagcca aaagctaaaa cgaattaaaa aaggctggga aaagagccaa 1800
tttctggaag aaggtattgg aggaacaatt cctcatgtct ccccggagag ggtcacagta 1860
atgtgatgat aaatggtgtt cacagctgcc atataaagtt ctactcatgc cattattttt 1920
atgacttcta cgttcagtta caagtatgct gtcaaattat cgtgggttga aacttgttaa 1980
atgagatttc aactgactta gtgatagagt tttcttcaag ttaattttca caaatgtcat 2040
gtttgccaat atgaattttt ctagtcaaca tattattgta atttaggtat gttttgtttt 2100
gttttgcaca actgtaaccc tgttgttact ttatatttca taatcaggca aaaatactta 2160
cagttaataa tatagatata atgttaaaaa caatttgcaa accagcagaa ttttaagctt 2220
ttaaaataat tcaatggata tacatttttt tctgaagatt aagattttaa ttattcaact 2280
taaaaagtag aaatgcatta ttatacattt ttttaagaaa ggacacgtta tgttagcatc 2340
taggtaaggc tgcatgatag cattcctata tttctctcat aaaataggat ttgaaggatg 2400
aaattaattg tatgaagcaa tgtgattata tgaagagaca caaattaaaa agacaaatta 2460
aacctgaaat tatatttaaa atatatttga gacatgaaat acatactgat aatacatacc 2520
tcatgaaaga ttttattctt tattgtgtta cagagcagtt tcattttcat attaatatac 2580
tgatcaggaa gaggattcag taacatttgg cctccaaaac tgctatctct aatacggtac 2640
caatcctagg aactgtatac tagttcctac ttagaacaaa agtatcaagt ttgcacacaa 2700
gtaatctgcc agctgacctt tgtcgcacct taaccagtca ccacttgcta tggtatagga 2760
ttatactgat gttctttgag ggattctgat gtgctaggca tggttctaag tactttactt 2820
gtattatccc atttaatact tagaacaacc ccgtgagata agtagttatt atcctcattt 2880
tacacatgag ggaccgaagg atagaaaagt tatttttcaa aggtcatgca gttaataaat 2940
ggcagagtga gcattcaagt ccaggtagtc atattccaga ggccacggtt ttaaccacta 3000
ggctctagag ctcccgccgc gcccctatgc attatgttca caatgccaat ctagatgctt 3060
cctcttttgt ataaagtcac tgacattctt tagagtgggt tgggtgcatc caaaaatgta 3120
taaaaatatt attataataa acttattact gcttgtaggg taattcacag ttacttaccc 3180
tattcttgct tggaacatga gcctggagac ccatggcagt ccatatgcct ccctatgcag 3240
tgaagggccc tagcagtgtt aacaaattgc tgagatccca cggagtcttt caaaaatctc 3300
tgtagagtta gtcttctcct tttctcttcc tgagaagttc tcctgcctgc ataaccattc 3360
attagggagt actttacaag catgaaggat attagggtaa gtggctaatt ataaatctac 3420
tctagagaca tataatcata cagattattc ataaaatttt tcagtgctgt ccttccacat 3480
ttaattgcat tttgctcaaa ctgtagaatg ccctacattc cccccacccc aatttgctat 3540
ttccttatta aaatagaaaa ttataggcaa gatacaatta tatgcgttcc tcttcctgaa 3600
attataacat ttctaaactt acccacgtag gtactactga atccaactgc caacaataaa 3660
aagactttta tttagtagag gctaccttc ccaccagtga ctctttttct acaactgcct 3720
tgtcagtttg gtaattcact tatgatttc taatgttctc ttggtgaatt ttattatctt 3780
gtaccctctt tttttttttt tttttttta aagacagagt cttgctctgt cacccaggct 3840
ggagtgcagt ggcacgatct cggctcactg caagctctgc ctcccgggtt cacgccattc 3900
tcctgcctca gcctcccgag tagctgggac tacaggtgcc cgccaccatg cccggctgat 3960
ttctttttgt atttttagta gagacggagt ttcaccgtgt tagccaggat ggtctcgatc 4020
tcctgacctc gtgatccgcc cgccttggcc tccaaagtgc tgggattaca ggtgtgagct 4080
accgcgcccg gcctattatc ttgtactttc taactgagcc ctctattttc tttattttaa 4140
taatatttct ccctacttga gaatcacttg ttagttcttg gtaggaattc agttgggcaa 4200
tgataacttt tatgggcaaa aacattctat tatagtgaac aaatgaaaat aacagcgtat 4260
tttcaatatt ttcttattcc ttaaattcca ctcttttaac actatgctta accacttaat 4320
gtgatgaaat attcctaaaa gttaaatgac tattaaagca tatattgttg catgtatata 4380
ttaagtagcc gatactctaa ataaaaatac cactgttaca gataaatggg gcctttaaaa 4440
atatgaaaaa caaacttgtg aaaatgtata aaagatgcat ctgttgtttc aaatggcact 4500
atcttctttt cagtactaca aaaacagaat aatttgaag ttttagaata aatgtaatat 4560
atttactata attctaaatg tttaaatgct tttctaaaaa tgcaaaacta tgatgtttag 4620

```
ttgctttatt ttacctctat gtgattattt ttcttaattg ttattttta taatcattat  4680
ttttctgaac cattcttctg gcctcagaag taggactgaa ttctactatt gctaggtgtg  4740
agaaagtggt ggtgagaacc ttagagcagt ggagatttgc tacctggtct gtgttttgag  4800
aagtgcccct tagaaagtta aaagaatgta gaaaagatac tcagtcttaa tcctatgcaa  4860
aaaaaaaaat caagtaattg ttttcctatg aggaaaataa ccatgagctg tatcatgcta  4920
cttagctttt atgtaaatat ttcttatgtc tcctctatta agagtattta aaatcatatt  4980
taaatatgaa tctattcatg ctaacattat ttttcaaaac atacatggaa atttagccca  5040
gattgtctac atataaggtt tttatttgaa ttgtaaaata tttaaaagta tgaataaaat  5100
atatttatag gtatttatca gagatgatta ttttgtgcta catacaggtt ggctaatgag  5160
ctctagtgtt aaactacctg attaatttct tataaagcag cataaccttg gcttgattaa  5220
ggaattctac tttcaaaaat taatctgata atagtaacaa ggtatattat actttcatta  5280
caatcaaatt atagaaatta cttgtgtaaa agggcttcaa gaatatatcc aattttttaaa  5340
tattttaata tatctcctat ctgataactt aattcttcta aattaccact tgccattaag  5400
ctatttcata ataaattctg tacagtttcc ccccaaaaaa gagatttatt tatgaaatat  5460
ttaaagtttc taatgtggta ttttaaataa agtatcataa atgtaataag taaatattta  5520
tttaggaata ctgtgaacac tgaactaatt attcctgtgt cagtctatga aatccctgtt  5580
ttgaaatacg taaacagcct aaaatgtgtt gaaattattt tgtaaatcca tgacttaaaa  5640
caagatacat acatagtata acacacctca cagtgttaag atttatattg tgaaatgaga  5700
caccctacct tcaattgttc atcagtgggt aaaacaaatt ctgatgtaca ttcaggacaa  5760
atgattagcc ctaaatgaaa ctgtaataat ttcagtggaa actcaatctg tttttacctt  5820
taaacagtga attttacatg aatgaatggg ttcttcactt tttttttagt atgagaaaat  5880
tatacagtgc ttaattttca gagattcttt ccatatgtta ctaaaaaatg ttttgttcag  5940
cctaacatac tgagtttttt ttaactttct aaattattga atttccatca tgcattcatc  6000
caaaattaag gcagactgtt tggattcttc cagtggccag atgagctaaa ttaaatcaca  6060
aaagcagatg cttttgtatg atctccaaat tgccaacttt aaggaaatat tctcttgaaa  6120
ttgtctttaa agatctttg cagctttgca gatacccaga ctgagctgga actggaattt  6180
gtcttcctat tgactctact tctttaaaag cggctgccca ttacattcct cagctgtcct  6240
tgcagttagg tgtacatgtg actgagtgtt ggccagtgag atgaagtctc ctcaaaggaa  6300
ggcagcatgt gtccttttc atcccttcat cttgctgctg ggattgtgga tataacagga  6360
gccctggcag ctgtctccag aggatcaaag ccacacccaa agagtaaggc agattagaga  6420
ccagaaagac cttgactact tccctacttc cactgctttt tcctgcattt aagccattgt  6480
aaatctgggt gtgttacatg aagtgaaaat taattctttc tgcccttcag ttctttatcc  6540
tgataccatt taacactgtc tgaattaact agactgcaat aattctttct tttgaaagct  6600
tttaaaggat aatgtgcaat tcacattaaa attgattttc cattgtcaat tagttatact  6660
cattttcctg ccttgatctt tcattagata ttttgtatct gcttggaata tattatcttc  6720
tttttaactg tgtaattggt aattactaaa actctgtaat ctccaaaata ttgctatcaa  6780
attacacacc atgttttcta tcattctcat agatctgcct tataaacatt taaataaaaa  6840
gtactattta atgattt                                                6857
```

```
SEQ ID NO: 66          moltype = AA  length = 490
FEATURE                Location/Qualifiers
source                 1..490
                       mol_type = protein
                       organism = Homo sapiens
SEQUENCE: 66
MESISMMGSP KSLSETVLPN GINGIKDARK VTVGVIGSGD FAKSLTIRLI RCGYHVVIGS  60
RNPKFASEFF PHVVDVTHHE DALTKTNIIF VAIHREHYTS LWDLRHLLVG KILIDVSNNM  120
RINQYPESNA EYLASLFPDS LIVKGFNVVS AWALQLGPKD ASRQVYICSN NIQARQQVIE  180
LARQLNFIPI DLGSLSSARE IENLPLRLFT LWRGPVVVAI SLATFFFLYS FVRDVIHPYA  240
RNQQSDFYKI PIEIVNKTLP IVAITLLSLV YLAGLLAAAY QLYYGTKYRR FPPWLETWLQ  300
CRKQLGLLSF FFAMVHVAYS LCLPMRRSER YLFLNMAYQQ VHANIENSWN EEEVWRIEMY  360
ISFGIMSLGL LSLLAVTSIP SVSNALNWRE FSFIQSTLGY VALLISTFHV LIYGWKRAFE  420
EEYYRFYTPP NFVLALVLPS IVILGKIILF LPCISQKLKR IKKGWEKSQF LEEGIGGTIP  480
HVSPERVTVM                                                     490
```

```
SEQ ID NO: 67          moltype = DNA  length = 4103
FEATURE                Location/Qualifiers
source                 1..4103
                       mol_type = other DNA
                       organism = synthetic construct
SEQUENCE: 67
aggctggaaa gtggaggatc cggtttgctc tgggcgggtc tggaagcaga gccggcggag  60
ggagcgccgg ggccctgggc tgcaggaggt tgcggcggcc gcggcagcat ggtggtgccg  120
gagaaggagc agagctggat ccccaagatc ttcaagaaga agacctgcac gacgttcata  180
gttgactcca cagatccggg agggaccttg tgccagtgtg ggcgccccccg gaccgcccac  240
cccgcagtgg ccatggagga tgccttcggg gcagccgtgg tgaccgtgtg ggacagcgat  300
gcacacacca cggagaagcc caccgatgcc tacggagagc tggacttcac gggggccggc  360
cgcaagcaca gcaatttcct ccggctctct gaccgaacgg atccagctgc agtttatagt  420
ctggtcacac gcacatgggg cttccgtgcc ccgaacctgg tggtgtcagt gctgggggga  480
tcggggggcc ccgtcctcca gacctggctg caggacctgc tgcgtcgtgg gctggtgcgg  540
gctgcccaga gcacaggagc ctggattgtc actgggggtc tgcacacggg catcggccgg  600
catgttggtg tggctgtacg ggaccatcag atggccagca ctgggggcac caaggtggtg  660
gccatgggtg tggccccctg ggtgtggtc cggaatagag acaccctcat caaccccaag  720
ggctcgttcc ctgcgaggta ccggtggcgc ggtgacccgg aggacggggt ccagtttccc  780
ctggactaca actactcggc cttcttcctg gtggacgacg gcacacacgg ctgcctgggg  840
ggcgagaacc gcttccgctt gcgcctggag tcctacatct cacagcagaa gacgggcgtg  900
ggagggactg gaattgacat ccctgtcctg ctcctcctga ttgatggtga tgagaagatg  960
ttgacgcgaa tagagaacgc cacccaggct cagctcccat gtctcctcgt ggctggctca  1020
gggggagctg cggactgcct ggcggagacc ctggaagaca ctctggcccc agggagtggg  1080
```

-continued

```
ggagccaggc aaggcgaagc ccgagatcga atcaggcgtt tctttcccaa aggggacctt  1140
gaggtcctgc aggcccaggt ggagaggatt atgacccgga aggagctcct gacagtctat  1200
tcttctgagg atgggtctga ggaattcgag accatagttt tgaaggccct tgtgaaggcc  1260
tgtgggagct cggaggcctc agcctacctg gatgagctgc gtttggctgt ggcttggaac  1320
cgcgtggaca ttgcccagag tgaactcttt cggggggaca tccaatggcg gtccttccat  1380
ctcgaagctt ccctcatgga cgccctgctg aatgaccggc ctgagttcgt gcgcttgctc  1440
atttcccacg gcctcagcct gggccacttc ctgaccccga tgcgcctggc ccaactctac  1500
agcgcggcgc cctccaactc gctcatccgc aacctttttgg accaggcgtc ccacagcgca  1560
ggcaccaaag ccccagccct aaaaggggga gctgcggagc tccggccccc tgacgtgggg  1620
catgtgctga ggatgctgct ggggaagatg tgcgcgccga ggtacccctc cgggggcgcc  1680
tgggaccctc acccaggcca gggcttcggg gagagcatgt atctgctctc ggacaaggcc  1740
acctcgccgc tctcgctgga tgctggcctc gggcaggccc cctggagcga cctgcttctt  1800
tgggcactgt tgctgaacag ggcacagatg gccatgtact tctgggagat gggttccaat  1860
gcagtttcct cagctcttgg ggcctgtttg ctgctccggg tgatggcacg cctggagcct  1920
gacgctgagg aggcagcacg gaggaaagac ctggcgttca agtttgaggg gatgggcgtt  1980
gacctctttg gcgagtgcta tcgcagcagt gaggtgaggg ctgcccgcct cctcctccgt  2040
cgctgcccgc tctgggggga tgccacttgc ctccagctgg ccatgcaagc tgacgcccgt  2100
gccttctttg cccaggatgg ggtacagtct ctgctgacac agaagtggtg gggagatatg  2160
gccagcacta cacccatctg ggccctggtt ctcgccttct ttgccctcc actcatctac  2220
acccgcctca tcaccttcag gaaatcagaa gaggagccca cacgggagga gctagagttt  2280
gacatggata gtgtcattaa tggggaaggg cctgtcggga cggcggaccc agccgagaag  2340
acgccgctgg gggtcccgcg ccagtcgggc cgtccgggtt gctgcggggg ccgctgcggg  2400
gggcgccggt gcctacgccg ctggttccac ttctggggcg cgccggtgac catcttcatg  2460
ggcaacgtgg tcagctacct gctgttcctg ctgcttttct cgcgggtgct gctcgtggat  2520
ttccagccgg cgccgcccgg ctccctggag ctgctgctct atttctgggc tttcacgctg  2580
ctgtgcgagg aactgcgcca gggcctgagc ggaggcgggg gcagcctcgc cagcgggggc  2640
cccgggcctg gccatgcctc actgagccag cgcctgcgcc tctacctcgc cgacagctgg  2700
aaccagtgcg acctagtggc tctcacctgc ttcctcctgg gcgtgggctg ccggctgacc  2760
ccgggtttgt accacctggg ccgcactgtc ctctgcatcg acttcatggt tttcacggtg  2820
cggctgcttc acatcttcac ggtcaacaaa cagctggggc ccaagatcgt catcgtgagc  2880
aagatgatga aggacgtgtt cttcttcctc ttcttcctcg gcgtgtggct ggtagcctat  2940
ggcgtggcca cggaggggct cctgaggcca cgggacagtg acttcccaag tatcctgcgc  3000
cgcgtcttct accgtcccta cctgcagatc ttcgggcaga ttccccagga ggacatggac  3060
gtggccctca tggagcacag caactgctcg tcggagcccg gcttctgggc acaccctcct  3120
ggggcccagg cgggcacctg cgtctcccag tatgccaact ggctggtggt gctgctcctc  3180
gtcatcttcc tgctcgtggc caacatcctg ctggtcaact tgctcattgc catgttcagt  3240
tacacattcg gcaaagtaca gggcaacagc gatctctact ggaaggcgca gcgttaccgc  3300
ctcatccggg aattccactc tcggcccgcg ctggccccgc cctttatcgt catctcccac  3360
ttgcgcctcc tgctcaggca attgtgcagg cgaccccgga gcccccagcc gtcctccccg  3420
gccctcgagc atttccgggt ttacctttct aaggaagccg agcggaagct gctaacgtgg  3480
gaatcggtgc ataaggagaa ctttctgctg gcacgcgcta gggacaagcg ggagagcgac  3540
tccgagcgtc tgaagcgcac gtcccagaag gtggacttgg cactgaaaca gctgggacac  3600
atccgcgagt acgaacagcg cctgaaagtg ctggagcggg aggtccagca gtgtagccgc  3660
gtcctggggt gggtggccga ggccctgagc cgctctgcct tgctgccccc aggtgggccg  3720
ccacccccctg acctgcctgg gtccaaagac tgagccctgc tggcggactt caaggagaag  3780
cccccacagg ggattttgct cctagagtaa ggctcatctg ggcctcggcc cccgcacctg  3840
gtggccttgt ccttgaggtg agccccatgt ccatctgggc cactgtcagg accacctttg  3900
ggagtgtcat ccttacaaac cacagcatgc ccggctcctc ccagaaccag tcccagcctg  3960
ggaggatcaa ggcctggatc ccgggccgtt atccatctgg aggctgcagg gtccttgggg  4020
taacagggac cacagacccc tcaccactca cagattcctc acactgggga aataaagcca  4080
tttcagagga atcgtgaaaa aaa                                         4103

SEQ ID NO: 68          moltype = AA  length = 1214
FEATURE                Location/Qualifiers
source                 1..1214
                       mol_type = protein
                       organism = Homo sapiens
SEQUENCE: 68
MVVPEKEQSW IPKIFKKKTC TTFIVDSTDP GGTLCQCGRP RTAHPAVAME DAFGAAVVTV  60
WDSDAHTTEK PTDAYGELDF TGAGRKHSNF LRLSDRTDPA AVYSLVTRTW GFRAPNLVVS  120
VLGGSGGPVL QTWLQDLLRR GLVRAAQSTG AWIVTGGLHT GIGRHVGVAV RDHQMASTGG  180
TKVVAMGVAP WGVVRNRDTL INPKGSFPAR YRWRGDPEDG VQFPLDYNYS AFFLVDDGTH  240
GCLGGENRFR LRLESYISQQ KTGVGGTGID IPVLLLLIDG DEKMLTRIEN ATQAQLPCLL  300
VAGSGGAADC LAETLEDTLA PGSGGARQGE ARDRIRRFFP KGDLEVLQAQ VERIMTRKEL  360
LTVYSSEDGS EEFETIVLKA LVKACGSSEA SAYLDELRLA VAWNRVDIAQ SELFRGDIQW  420
RSFHLEASLM DALLNDRPEF VRLLISHGLS LGHFLTPMRL AQLYSAAPSN SLIRNLLDQA  480
SHSAGTKAPA LKGGAAELRP PDVGHVLRML LGKMCAPRYP SGGAWDPHPG QGFGESMYLL  540
SDKATSPLSL DAGLGQAPWS DLLLWALLLN RAQMAMYFWE MGSNAVSSAL GACLLLRVMA  600
RLEPDAEEAA RRKDLAFKFE GMGVDLFGEC YRSSEVRAAR LLLRRCPLWG DATCLQLAMQ  660
ADARAFFAQD GVQSLLTQKW WGDMASTTPI WALVLAFFCP PLIYTRLITF RKSEEEPTRE  720
ELEFDMDSVI NGEGPVGTAD PAEKTPLGVP RQSGRPGCCG GRCGGRRCLR RWFHFWGAPV  780
TIFMGNVVSY LLFLLLFSRV LLVDFQPAPP GSLELLLYFW AFTLLCEELR QGLSGGGGSL  840
ASGGPGPGHA SLSQRLRLYL ADSWNQCDLV ALTCFLLGVG CRLTPGLYHL GRTVLCIDFM  900
VFTVRLLHIF TVNKQLGPKI VIVSKMMKDV FFFLFFLGVW LVAYGVATEG LLRPRDSDFP  960
SILRRVFYRP YLQIFGQIPQ EDMDVALMEH SNCSSEPGFW AHPPGAQAGT CVSQYANWLV  1020
VLLLVIFLLV ANILLVNLLI AMFSYTFGKV QGNSDLYWKA QRYRLIREFH SRPALAPPFI  1080
VISHLRLLLR QLCRRPRSPQ PSSPALEHFR VYLSKEAERK LLTWESVHKE NFLLARARDK  1140
RESDSERLKR TSQKVDLALK QLGHIREYEQ RLKVLEREVQ QCSRVLGWVA EALSRSALLP  1200
PGGPPPPDLP GSKD                                                   1214
```

```
SEQ ID NO: 69          moltype = DNA  length = 2174
FEATURE                Location/Qualifiers
source                 1..2174
                       mol_type = other DNA
                       organism = synthetic construct
SEQUENCE: 69
aatgatagag atattagggc tagttaacca cagttttaca agactcctct tcccgcgtgt  60
gggccattgt catgctggtg ggcgtcccgc ccacctgaaa ggtctccccg ccccgactgg  120
ggtttgttgt tgaagaagga gaatccccgg aaaggctgag tctccagctc aaggtcaaaa  180
cgtccaaggc cgaaagccct ccagtttccc ctggacgcct tgctcctgct tctgctacga  240
ccttctgggg aaaacgaatt tctcattttc ttcttaaatt gccattttcg ctttaggaga  300
tgaatgtttt cctttggctg ttttggcaat gactctgaat taaagcgatg ctaacgcctc  360
ttttcccccct aattgttaaa agctatggac tgcaggaaga tggcccgctt ctcttacagt  420
gtgatttgga tcatggccat ttctaaagtc tttgaactgg gattagttgc cgggctgggc  480
catcaggaat ttgctcgtcc atctcgggga tacctggcct tcagagatga cagcatttgg  540
ccccaggagg agcctgcaat tcggcctcgg tcttcccagc gtgtgccgcc catggggata  600
cagcacagta aggagctaaa cagaacctgc tgcctgaatg gggaacctg catgctgggg  660
tccttttgtg cctgccctcc ctccttctac ggacggaact gtgagcacga tgtgcgcaaa  720
gagaactgtg ggtctgtgcc ccatgacacc tggctgccca agaagtgttc cctgtgtaaa  780
tgctggcacg gtcagctccg ctgctttcct caggcatttc tacccggctg tgatggcctt  840
gtgatggatg agcacctcgt ggcttccagg actccagaac taccaccgtc tgcacgtact  900
accactttta tgctagttgg catctgcctt tctatacaaa gctactatta atcgacattg  960
acctatttcc agaaatacaa ttttagatat catgcaaatt tcatgaccag taaaggctgc  1020
tgctacaatg tcctaactga aagatgatca tttgtagttg ccttaaaata atgaatacat  1080
ttccaaaatg gtctctaaca tttccttaca gaactacttc ttacttcttt gccctgccct  1140
ctcccaaaaa actacttctt ttttcaaaag aaagtcagcc atatctccat tgtgcctaag  1200
tccagtgttt cttttttttt tttttttga gacggagtct cactctgtca cccaggctgg  1260
actgcaatga cgcgatcttg gttcactgca acctccgcat ccggggttca agccattctc  1320
ctgcctcagc ctcccaagta actgggatta caggcatgtg tcaccatgcc cagctaattt  1380
ttttgtattt ttagtagaga tggggtttc accatattgg ccagtctggt ctcgaactcc  1440
tgaccttgtg atccactcgc ctcagcctct cgaagtgctg agattacaca cgtgagcaac  1500
tgtgcaaggc ctggtgtttc ttgatacatg taattctacc aaggtcttct taatatgttc  1560
ttttaaatga ttgaattata tgttcagatt attggagact aattctaatg tggaccttag  1620
aatacagttt tgagtagagt tgatcaaaat caattaaaat agtctcttta aaaggaaaga  1680
aaacatcttt aaggggagga accagagtgc tgaagggaatg gaagtccatc tgcgtgtgtg  1740
cagggagact gggtaggaaa gaggaagcaa atagaagaga gaggttgaaa aacaaaatgg  1800
gttacttgat tggtgattag gtggtggtag agaagcaagt aaaaaggcta aatggaaggg  1860
caagtttcca tcatctatag aaagctatat aagacaagaa ctcccctttt tttcccaaag  1920
gcattataaa aagaatgaag cctccttaga aaaaaaatta tacctcaatg tccccaacaa  1980
gattgcttaa taaattgtgt ttcctccaag ctattcaatt cttttaactg ttgtagaaga  2040
caaaatgttc acaatatatt tagttgtaaa ccaagtgatc aaactacata ttgtaaagcc  2100
catttttaaa atacattgta tatatgtgta tgcacagtaa aaatggaaac tatattgacc  2160
taaaaaaaaa aaaa                                                    2174

SEQ ID NO: 70          moltype = AA  length = 188
FEATURE                Location/Qualifiers
source                 1..188
                       mol_type = protein
                       organism = Homo sapiens
SEQUENCE: 70
MDCRKMARFS YSVIWIMAIS KVFELGLVAG LGHQEFARPS RGYLAFRDDS IWPQEEPAIR  60
PRSSQRVPPM GIQHSKELNR TCCLNGGTCM LGSFCACPPS FYGRNCEHDV RKENCGSVPH  120
DTWLPKKCSL CKCWHGQLRC FPQAFLPGCD GLVMDEHLVA SRTPELPPSA RTTTFMLVGI  180
CLSIQSYY                                                           188

SEQ ID NO: 71          moltype = DNA  length = 3934
FEATURE                Location/Qualifiers
source                 1..3934
                       mol_type = other DNA
                       organism = synthetic construct
SEQUENCE: 71
gccctcccag agctgccgga cgctcgcggg tctcggaacg catcccgccg cgggggcttc  60
ggccgtggca tgggcgccgc ggcctgctc ggggtttct tggctctcgt cgcaccgggg  120
gtcctcggga tttcttgtgg ctctcctccg cctatcctaa atggccggat tagttattat  180
tctaccccca ttgctgttgg taccgtgata aggtacagtt gttcaggtac cttccgcctc  240
attggagaaa aaagtctatt atgcataact aaagacaaag tggatggaac ctgggataaa  300
cctgctccta aatgtgaata tttcaataaa tattcttctt gccctgagcc catagtacca  360
ggaggataca aaattagagg ctctacaccc tacagacatg gtgattctgt gacatttgcc  420
tgtaaaacca acttctccat gaacggaaac aagtctgttt ggtgtcaagc aaataatatg  480
tgggggccga cacgactacc aacctgtgta agtgttttcc ctctcgagtg tccagcactt  540
cctatgatcc acaatggaca tcacacaagt gagaatgttg gctccattgc tccaggattg  600
tctgtgactt acagctgtga atctggttac ttgcttgttg gagaaaagat cattaactgt  660
ttgtcttcgg gaaaatggag tgctgtcccc cccacatgtg aagaggcacg ctgtaaatct  720
ctaggacgat ttcccaatgg gaaggtaaag gagcctccaa ttctccgggt tggtgtaact  780
gcaaactttt tctgtgatga agggtatcga ctgcaaggcc caccttctag tcggtgtgta  840
attgctggac agggagttgc ttggaccaaa atgccagtat gtgaagaaat tttttgccca  900
tcacctcccc ctattctcaa tggaagacat ataggcaact cactagcaaa tgtctcatat  960
ggaagcatag tcacttacac ttgtgacccg gacccagagg aaggagtgaa cttcatcctt  1020
```

-continued

```
attggagaga gcactctccg ttgtacagtt gatagtcaga agactgggac ctggagtggc  1080
cctgccccac gctgtgaact ttctacttct gcggttcagt gtccacatcc ccagatccta  1140
agaggccgaa tggtatctgg gcagaaagat cgatatacct ataacgacac tgtgatattt  1200
gcttgcatgt ttggcttcac cttgaagggc agcaagcaaa tccgatgcaa tgcccaaggc  1260
acatgggagc catctgcacc agtctgtgaa aaggaatgcc aggcccctcc taacatcctc  1320
aatgggcaaa aggaagatag acacatggtc cgctttgacc ctggaacatc tataaaatat  1380
agctgtaacc ctggctatgt gctggtggga gaagaatcca tacagtgtac ctctgagggg  1440
gtgtggacac cccctgtacc ccaatgcaaa gtggcagcgt gtgaagctac aggaaggcaa  1500
ctcttgacaa aaccccagca ccaatttgtt agaccagatg tcaactcttc ttgtggtgaa  1560
gggtacaagt taagtgggag tgtttatcag gagtgtcaag gcacaattcc ttggtttatg  1620
gagattcgtc tttgtaaaga aatcacctgc ccaccacccc ctgttatcta caatggggca  1680
cacaccggga gttccttaga agattttcca tatggaacca cggtcactta cacatgtaac  1740
cctgggccag aaagaggagt ggaattcagc ctcattggag agagcaccat ccgttgtaca  1800
agcaatgatc aagaaagagg cacctggagt ggccctgctc ccctatgtaa actttccctc  1860
cttgctgtcc agtgctcaca tgtccatatt gcaaatggat acaagatatc tggcaaggaa  1920
gccccatatt tctacaatga cactgtgaca ttcaagtgtt atagtggatt tactttgaag  1980
ggcagtagtc agattcgttg caaagctgat aacacctggg atcctgaaat accagtttgt  2040
gaaaaagaaa catgccagca tgtgagacag agtcttcaag aacttccagc tggttcacgt  2100
gtggagctag ttaatacgtc ctgccaagat gggtaccagt tgactggaca tgcttatcag  2160
atgtgtcaag atgctgaaaa tggaatttgg ttcaaaaaga ttccactttg taaagttatt  2220
cactgtcacc ctccaccagt gattgtcaat gggaagcaca cagggatgat ggcagaaaac  2280
tttctatatg gaaatgaagt ctcttatgaa tgtgaccaag gattctatct cctgggagag  2340
aaaaaattgc agtgcagaag tgattctaaa ggacatggat cttggagcgg gccttcccca  2400
cagtgcttac gatctcctcc tgtgactcgc tgccctaatc cagaagtcaa acatgggtac  2460
aagctcaata aaacacattc tgcatattcc cacaatgaca tagtgtatgt tgactgcaat  2520
cctggcttca tcatgaatgg tagtcgcgtg attaggtgtc atactgataa cacatgggtg  2580
ccaggtgtgc caacttgtat gaaaaaagcc ttcatagggt gtccacctcc gcctaagacc  2640
cctaacggga accatactgg tggaaacata gctcgatttt ctcctggaat gtcaatcctg  2700
tacagctgtg accaaggcta cctgctggtg ggagaggcac tccttctttg cacacatgag  2760
ggaacctgga gccaacctgc ccctcattgt aaagaggtaa actgtagctc accagcagat  2820
atggatggaa tccagaaagg gctggaacca aggaaaatgt atcagtatgg agctgttgta  2880
actctggagt gtgaagatgg gtatatgctg gaaggcagtc cccagagcca gtgccaatcg  2940
gatcaccaat ggaaccctcc cctggcggtt tgcagatccc gttcacttgc tcctgtcctt  3000
tgtggtattg ctgcaggttt gatacttctt accttcttga ttgtcattac cttatacgtg  3060
atatcaaaac acagagaacg caattattat acagatacaa gccagaaaga agcttttcat  3120
ttagaagcac gagaagtata ttctgttgat ccatacaacc cagccagctg atcagaagac  3180
aaactggtgt gtgcctcatt gcttggaatt cagcggaata ttgattagaa agaaactgct  3240
ctaatatcag caagtctctt tatatggcct caagatcaat gaaatgatgt cataagcgat  3300
cacttcctat atgcacttat tctcaagaag aacatcttta tggtaaagat gggagcccag  3360
tttcactgcc atatactctt caaggacttt ctgaagcctc acttatgaga tgcctgaagc  3420
caggccatgg ctataaacaa ttacatggct ctaaaaagtt ttgccctttt taaggaaggc  3480
actaaaaaga gctgtcctgg tatctagacc catcttcttt ttgaaatcag catactcaat  3540
gttactatct gcttttggtt ataatgtgtt tttaattatc taaagtatga agcattttct  3600
ggggttatga tggccttacc tttattagga agtatggttt tattttgata gtagcttcct  3660
cctctggtgg tgttaatcat ttcattttta cccttactgt ttgagtttct ctcacattac  3720
tgtatatact ttgcctttcc ataatcactc agtgattgca atttgcacaa gttttttttaa  3780
attatgggaa tcaagattta atcctagaga tttggtgtac aattcaggct ttggatgttt  3840
ctttagcagt tttgtgataa gttctagttg cttgtaaaat ttcacttaat aatgtgtaca  3900
ttagtcattc aataaattgt aattgtaaag aaaa                              3934

SEQ ID NO: 72          moltype = AA  length = 1033
FEATURE                Location/Qualifiers
source                 1..1033
                       mol_type = protein
                       organism = Homo sapiens
SEQUENCE: 72
MGAAGLLGVF LALVAPGVLG ISCGSPPPIL NGRISYYSTP IAVGTVIRYS CSGTFRLIGE  60
KSLLCITKDK VDGTWDKPAP KCEYFNKYSS CPEPIVPGGY KIRGSTPYRH GDSVTFACKT  120
NFSMNGNKSV WCQANNMWGP TRLPTCVSVF PLECPALPMI HNGHHTSENV GSIAPGLSVT  180
YSCESGYLLV GEKIINCLSS GKWSAVPPTC EEARCKSLGR FPNGKVKEPP ILRVGVTANF  240
FCDEGYRLQG PPSSRCVIAG QGVAWTKMPV CEEIFCPSPP PILNGRHIGN SLANVSYGSI  300
VTYTCDPDPE EGVNFILIGE STLRCTVDSQ KTGTWSGPAP RCELSTSAVQ CPHPQILRGR  360
MVSGQKDRYT YNDTVIFACM FGFTLKGSKQ IRCNAQGTWE PSAPVCEKEC QAPPNILNGQ  420
KEDRHMVRFD PGTSIKYSCN PGYVLVGEES IQCTSEGVWT PPVPQCKVAA CEATGRQLLT  480
KPQHQFVRPD VNSSCGEGYK LSGSVYQECQ GTIPWFMEIR LCKEITCPPP PVIYNGAHTG  540
SSLEDFPYGT TVTYTCNPGP ERGVEFSLIG ESTIRCTSND QERGTWSGPA PLCKLSLLAV  600
QCSHVHIANG YKISGKEAPY FYNDTVTFKC YSGFTLKGSS QIRCKADNTW DPEIPVCEKE  660
TCQHVRQSLQ ELPAGSRVEL VNTSCQDGYQ LTGHAYQMCQ DAENGIWFKK IPLCKVIHCH  720
PPPVIVNGKH TGMMAENFLY GNEVSYECDQ GFYLLGEKKL QCRSDSKGHG SWSGPSPQCL  780
RSPPVTRCPN PEVKHGYKLN KTHSAYSHND IVYVDCNPGF IMNGSRVIRC HTDNTWVPGV  840
PTCMKKAFIG CPPPPKTPNG NHTGGNIARF SPGMSILYSC DQGYLLVGEA LLLCTHEGTW  900
SQPAPHCKEV NCSSPADMDG IQKGLEPRKM YQYGAVVTLE CEDGYMLEGS PQSQCQSDHQ  960
WNPPLAVCRS RSLAPVLCGI AAGLILLTFL IVITLYVISK HRERNYYTDT SQKEAFHLEA  1020
REVYSVDPYN PAS                                                     1033

SEQ ID NO: 73          moltype = DNA  length = 1300
FEATURE                Location/Qualifiers
source                 1..1300
                       mol_type = other DNA
```

```
                        organism = synthetic construct
SEQUENCE: 73
ctgcagccgg tgcagttaca cgttttcctc caaggagcct cggacgttgt cacgggtttg  60
gggtcgggga cagagcggtg accatggcca ggctggcgtt gtctcctgtg cccagccact  120
ggatggtggc gttgctgctg ctgctctcag ctgagccagt accagcagcc agatcggagg  180
accggtaccg gaatcccaaa ggtagtgctt gttcgcggat ctggcagagc ccacgtttca  240
tagccaggaa acggggcttc acggtgaaaa tgcactgcta catgaacagc gcctccggca  300
atgtgagctg gctctggaag caggagatgg acgagaatcc ccagcagctg aagctggaaa  360
agggccgcat ggaagagtcc cagaacgaat ctctcgccac cctcaccatc caaggcatcc  420
ggtttgagga caatggcatc tacttctgtc agcagaagtg caacaacacc tcggaggtct  480
accagggctg cggcacagag ctgcgagtca tgggattcag caccttggca cagctgaagc  540
agaggaacac gctgaaggat ggtatcatca tgatccagac gctgctgatc atcctcttca  600
tcatcgtgcc tatcttcctg ctgctggaca aggatgacag caaggctggc atggaggaag  660
atcacaccta cgagggcctg gacattgacc agacagccac ctatgaggac atagtgacgc  720
tgcggacagg ggaagtgaag tggtctgtag gtgagcaccc aggccaggag tgagagccag  780
gtcgccccat gacctgggtg caggctccct ggcctcagtg actgcttcgg agctgcctgg  840
ctcatggccc aacccctttc ctggaccccc cagctggcct ctgaagctgg cccaccagag  900
ctgccatttg tctccagccc ctggtcccca gctcttgcca aagggcctgg agtagaagga  960
caacagggca gcaacttgga gggagttctc tggggatgga cgggacccag ccttctgggg  1020
gtgctatgag gtgatccgtc cccacacatg ggatgggga ggcagagact ggtccagagc  1080
ccgcaaatgg actcggagcc gagggcctcc cagcagagct tgggaagggc catggaccca  1140
actgggcccc agaagagcca caggaacatc attcctctcc cgcaaccact cccaccccag  1200
ggaggccctg gcctccagtg ccttccccg tggaataaac ggtgtgtcct gagaaaccac  1260
aaaaaaaaaa aaaaaaaaaa aaaaaaaaaa aaaaaaaaaa                        1300

SEQ ID NO: 74           moltype = AA  length = 229
FEATURE                 Location/Qualifiers
source                  1..229
                        mol_type = protein
                        organism = Homo sapiens
SEQUENCE: 74
MARLALSPVP SHWMVALLLL LSAEPVPAAR SEDRYRNPKG SACSRIWQSP RFIARKRGFT  60
VKMHCYMNSA SGNVSWLWKQ EMDENPQQLK LEKGRMEESQ NESLATLTIQ GIRFEDNGIY  120
FCQQKCNNTS EVYQGCGTEL RVMGFSTLAQ LKQRNTLKDG IIMIQTLLII LFIIVPIFLL  180
LDKDDSKAGM EEDHTYEGLD IDQTATYEDI VTLRTGEVKW SVGEHPGQE             229

SEQ ID NO: 75           moltype = DNA  length = 2592
FEATURE                 Location/Qualifiers
source                  1..2592
                        mol_type = other DNA
                        organism = synthetic construct
SEQUENCE: 75
agagtctcca gttggtgacc aagagtacat ctcttttcaa atagctggat taggtcctca  60
tgctgctgtg gtcattgctg gtcatctttg atgcagtcac tgaacaggca gattcgctga  120
cccttgtggc gccctcttct gtcttcgaag gagacagcat cgttctgaaa tgccagggag  180
aacagaactg gaaaattcag aagatggctt accataagga taacaaagag ttatctgttt  240
tcaaaaaatt ctcagatttc cttatccaaa gtgcagtttt aagtgacagt ggtaactatt  300
tctgtagtac caaaggacaa ctctttctct gggataaaac ttcaaatata gtaaagataa  360
aagtccaaga gctctttcaa cgtcctgtgc tgactgccag ctccttccag cccatcgaag  420
gggtccagt gagcctgaaa tgtgagaccc ggctctctcc acagaggttg gatgttcaac  480
tccagttctg cttcttcaga gaaaaccagg tcctggggtc aggctggagc agctctccgg  540
agctccagat ttctgccgtg tggagtgaag acacagggtc ttactggtgc aaggcagaaa  600
cggtgactca caggatcaga aaacagagcc tccaatccca gattcacgtg cagagaatcc  660
ccatctctaa tgtaagcttg gagatccggg cccccgggg acaggtgact gaaggacaaa  720
aactgatcct gctctgctca gtggctgggg gtacaggaaa tgtcacattc tcctggtaca  780
gagaggccac aggaaccagt atgggaaaga aaacccagcg ttccctgtca gcagagctgg  840
agatcccagc tgtgaaagag agtgatgccg gcaaatatta ctgtagagct gacaacggcc  900
atgtgcctat ccagagcaag gtggtgaata tccctgtgag aattccagtg tctcgccctg  960
tcctcaccct caggtctcct ggggcccagg ctgcagtggg ggacctgctg gagcttcact  1020
gtgaggccct gagaggctct cccccaatct tgtaccaatt ttatcatgag gatgtcaccc  1080
ttgggaacag ctcggccccc tctggaggag gggcctcctt caacctctct ttgactgcag  1140
aacattctgg aaactactcc tgtgaggcca acaacggcct gggggcccag tgcagtgagg  1200
cagtgccagt ctccatctca ggacctgatg gctatagaag agacctcatg acagctggag  1260
ttctctgggg actgtttggt gtccttggtt tcactggtgt tgctttgctg ttgtatgcct  1320
tgttccacaa gatatcagga gaaagttctg ccactaatga acccagaggg gcttccaggc  1380
caaatcctca agagttcacc tattcaagcc caaccccaga catggaggag ctgcagccag  1440
tgtatgtcaa tgtgggctct gtagatgtgg atgtggttta ttctcaggtc tggagcatgc  1500
agcagccaga aagctcagca aacatcagga cacttctgga gaacaaggac tcccaagtca  1560
tctactcttc tgtgaagaaa tcataacact tggaggaatc agaagggaag atcaacagca  1620
aggatggggc atcattaaga cttgctataa aaccttatga aaatgcttga ggcttatcac  1680
ctgccacagc cagaacgtgc ctcaggaggc acctcctgtc atttttgtcc tgatgatgtt  1740
tcttctccaa tatcttcttt tacctatcaa tattcattga actgctgcta catccagaca  1800
ctgtgcaaat aaattatttc tgctaccttc tcttaagcaa tcagtgtgta aagatttgag  1860
ggaagaatga ataagagata caaggtctca ccttcatcta ctgtgaagtg atgagaacag  1920
gacttgatag tggtgtatta acttatttat gtgctgctgg atacagtttg ctaatatttt  1980
gttgagaatt tttgcaaata tgttcattgg gaatattggc ctgaaatttt cttttccact  2040
gtgtctctgc cagaatgttt gtatcaggct gatgctggct tcatagaatg agttaggcag  2100
gagcccttcc tccttgattt tttggcatag tttcagcagg attggtacca gttattcttt  2160
ctgcatcttg tagaattcag ctatgaatcc atctggtcta gggcttttgt gttggttggt  2220
```

```
aagtttttta ttactaattc aacttcagcg cttgatattg gtctaggagg ggtttctgtc  2280
tcttcctggt tcaatcttgg gagattgtgt gtttccagga atttagccgt ttcctccaga  2340
ttttcttctt tatgtgcatc gacttgagtg taaacataac ttatatgcac tgggaaacca  2400
aaaaatctgt gtgacttgct ttattgcagc atttgtttta ttttggtagt ctggaactga  2460
acctgcaata tcaccaaagt atgcatatag ttgcaaaaat gtgatttttg acatagtaaa  2520
tatgagtatt tgcaataaac tatgatatta cttttgtaag tatatagaat aaaatgtaaa  2580
taatctataa aa                                                      2592

SEQ ID NO: 76          moltype = AA  length = 508
FEATURE                Location/Qualifiers
source                 1..508
                       mol_type = protein
                       organism = Homo sapiens
SEQUENCE: 76
MLLWSLLVIF DAVTEQADSL TLVAPSSVFE GDSIVLKCQG EQNWKIQKMA YHKDNKELSV  60
FKKFSDFLIQ SAVLSDSGNY FCSTKGQLFL WDKTSNIVKI KVQELFQRPV LTASSFQPIE  120
GGPVSLKCET RLSPQRLDVQ LQFCFFRENQ VLGSGWSSSP ELQISAVWSE DTGSYWCKAE  180
TVTHRIRKQS LQSQIHVQRI PISNVSLEIR APGGQVTEGQ KLILLCSVAG GTGNVTFSWY  240
REATGTSMGK KTQRSLSAEL EIPAVKESDA GKYYCRADNG HVPIQSKVVN IPVRIPVSRP  300
VLTLRSPGAQ AAVGDLLELH CEALRGSPPI LYQFYHEDVT LGNSSAPSGG GASFNLSLTA  360
EHSGNYSCEA NNGLGAQCSE AVPVSISGPD GYRRDLMTAG VLWGLFGVLG FTGVALLLYA  420
LFHKISGESS ATNEPRGASR PNPQEFTYSS PTPDMEELQP VYVNVGSVDV DVVYSQVWSM  480
QQPESSANIR TLLENKDSQV IYSSVKKS                                     508

SEQ ID NO: 77          moltype = DNA  length = 4530
FEATURE                Location/Qualifiers
source                 1..4530
                       mol_type = other DNA
                       organism = synthetic construct
SEQUENCE: 77
aattctcgag ctcgtcgacc ggtcgacgag ctcgagggtc gacgagctcg agggcgcgcg  60
cccggccccc accccctcgca gcaccccgcg ccccgcgccc tcccagccgg gtccagccgg  120
agccatgggg ccggagccgc agtgagcacc atggagctgg cggccttgtg ccgctggggg  180
ctcctcctcg ccctcttgcc ccccggagcc gcgagcaccc aagtgtgcac cggcacagac  240
atgaagctgc ggctccctgc cagtcccgag acccacctgg acatgctccg ccacctctac  300
cagggctgcc aggtggtgca gggaaacctg gaactcacct acctgcccac caatgccagc  360
ctgtccttcc tgcaggatat ccaggaggtg cagggctacg tgctcatcgc tcacaaccaa  420
gtgaggcagg tcccactgca gaggctgcgg attgtgcgag gcacccagct ctttgaggac  480
aactatgccc tggccgtgct agacaatgga gacccgctga acaataccac ccctgtcaca  540
ggggcctccc caggaggcct gcgggagctg cagcttcgaa gcctcacaga gatcttgaaa  600
ggaggggtct tgatccagcg gaacccccag ctctgctacc aggacacgat tttgtggaag  660
gacatcttcc acaagaacaa ccagctggct ctcacactga tagacaccaa ccgctctcgg  720
gcctgccacc cctgttctcc gatgtgtaag ggctcccgct gctggggaga gagttctgag  780
gattgtcaga gcctgacgcg cactgtctgt gccggtggct gtgcccgctg caaggggcca  840
ctgcccactg actgctgcca tgagcagtgt gctgccggct gcacgggccc caagcactct  900
gactgcctgg cctgcctcca cttcaaccac agtggcatct gtgagctgca ctgcccagcc  960
ctggtcacct acaacacaga cacgtttgag tccatgccca atcccgaggg ccggtataca  1020
ttcggcgcca gctgtgtgac tgcctgtccc tacaactacc tttctacgga cgtgggatcc  1080
tgcaccctcg tctgccccct gcacaaccaa gaggtgacag cagaggatgg aacacagcgg  1140
tgtgagaagt gcagcaagcc ctgtgcccga gtgtgctatg gtctgggcat ggagcacttg  1200
cgagaggtga gggcagttac cagtgccaat atccaggagt ttgctggctg caagaagatc  1260
tttgggagcc tggcatttct gccggagagc tttgatgggg acccagcctc caacactgcc  1320
ccgctccagc cagagcagct ccaagtgttt gagactctgg aagagatcac aggttaccta  1380
tacatctcag catggccgga cagcctgcct gacctcagcg tcttccagaa cctgcaagta  1440
atccggggac gaattctgca caatggcgcc tactcgctga ccctgcaagg gctgggcatc  1500
agctggctgg ggctgcgctc actgagggaa ctgggcagtg gactggccct catccaccat  1560
aacacccacc tctgcttcgt gcacacggtg ccctgggacc agctctttcg gaacccgcac  1620
caagctctgc tccacactgc caaccggcca gaggacgagt gtgtgggcga gggcctggcc  1680
tgccaccagc tgtgcgcccg agggcactgc tggggtccag ggcccaccca gtgtgtcaac  1740
tgcagccagt tccttcgggg ccaggagtgc gtggaggaat gccgagtact gcaggggctc  1800
cccagggagt atgtgaatgc caggcactgt ttgccgtgcc accctgagtg tcagccccag  1860
aatggctcag tgacctgttt tggaccggag gctgaccagt gtgtggcctg tgcccactat  1920
aaggaccctc ccttctgcgt ggcccgctgc cccagcggtg tgaaacctga cctctcctac  1980
atgcccatct ggaagtttcc agatgaggag ggcgcatgcc agccttgccc catcaactgc  2040
acccactcct gtgtggacct ggatgacaag ggctgccccg ccgagcagag agccagccct  2100
ctgacgtcca tcgtctctgc ggtggttggc attctgctgg tcgtggtctt gggggtggtc  2160
tttgggatcc tcatcaagcg acggcagcag aagatccgga agtacacgat gcggagactg  2220
ctgcaggaaa cggagctggt ggagccgctg acacctagcg gagcgatgcc caaccaggcg  2280
cagatgcgga tcctgaaaga gacggagctg aggaaggtga aggtgcttgg atctggcgct  2340
tttggcacag tctacaaggg catctggatc cctgatgggg agaatgtgaa aattccagtg  2400
gccatcaaag tgttgaggga aaacacatcc cccaaagcca acaaagaaat cttagacgaa  2460
gcatacgtga tggctggtgt gggctcccca tatgtctccc gccttctggg catctgcctg  2520
acatccacgg tgcagctggt gacacagctt atgccctatg gctgcctctt agaccatgtc  2580
cgggaaaacc gcggacgcct gggctcccag gacctgctga actggtgtat gcagattgcc  2640
aaggggatga gctacctgga ggatgtgcgg ctcgtacaca gggacttggc cgctcggaac  2700
gtgctggtca agagtcccaa ccatgtcaaa attacagact tcgggctggc tcggctgctg  2760
gacattgacg agacagagta ccatgcagat gggggcaagg tgcccatcaa gtggatggcg  2820
ctggagtcca ttctccgccg gcggttcacc caccagagtg atgtgtggag ttatggtgtg  2880
actgtgtggg agctgatgac ttttggggcc aaaccttacg atgggatccc agcccgggag  2940
```

-continued

```
atccctgacc tgctggaaaa gggggagcgg ctgccccagc cccccatctg caccattgat  3000
gtctacatga tcatggtcaa atgttggatg attgactctg aatgtcggcc aagattccgg  3060
gagttggtgt ctgaattctc ccgcatggcc agggaccccc agcgctttgt ggtcatccag  3120
aatgaggact tgggcccagc cagtcccttg gacagcacct tctaccgctc actgctggag  3180
gacgatgaca tgggggacct ggtggatgct gaggagtatc tggtacccca gcagggcttc  3240
ttctgtccag accctgcccc gggcgctggg ggcatggtcc accacaggca ccgcagctca  3300
tctaccagga gtggcggtgg ggacctgaca ctagggctgg agccctctga agaggaggcc  3360
cccaggtctc cactggcacc ctccgaaggg gctggctccg atgtatttga tggtgacctg  3420
ggaatggggg cagccaaggg gctgcaaagc ctccccacac atgaccccag ccctctacag  3480
cggtacagtg aggaccccac agtacccctg ccctctgaga ctgatggcta cgttgccccc  3540
ctgacctgca gcccccagcc tgaatatgtg aaccagccag atgttcggcc ccagcccccct  3600
tcgccccgag agggccctct gcctgctgcc cgacctgctg gtgccactct ggaaagggcc  3660
aagactctct ccccagggaa gaatggggtc gtcaaagacg tttttgcctt tgggggtgcc  3720
gtggagaacc ccgagtactt gacaccccag ggaggagctg cccctcagcc ccaccctcct  3780
cctgccttca gcccagcctt cgacaacctc tattactggg accaggaccc accagagcgg  3840
ggggctccac ccagcacctt caaagggaca cctacggcag agaacccaga gtacctgggt  3900
ctggacgtgc cagtgtgaac cagaaggcca agtccgcaga agccctgatg tgtcctcagg  3960
gagcagggaa ggcctgactt ctgctggcat caagaggtgg gagggccctc cgaccacttc  4020
caggggaacc tgccatgcca ggaacctgtc ctaaggaacc ttccttcctg cttgagttcc  4080
cagatggctg gaaggggtcc agcctcgttg gaagaggaac agcactgggg agtctttgtg  4140
gattctgagg ccctgcccaa tgagactcta gggtccagtg gatgccacag cccagcttgg  4200
ccctttcctt ccagatcctg ggtactgaaa gccttaggga agctggcctg agaggggaag  4260
cggccctaag ggagtgtcta agaacaaaag cgacccattc agagactgtc cctgaaacct  4320
agtactgccc cccatgagga aggaacagca atggtgtcag tatccaggct ttgtacagag  4380
tgcttttctg tttagttttt actttttttg ttttgttttt ttaaagacga aataaagacc  4440
caggggagaa tgggtgttgt atggggaggc aagtgtgggg ggtccttctc cacacccact  4500
ttgtccattt gcaaatatat tttggaaaac                                4530
```

```
SEQ ID NO: 78          moltype = AA  length = 1255
FEATURE                Location/Qualifiers
source                 1..1255
                       mol_type = protein
                       organism = Homo sapiens
SEQUENCE: 78
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIVSAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERA KTLSPGKNGV VKDVFAFGGA VENPEYLTPQ  1200
GGAAPQPHPP PAFSPAFDNL YYWDQDPPER GAPPSTFKGT PTAENPEYLG LDVPV      1255
```

```
SEQ ID NO: 79          moltype = DNA  length = 2533
FEATURE                Location/Qualifiers
source                 1..2533
                       mol_type = other DNA
                       organism = synthetic construct
SEQUENCE: 79
ggagctcaag ctcctctaca aagaggtgga cagagaagac agcagagacc atgggacccc  60
cctcagcccc tccctgcaga ttgcatgtcc cctggaagga ggtcctgctc acagcctcac  120
ttctaacctt ctggaaccca cccaccactg ccaagctcac tattgaatcc acgccattca  180
atgtcgcaga ggggaaggag gttcttctac tcgcccacaa cctgccccag aatcgtattg  240
gttacagctg gtacaaaggc gaaagagtgg atggcaacag tctaattgta ggatatgtaa  300
taggaactca acaagctacc ccagggcccg catacagtgg tcgagagaca atataccccca  360
atgcatccct gctgatccag aacgtcaccc agaatgacac aggattctat accctacaag  420
tcataaagtc agatcttgtg aatgaagaag caaccggaca gttccatgta tacccggagc  480
tgcccaagcc ctccatctcc agcaacaact ccaaccccgt ggaggacaag gatgctgtgg  540
ccttcacctg tgaacctgag gttcagaaca caacctacct gtggtgggta aatggtcaga  600
gcctcccggt cagtcccagg ctgcagctgt ccaatggcaa catgacccctc actctactca  660
gcgtcaaaag gaacgatgca ggatcctatg aatgtgaaat acagaaccca gcgagtgcca  720
accgcagtga cccagtcacc ctgaatgtcc tctatggccc agatgtcccc accatttccc  780
cctcaaaggc caattaccgt ccaggggaaa atctgaacct ctcctgccac gcagcctcta  840
acccacctgc acagtactct tggtttatca atgggacgtt ccagcaatcc acacaagagc  900
tctttatccc caacatcact gtgaataata gcggatccta tatgtgccaa gcccataact  960
cagccactgg cctcaatagg accacagtca cgatgatcac agtctctgga agtgctcctg  1020
```

-continued

```
tcctctcagc tgtggccacc gtcggcatca cgattggagt gctggccagg gtggctctga  1080
tatagcagcc ctggtgtatt ttcgatattt caggaagact ggcagattgg accagaccct  1140
gaattcttct agctcctcca atcccatttt atcccatgga accactaaaa acaaggtctg  1200
ctctgctcct gaagccctat atgctggaga tggacaactc aatgaaaatt taaagggaaa  1260
accctcaggc ctgaggtgtg tgccactcag agacttcacc taactagaga cagtcaaact  1320
gcaaaccatg gtgagaaatt gacgacttca cactatggac agcttttccc aagatgtcaa  1380
aacaagactc ctcatcatga taaggctctt accccctttt aatttgtcct tgcttatgcc  1440
tgcctctttc gcttggcagg atgatgctgt cattagtatt tcacaagaag tagcttcaga  1500
gggtaactta acagagtgtc agatctatct tgtcaatccc aacgttttac ataaaataag  1560
agatccttta gtgcacccag tgactgacat tagcagcatc tttaacacag ccgtgtgttc  1620
aaatgtacag tggtcctttt cagagttgga cttctagact cacctgttct cactccctgt  1680
tttaattcaa cccagccatg caatgccaaa taatagaatt gctccctacc agctgaacag  1740
ggaggagtct gtgcagtttc tgacacttgt tgttgaacat ggctaaatac aatgggtatc  1800
gctgagacta agttgtagaa attaacaaat gtgctgcttg gttaaaatgg ctacactcat  1860
ctgactcatt ctttattcta ttttagttgg tttgtatctt gcctaaggtg cgtagtccaa  1920
ctcttggtat taccctccta atagtcatac tagtagtcat actccctggt gtagtgtatt  1980
ctctaaaagc tttaaatgtc tgcatgcagc cagccatcaa atagtgaatg gtctctcttt  2040
ggctggaatt acaaaactca gagaaatgtg tcatcaggag aacatcataa cccatgaagg  2100
ataaaagccc caaatggtgg taactgataa tagcactaat gctttaagat ttggtcacac  2160
tctcacctag gtgagcgcat tgagccagtg gtgctaaatg ctacatactc caactgaaat  2220
gttaaggaag aagatagatc caattaaaaa aaattaaaac caatttaaaa aaaaaaaaga  2280
acacaggaga ttccagtcta cttgagttag cataatacag aagtcccctc tactttaact  2340
tttacaaaaa agtaacctga actaatctga tgttaaccaa tgtatttatt tctgtggttc  2400
tgtttccttg ttccaatttg acaaaaccca ctgttcttgt attgtattgc ccagggggag  2460
ctatcactgt acttgtagag tggtgctgct ttaattcata aatcacaaat aaaagccaat  2520
tagctctata act                                                     2533

SEQ ID NO: 80          moltype = AA  length = 344
FEATURE                Location/Qualifiers
source                 1..344
                       mol_type = protein
                       organism = Homo sapiens
SEQUENCE: 80
MGPPSAPPCR LHVPWKEVLL TASLLTFWNP PTTAKLTIES TPFNVAEGKE VLLLAHNLPQ  60
NRIGYSWYKG ERVDGNSLIV GYVIGTQQAT PGPAYSGRET IYPNASLLIQ NVTQNDTGFY  120
TLQVIKSDLV NEEATGQFHV YPELPKPSIS SNNSNPVEDK DAVAFTCEPE VQNTTYLWWV  180
NGQSLPVSPR LQLSNGNMTL TLLSVKRNDA GSYECEIQNP ASANRSDPVT LNVLYGPDVP  240
TISPSKANYR PGENLNLSCH AASNPPAQYS WFINGTFQQS TQELFIPNIT VNNSGSYMCQ  300
AHNSATGLNR TTVTMITVSG SAPVLSAVAT VGITIGVLAR VALI                   344

SEQ ID NO: 81          moltype = DNA  length = 1583
FEATURE                Location/Qualifiers
source                 1..1583
                       mol_type = other DNA
                       organism = synthetic construct
SEQUENCE: 81
gtgcctctcc tggcaggcag agtggctcct cacagcctga agctcatcct tctgcacggg  60
ccagccaggc cagcacagag gcaccagggc agcagtgcac acaggtcccc ggggacccca  120
ccatgtggag cggatggtgg ctgtggcccc ttgtggccgt ctgcactgca gacttctttc  180
gggacgaggc agagaggatc atgagggact cccctgtcat tgatgggcac aatgacctcc  240
cctggcagct gctggatatg ttcaacaacc ggctgcagga cgagagggcc aacctgacca  300
ccttggccgg cacacacacc aacatcccca agctgagggc cggctttgtg ggaggccagt  360
tctggtccgt gtacacgccc tgcgacaccc agaacaaaga cgccgtgcgg aggacgctgg  420
agcagatgga cgtggtccac cgcatgtgcc ggatgtaccc ggagaccttc ctgtatgtca  480
ccagcagtgc aggcattcgg caggccttcc gggaagggaa ggtggccagc ctgatcggcg  540
tggagggcgg ccactccatt gacagcagtt tgggcgtcct gcgggcactc tatcagctgg  600
gcatgcggta cctgaccctc acccacagct gcaacacgcc ctgggctgac aactggctgg  660
tggacacggg agacagcgag ccccagagcc aaggcttgtc acccctttgg cagcgtgtgg  720
tgaaggagct gaaccgtctg gggtcctca tcgacttggc tcacgtgtct gtggccacca  780
tgaaggccac cctgcagctg tccagagccc cggtcatctt cagccactcc tcggcctaca  840
gcgtgtgcgc aagccggcgc aacgtgcctg acgacgtcct gaggctggtg aaacagacag  900
acagcctggt gatggtgaac ttctacaaca attacatttc ctgcaccaac aaggccaacc  960
tgtcccaagt ggccgaccat ctggatcaca tcaaggaggt ggcaggagcc agagccgtgg  1020
gttttggtgg ggactttgat ggtgttccaa gggtccctga ggggctggag gacgtctcca  1080
agtatccaga cctgatcgct gagctgctca ggaggaactg gacggaggcg gaggtcaagg  1140
gcgcactggc tgacaacctg ctgagggtct tcgaggctgt ggaacaggcc agcaacctca  1200
cacaggctcc cgaggaggag cccatcccgc tggaccagct gggtggctcc tgcaggaccc  1260
attacggcta ctcctctggg gcttccagcc tccatcgcca ctgggggctc ctgctggcct  1320
ccctcgctcc cctggtcctc tgtctgtctc tcctgtgaaa cctgggagac cagagtcccc  1380
tttagggttc ccggagctcc gggaagaccc gcccatccca ggactccaga tgccaggagc  1440
cctgctgccc acatgcaagg accagcatct cctgagagga cgcctgggct tacctggggg  1500
gcaggatgcc tggggacagt tcaggacaca cacacagtag gcccgcaata aaagcaacac  1560
cccttcaaaa aaaaaaaaaa aaa                                          1583

SEQ ID NO: 82          moltype = AA  length = 411
FEATURE                Location/Qualifiers
source                 1..411
                       mol_type = protein
                       organism = Homo sapiens
```

```
SEQUENCE: 82
MWSGWWLWPL VAVCTADFFR DEAERIMRDS PVIDGHNDLP WQLLDMFNNR LQDERANLTT  60
LAGTHTNIPK LRAGFVGGQF WSVYTPCDTQ NKDAVRRTLE QMDVVHRMCR MYPETFLYVT  120
SSAGIRQAFR EGKVASLIGV EGGHSIDSSL GVLRALYQLG MRYLTLTHSC NTPWADNWLV  180
DTGDSEPQSQ GLSPFGQRVV KELNRLGVLI DLAHVSVATM KATLQLSRAP VIFSHSSAYS  240
VCASRRNVPD DVLRLVKQTD SLVMVNFYNN YISCTNKANL SQVADHLDHI KEVAGARAVG  300
FGGDFDGVPR VPEGLEDVSK YPDLIAELLR RNWTEAEVKG ALADNLLRVF EAVEQASNLT  360
QAPEEEPIPL DQLGGSCRTH YGYSSGASSL HRHWGLLLAS LAPLVLCLSL L           411

SEQ ID NO: 83           moltype = DNA  length = 3485
FEATURE                 Location/Qualifiers
source                  1..3485
                        mol_type = other DNA
                        organism = synthetic construct
SEQUENCE: 83
tccagctggg tagccggggg agcgcgcgtg ggggctccgc gagtcgctcg cccttggttt  60
ctggggaagc ctgggggacg cggctgtggc ggaggcgccc tgggactcag gtcgcctgga  120
gcgtggcacg cagagcccca ggcgcggagc tgaggccgcg cggccgcgct tggccccagc  180
gggcgtggga ctgagcagtc tgctgccccc cgacatgtga cccagccccg ccgcccatgc  240
gggctcccgg ccgcccggcc ctgcggccgc tgccgctgcc gccgctgctg ctgttgctcc  300
tggcggcgcc ttggggacgg gcagttccct gtgtctctgg tggtttgcct aaacctgcaa  360
acatcacctt cttatccatc aacatgaaga atgtcctaca atggactcca ccagagggtc  420
ttcaaggagt taaagttact tacactgtgc agtatttcat atatgggcaa aagaaatggc  480
tgaataaatc agaatgcaga aatatcaata gaacctactg tgatctttct gctgaaactt  540
ctgactacga acaccagtat tatgccaaag ttaaggccat ttggggaaca aagtgttcca  600
aatgggctga aagtggacgg ttctatcctt ttttagaaac acaaattggc ccaccagagg  660
tggcactgac tacagatgag aagtccattt ctgttgtcct gacagctcca gagaagtgga  720
agagaaatcc agaagacctt cctgtttcca tgcaacaaat atactccaat ctgaagtata  780
acgtgtctgt gttgaatact aaatcaaaca gaacgtggtc ccagtgtgtg accaaccaca  840
cgctggtgct cacctggctg gagccgaaca ctctttactg cgtacacgtg gagtccttcg  900
tcccagggcc ccctcgccgt gctcagcctt ctgagaagca gtgtgccagg actttgaaag  960
atcaatcatc agagttcaag gctaaaatca tcttctggta tgttttgccc atatctatta  1020
ccgtgtttct tttttctgtg atgggctatt ccatctaccg atatatccac gttggcaaag  1080
agaaacaccc agcaaatttg attttgattt atggaaatga atttgacaaa agattctttg  1140
tgcctgctga aaaaatcgtg attaacttta tcaccctcaa tatctcggat gattctaaaa  1200
tttctcatca ggatatgagt ttactgggaa aaagcagtga tgtatccagc cttaatgatc  1260
ctcagcccag cgggaacctg aggccccctc aggaggaaga ggaggtgaaa catttaggt  1320
atgcttcgca tttgatggaa atttttgtg actctgaaga aaacacggaa ggtacttctt  1380
tcacccagca agagtccctc agcagaacaa tacccccgga taaaacagtc attgaatatg  1440
aatatgatgt cagaaccact gacatttgtg cggggcctga agagcaggag ctcagtttgc  1500
aggaggaggt gtccacacaa ggaacattat tggagtcgca ggcagcgttg gcagtcttgg  1560
gcccgcaaac gttacagtac tcatacaccc ctcagctcca agacttagac cccctggcgc  1620
aggagcacac agactcggag gaggggccgg aggaagagcc atcgacgacc ctggtcgact  1680
gggatcccca aactggcagg ctgtgtattc cttcgctgtc cagcttcgac caggattcag  1740
agggctgcga gccttctgag gggatgggc tcggagagga gggtcttcta tctagactct  1800
atgaggagcc ggctccagac aggccaccag gagaaaatga aacctatctc atgcaattca  1860
tggaggaatg gggttatat gtgcagatgg aaaactgatg ccaacacttc cttttgcctt  1920
ttgtttcctg tgcaaacaag tgagtcaccc ctttgatccc agccataaag tacctgggat  1980
gaaagaagtt ttttccagtt tgtcagtgtc tgtgagaatt acttatttct tttctctatt  2040
ctcatagcac gtgtgtgatt ggttcatgca tgtaggtctc ttaacaatga tggtgggcct  2100
ctggagtcca ggggctggcc ggttgttcta tgcagagaaa gcagtcaata aatgtttgcc  2160
agactgggtg cagaatttat tcaggtgggt gtactctggc ctcttggttc attattttca  2220
aacaagcaca cttgtacaat tattttctgg gtacttccca tatgcacata gcactgtaaa  2280
aaatatttcc caaagatcac tcattttata aataccactt tttcagaatt gggtttattg  2340
cgagcaggag gagatactta aaacatgcac atataccagg ttggtggtaa gttggtcaca  2400
tgtgaaaacc tcaactattt aatcatcatg attcatattt tgagtgaata catcaggcac  2460
agaccttcat gatatcacac actcttggct actttaagag gccatcttta atactttatg  2520
agtagttctg gagtgtaaac ataaacgagt attcttttgt agtcagaaaa gtgtcctctc  2580
aataatttag taggggctta ttgtctctca aaactaacct aaaagaaaat gacacatttt  2640
ataatagaat attacattta tttctggaag tgtgttttca aaaagatatt tacatagtct  2700
gtaaactaga aagtgttagg taaagctcta ggttactgtg ttactattat aatattaaac  2760
attcgaatag gcagtcgttc aaagactctt tggaatatct atgaatgaat atcctctatt  2820
cttataatat taaaacccat aagtaaatat aggacataca agagaaatga gttaaatgac  2880
tatgtaaggg agagtttatt aaaatttgat gaaatttact gtaggaacta aactatgcca  2940
taaaacaata gctttctagt tcatttccag taactgttcc catctccttt accacttgtt  3000
aagaaaatta aattcttcag tcacgctgct ttaaaatggg acaaaatcta ttaagttgaa  3060
ccatatataa ttgtggatat ttggctgttt ttaatctgac aagcagtaac ttcatatggt  3120
ttgccttaat atatatttgt tttagtcatg aactcataat ccattgatgc tctttcatga  3180
gaagagatat gacccatatt tccttattga tattattggt acaggcagac aaccctggta  3240
ggagagatgg attctggggt catgaccttt cgtgattatc cgcaaatgca aacagtttca  3300
gatctaatgg tttaatttag ggagtaatta tattaatcag agtgttctgt tattctcaat  3360
ctttatagaa acgattctgc tggttttgaa gaacagatgt attacactaa ctgtaaaagt  3420
agttcaagag tgagaaagaa taaattgtta ttaagagcaa aagaaaaata aagtgattga  3480
tgata                                                              3485

SEQ ID NO: 84           moltype = AA  length = 553
FEATURE                 Location/Qualifiers
source                  1..553
                        mol_type = protein
```

organism = Homo sapiens
SEQUENCE: 84
MRAPGRPALR PLPLPPLLLL LLAAPWGRAV PCVSGGLPKP ANITFLSINM KNVLQWTPPE 60
GLQGVKVTYT VQYFIYGQKK WLNKSECRNI NRTYCDLSAE TSDYEHQYYA KVKAIWGTKC 120
SKWAESGRFY PFLETQIGPP EVALTTDEKS ISVVLTAPEK WKRNPEDLPV SMQQIYSNLK 180
YNVSVLNTKS NRTWSQCVTN HTLVLTWLEP NTLYCVHVES FVPGPPRRAQ PSEKQCARTL 240
KDQSSEFKAK IIFWYVLPIS ITVFLFSVMG YSIYRYIHVG KEKHPANLIL IYGNEFDKRF 300
FVPAEKIVIN FITLNISDDS KISHQDMSLL GKSSDVSSLN DPQPSGNLRP PQEEEEVKHL 360
GYASHLMEIF CDSEENTEGT SFTQQESLSR TIPPDKTVIE YEYDVRTTDI CAGPEEQELS 420
LQEEVSTQGT LLESQAALAV LGPQTLQYSY TPQLQDLDPL AQEHTDSEEG PEEEPSTTLV 480
DWDPQTGRLC IPSLSSFDQD SEGCEPSEGD GLGEEGLLSR LYEEPAPDRP PGENETYLMQ 540
FMEEWGLYVQ MEN 553

SEQ ID NO: 85 moltype = DNA length = 2558
FEATURE Location/Qualifiers
source 1..2558
mol_type = other DNA
organism = synthetic construct
SEQUENCE: 85
tgtggcactg cctgcgtacc caaccccagc cctgggtagc ctgcagcatg gcccagctgt 60
tcctgcccct gctggcagcc ctggtcctgg cccaggctcc tgcagcttta gcagatgttc 120
tggaaggaga cagctcagag gaccgcgctt ttcgcgtgcg catcgcgggc gacgcgccac 180
tgcagggcgt gctcggcggc gccctcacca tcccttgcca cgtccactac ctgcggccac 240
cgccgagccg ccgggctgtg ctgggctctc cgcgggtcaa gtggactttc ctgtcccggg 300
gccgggaggc agaggtgctg gtggcgcggg gagtgcgcgt caaggtgaac gaggcctacc 360
ggttccgcgt ggcactgcct gcgtacccag cgtcgctcac cgacgtctcc ctggcgctga 420
gcgagctgcg ccccaacgac tcaggtatct atcgctgtga ggtccagcac ggcatcgatg 480
acagcagcga cgctgtggag gtcaaggtca aaggggtcgt ctttctctac cgagagggct 540
ctgcccgcta tgctttctcc ttttctgggg cccaggaggc ctgtgcccgc attggagccc 600
acatcgccac cccggagcag ctctatgccg cctaccttgg gggctatgag caatgtgatg 660
ctggctggct gtcggatcag accgtgaggt atcccatcca gaccccacga gaggcctgtt 720
acggagacat ggatggcttc cccggggtcc ggaactatgg tgtggtggac ccggatgacc 780
tctatgatgt gtactgttat gctgaagacc taaatggaga attgttcctg ggtgaccctc 840
cagagaagct gacattggag gaagcacggg cgtactgcca ggagcggggt gcagagattg 900
ccaccacggg ccaactgtat gcagcctggg atggtggcct ggaccactgc agcccagggt 960
ggctagctga tggcagtgtg cgctacccca tcgtcacacc cagccagcgc tgtggtgggg 1020
gcttgcctgg tgtcaagact ctcttcctct tccccaacca gactggcttc cccaataagc 1080
acagccgctt caacgtctac tgcttccgag actcggccca gccttctgcc atccctgagg 1140
cctccaaccc agcctccaac ccagcctctg atggactaga ggctatcgtc acagtgacag 1200
agaccctgga ggaactgcag ctgcctcagg aagccacaga gagtgaatcc cgtggggcca 1260
tctactccat ccccatcatg gaggacggag gaggtggaag ctccactcca gaagacccag 1320
cagaggcccc taggacgctc ctagaatttg aaacacaatc catggtaccg cccacggggt 1380
tctcagaaga ggaaggtaag gcattggagg aagaagagaa atatgaagat gaagaagaga 1440
aagaggagga agaagaagag gaggaggtgg aggatgaggc tctgtgggca tggcccagcg 1500
agctcagcag cccgggccct gaggcctctc tccccactga gccagcagcc caggaggagt 1560
cactctccca ggcgccagca agggcagtcc tgcagcctgg tgcatcacca cttcctgatg 1620
gagagtcaga agcttccagg cctccaaggg tccatggacc acctactgag actctgccca 1680
ctcccaggga gaggaaccta gcatccccat caccttccac tctggttgag gcaagagagg 1740
tgggggaggc aactggtggt cctgagctat ctggggtccc tcgaggagag agcgaggaga 1800
caggaagctc cgagggtgcc ccttccctgc ttccagccac acgggcccct gagggtacca 1860
gggagctgga ggcccccctct gaagataatt ctggaagaac tgccccagca gggacctcag 1920
tgcaggccca gccagtgctg cccactgaca gcgccagccg aggtggagtg gccgtggtcc 1980
ccgcatcagg taattctgcc caaggctcaa ctgccctctc tatcctactc cttttcttcc 2040
ccctgcagct ctgggtcacc tgacctgtag tcctttaacc caccatcatc ccaaactctc 2100
ctgtcctttg ccttcattct cttacccacc tctacctatg ggtctccaat ctcggatatc 2160
caccttgtgg gtatctcagc tctccgcgtc tttaccctgt gatcccagcc ccgccactga 2220
ccatctgtga cccttccctg ccattgggcc ctccacctgt ggctcacatc tcgccagccc 2280
cacagagcat cctcaggcct ctccaagggt cctcatcacc tattgcagcc ttcagggctc 2340
ggcctatttt ccactactcc cttcatccgc ctgtgtgccg tccccttttag ctgcctccta 2400
ttgatctcag ggaagcctgg gagtcccttc tcaccccctca acctccggag tccaggagaa 2460
cccgtacccc cacagagcct taagcaacta cttctgtgaa gtattttttg actgtttcat 2520
ggaaaacaag ccttggaaat aaatctctat taaaccgc 2558

SEQ ID NO: 86 moltype = AA length = 671
FEATURE Location/Qualifiers
source 1..671
mol_type = protein
organism = Homo sapiens
SEQUENCE: 86
MAQLFLPLLA ALVLAQAPAA LADVLEGDSS EDRAFRVRIA GDAPLQGVLG GALTIPCHVH 60
YLRPPPSRRA VLGSPRVKWT FLSRGREAEV LVARGVRVKV NEAYRFRVAL PAYPASLTDV 120
SLALSELRPN DSGIYRCEVQ HGIDDSSDAV EVKVKGVVFL YREGSARYAF SFSGAQEACA 180
RIGAHIATPE QLYAAYLGGY EQCDAGWLSD QTVRYPIQTP REACYGDMDG FPGVRNYGVV 240
DPDDLYDVYC YAEDLNGELF LGDPPEKLTL EEARAYCQER GAEIATTGQL YAAWDGGLDH 300
CSPGWLADGS VRYPIVTPSQ RCGGGLPGVK TLFLFPNQTG FPNKHSRFNV YCFRDSAQPS 360
AIPEASNPAS NPASDGLEAI VTVTETLEEL QLPQEATESE SRGAIYSIPI MEDGGGGSST 420
PEDPAEAPRT LLEFETQSMV PPTGFSEEEG KALEEEEKYE DEEEKEEEEE EEEVEDEALW 480
AWPSELSSPG PEASLPTEPA AQEESLSQAP ARAVLQPGAS PLPDGESEAS RPPRVHGPPT 540
ETLPTPRERN LASPSPSTLV EAREVGEATG GPELSGVPRG ESEETGSSEG APSLLPATRA 600

-continued

```
PEGTRELEAP SEDNSGRTAP AGTSVQAQPV LPTDSASRGG VAVVPASGNS AQGSTALSIL  660
LLFFPLQLWV T                                                        671

SEQ ID NO: 87          moltype = DNA  length = 4869
FEATURE                Location/Qualifiers
source                 1..4869
                       mol_type = other DNA
                       organism = synthetic construct
SEQUENCE: 87
cattctgctg gctgcgcggt ggcggcggct gtgtgtgcgc cgcgccttgc cgccccccct  60
ggccccccga gcccggggcg cgcgctcccg cccgggccgt ccgggccccg cggcgccgcg  120
gcccgaggcc ccgggaagcg cagccatggc tctgcggagg ctgggggccg cgctgctgct  180
gctgccgctg ctcgccgccg tggaagaaac gctaatggac tccactacag cgactgctga  240
gctgggctgg atggtgcatc ctccatcagg gtgggaagag gtgagtggct acgatgagaa  300
catgaacacg atccgcacgt accaggtgtg caacgtgttt gagtcaagcc agaacaactg  360
gctacggacc aagtttatcc ggcgccgtgg cgcccaccgc atccacgtgg agatgaagtt  420
ttcggtgcgt gactgcagca gcatccccag cgtgcctggc tcctgcaagg agaccttcaa  480
cctctattac tatgaggctg actttgactc ggccaccaag accttcccca actggatgga  540
gaatccatgg gtgaaggtgg ataccattgc agccgacgag agcttctccc aggtggacct  600
gggtggccgc gtcatgaaaa tcaacaccga ggtgcggagc ttcggacctg tgtcccgcag  660
cggcttctac ctggccttcc aggactatgg cggctgcatg tccctcatcg ccgtgcgtgt  720
cttctaccgc aagtgccccc gcatcatcca gaatggcgcc atcttccagg aaaccctgtc  780
gggggctgag agcacatcgc tggtggctgc ccggggcagc tgcatcgcca atgcggaaga  840
ggtggatgta cccatcaagc tctactgtaa cggggacggc gagtggctgg tgcccatcgg  900
gcgctgcatg tgcaaagcag gcttcgaggc cgttgagaat ggcaccgtct gccgaggttg  960
tccatctggg actttcaagg ccaaccaagg ggatgaggcc tgtacccact gtcccatcaa  1020
cagccggacc acttctgaag gggccaccaa ctgtgtctgc cgcaatggct actacagagc  1080
agacctggac cccctggaca tgccctgcac aaccatcccc tccgcgcccc aggctgtgat  1140
ttccagtgtc aatgagacct ccctcatgct ggagtggacc cctccccgcg actccggagg  1200
ccgagaggac ctcgtctaca acatcatctg caagagctgt ggctcgggcc ggggtgcctg  1260
cacccgctgc ggggacaatg tacagtacgc accacgccag ctaggcctga ccgagccacg  1320
catttacatc agtgacctgc tggcccacac ccagtacacc ttcgagatcc aggctgtgaa  1380
cggcgttact gaccagagcc ccttctcgcc tcagttcgcc tctgtgaaca tcaccaccaa  1440
ccaggcagct ccatcggcag tgtccatcat gcatcaggtg agccgcaccg tggacagcat  1500
taccctgtcg tggtcccagc cggaccagcc caatggcgtg atcctggact atgagctgca  1560
gtactatgag aaggagctca gtgagtacaa cgccacagcc ataaaaagcc ccaccaacac  1620
ggtcaccgtg cagggcctca aagccggcgc catctatgtc ttccaggtgc gggcacgcac  1680
cgtggcaggc tacgggcgct acagcggcaa gatgtacttc cagaccatga cagaagccga  1740
gtaccagaca agcatccagg agaagttgcc actcatcatc ggctcctcgg ccgctggcct  1800
ggtcttcctc attgctgtgg ttgtcatcgc catcgtgtgt aacagaagac gggggtttga  1860
gcgtgctgac tcggagtaca cggacaagct gcaacactac accagtggcc acatgacccc  1920
aggcatgaag atctacatcg atcctttcac ctacgaggac cccaacgagg cagtgcggga  1980
gtttgccaag gaaattgaca tctcctgtgt caaaattgag caggtgatcg gagcagggga  2040
gtttggcgag gtctgcagtg gccacctgaa gctgccaggc aagagagaga tctttgtggc  2100
catcaagacg ctcaagtcgg gctacacgga gaagcagcgc cgggacttcc tgagcgaagc  2160
ctccatcatg ggccagttcg accatcccaa cgtcatccac ctggagggtg tcgtgaccaa  2220
gagcacacct gtgatgatca tcaccgagtt catggagaat ggctccctgg actcctttct  2280
ccggcaaaac gatgggcagt tcacagtcat ccagctggtg ggcatgcttc ggggcatcgc  2340
agctggcatg aagtacctgg cagacatgaa ctatgttcac cgtgacctgg ctgcccgcaa  2400
catcctcgtc aacagcaacc tggtctgcaa ggtgtcggac tttgggctct cacgctttct  2460
agaggacgat acctcagacc ccacctacac cagtgccctg ggcggaaaga tccccatccg  2520
ctggacagcc ccggaagcca tccagtaccg gaagttcacc tcggccagtg atgtgtggag  2580
ctacggcatt gtcatgtggg aggtgatgtc ctatggggag cggccctact gggacatgac  2640
caaccaggat gtaatcaatg ccattgagca ggactatcgg ctgccaccgc ccatggactg  2700
cccgagcgcc ctgcaccaac tcatgctgga ctgttggcag aaggaccgca accaccggcc  2760
caagttcggc caaattgtca acacgctaga caagatgatc cgcaatccca acagcctcaa  2820
agccatggcg cccctctcct ctggcatcaa cctgccgctg ctggaccgca cgatccccga  2880
ctacaccagc tttaacacgg tggacgagtg gctggaggcc atcaagatgg ggcagtacaa  2940
ggagagcttc gccaatgccg gcttcacctc ctttgacgtc gtgtctcaga tgatgatgga  3000
ggacattctc cgggttgggg tcactttggc tggccaccag aaaaaaatcc tgaacagtat  3060
ccaggtgatg cgggcgcaga tgaaccagat tcagtctgtg gaggtttgac attcacctgc  3120
ctcggctcac ctcttcctcc aagccccgcc ccctctgccc cacgtgccgg ccctcctggt  3180
gctctatcca ctgcagggcc agccactcgc caggaggcca cgggccacgg gaagaaccaa  3240
gcggtgccag ccacgagacg tcaccaagaa aacatgcaac tcaaacgacg gaaaaaaaaa  3300
gggaatggga aaaaagaaaa cagatcctgg gagggggcgg gaaatacaag gaatattttt  3360
taaagaggat tctcataagg aaagcaatga ctgttcttgc gggggataaa aaagggcttg  3420
ggagattcat gcgatgtgtc caatcggaga caaaagcagt ttctctccaa ctccctctgg  3480
gaaggtgacc tggccagagc caagaaacac tttcagaaaa acaaatgtga aggggagaga  3540
caggggccgc ccttggctcc tgtccctgct gctcctctag gcctcactca acaaccaagc  3600
gcctggagga cgggacagat ggacagacag ccaccctgag aacccctctg ggaaaatcta  3660
ttcctgccac cactgggcaa acagaagaat ttttctgtct ttggagagta ttttagaaac  3720
tccaatgaaa gacactgttt ctcctgttgg ctcacagggc tgaaaggggc ttttgtcctc  3780
ctgggtcagg gagaacgcgg ggaccccaga aaggtcagcc ttcctgagga tgggcaaccc  3840
ccaggtctgc agctccaggt acatatcacg cgcacagcct ggcagcctgg ccctcctggt  3900
gcccactccc gccagcccct gcctcgagga ctgatactgc agtgactgcc gtcagctccg  3960
actgccgctg agaagggttg atcctgcatc tgggtttgtt tacagcaatt cctggactcg  4020
ggggtatttt ggtcacaggg tggttttggt ttagggggtt tgtttgttgg gttgtttttt  4080
gtttttttggt ttttttaat gacaatgaag tgacactttg acatttccta cctttgagg  4140
acttgatcct tctccaggaa gaaggtgctt tctgcttact gacttaggca atacaccaag  4200
```

```
ggcgagattt tatatgcaca tttctggatt tttttatacg gttttcattg acactcttcc  4260
ctcctcccac ctgccaccag gcctcaccaa agcccactgc catggggcca tctgggccat  4320
tcagagactg gagtgagatt tgggtgtgga gggggaggcg ccaaggtgga ggagcttccc  4380
actccaggac tgttgatgaa agggacagat tgaggaggaa gtgggctctg aggctgcagg  4440
gctggaagtc cttgcccact tcccactctc ctgccccaat ctatctagta cttcccaggc  4500
aaataggccc ctttgaggct cctgagtgcc ctcagatggt caaaacccag ttttccctct  4560
gggagcctaa accaggctgc atcggaggcc aggacccgga tcattcactg tgataccctg  4620
ccctccagag ggtgcgctca gagacacggg caagcatgcc tcttcccttc cctggagaga  4680
aagtgtgtga tttctctccc acctccttcc ccccaccaga cctttgctgg gcctaaaggt  4740
cttggccatg gggacgccct cagtctaggg atctggccac agactccctc ctgtgaacca  4800
acacagacac ccaagcagag caatcagtta gtgaattgaa tggaaataaa cgctttagtt  4860
ataatatga                                                          4869

SEQ ID NO: 88          moltype = AA  length = 987
FEATURE                Location/Qualifiers
source                 1..987
                       mol_type = protein
                       organism = Homo sapiens
SEQUENCE: 88
MALRRLGAAL LLLPLLAAVE ETLMDSTTAT AELGWMVHPP SGWEEVSGYD ENMNTIRTYQ  60
VCNVFESSQN NWLRTKFIRR RGAHRIHVEM KFSVRDCSSI PSVPGSCKET FNLYYYEADF  120
DSATKTFPNW MENPWVKVDT IAADESFSQV DLGGRVMKIN TEVRSFGPVS RSGFYLAFQD  180
YGGCMSLIAV RVFYRKCPRI IQNGAIFQET LSGAESTSLV AARGSCIANA EEVDVPIKLY  240
CNGDGEWLVP IGRCMCKAGF EAVENGTVCR GCPSGTFKAN QGDEACTHCP INSRTTSEGA  300
TNCVCRNGYY RADLDPLDMP CTTIPSAPQA VISSVNETSL MLEWTPPRDS GGREDLVYNI  360
ICKSCGSGRG ACTRCGDNVQ YAPRQLGLTE PRIYISDLLA HTQYTFEIQA VNGVTDQSPF  420
SPQFASVNIT TNQAAPSAVS IMHQVSRTVD SITLSWSQPD QPNGVILDYE LQYYEKELSE  480
YNATAIKSPT NTVTVQGLKA GAIYVFQVRA RTVAGYGRYS GKMYFQTMTE AEYQTSIQEK  540
LPLIIGSSAA GLVFLIAVVV IAIVCNRRRG FERADSEYTD KLQHYTSGHM TPGMKIYIDP  600
FTYEDPNEAV REFAKEIDIS CVKIEQVIGA GEFGEVCSGH LKLPGKREIF VAIKTLKSGY  660
TEKQRRDFLS EASIMGQFDH PNVIHLEGVV TKSTPVMIIT EFMENGSLDS FLRQNDGQFT  720
VIQLVGMLRG IAAGMKYLAD MNYVHRDLAA RNILVNSNLV CKVSDFGLSR FLEDDTSDPT  780
YTSALGGKIP IRWTAPEAIQ YRKFTSASDV WSYGIVMWEV MSYGERPYWD MTNQDVINAI  840
EQDYRLPPPM DCPSALHQLM LDCWQKDRNH RPKFGQIVNT LDKMIRNPNS LKAMAPLSSG  900
INLPLLDRTI PDYTSFNTVD EWLEAIKMGQ YKESFANAGF TSFDVVSQMM MEDILRVGVT  960
LAGHQKKILN SIQVMRAQMN QIQSVEV                                      987

SEQ ID NO: 89          moltype = DNA  length = 1658
FEATURE                Location/Qualifiers
source                 1..1658
                       mol_type = other DNA
                       organism = synthetic construct
SEQUENCE: 89
ggaaggcagc ggcagctcca ctcagccagt acccagatac gctgggaacc ttccccagcc  60
atggcttccc tggggcagat cctcttctgg agcataatta gcatcatcat tattctggct  120
ggagcaattg cactcatcat tggctttggt atttcaggga gacactccat cacagtcact  180
actgtcgcct cagctgggaa cattggggag gatggaatcc tgagctgcac ttttgaacct  240
gacatcaaac tttctgatat cgtgatacaa tggctgaagg aaggtgtttt aggcttggtc  300
catgagttca aagaaggcaa agatgagctg tcggagcagg atgaaatgtt cagaggccgg  360
acagcagtgt ttgctgatca agtgatagtt ggcaatgcct ctttgcggct gaaaaacgtg  420
caactcacag atgctggcac ctacaaatgt tatatcatca cttctaaagg caaggggaat  480
gctaaccttg agtataaaac tggagccttc agcatgccgg aagtgaatgt ggactataat  540
gccagctcag agaccttgcg gtgtgaggct ccccgatggt tcccccagcc cacagtggtc  600
tgggcatccc aagttgacca gggagccaac ttctcggaag tctccaatac cagctttgag  660
ctgaactctg agaatgtgac catgaaggtt gtgtctgtgc tctacaatgt tacgatcaac  720
aacacatact cctgtatgat tgaaaatgac attgccaaag caacagggga tatcaaagtg  780
acagaatcgg agatcaaaag gcggagtcac ctacagctgc taaactcaaa ggcttctctg  840
tgtgtctctt ctttctttgc catcagctgg gcacttctgc ctctcagccc ttacctgatg  900
ctaaaataat gtgccttggc cacaaaaaag catgcaaagt cattgttaca acagggatct  960
acagaactat ttcaccacca gatatgacct agttttatat ttctgggagg aaatgaattc  1020
atatctagaa gtctggagtg agcaaacaag agcaagaaac aaaaagaagc caaaagcaga  1080
aggctccaat atgaacaaga taaatctatc ttcaaagaca tattagaagt tgggaaaata  1140
attcatgtga actagacaag tgtgttaaga gtgataagta aaatgcacgt ggagacaagt  1200
gcatccccag atctcaggga cctccccctg cctgtcacct ggggagtgag aggacaggat  1260
agtgcatgtt ctttgtctct gaatttttag ttatatgtgc tgtaatgttg ctctgaggaa  1320
gcccctggaa agtctatccc aacatatcca catcttatat tccacaaatt aagctgtagt  1380
atgtacccta agacgctgct aattgactgc cacttcgcaa ctcaggggcg gctgcatttt  1440
agtaatgggt caaatgattc actttttatg atgcttccaa aggtgccttg gcttctcttc  1500
ccaactgaca aatgccaaag ttgagaaaaa tgatcataat tttagcataa acagagcagt  1560
cggggacacc gattttataa ataaactgag caccttcttt ttaaacaaaa aaaaaaaaaa  1620
aaaaaaaaaa aaaaaaaaaa aaaaaaaaaa aaaaaaaa                          1658

SEQ ID NO: 90          moltype = DNA  length = 946
FEATURE                Location/Qualifiers
source                 1..946
                       mol_type = other DNA
                       organism = synthetic construct
SEQUENCE: 90
tgacagccca ccagtgacca tgaaggctgt gctgcttgcc ctgttgatgg caggcttggc  60
```

-continued

```
cctgcagcca ggcactgccc tgctgtgcta ctcctgcaaa gcccaggtga gcaacgagga  120
ctgcctgcag gtggagaact gcacccagct gggggagcag tgctggaccg cgcgcatccg  180
cgcagttggc ctcctgaccg tcatcagcaa aggctgcagc ttgaactgcg tggatgactc  240
acaggactac tacgtgggca agaagaacat cacgtgctgt gacaccgact tgtgcaacgc  300
cagcggggcc catgccctgc agccggctgc cgccatcctt gcgctgctcc ctgcactcgg  360
cctgctgctc tggggacccg gccagctata ggctctgggg ggccccgctg cagcccacac  420
tgggtgtggt gccccaggcc tctgtgccac tcctcacaga cctggcccag tgggagcctg  480
tcctggttcc tgaggcacat cctaacgcaa gtctgaccat gtatgtttgc acccctgtcc  540
cccaccctga ccctcccatg gccctctcca ggactcccac ccggcagatc agctctagtg  600
acacagatcc gcctgcagat ggcccctcca accctctctg ctgctgtttc catggcccag  660
cattctccac ccttaaccct gtgctcaggc acctcttccc ccaggaagcc ttccctgccc  720
accccatcta tgacttgagc caggtctggt ccgtggtgtc cccgcaccc agcaggggac  780
aggcactcag gagggcccag taaaggctga gatgaagtgg actgagtaga actggaggac  840
aagagtcgac gtgagttcct gggagtctcc agagatgggg cctggaggcc tggaggaagg  900
ggccaggcct cacattcgtg gggctccctg aatggcagcc tgagca                 946

SEQ ID NO: 91          moltype = AA  length = 123
FEATURE                Location/Qualifiers
source                 1..123
                       mol_type = protein
                       organism = Homo sapiens
SEQUENCE: 91
MKAVLLALLM AGLALQPGTA LLCYSCKAQV SNEDCLQVEN CTQLGEQCWT ARIRAVGLLT  60
VISKGCSLNC VDDSQDYYVG KKNITCCDTD LCNASGAHAL QPAAAILALL PALGLLLWGP  120
GQL                                                                123

SEQ ID NO: 92          moltype = DNA  length = 1852
FEATURE                Location/Qualifiers
source                 1..1852
                       mol_type = other DNA
                       organism = synthetic construct
SEQUENCE: 92
ctgggctgag gcggaggcag gggagttgca gcgcgcgagg ctccgtgagt gtgtctcctg  60
cgcgctgaga ggcgggggga ggcggaggac caggaggagg aggaggagga ggaggagggg  120
gagaatgccc ggagccgccg ccgctgccgc cgccgccgcc gccgcgatgc tcccggctca  180
ggaggctgcc aagctgtacc acaccaacta tgtgcggaac tcgcgggcca tcggcgtgct  240
gtgggccatc ttcaccatct gctttgccat cgtcaacgtg gtgtgcttca tccagcccta  300
ctggataggc gacggcgtgg acaccccgca agccggctat ttcgggctct tccactactg  360
catcggcaac ggcttctccc gggagctgac ctgcaggggc agcttcacgg acttctccac  420
gctgccctcg ggcgccttca aagccgcctc cttctttatc ggcctctcca tgatgctcat  480
cattgcctgc atcatttgct ttaccctctt cttcttctgc aacacggcca ctgtgtacaa  540
gatatgtgcc tggatgcagc tcacctccgc tgcctgcctt gtgcttggct gtatgatttt  600
ccctgatggc tgggactcag atgaagtaaa acggatgtgt ggagaaaaga cagacaagta  660
cactcttggg gcttgctcag tccgctgggc atacatcctg gctattattg gaattttgga  720
tgccctgatc ctctcatttc tagcatttgt gcttggtaat cgacaagaca gcttgatggc  780
agaggaactg aaggcagaaa acaaagttct gctaagccaa tattctctag aatgagcaca  840
aaacaaatcg aataacagct aaacaaatcg aataacagct aaacgaatcg aataacagct  900
tttgtacatc aacatcaaga aggaatacgc ctgagagaga tcagagtata tagatgaata  960
tgaacaagaa tggaacattc acttgtcaac gcactttcta aatctagatc agcagagatg  1020
ggagtgattt tctggaaaga gatgtgatca tggattaaac accagctcat tggaaactca  1080
ttggatgaga tcagaaaacg ttcatgaaaa atcatattca ggaaataagg aagaggaata  1140
taaatgctct agagttaaca tgtaaaatat atacgtactg aggtttgtaa actgtccttt  1200
ttaaatcaaa ctgaaaacaa aaagctttaa cctttcaaca gaatttttaa aaaggcagtt  1260
agttctaaat tattcctatc tcaatagcca agaggctgat caagcgtcat ttattgagga  1320
agcatcttag aaaatgcctc tgaatgtttt cataggagcc gtgacctttg gttcttcatc  1380
tctaccattc atttacttca ctgtgtaatt agttacaacc actcagttat taagagacgt  1440
aacgcttcaa actttttacc aagtctgtgt tctgtttaat ctgtccatac aagttattac  1500
tgagaaagtg tttatgccat atactattac tccatcaagc tgtatattac aggaagtaca  1560
tctttacatc ataggttccc aagcaacata gatttcccta tctttcagga aacagcatca  1620
aggaactctg aaaaatatag aaaaagttca ttttcacctt ggaagctcac gtgtaatatt  1680
ataggctact atcaaataaa cacttttttt ctaattctcc ctagtatatg cataggaatt  1740
taatatactt tataaataag tatctaaaat gtctcctact tttttcctat ttctttgcca  1800
tacatgttat cagaaatcca tgtcttctat ttcccttact gatgggcact ca         1852

SEQ ID NO: 93          moltype = AA  length = 236
FEATURE                Location/Qualifiers
source                 1..236
                       mol_type = protein
                       organism = Homo sapiens
SEQUENCE: 93
MPGAAAAAAA AAAAMLPAQE AAKLYHTNYV RNSRAIGVLW AIFTICFAIV NVVCFIQPYW  60
IGDGVDTPQA GYFGLFHYCI GNGFSRELTC RGSFTDFSTL PSGAFKAASF FIGLSMMLII  120
ACIICFTLFF FCNTATVYKI CAWMQLTSAA CLVLGCMIFP DGWDSDEVKR MCGEKTDKYT  180
LGACSVRWAY ILAIIGILDA LILSFLAFVL GNRQDSLMAE ELKAENKVLL SQYSLE      236

SEQ ID NO: 94          moltype = DNA  length = 1052
FEATURE                Location/Qualifiers
source                 1..1052
                       mol_type = other DNA
```

```
                         organism = synthetic construct
SEQUENCE: 94
tgccaagccc tgccatgtag tgcacgcagg acatcaacaa acacagataa caggaaatga  60
tccattccct gtggtcactt attctaaagg ccccaacctt caaagttcaa gtagtgatat  120
ggatgactcc acagaaaggg agcagtcacg ccttacttct tgccttaaga aaagagaaga  180
aatgaaactg aaggagtgtg tttccatcct cccacggaag gaaagcccct ctgtccgatc  240
ctccaaagac ggaaagctgc tggctgcaac cttgctgctg gcactgctgt cttgctgcct  300
cacggtggtg tctttctacc aggtggccgc cctgcaaggg gacctggcca gcctccgggc  360
agagctgcag ggccaccacg cggagaagct gccagcagga gcaggagccc ccaaggccgg  420
cctggaggaa gctccagctg tcaccgcggg actgaaaatc tttgaaccac cagctccagg  480
agaaggcaac tccagtcaga acagcagaaa taagcgtgcc gttcagggtc cagaagaaac  540
agtcactcaa gactgcttgc aactgattgc agacagtgaa acaccaacta tacaaaaagg  600
atcttacaca tttgttccat ggcttctcag ctttaaaagg ggaagtgccc tagaagaaaa  660
agagaataaa atattggtca aagaaactgg ttacttttt atatatggtc aggttttata  720
tactgataag acctacgcca tgggacatct aattcagagg aagaaggtcc atgtctttgg  780
ggatgaattg agtctggtga ctttgtttcg atgtattcaa aatatgcctg aaacactacc  840
caataattcc tgctattcag ctggcattgc aaaactggaa gaaggagatg aactccaact  900
tgcaatacca agagaaaatg cacaaatatc actggatgga gatgtcacat tttttggtgc  960
attgaaactg ctgtgaccta cttacaccat gtctgtagct attttcctcc ctttctctgt  1020
acctctaaga agaaagaatc taactgaaaa ta                                1052

SEQ ID NO: 95            moltype = AA  length = 285
FEATURE                  Location/Qualifiers
source                   1..285
                         mol_type = protein
                         organism = Homo sapiens
SEQUENCE: 95
MDDSTEREQS RLTSCLKKRE EMKLKECVSI LPRKESPSVR SSKDGKLLAA TLLLALLSCC  60
LTVVSFYQVA ALQGDLASLR AELQGHHAEK LPAGAGAPKA GLEEAPAVTA GLKIFEPPAP  120
GEGNSSQNSR NKRAVQGPEE TVTQDCLQLI ADSETPTIQK GSYTFVPWLL SFKRGSALEE  180
KENKILVKET GYFFIYGQVL YTDKTYAMGH LIQRKKVHVF GDELSLVTLF RCIQNMPETL  240
PNNSCYSAGI AKLEEGDELQ LAIPRENAQI SLDGDVTFFG ALKLL                  285

SEQ ID NO: 96            moltype = DNA  length = 2544
FEATURE                  Location/Qualifiers
source                   1..2544
                         mol_type = other DNA
                         organism = synthetic construct
SEQUENCE: 96
agatgctgcc agggtccctg aagagggaag acacgcggaa acaggtaaaa atcattttgc  60
ttttattttg cattcaacaa gcaagttatt acggaacagc agttatgggc caggcatacc  120
tcccagagct gggaacacag tggggacctc cctggctctc tcttaccggt gttacaacag  180
gttgtagaca gacccctgtc ttgagcatcc tccttgccag gcctgctgag tcttctgaga  240
gtagggtagg ttattggatg cccaggaggg aagaaggagc cagggaggtc agccccaagg  300
ttctgcaagg ccctcaacag gcctggactg aggaggtctg gacagcatgg ccctgtcctg  360
agcctctgtg cataataact gctgtcccta acctccaccc caccctcagc cttccaattc  420
ccgggcctgg ggccctactc ctgtgctcca gagactcctg gagctccttg aggcagcaca  480
cagtcctgct ctggaggcgc ccatctccca ctcatgctgg gatgctccag cccgtcccag  540
agcaggttgt ggctggaggg tgctggcaga ggagggacaa tggcccggct cctggaggca  600
agtgttggct gcagggaacg gagtctagtc cttgccacag cccttgttac cccttaggta  660
accttaaggg gatttcaaag aactctggct ctgcaaccct gctaagtttt ttatggaaca  720
tgtaaaatag atcccatggc caaagaagta tggacaatgt attatactat actctaatcc  780
ccatgtctag agattaatgg tgtagataga gtttactgaa aggtttttaa agtcctgcaa  840
taaagaatct tacttaagcc aggtgcggtg gctcacgcct gtcatctcag cactttggga  900
ggccaaggcg ggaggatcac ttgaggtcag gagttcgaga ccagcctggc cagcatggcg  960
aaaccctgtc tctactagaa atacagaaaa attagctggg tgtggtggtg ggcacctgta  1020
atcccagcta ctcgggaggc tgaggcagga ggatcacttg aactggggag gtagaggtta  1080
cagcgagcca agatcgcgcc actgcactcc agcctgggtg acagagggaa actccatctc  1140
aaaaaaacaa caacacaaca acaacaacaa taacaacaaa aaaacaaagc aggactggag  1200
agaggtggaa tgaagtggca aggggttcct gaggggtgat ttgggacagg acatctaaag  1260
ccaggtgtac gctcacgtcc tcagtccccc aggctcctgc acgggctctg ttcttttgca  1320
gaaaggcctt ttccacctca tatccagctc cctccagaaa ttcaagagtc ccaggaagtc  1380
actctgacct gcttgctgaa tttctcctgc tatgggtatc cgatccaatt gcagtggctc  1440
ctagaggggg ttccaatgag gcaggctgct gtcacctcga cctccttgac catcaagtct  1500
gtcttcaccc ggagcgagct caagttctcc ccacagtgga gtcaccatgg gaagattgtg  1560
acctgccagc ttcaggatgc agatgggaag ttcctctcca atgacacggt gcagctgaac  1620
gtgaagcgtg agtctccccg gcatgcctgt gggaagggca aggtctgtgt caccttctcc  1680
ccagccccgc agggggcatg cacccagggc agggggaagc ctgcacagac ggcggcatcc  1740
tccagccctg gtcacgccgc cttgtcagcc ctggtgtttc gggaaaaaga tttgctctag  1800
cctaacagaa taaaatggtc caccctcaag ccatgacatg aattggggat tatctggtta  1860
ggtctttttg ttcccctctt ggtggggatt tttttcgcat cattatcttg tgcctcattc  1920
attcaataaa tacgtatcat gaacctacta ggtaccaggc cctattacgg ctgccaatgg  1980
ggggcatggg gcggtgggca gggtgcagca gtgagcaaaa ctcttgcccc acgcggagcc  2040
agcgctgcag tgaaagagac agacaacaaa tggattacca aagaaataca gagcatgagc  2100
caagacatta gaatctggaa caaagcaatg ttaacaaaga aatatacaac actattgtag  2160
gtagtgatat gtgtgttagg aaaaaaataa ggccgagaga ggggagtgat ggagagagac  2220
ctctctaaga aggtgagcac ttaggccggg tgcggtggct cacgcctgta atcctagcac  2280
tttggaaggc cgaggcgggg ggatcacaag gtcaggagat cgagaccatc ctggctaaca  2340
tggtgaaacc ccatctctag taaaaataca aaaaattagc caggcatgat ggcaggcgcc  2400
```

-continued

```
tgtagtccca gctacttggg aggccaaggc aggagaatga catgaaccca ggaggcggag  2460
cttgcagtga gctgagatcg caccactgca ctccaacctg ggtgacgagt gagactccat  2520
ctcaaaaaaa aaaaaaaaaa aaaa                                          2544

SEQ ID NO: 97          moltype = AA  length = 240
FEATURE                Location/Qualifiers
source                 1..240
                       mol_type = protein
                       organism = Homo sapiens
SEQUENCE: 97
MLPGSLKRED TRKQVKIILL LFCIQQASYY GTAVMGQAYL PELGTQWGPP WLSLTGVTTG  60
CRQTPVLSIL LARPAESSES RVGYWMPRRE EGAREVSPKV LQGPQQAWTE EVWTAWPCPE  120
PLCIITAVPN LHPTLSLPIP GPGALLLCSR DSWSSLRQHT VLLWRRPSPT HAGMLQPVPE  180
QVVAGGCWQR RDNGPAPGGK CWLQGTESSP CHSPCYPLGN LKGISKNSGS ATLLSFLWNM  240

SEQ ID NO: 98          moltype = DNA  length = 2116
FEATURE                Location/Qualifiers
source                 1..2116
                       mol_type = other DNA
                       organism = synthetic construct
SEQUENCE: 98
acgcggaaac aggcttgcac ccagacacga caccatgcat ctcctcggcc cctggctcct  60
gctcctggtt ctagaatact tggctttctc tgactcaagt aaatgggttt ttgagcaccc  120
tgaaaccctc tacgcctggg agggggcctg cgtctggatc cctgcacct acagagccct  180
agatggtgac ctggaaagct tcatcctgtt ccacaatcct gagtataaca agaacacctc  240
gaagtttgat gggacaagac tctatgaaag cacaaaggat gggaaggttc cttctgagca  300
gaaaagggtg caattcctgg gagacaagaa taagaactgc acactgagta tccacccggt  360
gcacctcaat gacagtggtc agctggggct gaggatggag tccaagactg agaaatggat  420
ggaacgaata cacctcaatg tctctgaaag gccttttcca cctcatatcc agctccctcc  480
agaaattcaa gagtcccagg aagtcactct gacctgcttg ctgaatttct cctgctatgg  540
gtatccgatc caattgcagt ggctcctaga gggggttcca atgaggcagg ctgctgtcac  600
ctcgacctcc ttgaccatca agtctgtctt cacccggagc gagctcaagt tctccccaca  660
gtggagtcac catgggaaga ttgtgacctg ccagcttcag gatgcagatg ggaagttcct  720
ctccaatgac acggtgcagc tgaacgtgaa gcatcctccc aagaaggtga ccacagtgat  780
tcaaaacccc atgccgattc gagaaggaga cacagtgacc ctttcctgta actacaattc  840
cagtaacccc agtgttaccc ggtatgaatg gaaaccccat ggcgcctggg aggagccatc  900
gcttggggtg ctgaagatcc aaaacgttgg ctgggacaac acaaccatcg cctgcgcagc  960
ttgtaatagt tggtgctcgt gggcctcccc tgtcgccctg aatgtccagt atgccccccg  1020
agacgtgagg gtccggaaaa tcaagcccct ttccgagatt cactctggaa actcggtcag  1080
cctccaatgt gacttctcaa gcagccaccc caaagaagtc cagttcttct gggagaaaaa  1140
tggcaggctt ctggggaaag aaagccagct gaattttgac tccatctccc cagaagatgc  1200
tgggagttac agctgctggg tgaacaactc cataggacag acagcgtcca aggcctggac  1260
acttgaagtg ctgtatgcac ccaggaggct gcgtgtgtcc atgagcccgg gggaccaagt  1320
gatggagggg aagagtgcaa ccctgacctg tgagagcgac gccaaccctc ccgtctccca  1380
ctacacctgg tttgactgga ataaccaaag cctcccctac cacagccaga agctgagatt  1440
ggagccggtg aaggtccagc actcgggtgc ctactggtgc caggggacca acagtgtggg  1500
caagggccgt tcgcctctca gcaccctcac cgtctactat agcccggaga ccatcggcag  1560
gcgagtggct gtgggactcg ggtcctgcct cgccatcctc atcctggcaa tctgtgggct  1620
caagctccag cgacgttgga agaggacaca gagccagcag gggcttcagg agaattccag  1680
cggccagagc ttctttgtga ggaataaaaa ggttagaagg gcccccctct ctgaaggccc  1740
ccactccctg ggatgctaca atccaatgat ggaagatggc attagctaca ccaccctgcg  1800
ctttcccgag atgaacatac cacgaactgg agatgcagag tcctcagaga tgcagagacc  1860
tcccccggac tgcgatgaca cggtcactta ttcagcattg cacaagcgcc aagtgggcac  1920
tatgagaacg tcattccaga ttttccagaa gatgaggggga ttcattactc agagctgatc  1980
cagtttgggg tcggggagcg gcctcaggca caagaaaatg tggactatgt gatcctcaaa  2040
cattgacact ggatgggctg cagcagaggc actgggggca gcgggggcca gggaagtccc  2100
cgagttttcc ccagac                                                   2116

SEQ ID NO: 99          moltype = AA  length = 647
FEATURE                Location/Qualifiers
source                 1..647
                       mol_type = protein
                       organism = Homo sapiens
SEQUENCE: 99
MHLLGPWLLL LVLEYLAFSD SSKWVFEHPE TLYAWEGACV WIPCTYRALD GDLESFILFH  60
NPEYNKNTSK FDGTRLYEST KDGKVPSEQK RVQFLGDKNK NCTLSIHPVH LNDSGQLGLR  120
MESKTEKWME RIHLNVSERP FPPHIQLPPE IQESQEVTLT CLLNFSCYGY PIQLQWLLEG  180
VPMRQAAVTS TSLTIKSVFT RSELKFSPQW SHHGKIVTCQ LQDADGKFLS NDTVQLNVKH  240
PPKKVTTVIQ NPMPIREGDT VTLSCNYNSS NPSVTRYEWK PHGAWEEPSL GVLKIQNVGW  300
DNTTIACAAC NSWCSWASPV ALNVQYAPRD VRVRKIKPLS EIHSGNSVSL QCDFSSSHPK  360
EVQFFWEKNG RLLGKESQLN FDSISPEDAG SYSCWVNNSI GQTASKAWTL EVLYAPRRLR  420
VSMSPGDQVM EGKSATLTCE SDANPPVSHY TWFDWNNQSL PYHSQKLRLE PVKVQHSGAY  480
WCQGTNSVGK GRSPLSTLTV YYSPETIGRR VAVGLGSCLA ILILAICGLK LQRRWKRTQS  540
QQGLQENSSG QSFFVRNKKV RRAPLSEGPH SLGCYNPMME DGISYTTLRF PEMNIPRTGD  600
AESSEMQRPP PDCDDTVTYS ALHKRQVGTM RTSFQIFQKM RGFITQS                 647

SEQ ID NO: 100         moltype = DNA  length = 1258
FEATURE                Location/Qualifiers
source                 1..1258
```

```
                         mol_type = other DNA
                         organism = synthetic construct
SEQUENCE: 100
tccactcaca gcctgaagca tacccggcag ggctgtcccc caggcccaac aagcaaaggg  60
cccagtagcg agggccactg gagcccatct ccggggggct gggcaggaag tagggtgggg  120
tttggggtag ggatctggta ccctgggact gctgcaactc aaactaacca acccactggg  180
agaagatgcc tgggggtcca ggagtcctcc aagctctgcc tgccaccatc ttcctcctct  240
tcctgctgtc tgctgtctac ctgggccctg ggtgccaggc cctgtggatg cacaaggtcc  300
cagcatcatt gatggtgagc ctgggggaag acgcccactt ccaatgcccg cacaatagca  360
gcaacaacgc caacgtcacc tggtggcgcg tcctccatgg caactacacg tggcccccctg  420
agttcttggg cccgggcgag gaccccaatg gtacgctgat catccagaat gtgaacaaga  480
gccatggggg catatacgtg tgccgggtcc aggagggcaa cgagtcatac cagcagtcct  540
gcggcaccta cctccgcgtg cgccagccgc cccccaggcc cttcctggac atgggggagg  600
gcaccaagaa ccgaatcatc acagccgagg ggatcatcct cctgttctgc gcggtggtgc  660
ctgggacgct gctgctgttc aggaaacgat ggcagaacga gaagctcggg ttggatgccg  720
gggatgaata tgaagatgaa aacctttatg aaggcctgaa cctggacgac tgctccatgt  780
atgaggacat ctcccggggc ctccagggca cctaccagga tgtgggcagc ctcaacatag  840
gagatgtcca gctggagaag ccgtgacacc cctactcctg ccaggctgcc cccgcctgct  900
gtgcacccag ctccagtgtc tcagctcact tccctgggac attctccttt cagcccttct  960
gggggcttcc ttagtcatat tcccccagtg gggggtggga gggtaacctc actcttctcc  1020
aggccaggcc tccttggact cccctggggg tgtcccactc ttcttccctc taaactgccc  1080
cacctcctaa cctaatcccc ccgccccgct gcctttccca ggctcccctc accccagcgg  1140
gtaatgagcc cttaatcgct gcctctaggg gagctgattg tagcagcctc gttagtgtca  1200
ccccctcctc cctgatctgt cagggccact tagtgataat aaattcttcc caactgca    1258

SEQ ID NO: 101           moltype = AA  length = 226
FEATURE                  Location/Qualifiers
source                   1..226
                         mol_type = protein
                         organism = Homo sapiens
SEQUENCE: 101
MPGGPGVLQA LPATIFLLFL LSAVYLGPGC QALWMHKVPA SLMVSLGEDA HFQCPHNSSN  60
NANVTWWRVL HGNYTWPPEF LGPGEDPNGT LIIQNVNKSH GGIYVCRVQE GNESYQQSCG  120
TYLRVRQPPP RPFLDMGEGT KNRIITAEGI ILLFCAVVPG TLLLFRKRWQ NEKLGLDAGD  180
EYEDENLYEG LNLDDCSMYE DISRGLQGTY QDVGSLNIGD VQLEKP                226

SEQ ID NO: 102           moltype = DNA  length = 2919
FEATURE                  Location/Qualifiers
source                   1..2919
                         mol_type = other DNA
                         organism = synthetic construct
SEQUENCE: 102
aaaaaaaaaa agtgatgagt tgtgaggcag gtcgcggccc tactgcctca ggagacgatg  60
cgcagctcat ttgcttaaat ttgcagctga cggctgccac ctctctagag gcacctggcg  120
gggagcctct caacataaga cagtgaccag tctggtgact cacagccggc acagccatga  180
actacccgct aacgctggaa atggacctcg agaacctgga ggacctgttc tgggaactgg  240
acagattgga caactataac gacacctccc tggtggaaaa tcatctctgc cctgccacag  300
aggggcccct catggcctcc ttcaaggccg tgttcgtgcc cgtggcctac agcctcatct  360
tcctcctggg cgtgatcggc aacgtcctgg tgctggtgat cctggagcgg caccggcaga  420
cacgcagttc cacggagacc ttcctgttcc acctggccgt ggccgacctc ctgctggtct  480
tcatcttgcc ctttgccgtg gccgagggct ctgtgggctg ggtcctgggg accttcctct  540
gcaaaactgt gattgccctg cacaaagtca acttctactg cagcagcctg ctcctggcct  600
gcatcgccgt ggaccgctac ctggccattg tccacgccgt ccatgcctac cgccaccgcc  660
gcctcctctc catccacatc acctgtggga ccatctggct ggtgggcttc ctccttgcct  720
tgccagagat tctcttcgcc aaagtcagcc aaggccatca caacaactcc ctgccacgtt  780
gcaccttctc ccaagagaac caagcagaaa cgcatgcctg gttcacctcc cgattcctct  840
accatgtggc gggattcctg ctgcccatgc tggtgatggg ctggtgctac gtgggggtag  900
tgcacaggtt gcgccaggcc cagcggcgcc ctcagcggca gaaggcagtc agggtggcca  960
tcctggtgac aagcatcttc ttcctctgct ggtcacccta ccacatcgtc atcttcctgg  1020
acaccctggc gaggctgaag gccgtggaca atacctgcaa gctgaatggc tctctccccg  1080
tggccatcac catgtgtgag ttcctgggcc tggcccactg ctgcctcaac cccatgctct  1140
acactttcgc cggcgtgaag ttccgcagtg acctgtcgcg gctcctgacg aagctgggct  1200
gtaccggccc tgcctccctg tgccagctct tccctagctg gcgcaggagc agtctctctg  1260
agtcagagaa tgccacctct ctcaccacgt tctaggtccc agtgtcccct tttattgctg  1320
cttttccttg gggcaggcag tgatgctgga tgctccttcc aacaggagct gggatcctaa  1380
gggctcaccg tggctaagag tgtcctagga gtatcctcat ttggggtagc tagaggaacc  1440
aacccccatt tctagaacat ccctgccagc tcttctgccg gccctggggc taggctggag  1500
cccagggagc ggaaagcagc tcaaaggcac agtgaaggct gtccttaccc atctgcaccc  1560
ccctgggctg agagaacctc acgcacctcc catcctaatc atccaatgct caagaaacaa  1620
cttctacttc tgcccttgcc aacggagagc gcctgcccct cccagaacac actccatcag  1680
cttaggggct gctgacctcc acagcttccc ctctctcctc ctgcccacct gtcaaacaaa  1740
gccagaagct gagcaccagg ggatgagtgg aggttaaggc tgaggaaagg ccagctggca  1800
gcagagtgtg gccttcggac aactcagtcc ctaaaaacac agacattctg ccaggccccc  1860
aagcctgcag tcatcttgac caagcaggaa gctcagactg gttgagttca ggtagctgcc  1920
cctggctctg accgaaacag cgctgggtcc accccatgtc accggatcct gggtggtctg  1980
caggcagggc tgactctagg tgcccttgga ggccagccag tgacctgagg aagcgtgaag  2040
gccgagaagc aagaaagaaa cccgacagag ggaagaaaag agctttcttc ccgaacccca  2100
aggagggaga tggatcaatc aaacccggcg gtcccctccg ccaggcgaga tggggtgggg  2160
tggagaactc ctagggtggc tgggtccagg ggatgggagg ttgtgggcat tgatggggaa  2220
```

```
ggaggctggc ttgtcccctc ctcactccct tcccataagc tatagacccg aggaaactca  2280
gagtcggaac ggagaaaggt ggactggaag gggcccgtgg gagtcatctc aaccatcccc  2340
tccgtggcat caccttaggc agggaagtgt aagaaacaca ctgaggcagg gaagtcccca  2400
ggccccagga agccgtgccc tgcccccgtg aggatgtcac tcagatggaa ccgcaggaag  2460
ctgctccgtg cttgtttgct cacctggggt gtgggaggcc cgtccggcag ttctgggtgc  2520
tccctaccac ctccccagcc tttgatcagg tggggagtca gggacccctg cccttgtccc  2580
actcaagcca agcagccaag ctccttggga ggccccactg ggaaataac agctgtggct  2640
cacgtgagag tgtcttcacg gcaggacaac gaggaagccc taagacgtcc ctttttctc  2700
tgagtatctc ctcgcaagct gggtaatcga tgggggagtc tgaagcagat gcaaagaggc  2760
aagaggctgg attttgaatt ttctttttaa taaaaaggca cctataaaac aggtcaatac  2820
agtacaggca gcacagagac ccccggaaca agcctaaaaa ttgtttcaaa ataaaaacca  2880
agaagatgtc ttcacatatt gtaaaaaaaa aaaaaaaaa                        2919

SEQ ID NO: 103         moltype = AA  length = 372
FEATURE                Location/Qualifiers
source                 1..372
                       mol_type = protein
                       organism = Homo sapiens
SEQUENCE: 103
MNYPLTLEMD LENLEDLFWE LDRLDNYNDT SLVENHLCPA TEGPLMASFK AVFVPVAYSL  60
IFLLGVIGNV LVLVILERHR QTRSSTETFL FHLAVADLLL VFILPFAVAE GSVGWVLGTF  120
LCKTVIALHK VNFYCSSLLL ACIAVDRYLA IVHAVHAYRH RRLLSIHITC GTIWLVGFLL  180
ALPEILFAKV SQGHHNNSLP RCTFSQENQA ETHAWFTSRF LYHVAGFLLP MLVMGWCYVG  240
VVHRLRQAQR RPQRQKAVRV AILVTSIFFL CWSPYHIVIF LDTLARLKAV DNTCKLNGSL  300
PVAITMCEFL GLAHCCLNPM LYTFAGVKFR SDLSRLLTKL GCTGPASLCQ LFPSWRRSSL  360
SESENATSLT TF                                                     372

SEQ ID NO: 104         moltype = DNA  length = 1388
FEATURE                Location/Qualifiers
source                 1..1388
                       mol_type = other DNA
                       organism = synthetic construct
SEQUENCE: 104
gatttatact cttaatgggt actttctgac tgaattttat gagctcattc tgaagaggct  60
gacgatttta ctatctcatt tttttccttt ctccagaatg ggttctgggt gggtcccctg  120
ggtggtggct ctgctagtga atctgacccg actggattcc tccatgactc aaggcacaga  180
ctctccagaa gattttgtga ttcaggcaaa ggctgactgt tacttcacca acgggacaga  240
aaaggtgcag tttgtggtca gattcatctt taacttggag gagtatgtac gtttcgacag  300
tgatgtgggg atgtttgtgg cattgaccaa gctggggcag ccagatgctg agcagtggaa  360
cagccggctg gatctcttgg agaggagcag acaggccgtg gatggggtct gtagacacaa  420
ctacaggctg ggcgcaccct tcactgtggg gagaaaagtg caaccagagg tgacagtgta  480
cccagagagg accccactcc tgcaccagca taatctgctg cactgctctg tgacaggctt  540
ctatccaggg gatatcaaga tcaagtggtt cctgaatggg caggaggaga gagctggggt  600
catgtccact ggccctatca ggaatggaga ctggaccttt cagactgtgg tgatgctaga  660
aatgactcct gaacttggac atgtctacac ctgccttgtc gatcactcca gcctgctgag  720
ccctgtttct gtggagtgga gagctcagtc tgaatattct tggagaaaga tgctgagtgg  780
cattgcagcc ttcctacttg ggctaatctt ccttctggtg ggaatcgtca tccagctaag  840
ggctcagaaa ggatatgtga ggacgcagat gtctggtaat gaggtctcaa gagctgttct  900
gctccctcag tcatgctaag gtcctcactg aagcttctct ctctggagcc tgaagtagtg  960
atgagtagtc tgggccctgg gtgaggtaaa ggacattcat gaggtcaatg ttctgggaat  1020
aactctcttc cctgatcctt ggaggagccc gaactgattc tggagctctg tgttctgaga  1080
tcatgcatct cccacccatc tgcccttctc ccttctacgt gtacatcatt aatccccatt  1140
gccaagggca ttgtccagaa actcccctga gaccttactc cttccagccc caaatcattt  1200
acttttctgt ggtccagccc tactcctata agtcatgatc tccaaagctt tctgtcttcc  1260
aactgcagtc tccacagtct tcagaagaca aatgctcagg tagtcactgt ttcctttca   1320
ctgtttttaa aaacctttta ttgtcaaata aaatggagat acaaaaaatg taaaaaaaaa  1380
aaaaaaaa                                                          1388

SEQ ID NO: 105         moltype = AA  length = 273
FEATURE                Location/Qualifiers
source                 1..273
                       mol_type = protein
                       organism = Homo sapiens
SEQUENCE: 105
MGSGWVPWVV ALLVNLTRLD SSMTQGTDSP EDFVIQAKAD CYFTNGTEKV QFVVRFIFNL  60
EEYVRFDSDV GMFVALTKLG QPDAEQWNSR LDLLERSRQA VDGVCRHNYR LGAPFTVGRK  120
VQPEVTVYPE RTPLLHQHNL LHCSVTGFYP GDIKIKWFLN GQEERAGVMS TGPIRNGDWT  180
FQTVVMLEMT PELGHVYTCL VDHSSLLSPV SVEWRAQSEY SWRKMLSGIA AFLLGLIFLL  240
VGIVIQLRAQ KGYVRTQMSG NEVSRAVLLP QSC                              273

SEQ ID NO: 106         moltype = DNA  length = 2341
FEATURE                Location/Qualifiers
source                 1..2341
                       mol_type = other DNA
                       organism = synthetic construct
SEQUENCE: 106
tccgcgatcg ctgctttcag ctgggcaaca gcacagggcg gtcctgcgca tccgggggc  60
tgcgctccca gaccggtggc tggggagtag gttgcagggg tgtcactgtg tcaggggagg  120
aggaggagga ggaggaagaa gaggtagcgg caaggtcgcg gtctgaggtt ccggtgctcg  180
```

-continued

```
ccgccgccca gctcccagcc gaggctttct caaccgcgtc aataaaaggc cgccccgacc  240
cgccccccgcg ccccgcagcc ctgccggaca ccccgggctg cagctgagcg ggcgcagacg  300
ggccgaggcg ggcgccgggc gcgcagggac cgagggaccg agtgctcccc atgagcgcac  360
gtgggccggg cggtccgcaa gcccggctga gagcgcgcca tggggcaggc gggctgcaag  420
ggctctgcc tgtcgctgtt cgactacaag accgagaagt atgtcatcgc caagaacaag  480
aaggtgggcc tgctgtaccg gctgctgcag gcctccatcc tggcgtacct ggtcgtatgg  540
gtgttcctga taaagaaggg ttaccaagac gtcgacacct ccctgcagag tgctgtcatc  600
accaaagtca agggcgtggc cttcaccaac acctcggatc ttgggcagcg gatctgggat  660
gtcgccgact acgtcattcc agcccaggga gagaacgtct tttttgtggt caccaacctg  720
attgtgaccc ccaaccagcg gcagaacgtc tgtgctgaga atgaaggcat tcctgatggc  780
gcgtgctcca aggacagcga ctgccacgct ggggaagcgg ttacagctgg aaacggagtg  840
aagaccggcc gctgcctgcg gagagagaac ttggccaggg gcacctgtga gatctttgcc  900
tggtgcccgt tggagacaag ctccaggccg gaggagccat tcctgaagga ggccgaagac  960
ttcaccattt tcataaagaa ccacatccgt ttccccaaat tcaacttctc caaaagcaat  1020
gtgatggacg tcaaggacag atctttcctg aaatcatgcc actttggccc caagaaccac  1080
tactgcccca tcttccgact gggctccgtg atccgctggg ccgggagcga cttccaggat  1140
atagccctgg agggtggcgt gataggaatt aatattgaat ggaactgtga tcttgataaa  1200
gctgcctctg agtgccaccc tcactattct tttagccgtc tggacaataa actttcaaag  1260
tctgtctcct ccgggtacaa cttcagattt gccagatatt accgagacgc agccggggtg  1320
gagttccgca ccctgatgaa agcctacggg atccgctttg acgtgatggt gaacggcaag  1380
ggtgctttct tctgcgacct ggtactcatc tacctcatca aaaagagaga gttttaccgt  1440
gacaagaagt acgaggaagt gaggggccta gaagacagtt cccaggaggc cgaggacgag  1500
gcatcggggc tggggctatc tgagcagctc acatctgggc cagggctgct ggggatgccg  1560
gagcagcagg agctgcagga gccacccgag gcgaagcgtg gaagcagcag tcagaagggg  1620
aacggatctg tgtgcccaca gctcctggag ccccacagga gcacgtgaat tgcctctgct  1680
tacgttcagg ccctgtccta aacccagccg tctagcaccc agtgatccca tgcctttggg  1740
aatcccagga tgctgcccaa cgggaaattt gtacattggg tgctatcaat gccacatcac  1800
agggaccagc catcacagag caaagtgacc tccacgtctg atgctggggt catcaggacg  1860
gacccatcat ggctgtcttt ttgccccacc ccctgccgtc agttcttcct ttctccgtgg  1920
ctggcttccc gcactaggga acgggttgta aatggggaac atgacttcct tccggagtcc  1980
ttgagcacct cagctaagga ccgcagtgcc ctgtagagtt cctagattac ctcactggga  2040
atagcattgt gcgtgtccgg aaaagggctc catttggttc cagcccactc ccctctgcaa  2100
gtgccgcagc ttccctcaga gcatactctc cagtggatcc aagtactctc tctcctaaag  2160
acaccacctt cctgccagct gtttgccctt aggccagtac acagaattaa agtgggggag  2220
atggcagacg ctttctggga cctgcccaag atatgtattc tctgacactc ttatttggtc  2280
ataaaacaat aaatggtgtc aatttcaaaa aaaaaaaaaa aaaaaaaaaa aaaaaaaaaa  2340
a                                                                  2341

SEQ ID NO: 107          moltype = AA  length = 422
FEATURE                 Location/Qualifiers
source                  1..422
                        mol_type = protein
                        organism = Homo sapiens
SEQUENCE: 107
MGQAGCKGLC LSLFDYKTEK YVIAKNKKVG LLYRLLQASI LAYLVVWVFL IKKGYQDVDT  60
SLQSAVITKV KGVAFTNTSD LGQRIWDVAD YVIPAQGENV FFVVTNLIVT PNQRQNVCAE  120
NEGIPDGACS KDSDCHAGEA VTAGNGVKTG RCLRRENLAR GTCEIFAWCP LETSSRPEEP  180
FLKEAEDFTI FIKNHIRFPK FNFSKSNVMD VKDRSFLKSC HFGPKNHYCP IFRLGSVIRW  240
AGSDFQDIAL EGGVIGINIE WNCDLDKAAS ECHPHYSFSR LDNKLSKSVS SGYNFRFARY  300
YRDAAGVEFR TLMKAYGIRF DVMVNGKGAF FCDLVLIYLI KKREFYRDKK YEEVRGLEDS  360
SQEAEDEASG LGLSEQLTSG PGLLGMPEQQ ELQEPPEAKR GSSSQKGNGS VCPQLLEPHR  420
ST                                                                 422

SEQ ID NO: 108          moltype = DNA  length = 1548
FEATURE                 Location/Qualifiers
source                  1..1548
                        mol_type = other DNA
                        organism = synthetic construct
SEQUENCE: 108
aattgctaag ccgtgcagtc acagagggaa cacagagcct agttgtaaac ggacagagac  60
gagaggggca agggaggaca gtggatgaca gggaagacga gtgggggcag agctgctcag  120
gaccatggct gaggccatca cctatgcaga tctgaggttt gtgaaggctc ccctgaagaa  180
gagcatctcc agccggttag gacaggaccc aggggctgat gatgatgggg aaatcaccta  240
cgagaatgtt caagtgcccg cagtcctagg ggtgccctca agcttggctt cttctgtact  300
aggggacaaa gcagcggtca agtcggagca gccaactgcg tcctggagag ccgtgacgtc  360
accagctgtc gggcggattc tcccctgccg cacaacctgc ctgcgatacc tcctgctcgg  420
cctgctcctc acctgcctgc tgttaggagt gaccgccatc tgcctgggag tgcgctatct  480
gcaggtgtct cagcagctcc agcagacgaa cagggttctg gaagtcacta acagcagcct  540
gaggcagcag ctccgcctca agataacgca gctgggacag agtgcagagg atctgcaggg  600
gtccaggaga gagctggcgc agagtcagga agcactacag gtggaacaga gggctcatca  660
ggcggccgaa gggcagctac aggcctgcca ggcagacaga cagaagacga aggagacctt  720
gcaaagtgag gagcaacaga ggagggcctt ggagcagaag ctgagcaaca tggagaacag  780
actgaagccc ttcttcacat gcggctcagc agacacctgc tgtccgtcgg gatggataat  840
gcatcagaaa agctgctttt acatctcact tacttcaaaa aattggcagg agagccaaaa  900
acaatgtgaa actctgtctt ccaagctggc cacattcagt gaaatttatc cacaatcaca  960
ctcttactac ttcttaaatt cactgttgcc aaatggtggt tcagggaatt catattggac  1020
tggcctcagc tctaacaagg attggaagtt gactgatgat acacaacgca ctaggactta  1080
tgctcaaagc tcaaaatgta acaaggtaca taaaacttgg tcatggtgga cactggagtc  1140
agagtcatgt agaagttctc ttccctacat ctgtgagatg acagctttca ggtttccaga  1200
```

-continued

```
ttaggacagt cctttgcact gagttgacac tcatgccaac aagaacctgt gcccctcctt  1260
cctaacctga ggcctggggt tcctcagacc atctccttca ttctgggcag tgcccagcca  1320
ccggctgacc cacacctgac acttccagcc agtctgctgc ctgctccctc ttcctgaaac  1380
tggactgttc ctgggaaaag ggtgaagcca cctctagaag ggactttggc ctccccccaa  1440
gaacttccca tggtagaatg gggtgggga ggagggcgca cgggctgagc ggataggggc  1500
ggcccggagc cagccaggca gttttattga aatcttttta aataattg              1548

SEQ ID NO: 109         moltype = AA  length = 359
FEATURE                Location/Qualifiers
source                 1..359
                       mol_type = protein
                       organism = Homo sapiens
SEQUENCE: 109
MAEAITYADL RFVKAPLKKS ISSRLGQDPG ADDDGEITYE NVQVPAVLGV PSSLASSVLG  60
DKAAVKSEQP TASWRAVTSP AVGRILPCRT TCLRYLLLGL LLTCLLLGVT AICLGVRYLQ  120
VSQQLQQTNR VLEVTNSSLR QQLRLKITQL GQSAEDLQGS RRELAQSQEA LQVEQRAHQA  180
AEGQLQACQA DRQKTKETLQ SEEQQRRALE QKLSNMENRL KPFFTCGSAD TCCPSGWIMH  240
QKSCFYISLT SKNWQESQKQ CETLSSKLAT FSEIYPQSHS YYFLNSLLPN GGSGNSYWTG  300
LSSNKDWKLT DDTQRTRTYA QSSKCNKVHK TWSWWTLESE SCRSSLPYIC EMTAFRFPD   359

SEQ ID NO: 110         moltype = DNA  length = 2725
FEATURE                Location/Qualifiers
source                 1..2725
                       mol_type = other DNA
                       organism = synthetic construct
SEQUENCE: 110
agaatgctga gcagtcaaca gcatttcttg ttccaagatc acccttctga gtacctctct  60
ggctgccaaa ttgccagggc cttcacagtt tgattccatt tctcagctcc aagcattagg  120
taaacccacc aagcaatcct agcctgtgat ggcgtttgac gtcagctgct tcttttgggt  180
ggtgctgttt tctgccggct gtaaagtcat cacctcctgg gatcagatgt gcattgagaa  240
agaagccaac aaaacatata actgtgaaaa tttaggtctc agtgaaatcc ctgacactct  300
accaaacaca acagaatttt tggaattcag ctttaatttt ttgcctacaa ttcacaatag  360
aaccttcagc agactcatga atcttacctt tttggattta actaggtgcc agattaactg  420
gatacatgaa gacacttttc aaagccatca tcaattaagc acacttgtgt taactggaaa  480
tcccctgata ttcatggcag aaacatcgct taatgggccc aagtcactga agcatctttt  540
cttaatccaa acgggaatat ccaatctcga gtttattcca gtgcacaatc tggaaaactt  600
ggaaagcttg tatcttggaa gcaaccatat ttcctccatt aagttcccca aagacttccc  660
agcacggaat ctgaaagtac tggattttca gaataatgct atacactaca tctctagaga  720
agacatgagg tctctggagc aggccatcaa cctaagcctg aacttcaatg gcaataatgt  780
taaaggtatt gagcttgggg cttttgattc aacgatcttc caaagtttga actttggagg  840
aactccaaat ttgtctgtta tattcaatgg tctgcagaac tctactactc agtctctctg  900
gctgggaaca tttgaggaca ttgatgacga agatattagt tcagccatgc tcaagggact  960
ctgtgaaatg tctgttgaga gcctcaacct gcaggaacac cgcttctctg acatctcatc  1020
caccacattt cagtgcttca cccaactcca agaattggat ctgacagcaa ctcacttgaa  1080
agggttaccc tctgggatga agggtctgaa cttgctcaag aaattagttc tcagtgtaaa  1140
tcatttcgat caattgtgtc aaatcagtgc tgccaatttc ccctccctta cacacctcta  1200
catcagaggc aacgtgaaga aacttcacct tggtgttggc tgcttggaga aactaggaaa  1260
ccttcagaca cttgatttaa gccataatga catagaggct tctgactgct gcagtctgca  1320
actcaaaaac ctgtcccact tgcaaacctt aaacctgagc cacaatgagc ctcttggtct  1380
ccagagtcag gcattcaaag aatgtcctca gctagaactc ctcgatttgg catttacccg  1440
cttacacatt aatgctccac aaagtccctt ccaaaacctc catttccttc aggttctgaa  1500
tctcacttac tgcttccttg ataccagcaa tcagcatctt ctagcaggcc taccagttct  1560
ccggcatctc aacttaaaag ggaatcactt tcaagatggg actatcacga agaccaacct  1620
acttcagacc gtgggcagct tggaggttct gattttgtcc tcttgtggtc tcctctctat  1680
agaccagcaa gcattccaca gcttgggaaa aatgagccat gtagacttaa gccacaacag  1740
cctgacatgc gacagcattg attctcttag ccatcttaag ggaatctacc tcaatctggc  1800
tgccaacagc attaacatca tctcaccccg tctcctccct atcttgtccc agcagagcac  1860
cattaattta agtcataacc ccctggactg cacttgctcg aatattcatt tcttaacatg  1920
gtacaaagaa aacctgcaca aacttgaagg ctcggaggag accacgtgtg caaacccgcc  1980
atctctaagg ggagttaagc tatctgatgt caagctttcc tgtgggatta cagccatagg  2040
cattttcttt ctcatagtat ttctattatt gttggctatt ctgctatttt ttgcagttaa  2100
ataccttctc aggtggaaat accaacacat ttagtgctga aggtttccag agaaagcaaa  2160
taagtgtgct tagcaaaatt gctctaagtg aaagaactgt catctgctgg tgaccagacc  2220
agacttttca gattgcttcc tggaactggg cagggactca ctgtgctttt ctgagcttct  2280
tactcctgtg agtcccagag ctaaagaacc ttctaggcaa gtacaccgaa tgactcagtc  2340
cagagggtca gatgctgctg tgagaggcac agagcccttt ccgcatgtgg aagagtggga  2400
ggaagcagag ggagggactg ggcagggact gccggccccg gagtctccca cagggaggcc  2460
attccccttc tactcaccga catccctccc agcaccacac accccgcccc tgaaaggaga  2520
tcatcagccc ccacaatttg tcagagctga agccagccca ctacccaccc ccactacagc  2580
attgtgcttg ggtctgggtt ctcagtaatg tagccatttg agaaacttac ttggggacaa  2640
agtctcaatc cttattttaa atgaaaaaag aaaagaaaag cataataaat ttaaaagaaa  2700
aggctgagaa atgaaaaaaa aaaaa                                       2725

SEQ ID NO: 111         moltype = AA  length = 661
FEATURE                Location/Qualifiers
source                 1..661
                       mol_type = protein
                       organism = Homo sapiens
SEQUENCE: 111
```

```
MAFDVSCFFW VVLFSAGCKV ITSWDQMCIE KEANKTYNCE NLGLSEIPDT LPNTTEFLEF  60
SFNFLPTIHN RTFSRLMNLT FLDLTRCQIN WIHEDTFQSH HQLSTLVLTG NPLIFMAETS  120
LNGPKSLKHL FLIQTGISNL EFIPVHNLEN LESLYLGSNH ISSIKFPKDF PARNLKVLDF  180
QNNAIHYISR EDMRSLEQAI NLSLNFNGNN VKGIELGAFD STIFQSLNFG GTPNLSVIFN  240
GLQNSTTQSL WLGTFEDIDD EDISSAMLKG LCEMSVESLN LQEHRFSDIS STTFQCFTQL  300
QELDLTATHL KGLPSGMKGL NLLKKLVLSV NHFDQLCQIS AANFPSLTHL YIRGNVKKLH  360
LGVGCLEKLG NLQTLDLSHN DIEASDCCSL QLKNLSHLQT LNLSHNEPLG LQSQAFKECP  420
QLELLDLAFT RLHINAPQSP FQNLHFLQVL NLTYCFLDTS NQHLLAGLPV LRHLNLKGNH  480
FQDGTITKTN LLQTVGSLEV LILSSCGLLS IDQQAFHSLG KMSHVDLSHN SLTCDSIDSL  540
SHLKGIYLNL AANSINIISP RLLPILSQQS TINLSHNPLD CTCSNIHFLT WYKENLHKLE  600
GSEETTCANP PSLRGVKLSD VKLSCGITAI GIFFLIVFLL LLAILLFFAV KYLLRWKYQH  660
I                                                                 661

SEQ ID NO: 112          moltype = DNA  length = 3116
FEATURE                 Location/Qualifiers
source                  1..3116
                        mol_type = other DNA
                        organism = synthetic construct
SEQUENCE: 112
aacttccgat atcaacttcc tcaaacctct gatgagctgc tgctgctcga ctctgaggtg  60
cattcttttt ttgatgagag gcatctctag gtaccatccc tgacctggtc ctcatgctgc  120
cgaggctgtt gctgttgatc tgtgctccac tctgtgaacc tgccgagctg tttttgatag  180
ccagcccctc ccatcccaca gaggggagcc cagtgaccct gacgtgtaag atgccctttc  240
tacagagttc agatgcccag ttccagttct gcttttttcag agacacccgg gccttgggcc  300
caggctggag cagctccccc aagctccaga tcgctgccat gtggaaagaa gacacagggt  360
catactggtg cgaggcacag acaatggcgt ccaaagtctt gaggagcagg agatcccaga  420
taaatgtgca cagggtccct gtcgctgatg tgagcttgga gactcagccc ccaggaggac  480
aggtgatgga gggagacagg ctggtcctca tctgctcagt tgctatgggc acaggagaca  540
tcaccttcct ttggtacaaa ggggctgtag gtttaaacct tcagtcaaag acccagcgtt  600
cactgacagc agagtatgag attccttcag tgagggagag tgatgctgag caatattact  660
gtgtagctga aaatggctat ggtcccagcc ccagtgggct ggtgagcatc actgtcagaa  720
tcccggtgtc tcgcccaatc ctcatgctca gggctcccag ggcccaggct gcagtggagg  780
atgtgctgga gcttcactgt gaggccctga gaggctctcc tccgatcctg tactggtttt  840
atcacgagga tatcaccctg ggagcaggt cggcccccctc tggaggagga gcctccttca  900
acctttccct gactgaagaa cattctggaa actactcctg tgaggccaac aatggcctgg  960
gggcccagcg cagtgaggcg gtgacactca acttcacagt gcctactggg gccagaagca  1020
atcatcttac ctcaggagtc attgaggggc tgctcagcac ccttggtcca gccaccgtgg  1080
ccttattatt ttgctacggc ctcaaaagaa aaataggaag acgttcagcc agggatccac  1140
tcaggagcct tcccagccct ctaccccaag agttcaccta cctcaactca cctaccccag  1200
ggcagctaca gcctatatat gaaaatgtga atgttgtaag tggggatgag gtttattcac  1260
tggcgtacta taaccagccg gagcaggaat cagtagcagc agaaaccctg ggacacata  1320
tggaggacaa ggtttcctta gacatctatt ccaggctgag gaaagcaaac attacagatg  1380
tggactatga agatgctatg taaggttatg gaagattctg ctctttgaaa accatccatg  1440
accccaagcc tcaggcctga tatgttcttc agagatcctg ggcattagc tttccagtat  1500
acctcttctg gatgccattc tccatggcac tattccttca tctactgtga agtgaagttg  1560
gcgcagccct gaagaaacta cctaggagaa ctaatagaca caggagtgac agggactttg  1620
ttatcagaac cagattcctg ccggctcctt tgaaaacagg tcatattgtg ctcttctgtt  1680
tacaagagga aacaagatgg aataaaagaa attgggatct tgggttggag ggacagtgaa  1740
gcttagagca catgaactca aggttagtga ctctgcagga cttcacagag agagctgtgc  1800
ccatcattca gtccaagtgc tttctctgcc cagacagcac agaactccag ccccgctact  1860
tacatggatc atcgagtttc cacctaaaat atgattctat ttattttgag tcactgttac  1920
caaattagaa ctaaaacaaa gttacataaa aagttattgt gactccactt aattttagtg  1980
acgtattttt gtatatatag gccaacctat accacatcca aaattatgta tctattacag  2040
cccctagaag ctttataaat acagtgtgtc ttcttttatt cacaaaattt ttgaaatcgt  2100
ggtaatatgg tttgaaacct gtatcttaat tattttttttt ttaaattgag acagggtctc  2160
actctgtcac tcaatctgga atgcagtggc acaatcttgc ctcactgcaa cgcctgcctc  2220
tcaggctcaa gcaaacctct cacctcagcc tgctgagtag ctgggactac aggcacatgc  2280
caccaaactt ggccattttt tgtcttacgt agagacaaga tttcaccgtt ttgcccaggc  2340
tggtctcaaa ctcctgggct caagcaatgt attgaatttt aaaataacca ggcactcact  2400
cttatgaatt aataaacatt tggaggtata taaagtaaaa agttaaagtc tttcctgtaa  2460
gttaacacaa atgttaacta ttgttaaaaa ctttacaggt agctctctag atatttttct  2520
atttttgtat gtatacttat gcatacatgt aagtatataa acatttagaa gtgtacctat  2580
ctaacaaact attatgaaat actttcaaat ctgtaaatag atctattata ctattttaaa  2640
agtctctata gtagtgtgtt atatagataa atcataactt ttttcttttt ttattgtagt  2700
aaatatgcac aacataaaat tgatcatttt aaccattttt aagtgtacaa ttcagtggca  2760
ttaagtacta tcataatata ttttaatcct tctcatcact ggtggacatt aaggagactc  2820
tcaaaaaatt catattataa aaacaaagtt caaacaaatg tctttgtact agcatattat  2880
ggcactcctg ctggattatc tgaaggataa atttgtaaat ctagtattgc tagattatgc  2940
atattaaata ttcttgttaa atagtcttca atgtctctca ggtaaggctg tatcaattta  3000
tatcttcacc aacaacgtct gggaaatcag tttgtggggt gtattactta gttttcacat  3060
tgctaataaa gacatatcca agactgggta atttataaaa aaaaaaaaaa aaaaaa      3116

SEQ ID NO: 113          moltype = AA  length = 429
FEATURE                 Location/Qualifiers
source                  1..429
                        mol_type = protein
                        organism = Homo sapiens
SEQUENCE: 113
MLPRLLLLIC APLCEPAELF LIASPSHPTE GSPVTLTCKM PFLQSSDAQF QFCFFRDTRA  60
```

-continued

```
LGPGWSSSPK LQIAAMWKED TGSYWCEAQT MASKVLRSRR SQINVHRVPV ADVSLETQPP  120
GGQVMEGDRL VLICSVAMGT GDITFLWYKG AVGLNLQSKT QRSLTAEYEI PSVRESDAEQ  180
YYCVAENGYG PSPSGLVSIT VRIPVSRPIL MLRAPRAQAA VEDVLELHCE ALRGSPPILY  240
WFYHEDITLG SRSAPSGGGA SFNLSLTEEH SGNYSCEANN GLGAQRSEAV TLNFTVPTGA  300
RSNHLTSGVI EGLLSTLGPA TVALLFCYGL KRKIGRRSAR DPLRSLPSPL PQEFTYLNSP  360
TPGQLQPIYE NVNVVSGDEV YSLAYYNQPE QESVAAETLG THMEDKVSLD IYSRLRKANI  420
TDVDYEDAM                                                         429

SEQ ID NO: 114         moltype = DNA  length = 2797
FEATURE                Location/Qualifiers
source                 1..2797
                       mol_type = other DNA
                       organism = synthetic construct
SEQUENCE: 114
gtgcagtgtc ctgactgtaa gatcaagtcc aaacctgttt tggaattgag gaaacttctc  60
ttttgatctc agcccttggt ggtccaggtc ttcatgctgc tgtgggtgat attactggtc  120
ctggctcctg tcagtggaca gtttgcaagg acacccaggc ccattatttt cctccagcct  180
ccatggacca cagtcttcca aggagagaga gtgaccctca cttgcaaggg atttcgcttc  240
tactcaccac agaaaacaaa atggtaccat cggtaccttg ggaaagaaat actaagagaa  300
accccagaca atatccttga ggttcaggaa tctggagagt acagatgcca ggcccagggc  360
tcccctctca gtagccctgt gcacttggat ttttcttcag cttcgctgat cctgcaagct  420
ccactttctg tgtttgaagg agactctgtg gttctgaggt gccgggcaaa ggcggaagta  480
acactgaata atactattta caagaatgat aatgtcctgg cattccttaa taaaagaact  540
gacttccata ttcctcatgc atgtctcaag gacaatggtg catatcgctg tactggatat  600
aaggaaagtt gttgccctgt ttcttccaat acagtcaaaa tccaagtcca agagccattt  660
acacgtccag tgctgagagc cagctccttc cagcccatca gcgggaaccc agtgaccctg  720
acctgtgaga cccagctctc tctagagagg tcagatgtcc cgctccggtt ccgcttcttc  780
agagatgacc agaccctggg attaggctgg agtctctccc cgaatttcca gattactgcc  840
atgtggagta aagattcagg gttctactgg tgtaaggcag caacaatgcc tcacagcgtc  900
atatctgaca gcccgagatc ctggatacag gtgcagatcc ctgcatctca tcctgtcctc  960
actctcagcc ctgaaaaggc tctgaatttt gagggaacca aggtgacact tcactgtgaa  1020
acccaggaag attctctgcg cactttgtac aggttttatc atgagggtgt ccccctgagg  1080
cacaagtcag tccgctgtga aaggggagca tccatcagct tctcactgac tacagagaat  1140
tcagggaact actactgcac agctgacaat ggccttggcg ccaagcccag taaggctgtg  1200
agcctctcag tcactgttcc cgtgtctcat cctgtcctca acctcagctc tcctgaggac  1260
ctgatttttg agggagccaa ggtgacactt cactgtgaag cccagagagg ttcactcccc  1320
atcctgtacc agtttcatca tgaggatgct gccctggagc gtaggtcggc caactctgca  1380
ggaggagtgg ccatcagctt ctctctgact gcagagcatt cagggaacta ctactgcaca  1440
gctgacaatg gctttggccc ccagcgcagt aaggcggtga gcctctccat cactgtccct  1500
gtgtctcatc ctgtcctcac cctcagctct gctgaggccc tgacttttga aggagccact  1560
gtgacacttc actgtgaagt ccagagaggt tccccacaaa tcctatacca gttttatcat  1620
gaggacatgc ccctgtggag cagctcaaca ccctctgtgg gaagagtgtc cttcagcttc  1680
tctctgactg aaggacattc agggaattac tactgcacag ctgacaatgg ctttggtccc  1740
cagcgcagtg aagtggtgag cctttttgtc actgttccag tgtctcgccc catcctcacc  1800
ctcagggttc ccagggccca ggctgtggtg ggggacctgc tggagcttca ctgtgaggcc  1860
ccgagaggct ctcccccaat cctgtactgg ttttatcatg aggatgtcac cctggggagc  1920
agctcagccc cctctggagg agaagcttct ttcaacctct ctctgactgc agaacattct  1980
ggaaactact catgtgaggc caacaatggc ctagtggccc agcacagtga cacaatatca  2040
ctcagtgtta tagttccagt atctcgtccc atcctcacct tcagggctcc cagggcccag  2100
gctgtggtgg gggacctgct ggagcttcac tgtgaggccc tgagaggctc ctccccaatc  2160
ctgtactggt tttatcatga agatgtcacc ctgggtaaga tctcagcccc ctctggagga  2220
ggggcctcct tcaacctctc tctgactaca gaacattctg gaatctactc ctgtgaggca  2280
gacaatggtc tggaggccca gcgcagtgag atggtgacac tgaaagttgc aggtgagtgg  2340
gccctgccca ccagcagcac atctgagaac tgactgtgcc tgttctccct gcagctgaaa  2400
atggagccac agagctcctc agggctgttt gcttgtgtgg catcccagca cacttcctgc  2460
ctgcagaacc tccctgtgaa agtctcggat cctttgtggt atggttccag gaatctgatg  2520
tttcccagca gtcttcttga agatgatcaa agcacctcac taaaaatgca aataagactt  2580
ttttagaaca taaactatat tctgaactga aattattaca tgaaaatgaa accaaagaat  2640
tctgagcata tgtttctctg ccgtagaaag gattaagctg tttcttgtcc ggattcttct  2700
ctcattgact tctaagaagc ctctactctt gagtctcttt cattactggg gatgtaaatg  2760
ttccttacat ttccacatta aaaatcctat gttaacg                          2797

SEQ ID NO: 115         moltype = AA  length = 759
FEATURE                Location/Qualifiers
source                 1..759
                       mol_type = protein
                       organism = Homo sapiens
SEQUENCE: 115
MLLWVILLVL APVSGQFART PRPIIFLQPP WTTVFQGERV TLTCKGFRFY SPQKTKWYHR  60
YLGKEILRET PDNILEVQES GEYRCQAQGS PLSSPVHLDF SSASLILQAP LSVFEGDSVV  120
LRCRAKAEVT LNNTIYKNDN VLAFLNKRTD FHIPHACLKD NGAYRCTGYK ESCCPVSSNT  180
VKIQVQEPFT RPVLRASSFQ PISGNPVTLT CETQLSLERS DVPLRFRFFR DDQTLGLGWS  240
LSPNFQITAM WSKDSGFYWC KAATMPHSVI SDSPRSWIQV QIPASHPVLT LSPEKALNFE  300
GTKVTLHCET QEDSLRTLYR FYHEGVPLRH KSVRCERGAS ISFSLTTENS GNYYCTADNG  360
LGAKPSKAVS LSVTVPVSHP VLNLSSPEDL IFEGAKVTLH CEAQRGSLPI LYQFHHEDAA  420
LERRSANSAG GVAISFSLTA EHSGNYYCTA DNGFGPQRSK AVSLSITVPV SHPVLTLSSA  480
EALTFEGATV TLHCEVQRGS PQILYQFYHE DMPLWSSSTP SVGRVSFSFS LTEGHSGNYY  540
CTADNGFGPQ RSEVVSLFVT VPVSRPILTL RVPRAQAVVG DLLELHCEAP RGSPPILYWF  600
YHEDVTLGSS SAPSGGEASF NLSLTAEHSG NYSCEANNGL VAQHSDTISL SVIVPVSRPI  660
```

-continued

```
LTFRAPRAQA VVGDLLELHC EALRGSSPIL YWFYHEDVTL GKISAPSGGG ASFNLSLTTE  720
HSGIYSCEAD NGLEAQRSEM VTLKVAGEWA LPTSSTSEN                         759

SEQ ID NO: 116          moltype = DNA  length = 1814
FEATURE                 Location/Qualifiers
source                  1..1814
                        mol_type = other DNA
                        organism = synthetic construct
SEQUENCE: 116
gcagagctcg agaggcggct gccgggctgc ggggcgcctt gactctccct ccaccctgcc  60
tcctcgggct ccactcgtct gcccctggac tcccgtctcc tcctgtcctc cggcttccca  120
gagctccctc cttatggcag cagcttcccg cgtctccggc gcagcttctc agcggacgac  180
cctctcgctc cggggctgag cccagtccct ggatgttgct gaaactctcg agatcatgcg  240
cgggtttggc tgctgcttcc ccgccgggtg ccactgccac cgccgccgcc tctgctgccg  300
ccgtccgcgg gatgctcagt agcccgctgc ccggcccccg cgatcctgtg ttcctcggaa  360
gccgtttgct gctgcagagt tgcacgaact agtcatggtg ctgtgggagt ccccgcggca  420
gtgcagcagc tggacacttt gcgagggctt ttgctggctg ctgctgctgc ccgtcatgct  480
actcatcgta gcccgcccgg tgaagctcgc tgctttccct acctccttaa gtgactgcca  540
aacgcccacc ggctggaatt gctctggtta tgatgacaga gaaaatgatc tcttcctctg  600
tgacaccaac acctgtaaat ttgatgggga atgtttaaga attggagaca ctgtgacttg  660
cgtctgtcag ttcaagtgca acaatgacta tgtgcctgtg tgtggctcca atggggagag  720
ctaccagaat gagtgttacc tgcgacaggc tgcatgcaaa cagcagagtg agatacttgt  780
ggtgtcagaa ggatcatgtg ccacagatgc aggatcagga tctggagatg gagtccatga  840
aggctctgga gaaactagtc aaaaggagac atccacctgt gatatttgcc agtttggtgc  900
agaatgtgac gaagatgccg aggatgtctg gtgtgtgtgt aatattgact gttctcaaac  960
caacttcaat cccctctgcg cttctgatgg gaaatcttat gataatgcat gccaaatcaa  1020
agaagcatcg tgtcagaaac aggagaaaat tgaagtcatg tctttgggtc gatgtcaaga  1080
taacacaact acaactacta agtctgaaga tgggcattat gcaagaacag attatgcaga  1140
gaatgctaac aaattagaag aaagtgccag agaacaccac ataccttgtc cggaacatta  1200
caatggcttc tgcatgcatg ggaagtgtga gcattctatc aatatgcagg agccatcttg  1260
caggtgtgat gctggttata ctggacaaca ctgtgaaaaa aaggactaca gtgttctata  1320
cgttgttccc ggtcctgtac gatttcagta tgtcttaatc gcagctgtga ttggaacaat  1380
tcagattgct gtcatctgtg tggtggtcct ctgcatcaca aggaaatgcc ccagaagcaa  1440
cagaattcac agacagaagc aaaatacagg gcactacagt tcagacaata caacaagagc  1500
gtccacgagg ttaatctaaa gggagcatgt ttcacagtgg ctggactacc gagagcttgg  1560
actacacaat acagtattat agacaaaaga ataagacaag agatctacac atgttgcctt  1620
gcatttgtgg taatctacac caatgaaaac atgtactaca gctatatttg attatgtatg  1680
gatatatttg aaatagtata cattgtcttg atgtttttc tgtaatgtaa ataaactatt  1740
tatatcacac aatatagttt tttctttccc atgtatttgt tatatataat aaatactcag  1800
tgatgagaaa aaaa                                                    1814

SEQ ID NO: 117          moltype = AA  length = 374
FEATURE                 Location/Qualifiers
source                  1..374
                        mol_type = protein
                        organism = Homo sapiens
SEQUENCE: 117
MVLWESPRQC SSWTLCEGFC WLLLLPVMLL IVARPVKLAA FPTSLSDCQT PTGWNCSGYD  60
DRENDLFLCD TNTCKFDGEC LRIGDTVTCV CQFKCNNDYV PVCGSNGESY QNECYLRQAA  120
CKQQSEILVV SEGSCATDAG SGSGDGVHEG SGETSQKETS TCDICQFGAE CDEDAEDVWC  180
VCNIDCSQTN FNPLCASDGK SYDNACQIKE ASCQKQEKIE VMSLGRCQDN TTTTTKSEDG  240
HYARTDYAEN ANKLEESARE HHIPCPEHYN GFCMHGKCEH SINMQEPSCR CDAGYTGQHC  300
EKKDYSVLYV VPGPVRFQYV LIAAVIGTIQ IAVICVVVLC ITRKCPRSNR IHRQKQNTGH  360
YSSDNTTRAS TRLI                                                    374

SEQ ID NO: 118          moltype = DNA  length = 2653
FEATURE                 Location/Qualifiers
source                  1..2653
                        mol_type = other DNA
                        organism = synthetic construct
SEQUENCE: 118
ctcaaaaggg gccggatttc cttctcctgg aggcagatgt tgcctctctc tctcgctcgg  60
attggttcag tgcactctag aaacactgct gtggtggaga aactggaccc caggtctgga  120
gcgaattcca gcctgcaggg ctgataagcg aggcattagt gagattgaga gagactttac  180
cccgccgtgg tggttggagg gcgcgcagta gagcagcagc acaggcgcgg gtcccgggag  240
gccggctctg ctcgcgccga gatgtggaat ctccttcacg aaaccgactc ggctgtggcc  300
accgcgcgcc gcccgcgctg gctgtgcgct ggggcgctgg tgctggcggg tggcttcttt  360
ctcctcggct tcctcttcgg gtggtttata aaatcctcca atgaagctac taacattact  420
ccaaagcata atatgaaagc atttttggat gaattgaaag ctgagaacat caagaagttc  480
ttatataatt ttacacagat accacattta gcaggaacag aacaaaactt tcagcttgca  540
aagcaaattc aatcccagtg gaaagaattt ggcctggatt ctgttgagct agcacattat  600
gatgtcctgt tgtcctaccc aaataagact catcccaact acatctcaat aattaatgaa  660
gatggaaatg agattttcaa cacatcatta tttgaaccac ctcctccagg atatgaaaat  720
gtttcggata ttgtaccacc tttcagtgct ttctctcctc aaggaatgcc agagggcgat  780
ctagtgtatg ttaactatgc acgaactgaa gacttcttta aattggaacg ggacatgaaa  840
atcaattgct ctgggaaaat tgtaattgcc agatatggga aagttttcag aggaaataag  900
gttaaaaatg cccagctggc aggggccaaa ggagtcattc tctactccga ccctgctgac  960
tactttgctc ctggggtgaa gtcctatcca gatggttgga atcttcctgg aggtggtgtc  1020
cagcgtggaa atatcctaaa tctgaatggt gcaggagacc ctctcacacc aggttaccca  1080
```

-continued

```
gcaaatgaat atgcttatag gcgtggaatt gcagaggctg ttggtcttcc aagtattcct  1140
gttcatccaa ttggatacta tgatgcacag aagctcctag aaaaaatggg tggctcagca  1200
ccaccagata gcagctggag aggaagtctc aaagtgccct acaatgttgg acctggcttt  1260
actggaaact tttctacaca aaaagtcaag atgcacatcc actctaccaa tgaagtgaca  1320
agaatttaca atgtgatagg tactctcaga ggagcagtgg aaccagacag atatgtcatt  1380
ctgggaggtc accgggactc atgggtgttt ggtggtattg accctcagag tggagcagct  1440
gttgttcatg aaattgtgag gagctttgga acactgaaaa aggaagggtg gagacctaga  1500
agaacaattt tgtttgcaag ctgggatgca gaagaatttg gtcttcttgg ttctactgag  1560
tggcagagg agaattcaag actccttcaa gagcgtggcg tggcttatat taatgctgac  1620
tcatctatag aaggaaacta cactctgaga gttgattgta caccgctgat gtacagcttg  1680
gtacacaacc taacaaaaga gctgaaaagc cctgatgaag gctttgaagg caaatctctt  1740
tatgaaagtt ggactaaaaa aagtccttcc ccagagttca gtggcatgcc caggataagc  1800
aaattgggat ctggaaatga ttttgaggtg ttcttccaac gacttggaat tgcttcaggc  1860
agagcacggt atactaaaaa ttgggaaaca aacaaattca gcggctatcc actgtatcac  1920
agtgtctatg aaacatatga gttggtggaa aagttttatg atccaatgtt taaatatcac  1980
ctcactgtgg cccaggttcg aggagggatg gtgtttgagc tagccaattc catagtgctc  2040
ccttttgatt gtcgagatta tgctgtagtt ttaagaaagt atgctgacaa aatctacagt  2100
atttctatga aacatccaca ggaaatgaag acatacagtg tatcatttga ttcacttttt  2160
tctgcagtaa agaattttac agaaattgct tccaagttca gtgagagact ccaggacttt  2220
gacaaaagca acccaatagt attaagaatg atgaatgatc aactcatgtt tctggaaaga  2280
gcatttattg atccattagg gttaccagac aggccttttt ataggcatgt catctatgct  2340
ccaagcagcc acaacaagta tgcaggggag tcattcccag gaatttatga tgctctgttt  2400
gatattgaaa gcaaagtgga cccttccaag gcctggggag aagtgaagag acagatttat  2460
gttgcagcct tcacagtgca ggcagctgca gagactttga gtgaagtagc ctaagaggat  2520
tctttagaga atccgtattg aatttgtgtg gtatgtcact cagaaagaat cgtaatgggt  2580
atattgataa attttaaaat tggtatattt gaaataaagt tgaatattat atataaaaaa  2640
aaaaaaaaaa aaa                                                    2653

SEQ ID NO: 119         moltype = AA  length = 750
FEATURE                Location/Qualifiers
source                 1..750
                       mol_type = protein
                       organism = Homo sapiens
SEQUENCE: 119
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP  120
NKTHPNYISI INEDGNEIFN TSLFEPPPPG YENVSDIVPP FSAFSPQGMP EGDLVYVNYA  180
RTEDFFKLER DMKINCSGKI VIARYGKVFR GNKVKNAQLA GAKGVILYSD PADYFAPGVK  240
SYPDGWNLPG GGVQRGNILN LNGAGDPLTP GYPANEYAYR RGIAEAVGLP SIPVHPIGYY  300
DAQKLLEKMG GSAPPDSSWR GSLKVPYNVG PGFTGNFSTQ KVKMHIHSTN EVTRIYNVIG  360
TLRGAVEPDR YVILGGHRDS WVFGGIDPQS GAAVVHEIVR SFGTLKKEGW RPRRTILFAS  420
WDAEEFGLLG STEWAEENSR LLQERGVAYI NADSSIEGNY TLRVDCTPLM YSLVHNLTKE  480
LKSPDEGFEG KSLYESWTKK SPSPEFSGMP RISKLGSGND FEVFFQRLGI ASGRARYTKN  540
WETNKFSGYP LYHSVYETYE LVEKFYDPMF KYHLTVAQVR GGMVFELANS IVLPFDCRDY  600
AVVLRKYADK IYSISMKHPQ EMKTYSVSFD SLFSAVKNFT EIASKFSERL QDFDKSNPIV  660
LRMMNDQLMF LERAFIDPLG LPDRPFYRHV IYAPSSHNKY AGESFPGIYD ALFDIESKVD  720
PSKAWGEVKR QIYVAAFTVQ AAAETLSEVA                                  750

SEQ ID NO: 120         moltype = DNA  length = 2996
FEATURE                Location/Qualifiers
source                 1..2996
                       mol_type = other DNA
                       organism = synthetic construct
SEQUENCE: 120
cgcagccacc catgcgcgcg cgctcgcaag accaccagcg cccagagccc cagtctgagg  60
cttggcgccg ggggtctgcg ggcgagggga gctctctacg tgcgaggggc tagcgggagc  120
cggcacaaga gggtcgagga gccaggaacc ccaaacgtcc ggcgccaggc gctagccaag  180
ctgctgcgcg ccccggcgcc cagctggctc ggggacagcc gctgggtgtc ggagaccgga  240
gctagcggat tgcagcggaa aagcaaagat gtcacactgg atccttggcc tccagggtcc  300
attaaggtga gaataagatc tctgggctgg ctggaactag cctaagactg aaaagcagcc  360
atggacatgg cggatgagcc actcaatgga agccacacat ggctatccat tccatttgac  420
ctcaatggct ctgtggtgtc aaccaacacc tcaaaccaga cagagccgta ctatgacctg  480
acaagcaatg cagtcctcac attcatctat tttgtggtct gcatcattgg gttgtgtggc  540
aacacacttg tcatttatgt catcctccgc tatgccaaga tgaagaccat caccaacatt  600
tacatcctca acctggccat cgcagatgag ctcttcatgc tgggtctgcc tttcttggct  660
atgcaggtgg ctctggtcca ctggcccttt ggcaaggcca tttgccgggt ggtcatgact  720
gtggatggca tcaatcagtt caccagcatc ttctgcctga cagtcatgag catcgaccga  780
tacctggctg tggtccaccc catcaagtcg gccaagtgga ggagaccccg gacggccaag  840
atgatcacca tggctgtgtg gggagtctct ctgctggtca tcttgcccat catgatatat  900
gctgggctcc ggagcaacca gtgggggaga agcagctgca ccatcaactg gccaggtgaa  960
tctggggctt ggtacacagg gttcatcatc tacactttca ttctggggtt cctggtaccc  1020
ctcaccatca tctgtctttg ctacctgttc attatcatca aggtgaagtc ctctggaatc  1080
cgagtgggct cctctaagag gaagaagtct gagaagaagg tcacccgaat ggtgtccatc  1140
gtggtggctg tcttcatctt ctgctggctt cccttctaca tattcaacgt ttcttccgtc  1200
tccatggcca tcagccccac cccagccctt aaaggcatgt ttgactttgt ggtggtcctc  1260
acctatgcta acagctgtgc caaccctatc ctatatgcct tcttgtctga caacttcaag  1320
aagagcttcc agaatgtcct ctgcttggtc aaggtgagcg gcacagatga tggggagcgg  1380
agtgacagta agcaggacaa atcccggctg aatgagacca cggagaccca gaggaccctc  1440
ctcaatggag acctccaaac cagtatctga actgcttggg gggtgggaaa gaaccaagcc  1500
```

```
atgctctgtc tactggcaat gggctcccta cccacactgg cttcctgcct cccacccctc  1560
acacctggct tctagaatag aggattgctc agcatgagtc caattcagag aacggtgttt  1620
gagtcagctt gtctgattga atgataatgt gctaaattga ttacctcccc cttaaagcga  1680
acactgaaat gcaggtagac aattcaaagt ctggagaaga gggatcatgc ctggatatga  1740
tctttagaaa caacaaaaat agaaaaaaat aagtatctgt gtgtttgtgt attgaaaact  1800
caatatgtaa tcttgtgttt ttatatgtat acttgtatat tcctatttat tctctgtata  1860
ggcattacct acgttcctgt gtttacatac acaagtagca aattcgagta tgcatagtgt  1920
agatggacat ttgccacaac acactgcccg cagaaatgga cttaccgtga agccaataaa  1980
gttcaagctt cagggatctc tcttgcacgg gccttgccaa ggcccaggag ggacttgggc  2040
agtatgttca tgtggtcata tgtttttgta aaaaattgtg aaagtaagat atgtttgtat  2100
tgtttttctt aaagaggaac ctcgtataag cttcaagcct cacaaacctt ctagcctctg  2160
cccttgggga tttgcttcat taatttcagg caagtgaggt caatgtaaga agggaaaggg  2220
agaagatatt tgaagaacca gaatgtaaat tcatgtgttt ccacttctca gatatagtca  2280
gagaattatt catttgccca aaaggactta agtggttgtg gtcatccatc attgtattta  2340
tcaagacaaa gccaactttg ttataagatt gcattttttt cttttcaaat tgctttagtt  2400
tttcttaggg agctatgagg gggaaaaatc actaacatga aaggcaaaaa atggactatg  2460
attcctgtgg ggaaacaatt tcattctctc catcgtgaaa ataagtgaat aagagtgaag  2520
caaaattaca cctttatgag aaaccataaa attgttttta tttttcaggc cagacatagc  2580
ttcctaatga aagaaaatgg aaatgtaatt cgacgactcc tcaaagggga ctttagagga  2640
cttcatacaa agctgggcat taagaaaacc acaatgcatg gccgggcgtg gtggcttaca  2700
cctgtaatcc cagcactttg ggaggccgag gtgggtggat cacccgaggt caggagttcg  2760
agaccagcct ggccaacatg gtgaaacccc atcactacta aaaatatgta aattagtcgg  2820
gcgtggtgtc acgtgcctgt aatcctagct gctcgggagg ctgaggcagg agaatcactt  2880
gaacttggga ggtggaggtt gcagtaagct gagattgtgc cactgcactc tagcctgagc  2940
aacaagagca aaactcagtc tcaaaaaaaa aaaaaaaaaa aaaaaaaaaa aaaaaa      2996

SEQ ID NO: 121          moltype = AA  length = 369
FEATURE                 Location/Qualifiers
source                  1..369
                        mol_type = protein
                        organism = Homo sapiens
SEQUENCE: 121
MDMADEPLNG SHTWLSIPFD LNGSVVSTNT SNQTEPYYDL TSNAVLTFIY FVVCIIGLCG  60
NTLVIYVILR YAKMKTITNI YILNLAIADE LFMLGLPFLA MQVALVHWPF GKAICRVVMT  120
VDGINQFTSI FCLTVMSIDR YLAVVHPIKS AKWRRPRTAK MITMAVWGVS LLVILPIMIY  180
AGLRSNQWGR SSCTINWPGE SGAWYTGFII YTFILGFLVP LTIICLCYLF IIIKVKSSGI  240
RVGSSKRKKS EKKVTRMVSI VVAVFIFCWL PFYIFNVSSV SMAISPTPAL KGMFDFVVVL  300
TYANSCANPI LYAFLSDNFK KSFQNVLCLV KVSGTDDGER SDSKQDKSRL NETTETQRTL  360
LNGDLQTSI                                                        369

SEQ ID NO: 122          moltype = DNA  length = 1245
FEATURE                 Location/Qualifiers
source                  1..1245
                        mol_type = other DNA
                        organism = synthetic construct
SEQUENCE: 122
cgtcctccct tcttctcttg cagagcctga cgcaccccag ggctgccgcc atggagcccc  60
tgttcccagc ctccacgccc agctggaacg cctcctcccc gggggctgcc tctggaggcg  120
gtgacaacag gacgctggtg gggccggcgc cctcggcagg ggcccgggcg gtgctggtgc  180
ccgtgctgta cctgctggtg tgtgcggccg ggctgggcgg gaacacgctg gtcatctacg  240
tggtgctgcg cttcgccaag atgaagaccg tcaccaacat ctacattctc aacctggcag  300
tggccgacgt cctgtacatg ctggggctgc ctttcctggc cacgcagaac gccgcgtcct  360
tctggccctt cggccccgtc ctgtgccgcc tggtcatgac gctggacggc gtcaaccagt  420
tcaccagtgt cttctgcctg acagtcatga gcgtggaccg ctacctggca gtggtgcacc  480
cgctgagctc ggcccgctgg cgccgcccgc gtgtggccaa gctggcgagc gccgcggcct  540
gggtcctgtc tctgtgcatg tcgctgccgc tcctggtgtt cgcggacgtg caggagggcg  600
gtacctgcaa cgccagctgg ccggagcccg tggggctgtg ggcgccgtc ttcatcatct   660
acacggccgt gctgggcttc ttcgcgccgc tgctggtcat ctgcctgtgc tacctgctca  720
tcgtggtgaa ggtgagggcg gcgggcgtgc gcgtgggctg cgtgcggcgg cgctcggagc  780
ggaaggtgac gcgcatggtg ttggtggtgg tgctggtgtt tgcgggatgt tggctgccct  840
tcttcaccgt caacatcgtc aacctggccg tggcgctgcc ccaggagccc gcctccgccg  900
gcctctactt cttcgtggtc atcctctcct acgccaacag ctgtgccaac cccgtcctct  960
acggcttcct ctctgacaac ttccgccaga gcttccagaa ggttctgtgc ctccgcaagg  1020
gctctggtgc caaggacgct gacgccacgg agccgcgtcc agacaggatc cggcagcagc  1080
aggaggccac gccgcccgcg caccgcgccg cagccaacgg gcttatgcag accagcaagc  1140
tgtgagagtg caggcggggg gtgggcggcc ccgtgtcacc cccaggagcg gaggttgcac  1200
tgcggtgacc cccacccatg acctgccagt caggatgctc cccgg                 1245

SEQ ID NO: 123          moltype = AA  length = 364
FEATURE                 Location/Qualifiers
source                  1..364
                        mol_type = protein
                        organism = Homo sapiens
SEQUENCE: 123
MEPLFPASTP SWNASSPGAA SGGGDNRTLV GPAPSAGARA VLVPVLYLLV CAAGLGGNTL  60
VIYVVLRFAK MKTVTNIYIL NLAVADVLYM LGLPFLATQN AASFWPFGPV LCRLVMTLDG  120
VNQFTSVFCL TVMSVDRYLA VVHPLSSARW RRPRVAKLAS AAAWVLSLCM SLPLLVFADV  180
QEGGTCNASW PEPVGLWGAV FIIYTAVLGF FAPLLVICLC YLLIVVKVRA AGVRVGCVRR  240
RSERKVTRMV LVVVLVFAGC WLPFFTVNIV NLAVALPQEP ASAGLYFFVV ILSYANSCAN  300
```

-continued

```
PVLYGFLSDN FRQSFQKVLC LRKGSGAKDA DATEPRPDRI RQQQEATPPA HRAAANGLMQ  360
TSKL                                                               364

SEQ ID NO: 124          moltype = DNA  length = 5717
FEATURE                 Location/Qualifiers
source                  1..5717
                        mol_type = other DNA
                        organism = synthetic construct
SEQUENCE: 124
ggctaccgct cccggcttgg cgtcccgcgc gcacttcggc gatggctttt ccgccgcggc  60
gacggctgcg cctcggtccc cgcggcctcc cgcttcttct ctcgggactc ctgctacctc  120
tgtgccgcgc cttcaaccta gacgtggaca gtcctgccga gtactctggc cccgagggaa  180
gttacttcgg cttcgccgtg gatttcttcg tgcccagcgc gtcttcccgg atgtttcttc  240
tcgtgggagc tcccaaagca aacaccaccc agcctgggat tgtggaagga gggcaggtcc  300
tcaaatgtga ctggtcttct acccgccggt gccagccaat tgaatttgat gcaacaggca  360
atagagatta tgccaaggat gatccattgg aatttaagtc ccatcagtgg tttggagcat  420
ctgtgaggtc gaaacaggat aaaattttgg cctgtgcccc attgtaccat tggagaactg  480
agatgaaaca ggagcgagag cctgttggaa catgcttttct tcaagatgga acaaagactg  540
ttgagtatgc tccatgtaga tcacaagata ttgatgctga tggacaggga ttttgtcaag  600
gaggattcag cattgatttt actaaagctg acagagtact tcttggtggt cctggtagct  660
tttattggca aggtcagctt atttcggatc aagtggcaga aatcgtatct aaatacgacc  720
ccaatgttta cagcatcaag tataataacc aattagcaac tcggactgca caagctattt  780
ttgatgacag ctatttgggt tattctgtgg ctgtcggaga tttcaatggt gatggcatag  840
atgactttgt ttcaggagtt ccaagagcag caaggacttt gggaatggtt tatatttatg  900
atgggaagaa catgtcctcc ttatacaatt ttactggcga gcagatggct gcatatttcg  960
gattttctgt agctgccact gacattaatg gagatgatta tgcagatgtg tttattggag  1020
cacctctctt catggatcgt ggctctgatg gcaaactcca agaggtgggg caggtctcag  1080
tgtctctaca gagagcttca ggagacttcc agacgacaaa gctgaatgga tttgaggtct  1140
ttgcacggtt tggcagtgcc atagctcctt tgggagatct ggaccaggat ggtttcaatg  1200
atattgcaat tgctgctcca tatgggggtg aagataaaaa aggaattgtt tatatcttca  1260
atggaagatc aacaggcttg aacgcagtcc catctcaaat ccttgaaggg cagtgggctg  1320
ctcgaagcat gccaccaagc tttggctatt caatgaaagg agccacagat atagacaaaa  1380
atggatatcc agacttaatt gtaggagctt ttggtgtaga tcgagctatc ttatacaggg  1440
ccagaccagt tatcactgta aatgctggtc ttgaagtgta ccctagcatt ttaaatcaag  1500
acaataaaac ctgctcactg cctggaacag ctctcaaagt ttcctgtttt aatgttaggt  1560
tctgcttaaa ggcagatggc aaaggagtac ttcccaggaa acttaatttc caggtggaac  1620
ttcttttgga taaactcaag caaaagggag caattcgacg agcactgttt ctctacagca  1680
ggtccccaag tcactccaag aacatgacta tttcaagggg gggactgatg cagtgtgagg  1740
aattgatagc gtatctgcgg gatgaatctg aatttagaga caaactcact ccaattacta  1800
tttttatgga atatcggttg gattatagaa cagctgctga tacaacaggc ttgcaaccca  1860
ttcttaacca gttcacgcct gctaacatta gtcgacaggc tcacattcta cttgactgtg  1920
gtgaagacaa tgtctgtaaa cccaagctgg aagtttctgt agatagtgat caaaagaaga  1980
tctatattgg ggatgacaac cctctgacat tgattgttaa ggctcagaat caaggagaag  2040
gtgcctacga agctgagctc atcgtttcca ttccactgca ggctgatttc atcggggttg  2100
tccgaaacaa tgaagcctta gcaagacttt cctgtgcatt taagacagaa aaccaaactc  2160
gccaggtggt atgtgacctt ggaaacccaa tgaaggctgg aactcaactc ttagctggtc  2220
ttcgtttcag tgtgcaccag cagtcagaga tggatacttc tgtgaaattt gacttacaaa  2280
tccaaagctc aaatctattt gacaaagtaa gcccagttgt atctcacaaa gttgatcttg  2340
ctgttttagc tgcagttgag ataagaggag tctcgagtcc tgatcatatc tttcttccga  2400
ttccaaactg ggagcacaag gagaaccctg agactgaaga agatgttggg ccagttgttc  2460
agcacatcta tgagctgaga aacaatggtc caagttcatt cagcaaggca atgctccatc  2520
ttcagtggcc ttacaaatat aataataaca ctctgttgta tatccttcat tatgatattg  2580
atggaccaat gaactgcact tcagatatgg agatcaaccc tttgagaatt aagatctcat  2640
ctttgcaaac aactgaaaag aatgacacgg ttgccgggca aggtgagcgg gaccatctca  2700
tcactaagcg ggatcttgcc ctcagtgaag gagatattca cactttgggt tgtggagttg  2760
ctcagtgctt gaagattgtc tgccaagttg ggagattaga cagaggaaag agtgcaatct  2820
tgtacgtaaa gtcattactg tggactgaga cttttatgaa taaagaaaat cagaatcatt  2880
cctattctct gaagtcgtct gcttcattta atgtcataga gtttccttat aagaatcttc  2940
caattgagga tatcaccaac tccacattgg ttaccactaa tgtcacctgg ggcattcagc  3000
cagcgcccat gcctgtgcct gtgtgggtga tcattttagc agttctagca ggattgttgc  3060
tactggctgt tttggtattt gtaatgtaca ggatgggctt ttttaaacgg gtccggccac  3120
ctcaagaaga acaagaaagg gagcagcttc aacctcatga aaatggtgaa ggaaactcag  3180
aaacttaact gcagttttta agttatgcta catcttgacc cactagaatt agcaacttta  3240
ttatagattt aaactttctt catgaggagt aaaaatccaa ggctttactg ctgatagtgc  3300
taattggcat taaccacaaa atgagaatta tatttgtcaa ccttctcctt ataaataagt  3360
tcagacatac atttaataac atagggtgac ttgtgttttt aggtatttaa ataataaaat  3420
ttcaagggat agtttttatt caatgtatat aagacaggta gtgcctgatt tactacttta  3480
tataaaatag tacctccttc agttactgtt tctgatttaa tgtacggaac tttatttgtt  3540
gttgttgttg ttgttgttgt tgttgtttta aagcagtcca aatttggacc ttagcaatca  3600
tgtcttttgt ataggtactt aatgttaata catattacac tacagtttac ttttcagaat  3660
actaaagact ttataactgc atgaacttgg attttttttaa tcactcatat ggtagaattt  3720
tataaacaca tacatgatac catccaaatt cttgctttta ataacaaagg tacaatattt  3780
tgttttagta tgaaaatctg gtagatccta ttacacttct gtttatatta aatccacaat  3840
attttattac atttttaact tgtataaatt ttaggtcaaa tccttcaagc caacctatac  3900
taaaaattag ttccataatc acaaatggct cttttgtgta attgtttaat ttcacctgaa  3960
tatcataatg cttaaagcca tatggagttg gaaattattt ccaaagcata tttattccat  4020
tgttttagtc tggctattta cagtataaaa aaagcatttt attaaaatac tgtgtagttc  4080
tttgagatag ttgcttatgc atatagtaag tattacattc ttagagtaga gcagagtttt  4140
tagttagtat taatttattt tcctccattc atgtactttt ccttatattt ccaaaactgt  4200
```

-continued

```
tactgagaat gggtcaagat cagtgagaaa tctttacagt tgacaggaac ctggacccct  4260
taccccaact ttatgagtaa tgcttggaat aaaaaactct taaggcaact cactgattta  4320
cttctagcaa tagcatgatg ttacaggaat attacctctg tttaagcaag gtaatgtgta  4380
aaatcagtct cggctgtcag aataacttct aaaaggtatt tttataagca gttcaagtta  4440
ctgaaaacct tttaaacctt tctgaagttc gttagtataa attactttc taggattatt  4500
aataaaagcc acataggtgg caagttgtag ttttatatgg ctctgtagag tggtgaacct  4560
tctagaggaa tatatgattt attcacagtt cctcaaggcc tggggatgat gatcagttat  4620
acctattttt gtgcaattac atcatgttgt acattagaaa tggagagttt aatagctctt  4680
taactgctgt cctcattagg taatgataaa tatttccctt aaataattga ctattttgct  4740
gtgttttaaa aatgattgaa atttatcttg ccatatctca taatttcatg cacaagttga  4800
ctgagctaat cttgagaata tattcgtaaa ataggagcac atttagttga ggtatacaag  4860
gtaggactct agacaaaacc ttctatttta gctttagtga atttcaaaag taatgggtct  4920
tggagtatag atttttatta gtagcttgaa agagcttaat catatgcagt aagtattttt  4980
attaccaata aatttaaaat tttttaagaa aaatattttt atcctagggc caagtgttgc  5040
ctgccaccaa tcagtaagtt agtctataac aaattttacc ctaacagttt taccacctag  5100
caacagtcat ttctgaaaat atgttggata gaaagtcact ctttggcaaa agtgttagaa  5160
tttgcttttg tgccatctat tccttttatg gcatctatct tgaaagtaat cttgtattgg  5220
agattgaaag atgctgtaat ttagaaatta acatgatatc ttaaattacc tttatgaaat  5280
atagttttgt ataatagcat agattttcct tcaaaaaatg aacatttata tatctacaaa  5340
aatatggaga agagcaattt gaaagcctac tttctgaaga aaatggtggg attttttttt  5400
atcatgatta aatatcaaaa aattgcccta tgaaaacttt aaatctctaa aacatttgaa  5460
atactaccat atttgtgatt tattgagaat aaaaaatccat tttgaaatgt aaaattttta  5520
tgatctgatt cagttttaag aaaacatgaa tgaactagaa gatattaaaa acatttgaca  5580
ttggtaagaa atattgatac tgatattgat ttttatatag gtatttattt cagaattgat  5640
attttgagaa aaatacatgt gagtcatttt ttctgtttct cttttctctt aacgattatc  5700
actgtaattc tgaatct                                               5717
```

```
SEQ ID NO: 125          moltype = AA  length = 1048
FEATURE                 Location/Qualifiers
source                  1..1048
                        mol_type = protein
                        organism = Homo sapiens
SEQUENCE: 125
MAFPPRRRLR LGPRGLPLLL SGLLLPLCRA FNLDVDSPAE YSGPEGSYFG FAVDFFVPSA  60
SSRMFLLVGA PKANTTQPGI VEGGQVLKCD WSSTRRCQPI EFDATGNRDY AKDDPLEFKS  120
HQWFGASVRS KQDKILACAP LYHWRTEMKQ EREPVGTCFL QDGTKTVEYA PCRSQDIDAD  180
GQGFCQGGFS IDFTKADRVL LGGPGSFYWQ GQLISDQVAE IVSKYDPNVY SIKYNNQLAT  240
RTAQAIFDDS YLGYSVAVGD FNGDGIDDFV SGVPRAARTL GMVYIYDGKN MSSLYNFTGE  300
QMAAYFGFSV AATDINGDDY ADVFIGAPLF MDRGSDGKLQ EVGQVSVSLQ RASGDFQTTK  360
LNGFEVFARF GSAIAPLGDL DQDGFNDIAI AAPYGGEDKK GIVYIFNGRS TGLNAVPSQI  420
LEGQWAARSM PPSFGYSMKG ATDIDKNGYP DLIVGAFGVD RAILYRARPV ITVNAGLEVY  480
PSILNQDNKT CSLPGTALKV SCFNVRFCLK ADGKGVLPRK LNFQVELLLD KLKQKGAIRR  540
ALFLYSRSPS HSKNMTISRG GLMQCEELIA YLRDESEFRD KLTPITIFME YRLDYRTAAD  600
TTGLQPILNQ FTPANISRQA HILLDCGEDN VCKPKLEVSV DSDQKKIYIG DDNPLTLIVK  660
AQNQGEGAYE AELIVSIPLQ ADFIGVVRNN EALARLSCAF KTENQTRQVV CDLGNPMKAG  720
TQLLAGLRFS VHQQSEMDTS VKFDLQIQSS NLFDKVSPVV SHKVDLAVLA AVEIRGVSSP  780
DHIFLPIPNW EHKENPETEE DVGPVVQHIY ELRNNGPSSF SKAMLHLQWP YKYNNNTLLY  840
ILHYDIDGPM NCTSDMEINP LRIKISSLQT TEKNDTVAGQ GERDHLITKR DLALSEGDIH  900
TLGCGVAQCL KIVCQVGRLD RGKSAILYVK SLLWTETFMN KENQNHSYSL KSSASFNVIE  960
FPYKNLPIED ITNSTLVTTN VTWGIQPAPM PVPVWVIILA VLAGLLLLAV LVFVMYRMGF  1020
FKRVRPPQEE QEREQLQPHE NGEGNSET                                   1048
```

```
SEQ ID NO: 126          moltype = DNA  length = 2397
FEATURE                 Location/Qualifiers
source                  1..2397
                        mol_type = other DNA
                        organism = synthetic construct
SEQUENCE: 126
gcaagaactg aaacgaatgg ggattgaact gctttgcctg ttctttctat ttctaggaag  60
gaatgatcac gtacaaggtg gctgtgccct gggaggtgca gaaacctgtg aagactgcct  120
gcttattgga cctcagtgtg cctggtgtgc tcaggagaat tttactcatc catctggagt  180
tggcgaaagg tgtgataccc cagcaaacct tttagctaaa ggatgtcaat taaacttcat  240
cgaaaaccct gtctcccaag tagaaatact taaaaataag cctctcagtg taggcagaca  300
gaaaaatagt tctgacattg ttcagattgc gcctcaaagc ttgatcctta agttgagacc  360
aggtggtgcg cagactctgc aggtgcatgt ccgccagact gaggactacc cggtggattt  420
gtattacctc atggacctct ccgcctccat ggatgacgac ctcaacacaa taaaggagct  480
gggctcccgg ctttccaaag agatgtctaa attaaccagc aactttagac tgggcttcgg  540
atcttttgtg gaaaaacctg tatccccttt cgtgaaaaca acaccagaag aaattgccaa  600
cccttgcagt agtattccat acttctgttt acctacattt ggattcaagc acattttgcc  660
attgacaaat gatgctgaaa gattcaatga aattgtgaag aatcagaaaa tttctgctaa  720
tattgacaca cccgaaggtg gatttgatgc aattatgcaa gctgctgtgt gtaaggaaaa  780
aattggctgg cggaatgact ccctccacct cctggtcttt gtgagtgatg ctgattctca  840
ttttggaatg gacagcaaac tagcaggcat cgtcattcct aatgacgggc tctgtcactt  900
ggacagcaag aatgaatact ccatgtcaac tgtcttggaa tatccaacaa ttggacaact  960
cattgataaa ctggtacaaa acaacgtgtt attgatcttc gctgtaaccc aagaacaagt  1020
tcatttatat gagaattacg caaaacttat tcctggagct acagtaggtc tacttcagaa  1080
ggactccgga aacattctcc agctgatcat ctcagcttat gaagaactgc ggtctgaggt  1140
ggaactggaa gtattaggag acactgaagg actcaacttg tcatttacag ccatctgtaa  1200
caacggtacc ctcttccaac accaaaagaa atgctctcac atgaaagtgg gagacacagc  1260
```

```
ttccttcagc gtgactgtga atatcccaca ctgcgagaga agaagcaggc acattatcat  1320
aaagcctgtg gggctggggg atgccctgga attacttgtc agcccagaat gcaactgcga  1380
ctgtcagaaa gaagtggaag tgaacagctc caaatgtcac cacgggaacg gctctttcca  1440
gtgtggggtg tgtgcctgcc accctggcca catggggcct cgctgtgagt gtggcgagga  1500
catgctgagc acagattcct gcaaggaggc cccagatcat ccctcctgca gcggaagggg  1560
tgactgctac tgtgggcagt gtatctgcca cttgtctccc tatggaaaca tttatgggcc  1620
ttattgccag tgtgacaatt tctcctgcgt gagacacaaa gggctgctct gcggaggtaa  1680
cggcgactgt gactgtggtg aatgtgtgtg caggagcggc tggactggcg agtactgcaa  1740
ctgcaccacc agcacggact cctgcgtctc tgaagatgga gtgctctgca gcgggcgcgg  1800
ggactgtgtt tgtggcaagt gtgtttgcac aaaccctgga gcctcaggac caacctgtga  1860
acgatgtcct acctgtggtg acccctgtaa ctctaaacgg agctgcattg agtgccacct  1920
gtcagcagct ggccaagccc gagaagaatg tgtggacaag tgcaaactag ctggtgcgac  1980
catcagtgaa gaagaagatt tctcaaagga tggttctgtt tcctgctctc tgcaaggaga  2040
aaatgaatgt cttattacat tcctaataac tacagataat gaggggaaaa ccatcattca  2100
cagcatcaat gaaaaagatt gtccgaagcc tccaaacatt cccatgatca tgttaggggt  2160
ttccctggct attcttctca tcggggttgt cctactgtgc atctggaagc tactggtgtc  2220
atttcatgat cgtaaagaag ttgccaaatt tgaagcagaa cgatcaaaag ccaagtggca  2280
aacgggaacc aatccactct acagaggatc cacaagtact tttaaaaatg taacttataa  2340
acacagggaa aaacaaaagg tagacctttc cacagattgc tagaactact ttatgca     2397

SEQ ID NO: 127         moltype = AA  length = 788
FEATURE                Location/Qualifiers
source                 1..788
                       mol_type = protein
                       organism = Homo sapiens
SEQUENCE: 127
MGIELLCLFF LFLGRNDHVQ GGCALGGAET CEDCLLIGPQ CAWCAQENFT HPSGVGERCD  60
TPANLLAKGC QLNFIENPVS QVEILKNKPL SVGRQKNSSD IVQIAPQSLI LKLRPGGAQT  120
LQVHVRQTED YPVDLYYLMD LSASMDDDLN TIKELGSRLS KEMSKLTSNF RLGFGSFVEK  180
PVSPFVKTTP EEIANPCSSI PYFCLPTFGF KHILPLTNDA ERFNEIVKNQ KISANIDTPE  240
GGFDAIMQAA VCKEKIGWRN DSLHLLVFVS DADSHFGMDS KLAGIVIPND GLCHLDSKNE  300
YSMSTVLEYP TIGQLIDKLV QNNVLLIFAV TQEQVHLYEN YAKLIPGATV GLLQKDSGNI  360
LQLIISAYEE LRSEVELEVL GDTEGLNLSF TAICNNGTLF QHQKKCSHMK VGDTASFSVT  420
VNIPHCERRS RHIIIKPVGL GDALELLVSP ECNCDCQKEV EVNSSKCHHG NGSFQCGVCA  480
CHPGHMGPRC ECGEDMLSTD SCKEAPDHPS CSGRGDCYCG QCICHLSPYG NIYGPYCQCD  540
NFSCVRHKGL LCGGNGDCDC GECVCRSGWT GEYCNCTTST DSCVSEDGVL CSGRGDCVCG  600
KCVCTNPGAS GPTCERCPTC GDPCNSKRSC IECHLSAAGQ AREECVDKCK LAGATISEEE  660
DFSKDGSVSC SLQGENECLI TFLITTDNEG KTIIHSINEK DCPKPPNIPM IMLGVSLAIL  720
LIGVVLLCIW KLLVSFHDRK EVAKFEAERS KAKWQTGTNP LYRGSTSTFK NVTYKHREKQ  780
KVDLSTDC                                                          788

SEQ ID NO: 128         moltype = DNA  length = 3036
FEATURE                Location/Qualifiers
source                 1..3036
                       mol_type = other DNA
                       organism = synthetic construct
SEQUENCE: 128
cgaccagcag accagacagt cacagcagcc ttgacaaaac gttcctggaa ctcaagcact  60
tctccacaga ggaggacaga gcagacagca gagaccatgg agtctccctc ggcccctccc  120
cacagatggt gcatcccctg gcagaggctc ctgctcacag cctcacttct aaccttctgg  180
aacccgccca ccactgccaa gctcactatt gaatccacgc cgttcaatgt cgcagagggg  240
aaggaggtgc ttctacttgt ccacaatctg ccccagcatc tttttggcta cagctggtac  300
aaaggtgaaa gagtggatgg caaccgtcaa attataggat atgtaatagg aactcaacaa  360
gctaccccag ggcccgcata cagtggtcga gagataatat accccaatgc atccctgctg  420
atccagaaca tcatccagaa tgacacagga ttctacaccc tacacgtcat aaagtcagat  480
cttgtgaatg aagaagcaac tggccagttc cgggtatacc cggagctgcc caagccctcc  540
atctccagca acaactccaa acccgtggag gacaaggatg ctgtggcctt cacctgtgaa  600
cctgagactc aggacgcaac ctacctgtgg tgggtaaaca atcagagcct cccggtcagt  660
cccaggctgc agctgtccaa tggcaacagg accctcactc tattcaatgt cacaagaaat  720
gacacagcaa gctacaaatg tgaaacccag aacccagtga gtgccaggcg cagtgattca  780
gtcatcctga atgtcctcta tggcccggat gcccccacca tttcccctct aaacacatct  840
tacagatcag gggaaaatct gaacctctcc tgccatgcag cctctaaccc acctgcacag  900
tactcttggt ttgtcaatgg gactttccag caatccaccc aagagctctt tatccccaac  960
atcactgtga ataatagtgg atcctatacg tgccaagccc ataactcaga cactggcctc  1020
aataggacca cagtcacgac gatcacagtc tatgcagagc cacccaaacc cttcatcacc  1080
agcaacaact ccaaccccgt ggaggatgag gatgctgtag ccttaacctg tgaacctgag  1140
attcagaaca caacctacct gtggtgggta aataatcaga gcctcccggt cagtcccagg  1200
ctgcagctgt ccaatgacaa caggaccctc actctactca gtgtcacaag gaatgatgta  1260
ggaccctatg agtgtggaat ccagaacgaa ttaagtgttg accacagcga cccagtcatc  1320
ctgaatgtcc tctatggccc agacgacccc accatttccc cctcatacac ctattaccgt  1380
ccaggggtga acctcagcct ctcctgccat gcagcctcta acccacctgc acagtattct  1440
tggctgattg atgggaacat ccagcaacac acacaagagc tctttatctc caacatcact  1500
gagaagaaca gcggactcta tacctgccag gccaataact cagccagtgg ccacagcagg  1560
actacagtca agacaatcac agtctctgcg gagctgccca agccctccat ctccagcaac  1620
aactccaaac ccgtggagga caaggatgct gtggccttca cctgtgaacc tgaggctcag  1680
aacacaacct acctgtggtg ggtaaatggt cagagcctcc cagtcagtcc caggctgcag  1740
ctgtccaatg gcaacaggac cctcactcta ttcaatgtca caagaaatga cgcaagagcc  1800
tatgtatgtg gaatccagaa ctcagtgagt gcaaaccgca gtgacccagt caccctggat  1860
gtcctctatg ggccggacac ccccatcatt tccccccag actcgtctta cctttcggga   1920
```

-continued

```
gcgaacctca acctctcctg ccactcggcc tctaacccat ccccgcagta ttcttggcgt  1980
atcaatggga taccgcagca acacacacaa gttctcttta tcgccaaaat cacgccaaat  2040
aataacggga cctatgcctg ttttgtctct aacttggcta ctggccgcaa taattccata  2100
gtcaagagca tcacagtctc tgcatctgga acttctcctg gtctctcagc tggggccact  2160
gtcggcatca tgattggagt gctggttggg gttgctctga tatagcagcc ctggtgtagt  2220
ttcttcattt caggaagact gacagttgtt ttgcttcttc cttaaagcat ttgcaacagc  2280
tacagtctaa aattgcttct ttaccaagga tatttacaga aaagactctg accagagatc  2340
gagaccatcc tagccaacat cgtgaaaccc catctctact aaaaatacaa aaatgagctg  2400
ggcttggtgg cgcgcacctg tagtcccagt tactcgggag gctgaggcag gagaatcgct  2460
tgaacccggg aggtggagat tgcagtgagc ccagatcgca ccactgcact ccagtctggc  2520
aacagagcaa gactccatct caaaaagaaa agaaaagaag actctgacct gtactcttga  2580
atacaagttt ctgataccac tgcactgtct gagaatttcc aaaactttaa tgaactaact  2640
gacagcttca tgaaactgtc caccaagatc aagcagagaa aataattaat ttcatgggac  2700
taaatgaact aatgaggata atattttcat aattttttat ttgaaatttt gctgattctt  2760
taaatgtctt gtttcccaga tttcaggaaa cttttttttct tttaagctat ccacagctta  2820
cagcaatttg ataaaatata cttttgtgaa caaaaattga gacatttaca ttttctccct  2880
atgtggtcgc tccagacttg ggaaactatt catgaatatt tatattgtat ggtaatatag  2940
ttattgcaca agttcaataa aaatctgctc tttgtatgac agaatacatt tgaaaacatt  3000
ggttatatta ccaagacttt gactagaatg tcgtat                            3036

SEQ ID NO: 129          moltype = AA  length = 702
FEATURE                 Location/Qualifiers
source                  1..702
                        mol_type = protein
                        organism = Homo sapiens
SEQUENCE: 129
MESPSAPPHR WCIPWQRLLL TASLLTFWNP PTTAKLTIES TPFNVAEGKE VLLLVHNLPQ  60
HLFGYSWYKG ERVDGNRQII GYVIGTQQAT PGPAYSGREI IYPNASLLIQ NIIQNDTGFY  120
TLHVIKSDLV NEEATGQFRV YPELPKPSIS SNNSKPVEDK DAVAFTCEPE TQDATYLWWV  180
NNQSLPVSPR LQLSNGNRTL TLFNVTRNDT ASYKCETQNP VSARRSDSVI LNVLYGPDAP  240
TISPLNTSYR SGENLNLSCH AASNPPAQYS WFVNGTFQQS TQELFIPNIT VNNSGSYTCQ  300
AHNSDTGLNR TTVTTITVYA EPPKPFITSN NSNPVEDEDA VALTCEPEIQ NTTYLWWVNN  360
QSLPVSPRLQ LSNDNRTLTL LSVTRNDVGP YECGIQNELS VDHSDPVILN VLYGPDDPTI  420
SPSYTYYRPG VNLSLSCHAA SNPPAQYSWL IDGNIQQHTQ ELFISNITEK NSGLYTCQAN  480
NSASGHSRTT VKTITVSAEL PKPSISSNNS KPVEDKDAVA FTCEPEAQNT TYLWWVNGQS  540
LPVSPRLQLS NGNRTLTLFN VTRNDARAYV CGIQNSVSAN RSDPVTLDVL YGPDTPIISP  600
PDSSYLSGAN LNLSCHSASN PSPQYSWRIN GIPQQHTQVL FIAKITPNNN GTYACFVSNL  660
ATGRNNSIVK SITVSASGTS PGLSAGATVG IMIGVLVGVA LI                     702

SEQ ID NO: 130          moltype = DNA  length = 90
FEATURE                 Location/Qualifiers
source                  1..90
                        mol_type = other DNA
                        organism = synthetic construct
SEQUENCE: 130
ttggctttgg tcttcaagta gccaaagcga tgaaatatct tgcaagcaaa aagtttgtcc  60
acagagactt ggctgcaaga aactgtatgt                                   90

SEQ ID NO: 131          moltype = AA  length = 22
FEATURE                 Location/Qualifiers
source                  1..22
                        mol_type = protein
                        organism = Homo sapiens
SEQUENCE: 131
KAMKYLASKK FVHRDLAARN CM                                           22

SEQ ID NO: 132          moltype = DNA  length = 1804
FEATURE                 Location/Qualifiers
source                  1..1804
                        mol_type = other DNA
                        organism = synthetic construct
SEQUENCE: 132
cgctccacct ctcaagcagc cagcgcctgc ctgaatctgt tctgcccct ccccacccat  60
ttcaccacca ccatgacacc gggcacccag tctcctttct tcctgctgct gctcctcaca  120
gtgcttacag ttgttacagg ttctggtcat gcaagctcta ccccaggtgg agaaaaggag  180
acttcggcta cccagagaag ttcagtgccc agctctactg agaagaatgc tgtgagtatg  240
accagcagcg tactctccag ccacagcccc ggttcaggct cctccaccac tcagggacag  300
gatgtcactc tggccccggc cacggaacca gcttcaggtt cagctgccac ctggggacag  360
gatgtcacct cggtcccagt caccaggcca gccctgggct ccaccacccc gccagcccac  420
gatgtcacct cagccccgga caacaagcca gccccgggct ccaccgcccc cccagcccac  480
ggtgtcacct cggccccgga caccaggccg gccccgggct ccaccgcccc cccagcccat  540
ggtgtcacct cggccccgga caacaggccc gccttgggct ccaccgcccc tccagtccac  600
aatgtcacct cggcctcagg ctctgcatca ggctcagctt ctactctggt gcacaacggc  660
acctctgcca gggctaccac aaccccagcc agcaagagca ctccattctc aattcccagc  720
caccactctg atactcctac cacccttgcc agccatagca ccaagactga tgccagtagc  780
actcaccata gcacggtacc tcctctcacc tcctccaatc acagcacttc tccccagttg  840
tctactgggg tctctttctt tttcctgtct tttcacattt caaacctcca gtttaattcc  900
tctctggaag atcccagcac cgactactac caagagctgc agagagacat ttctgaaatg  960
tttttgcaga tttataaaca agggggtttt ctgggcctct ccaatattaa gttcaggcca  1020
```

-continued

```
ggatctgtgg tggtacaatt gactctggcc ttccgagaag gtaccatcaa tgtccacgac  1080
gtggagacac agttcaatca gtataaaacg gaagcagcct ctcgatataa cctgacgatc  1140
tcagacgtca gcgtgagtga tgtgccattt cctttctctg cccagtctgg ggctggggtg  1200
ccaggctggg gcatcgcgct gctggtgctg gtctgtgttc tggttgcgct ggccattgtc  1260
tatctcattg ccttggctgt ctgtcagtgc cgccgaaaga actacgggca gctggacatc  1320
tttccagccc gggataccta ccatcctatg agcgagtacc ccacctacca cacccatggg  1380
cgctatgtgc cccctagcag taccgatcgt agcccctatg agaaggtttc tgcaggtaat  1440
ggtggcagca gcctctctta cacaaaccca gcagtggcag ccacttctgc caacttgtag  1500
gggcacgtcg cccgctgagc tgagtggcca gccagtgcca ttccactcca ctcaggttct  1560
tcagggccag agcccctgca ccctgtttgg gctggtgagc tgggagttca ggtgggctgc  1620
tcacaccgtc cttcagaggc cccaccaatt tctcggacac ttctcagtgt gtggaagctc  1680
atgtgggccc ctgaggctca tgcctgggaa gtgttgtggt gggggctccc aggaggactg  1740
gcccagagag ccctgagata gcggggatcc tgaactggac tgaataaaac gtggtctccc  1800
actg                                                               1804

SEQ ID NO: 133          moltype = AA  length = 475
FEATURE                 Location/Qualifiers
source                  1..475
                        mol_type = protein
                        organism = Homo sapiens
SEQUENCE: 133
MTPGTQSPFF LLLLLTVLTV VTGSGHASST PGGEKETSAT QRSSVPSSTE KNAVSMTSSV  60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDNRPALGS TAPPVHNVTS  180
ASGSASGSAS TLVHNGTSAR ATTTPASKST PFSIPSHHSD TPTTLASHST KTDASSTHHS  240
TVPPLTSSNH STSPQLSTGV SFFFLSFHIS NLQFNSSLED PSTDYYQELQ RDISEMFLQI  300
YKQGGFLGLS NIKFRPGSVV VQLTLAFREG TINVHDVETQ FNQYKTEAAS RYNLTISDVS  360
VSDVPFPFSA QSGAGVPGWG IALLVLVCVL VALAIVYLIA LAVCQCRRKN YGQLDIFPAR  420
DTYHPMSEYP TYHTHGRYVP PSSTDRSPYE KVSAGNGGSS LSYTNPAVAA TSANL       475

SEQ ID NO: 134          moltype = DNA  length = 1552
FEATURE                 Location/Qualifiers
source                  1..1552
                        mol_type = other DNA
                        organism = synthetic construct
SEQUENCE: 134
gcccgtacac accgtgtgct gggacacccc acagtcagcc gcatggctcc cctgtgcccc  60
agcccctggc tccctctgtt gatcccggcc cctgctccag gcctcactgt gcaactgctg  120
ctgtcactgc tgcttctgat gcctgtccat ccccagaggt tgccccggat gcaggaggat  180
tccccccttgg gaggaggctc ttctggggaa gatgacccac tgggcgagga ggatctgccc  240
agtgaagagg attcacccag agaggaggat ccacccggag aggaggatct acctggagag  300
gaggatctac ctggagagga ggatctacct gaagttaagc ctaaatcaga agaagagggc  360
tccctgaagt tagaggatct acctactgtt gaggctcctg gagatcctca agaaccccag  420
aataatgccc acagggacaa agaaggggat gaccagagtc attggcgcta tggaggcgac  480
ccgccctggc cccgggtgtc cccagcctgc gcgggccgct tccagtcccc ggtggatatc  540
cgcccccagc tcgccgcctt ctgcccggcc ctgcgccccc tggaactcct gggcttccag  600
ctcccgccgc tcccagaact gcgcctgcgc aacaatggcc acagtgtgca actgaccctg  660
cctcctgggc tagagatggc tctgggtccc gggcgggagt accgggctct gcagctgcat  720
ctgcactggg gggctgcagg tcgtccgggc tcggagcaca ctgtggaagg ccaccgtttc  780
cctgccgaga tccacgtggt tcacctcagc accgcctttg ccagagttga cgaggccttg  840
gggcgcccgg gaggcctggc cgtgttggcc gcctttctgg aggagggccc ggaagaaaac  900
agtgcctatg agcagttgct gtctcgcttg gaagaaatcg ctgaggaagg ctcagagact  960
caggtcccag gactggacat atctgcactc ctgccctctg acttcagccg ctacttccaa  1020
tatgaggggt ctctgactac accgccctgt gcccagggtg tcatctggac tgtgtttaac  1080
cagacagtga tgctgagtgc taagcagctc cacaccctct ctgacaccct gtggggacct  1140
ggtgactctc ggctacagct gaacttccga gcgacgcagc ctttgaatgg gcgagtgatt  1200
gaggcctcct tccctgctgg agtggacagc agtcctcggg ctgctgagcc agtccagctg  1260
aattcctgcc tggctgctgg tgacatccta gccctggttt ttggcctcct ttttgctgtc  1320
accagcgtcg cgttccttgt gcagatgaga aggcagcaca gaaggggaac caaagggggt  1380
gtgagctacc gcccagcaga ggtagccgag actggagcct agaggctgga tcttggagaa  1440
tgtgagaagc cagccagagg catctgaggg ggagccggta actgtcctgt cctgctcatt  1500
atgccacttc cttttaactg ccaagaaatt ttttaaaata aatatttata at          1552

SEQ ID NO: 135          moltype = AA  length = 459
FEATURE                 Location/Qualifiers
source                  1..459
                        mol_type = protein
                        organism = Homo sapiens
SEQUENCE: 135
MAPLCPSPWL PLLIPAPAPG LTVQLLLSLL LLMPVHPQRL PRMQEDSPLG GGSSGEDDPL  60
GEEDLPSEED SPREEDPPGE EDLPGEEDLP GEEDLPEVKP KSEEEGSLKL EDLPTVEAPG  120
DPQEPQNNAH RDKEGDDQSH WRYGGDPPWP RVSPACAGRF QSPVDIRPQL AAFCPALRPL  180
ELLGFQLPPL PELRLRNNGH SVQLTLPPGL EMALGPGREY RALQLHLHWG AAGRPGSEHT  240
VEGHRFPAEI HVVHLSTAFA RVDEALGRPG GLAVLAAFLE EGPEENSAYE QLLSRLEEIA  300
EEGSETQVPG LDISALLPSD FSRYFQYEGS LTTPPCAQGV IWTVFNQTVM LSAKQLHTLS  360
DTLWGPGDSR LQLNFRATQP LNGRVIEASF PAGVDSSPRA AEPVQLNSCL AAGDILALVF  420
GLLFAVTSVA FLVQMRRQHR RGTKGGVSYR PAEVAETGA                         459

SEQ ID NO: 136          moltype = DNA  length = 1595
```

-continued

```
FEATURE                 Location/Qualifiers
source                  1..1595
                        mol_type = other DNA
                        organism = synthetic construct
SEQUENCE: 136
ccccggcgca gcgcggccgc agcagcctcc gcccccgcca cggtgtgagc gcccgacgcg  60
gccgaggcgg ccggagtccc gagctagccc cggcggccgc cgccgcccag accggacgac  120
aggccacctc gtcggcgtcc gcccgagtcc ccgcctcgcc gccaacgcca caaccaccgc  180
gcacggcccc ctgactccgt ccagtattga tcgggagagc cggagcgagc tcttcgggga  240
gcagcgatgc gaccctccgg gacggccggg gcagcgctcc tggcgctgct ggctgcgctc  300
tgcccggcga gtcgggctct ggaggaaaag aaagtttgcc aaggcacgag taacaagctc  360
acgcagttgg gcacttttga agatcatttt ctcagcctcc agaggatgtt caataactgt  420
gaggtggtcc ttgggaattt ggaaattacc tatgtgcaga ggaattatga tctttccttc  480
ttaaagacca tccaggaggt ggctggttat gtcctcattg ccctcaacac agtggagcga  540
attcctttgg aaaacctgca gatcatcaga ggaaatatgt actacgaaaa ttcctatgcc  600
ttagcagtct tatctaacta tgatgcaaat aaaaccggac tgaaggagct gcccatgaga  660
aatttacagg aaatcctgca tggcgccgtg cggttcagca acaaccctgc cctgtgcaac  720
gtggagagca tccagtggcg ggacatagtc agcagtgact ttctcagcaa catgtcgatg  780
gacttccaga accacctggg cagctgccaa aagtgtgatc caagctgtcc caatgggagc  840
tgctggggtg caggagagga gaactgccag aaactgacca aaatcatctg tgcccagcag  900
tgctccgggc gctgccgtgg caagtccccc agtgactgct gccacaacca gtgtgctgca  960
ggctgcacag gcccccggga gagcgactgc ctggtctgcc gcaaattccg agacgaagcc  1020
acgtgcaagg acacctgccc cccactcatg ctctacaacc ccaccacgta ccagatggat  1080
gtgaaccccg agggcaaata cagctttggt gccacctgcg tgaagaagtg tccccgtaat  1140
tatgtggtga cagatcacgg ctcgtgcgtc cgagcctgtg gggccgacag ctatgagatg  1200
gaggaagacg gcgtccgcaa gtgtaagaag tgcgaagggc cttgccgcaa agtgtgtaac  1260
ggaataggta ttggtgaatt taaagactca ctctccataa atgctacgaa tattaaacac  1320
ttcaaaaact gcacctccat cagtggcgat ctccacatcc tgccggtggc atttaggggt  1380
gactccttca cacatactcc tcctctggat ccacaggaac tggatattct gaaaaccgta  1440
aaggaaatca caggtttgag ctgaattatc acatgaatat aaatgggaaa tcagtgtttt  1500
agagagagaa cttttcgaca tatttcctgt tcccttggaa taaaaacatt tcttctgaaa  1560
ttttaccgtt aaaaaaaaaa aaaaaaaaaa aaaaa                            1595

SEQ ID NO: 137          moltype = AA  length = 405
FEATURE                 Location/Qualifiers
source                  1..405
                        mol_type = protein
                        organism = Homo sapiens
SEQUENCE: 137
MRPSGTAGAA LLALLAALCP ASRALEEKKV CQGTSNKLTQ LGTFEDHFLS LQRMFNNCEV  60
VLGNLEITYV QRNYDLSFLK TIQEVAGYVL IALNTVERIP LENLQIIRGN MYYENSYALA  120
VLSNYDANKT GLKELPMRNL QEILHGAVRF SNNPALCNVE SIQWRDIVSS DFLSNMSMDF  180
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGAT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGLS                 405

SEQ ID NO: 138          moltype = DNA  length = 1437
FEATURE                 Location/Qualifiers
source                  1..1437
                        mol_type = other DNA
                        organism = synthetic construct
SEQUENCE: 138
gcttcctcag acatgccgct gctgctactg ctgcccctgc tgtgggcagg ggccctggct  60
atggatccaa atttctggct gcaagtgcag gagtcagtga cggtacagga gggtttgtgc  120
gtcctcgtgc cctgcacttt cttccatccc ataccctact acgacaagaa ctccccagtt  180
catggttact ggttccggga aggagccatt atatccgggg actctccagt ggccacaaac  240
aagctagatc aagaagtaca ggaggagact cagggcagat tccgcctcct tggggatccc  300
agtaggaaca actgctccct gagcatcgta gacgccagga ggagggataa tggttcatac  360
ttctttcgga tggagagagg aagtaccaaa tacagttaca aatctcccca gctctctgtg  420
catgtgacag acttgaccca caggcccaaa atcctcatcc ctggcactct agaacccggc  480
cactccaaaa accttacctg ctctgtgtcc tgggcctgtg agcagggaac acccccgatc  540
ttctcctggt tgtcagctgc ccccacctcc ctgggcccca ggactactca ctcctcggtg  600
ctcataatca ccccacggcc ccaggaccac ggcaccaacc tgacctgtca ggtgaagttc  660
gctggagctg gtgtgactac ggagagaacc atccagctca acgtcaccta tgttccacag  720
aacccaacaa ctggtatctt tccaggagat ggctcaggga aacaagagac cagagcagga  780
ctggttcatg gggccattgg aggagctggt gttacagccc tgctcgctct ttgtctctgc  840
ctcatcttct tcatagtgaa gacccacagg aggaaagcag ccaggacagc agtgggcagc  900
aatgacaccc accctaccac agggtcagcc tccccgaaac accagaagaa ctccaagtta  960
catggcccca ctgaaacctc aagctgttca ggtgccgccc ctactgtgga gatggatgag  1020
gagctgcatt atgcttccct caactttcat gggatgaatc cttccaagga cacctccacc  1080
gaatactcag aggtcaggac ccagtgagga accctcaaga gcatcaggct cagctagaag  1140
atccacatcc tctacaggtc ggggaccaaa ggctgattct tggagattta actccccaca  1200
ggcaatgggt ttatagacat tatgtgagtt tcctgctata ttaacatcat cttgagactt  1260
tgcaagcaga gagtcgtgga atcaaatctg tgctctttca tttgctaagt gtatgatgtc  1320
acacaagctc cttaaccttc catgtctcca ttttcttctc tgtgaagtag gtataagaag  1380
tcctatctca tagggatgct gtgagcatta aataaaggta cacatggaaa acaccag     1437

SEQ ID NO: 139          moltype = AA  length = 364
```

```
FEATURE                Location/Qualifiers
source                 1..364
                       mol_type = protein
                       organism = Homo sapiens
SEQUENCE: 139
MPLLLLLPLL WAGALAMDPN FWLQVQESVT VQEGLCVLVP CTFFHPIPYY DKNSPVHGYW  60
FREGAIISGD SPVATNKLDQ EVQEETQGRF RLLGDPSRNN CSLSIVDARR RDNGSYFFRM  120
ERGSTKYSYK SPQLSVHVTD LTHRPKILIP GTLEPGHSKN LTCSVSWACE QGTPPIFSWL  180
SAAPTSLGPR TTHSSVLIIT PRPQDHGTNL TCQVKFAGAG VTTERTIQLN VTYVPQNPTT  240
GIFPGDGSGK QETRAGLVHG AIGGAGVTAL LALCLCLIFF IVKTHRRKAA RTAVGSNDTH  300
PTTGSASPKH QKNSKLHGPT ETSSCSGAAP TVEMDEELHY ASLNFHGMNP SKDTSTEYSE  360
VRTQ                                                              364

SEQ ID NO: 140         moltype = DNA  length = 1968
FEATURE                Location/Qualifiers
source                 1..1968
                       mol_type = other DNA
                       organism = synthetic construct
SEQUENCE: 140
aggcccctgc ctgccccagc atcccctgcg cgaagctggg tgccccggag agtctgacca  60
ccatgccacc tcctcgcctc ctcttcttcc tcctcttcct cacccccatg gaagtcaggc  120
ccgaggaacc tctagtggtg aaggtggaag agggagataa cgctgtgctg cagtgcctca  180
aggggacctc agatggcccc actcagcagc tgacctggtc tcgggagtcc ccgcttaaac  240
ccttcttaaa actcagcctg gggctgccag gcctgggaat ccacatgagg cccctggcca  300
tctggctttt catcttcaac gtctctcaac agatgggggg cttctacctg tgccagccgg  360
ggcccccctc tgagaaggcc tggcagcctg gctggacagt caatgtggag ggcagcgggg  420
agctgttccg gtggaatgtt tcggacctag gtggcctggg ctgtggcctg aagaacaggt  480
cctcagaggg ccccagctcc ccttccggga agctcatgag ccccaagctg tatgtgtggg  540
ccaaagaccg ccctgagatc tgggagggag agcctccgtg tctcccaccg agggacagcc  600
tgaaccagag cctcagccag gacctcacca tggcccctgg ctccacactc tggctgtcct  660
gtggggtacc ccctgactct gtgtccaggg gccccctctc ctggacccat gtgcacccca  720
aggggcctaa gtcattgctg agcctagagc tgaaggacga tcgcccggcc agagatatgt  780
gggtaatgga gacgggtctg ttgttgcccc gggccacagc tcaagacgct ggaaagtatt  840
attgtcaccg tggcaacctg accatgtcat tccacctgga gatcactgct cggccagtac  900
tatggcactg gctgctgagg actggtggct ggaaggtctc agctgtgact ttggcttatc  960
tgatcttctg cctgtgttcc cttgtgggca ttcttcatct tcaaagagcc ctggtcctga  1020
ggaggaaaag aaagcgaatg actgacccca ccaggagatt cttcaaagtg acgcctcccc  1080
caggaagcgg gccccagaac cagtacggga acgtgctgtc tctccccaca cccacctcag  1140
gcctcggacg cgcccagcgt tgggccgcag gcctgggggg cactgccccg tcttatggaa  1200
acccgagcag cgacgtccag gcggatggag ccttggggtc ccggagcccg ccgggagtgg  1260
gcccagaaga agaggaaggg gagggctatg aggaacctga cagtgaggag gactccgagt  1320
tctatgagaa cgactccaac cttgggcagg accagctctc ccaggatggc agcggctacg  1380
agaaccctga ggatgagccc ctgggtcctg aggatgaaga ctccttctcc aacgctgagt  1440
cttatgagaa cgaggatgaa gagctgaccc agccggtcgc caggacaatg gacttcctga  1500
gccctcatgg gtcagcctgg gaccccagcc gggaagcaac ctccctggca gggtcccagt  1560
cctatgagga tatgagagga atcctgtatg cagccccccca gctccgctcc attcggggcc  1620
agcctggacc caatcatgag gaagatgcag actcttatga gaacatggat aatcccgatg  1680
ggccagaccc agcctgggga ggagggggcc gcatgggcac ctggagcacc aggtgatcct  1740
caggtggcca gcctggatct cctcaagtcc ccaagattca cacctgactc tgaaatctga  1800
agacctcgag cagatgatgc caacctctgg agcaatgttg cttaggatgt gtgcatgtgt  1860
gtaagtgtgt gtgtgtgtgt gtgtgtgtat acatgccagt gacacttcca gtcccctttg  1920
tattccttaa ataaactcaa tgagctcttc caatcctaaa aaaaaaaa                1968

SEQ ID NO: 141         moltype = AA  length = 557
FEATURE                Location/Qualifiers
source                 1..557
                       mol_type = protein
                       organism = Homo sapiens
SEQUENCE: 141
MPPPRLLFFL LFLTPMEVRP EEPLVVKVEE GDNAVLQCLK GTSDGPTQQL TWSRESPLKP  60
FLKLSLGLPG LGIHMRPLAI WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCLPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW KVSAVTLAYL  300
IFCLCSLVGI LHLQRALVLR RKRKRMTDPT RRFFKVTPPP GSGPQNQYGN VLSLPTPTSG  360
LGRAQRWAAG LGGTAPSYGN PSSDVQADGA LGSRSPPGVG PEEEEGEGYE EPDSEEDSEF  420
YENDSNLGQD QLSQDGSGYE NPEDEPLGPE DEDSFSNAES YENEDEELTQ PVARTMDFLS  480
PHGSAWDPSR EATSLAGSQS YEDMRGILYA APQLRSIRGQ PGPNHEEDAD SYENMDNPDG  540
PDPAWGGGGR MGTWSTR                                                557

SEQ ID NO: 142         moltype = DNA  length = 3216
FEATURE                Location/Qualifiers
source                 1..3216
                       mol_type = other DNA
                       organism = synthetic construct
SEQUENCE: 142
ggcagtttcc tggctgaaca cgccagccca atacttaaag agagcaactc ctgactccga  60
tagagactgg atggacccac aagggtgaca gcccaggcgg accgatcttc ccatcccaca  120
tcctccggcg cgatgccaaa aagaggctga cggcaactgg gccttctgca gagaaagacc  180
```

-continued

```
tccgcttcac tgccccggct ggtcccaagg gtcaggaaga tggattcata cctgctgatg  240
tggggactgc tcacgttcat catggtgcct ggctgccagg cagagctctg tgacgatgac  300
ccgccagaga tcccacacgc cacattcaaa gccatggcct acaaggaagg aaccatgttg  360
aactgtgaat gcaagagagg tttccgcaga ataaaaagcg ggtcactcta tatgctctgt  420
acaggaaact ctagccactc gtcctgggac aaccaatgtc aatgcacaag ctctgccact  480
cggaacacaa cgaaacaagt gacacctcaa cctgaagaac agaaagaaag gaaaaccaca  540
gaaatgcaaa gtccaatgca gccagtggac caagcgagcc ttccaggtca ctgcagggaa  600
cctccaccat gggaaaatga agccacagag agaatttatc atttcgtggt ggggcagatg  660
gtttattatc agtgcgtcca gggatacagg gctctacaca gaggtcctgc tgagagcgtc  720
tgcaaaatga cccacgggaa gacaaggtgg acccagcccc agctcatatg cacaggtgaa  780
atggagacca gtcagtttcc aggtgaagag aagcctcagg caagccccga aggccgtcct  840
gagagtgaga cttcctgcct cgtcacaaca acagattttc aaatacagac agaaatggct  900
gcaaccatgg agacgtccat atttacaaca gagtaccagg tagcagtggc cggctgtgtt  960
ttcctgctga tcagcgtcct cctcctgagt gggctcacct ggcagcggag acagaggaag  1020
agtagaagaa caatctagaa aaccaaaaga acaagaattt cttggtaaga agccgggaac  1080
agacaacaga agtcatgaag cccaagtgaa atcaaaggtg ctaaatggtc gcccaggaga  1140
catccgttgt gcttgcctgc gttttggaag ctctgaagtc acatcacagg acacggggca  1200
gtggcaacct tgtctctatg ccagctcagt cccatcagag agcgagcgct acccacttct  1260
aaatagcaat ttcgccgttg aagaggaagg gcaaaaccac tagaactctc catcttattt  1320
tcatgtatat gtgttcatta aagcatgaat ggtatggaac tctctccacc ctatatgtag  1380
tataaagaaa agtaggttta cattcatctc attccaactt cccagttcag gagtcccaag  1440
gaaagcccca gcactaacgt aaatacacaa cacacacact ctaccctata caactggaca  1500
ttgtctgcgt ggttcctttc tcagccgctt ctgactgctg attctcccgt tcacgttgcc  1560
taataaacat ccttcaagaa ctctgggctg ctacccagaa atcattttac ccttggctca  1620
atcctctaag ctaacccccct tctactgagc cttcagtctt gaatttctaa aaaacagagg  1680
ccatggcaga ataatctttg ggtaacttca aaacggggca gccaaaccca tgaggcaatg  1740
tcaggaacag aaggatgaat gaggtcccag gcagagaatc atacttagca aagttttacc  1800
tgtgcgttac taattggcct ctttaagagt tagtttcttt gggattgcta tgaatgatac  1860
cctgaatttg gcctgcacta atttgatgtt tacaggtgga cacacaaggt gcaaatcaat  1920
gcgtacgttt cctgagaagt gtctaaaaac accaaaaagg gatccgtaca ttcaatgttt  1980
atgcaaggaa ggaaagaaag aaggaagtga agagggagaa gggatggagg tcacactggt  2040
agaacgtaac cacggaaaag agcgcatcag gcctggcacg gtggctcagg cctataaccc  2100
cagctcccta ggagaccaag gcgggagcat ctcttgaggc caggagtttg agaccagcct  2160
gggcagcata gcaagacaca tccctacaaa aaattagaaa ttggctggat gtggtggcat  2220
acgcctgtag tcctagccac tcaggaggct gaggcaggag gattgcttga gcccaggagt  2280
tcgaggctgc agtcagtcat gatggcacca ctgcactcca gcctgggcaa cagagcaaga  2340
tcctgtcttt aaggaaaaaa agacaagatg agcataccag cagtccttga acattatcaa  2400
aaagttcagc atattagaat caccgggagg ccttgttaaa agagttcgct gggcccatct  2460
tcagagtctc tgagttgttg gtctggaata gagccaaatg ttttgtgtgt ctaacaattc  2520
ccaggtgctg ttgctgctgc tactattcca ggaacacact ttgagaacca ttgtgttatt  2580
gctctgcacg cccacccact ctcaactccc acgaaaaaaa tcaacttcca gagctaagat  2640
ttcggtggaa gtcctggttc catatctggt gcaagatctc ccctcacgaa tcagttgagt  2700
caacattcta gctcaacaac atcacacgat taacattaac gaaaattatt catttgggaa  2760
actatcagcc agttttcact tctgaagggg caggagagtg ttatgagaaa tcacggcagt  2820
tttcagcagg gtccagattc agattaaata actattttct gtcatttctg tgaccaacca  2880
catacaaaca gactcatctg tgcactctcc ccctccccct tcaggtatat gttttctgag  2940
taaagttgaa aagaatctca gaccagaaaa tatagatata tatttaaatc ttacttgagt  3000
agaactgatt acgacttttg ggtgttgagg ggtctataag atcaaaactt ttccatgata  3060
atactaagat gttatcgacc atttatctgt ccttctctca aaagtgtatg gtggaatttt  3120
ccagaagcta tgtgatacgt gatgatgtca tcactctgct gttaacatat aataaattta  3180
ttgctattgt ttataaaaga ataaatgata tttttt                           3216

SEQ ID NO: 143          moltype = AA  length = 272
FEATURE                 Location/Qualifiers
source                  1..272
                        mol_type = protein
                        organism = Homo sapiens
SEQUENCE: 143
MDSYLLMWGL LTFIMVPGCQ AELCDDDPPE IPHATFKAMA YKEGTMLNCE CKRGFRRIKS  60
GSLYMLCTGN SSHSSWDNQC QCTSSATRNT TKQVTPQPEE QKERKTTEMQ SPMQPVDQAS  120
LPGHCREPPP WENEATERIY HFVVGQMVYY QCVQGYRALH RGPAESVCKM THGKTRWTQP  180
QLICTGEMET SQFPGEEKPQ ASPEGRPESE TSCLVTTTDF QIQTEMAATM ETSIFTTEYQ  240
VAVAGCVFLL ISVLLLSGLT WQRRQRKSRR TI                                272

SEQ ID NO: 144          moltype = DNA  length = 3227
FEATURE                 Location/Qualifiers
source                  1..3227
                        mol_type = other DNA
                        organism = synthetic construct
SEQUENCE: 144
gctgggcaaa gccggtggca agggcctccc ctgccgctgt gccaggcagg cagtgccaaa  60
tccggggagc ctggagctgg ggggagggcc ggggacagcc cggccctgcc ccctccccg  120
ctgggagccc agcaacttct gaggaaagtt tggcacccat ggcgtggcgg tgccccagga  180
tgggcagggt cccgctggcc tggtgcttgg cgctgtgcgg ctgggcgtgc atggccccca  240
ggggcacgca ggctgaagaa agtcccttcg tgggcaaccc agggaatatc acaggtgccc  300
ggggactcac gggcaccctt cggtgtcagc tccaggttca gggagagccc cccgaggtac  360
attggcttcg ggatggacag atcctggagc tcgcggacag cacccagacc caggtgcccc  420
tgggtgagga tgaacaggat gactggatag tggtcagcca gctcagaatc acctccctgc  480
agctttccga cacgggacag taccagtgtt tggtgtttct gggacatcag accttcgtgt  540
```

```
cccagcctgg ctatgttggg ctggagggct tgccttactt cctggaggag cccgaagaca  600
ggactgtggc cgccaacacc cccttcaacc tgagctgcca agctcaggga cccccagagc  660
ccgtggacct actctggctc caggatgctg tcccccctggc cacggctcca ggtcacggcc  720
cccagcgcag cctgcatgtt ccagggctga acaagacatc ctctttctcc tgcgaagccc  780
ataacgccaa gggggtcacc acatcccgca cagccaccat cacagtgctc ccccagcagc  840
cccgtaacct ccacctggtc tcccgccaac ccacggagct ggaggtggct tggactccag  900
gcctgagcgg catctacccc ctgacccact gcaccctgca ggctgtgctg tcagacgatg  960
ggatgggcat ccaggcggga gaaccagacc ccccagagga gcccctcacc tcgcaagcat  1020
ccgtgccccc ccatcagctt cggctaggca gcctccatcc tcacacccct tatcacatcc  1080
gcgtggcatg caccagcagc cagggcccct catcctggac ccactggctt cctgtggaga  1140
cgccggaggg agtgcccctg ggcccccccta agaacattag tgctacgcgg aatgggagcc  1200
aggccttcgt gcattggcaa gagccccggg cgcccctgca gggtaccctg ttagggtacc  1260
ggctggcgta tcaaggccag gacaccccag aggtgctaat ggacataggg ctaaggcaag  1320
aggtgaccct ggagctgcag ggggacgggt ctgtgtccaa tctgacagtg tgtgtggcag  1380
cctacactgc tgctggggat ggaccctgga gcctcccagt acccctggag gcctggcgcc  1440
cagtgaagga accttcaact cctgccttct cgtggccctg gtggtatgta ctgctaggag  1500
cagtcgtggc cgctgcctgt gtcctcatct tggctctctt ccttgtccac cggcgaaaga  1560
aggagacccg ttatggagaa gtgtttgaac caacagtgga aagaggtgaa ctggtagtca  1620
ggtaccgcgt gcgcaagtcc tacagtcgtc ggaccactga agctaccttg aacagcctgg  1680
gcatcagtga agagctgaag gagaagctgc gggatgtgat ggtggaccgg cacaaggtgg  1740
ccctggggaa gactctggga gagggagagt ttggagctgt gatggaaggc cagctcaacc  1800
aggacgactc catcctcaag gtggctgtga agacgatgaa gattgccatc tgcacgaggt  1860
cagagctgga ggatttcctg agtgaagcgg tctgcatgaa ggaatttgac catcccaacg  1920
tcatgaggct catcggtgtc tgtttccagg gttctgaacg agagagcttc ccagcacctg  1980
tggtcatctt acctttcatg aaacatggag acctacacag cttcctcctc tattcccggc  2040
tcggggacca gccagtgtac ctgcccactc agatgctagt gaagttcatg gcagacatcg  2100
ccagtggcat ggagtatctg agtaccaaga gattcataca ccgggacctg gcggccagga  2160
actgcatgct gaatgagaac atgtccgtgt gtgtggcgga cttcgggctc tccaagaaga  2220
tctacaatgg ggactactac cgccagggac gtatcgccaa gatgccagtc aagtggattg  2280
ccattgagag tctagctgac cgtgtctaca ccagcaagag cgatgtgtgg tccttcgggg  2340
tgacaatgtg ggagattgcc acaagaggcc aaaccccata tccgggcgtg gagaacagcg  2400
agatttatga ctatctgcgc cagggaaatc gcctgaagca gcctgcggac tgtctggatg  2460
gactgtatgc cttgatgtcg cggtgctggg agctaaatcc ccaggaccgg ccaagtttta  2520
cagagctgcg ggaagatttg gagaacacac tgaaggcctt gcctcctgcc caggagcctg  2580
acgaaatcct ctatgtcaac atggatgagg gtggaggtta tcctgaaccc cctggagctg  2640
caggaggagc tgaccccccca acccagccag accctaagga ttcctgtagc tgcctcactg  2700
cggctgaggt ccatcctgct ggacgctatg tcctctgccc ttccacaacc cctagccccg  2760
ctcagcctgc tgataggggc tccccagcag ccccagggca ggaggatggt gcctgagaca  2820
accctccacc tggtactccc tctcaggatc caagctaagc actgccactg gggaaaactc  2880
caccttccca cttttccacc ccacgcctta tccccacttg cagccctgtc ttcctaccta  2940
tcccacctcc atcccagaca ggtccctccc cttctctgtg cagtagcatc accttgaaag  3000
cagtagcatc accatctgta aaaggaaggg gttggattgc aatatctgaa gccctcccag  3060
gtgttaacat tccaagactc tagagtccaa ggtttaaaga gtctagattc aaaggttcta  3120
ggtttcaaag atgctgtgag tctttggttc taaggacctg aaattccaaa gtctctaatt  3180
ctattaaagt gctaaggttc taaggcaaaa aaaaaaaaaa aaaaaaa              3227
```

```
SEQ ID NO: 145          moltype = AA  length = 885
FEATURE                 Location/Qualifiers
source                  1..885
                        mol_type = protein
                        organism = Homo sapiens
SEQUENCE: 145
MAWRCPRMGR VPLAWCLALC GWACMAPRGT QAEESPFVGN PGNITGARGL TGTLRCQLQV  60
QGEPPEVHWL RDGQILELAD STQTQVPLGE DEQDDWIVVS QLRITSLQLS DTGQYQCLVF  120
LGHQTFVSQP GYVGLEGLPY FLEEPEDRTV AANTPFNLSC QAQGPPEPVD LLWLQDAVPL  180
ATAPGHGPQR SLHVPGLNKT SSFSCEAHNA KGVTTSRTAT ITVLPQQPRN LHLVSRQPTE  240
LEVAWTPGLS GIYPLTHCTL QAVLSDDGMG IQAGEPDPPE EPLTSQASVP PHQLRLGSLH  300
PHTPYHIRVA CTSSQGPSSW THWLPVETPE GVPLGPPKNI SATRNGSQAF VHWQEPRAPL  360
QGTLLGYRLA YQGQDTPEVL MDIGLRQEVT LELQGDGSVS NLTVCVAAYT AAGDGPWSLP  420
VPLEAWRPVK EPSTPAFSWP WWYVLLGAVV AAACVLILAL FLVHRRKKET RYGEVFEPTV  480
ERGELVVRYR VRKSYSRRTT EATLNSLGIS EELKEKLRDV MVDRHKVALG KTLGEGEFGA  540
VMEGQLNQDD SILKVAVKTM KIAICTRSEL EDFLSEAVCM KEFDHPNVMR LIGVCFQGSE  600
RESFPAPVVI LPFMKHGDLH SFLLYSRLGD QPVYLPTQML VKFMADIASG MEYLSTKRFI  660
HRDLAARNCM LNENMSVCVA DFGLSKKIYN GDYYRQGRIA KMPVKWIAIE SLADRVYTSK  720
SDVWSFGVTM WEIATRGQTP YPGVENSEIY DYLRQGNRLK QPADCLDGLY ALMSRCWELN  780
PQDRPSFTEL REDLENTLKA LPPAQEPDEI LYVNMDEGGG YPEPPGAAGG ADPPTQPDPK  840
DSCSCLTAAE VHPAGRYVLC PSTTPSPAQP ADRGSPAAPG QEDGA                 885
```

```
SEQ ID NO: 146          moltype = DNA  length = 3630
FEATURE                 Location/Qualifiers
source                  1..3630
                        mol_type = other DNA
                        organism = synthetic construct
SEQUENCE: 146
atacgggaga actaaggctg aaacctcgga ggaacaacca cttttgaagt gacttcgcgg  60
cgtgcgttgg gtgcggacta ggtggccccg gcgggagtgt gctggagcct gaagtccacg  120
cgcgcggctg agaaccgccg ggaccgcacg tgggcgccgc gcgcttcccc cgcttcccag  180
gtgggcgccg gccgccaggc cacctcacgt ccggccccgg ggatgcgcgt cctcctcgcc  240
gcgctgggac tgctgttcct gggggcgcta cgagccttcc cacaggatcg acccttcgag  300
```

```
gacacctgtc atggaaaccc cagccactac tatgacaagg ctgtcaggag gtgctgttac  360
cgctgcccca tggggctgtt cccgacacag cagtgcccac agaggcctac tgactgcagg  420
aagcagtgtg agcctgacta ctacctggat gaggccgacc gctgtacagc ctgcgtgact  480
tgttctcgag atgacctcgt ggagaagacg ccgtgtgcat ggaactcctc ccgtgtctgc  540
gaatgtcgac ccggcatgtt ctgttccacg tctgccgtca actcctgtgc ccgctgcttc  600
ttccattctg tctgtccggc agggatgatt gtcaagttcc caggcacggc gcagaagaac  660
acggtctgtg agccggcttc cccaggggtc agccctgcct gtgccagccc agagaactgc  720
aaggaaccct ccagtggcac catcccccag gccaagccca ccccggtgtc cccagcaacc  780
tccagtgcca gcaccatgcc tgtaagaggg ggcacccgcc tcgcccagga agctgcttct  840
aaactgacga gggctcccga ctctccctcc tctgtgggaa ggcctagttc agatccaggt  900
ctgtccccaa cacagccatg cccagagggg tctggtgatt gcagaaagca gtgtgagccc  960
gactactacc tggacgaggc cggccgctgc acagcctgcg tgagctgttc tcgagatgac  1020
cttgtggaga agacgccatg tgcatggaac tcctcccgca cctgcgaatg tcgacctggc  1080
atgatctgtg ccacatcagc caccaactcc tgtgcccgct gtgtccccta cccaatctgt  1140
gcagcagaga cggtcaccaa gccccaggat atggctgaga aggacaccac ctttgaggcg  1200
ccacccctgg ggacccagcc ggactgcaac cccaccccag agaatggcga ggcgcctgcc  1260
agcaccagcc ccactcagag cttgctggtg gactcccagg ccagtaagac gctgcccatc  1320
ccaaccagcg ctcccgtcgc tctctcctcc acggggaagc ccgttctgga tgcagggcca  1380
gtgctcttct gggtgatcct ggtgttggtt gtggtggtcg gctccagcgc cttcctcctg  1440
tgccaccgga gggcctgcag gaagcgaatt cggcagaagc tccacctgtg ctacccggtc  1500
cagacctccc agcccaagct agagcttgtg gattccagac ccaggaggag ctcaacgcag  1560
ctgaggagtg gtgcgtcggt gacagaaccc gtcgcggaag agcgagggtt aatgagccag  1620
ccactgatgg agacctgcca cagcgtgggg gcagcctacc tggagagcct gccgctgcag  1680
gatgccagcc cggccggggg cccctcgtcc cccagggacc ttcctgagcc ccgggtgtcc  1740
acggagcaca ccaataacaa gattgagaaa atctacatca tgaaggctga caccgtgatc  1800
gtggggaccg tgaaggctga gctgccggag ggccggggcc tggcggggcc agcagagccc  1860
gagttggagg aggagctgga ggcggaccat accccccact accccgagca ggagacagaa  1920
ccgcctctgg gcagctgcag cgatgtcatg ctctcagtgg aagaggaagg gaaagaagac  1980
cccttgccca cagctgcctc tggaaagtga ggcctgggct gggctggggc taggagggca  2040
gcagggtggc ctctgggagg ccaggatggc actgttggca ccgaggttgg gggcagaggc  2100
ccatctggcc tgaactgagg ctccagcatc tagtggtgga ccggccggtc actgcagggg  2160
tctggtggtc tctgcttgca tccccaactt agctgtcccc tgacccagag cctaggggat  2220
ccggggcttg tacagaagag acagtccaag ggactggat cccagcagtg atgttggttg  2280
aggcagcaaa cagatggcag gatgggcact gccgagaaca gcattggtcc cagagccctg  2340
ggcatcagac cttaaccacc aggcccacag cccagcgagg gagaggtcgt gaggccagct  2400
cccggggccc ctgtaaccct actctcctct ctccctggac ctcagaggtg acacccattg  2460
ggcccttccg gcatgccccc agttactgta aatgtggccc ccagtgggca tggagccagt  2520
gcctgtggtt gtttctccag agtcaaaagg gaagtcgagg gatggggcgt cgtcagctgg  2580
cactgtctct gctgcagcgg ccacactgta ctctgcactg gtgtgagggc ccctgcctgg  2640
actgtgggac cctcctggtg ctgcccacct tccctgtcct gtagcccccct cggtgggccc  2700
agggcctagg ggcccaggat caagtcactc atctcagaat gtccccacca atccccgcca  2760
cagcaggcgc ctcgggtccc agatgtctgc agccctcagc agctgcagac cgcccctcac  2820
caacccagag aacctgcttt actttgccca gggacttcct ccccatgtga acatggggaa  2880
cttcgggccc tgcctggagt ccttgaccgc tctctgtggg ccccacccac tctgtcctgg  2940
gaaatgaaga agcatcttcc ttaggtctgc cctgcttgca aatccactag caccgacccc  3000
accacctggt tccggctctg cacgctttgg ggtgtggatg tcgagaggca ccacggcctc  3060
acccaggcat ctgctttact ctggaccata ggaaacaaga ccgtttggag gtttcatcag  3120
gattttgggt ttttcacatt tcacgctaag gagtagtggc cctgacttcc ggtcggctgg  3180
ccagctgact ccctagggcc ttcagacgtg tatgcaaatg agtgatggat aaggatgagt  3240
cttggagttg cgggcagcct ggagactcgt ggacttaccg cctggaggca ggcccgggaa  3300
ggctgctgtt tactcatcgg gcagccacgt gctctctgga ggaagtgata gtttctgaaa  3360
ccgctcagat gttttgggga aagttggaga agccgtggcc ttgcgagagg tggttacacc  3420
agaacctgga cattggccag aagaagctta agtgggcaga cactgtttgc ccagtgtttg  3480
tgcaaggatg gagtgggtgt ctctgcatca cccacagccg cagctgtaag gcacgctgga  3540
aggcacacgc ctgccaggca gggcagtctg gcgcccatga tgggagggat tgacatgttt  3600
caacaaaata atgcacttcc ttaaaaaaaa                                   3630
```

```
SEQ ID NO: 147          moltype = AA  length = 595
FEATURE                 Location/Qualifiers
source                  1..595
                        mol_type = protein
                        organism = Homo sapiens
SEQUENCE: 147
MRVLLAALGL LFLGALRAFP QDRPFEDTCH GNPSHYYDKA VRRCCYRCPM GLFPTQQCPQ  60
RPTDCRKQCE PDYYLDEADR CTACVTCSRD DLVEKTPCAW NSSRVCECRP GMFCSTSAVN  120
SCARCFFHSV CPAGMIVKFP GTAQKNTVCE PASPGVSPAC ASPENCKEPS SGTIPQAKPT  180
PVSPATSSAS TMPVRGGTRL AQEAASKLTR APDSPSSVGR PSSDPGLSPT QPCPEGSGDC  240
RKQCEPDYYL DEAGRCTACV SCSRDDLVEK TPCAWNSSRT CECRPGMICA TSATNSCARC  300
VPYPICAAET VTKPQDMAEK DTTFEAPPLG TQPDCNPTPE NGEAPASTSP TQSLLVDSQA  360
SKTLPIPTSA PVALSSTGKP VLDAGPVLFW VILVLVVVVG SSAFLLCHRR ACRKRIRQKL  420
HLCYPVQTSQ PKLELVDSRP RRSSTQLRSG ASVTEPVAEE RGLMSQPLME TCHSVGAAYL  480
ESLPLQDASP AGGPSSPRDL PEPRVSTEHT NNKIEKIYIM KADTVIVGTV KAELPEGRGL  540
AGPAEPELEE ELEADHTPHY PEQETEPPLG SCSDVMLSVE EEGKEDPLPT AASGK       595
```

```
SEQ ID NO: 148          moltype = DNA  length = 3802
FEATURE                 Location/Qualifiers
misc_feature            1064..1065
                        note = n is a, c, g, or t
misc_feature            1240
```

```
                          note = n is a, c, g, or t
misc_feature              1862
                          note = n is a, c, g, or t
misc_feature              1878
                          note = n is a, c, g, or t
misc_feature              1899..1900
                          note = n is a, c, g, or t
misc_feature              1906
                          note = n is a, c, g, or t
misc_feature              1917
                          note = n is a, c, g, or t
misc_feature              1928..1929
                          note = n is a, c, g, or t
misc_feature              2395
                          note = n is a, c, g, or t
source                    1..3802
                          mol_type = other DNA
                          organism = synthetic construct
SEQUENCE: 148
cccctgcagc tggcctcaat gttaagatct taaggggcac agcacagacc ttgtcttgtc  60
tatctccctg gcacctctca cagagtacag cttattaaca gatgttccag aaactgttac  120
tgaacaatcg gcttgatgct gtgggcttgt ctgcatcttg caactgtcac ctggctgaga  180
aatttcttct ataaataagc agtttctgtt tcagatgtga tatgccctga tatttacacc  240
ctgtctctta ccccatccaa gactcaaact tagaaacttg aattagatgt ggtattcaaa  300
tccttacgtg ccgcgaagac acagacagcc cccgtaagaa cccacgaagc aggcgaagtt  360
cattgttctc aacattctag ctgctcttgc tgcatttgct ctggaattct tgtagagata  420
ttacttgtcc ttccaggctg ttctttctgt agctcccttg ttttcttttt gtgatcatgt  480
tgcagatggc tgggcagtgc tcccaaaatg aatattttga cagtttgttg catgcttgca  540
taccttgtca acttcgatgt tcttctaata ctcctcctct aacatgtcag cgttattgta  600
atgcaagtaa gtaatattgc ttgaacgatt attcattggt gtgaactatt ctgtctatat  660
ggactgctta ttcagagaat caacataatg ggcatgatgg tgagttttct tgaatcaaaa  720
agagaaagga agcaaggcag tgattttaat gtttatggaa acaaagtaat tatttggaac  780
tgaacttgat atgattcagc actattagca acatagattt tttttaaaaa tcagctcttc  840
taattaagtg atatttagaa tttaaaagtc aatgttcatt aattaaggtg attgaatgga  900
aataatccat acttgattat tttgctatca aaacaatcca taattcatta tttttagcaa  960
aataatcaag tatgacagcc gggtgcggtg gatggctcac acctgtaatc ccagcacttt  1020
gggaggccga gatgggtgaa tcacctgagg tcggcagttt gagnncagcc tggccaacct  1080
ggtgaaaccc tgtctctact aaaaatacaa aaaattagct gggcatggtg gcacaggtct  1140
gtaatcccag ctactcggga ggctgaggca ggagaatcgt ttgaacttgg gaggtggagg  1200
ttgcagtgag ccgagatcgc gccactgcaa ctctagcctn ggcaacagag caagactttg  1260
tctcaaaata aataaataaa taataacaat aaagtatgtg aatattatgt tatcagctca  1320
ttatctgtct gatgttcttt tcataaaggt gtgaccaatt cagtgaaagg aacgaatgcg  1380
attctctgga cctgtttggg actgagctta ataatttctt tggcagtttt cgtgctaatg  1440
tttttgctaa ggaagataag ctctgaacca ttaaaggacg agtttaaaaa cacaggttgg  1500
tttgatggtg aatctttgaa atctatttcc aggggatggc tattgtgagt ttcagttcct  1560
tttctttttt tagcgttgac tatttcactt cgttacagcc ctttcgaatg tgttagaaca  1620
ttgttacatt aaatgaactt ggtagaggtg agccatcttc attctgattt tgacaccttg  1680
gcagattttc tacaatgtca gtcttctcca ggattcttcc actgttaatt actctattga  1740
aagtactaag gctttcttgg gaaacatcag tctctttgac taaagttagc acatcgatta  1800
aatgccacat tatcagaaac tcctagccag gtctgctact gtcaggaaaa gcatatttgt  1860
cnagatctat ggtcakgntt ttatacaaat ataggtgtnn yttgcntgag tgaacanttt  1920
actactgnna aaatgttaga aatgaataac cagttgctcc tgaattattt gaggaatcat  1980
ctaaaaaata attattttta agcaatagag aaccagtccc agaaaaatga atgttctact  2040
taagtgcctc ttaagataaa aaatacttct gcagcacctt tgctcatgat tggattccca  2100
agcatgtaca gccactgccc tatttctgta tgcatttatt tatttattta tttatttatt  2160
tatttagaga tggagtctcg ctctgtggcc caaggctgga gtgcagtggc gtgatctcaa  2220
ctcactgcag cctctgcctc ttgggttcaa acaattctcc catctcagcc tcctgagtaa  2280
ctggactata ggtatgtgcc atcacctccg actaattttt gtactttttg gtagagacag  2340
ggtttcatca tgttggccag gatggtctca agctcctgac cacaagtgat ctgcncgcct  2400
cagcttccca aagtgctggg attacaggcg tgagccacag ggcccagcac atactcattc  2460
ttttttactg aaaagatctg tttcaagctg ggtgttggtg gctatggagc tgtagtccga  2520
ctgctctgta ggctaacgtg ggaggattgc ttgagcccag agtttgaatg cagcctgggc  2580
aacacagtaa gaccccacct ctaaaaaatg aaaaaatctc tctcacattg ctttgagtcc  2640
cgatgtgtac tgctaagact ctcatgacca cattctctgt gaagtttggg ttaagttccg  2700
ttctacataa ttaggatcag gtctcctggg catggctaac attgacctgg aaaagagcag  2760
gactggtgat gaaattattc ttccgagagg cctcgagtac acggtggaag aatgcacctg  2820
tgaagactgc atcaagagca aaccgaaggt cgactctgac cattgctttc cactcccagc  2880
tatggaggaa ggcgcaacca ttcttgtcac cacgaaaacg aatgactatt gcaagagcct  2940
gccagctgct ttgagtgcta cggagataga gaaatcaatt tctgctaggt aattaaccat  3000
ttcgactcga gcagtgccac tttaaaaatc ttttgtcaga atagatgatg tgtcagatct  3060
ctttaggatg actgtatttt tcagttgccg atacagcttt ttgtcctcta actgtggaaa  3120
ctctttatgt tagatatatt tctctaggtt actgttggga gcttaatggt agaaacttcc  3180
ttggtttcat gattaaagtc tttttttttc ctgacatcta agtttttatt aacgtgagtt  3240
tttaaaaaca agcatgtata ccagtgtggg gggtgagggt gggagagaaa ggtgggaggg  3300
ggaaagaatt ctaacctatt gataataaag ctccagtttt ggccaggcgc ggtgctcatg  3360
cctgtaatcc cagcactttg aaaggccgag gcgggcagat tacctgaggt caggaatttg  3420
agaccagcct ggccaacatg gtgaaaccct gtctttacta aaaatacaaa aattagctgg  3480
gcatggtggt aggcacctgt aatcccagct actcaggagg ctgaggcagg agaatcgctt  3540
gaacctggga ggtggaggtt gcaatgagct gagatagcat ccctgcactc cagcctgggc  3600
```

-continued

```
aagagggtga gactccgtct caaaacaaaa caacacaaac aaacaaaaag tacctccagc  3660
ttcatcttct gctggatttt atagcgcccc caaagatatg tggtccttaa aaattgtata  3720
ccacttattc aggagtcttg ttcctgaaag ggttgttctt gttacagccc tagtctgggc  3780
tgtaatcagc ttcttaaggt cc                                           3802

SEQ ID NO: 149         moltype = AA  length = 184
FEATURE                Location/Qualifiers
source                 1..184
                       mol_type = protein
                       organism = Homo sapiens
SEQUENCE: 149
MLQMAGQCSQ NEYFDSLLHA CIPCQLRCSS NTPPLTCQRY CNASVTNSVK GTNAILWTCL  60
GLSLIISLAV FVLMFLLRKI SSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                               184

SEQ ID NO: 150         moltype = DNA  length = 2607
FEATURE                Location/Qualifiers
source                 1..2607
                       mol_type = other DNA
                       organism = synthetic construct
SEQUENCE: 150
tctgttccca cttcctcccc gccccaggaa acctgccatg gcctcctggt gagctgtcct  60
catccactgc tcgctgcctc tccagatctt cagttgcttc aggccatttg aacgtatatg  120
agccggtcgt aggggatatg atggcttagc ttgggctcag aggcctgaaa atcgccccca  180
ccaatcacct gtttccccca atctaccctc ctgaaggtca ctgacaaaga cttcattgtc  240
tcctaggaga ggctgccata tatccagggc tgacgtaatt ccatcttaat atcagttaca  300
ttataaaaat ttacctcgtg cctgaggccc cagagcccaa gggtgcaaag cagtaattgg  360
tcaaagttca acttccctcc cactctgggc tcaggctgtc cctgagggc ctgtgttttg  420
agtctctttc cagaaccttg gtgtgaactt aggtcttggc gtcgggatcc cttttcgtca  480
cactcaggtg acctacaggg agctccgctc gacactgcaa ggcttagacc agttcggtcc  540
aacagagaaa gcaggcaacc accatgtcat ttgaaaacag tttcatcggg atataattcg  600
caacccatac agtgaatcca tttaagatac tctgacccat ggatcccctg ggtgcagcca  660
agccacaatg gccatggcgc cgctgtctgg ccgcactgct atttcagctg ctggtggctg  720
tgtgtttctt ctcctacctg cgtgtgtccc gagacgatgc cactggatcc cctagggctc  780
ccagtgggtc ctcccgacag gacaccactc ccacccgccc caccctcctg atcctgctat  840
ggacatggcc tttccacatc cctgtggctc tgtcccgctg ttcagagatg gtgcccggca  900
cagccgactg ccacatcact gccgaccgca aggtgtaccc acaggcagac acggtcatcg  960
tgcaccactg ggatatcatg tccaacccta agtcacgcct cccaccttcc ccgaggccgc  1020
aggggcagcg ctggatctgg ttcaacttgg agccaccccc taactgccag cacctggaag  1080
ccctggacag atacttcaat ctcaccatgt cctaccgcag cgactccgac atcttcacgc  1140
cctacggctg gctggagccg tggtccggcc agcctgccca cccaccgctc aacctctcgg  1200
ccaagaccga gctggtggcc tgggcggtgt ccaactggaa gccggactca gccagggtgc  1260
gctactacca gagcctgcag gctcatctca aggtggacgt gtacggacgc tcccacaagc  1320
ccctgcccaa ggggaccatg atggagacgc tgtcccggta caagttctac ctggccttcg  1380
agaactcctt gcaccccgac tacatcaccg agaagctgtg gaggaacgcc ctggaggcct  1440
gggccgtgcc cgtggtgctg ggccccagca gaagcaacta cgagaggttc ctgccacccg  1500
acgccttcat ccacgtggac gacttccaga gccccaagga cctggcccgg tacctgcagg  1560
agctggacaa ggaccacgcc cgctacctga gctactttcg ctggcgggag acgctgcggc  1620
ctcgctcctt cagctgggca ctggatttct gcaaggcctg ctggaaactg cagcaggaat  1680
ccaggtacca gacggtgcgc agcatagcgg cttggttcac ctgagaggcc ggcatggtgc  1740
ctgggctgcc gggaacctca tctgcctggg gcctcacctg ctggagtcct ttgtggccaa  1800
ccctctctct tacctgggac ctcacacgct gggcttcacg gctgccagga gcctctcccc  1860
tccagaagac ttgcctgcta gggacctcgc ctgctgggga cctcgcctgt tggggacctc  1920
acctgctggg gacctcacct gctggggacc ttggctgctg gaggctgcac ctactgagga  1980
tgtcggcggt cggggacttt acctgctggg acctgctccc agagaccttg ccacactgaa  2040
tctcacctgc tggggacctc accctggagg gccctgggcc ctggggaact ggcttacttg  2100
gggccccacc cgggagtgat ggttctggct gatttgtttg tgatgttgtt agccgcctgt  2160
gaggggtgca gagagatcat cacggcacgg tttccagatg taatactgca aggaaaaatg  2220
atgacgtgtc tcctcactct agaggggttg gtcccatggg ttaagagctc accccaggtt  2280
ctcacctcag ggttaagag ctcagagttc agacaggtcc aagttcaagc ccaggaccac  2340
cacttatagg gtacaggtgg gatcgactgt aaatgaggac ttctggaaca ttccaaatat  2400
tctggggttg agggaaattg ctgctgtcta caaaatgcca agggtggaca ggcgctgtgg  2460
ctcacgcctg taatcccagc actttgggag gctgaggtag gaggattgat tgaggccaag  2520
agttaaagac cagcctggtc aatatagcaa gaccacgtct ctaaataaaa aataataggc  2580
cggccaggca aaaaaaaaaa aaaaaaa                                      2607

SEQ ID NO: 151         moltype = AA  length = 361
FEATURE                Location/Qualifiers
source                 1..361
                       mol_type = protein
                       organism = Homo sapiens
SEQUENCE: 151
MDPLGAAKPQ WPWRRCLAAL LFQLLVAVCF FSYLRVSRDD ATGSPRAPSG SSRQDTTPTR  60
PTLLILLWTW PFHIPVALSR CSEMVPGTAD CHITADRKVY PQADTVIVHH WDIMSNPKSR  120
LPPSPRPQGQ RWIWFNLEPP PNCQHLEALD RYFNLTMSYR SDSDIFTPYG WLEPWSGQPA  180
HPPLNLSAKT ELVAWAVSNW KPDSARVRYY QSLQAHLKVD VYGRSHKPLP KGTMMETLSR  240
YKFYLAFENS LHPDYITEKL WRNALEAWAV PVVLGPSRSN YERFLPPDAF IHVDDFQSPK  300
DLARYLQELD KDHARYLSYF RWRETLRPRS FSWALDFCKA CWKLQQESRY QTVRSIAAWF  360
```

```
T                                                                   361

SEQ ID NO: 152         moltype = DNA  length = 2371
FEATURE                Location/Qualifiers
source                 1..2371
                       mol_type = other DNA
                       organism = synthetic construct
SEQUENCE: 152
tctcctcttg ctctaagcag ggtgtttgac cttctagtcg actgcgtccc ctgtacccgg  60
cgccagctgt gttcctgacc ccagaataac tcagggctgc accgggcctg gcagcgctcc  120
gcacacattt cctgtcgcgg cctaagggaa actgttggcc gctgggcccg cggggggatt  180
cttggcagtt ggggggtccg tcgggagcga gggcggaggg gaagggaggg ggaaccgggt  240
tggggaagcc agctgtagag ggcggtgacc gcgctccaga cacagctctg cgtcctcgag  300
cgggacagat ccaagttggg agcagctctg cgtgcggggc ctcagagaat gaggccggcg  360
ttcgccctgt gcctcctctg gcaggcgctc tggcccgggc cgggcggcgg cgaacacccc  420
actgccgacc gtgctggctg ctcggcctcg gggcctgct acagcctgca ccacgctacc  480
atgaagcggc aggcggccga ggaggcctgc atcctgcgag gtggggcgct cagcaccgtg  540
cgtgcgggcg ccgagctgcg cgctgtgctc gcgctcctgc gggcaggccc agggcccgga  600
gggggctcca aagacctgct gttctgggtc gcactggagc gcaggcgttc ccactgcacc  660
ctggagaacg agcctttgcg gggtttctcc tggctgtcct ccgaccccgg cggtctcgaa  720
agcgacacgc tgcagtgggt ggaggagccc caacgctcct gcaccgcgcg gagatgcgcg  780
gtactccagg ccaccggtgg ggtcgagccc gcaggctgga aggagatgcg atgccacctg  840
cgcgccaacg gctacctgtg caagtaccag tttgaggtct tgtgtcctgc gccgcgcccc  900
ggggccgcct ctaacttgag ctatcgcgcg cccttccagc tgcacagcgc cgctctggac  960
ttcagtccac ctgggaccga ggtgagtgcg ctctgccggg gacagctccc gatctcagtt  1020
acttgcatcg cggacgaaat cggcgctcgc tgggacaaac tctcgggcga tgtgttgtgt  1080
ccctgccccg ggaggtacct ccgtgctggc aaatgcgcag agctccctaa ctgcctagac  1140
gacttgggag gctttgcctg cgaatgtgct acgggcttcg agctggggaa ggacggccgc  1200
tcttgtgtga ccagtgggga aggacagccg acccttgggg ggaccggggt gcccaccagg  1260
cgcccgccgg ccactgcaac cagccccgtg ccgcagagaa catggccaat cagggtcgac  1320
gagaagctgg gagagacacc acttgtccct gaacaagaca attcagtaac atctattcct  1380
gagattcctc gatggggatc acagagcacg atgtctaccc ttcaaatgtc ccttcaagcc  1440
gagtcaaagg ccactatcac cccatcaggg agcgtgattt ccaagtttaa ttctacgact  1500
tcctctgcca ctcctcaggc tttcgactcc tcctctgccg tggtcttcat atttgtgagc  1560
acagcagtag tagtgttggt gatcttgacc atgacagtac tggggcttgt caagctctgc  1620
tttcacgaaa gcccctcttc ccagccaagg aaggagtcta tgggcccgcc gggcctggag  1680
agtgatcctg agcccgctgc tttgggctcc agttctgcac attgcacaaa caatggggtg  1740
aaagtcgggg actgtgatct gcgggacaga gcagagggtg ccttgctggc ggagtcccct  1800
cttggctcta gtgatgcata gggaaacagg ggacatgggc actcctgtga acagtttttc  1860
acttttgatg aaacggggaa ccaagaggaa cttacttgtg taactgacaa tttctgcaga  1920
aatccccctt cctctaaatt ccctttactc cactgaggag ctaaatcaga actgcacact  1980
ccttccctga tgatagagga agtggaagtg cctttaggat ggtgatactg gggaccgggg  2040
tagtgctggg gagagatatt ttcttatgtt tattcggaga atttggagaa gtgattgaac  2100
ttttcaagac attggaaaca aatagaacac aatataattt acattaaaaa ataatttcta  2160
ccaaaatgga aaggaaatgt tctatgttgt tcaggctagg agtatattgg ttcgaaatcc  2220
cagggaaaaa aataaaaata aaaaattaaa ggattgttga taacccagac tcaaatatca  2280
ttgccttcct ccaggagtaa ttaggaacag ctgagggcat gctgggagta agcagcaaga  2340
gtgcattctg cttttagatt gagggagagg t                                 2371

SEQ ID NO: 153         moltype = AA  length = 490
FEATURE                Location/Qualifiers
source                 1..490
                       mol_type = protein
                       organism = Homo sapiens
SEQUENCE: 153
MRPAFALCLL WQALWPGPGG GEHPTADRAG CSASGACYSL HHATMKRQAA EEACILRGGA  60
LSTVRAGAEL RAVLALLRAG PGPGGGSKDL LFWVALERRR SHCTLENEPL RGFSWLSSDP  120
GGLESDTLQW VEEPQRSCTA RRCAVLQATG GVEPAGWKEM RCHLRANGYL CKYQFEVLCP  180
APRPGAASNL SYRAPFQLHS AALDFSPPGT EVSALCRGQL PISVTCIADE IGARWDKLSG  240
DVLCPCPGRY LRAGKCAELP NCLDDLGGFA CECATGFELG KDGRSCVTSG EGQPTLGGTG  300
VPTRRPPATA TSPVPQRTWP IRVDEKLGET PLVPEQDNSV TSIPEIPRWG SQSTMSTLQM  360
SLQAESKATI TPSGSVISKF NSTTSSATPQ AFDSSSAVVF IFVSTAVVVL VILTMTVLGL  420
VKLCFHESPS SQPRKESMGP PGLESDPEPA ALGSSSAHCT NNGVKVGDCD LRDRAEGALL  480
AESPLGSSDA                                                          490

SEQ ID NO: 154         moltype = DNA  length = 3973
FEATURE                Location/Qualifiers
source                 1..3973
                       mol_type = other DNA
                       organism = synthetic construct
SEQUENCE: 154
gggctggggg agggtatata agccgagtag gcgacggtga ggtcgacgcc ggccaagaca  60
gcacagacag attgacctat tggggtgttt cgcgagtgtg agagggaagc gccgcggcct  120
gtatttctag acctgccctt cgcctggttc gtggcgcctt gtgaccccgg gcccctgccg  180
cctgcaagtc ggaaattgcg ctgtgctcct gtgctacggc ctgtggctgg actgcctgct  240
gctgcccaac tggctggcaa gatgaagctc tccctggtgg ccgcgatgct gctgctgctc  300
agcgcggcgc gggccgagga ggaggacaag aaggaggacg tgggcacggt ggtcggcatc  360
gacctgggga ccacctactc ctgcgtcggc gtgttcaaga acggccgcgt ggagatcatc  420
gccaacgatc agggcaaccg catcacgccg tcctatgtcg ccttcactcc tgaaggggaa  480
```

-continued

```
cgtctgattg gcgatgccgc caagaaccag ctcacctcca accccgagaa cacggtcttt  540
gacgccaagc ggctcatcgg ccgcacgtgg aatgacccgt ctgtgcagca ggacatcaag  600
ttcttgccgt tcaaggtggt tgaaaagaaa actaaaccat acattcaagt tgatattgga  660
ggtgggcaaa caaagacatt tgctcctgaa gaaatttctg ccatggttct cactaaaatg  720
aaagaaaccg ctgaggctta tttgggaaag aaggttaccc atgcagttgt tactgtacca  780
gcctatttta atgatgccca acgccaagca accaaagacg ctggaactat tgctggccta  840
aatgttatga ggatcatcaa cgagcctacg gcagctgcta ttgcttatgg cctggataag  900
agggaggggg agaagaacat cctggtgttt gacctgggtg gcggaacctt cgatgtgtct  960
cttctcacca ttgacaatgg tgtcttcgaa gttgtggcca ctaatggaga tactcatctg  1020
ggtggagaag actttgacca gcgtgtcatg gaacacttca tcaaactgta caaaaagaag  1080
acgggcaaag atgtcaggaa agacaataga gctgtgcaga aactccggcg cgaggtagaa  1140
aaggccaaac gggccctgtc ttctcagcat caagcaagaa ttgaaattga gtccttctat  1200
gaaggagaag acttttctga gaccctgact cgggccaaat ttgaagagct caacatggat  1260
ctgttccggt ctactatgaa gcccgtccag aaagtgttgg aagattctga tttgaagaag  1320
tctgatattg atgaaattgt tcttgttggt ggctcgactc gaattccaaa gattcagcaa  1380
ctggttaaag agttcttcaa tggcaaggaa ccatcccgtg gcataaaccc agatgaagct  1440
gtagcgtatg gtgctgctgt ccaggctggt gtgctctctg gtgatcaaga tacaggtgac  1500
ctggtactgc ttgatgtatg tccccttaca cttggtattg aaactgtggg aggtgtcatg  1560
accaaactga ttccaaggaa cacagtggtg cctaccaaga agtctcagat cttttctaca  1620
gcttctgata atcaaccaac tgttacaatc aaggtctatg aaggtgaaag accccctgaca  1680
aaagacaatc atcttctggg tacatttgat ctgactggaa ttcctcctgc tcctcgtggg  1740
gtcccacaga ttgaagtcac ctttgagata gatgtgaatg gtattcttcg agtgacagct  1800
gaagacaagg gtacagggaa caaaaataag atcacaatca ccaatgacca gaatcgcctg  1860
acacctgaag aaatcgaaag gatggttaat gatgctgaga agtttgctga ggaagacaaa  1920
aagctcaagg agcgcattga tactagaaat gagttggaaa gctatgccta ttctctaaag  1980
aatcagattg gagataaaga aaagctggga ggtaaacttt cctctgaaga taaggagacc  2040
atggaaaaag ctgtagaaga aaagattgaa tggctggaaa gccaccaaga tgctgacatt  2100
gaagacttca aagctaagaa gaaggaactg gaagaaattg ttcaaccaat tatcagcaaa  2160
ctctatggaa gtgcaggccc tcccccaact ggtgaagagg atacagcaga aaaagatgag  2220
ttgtagacac tgatctgcta gtgctgtaat attgtaaata ctggactcag gaacttttgt  2280
taggaaaaaa ttgaaagaac ttaagtctcg aatgtaattg gaatcttcac ctcagagtgg  2340
agttgaaact gctatagcct aagcggctgt ttactgcttt tcattagcag ttgctcacat  2400
gtctttgggt gggggggaga agaagaattg gccatcttaa aaagcgggta aaaaacctgg  2460
gttagggtgt gtgttcacct tcaaaatgtt ctatttaaca actgggtcat gtgcatctgg  2520
tgtaggaagt tttttctacc ataagtgaca ccaataaatg tttgttattt acactggtct  2580
aatgtttgtg agaagcttct aattagatca attacttatt ttaggaaatt taagactaga  2640
tactcgtgtg tggggtgagg ggagggagta tttggtatgt tgggataagg aaacacttct  2700
atttaatgct tccagggatt ttttttttt tttttaaccc tcctgggccc aagtgatcct  2760
tccacctcag tctcccagct aattgagacc acaggcttgt taccaccatg ctcggctttt  2820
gcattaatct aagaaaaggg gagagaagtt aatccacatc tttactcagg caaggggcat  2880
ttcacagtgc ccaagagtgg ggttttcttg aacatacttg gtttcctatt tccccttatc  2940
tttctaaaac tgcctttctg gtggcttttt ttaaaattat tactaatgat gcttttatag  3000
ctgcttggat tctctgagaa atgatgggga gtgagtgatc actggtatta actttataca  3060
cttggatttc atttgtaact ttaggatgta aaggtatatt gtgaacccta gctgtgtcag  3120
aatctccatc cctgaaattt ctcattagtg gtactggggt gggatcttgg atggtgacat  3180
tgaaactaca ctaaatcccc tcactatgaa tgggttgtta aaggcaatgg tttgtgtcaa  3240
aactggttta ggattactta gattgtgttc ctgaagaaaa gagtccaggt aaatggtatg  3300
atcaataaag gacaggctgg tgctaacata aaatccaata ttgtaatcct agcactttgg  3360
gaggccaagg cgggtggatc acaaggtcaa gagatagaga ccatctttgc caacatggtg  3420
aaactccatc tctactgaaa atacaaaaat tagctgggcg tggtagtgca agctgaaggc  3480
tgaggcagga gaatcactcg aacccgggag gcagaggttg cagtgagccg agatcacacc  3540
actgtactcc agcccggcac tccagcctgg cgacaagagt gagactccac ctcaaaaaaa  3600
aaaaaaagaa tccaatactg cccaaggata ggtattttat agatgggcaa ctggctgaaa  3660
ggttaattct ctagggctag tagaactgga tcccaacacc aaactcttaa ttagacctag  3720
gcctcagctg cactgcccga aaagcatttg ggcagaccct gagcagaata ctggtctcag  3780
gccaagccca atacagccat taaagatgac ctacagtgct gtgtaccctg gggcaatagg  3840
gttaaatggt agttagcaac tagggctagt cttcccttac ctcaaaggct ctcactaccg  3900
tggaccacct agtctgtaac tctttctgag gagctgttac tgaatattaa aaagatagac  3960
ttcaactatg aaa                                                    3973
```

```
SEQ ID NO: 155         moltype = AA  length = 654
FEATURE                Location/Qualifiers
source                 1..654
                       mol_type = protein
                       organism = Homo sapiens
SEQUENCE: 155
MKLSLVAAML LLLSAARAEE EDKKEDVGTV VGIDLGTTYS CVGVFKNGRV EIIANDQGNR  60
ITPSYVAFTP EGERLIGDAA KNQLTSNPEN TVFDAKRLIG RTWNDPSVQQ DIKFLPFKVV  120
EKKTKPYIQV DIGGGQTKTF APEEISAMVL TKMKETAEAY LGKKVTHAVV TVPAYFNDAQ  180
RQATKDAGTI AGLNVMRIIN EPTAAAIAYG LDKREGEKNI LVFDLGGGTF DVSLLTIDNG  240
VFEVVATNGD THLGGEDFDQ RVMEHFIKLY KKKTGKDVRK DNRAVQKLRR EVEKAKRALS  300
SQHQARIEIE SFYEGEDFSE TLTRAKFEEL NMDLFRSTMK PVQKVLEDSD LKKSDIDEIV  360
LVGGSTRIPK IQQLVKEFFN GKEPSRGINP DEAVAYGAAV QAGVLSGDQD TGDLVLLDVC  420
PLTLGIETVG GVMTKLIPRN TVVPTKKSQI FSTASDNQPT VTIKVYEGER PLTKDNHLLG  480
TFDLTGIPPA PRGVPQIEVT FEIDVNGILR VTAEDKGTGN KNKITITNDQ NRLTPEEIER  540
MVNDAEKFAE EDKKLKERID TRNELESYAY SLKNQIGDKE KLGGKLSSED KETMEKAVEE  600
KIEWLESHQD ADIEDFKAKK KELEEIVQPI ISKLYGSAGP PPTGEEDTAE KDEL        654

SEQ ID NO: 156         moltype = DNA  length = 926
```

-continued

```
FEATURE                Location/Qualifiers
source                 1..926
                       mol_type = other DNA
                       organism = synthetic construct
SEQUENCE: 156
ccagagaggg gcaggcttgt cccctgacag gttgaagcaa gtagacgccc aggagccccg  60
ggaggggggct gcagtttcct tccttccttc tcggcagcgc tccgcgcccc catcgcccct  120
cctgcgctag cggaggtgat cgccgcggcg atgccggagg agggttcggg ctgctcggtg  180
cggcgcaggc cctatgggtg cgtcctgcgg gctgctttgg tcccattggt cgcgggcttg  240
gtgatctgcc tcgtggtgtg catccagcgc ttcgcacagg ctcagcagca gctgccgctc  300
gagtcacttg ggtgggacgt agctgagctg cagctgaatc acacaggacc tcagcaggac  360
cccaggctat actggcaggg gggcccagca ctgggccgct ccttcctgca tggaccagag  420
ctggacaagg ggcagctacg tatccatcgt gatggcatct acatggtaca catccaggtg  480
acgctggcca tctgctcctc cacgacggcc tccaggcacc accccaccac cctggccgtg  540
ggaatctgct ctcccgcctc ccgtagcatc agcctgctgc gtctcagctt ccaccaaggt  600
tgtaccattg tctcccagcg cctgacgccc ctggcccgag gggacacact ctgcaccaac  660
ctcactggga cacttttgcc ttcccgaaac actgatgaga ccttctttgg agtgcagtgg  720
gtgcgcccct gaccactgct gctgattagg gtttttttaaa ttttatttta ttttatttaa  780
gttcaagaga aaaagtgtac acacaggggc cacccggggt tggggtggga gtgtggtggg  840
gggtagtttg tggcaggaca agagaaggca ttgagctttt tctttcattt tcctattaaa  900
aaatacaaaa atcaaaacaa aaaaaa                                        926

SEQ ID NO: 157         moltype = AA  length = 193
FEATURE                Location/Qualifiers
source                 1..193
                       mol_type = protein
                       organism = Homo sapiens
SEQUENCE: 157
MPEEGSGCSV RRRPYGCVLR AALVPLVAGL VICLVVCIQR FAQAQQQLPL ESLGWDVAEL  60
QLNHTGPQQD PRLYWQGGPA LGRSFLHGPE LDKGQLRIHR DGIYMVHIQV TLAICSSTTA  120
SRHHPTTLAV GICSPASRSI SLLRLSFHQG CTIVSQRLTP LARGDTLCTN LTGTLLPSRN  180
TDETFFGVQW VRP                                                      193

SEQ ID NO: 158         moltype = AA  length = 293
FEATURE                Location/Qualifiers
REGION                 1..293
                       note = Synthetic construct
source                 1..293
                       mol_type = protein
                       organism = synthetic construct
SEQUENCE: 158
MGILPFLLIP MESNWTVHVF SRTLCHMLLW TAVLNLAAGT HDLPKAVVKL EPPWIQVLKE  60
DTVTLTCEGT HNPGNSSTQW FHNGRSIRSQ VQASYTFKAT VNDSGEYRCQ MEQTRLSDPV  120
DLGVISDWLL LQTPQLVFLE GETITLRCHS WRNKLLNRIS FFHNEKSVRY HHYSSNFSIP  180
KANHSHSGDY YCKGSLGRTQ HQSKTVTITV QGPKSSRSLP VLTIVAAVTG IAVAAIVIIL  240
VSLVYLKKKQ VPDNPPDLEE AAKTEAENTI TYSLLKHPEA LDEETEHDYQ NHI          293

SEQ ID NO: 159         moltype = DNA  length = 2880
FEATURE                Location/Qualifiers
source                 1..2880
                       mol_type = other DNA
                       organism = synthetic construct
SEQUENCE: 159
tgctgctctc cgcccgcgtc cggctcgtgg ccccctactt cgggcaccat ggacacctcc  60
cggctcggtg tgctcctgtc cttgcctgtg ctgctgcagc tggcgaccgg gggcagctct  120
cccaggtctg gtgtgttgct gaggggctgc cccacacact gtcattgcga gcccgacggc  180
aggatgttgc tcagggtgga ctgctccgac ctggggctct cggagctgcc ttccaacctc  240
agcgtcttca cctcctacct agacctcagt atgaacaaca tcagtcagct gctcccgaat  300
cccctgccca gtctccgctt cctggaggag ttacgtcttg cgggaaacgc tctgacatac  360
attcccaagg gagcattcac tggcctttac agtcttaaag ttcttatgct gcagaataat  420
cagctaagac acgtacccac agaagctctg cagaatttgc gaagccttca atccctgcgt  480
ctggatgcta accacatcag ctatgtgccc ccaagctgtt tcagtggcct gcattccctg  540
aggcacctgt ggctggatga caatgcgtta acagaaatcc ccgtccaggc ttttagaagt  600
ttatcggcat tgcaagccat gaccttggcc ctgaacaaaa tacaccacat accagactat  660
gcctttggaa acctctccag cttggtagtt ctacatctcc ataacaatag aatccactcc  720
ctgggaaaga aatgctttga tggctccac agcctagaga ctttagattt aaattacaat  780
aaccttgatg aattccccac tgcaattagg acactctcca accttaaaga actaggattt  840
catagcaaca atatcaggtc gatacctgag aaagcatttg taggcaaccc ttctcttatt  900
acaatacatt tctatgacaa tcccatccaa tttgttggga gatctgcttt tcaacattta  960
cctgaactaa gaacactgac tctgaatggt gcctcacaaa taactgaatt tcctgattta  1020
actggaactg caaacctgga gagtctgact ttaactggag cacagatctc atctcttcct  1080
caaaccgtct gcaatcagtt acctaatctc caagtgctag atctgtctta caacctatta  1140
gaagatttac ccagtttttc agtctgccaa aagcttcaga aaattgacct aagacataat  1200
gaaatctacg aaattaaagt tgacactttc cagcagttgc ttagcctccg atcgctgaat  1260
ttggcttgga acaaaattgc tattattcac cccaatgcat tttccacttt gccatcccta  1320
ataaagctgg acctatcgtc caacctcctg tcgtcttttc ctataactgg gttacatggt  1380
ttaactcact taaaattaac aggaaatcat gccttacaga gcttgatatc atctgaaaac  1440
tttccagaac tcaaggttat agaaatgcct tatgcttacc agtgctgtgc atttggagtg  1500
tgtgagaatg cctataagat ttctaatcaa tggaataaag gtgacaacag cagtatggac  1560
```

```
gaccttcata agaaagatgc tggaatgttt caggctcaag atgaacgtga ccttgaagat  1620
ttcctgcttg actttgagga agacctgaaa gcccttcatt cagtgcagtg ttcaccttcc  1680
ccaggcccct tcaaaccctg tgaacacctg cttgatggct ggctgatcag aattggagtg  1740
tggaccatag cagttctggc acttacttgt aatgctttgg tgacttcaac agttttcaga  1800
tcccctctgt acatttcccc cattaaactg ttaattgggg tcatcgcagc agtgaacatg  1860
ctcacgggag tctccagtgc cgtgctggct ggtgtggatg cgttcacttt tggcagcttt  1920
gcacgacatg gtgcctggtg ggagaatggg gttggttgcc atgtcattgg ttttttgtcc  1980
atttttgctt cagaatcatc tgttttcctg cttactctgg cagccctgga gcgtgggttc  2040
tctgtgaaat attctgcaaa atttgaaacg aaagctccat tttctagcct gaaagtaatc  2100
attttgctct gtgccctgct ggccttgacc atggccgcag ttcccctgct gggtggcagc  2160
aagtatggcg cctcccctct ctgcctgcct ttgccttttg gggagcccag caccatgggc  2220
tacatggtcg ctctcatctt gctcaattcc ctttgcttcc tcatgatgac cattgcctac  2280
accaagctct actgcaattt ggacaaggga gacctggaga atatttggga ctgctctatg  2340
gtaaaacaca ttgccctgtt gctcttcacc aactgcatcc taaactgccc tgtggctttc  2400
ttgtccttct cctctttaat aaaccttaca tttatcagtc ctgaagtaat taagtttatc  2460
cttctggtgg tagtcccact tcctgcatgt ctcaatcccc ttctctacat cttgttcaat  2520
cctcacttta aggaggatct ggtgagcctg agaaagcaaa cctacgtctg gacaagatca  2580
aaacacccaa gcttgatgtc aattaactct gatgatgtcg aaaaacagtc ctgtgactca  2640
actcaagcct tggtaacctt taccagctcc agcatcactt atgacctgcc tcccagttcc  2700
gtgccatcac cagcttatcc agtgactgag agctgccatc tttcctctgt ggcatttgtc  2760
ccatgtctct aattaatatg tgaaggaaaa tgttttcaaa ggttgagaac ctgaaaatgt  2820
gagattgagt atatcagagc agtaattaat aagaagagct gaggtgaaac tcggtttaaa  2880

SEQ ID NO: 160         moltype = AA  length = 907
FEATURE                Location/Qualifiers
source                 1..907
                       mol_type = protein
                       organism = Homo sapiens
SEQUENCE: 160
MDTSRLGVLL SLPVLLQLAT GGSSPRSGVL LRGCPTHCHC EPDGRMLLRV DCSDLGLSEL  60
PSNLSVFTSY LDLSMNNISQ LLPNPLPSLR FLEELRLAGN ALTYIPKGAF TGLYSLKVLM  120
LQNNQLRHVP TEALQNLRSL QSLRLDANHI SYVPPSCFSG LHSLRHLWLD DNALTEIPVQ  180
AFRSLSALQA MTLALNKIHH IPDYAFGNLS SLVVLHLHNN RIHSLGKKCF DGLHSLETLD  240
LNYNNLDEFP TAIRTLSNLK ELGFHSNNIR SIPEKAFVGN PSLITIHFYD NPIQFVGRSA  300
FQHLPELRTL TLNGASQITE FPDLTGTANL ESLTLTGAQI SSLPQTVCNQ LPNLQVLDLS  360
YNLLEDLPSF SVCQKLQKID LRHNEIYEIK VDTFQQLLSL RSLNLAWNKI AIIHPNAFST  420
LPSLIKLDLS SNLLSSFPIT GLHGLTHLKL TGNHALQSLI SSENFPELKV IEMPYAYQCC  480
AFGVCENAYK ISNQWNKGDN SSMDDLHKKD AGMFQAQDER DLEDFLLDFE EDLKALHSVQ  540
CSPSPGPFKP CEHLLDGWLI RIGVWTIAVL ALTCNALVTS TVFRSPLYIS PIKLLIGVIA  600
AVNMLTGVSS AVLAGVDAFT FGSFARHGAW WENGVGCHVI GFLSIFASES SVFLLTLAAL  660
ERGFSVKYSA KFETKAPFSS LKVIILLCAL LALTMAAVPL LGGSKYGASP LCLPLPFGEP  720
STMGYMVALI LLNSLCFLMM TIAYTKLYCN LDKGDLENIW DCSMVKHIAL LLFTNCILNC  780
PVAFLSFSSL INLTFISPEV IKFILLVVVP LPACLNPLLY ILFNPHFKED LVSLRKQTYV  840
WTRSKHPSLM SINSDDVEKQ SCDSTQALVT FTSSSITYDL PPSSVPSPAY PVTESCHLSS  900
VAFVPCL                                                            907

SEQ ID NO: 161         moltype = DNA  length = 3977
FEATURE                Location/Qualifiers
source                 1..3977
                       mol_type = other DNA
                       organism = synthetic construct
SEQUENCE: 161
ggatggtgcc ttgagtgaat gaccccccttg gagaacattc ttccgcatcc ctcgcctcaa  60
gccagcctca gacagaaaac tgaagattca gcagatccag tgcttcctgc tcctcttctg  120
cccaggaaca cgcttgcctt ccccaaggct tccagaagct ctgaggcagg aggcaccaag  180
ttctacctca tgtttggagg atcttgctag ctatggccct cgtactcggc tccctgttgc  240
tgctggggct gtgcgggaac tccttttcag gagggcagcc ttcatccaca gatgctccta  300
aggcttggaa ttatgaattg cctgcaacaa attatgagac ccaagactcc cataaagctg  360
gacccattgg cattctcttt gaactagtgc atatctttct ctatgtggta cagccgcgtg  420
atttcccaga agatactttg agaaaattct tacagaaggc atatgaatcc aaaattgatt  480
atgacaagcc agaaactgta atcttaggtc taaagattgt ctactatgaa gcagggatta  540
ttctatgctg tgtcctgggg ctgctgttta ttattctgat gcctctggtg gggtatttct  600
tttgtatgtg tcgttgctgt aacaaatgtg gtggagaaat gcaccagcga cagaaggaaa  660
atgggccctt cctgaggaaa tgctttgcaa tctccctgtt ggtgatttgt ataataataa  720
gcattggcat cttctatggt tttgtggcaa atcaccaggt aagaacccgg atcaaaagga  780
gtcggaaact ggcagatagc aatttcaagg acttgcgaac tctcttgaat gaaactccag  840
agcaaatcaa atatatattg gcccagtaca acactaccaa ggacaaggcg ttcacagatc  900
tgaacagtat caattcagtg ctaggaggcg gaattcttga ccgactgaga cccaacatca  960
tccctgttct tgatgagatt aagtccatgg caacagcgat caaggagacc aaagaggcgt  1020
tggagaacat gaacagcacc ttgaagagct tgcaccaaca aagtacacag cttagcagca  1080
gtctgaccag cgtgaaaact agcctgcggt catctctcaa tgaccctctg tgcttggtgc  1140
atccatcaag tgaaacctgc aacagcatca gattgtctct aagccagctg aatagcaacc  1200
ctgaactgag gcagcttcca cccgtggatg cagaacttga caacgttaat aacgttctta  1260
ggacagattt ggatggcctg gtccaacagg gctatcaatc ccttaatgat atacctgaca  1320
gagtacaacg ccaaaccacg actgtcgtag caggtatcaa aagggtcttg aattccattg  1380
gttcagatat cgacaatgta actcagcgtc ttcctattca ggatatactc tcagcattct  1440
ctgtttatgt taataacact gaaagttaca tccacagaaa tttacctaca ttggaagagt  1500
atgattcata ctggtggctg ggtggcctgg tcatctgctc tctgctgacc ctcatcgtga  1560
ttttttacta cctgggctta ctgtgtggcg tgtgcggcta tgacaggcat gccaccccga  1620
```

-continued

```
ccacccgagg ctgtgtctcc aacaccggag gcgtcttcct catggttgga gttggattaa  1680
gtttcctctt ttgctggata ttgatgatca ttgtggttct tacctttgtc tttggtgcaa  1740
atgtggaaaa actgatctgt gaaccttaca cgagcaagga attattccgg gttttggata  1800
caccctactt actaaatgaa gactgggaat actatctctc tgggaagcta tttaataaat  1860
caaaaatgaa gctcactttt gaacaagttt acagtgactg caaaaaaaat agaggcactt  1920
acggcactct tcacctgcag aacagcttca atatcagtga acatctcaac attaatgagc  1980
atactggaag cataagcagt gaattggaaa gtctgaaggt aaatcttaat atctttctgt  2040
tgggtgcagc aggaagaaaa aaccttcagg attttgctgc ttgtggaata gacagaatga  2100
attatgacag ctacttggct cagactggta aatcccccgc aggagtgaat cttttatcat  2160
ttgcatatga tctagaagca aaagcaaaca gtttgccccc aggaaatttg aggaactccc  2220
tgaaaagaga tgcacaaact attaaaacaa ttcaccagca acgagtcctt cctatagaac  2280
aatcactgag cactctatac caaagcgtca agatacttca acgcacaggg aatggattgt  2340
tggagagagt aactaggatt ctagcttctc tggattttgc tcagaacttc atcacaaaca  2400
atacttcctc tgttattatt gaggaaacta agaagtatgg gagaacaata ataggatatt  2460
ttgaacatta tctgcagtgg atcgagttct ctatcagtga gaaagtggca tcgtgcaaac  2520
ctgtggccac cgctctagat actgctgttg atgtctttct gtgtagctac attatcgacc  2580
ccttgaattt gttttggttt ggcataggaa aagctactgt atttttactt ccggctctaa  2640
tttttgcggt aaaactggct aagtactatc gtcgaatgga ttcggaggac gtgtacgatg  2700
atgttgaaac tatacccatg aaaaatatgg aaaatggtaa taatggttat cataaagatc  2760
atgtatatgg tattcacaat cctgttatga caagcccatc acaacattga tagctgatgt  2820
tgaaactgct tgagcatcag gatactcaaa gtggaaagga tcacagattt ttggtagttt  2880
ctgggtctac aaggactttc caaatccagg agcaacgcca gtggcaacgt agtgactcag  2940
gcgggcacca aggcaacggc accattggtc tctgggtagt gctttaagaa tgaacacaat  3000
cacgttatag tccatggtcc atcactattc aaggatgact ccctcccttc ctgtctattt  3060
ttgtttttta ctttttttaca ctgagtttct atttagacac tacaacatat ggggtgtttg  3120
ttcccattgg atgcatttct atcaaaactc tatcaaatgt gatggctaga ttctaacata  3180
ttgccatgtg tggagtgtgc tgaacacaca ccagtttaca ggaaagatgc attttgtgta  3240
cagtaaacgg tgtatatacc ttttgttacc acagagtttt ttaaacaaat gagtattata  3300
ggactttctt ctaaatgagc taaataagtc accattgact tcttggtgct gttgaaaata  3360
atccattttc actaaaagtg tgtgaaacct acagcatatt cttcacgcag agattttcat  3420
ctattatact ttatcaaaga ttggccatgt tccacttgga aatggcatgc aaaagcaatc  3480
atagagaaac ctgcgtaact ccatctgaca aattcaaaag agagagagag atcttgagag  3540
agaaatgctg ttcgttcaaa agtggagttg ttttaacaga tgccaattac ggtgtacagt  3600
ttaacagagt tttctgttgc attaggataa acattaattg gagtgcagct aacatgagta  3660
tcatcagact agtatcaagt gttctaaaat gaaatatgag aagatcctgt cacaattctt  3720
agatctggtg tccagcatgg atgaaacctt tgagtttggt ccctaaattt gcatgaaagc  3780
acaaggtaaa tattcatttg cttcaggagt ttcatgttgg atctgtcatt atcaaaagtg  3840
atcagcaatg aagaactggt cggacaaaat ttaacgttga tgtaatgaaa ttccagatgt  3900
aggcattccc cccaggtctt ttcatgtgca gattgcagtt ctgattcatt tgaataaaaa  3960
ggaacttgga aaacatg                                                 3977
```

```
SEQ ID NO: 162         moltype = AA  length = 865
FEATURE                Location/Qualifiers
source                 1..865
                       mol_type = protein
                       organism = Homo sapiens
SEQUENCE: 162
MALVLGSLLL LGLCGNSFSG GQPSSTDAPK AWNYELPATN YETQDSHKAG PIGILFELVH  60
IFLYVVQPRD FPEDTLRKFL QKAYESKIDY DKPETVILGL KIVYYEAGII LCCVLGLLFI  120
ILMPLVGYFF CMCRCCNKCG GEMHQRQKEN GPFLRKCFAI SLLVICIIIS IGIFYGFVAN  180
HQVRTRIKRS RKLADSNFKD LRTLLNETPE QIKYILAQYN TTKDKAFTDL NSINSVLGGG  240
ILDRLRPNII PVLDEIKSMA TAIKETKEAL ENMNSTLKSL HQQSTQLSSS LTSVKTSLRS  300
SLNDPLCLVH PSSETCNSIR LSLSQLNSNP ELRQLPPVDA ELDNVNNVLR TDLDGLVQQG  360
YQSLNDIPDR VQRQTTTVVA GIKRVLNSIG SDIDNVTQRL PIQDILSAFS VYVNNTESYI  420
HRNLPTLEEY DSYWWLGGLV ICSLLTLIVI FYYLGLLCGV CGYDRHATPT TRGCVSNTGG  480
VFLMVGVGLS FLFCWILMII VVLTFVFGAN VEKLICEPYT SKELFRVLDT PYLLNEDWEY  540
YLSGKLFNKS KMKLTFEQVY SDCKKNRGTY GTLHLQNSFN ISEHLNINEH TGSISSELES  600
LKVNLNIFLL GAAGRKNLQD FAACGIDRMN YDSYLAQTGK SPAGVNLLSF AYDLEAKANS  660
LPPGNLRNSL KRDAQTIKTI HQQRVLPIEQ SLSTLYQSVK ILQRTGNGLL ERVTRILASL  720
DFAQNFITNN TSSVIIEETK KYGRTIIGYF EHYLQWIEFS ISEKVASCKP VATALDTAVD  780
VFLCSYIIDP LNLFWFGIGK ATVFLLPALI FAVKLAKYYR RMDSEDVYDD VETIPMKNME  840
NGNNGYHKDH VYGIHNPVMT SPSQH                                        865
```

```
SEQ ID NO: 163         moltype = DNA  length = 3858
FEATURE                Location/Qualifiers
source                 1..3858
                       mol_type = other DNA
                       organism = synthetic construct
SEQUENCE: 163
ctactttatt ctgataaaac aggtctatgc agctaccagg acaatggaat ctacgttgac  60
tttagcaacg gaacaacctg ttaagaagaa cactcttaag aaatataaaa tagcttgcat  120
tgttcttctt gctttgctgg tgatcatgtc acttggatta ggcctggggc ttggactcag  180
gaaactggaa aagcaaggca gctgcaggaa gaagtgcttt gatgcatcat ttagaggact  240
ggagaactgc cggtgtgatg tggcatgtaa agaccgaggt gattgctgct gggattttga  300
agacacctgt gtggaatcaa ctcgaatatg gatgtgcaat aaatttcgtt gtggagagac  360
cagattagag gccagccttt gctcttgttc agatgactgt ttgcagaaga aagattgctg  420
tgctgactat aagagtgttt gccaaggaga aacctcatgg ctggaagaaa actgtgacac  480
agcccagcag tctcagtgcc cagaagggtt tgacctgcca ccagttatct tgttttctat  540
ggatggattt agagctgaat atttatacac atgggatact ttaatgccaa atatcaataa  600
```

-continued

```
actgaaaaca tgtggaattc attcaaaata catgagagct atgtatccta ccaaaacctt  660
cccaaatcat tacaccattg tcacgggctt gtatccagag tcacatggca tcattgacaa  720
taatatgtat gatgtaaatc tcaacaagaa tttttcactt tcttcaaagg aacaaaataa  780
tccagcctgg tggcatgggc aaccaatgtg gctgacagca atgtatcaag gtttaaaagc  840
cgctacctac ttttggcccg gatcagaagt ggctataaat ggctcctttc cttccatata  900
catgccttac aacggaagtg tcccatttga agagaggatt tctacactgt taaaatggct  960
ggacctgccc aaagctgaaa gacccaggtt ttataccatg tattttgaag aacctgattc  1020
ctctggacat gcaggtggac cagtcagtgc cagagtaatt aaagccttac aggtagtaga  1080
tcatgctttt gggatgttga tggaaggcct gaagcagcgg aatttgcaca actgtgtcaa  1140
tatcatcctt ctggctgacc atggaatgga ccagacttat tgtaacaaga tggaatacat  1200
gactgattat tttcccagaa taaacttctt ctacatgtac gaagggcctg ccccccgcat  1260
ccgagctcat aatatacctc atgacttttt tagttttaat tctgaggaaa ttgttagaaa  1320
cctcagttgc cgaaaacctg atcagcattt caagccctat ttgactcctg atttgccaaa  1380
gcgactgcac tatgccaaga acgtcagaat cgacaaagtt catctctttg tggatcaaca  1440
gtggctggct gttaggagta aatcaaatac aaattgtgga ggaggcaacc atggttataa  1500
caatgagttt aggagcatgg aggctatctt tctggcacat ggacccagtt ttaaagagaa  1560
gactgaagtt gaaccatttg aaaatattga agtctataac ctaatgtgtg atcttctacg  1620
cattcaacca gcaccaaaca atggaaccca tggtagttta aaccatcttc tgaaggtgcc  1680
tttttatgag ccatcccatg cagaggaggt gtcaaagttt tctgtttgtg gctttgctaa  1740
tccattgccc acagagtctc ttgactgttt ctgccctcac ctacaaaata gtactcagct  1800
ggaacaagtg aatcagatgc taaatctcac ccaagaagaa ataacagcaa cagtgaaagt  1860
aaatttgcca tttgggaggc ctagggtact gcagaagaac gtggaccact gtctccttta  1920
ccacagggaa tatgtcagtg gatttggaaa agctatgagg atgcccatgt ggagttcata  1980
cacagtcccc cagttgggag acacatcgcc tctgcctccc actgtcccag actgtctgcg  2040
ggctgatgtc agggttcctc cttctgagag ccaaaaatgt tccttctatt tagcagacaa  2100
gaatatcacc cacggcttcc tctatcctcc tgccagcaat agaacatcag atagccaata  2160
tgatgcttta attactagca atttggtacc tatgtatgaa gaattcagaa aaatgtggga  2220
ctacttccac agtgttcttc ttataaaaca tgccacagaa agaaatggag taaatgtggt  2280
tagtggacca atatttgatt ataattatga tggccatttt gatgctccag atgaaattac  2340
caaacattta gccaacactg atgttcccat cccaacacac tactttgtgg tgctgaccag  2400
ttgtaaaaac aagagccaca caccggaaaa ctgccctggg tggctggatg tcctaccctt  2460
tatcatccct caccgaccta ccaacgtgga gagctgtcct gaaggtaaac cagaagctct  2520
ttgggttgaa gaaagattta cagctcacat tgcccgggtc cgtgatgtag aacttctcac  2580
tgggcttgac ttctatcagg ataaagtgca gcctgtctct gaaattttgc aactaaagac  2640
atatttacca acatttgaaa ccactattta acttaataat gtctacttaa tatataattt  2700
actgtataaa gtaattttgg caaaatataa gtgatttttt ctggagaatt gtaaaataaa  2760
gttttctatt tttccttaaa aaaaaaaccg gaattccggg cttgggaggc tgaggcagga  2820
gactcgcttg aacccgggag gcagaggttg cagtgagcca agattgcgcc attgcactcc  2880
agagcctggg tgacagagca agactacatc tcaaaaaata aataaataaa ataaaagtaa  2940
caataaaaat aaaaagaaca gcagagagaa tgagcaagga gaaatgtcac aaactattgc  3000
aaaatactgt tacactgggt tggctctcca agaagatact ggaatctctt cagccatttg  3060
cttttcagaa gtagaaacca gcaaaccacc tctaagcgga gaacatacga ttctttatta  3120
agtagctctg gggaaggaaa gaataaaagt tgatagctcc ctgattggga aaaaatgcac  3180
aattaataaa gaatgaagat gaaagaaagc atgcttatgt tgtaacacaa aaaaaattca  3240
caaacgttgg tggaaggaaa acagtataga aaacattact ttaactaaaa gctggaaaaa  3300
ttttcagttg ggatgcgact gacaaaaaga acgggatttc caggcataaa gttggcgtga  3360
gctacagagg gcaccatgtg gctcagtgga agaccccttca agattcaaag ttccatttga  3420
cagagcaaag gcacttcgca aggagaaggg tttaaattat gggtccaaaa gccaagtggt  3480
aaagcgagca atttgcagca taactgcttc tcctagacag ggctgagtgg gcaaaatacg  3540
acagtacaca cagtgactat tagccactgc cagaaacagg ctgaacagcc ctgggagaca  3600
agggaaggca ggtggtggga gttgttcatg gagagaaagg agagttttag aaccagcaca  3660
tccactggag atgctgggcc accagacccc tcccagtcaa taaagtctgg tgcctcattt  3720
gatctcagcc tcatcatgac cctggagaga ccctgatacc atctgccagt ccccgacagc  3780
ttaggcactc cttgccatca acctgacccc ccgagtggtt ctccaggctc cctgccccac  3840
ccattcaggc cggaattc                                                 3858
```

```
SEQ ID NO: 164         moltype = AA  length = 875
FEATURE                Location/Qualifiers
source                 1..875
                       mol_type = protein
                       organism = Homo sapiens
SEQUENCE: 164
MESTLTLATE QPVKKNTLKK YKIACIVLLA LLVIMSLGLG LGLGLRKLEK QGSCRKKCFD  60
ASFRGLENCR CDVACKDRGD CCWDFEDTCV ESTRIWMCNK FRCGETRLEA SLCSCSDDCL  120
QKKDCCADYK SVCQGETSWL EENCDTAQQS QCPEGFDLPP VILFSMDGFR AEYLYTWDTL  180
MPNINKLKTC GIHSKYMRAM YPTKTFPNHY TIVTGLYPES HGIIDNNMYD VNLNKNFSLS  240
SKEQNNPAWW HGQPMWLTAM YQGLKAATYF WPGSEVAING SFPSIYMPYN GSVPFEERIS  300
TLLKWLDLPK AERPRFYTMY FEEPDSSGHA GGPVSARVIK ALQVVDHAFG MLMEGLKQRN  360
LHNCVNIILL ADHGMDQTYC NKMEYMTDYF PRINFFYMYE GPAPRIRAHN IPHDFFSFNS  420
EEIVRNLSCR KPDQHFKPYL TPDLPKRLHY AKNVRIDKVH LFVDQQWLAV RSKSNTNCGG  480
GNHGYNNEFR SMEAIFLAHG PSFKEKTEVE PFENIEVYNL MCDLLRIQPA PNNGTHGSLN  540
HLLKVPFYEP SHAEEVSKFS VCGFANPLPT ESLDCFCPHL QNSTQLEQVN QMLNLTQEEI  600
TATVKVNLPF GRPRVLQKNV DHCLLYHREY VSGFGKAMRM PMWSSYTVPQ LGDTSPLPPT  660
VPDCLRADVR VPPSESQKCS FYLADKNITH GFLYPPASNR TSDSQYDALI TSNLVPMYEE  720
FRKMWDYFHS VLLIKHATER NGVNVVSGPI FDYNYDGHFD APDEITKHLA NTDVPIPTHY  780
FVVLTSCKNK SHTPENCPGW LDVLPFIIPH RPTNVESCPE GKPEALWVEE RFTAHIARVR  840
DVELLTGLDF YQDKVQPVSE ILQLKTYLPT FETTI                               875

SEQ ID NO: 165         moltype = DNA  length = 585
```

-continued

```
FEATURE                Location/Qualifiers
source                 1..585
                       mol_type = other DNA
                       organism = synthetic construct
SEQUENCE: 165
caacgcagag ttgggagcaa ctccagagcc tccttcaaga tgctgctggt cctgctctca  60
gtggtccttc tggctctgag ctcagctcag agcacagata atgatgtgaa ctatgaagac  120
tttactttca ccataccaga tgtagaggac tcaagtcaga gaccagatca gggaccccag  180
agacctcctc ctgaaggact cctacctaga ccccctggtg atagtggtaa ccaagatgat  240
ggtcctcagc agagaccacc aaaaccagga ggccatcacc gccatcctcc cccacctcct  300
tttcaaaatc agcaacgacc accccgacga ggacaccgtc aactctctct accccgattt  360
ccttctgtca gcctgcagga agcatcatca ttcttccaga gggacagacc agcaagacat  420
ccccaggagc aaccactctg gtaatctaga attcagtggc agaaaataaa taagaagata  480
acttccttca gaaagccatg acattgaaat aatgtggtca taactctttc ttcagtatac  540
caataaaata ttaatagcat gcaaaaaaaa aaaaaaaaaa aaaaa                   585

SEQ ID NO: 166         moltype = AA  length = 134
FEATURE                Location/Qualifiers
source                 1..134
                       mol_type = protein
                       organism = Homo sapiens
SEQUENCE: 166
MLLVLLSVVL LALSSAQSTD NDVNYEDFTF TIPDVEDSSQ RPDQGPQRPP PEGLLPRPPG  60
DSGNQDDGPQ QRPPKPGGHH RHPPPPPFQN QQRPPRRGHR QLSLPRFPSV SLQEASSFFQ  120
RDRPARHPQE QPLW                                                    134

SEQ ID NO: 167         moltype = DNA  length = 3850
FEATURE                Location/Qualifiers
source                 1..3850
                       mol_type = other DNA
                       organism = synthetic construct
SEQUENCE: 167
gaccagagag aagcgtgggg aagagtgggc tgagggactc cactagaggc tgtccatctg  60
gattccctgc ctccctagga gcccaacaga gcaaagcaag tgggcacaag gagtatggtt  120
ctaacgtgat tggggtcatg aagacgttgc tgttggactt ggctttgtgg tcactgctct  180
tccagcccgg gtggctgtcc tttagttccc aggtgagtca gaactgccac aatggcagct  240
atgaaatcag cgtcctgatg atgggcaact cagcctttgc agagcccctg aaaaacttgg  300
aagatgcggt gaatgagggg ctggaaatag tgagaggacg tctgcaaaat gctggcctaa  360
atgtgactgt gaacgctact ttcatgtatt cggatggtct gattcataac tcaggcgact  420
gccggagtag cacctgtgaa ggcctcgacc tactcaggaa aatttcaaat gcacaacgga  480
tgggctgtgt cctcataggg ccctcatgta catactccac cttccagatg taccttgaca  540
cagaattgag ctaccccatg atctcagctg gaagttttgg attgtcatgt gactataaag  600
aaaccttaac caggctgatg tctccagcta gaaagttgat gtacttcttg gttaactttt  660
ggaaaaccaa cgatctgccc ttcaaaactt attcctggag cacttcgtat gtttacaaga  720
atggtacaga aactgaggac tgtttctggt accttaatgc tctggaggct agcgtttcct  780
atttctccca cgaactcggc tttaaggtgg tgttaagaca agataaggag tttcaggata  840
tcttaatgga ccacaacagg aaaagcaatg tgattattat gtgtggtggt ccagagttcc  900
tctacaagct gaagggtgac cgagcagtgg ctgaagacat tgtcattatt ctagtggatc  960
ttttcaatga ccagtacttt gaggacaatg tcacagcccc tgactatatg aaaaatgtcc  1020
ttgttctgac gctgtctcct gggaattccc ttctaaatag ctctttctcc aggaatctat  1080
caccaacaaa acgagacttt gctcttgcct atttgaatgg aatcctgctc tttggacata  1140
tgctgaagat atttcttgaa aatggagaaa atattaccac ccccaaattt gctcatgctt  1200
tcaggaatct cacttttgaa gggtatgacg gtccagtgac cttggatgac tggggggatg  1260
ttgacagtac catggtgctt ctgtatacct ctgtggacac caagaaatac aaggttcttt  1320
tgacctatga tacccacgta aataagacct atcctgtgga tatgagcccc acattcactt  1380
ggaagaactc taaacttcct aatgatatta caggccgggg ccctcagatc ctgatgattg  1440
cagtcttcac cctcactgga gctgtggtgc tgctcctgct cgtcgctctc ctgatgctca  1500
gaaaatatag aaaagattat gaacttcgtc agaaaaaatg gtcccacatt cctcctgaaa  1560
atatctttcc tctggagacc aatgagacca atcatgttag cctcaagatc gatgatgaca  1620
aaagacgaga tacaatccag agactacgac agtgcaaata cgacaaaaag cgagtgattc  1680
tcaaagatct caagcacaat gatggtaatt tcactgaaaa acagaagata gaattgaaca  1740
agttgcttca gattgactat tacaacctga ccaagttcta cggcacagtg aaacttgata  1800
ccatgatctt cggggtgata gaatactgtg agagaggatc cctccgggaa gttttaaatg  1860
acacaatttc ctaccctgat ggcacattca tggattggga gtttaagatc tctgtcttgt  1920
atgacattgc taagggaatg tcatatctgc actccagtaa gacagaagtc catggtcgtc  1980
tgaaatctac caactgcgta gtggacagta gaatggtggt gaagatcact gatttggct  2040
gcaattccat ttacctcca aaaaaggacc tgtggacagc tccagagcac ctccgccaag  2100
ccaacatctc tcagaaagga gatgtgtaca gctatgggat catcgcacag gagatcatcc  2160
tgcggaaaga aaccttctac actttgagct gtcgggaccg gaatgagaag attttcagag  2220
tggaaaattc caatggaatg aaacccttcc gcccagattt attcttggaa acagcagagg  2280
aaaaagagct agaagtgtac ctacttgtaa aaaactgttg ggaggaagat ccagaaaaga  2340
gaccagattt caaaaaaatt gagactacac ttgccaagat atttggactt tttcatgacc  2400
aaaaaaatga aagctatatg gataccttga tccgacgtct acagctatat tctcgaaacc  2460
tggaacatct ggtagaggaa aggacacagc tgtacaaggc agagagggac agggctgaca  2520
gacttaactt tatgttgctt ccaaggctag tggtaaagtc tctgaaggag aaaggctttg  2580
tggagccgga actatatgag gaagttacaa tctacttcag tgacattgta ggtttcacta  2640
ctatctgcaa atacagcacc cccatggaag tggtggacat gcttaatgac atctataaga  2700
gttttgacca cattgttgat catcatgatg tctacaaggt ggaaaccatc ggtgatgcgt  2760
acatggtggc tagtggtttg cctaagagaa atggcaatcg gcatgcaata gacattgcca  2820
```

-continued

```
agatggcctt ggaaatcctc agcttcatgg ggacctttga gctggagcat cttcctggcc  2880
tcccaatatg gattcgcatt ggagttcact ctggtccctg tgctgctgga gttgtgggaa  2940
tcaagatgcc tcgttattgt ctatttggag atacggtcaa cacagcctct aggatggaat  3000
ccactggcct ccctttgaga attcacgtga gtggctccac catagccatc ctgaagagaa  3060
ctgagtgcca gttcctttat gaagtgagag gagaaacata cttaaaggga agaggaaatg  3120
agactaccta ctggctgact gggatgaagg accagaaatt caacctgcca acccctccta  3180
ctgtggagaa tcaacagcgt ttgcaagcag aattttcaga catgattgcc aactctttac  3240
agaaaagaca ggcagcaggg ataagaagcc aaaaacccag acgggtagcc agctataaaa  3300
aaggcactct ggaatacttg cagctgaata ccacagacaa ggagagcacc tatttttaaa  3360
cctaaatgag gtataaggac tcacacaaat taaaatacag ctgcactgag gcagcgacct  3420
caagtgtcct gaaagcttac attttcctga gacctcaatg aagcagaaat gtacttaggc  3480
ttggctgccc tgtctggaac atggactttc ttgcatgaat cagatgtgtg ttctcagtga  3540
aataactacc ttccactctg gaaccttatt ccagcagttg ttccagggag cttctacctg  3600
gaaaagaaaa gaaatgaata gactatctag aacttgagaa gattttattc ttatttcatt  3660
tattttttgt ttgtttattt ttatcgtttt tgtttactgg ctttccttct gtattcataa  3720
gatttttttaa attgtcataa ttatatttta aataccatc ttcattaaag tatatttaac  3780
tcataatttt tgcagaaaat atgctatata ttaggcaaga ataaaagcta aaggtttccc  3840
aaaaaaaaaa                                                         3850

SEQ ID NO: 168          moltype = AA  length = 1073
FEATURE                 Location/Qualifiers
source                  1..1073
                        mol_type = protein
                        organism = Homo sapiens
SEQUENCE: 168
MKTLLLDLAL WSLLFQPGWL SFSSQVSQNC HNGSYEISVL MMGNSAFAEP LKNLEDAVNE  60
GLEIVRGRLQ NAGLNVTVNA TFMYSDGLIH NSGDCRSSTC EGLDLLRKIS NAQRMGCVLI  120
GPSCTYSTFQ MYLDTELSYP MISAGSFGLS CDYKETLTRL MSPARKLMYF LVNFWKTNDL  180
PFKTYSWSTS YVYKNGTETE DCFWYLNALE ASVSYFSHEL GFKVVLRQDK EFQDILMDHN  240
RKSNVIIMCG GPEFLYKLKG DRAVAEDIVI ILVDLFNDQY FEDNVTAPDY MKNVLVLTLS  300
PGNSLLNSSF SRNLSPTKRD FALAYLNGIL LFGHMLKIFL ENGENITTPK FAHAFRNLTF  360
EGYDGPVTLD DWGDVDSTMV LLYTSVDTKK YKVLLTYDTH VNKTYPVDMS PTFTWKNSKL  420
PNDITGRGPQ ILMIAVFTLT GAVVLLLLVA LLMLRKYRKD YELRQKKWSH IPPENIFPLE  480
TNETNHVSLK IDDDKRRDTI QRLRQCKYDK KRVILKDLKH NDGNFTEKQK IELNKLLQID  540
YYNLTKFYGT VKLDTMIFGV IEYCERGSLR EVLNDTISYP DGTFMDWEFK ISVLYDIAKG  600
MSYLHSSKTE VHGRLKSTNC VVDSRMVVKI TDFGCNSILP PKKDLWTAPE HLRQANISQK  660
GDVYSYGIIA QEIILRKETF YTLSCRDRNE KIFRVENSNG MKPFRPDLFL ETAEEKELEV  720
YLLVKNCWEE DPEKRPDFKK IETTLAKIFG LFHDQKNESY MDTLIRRLQL YSRNLEHLVE  780
ERTQLYKAER DRADRLNFML LPRLVVKSLK EKGFVEPELY EEVTIYFSDI VGFTTICKYS  840
TPMEVVDMLN DIYKSFDHIV DHHDVYKVET IGDAYMVASG LPKRNGNRHA IDIAKMALEI  900
LSFMGTFELE HLPGLPIWIR IGVHSGPCAA GVVGIKMPRY CLFGDTVNTA SRMESTGLPL  960
RIHVSGSTIA ILKRTECQFL YEVRGETYLK GRGNETTYWL TGMKDQKFNL PTPPTVENQQ  1020
RLQAEFSDMI ANSLQKRQAA GIRSQKPRRV ASYKKGTLEY LQLNTTDKES TYF         1073

SEQ ID NO: 169          moltype = DNA  length = 2744
FEATURE                 Location/Qualifiers
source                  1..2744
                        mol_type = other DNA
                        organism = synthetic construct
SEQUENCE: 169
ctcgtgccga attcggcacg agaccgcgtg ttcgcgcctg gtagagattt ctcgaagaca  60
ccagtgggcc cgtgtggaac caaacctgcg cgcgtggccg ggccgtggga caacgaggcc  120
gcggagacga aggcgcaatg gcgaggaagt tatctgtaat cttgatcctg acctttgccc  180
tctctgtcac aaatcccctt catgaactaa aagcagctgc tttcccccag accactgaga  240
aaattagtcc gaattgggaa tctggcatta atgttgactt ggcaatttcc acacggcaat  300
atcatctaca acagcttttc taccgctatg gagaaaataa ttctttgtca gttgaagggt  360
tcagaaaatt acttcaaaat ataggcatag ataagattaa aagaatccat atacaccatg  420
accacgacca tcactcagac cacgagcatc actcagacca tgagcgtcac tcagaccatg  480
agcatcactc agaccacgag catcactctg accataatca tgctgcttct ggtaaaaata  540
agcgaaaagc tctttgccca gaccatgact cagatagttc aggtaaagat cctagaaaca  600
gccaggggaa aggagctcac cgaccagaac atgccagtgg tagaaggaat gtcaaggaca  660
gtgttagtgc tagtgaagtg acctcaactg tgtacaacac tgtctctgaa ggaactcact  720
ttctagagac aatagagact ccaagacctg gaaaactctt ccccaaagat gtaagcagct  780
ccactccacc cagtgtcaca tcaaagagcc gggtgagccg gctggctggt aggaaaacaa  840
atgaatctgt gagtgagccc cgaaaaggct ttatgtattc cagaaacaca aatgaaaatc  900
ctcaggagtg tttcaatgca tcaaagctac tgacatctca tggcatgggc atccaggttc  960
cgctgaatgc aacagagttc aactatctct gtccagccat catcaaccaa attgatgcta  1020
gatcttgtct gattcataca agtgaaaaga aggctgaaat ccctccaaag acctattcat  1080
tacaaatagc ctgggttggt ggttttatag ccatttccat catcagtttc ctgtctctgc  1140
tgggggttat cttagtgcct ctcatgaatc gggtgttttt caaatttctc ctgagtttcc  1200
ttgtggcact ggccgttggg actttgagtg gtgatgcttt tttacacctt cttccacatt  1260
ctcatgcaag tcaccaccat agtcatagcc atgaagaacc agcaatggaa atgaaaagag  1320
gaccactttt cagtcatctg tcttctcaaa acatagaaga aagtgcctat tttgattcca  1380
cgtggaaggg tctaacagct ctaggaggcc tgtatttcat gtttcttgtt gaacatgtcc  1440
tcacattgat caaacaattt aaagataaga agaaaaagaa tcagaagaaa cctgaaaatg  1500
atgatgatgt ggagattaag aagcagttgt ccaagtatga atctcaactt tcaacaaatg  1560
aggagaaagt agatacagat gatcgaactg aaggctattt acgagcagac tcacaagagc  1620
cctcccactt tgattctcag cagcctgcag tcttggaaga agaagaggtc atgatagctc  1680
atgctcatcc acaggaagtc tacaatgaat atgtacccag agggtgcaag aataaatgcc  1740
```

-continued

```
attcacattt ccacgataca ctcggccagt cagacgatct cattcaccac catcatgact  1800
accatcatat tctccatcat caccaccacc aaaaccacca tcctcacagt cacagccagc  1860
gctactctcg ggaggagctg aaagatgccg gcgtcgccac tttggcctgg atggtgataa  1920
tgggtgatgg cctgcacaat ttcagcgatg gcctagcaat tggtgctgct tttactgaag  1980
gcttatcaag tggtttaagt acttctgttg ctgtgttctg tcatgagttg cctcatgaat  2040
taggtgactt tgctgttcta ctaaaggctg gcatgaccgt taagcaggct gtcctttata  2100
atgcattgtc agccatgctg gcgtatcttg gaatggcaac aggaattttc attggtcatt  2160
atgctgaaaa tgtttctatg tggatatttg cacttactgc tggcttattc atgtatgttg  2220
ctctggttga tatggtacct gaaatgctgc acaatgatgc tagtgaccat ggatgtagcc  2280
gctgggggta tttcttttta cagaatgctg ggatgctttt gggttttgga attatgttac  2340
ttatttccat atttgaacat aaaatcgtgt ttcgtataaa tttctagtta aggtttaaat  2400
gctagagtag cttaaaaagt tgtcatagtt tcagtaggtc atagggagat gagtttgtat  2460
gctgtactat gcagcgttta aagttagtgg gttttgtgat ttttgtattg aatattgctg  2520
tctgttacaa agtcagttaa aggtacgttt taatatttaa gttattctat cttggagata  2580
aaatctgtat gtgcaattca ccggtattac cagtttatta tgtaaacaag agatttggca  2640
tgacatgttc tgtatgtttc agggaaaaat gtctttaatg ctttttcaag aactaacaca  2700
gttattccta tactggattt taggtctctg aagaactgct ggtg                    2744

SEQ ID NO: 170         moltype = AA  length = 749
FEATURE                Location/Qualifiers
source                 1..749
                       mol_type = protein
                       organism = Homo sapiens
SEQUENCE: 170
MARKLSVILI LTFALSVTNP LHELKAAAFP QTTEKISPNW ESGINVDLAI STRQYHLQQL  60
FYRYGENNSL SVEGFRKLLQ NIGIDKIKRI HIHHDHDHHS DHEHHSDHER HSDHEHHSDH  120
EHHSDHNHAA SGKNKRKALC PDHDSDSSGK DPRNSQGKGA HRPEHASGRR NVKDSVSASE  180
VTSTVYNTVS EGTHFLETIE TPRPGKLFPK DVSSSTPPSV TSKSRVSRLA GRKTNESVSE  240
PRKGFMYSRN TNENPQECFN ASKLLTSHGM GIQVPLNATE FNYLCPAIIN QIDARSCLIH  300
TSEKKAEIPP KTYSLQIAWV GGFIAISIIS FLSLLGVILV PLMNRVFFKF LLSFLVALAV  360
GTLSGDAFLH LLPHSHASHH HSHSHEEPAM EMKRGPLFSH LSSQNIEESA YFDSTWKGLT  420
ALGGLYFMFL VEHVLTLIKQ FKDKKKKNQK KPENDDDVEI KKQLSKYESQ LSTNEEKVDT  480
DDRTEGYLRA DSQEPSHFDS QQPAVLEEEE VMIAHAHPQE VYNEYVPRGC KNKCHSHFHD  540
TLGQSDDLIH HHHDYHHILH HHHHQNHHPH SHSQRYSREE LKDAGVATLA WMVIMGDGLH  600
NFSDGLAIGA AFTEGLSSGL STSVAVFCHE LPHELGDFAV LLKAGMTVKQ AVLYNALSAM  660
LAYLGMATGI FIGHYAENVS MWIFALTAGL FMYVALVDMV PEMLHNDASD HGCSRWGYFF  720
LQNAGMLLGF GIMLLISIFE HKIVFRINF                                    749

SEQ ID NO: 171         moltype = DNA  length = 5551
FEATURE                Location/Qualifiers
misc_feature           1769
                       note = n is a, c, g, or t
source                 1..5551
                       mol_type = other DNA
                       organism = synthetic construct
SEQUENCE: 171
ttttcatgga aatatcttca aatttcatta gtggtcctat tatagaagac acacagcagg  60
caagtgtcag agctagaaat gaccctaaat ttctgggtcc ctattcagca gccataagca  120
attgccagct gcaggaaggt ggaggcagaa gaagtaaaaa gggaacaaga ggtgaggttt  180
acgttctgcc taagtggaac agagtagaac tttgcacaaa ctccttaatc ttgcctagag  240
gcagaatgtg ggatgtacta tatgggaggc aggcaaatct gggcctggtt cccacctcca  300
tcactcattt gaacaagtta tgtaatttat ttttgcgtca atttcttgt ctgtaaaact  360
ggagtgagag gacctaactt gagtaccgaa gtgaagagtc aatgagataa tatctgtgat  420
cagcacagtg cttggcaagt ggaagacact cagtcaagct aacttaaagc cccagttttt  480
tcatttgtac aacagaacaa caacaataat agcaacaagc aataatacta acaatattta  540
tcttgcctct gagttgtctt gaaaatcaga tgagtatata tattatgttt ctaaattcta  600
aagtgtatct cactctccta acaaagcagt tggtcttcag atcaggacca gagttaatac  660
catgccagag cattattaca ggttttttcc aatgagtaat taattttatt tttaaactta  720
tcatacagta aaattgactc ttttggttta caaagttcta tgagttatag cacgttgtat  780
aggtttatgt aaccaccacc acaatccgga tacagaacat gactacagct ttagagattc  840
tttttcaaag tgttttacat tcatgttgca aaacactttt aaaaataaga aaagagatgt  900
agataaacgt gctgaagatg caaattaatg aaaccagctt ttgtgcacaa atctctgcag  960
tttccagtgt tttcagcttt tgtctgagcc atttttgctg tcggctttgc agactatctc  1020
tttctataaa agtaatcagg cgtccgttgg agagttgggt ctttcttcac attaaaggca  1080
catgtcccag gcacaagcct caggatcctt atttgatctt ttttaatacg accaggtctt  1140
aaatttccga accatgtttt ccctaattgc cattttctct ctaaaatgaa gaagcctgga  1200
agaaccttct tatcccttcg gggaaattat ttaattggga caaaggggat gtggagttac  1260
agagagcaac gatagggctt tcaggaaccc aaaacctgtc tggtataata acagatcctt  1320
ccggtaacca accattcaat ttgtccctct cccccaaccc catcctctcc atcaccatct  1380
gccagatggc cccctgggac caatcgactt tgaaaccaaa cttctctccc aggtcagctc  1440
ctgcaatccc cactcctcgt cccttggagc tttctccaca gaagtgactt gacacaccgc  1500
gctacatctg ggagggggg cggtccgct ttccgggaga ctcaagtctt tgctatttgc  1560
cttttgtttc tgggatgcct ttggctgcct ttctcttcca tctgctttta attttggtaa  1620
gagaaaagct aatgaatcag gaatgaatct cctctccact aatctttwtg ttttctttct  1680
ctctctctct ctcttagagt tggcgcgctc tcttcacgag ttccatcact acccaagaag  1740
tgagggggcg ggggggacag gcgggaagnc attaattaca cctaaatctg aagtttgcgg  1800
cctcaagtac cactttgatg gggagagctt ctgaagcttc catacaacct gccgtgcctt  1860
tgctgctgcc gcagtagatt ttcagctcat ttctttctgc tgctgcttcg cgctgctctg  1920
tcatgcctaa atctatctcg tcactgccaa aggtgcctga atcagggtga attccacgag  1980
```

-continued

```
attcaccagc ggttttgctc cagtccaagg taaatacagt atgcaaaatg aggaaccacc  2040
caaggatgtc ggggaggggg gagagaaagg gattccctca ccttttccgg cacattcctc  2100
gttaatttcc accaggagga ggcgcgcagc ccagctcccc tagtctctct tcttaaatcc  2160
ccctacctac ggctgccgag gttggccgcg cgtcgggagt ctccccgaca gtcctggccc  2220
tcccccgccc cccgggttgg tttttcccag ctgcggaggt tgggaggttg ggccaggggc  2280
tggggtgcga agagagtcgg cgcccgcaac gcggagccgg gaagtcgtcg ctactctggt  2340
ggaactcaga gttggttctg gaggcggcgg acgcggaggt gagcagtggg agcccgcggc  2400
ctgggagaga cccgggaggc gtcgttgggg cccctcccca tcctcgggtg gagagtaggg  2460
ttggttcggg ttgccactgt accccgagtc ccactgctgc tttgttccca gactctcccc  2520
tcctctttgg agatgacttg aacccctttg agatccgagg ggctggcggg gcgcgggctg  2580
gggggcgaca gttgtagctc cacttcctgc taatgcgaga aggtacaaaa agagatcaaa  2640
aagtcctgta acctgaaact tccctcgcat cctaaccggg accgggtgga gaggtctggg  2700
cgggggcgga gacacccgga ggccgacctt ccgccgaggc ggtgcaggaa ggaacgggag  2760
agggagaagt ttggtaggga aggaattggg gattaagcgg taagttagac gcgggagacg  2820
atctcctcgg gaaaggcgga gggcgggagg ccggtcgggt ttatttagtg tgggccaggg  2880
aagaaggaag actttgcggt ctgggtgtcg gatgcgcgtc cccctccgga gtaaaagtga  2940
ccggaggggt tggggaggcg aggccggggc gggcttttgg aaggaggtct ctgggacaga  3000
ctggagacga ctagactcga aaaggccggt ttttgcactc cggaagccgc ggcagccacc  3060
gctgttcacg cctctctcct gcttgtccca ggtccctcag aggatccagc gaggggtgcc  3120
aacaagaggc gaagaggtgg caccagggcg gcggcaggaa gaggagcggg agcaggagcg  3180
cggagcggag cgtcccgacc cgccgtgcgt actttctgga gggaagggggc gggggaatcg  3240
gcccctgagg gaagcgcccg gtggcgaggg ggttagccaa gttccggctg cggcgccact  3300
ccctcggttc cacgagagga aagttttttt tttccagacg cttccgccgg ctcgcgccct  3360
ccgggcccag cctcccgagc cttcggagcg ggcgccgtcc cagcccagct ccggggaaac  3420
gcgagccgcg atgcctgggg ggtgctcccg gggccccgcc gccggggacg ggcgtctgcg  3480
gctggcgcga ctagcgctgg tactcctggg ctgggtctcc tcgtcttctc ccacctcctc  3540
ggcatcctcc ttctcctcct cggcgccgtt cctggcttcc gccgtgtccg cccagccccc  3600
gctgccggac cagtgccccg cgctgtgcga gtgctccgag gcagcgcgca cagtcaagtg  3660
cgttaaccgc aatctgaccg aggtgcccac ggacctgccc gcctacgtgc gcaacctctt  3720
ccttaccggc aaccagctgg ccgtgctccc tgccggcgcc ttcgcccgcc ggccgccgct  3780
ggcggagctg gccgcgctca acctcagcgg cagccgcctg gacgaggtgc gcgcgggcgc  3840
cttcgagcat ctgcccagcc tgcgccagct cgacctcagc cacaacccac tggccgacct  3900
cagtcccttc gctttctcgg gcagcaatgc cagcgtctcg gcccccagtc cccttgtgga  3960
actgatcctg aaccacatcg tgccccctga agatgagcgg cagaaccgga gcttcgaggg  4020
catggtggtg gcggccctgc tggcgggccg tgcactgcag gggctccgcc gcttggagct  4080
ggccagcaac cacttccttt acctgccgcg ggatgtgctg gcccaactgc ccagcctcag  4140
gcacctggac ttaagtaata attcgctggt gagcctgacc tacgtgtcct tccgcaacct  4200
gacacatcta gaaagcctcc acctggagga caatgccctc aaggtccttc acaatggcac  4260
cctggctgag ttgcaaggtc taccccacat tagggttttc ctggacaaca atccctgggt  4320
ctgcgactgc cacatggcag acatggtgac ctggctcaag gaaacagagg tagtgcaggg  4380
caaagaccgg ctcacctgtg catatccgga aaaaatgagg aatcgggtcc tcttggaact  4440
caacagtgct gacctggact gtgacccgat tcttccccca tccctgcaaa cctcttatgt  4500
cttcctgggt attgttttag ccctgatagg cgctattttc ctcctggttt tgtatttgaa  4560
ccgcaagggg ataaaaaagt ggatgcataa catcagagat gcctgcaggg atcacatgga  4620
agggtatcat tacagatatg aaatcaatgc ggaccccaga ttaacaaacc tcagttctaa  4680
ctcggatgtc tgagaaatat tagaggacag accaaggaca actctgcatg agatgtagac  4740
ttaagcttta tccctactag gcttgctcca ctttcatcct ccactataga tacaacggac  4800
tttgactaaa agcagtgaag ggatttgct tccttgttat gtaaagtttc tcggtgtgtt  4860
ctgttaatgt aagacgatga acagttgtgt atagtgtttt accctcttct ttttcttgga  4920
actcctcaac acgtatggag ggatttttca ggtttcagca tgaacatggg cttcttgctg  4980
tctgtctctc tctcagtaca gttcaaggtg tagcaagtgt acccacacag atagcattca  5040
acaaaagctg cctcaacttt ttcgagaaaa atactttatt cataaatatc agttttattc  5100
tcatgtacct aagttgtgga gaaaataatt gcatcctata aactgcctgc agacgttagc  5160
aggctcttca aaataactcc atggtgcaca ggagcacctg catccaagag catgcttaca  5220
ttttactgtt ctgcatatta caaaaaaataa cttgcaactt cataacttct ttgacaaagt  5280
aaattacttt tttgattgca gtttatatga aaatgtactg attttttttt aataaactgc  5340
atcgagatcc aaccgactga attgttaaaa aaaaaaaaaa ataaacattg ttaaaacaat  5400
tacagtgtgt gcaagtttgc tttgaaaaaa ggatgaaggg caggagtatt caatggtctt  5460
ggttccgatg ataattatta cttaacatag ctgagaatca aactgtagca atgtctaata  5520
taaatagact tgggagatcg tttcgaaatg g                                 5551

SEQ ID NO: 172          moltype = AA  length = 420
FEATURE                 Location/Qualifiers
source                  1..420
                        mol_type = protein
                        organism = Homo sapiens
SEQUENCE: 172
MPGGCSRGPA AGDGRLRLAR LALVLLGWVS SSSPTSSASS FSSSAPFLAS AVSAQPPLPD  60
QCPALCECSE AARTVKCVNR NLTEVPTDLP AYVRNLFLTG NQLAVLPAGA FARRPPLAEL  120
AALNLSGSRL DEVRAGAFEH LPSLRQLDLS HNPLADLSPF AFSGSNASVS APSPLVELIL  180
NHIVPPEDER QNRSFEGMVV AALLAGRALQ GLRRLELASN HFLYLPRDVL AQLPSLRHLD  240
LSNNSLVSLT YVSFRNLTHL ESLHLEDNAL KVLHNGTLAE LQGLPHIRVF LDNNPWVCDC  300
HMADMVTWLK ETEVVQGKDR LTCAYPEKMR NRVLLELNSA DLDCDPILPP SLQTSYVFLG  360
IVLALIGAIF LLVLYLNRKG IKKWMHNIRD ACRDHMEGYH YRYEINADPR LTNLSSNSDV  420

SEQ ID NO: 173          moltype = DNA  length = 5977
FEATURE                 Location/Qualifiers
source                  1..5977
                        mol_type = other DNA
```

```
                         organism = synthetic construct
SEQUENCE: 173
tgtctctctt acctccttga tgttcggcac tatttgtggc cggcgtggtg gaaggacaca  60
gtgaggttct cacccccgcc ccccgctcct cgctcccatc ccagttccat caaaacgaac  120
ccgggccagc gcaaggatct ccgagttgcg agtgtgctga ggctgggact gtcactcatt  180
ctccgatcag cgcgtgaacg cagctcggct gccgctggca ggaaacaatt ctgcaaaaat  240
aatcatactc agcctggcaa ttgtctgccc ctaggtctgt cgctcagccg ccgtccacac  300
tcgctgcagg ggggggggca cagaatttac cgcggcaaga acatccctcc cagccagcag  360
attacaatgc tgcaaactaa ggatctcatc tggactttgt ttttcctggg aactgcagtt  420
tctctgcagg tggatattgt tcccagccag ggggagatca gcgttggaga gtccaaattc  480
ttcttatgcc aagtggcagg agatgccaaa gataaagaca tctcctggtt ctcccccaat  540
ggagaaaagc tcaccccaaa ccagcagcgg atctcagtgg tgtggaatga tgattcctcc  600
tccaccctca ccatctataa cgccaacatc gacgacgccg gcatttacaa gtgtgtggtt  660
acaggcgagg atggcagtga gtcagaggcc accgtcaacg tgaagatctt tcagaagctc  720
atgttcaaga atgcgccaac cccacaggag ttccgggagg gggaagatgc cgtgattgtg  780
tgtgatgtgg tcagctccct cccaccaacc atcatctgga aacacaaagg ccgagatgtc  840
atcctgaaaa aagatgtccg attcatagtc ctgtccaaca actacctgca gatccggggc  900
atcaagaaaa cagatgaggg cacttatcgc tgtgagggca gaatcctggc acggggggag  960
atcaacttca aggacattca ggtcattgtg aatgtgccac ctaccatcca ggccaggcag  1020
aatattgtga atgccaccgc caacctcggc cagtccgtca ccctggtgtg cgatgccgaa  1080
ggcttcccag agcccaccat gagctggaca aaggatgggg aacagataga gcaagaggaa  1140
gacgatgaga agtacatctt cagcgacgat agttcccagc tgaccatcaa aaaggtggat  1200
aagaacgacg aggctgagta catctgcatt gctgagaaca aggctggcga gcaggatgcg  1260
accatccacc tcaaagtctt tgcaaaaccc aaaatcacat atgtagagaa ccagactgcc  1320
atggaattag aggagcaggt cactcttacc tgtgaagcct ccggagaccc cattccctcc  1380
atcacctgga ggacttctac ccggaacatc agcagcgaag aaaagactct ggatgggcac  1440
atggtggtgc gtagccatgc ccgtgtgtcg tcgctgaccc tgaagagcat ccagtacact  1500
gatgccggag agtacatctg caccgccagc aacaccatcg gccaggactc ccagtccatg  1560
taccttgaag tgcaatatgc cccaaagcta cagggccctg tggctgtgta cacttgggag  1620
gggaaccagg tgaacatcac ctgcgaggta tttgcctatc ccagtgccac gatctcatgg  1680
tttcgggatg gccagctgct gccaagctcc aattacagca atatcaagat ctacaacacc  1740
ccctctgcca gctatctgga ggtgacccca gactctgaga atgattttgg gaactacaac  1800
tgtactgcag tgaaccgcat tgggcaggag tccttggaat tcatccttgt tcaagcagac  1860
accccctctt caccatccat cgaccaggtg gagccatact ccagcacagc ccaggtgcag  1920
tttgatgaac cagaggccac aggtggggtg cccatcctca aatacaaagc tgagtggaga  1980
gcagttggtg aagaagtatg gcattccaag tggtatgatg ccaaggaagc cagcatggag  2040
ggcatcgtca ccatcgtggg cctgaagccc gaaacaacgt acgccgtaag gctggcggcg  2100
ctcaatggca aagggctggg tgagatcagc gcggcctccg agttcaagac gcagccagtc  2160
caaggggaac ccagtgcacc taagctcgaa gggcagatgg gagaggatgg aaactctatt  2220
aaagtgaacc tgatcaagca ggatgacggc ggctccccca tcagacacta tctggtcagg  2280
taccgagcgc tctcctccga gtggaaacca gagatcaggc tcccgtctgg cagtgaccac  2340
gtcatgctga agtccctgga ctggaatgct gagtatgagg tctacgtggt ggctgagaac  2400
cagcaaggaa aatccaaggc ggctcatttt gtgttcagga cctcggccca gcccacagcc  2460
atcccagcca acggcagccc cacctcaggc ctgagcaccg gggccatcgt gggcatcctc  2520
atcgtcatct tcgtcctgct cctggtggtt gtggacatca cctgctactt cctgaacaag  2580
tgtggcctgt tcatgtgcat tgcggtcaac ctgtgtggaa aagccgggcc cggggccaag  2640
ggcaaggaca tggaggaggg caaggccgcc ttctcgaaag atgagtccaa ggagcccatc  2700
gtggaggttc gaacggagga ggagaggacc cccaaaccatg atggagggaa acacacagag  2760
cccaacgaga ccacgccact gacggagccc gagaagggcc ccgtagaagc aaagccagag  2820
tgccaggaga cagaaacgaa gccagcgcca gccgaagtca agacggtccc caatgacgcc  2880
acacagacaa aggagaacga gagcaaagca tgatgggtga agagaaccga gcaaagatca  2940
aaataaaaag tgacacagca gcttcaccag agcatttcca acaccacaga cacacacacg  3000
cacgcacaca cacaaacaca catgcacaca cacacatctc atttctctag tgtcttttgc  3060
ctttaaaaaa aactaaacag ataaaacatg ggaatctcct ttttgtaggt ttatagaaag  3120
ggtccctttg ttgcacactc acttgtaaga aaatgagaca aaaaggttaa acccacagcc  3180
aaactaggac actccgttcc ctgaaaccgt taaaaaatca aacaaaagga ccccaaatta  3240
agaatctagg aagctcagaa acgaaatcta ggttcaggaa gaccacactt ggtgttaccc  3300
gattggcaca gaccagtttc agagaaatac tttcaggcac taagactaat cgaatgaaca  3360
aagtccacag tttattttta tactttcagt caagtttgaa ctctgtaaaa cctcataaat  3420
aagttataat ttctgttcac tttgtatttg ttcagtatgc aaagtgtgtc accctttcta  3480
gctgaattca attcccacgt agactcttat tttataggac gaatgccaaa ttgcagcttc  3540
tgggggtaga tctcaatttg cagtattcag acttcttttt ctttctttta cattcttttt  3600
tctttctttc tttctgccaa ctttgttttc cagtgtttac aaggtgacaa atgtttgact  3660
ttggttgtgt ttaaatgtcc gtgtaaaata gctgcctttt attttttaag gtaacaaata  3720
ccacctagag gtaggtagga tcatcccacg cttgctttag cacaggacaa ctttacaaaa  3780
catgattgtt tacagctgct cttcccctct tttctgatct gcagtttttg cctgggtccc  3840
actcaggtga aaatccatct cattctggaa tggttttgct tttgaatttt tggttatttt  3900
tgtgtttctt tgggggttag accactttct gattagccgc cacctgcctg catctgtgaa  3960
aagggatctg ctcccaggcg ttctcaccct tcttttgaag gactccttag gctttgttga  4020
atgaagcaga gaagattgta tagttggggc tggtcttggt gaacacacat tattacccca  4080
cacatcccct ttgtgtagaa agccaaataa aatctataca taccatttcc ttttgagccc  4140
agaatctaga tttgagcgga agagcatgtg tgcttcaggg aattagtgtc ttttttttgga  4200
aatctgttga agtaaagtaa catcggcctt ctgttcactt aggcagcatt tatagaaaca  4260
aaagaagaaa gaaacaacct actgtctgga gtcataacac aactttcctg gattggaaac  4320
caagtggggg aaaaaataca gaaactttaa gggggatggg aggggggga gaagggaaaa  4380
gccagccctt tgtatagaaa ttttgctttt ttttccctca ttctacttta gaactgcaag  4440
cttgtgcact gtggatgcgt gaatatttta gtgtgaaacg tgtttttgtc atagtattga  4500
aataaaactt caacatagtt tggttgtgga aggtatagca gatagttcag aaaaaatatt  4560
caggaaacaa aaatcactca aacggaatcg aagcctttta acaaagaaaa tgaaatacag  4620
```

-continued

```
atgatgatga tgatgatgaa gatgatgcta agtaaacaga aatcagtact ccgcatgcgc  4680
tcctctccta aggtacaaag cagcaagagg ttagggtggc aaggctgcct ctgggtccat  4740
tctgtgggcc actctcccca acgttctgac acttctgcag tctgatcagt ggcgatgcta  4800
gattataatt tcaaactgtg aagaataatg gtcttgtcat ttgctcaatg tggggttatg  4860
ttgcattttc tcagctcctg gggatggaaa tggaggatcc cagaacacac agccctggcc  4920
cctttgattc tagggcctgc acagatctct ggttcaaatg cacaggccct cagaatagag  4980
gaacatgaag agagatctta gagcacacag tagaatgtga gagcctgggt gtctgagacc  5040
gggagggccc agcagtgagg ggcaggctct tctggtcacc aggctgttca gtggactcag  5100
ttcttcatct tgtaatgtcg atggctttgc cacaccaggc caagcccatg ccataccttg  5160
tcaagactgt caaagtggtt gtggttaggt caaactggtt ttggttctga tggttaggaa  5220
gaaacaggtc agccctcaga tcacctggcc cgggacagct gaccccctag aaccctggct  5280
ctgccattag ctaggaccta agactctgcc cacattttgg tctgttctct cccattacac  5340
ataggtttgt ctcagcatgc aagagttttt cctttaaaaa aaaaaaaaaa aaaaaaaaaa  5400
aagcaatgct ttctctaaaa tcaaagaggg agtcatttta ttccaagatg ttttatcttt  5460
tatgttaaga gatcaaagct tataattttc ttttttaatt tttgaaggag ggatcaactc  5520
cagtttccaa tgtctatgtg tctatgtgtg tatgtgccat acatatgtat tcacatgaag  5580
accggcatgg ccaagttctg ctggaggagc actcaagtgt gacgagcagg gccactggac  5640
cctgcagggc tgtggtgtat atagtgcagc tttggaggtg gaactctatt ttcacacttt  5700
tctatggagc cttccgagtc ccaggttttc acttgaggct gtctgtctgg atggcggttt  5760
tcagacctcc attaacatcc ctacccagca ttctgtactt cgggggcctt ctctcttgtt  5820
ataaaacttt ttaccaagtg aaacatcgat accacctttg tttccattct cactggtgta  5880
aatactgagt actaactgag aattttgact ttgcattctg tcggaatact tgtgttcaat  5940
aaaaattgaa agaaaaaagc taaaaaaaaa aaaaaaa                           5977

SEQ ID NO: 174          moltype = AA  length = 848
FEATURE                 Location/Qualifiers
source                  1..848
                        mol_type = protein
                        organism = Homo sapiens
SEQUENCE: 174
MLQTKDLIWT LFFLGTAVSL QVDIVPSQGE ISVGESKFFL CQVAGDAKDK DISWFSPNGE  60
KLTPNQQRIS VVWNDDSSST LTIYNANIDD AGIYKCVVTG EDGSESEATV NVKIFQKLMF  120
KNAPTPQEFR EGEDAVIVCD VVSSLPPTII WKHKGRDVIL KKDVRFIVLS NNYLQIRGIK  180
KTDEGTYRCE GRILARGEIN FKDIQVIVNV PPTIQARQNI VNATANLGQS VTLVCDAEGF  240
PEPTMSWTKD GEQIEQEEDD EKYIFSDDSS QLTIKKVDKN DEAEYICIAE NKAGEQDATI  300
HLKVFAKPKI TYVENQTAME LEEQVTLTCE ASGDPIPSIT WRTSTRNISS EEKTLDGHMV  360
VRSHARVSSL TLKSIQYTDA GEYICTASNT IGQDSQSMYL EVQYAPKLQG PVAVYTWEGN  420
QVNITCEVFA YPSATISWFR DGQLLPSSNY SNIKIYNTPS ASYLEVTPDS ENDFGNYNCT  480
AVNRIGQESL EFILVQADTP SSPSIDQVEP YSSTAQVQFD EPEATGGVPI LKYKAEWRAV  540
GEEVWHSKWY DAKEASMEGI VTIVGLKPET TYAVRLAALN GKGLGEISAA SEFKTQPVQG  600
EPSAPKLEGQ MGEDGNSIKV NLIKQDDGGS PIRHYLVRYR ALSSEWKPEI RLPSGSDHVM  660
LKSLDWNAEY EVYVVAENQQ GKSKAAHFVF RTSAQPTAIP ANGSPTSGLS TGAIVGILIV  720
IFVLLLVVVD ITCYFLNKCG LFMCIAVNLC GKAGPGAKGK DMEEGKAAFS KDESKEPIVE  780
VRTEEERTPN HDGGKHTEPN ETTPLTEPEK GPVEAKPECQ ETETKPAPAE VKTVPNDATQ  840
TKENESKA                                                           848

SEQ ID NO: 175          moltype = DNA  length = 1108
FEATURE                 Location/Qualifiers
source                  1..1108
                        mol_type = other DNA
                        organism = synthetic construct
SEQUENCE: 175
ctggaggcct ggctggtgct cacatacaat aattaactgc tgagtggcct tcgcccaatc  60
ccaggctcca ctcctgggct ccattcccac tccctgcctg tctcctaggc cactaaacca  120
cagctgtccc ctggaataag gcaaggggga gtgtagagca gagcagaagc ctgagccaga  180
cggagagcca cctcctctcc cagggacaga catggctcag cggatgacaa cacagctgct  240
gctccttcta gtgtgggtgg ctgtagtagg ggaggctcag acaaggattg catgggccag  300
gactgagctt ctcaatgtct gcatgaacgc caagcaccac aaggaaaagc caggccccga  360
ggacaagttg catgagcagt gtcgaccctg gaggaagaat gcctgctgtt ctaccaacac  420
cagccaggaa gcccataagg atgtttccta cctatataga ttcaactgga accactgtgg  480
agagatggca cctgcctgca aacggcattt catccaggac acctgcctct acgagtgctc  540
ccccaacttg gggccctgga tccagcaggt ggatcagagc tggcgcaaag agcgggtact  600
gaacgtgccc ctgtgcaaag aggactgtga gcaatggtgg gaagattgtc gcacctccta  660
cacctgcaag agcaactggc acaagggctg gaactggact tcagggttta acaagtgcgc  720
agtgggagct gcctgccaac ctttccattt ctacttcccc acacccactg ttctgtgcaa  780
tgaaatctgg actcactcct acaaggtcag caactacagc cgagggagtg gccgctgcat  840
ccagatgtgg ttcgacccag cccagggcaa ccccaatgag gaggtggcga ggttctatgc  900
tgcagccatg agtggggctg ggccctgggc agcctggcct ttcctgctta gcctggccct  960
aatgctgctg tggctgctca gctgacctcc ttttaccttc tgatacctgg aaatccctgc  1020
cctgttcagc cccacagctc ccaactattt ggttcctgct ccatggtcgg gcctctgaca  1080
gccactttga ataaaccaga caccgcac                                     1108

SEQ ID NO: 176          moltype = AA  length = 257
FEATURE                 Location/Qualifiers
source                  1..257
                        mol_type = protein
                        organism = Homo sapiens
SEQUENCE: 176
MAQRMTTQLL LLLVWVAVVG EAQTRIAWAR TELLNVCMNA KHHKEKPGPE DKLHEQCRPW  60
```

```
RKNACCSTNT SQEAHKDVSY LYRFNWNHCG EMAPACKRHF IQDTCLYECS PNLGPWIQQV  120
DQSWRKERVL NVPLCKEDCE QWWEDCRTSY TCKSNWHKGW NWTSGFNKCA VGAACQPFHF  180
YFPTPTVLCN EIWTHSYKVS NYSRGSGRCI QMWFDPAQGN PNEEVARFYA AAMSGAGPWA  240
AWPFLLSLAL MLLWLLS                                                257

SEQ ID NO: 177         moltype = DNA  length = 2669
FEATURE                Location/Qualifiers
source                 1..2669
                       mol_type = other DNA
                       organism = synthetic construct
SEQUENCE: 177
cagatgccag aagaacactg ttgctcttgg tggacgggcc cagaggaatt cagagttaaa  60
ccttgagtgc ctgcgtccgt gagaattcag catggaatgt ctctactatt tcctgggatt  120
tctgctcctg gctgcaagat tgccacttga tgccgccaaa cgatttcatg atgtgctggg  180
caatgaaaga ccttctgctt acatgaggga gcacaatcaa ttaaatggct ggtcttctga  240
tgaaaatgac tggaatgaaa aactctaccc agtgtggaag cggggagaca tgaggtggaa  300
aaactcctgg aagggaggcc gtgtgcaggc ggtcctgacc agtgactcac cagccctcgt  360
gggctcaaat ataacatttg cggtgaacct gatattccct agatgccaaa aggaagatgc  420
caatggcaac atagtctatg agaagaactg cagaaatgag gctggtttat ctgctgatcc  480
atatgtttac aactggacag catggtcaga ggacagtgac ggggaaaatg gcaccggcca  540
aagccatcat aacgtcttcc ctgatgggaa accttttcct caccaccccg gatggagaag  600
atggaatttc atctacgtct tccacacact tggtcagtat ttccagaaat tgggacgatg  660
ttcagtgaga gtttctgtga acacagccaa tgtgacactt gggcctcaac tcatggaagt  720
gactgtctac agaagacatg gacgggcata tgttcccatc gcacaagtga aagatgtgta  780
cgtggtaaca gatcagattc ctgtgtttgt gactatgttc cagaagaacg atcgaaattc  840
atccgacgaa accttcctca aagatctccc cattatgttt gatgtcctga ttcatgatcc  900
tagccacttc ctcaattatt ctaccattaa ctacaagtgg agcttcgggg ataatactgg  960
cctgtttgtt tccaccaatc atactgtgaa tcacacgtat gtgctcaatg gaaccttcag  1020
ccttaacctc actgtgaaag ctgcagcacc aggaccttgt ccgccaccgc caccaccacc  1080
cagaccttca aaacccaccc cttctttagg acctgctggt gacaaccccc tggagctgag  1140
taggattcct gatgaaaact gccagattaa cagatatggc cactttcaag ccaccatcac  1200
aattgtagag ggaatcttag aggttaacat catccagatg acagacgtcc tgatgccggt  1260
gccatggcct gaaagctccc taatagactt tgtcgtgacc tgccaaggga gcattcccac  1320
ggaggtctgt accatcattt ctgaccccac ctgcgagatc acccagaaca cagtctgcag  1380
ccctgtggat gtggatgaga tgtgtctgct gactgtgaga cgaaccttca atgggtctgg  1440
gacgtactgt gtgaacctca ccctgggggga tgacacaagc ctggctctca cgagcaccct  1500
gatttctgtt cctgacagag acccagcctc gcctttaagg atggcaaaca gtgccctgat  1560
ctccgttggc tgcttggcca tatttgtcac tgtgatctcc ctcttggtgt acaaaaaaca  1620
caaggaatac aacccaatag aaaatagtcc tgggaatgtg gtcagaagca aaggcctgag  1680
tgtctttctc aaccgtgcaa aagccgtgtt cttcccggga aaccaggaaa aggatccgct  1740
actcaaaaac caagaattta aaggagtttc ttaaatttcg accttgtttc tgaagctcac  1800
ttttcagtgc cattgatgtg agatgtgctg gagtggctat taaccttttt ttcctaaaga  1860
ttattgttaa atagatattg tggtttgggg aagttgaatt ttttataggt taaatgtcat  1920
tttagagatg gggagaggga ttatactgca ggcagcttca gccatgttgt gaaactgata  1980
aaagcaactt agcaaggctt cttttcatta ttttttatgt ttcacttata aagtcttagg  2040
taactagtag gatagaaaca ctgtgtcccg agagtaagga gagaagctac tattgattag  2100
agcctaaccc aggttaactg caagaagagg cgggatactt tcagctttcc atgtaactgt  2160
atgcataaag ccaatgtagt ccagtttcta agatcatgtt ccaagctaac tgaatcccac  2220
ttcaatacac actcatgaac tcctgatgga acaataacag gcccaagcct gtggtatgat  2280
gtgcacactt gctagactca gaaaaaatac tactctcata aatgggtggg agtattttgg  2340
tgacaaccta ctttgcttgg ctgagtgaag gaatgatatt catatattca tttattccat  2400
ggacatttag ttagtgcttt ttatatacca ggcatgatgc tgagtgacac tcttgtgtat  2460
atttccaaat ttttgtatag tcgctgcaca tatttgaaat catatattaa gactttccaa  2520
agatgaggtc cctggttttt catggcaact tgatcagtaa ggatttcacc tctgtttgta  2580
actaaaacca tctactatat gttagacatg acattctttt tctctccttc ctgaaaaata  2640
aagtgtggga agagacaaaa aaaaaaaaa                                   2669

SEQ ID NO: 178         moltype = AA  length = 560
FEATURE                Location/Qualifiers
source                 1..560
                       mol_type = protein
                       organism = Homo sapiens
SEQUENCE: 178
MECLYYFLGF LLLAARLPLD AAKRFHDVLG NERPSAYMRE HNQLNGWSSD ENDWNEKLYP  60
VWKRGDMRWK NSWKGGRVQA VLTSDSPALV GSNITFAVNL IFPRCQKEDA NGNIVYEKNC  120
RNEAGLSADP YVYNWTAWSE DSDGENGTGQ SHHNVFPDGK PFPHHPGWRR WNFIYVFHTL  180
GQYFQKLGRC SVRVSVNTAN VTLGPQLMEV TVYRRHGRAY VPIAQVKDVY VVTDQIPVFV  240
TMFQKNDRNS SDETFLKDLP IMFDVLIHDP SHFLNYSTIN YKWSFGDNTG LFVSTNHTVN  300
HTYVLNGTFS LNLTVKAAAP GPCPPPPPPP RPSKPTPSLG PAGDNPLELS RIPDENCQIN  360
RYGHFQATIT IVEGILEVNI IQMTDVLMPV PWPESSLIDF VVTCQGSIPT EVCTIISDPT  420
CEITQNTVCS PVDVDEMCLL TVRRTFNGSG TYCVNLTLGD DTSLALTSTL ISVPDRDPAS  480
PLRMANSALI SVGCLAIFVT VISLLVYKKH KEYNPIENSP GNVVRSKGLS VFLNRAKAVF  540
FPGNQEKDPL LKNQEFKGVS                                             560

SEQ ID NO: 179         moltype = DNA  length = 1440
FEATURE                Location/Qualifiers
source                 1..1440
                       mol_type = other DNA
                       organism = synthetic construct
```

SEQUENCE: 179
gttacccagc attgtgagtg acagagcctg gatctgaacg ctgatcccat aatgcatcct 60
caagtggtca tcttaagcct catcctacat ctggcagatt ctgtagctgg ttctgtaaag 120
gttggtggag aggcaggtcc atctgtcaca ctaccctgcc actacagtgg agctgtcaca 180
tcaatgtgct ggaatagagg ctcatgttct ctattcacat gccaaaatgg cattgtctgg 240
accaatggaa cccacgtcac ctatcggaag gacacacgct ataagctatt gggggacctt 300
tcaagaaggg atgtctcttt gaccatagaa aatacagctg tgtctgacag tggcgtatat 360
tgttgccgtg ttgagcaccg tgggtggttc aatgacatga aaatcaccgt atcattggag 420
attgtgccac ccaaggtcac gactactcca attgtcacaa ctgttccaac cgtcacgact 480
gttcgaacga gcaccactgt tccaacgaca acgactgttc caacgacaac tgttccaaca 540
acaatgagca ttccaacgac aacgactgtt ccgacgacaa tgactgtttc aacgacaacg 600
agcgttccaa cgacaacgag cattccaaca acaacaagtg ttccagtgac aacaacggtc 660
tctacctttg ttcctccaat gcctttgccc aggcagaacc atgaaccagt agccacttca 720
ccatcttcac ctcagccagc agaaacccac cctacgacac tgcagggagc aataaggaga 780
gaacccacca gctcaccatt gtactcttac acaacagatg ggaatgacac cgtgacagag 840
tcttcagatg gcctttggaa taacaatcaa actcaactgt tcctagaaca tagtctactg 900
acggccaata ccactaaagg aatctatgct ggagtctgta tttctgtctt ggtgcttctt 960
gctcttttgg gtgtcatcat tgccaaaaag tatttcttca aaaaggaggt tcaacaacta 1020
agtgtttcat ttagcagcct tcaaattaaa gctttgcaaa atgcagttga aaaggaagtc 1080
caagcagaag acaatatcta cattgagaat agtctttatg ccacggacta agacccagtg 1140
gtgctctttg agagtttacg cccatgactg cagaagactg aacaggtatc agcacatcag 1200
atgtctttta gactccaaga caatttttct gtttcagttt catctggcat tccaacatgt 1260
cagtgatact gggtagagta actctcccac tccaaactgt gtatagtcaa cctcatcatt 1320
aatgtagtcc taatttgttt tgctaaaact ggctcaatcc ttctgatcat tgcagagttt 1380
tctctcaaac atgaacactt tagaattgta tgttctcttt agaccccata aatcctgtat 1440

SEQ ID NO: 180 moltype = AA length = 359
FEATURE Location/Qualifiers
source 1..359
mol_type = protein
organism = Homo sapiens
SEQUENCE: 180
MHPQVVILSL ILHLADSVAG SVKVGGEAGP SVTLPCHYSG AVTSMCWNRG SCSLFTCQNG 60
IVWTNGTHVT YRKDTRYKLL GDLSRRDVSL TIENTAVSDS GVYCCRVEHR GWFNDMKITV 120
SLEIVPPKVT TTPIVTTVPT VTTVRTSTTV PTTTTVPTTT VPTTMSIPTT TTVPTTMTVS 180
TTTSVPTTTS IPTTTSVPVT TTVSTFVPPM PLPRQNHEPV ATSPSSPQPA ETHPTTLQGA 240
IRREPTSSPL YSYTTDGNDT VTESSDGLWN NNQTQLFLEH SLLTANTTKG IYAGVCISVL 300
VLLALLGVII AKKYFFKKEV QQLSVSFSSL QIKALQNAVE KEVQAEDNIY IENSLYATD 359

SEQ ID NO: 181 moltype = DNA length = 2671
FEATURE Location/Qualifiers
source 1..2671
mol_type = other DNA
organism = synthetic construct
SEQUENCE: 181
ggtgagtcac caaggaaggc agcggcagct ccactcagcc actgcaattg tgtccggaat 60
ttattccttc tggtgggttc atggtcttgc tgacttcaag aatgaagccg ctgacctcgc 120
gcataattag catcatcatt attctggctg gagcaattgc actcatcatt ggctttggta 180
tttcagggag acactccatc acagtcacta ctgtcgcctc agctgggaac attggggagg 240
atggaatcct gagctgcact tttgaacctg acatcaaact ttctgatatc gtgatacaat 300
ggctgaagga aggtgtttta ggcttggtcc atgagttcaa agaaggcaaa gatgagctgt 360
cggagcagga tgaaatgttc agaggccgga cagcagtgtt tgctgatcaa gtgatagttg 420
gcaatgcctc tttgcggctg aaaaacgtgc aactcacaga tgctggcacc tacaaatgtt 480
atatcatcac ttctaaaggc aaggggaatg ctaaccttga gtataaaact ggagccttca 540
gcatgccgga agtgaatgtg gactataatg ccagctcaga gaccttgcgg tgtgaggctc 600
cccgatggtt cccccggccc acagtggtct gggcatccca agttgaccag ggagccaact 660
tctcggaagt ctccaatacc agctttgagc tgaactctga gaatgtgacc atgaaggtag 720
tgtctgtgct ctacaatgtt acgatcaaca acacatactc ctgtatggtt gaaaatgaca 780
ttgccaaagc aacaggggat atcaaagtga cagaatcgga gatcaaaagg cggagtcacc 840
tacagctgct aaactcaaag gcttctctgt gtgtctcttc tttctttgcc atcagctggg 900
cacttctgcc tctcagccct tacctgatgc taaaataatg tgccttggcc acaaaaaagc 960
atgcaaagtc attgttacaa cagggatcta cagaactatt tcaccaccag atatgaccta 1020
gttttatatt tctgggagga aatgaattca tatctagaag tctggagtga gcaaacaaga 1080
gcaagaaaca aaaagaagcc aaaagcagaa ggctccaata tgaacaagat aaatctatct 1140
tcaaagacat attagaagtt gggaaaataa ttcatgtgaa ctagacaagt gtgttaagag 1200
tgataagtaa aatgcacgtg gagacaagtg catccccaga tctcagggac ctccccctgc 1260
ctgtcacctg gggagtgaga ggacaggata gtgcatgttc tttgtctctg aatttttagt 1320
tatatgtgcc gtaatgttgc tctgaggaag cccctggaaa gtctatccca acatatccac 1380
atcttatatt ccacaaatta agctgtagta tgtaccctaa gacgctgcta attgactgcc 1440
acttcgcaac tcaggggcgg ctgcatttta gtaatgggtc aaatgattca ctttttatga 1500
tgcttccaaa ggtgccttgg cttctcttcc caactgacaa atgccaaagt tgagaaaaat 1560
gatcataatt ttagcataaa cagagcagtc ggcgacaccg attttataaa taaactgagc 1620
accttctttt taaacaaaca aatgcgggtt tatttctcag atgatgttca tccgtgaatg 1680
gtccagggaa ggacctttca ccttgtctat atggcattat gtcatcacaa gctctgaggc 1740
ttctcctttc catcctgcgt ggacagctaa gacctcagtt ttcaatagca tctagagcag 1800
tgggactcag ctggggtgat ttcgcccccc atctccgggg gaatgtctga agacaatttt 1860
ggttacctca atgagggagt ggaggaggat acagtgccac taccaactag tggatagagg 1920
ccagggatgc tgctcaacct cctaccatgt acaggacgtc tccccattac aactacccaa 1980
tccgaagtgt caactgtgtc agggctaagg aaccctggtt ttgagtagaa aagggcctgg 2040

```
aaagagggga gccaacaaat ctgtctgctt cctcacatta gtcattggca aataagcatt  2100
ctgtctcttt ggctgctgcc tcagcacaga gagccagaac tctatcgggc accaggataa  2160
catctctcag tgaacagagt tgacaaggcc tatgggaaat gcctgatggg attatcttca  2220
gcttgttgag cttctaagtt tctttccctt cattctaccc tgcaagccaa gttctgtaag  2280
agaaatgcct gagttctagc tcaggttttc ttactctgaa tttagatctc cagaccctgc  2340
ctggccacaa ttcaaattaa ggcaacaaac atataccttc catgaagcac acacagactt  2400
ttgaaagcaa ggacaatgac tgcttgaatt gaggccttga ggaatgaagc tttgaaggaa  2460
aagaatactt tgtttccagc ccccttccca cactcttcat gtgttaacca ctgccttcct  2520
ggaccttgga gccacggtga ctgtattaca tgttgttata gaaaactgat tttagagttc  2580
tgatcgttca agagaatgat taaatataca tttcctacaa aaaaaaaaaa aaaaaaaaaa  2640
aaaaaaaaaa aataaaaaaa aaaaaaaaaa a                                 2671

SEQ ID NO: 182          moltype = DNA  length = 1164
FEATURE                 Location/Qualifiers
source                  1..1164
                        mol_type = other DNA
                        organism = synthetic construct
SEQUENCE: 182
agtggggcca ggggagtcat ctttttccgt tgcgggtacc cacctgccgc tggccagcat  60
tgccccagag gcatccttgg gtggctgctt gtataaactg caaggtccac aaagtgttga  120
acaagttgtt gaatgttttg gccaacactg cacctgctgt cttccctaca gatttgcagg  180
ctgggaaggc tagacttcct cagcccgagg gctgcccttc caaactctat cggctgatgc  240
agcgctgctg ggccctcagc cccaaggacc ggccctcctt cagtgagatt gccagcgccc  300
tgggagacag caccgtggac agcaagccgt gaggagggag cccgctcagg atggcctggg  360
caggggagga catctctaga gggaagctca cagcatgatg ggcaagatcc ctgtcctcct  420
gggccctgag gcccctgccc tagtgcaaca ggcattgctg aggtctgagc agggcctggc  480
ctttcctcct cttcctcacc ctcatccttt gggaggctga cttggaccca aactgggcga  540
ctagggcttt gagctgggca gttttccctg ccacctcttc ctctatcagg gacagtgtgg  600
gtgccacagg taaccccaat ttctggcctt caacttctcc ccttgaccgg gtccaactct  660
gccactcatc tgccaacttt gcctggggag ggctaggctt gggatgagct gggtttgtgg  720
ggagttcctt aatattctca agttctgggc acacagggtt aatgagtctc ttggcccact  780
ggtcccactt gggggtctag accaggatta tagaggacac agcaagtgag tcctccccac  840
tctgggcttg tgcacactga cccagaccca cgtcttcccc acccttctct cctttcctca  900
tcctaagtgc ctggcagatg aaggagtttt caggagcttt tgacactata taaaccgccc  960
tttttgtatg caccacgggc ggcttttata tgtaattgca gcgtggggtg ggtgggcatg  1020
ggaggtaggg gtgggccctg gagatgagga gggtgggcca tccttacccc acacttttat  1080
tgttgtcgtt ttttgtttgt ttttgttttt ttgtttttgt ttttgttttt acactcgctg  1140
ctctcaataa ataagccttt ttta                                         1164

SEQ ID NO: 183          moltype = AA  length = 1070
FEATURE                 Location/Qualifiers
source                  1..1070
                        mol_type = protein
                        organism = Homo sapiens
SEQUENCE: 183
MGAARGSPAR PRRLPLLSVL LLPLLGGTQT AIVFIKQPSS QDALQGRRAL LRCEVEAPGP  60
VHVYWLLDGA PVQDTERRFA QGSSLSFAAV DRLQDSGTFQ CVARDDVTGE EARSANASFN  120
IKWIEAGPVV LKHPASEAEI QPQTQVTLRC HIDGHPRPTY QWFRDGTPLS DGQSNHTVSS  180
KERNLTLRPA GPEHSGLYSC CAHSAFGQAC SSQNFTLSIA DESFARVVLA PQDVVVARYE  240
EAMFHCQFSA QPPPSLQWLF EDETPITNRS RPPHLRRATV FANGSLLLTQ VRPRNAGIYR  300
CIGQGQRGPP IILEATLHLA EIEDMPLFEP RVFTAGSEER VTCLPPKGLP EPSVWWEHAG  360
VRLPTHGRVY QKGHELVLAN IAESDAGVYT CHAANLAGQR RQDVNITVAT VPSWLKKPQD  420
SQLEEGKPGY LDCLTQATPK PTVVWYRNQM LISEDSRFEV FKNGTLRINS VEVYDGTWYR  480
CMSSTPAGSI EAQARVQVLE KLKFTPPPQP QQCMEFDKEA TVPCSATGRE KPTIKWERAD  540
GSSLPEWVTD NAGTLHFARV TRDDAGNYTC IASNGPQGQI RAHVQLTVAV FITFKVEPER  600
TTVYQGHTAL LQCEAQGDPK PLIQWKGKDR ILDPTKLGPR MHIFQNGSLV IHDVAPEDSG  660
RYTCIAGNSC NIKHTEAPLY VVDKPVPEES EGPGSPPPYK MIQTIGLSVG AAVAYIIAVL  720
GLMFYCKKRC KAKRLQKQPE GEEPEMECLN GGPLQNGQPS AEIQEEVALT SLGSGPAATN  780
KRHSTSDKMH FPRSSLQPIT TLGKSEFGEV FLAKAQGLEE GVAETLVLVK SLQSKDEQQQ  840
LDFRRELEMF GKLNHANVVR LLGLCREAEP HYMVLEYVDL GDLKQFLRIS KSKDEKLKSQ  900
PLSTKQKVAL CTQVALGMEH LSNNRFVHKD LAARNCLVSA QRQVKVSALG LSKDVYNSEY  960
YHFRQAWVPL RWMSPEAILE GDFSTKSDVW AFGVLMWEVF THGEMPHGGQ ADDEVLADLQ  1020
AGKARLPQPE GCPSKLYRLM QRCWALSPKD RPSFSEIASA LGDSTVDSKP             1070

SEQ ID NO: 184          moltype = DNA  length = 1229
FEATURE                 Location/Qualifiers
source                  1..1229
                        mol_type = other DNA
                        organism = synthetic construct
SEQUENCE: 184
ttcctttctc tctcagctct ccgtctctct ttctctctca gcctctttct ttctccctgt  60
ctcccccact gtcagcacct cttctgtgtg gtgagtggac cgcttacccc actaggtgaa  120
gatgtcagcc caggagagct gcctcagcct catcaagtcc tcggcagcct gatcttctgc  180
ttcggcatct ggatcctcat tgacaagacc agcttcgtgt cctttgtggg cttggccttc  240
gtgcctctgc agatctggtc caaagtcctg gccatctcag gaatcttcac catgggcatc  300
gccctcctgg gttgtgtggg ggccctcaag gagctccgct gcctcctggg cctgtatttt  360
gggatgctgc tgctcctgtt tgccacacag atcaccctgg gaatcctcat ctccactcag  420
cgggcccagc tggagcgaag cttgcgggac gtcgtagaga aaccatccca aaagtacggc  480
accaaccccg aggagaccgc ggccgaggag agctgggact atgtgcagtt ccagctgcgc  540
```

```
tgctgcggct ggcactaccc gcaggactgg ttccaagtcc tcatcctgag aggtaacggg  600
tcggaggcgc accgcgtgcc ctgctcctgc tacaacttgt cggcgaccaa cgactccaca  660
atcctagata aggtgatctt gccccagctc agcaggcttg gacacctggc gcggtccaga  720
cacagtgcag acatctgcgc tgtccctgca gagagccaca tctaccgcga gggctgcgcg  780
cagggcctcc agaagtggct gcacaacaac cttatttcca tagtgggcat ttgcctgggc  840
gtcggcctac tcgagctcgg gttcatgacg ctctcgatat tcctgtgcag aaacctggac  900
cacgtctaca accggctcgc tcgataccgt taggccccgc cctccccaaa gtcccgcccc  960
gcccccgtca cgtgcgctgg gcacttccct gctgcctgta aatatttgtt taatccccag  1020
ttcgcctgga gccctccgcc ttcacattcc cctggggacc cacgtggctg cgtgcccctg  1080
ctgctgtcac ctctcccacg ggacctgggg ctttcgtcca cagcttcctg tccccatctg  1140
tcggcctacc accacccaca agattatttt tcacccaaac ctcaaataaa tcccctgcgt  1200
ttttggtaaa aaaaaaaaaa aaaaaaaaa                                  1229

SEQ ID NO: 185          moltype = AA  length = 213
FEATURE                 Location/Qualifiers
source                  1..213
                        mol_type = protein
                        organism = Homo sapiens
SEQUENCE: 185
MGIALLGCVG ALKELRCLLG LYFGMLLLLF ATQITLGILI STQRAQLERS LRDVVEKTIQ  60
KYGTNPEETA AEESWDYVQF QLRCCGWHYP QDWFQVLILR GNGSEAHRVP CSCYNLSATN  120
DSTILDKVIL PQLSRLGHLA RSRHSADICA VPAESHIYRE GCAQGLQKWL HNNLISIVGI  180
CLGVGLLELG FMTLSIFLCR NLDHVYNRLA RYR                             213

SEQ ID NO: 186          moltype = DNA  length = 3148
FEATURE                 Location/Qualifiers
source                  1..3148
                        mol_type = other DNA
                        organism = synthetic construct
SEQUENCE: 186
gtgggaaggg cctgtgggtt tattataagg cggagctcgg cgggagaggt gcgggccgaa  60
tccgagccga gcggagagga atccggcagt agagagcgga ctccagccgg cggaccctgc  120
agccctcgcc tgggacagcg gcgcgctggg caggcgccca agagagcatc gagcagcgga  180
acccgcgaag ccggcccgca gccgcgaccc gcgcagcctg ccgctctccc gccgccggtc  240
cgggcagcat gaggcgcgcg gcgctctggc tctggctgtg cgcgctggcg ctgagcctgc  300
agccggccct gccgcaaatt gtggctacta atttgccccc tgaagatcaa gatggctctg  360
gggatgactc tgacaacttc tccggctcag gtgcaggtgc tttgcaagat atcaccttgt  420
cacagcagac cccctccact tggaaggaca cgcagctcct gacggctatt cccacgtctc  480
cagaacccac cggcctggag gctacagctg cctccacctc caccctgccg gctggagagg  540
ggcccaagga gggagaggct gtagtcctgc cagaagtgga gcctggcctc accgcccggg  600
agcaggaggc cacccccccga cccagggaga ccacacagct cccgaccact catcaggcct  660
caacgaccac agccaccacg gcccaggagc ccgccacctc ccaccccccac agggacatgc  720
agcctggcca ccatgagacc tcaacccctg caggacccag ccaagctgac cttcacactc  780
cccacacaga ggatggaggt ccttctgcca ccgagagggc tgctgaggat ggagcctcca  840
gtcagctccc agcagcagag ggctctgggg agcaggactt caccttttgaa acctcggggg  900
agaatacggc tgtagtggcc gtggagcctg accgccggaa ccagtcccca gtggatcagg  960
gggccacggg ggcctcacag ggcctcctgg acaggaaaga ggtgctggga ggggtcattg  1020
ccggaggcct cgtggggctc atctttgctg tgtgcctggt gggtttcatg ctgtaccgca  1080
tgaagaagaa ggacgaaggc agctactcct tggaggagcc gaaacaagcc aacggcgggg  1140
cctaccagaa gcccaccaaa caggaggaat tctatgcctg acgcgggagc catgcgcccc  1200
ctccgccctg ccactcacta ggcccccact tgcctcttcc ttgaagaact gcaggccctg  1260
gcctcccctg ccaccaggcc acctccccag cattccagcc cctctggtcg ctcctgccca  1320
cggagtcgtg ggtgtgctg ggagctccac tctgcttctc tgacttctgc ctggagactt  1380
agggcaccag gggtttctcg cataggacct ttccaccaca gccagcacct ggcatcgcac  1440
cattctgact cggtttctcc aaactgaagc agcctctccc caggtccagc tctggagggg  1500
agggggatcc gactgctttg gacctaaatg gcctcatgtg gctggaagat cctgcgggtg  1560
gggcttgggg ctcacacacc tgtagcactt actggtagga ccaagcatct tggggggggtg  1620
gccgctgagt ggcaggggac aggagtccac tttgtttcgt ggggaggtct aatctagata  1680
tcgacttgtt tttgcacatg tttcctctag ttctttgttc atagcccagt agaccttgtt  1740
acttctgagg taagttaagt aagttgattc ggtatccccc catcttgctt ccctaatcta  1800
tggtcgggag acagcatcag ggttaagaag actttttttt ttttttttaa actaggagaa  1860
ccaaatctgg aagccaaaat gtaggcttag tttgtgtgtt gtctcttgag tttgtcgctc  1920
atgtgtgcaa cagggtatgg actatctgtc tggtggcccc gtttctggtg gtctgttggc  1980
aggctggcca gtccaggctg ccgtggggcc gccgcctctt tcaagcagtc gtgcctgtgt  2040
ccatgcgctc agggccatgc tgaggcctgg gccgctgcca cgttggagaa gcccgtgtga  2100
gaagtgaatg ctgggactca gccttcagac agagaggact gtagggaggg cggcaggggc  2160
ctggagatcc tcctgcagac cacgcccgtc ctgcctgtgg cgccgtctcc aggggctgct  2220
tcctcctgga aattgacgag ggtgtcttg ggcagagctg gctctgagcg cctccatcca  2280
aggccaggtt ctccgttagc tcctgtggcc ccaccctggg ccctgggctg gaatcaggaa  2340
tattttccaa agagtgatag tcttttgctt ttggcaaaac tctacttaat ccaatgggtt  2400
tttccctgta cagtagattt tccaaatgta ataaacttta atataaagta gtcctgtgaa  2460
tgccactgcc ttcgcttctt gcctctgtgc tgtgtgtgac gtgaccggac ttttctgcaa  2520
acaccaacat gttgggaaac ttggctcgaa tctctgtgcc ttcgtctttc ccatggggag  2580
ggattctggt tccagggtcc ctctgtgtat ttgctttttt gttttggctg aaattctcct  2640
ggaggtcggt aggttcagcc aaggttttat aaggctgatg tcaatttctg tgttgccaag  2700
ctccaagccc catcttctaa atggcaaagg aaggtggatg gccccagcac agcttgacct  2760
gaggctgtgg tcacagcgga ggtgtggagc cgaggcctac cccgcagaca ccttggacat  2820
cctcctccca cccggctgca gaggccagag gcccccagcc cagggctcct gcacttactt  2880
gcttatttga caacgtttca gcgactccgt tggccactcc gagaggtggg ccagtctgtg  2940
```

```
gatcagagat gcaccaccaa gccaagggaa cctgtgtccg gtattcgata ctgcgacttt  3000
ctgcctggag tgtatgactg cacatgactc gggggtgggg aaaggggtcg gctgaccatg  3060
ctcatctgct ggtccgtggg acggtgccca agccagaggc tgggttcatt tgtgtaacga  3120
caataaacgg tacttgtcat ttcgggca                                    3148

SEQ ID NO: 187         moltype = AA  length = 310
FEATURE                Location/Qualifiers
source                 1..310
                       mol_type = protein
                       organism = Homo sapiens
SEQUENCE: 187
MRRAALWLWL CALALSLQPA LPQIVATNLP PEDQDGSGDD SDNFSGSGAG ALQDITLSQQ  60
TPSTWKDTQL LTAIPTSPEP TGLEATAAST STLPAGEGPK EGEAVVLPEV EPGLTAREQE  120
ATPRPRETTQ LPTTHQASTT TATTAQEPAT SHPHRDMQPG HHETSTPAGP SQADLHTPHT  180
EDGGPSATER AAEDGASSQL PAAEGSGEQD FTFETSGENT AVVAVEPDRR NQSPVDQGAT  240
GASQGLLDRK EVLGGVIAGG LVGLIFAVCL VGFMLYRMKK KDEGSYSLEE PKQANGGAYQ  300
KPTKQEEFYA                                                        310

SEQ ID NO: 188         moltype = DNA  length = 1506
FEATURE                Location/Qualifiers
source                 1..1506
                       mol_type = other DNA
                       organism = synthetic construct
SEQUENCE: 188
ctgcctgggg agcccccccg ccccacatcc tgccccgcaa aaggcagctt caccaaagtg  60
gggtatttcc agcctttgta gctttcactt ccacatctac caagtgggcg gagtggcctt  120
ctgtggacga atcagattcc tctccagcac cgactttaag aggcgagccg gggggtcagg  180
gtcccagatg cacaggagga gaagcaggag ctgtcgggaa gatcagaagc cagtcatgga  240
tgaccagcgc gaccttatct ccaacaatga gcaactgccc atgctgggcc ggcgccctgg  300
ggccccggag agcaagtgca gccgcggagc cctgtacaca ggcttttcca tcctggtgac  360
tctgctcctc gctggccagg ccaccaccgc ctacttcctg taccagcagc agggccggct  420
ggacaaactg acagtcacct cccagaacct gcagctggag aacctgcgca tgaagcttcc  480
caagcctccc aagcctgtga gcaagatgcg catggccacc ccgctgctga tgcaggcgct  540
gcccatggga gccctgcccc aggggcccat gcagaatgcc accaagtatg gcaacatgac  600
agaggaccat gtgatgcacc tgctccagaa tgctgacccc ctgaaggtgt acccgccact  660
gaaggggagc ttcccggaga acctgagaca ccttaagaac accatggaga ccatagactg  720
gaaggtcttt gagagctgga tgcaccattg gctcctgttt gaaatgagca ggcactcctt  780
ggagcaaaag cccactgacg ctccaccgaa agagtcactg gaactggagg acccgtcttc  840
tgggctgggt gtgaccaagc aggatctggg cccagtcccc atgtgagagc agcagaggcg  900
gtcttcaaca tcctgccagc cccacacagc tacagctttc ttgctccctt cagcccccag  960
cccctccccc atctcccacc ctgtacctca tcccatgaga ccctggtgcc tggctctttc  1020
gtcacccttg gacaagacaa accaagtcgg aacagcagat aacaatgcag caaggccctg  1080
ctgcccaatc tccatctgtc aacaggggcg tgaggtccca ggaagtggcc aaaagctaga  1140
cagatccccg ttcctgacat cacagcagcc tccaacacaa ggctccaaga cctaggctca  1200
tggacgagat gggaaggcac agggagaagg gataacccta cacccagacc ccaggctgga  1260
catgctgact gtcctctccc ctccagcctt tggccttggc ttttctagcc tatttacctg  1320
caggctgagc cactctcttc cctttcccca gcatcactcc ccaaggaaga gccaatgttt  1380
tccacccata atcctttctg ccgaccccta gttccctctg ctcagccaag cttgttatca  1440
gctttcaggg ccatggttca cattagaata aaaggtagta attagaacaa aaaaaaaaaa  1500
aaaaaa                                                            1506

SEQ ID NO: 189         moltype = AA  length = 232
FEATURE                Location/Qualifiers
source                 1..232
                       mol_type = protein
                       organism = Homo sapiens
SEQUENCE: 189
MHRRRSRSCR EDQKPVMDDQ RDLISNNEQL PMLGRRPGAP ESKCSRGALY TGFSILVTLL  60
LAGQATTAYF LYQQQGRLDK LTVTSQNLQL ENLRMKLPKP PKPVSKMRMA TPLLMQALPM  120
GALPQGPMQN ATKYGNMTED HVMHLLQNAD PLKVYPPLKG SFPENLRHLK NTMETIDWKV  180
FESWMHHWLL FEMSRHSLEQ KPTDAPPKES LELEDPSSGL GVTKQDLGPV PM          232

SEQ ID NO: 190         moltype = DNA  length = 5616
FEATURE                Location/Qualifiers
source                 1..5616
                       mol_type = other DNA
                       organism = synthetic construct
SEQUENCE: 190
ccccggcgca gcgcggccgc agcagcctcc gccccccgca cggtgtgagc gcccgacgcg  60
gccgaggcgg ccggagtccc gagctagccc cggcggccgc cgccgcccag accggacgac  120
aggccacctc gtcggcgtcc gcccgagtcc ccgcctcgcc gccaacgcca caaccaccgc  180
gcacggcccc ctgactccgt ccagtattga tcgggagagc cggagcgagc tcttcgggga  240
gcagcgatgc gaccctccgg gacggccggg gcagcgctcc tggcgctgct ggctgcgctc  300
tgcccggcga gtcgggctct ggaggaaaag aaagtttgcc aaggcacgag taacaagctc  360
acgcagttgg gcacttttga agatcatttt ctcagcctcc agaggatgtt caataactgt  420
gaggtggtcc ttgggaattt ggaaattacc tatgtgcaga ggaattatga tctttccttc  480
ttaaagacca tccaggaggt ggctggttat gtcctcattg ccctcaacac agtggagcga  540
attcctttgg aaaacctgca gatcatcaga ggaaatatgt actacgaaaa ttcctatgcc  600
ttagcagtct tatctaacta tgatgcaaat aaaaccggac tgaaggagct gcccatgaga  660
```

-continued

```
aatttacagg aaatcctgca tggcgccgtg cggttcagca acaaccctgc cctgtgcaac  720
gtggagagca tccagtggcg ggacatagtc agcagtgact ttctcagcaa catgtcgatg  780
gacttccaga accacctggg cagctgccaa aagtgtgatc caagctgtcc caatgggagc  840
tgctggggtg caggagagga gaactgccag aaactgacca aaatcatctg tgcccagcag  900
tgctccgggc gctgccgtgg caagtccccc agtgactgct gccacaacca gtgtgctgca  960
ggctgcacag gcccccggga gagcgactgc ctggtctgcc gcaaattccg agacgaagcc  1020
acgtgcaagg acacctgccc cccactcatg ctctacaacc ccaccacgta ccagatggat  1080
gtgaaccccg agggcaaata cagctttggt gccacctgcg tgaagaagtg tccccgtaat  1140
tatgtggtga cagatcacgg ctcgtgcgtc cgagcctgtg ggccgacag ctatgagatg  1200
gaggaagacg gcgtccgcaa gtgtaagaag tgcgaagggc cttgccgcaa agtgtgtaac  1260
ggaataggta ttggtgaatt taaagactca ctctccataa atgctacgaa tattaaacac  1320
ttcaaaaact gcacctccat cagtggcgat ctccacatcc tgccggtggc atttaggggt  1380
gactccttca cacatactcc tcctctggat ccacaggaac tggatattct gaaaaccgta  1440
aaggaaatca cagggttttt gctgattcag gcttggcctg aaaacaggac ggacctccat  1500
gcctttgaga acctagaaat catacgcggc aggaccaagc aacatggtca gttttctctt  1560
gcagtcgtca gcctgaacat aacatccttg ggattacgct ccctcaagga gataagtgat  1620
ggagatgtga taatttcagg aaacaaaaat ttgtgctatg caaatacaat aaactggaaa  1680
aaactgtttg ggacctccgg tcagaaaacc aaaattataa gcaacagagg tgaaaacagc  1740
tgcaaggcca caggccaggt ctgccatgcc ttgtgctccc ccgagggctg ctggggcccg  1800
gagcccaggg actgcgtctc ttgccggaat gtcagccgag gcagggaatg cgtggacaag  1860
tgcaaccttc tggagggtga gccaagggag tttgtggaga actctgagtg catacagtgc  1920
cacccagagt gcctgcctca ggccatgaac atcacctgca caggacgggg accagacaac  1980
tgtatccagt gtgcccacta cattgacggc ccccactgcg tcaagacctg cccggcagga  2040
gtcatgggag aaaacaacac cctggtctgg aagtacgcag acgccggcca tgtgtgccac  2100
ctgtgccatc caaactgcac ctacggatgc actgggccag gtcttgaagg ctgtccaacg  2160
aatgggccta agatcccgtc catcgccact gggatggtgg gggccctcct cttgctgctg  2220
gtggtggccc tggggatcgg cctcttcatg cgaaggcgcc acatcgttcg gaagcgcacg  2280
ctgcggaggc tgctgcagga gagggagctt gtggagcctc ttacacccag tggagaagct  2340
cccaaccaag ctctcttgag gatcttgaag gaaactgaat tcaaaaagat caaagtgctg  2400
ggctccggtg cgttcggcac ggtgtataag ggactctgga tcccagaagg tgagaaagtt  2460
aaaattcccg tcgctatcaa ggaattaaga gaagcaacat ctccgaaagc caacaaggaa  2520
atcctcgatg aagcctacgt gatggccagc gtggacaacc cccacgtgtg ccgcctgctg  2580
ggcatctgcc tcacctccac cgtgcagctc atcacgcagc tcatgccctt cggctgcctc  2640
ctggactatg tccgggaaca caaagacaat attggctccc agtacctgct caactggtgt  2700
gtgcagatcg caaagggcat gaactacttg gaggaccgtc gcttggtgca ccgcgacctg  2760
gcagccagga acgtactggt gaaaacaccg cagcatgtca agatcacaga ttttgggctg  2820
gccaaactgc tgggtgcgga agagaaagaa taccatgcag aaggaggcaa agtgcctatc  2880
aagtggatgg cattggaatc aattttacac agaatctata cccaccagag tgatgtctgg  2940
agctacgggg tgaccgtttg ggagttgatg acctttggat ccaagccata tgacggaatc  3000
cctgccagcg agatctcctc catcctggag aaaggagaac gcctccctca gccacccata  3060
tgtaccatcg atgtctacat gatcatggtc aagtgctgga tgatagacgc agatagtcgc  3120
ccaaagttcc gtgagttgat catcgaattc tccaaaatgg cccgagaccc ccagcgctac  3180
cttgtcattc agggggatga aagaatgcat ttgccaagtc ctacagactc caacttctac  3240
cgtgccctga tggatgaaga agacatggac gacgtggtgg atgccgacga gtacctcatc  3300
ccacagcagg gcttcttcag cagcccctcc acgtcacgga ctcccctcct gagctctctg  3360
agtgcaacca gcaacaattc caccgtggct tgcattgata gaaatgggct gcaaagctgt  3420
cccatcaagg aagacagctt cttgcagcga tacagctcag accccacagg cgccttgact  3480
gaggacagca tagacgacac cttcctccca gtgcctgaat acataaacca gtccgttccc  3540
aaaaggcccg ctggctctgt gcagaatcct gtctatcaca atcagcctct gaaccccgcg  3600
cccagcagag acccacacta ccaggacccc cacagcactg cagtgggcaa ccccgagtat  3660
ctcaacactg tccagcccac ctgtgtcaac agcacattcg acagccctgc ccactgggcc  3720
cagaaaggca gccaccaaat tagcctggac aaccctgact accagcagga cttctttccc  3780
aaggaagcca agccaaatgg catctttaag ggctccacag ctgaaaatgc agaataccta  3840
agggtcgcgc cacaaagcag tgaatttatt ggagcatgac cacggaggat agtatgagcc  3900
ctaaaaatcc agactctttc gatacccagg accaagccac agcaggtcct ccatcccaac  3960
agccatgccc gcattagctc ttagacccac agactggttt tgcaacgttt acaccgacta  4020
gccaggaagt acttccacct cgggcacatt ttgggaagtt gcattccttt gtcttcaaac  4080
tgtgaagcat ttacagaaac gcatccagca agaatattgt ccctttgagc agaaatttat  4140
ctttcaaaga ggtatatttg aaaaaaaaaa aaagtatatg tgaggatttt tattgattgg  4200
ggatcttgga gtttttcatt gtcgctattg atttttactt caatgggctc ttccaacaag  4260
gaagaagctt gctggtagca cttgctaccc tgagttcatc caggcccaac tgtgagcaag  4320
gagcacaagc cacaagtctt ccagaggatg cttgattcca gtggttctgc ttcaaggctt  4380
ccactgcaaa acactaaaga tccaagaagg ccttcatggc cccagcaggc cggatcggta  4440
ctgtatcaag tcatggcagg tacagtagga taagccactc tgtcccttcc tgggcaaaga  4500
agaaacggag gggatggaat tcttccttag acttactttt gtaaaaatgt ccccacggta  4560
cttactcccc actgatggac cagtggtttc cagtcatgag cgttagactg acttgtttgt  4620
cttccattcc attgttttga aactcagtat gctgcccctg tcttgctgtc atgaaatcag  4680
caagagagga tgacacatca aataataact cggattccag cccacattgg attcatcagc  4740
atttggacca atagcccaca gctgagaatg tggaatacct aaggatagca ccgcttttgt  4800
tctcgcaaaa acgtatctcc taatttgagg ctcagatgaa atgcatcagg tcctttgggg  4860
catagatcag aagactacaa aaatgaagct gctctgaaat ctcctttagc catcacccca  4920
accccccaaa attagtttgt gttacttatg gaagatagtt ttctcctttt acttcacttc  4980
aaaagctttt tactcaaaga gtatatgttc cctccaggtc agctgccccc aaacccccctc  5040
cttacgcttt gtcacacaaa aagtgtctct gccttgagtc atctattcaa gcacttacag  5100
ctctggccac aacagggcat tttacaggtg cgaatgacag tagcattatg agtagtgtgg  5160
aattcaggta gtaaatatga aactagggtt tgaaattgat aatgctttca caacatttgc  5220
agatgtttta gaaggaaaaa agttccttcc taaaataatt tctctacaat tggaagattg  5280
gaagattcag ctagttagga gcccaccttt tttcctaatc tgtgtgtgcc ctgtaacctg  5340
actggttaac agcagtcctt tgtaaacagt gttttaaact ctcctagtca atatccaccc  5400
```

```
catccaattt atcaaggaag aaatggttca gaaaatattt tcagcctaca gttatgttca  5460
gtcacacaca catacaaaat gttccttttg cttttaaagt aatttttgac tcccagatca  5520
gtcagagccc ctacagcatt gttaagaaag tatttgattt ttgtctcaat gaaaataaaa  5580
ctatattcat ttccactcta aaaaaaaaaa aaaaaa                            5616

SEQ ID NO: 191         moltype = AA  length = 1210
FEATURE                Location/Qualifiers
source                 1..1210
                       mol_type = protein
                       organism = Homo sapiens
SEQUENCE: 191
MRPSGTAGAA LLALLAALCP ASRALEEKKV CQGTSNKLTQ LGTFEDHFLS LQRMFNNCEV  60
VLGNLEITYV QRNYDLSFLK TIQEVAGYVL IALNTVERIP LENLQIIRGN MYYENSYALA  120
VLSNYDANKT GLKELPMRNL QEILHGAVRF SNNPALCNVE SIQWRDIVSS DFLSNMSMDF  180
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGAT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGFLLIQAW PENRTDLHAF  420
ENLEIIRGRT KQHGQFSLAV VSLNITSLGL RSLKEISDGD VIISGNKNLC YANTINWKKL  480
FGTSGQKTKI ISNRGENSCK ATGQVCHALC SPEGCWGPEP RDCVSCRNVS RGRECVDKCN  540
LLEGEPREFV ENSECIQCHP ECLPQAMNIT CTGRGPDNCI QCAHYIDGPH CVKTCPAGVM  600
GENNTLVWKY ADAGHVCHLC HPNCTYGCTG PGLEGCPTNG PKIPSIATGM VGALLLLLVV  660
ALGIGLFMRR RHIVRKRTLR RLLQERELVE PLTPSGEAPN QALLRILKET EFKKIKVLGS  720
GAFGTVYKGL WIPEGEKVKI PVAIKELREA TSPKANKEIL DEAYVMASVD NPHVCRLLGI  780
CLTSTVQLIT QLMPFGCLLD YVREHKDNIG SQYLLNWCVQ IAKGMNYLED RRLVHRDLAA  840
RNVLVKTPQH VKITDFGLAK LLGAEEKEYH AEGGKVPIKW MALESILHRI YTHQSDVWSY  900
GVTVWELMTF GSKPYDGIPA SEISSILEKG ERLPQPPICT IDVYMIMVKC WMIDADSRPK  960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLPVP EYINQSVPKR PAGSVQNPVY HNQPLNPAPS RDPHYQDPHS TAVGNPEYLN  1140
TVQPTCVNST FDSPAHWAQK GSHQISLDNP DYQQDFFPKE AKPNGIFKGS TAENAEYLRV  1200
APQSSEFIGA                                                         1210

SEQ ID NO: 192         moltype = DNA  length = 4975
FEATURE                Location/Qualifiers
source                 1..4975
                       mol_type = other DNA
                       organism = synthetic construct
SEQUENCE: 192
ctctcacaca cacacacccc tcccctgcca tccctccccg gactccggct ccggctccga  60
ttgcaatttg caacctccgc tgccgtcgcc gcagcagcca ccaattcgcc agcggttcag  120
gtggctcttg cctcgatgtc ctagcctagg ggcccccggg ccggacttgg ctgggctccc  180
ttcaccctct gcggagtcat gagggcgaac gacgctctgc aggtgctggg cttgcttttc  240
agcctggccc ggggctccga ggtgggcaac tctcaggcag tgtgtcctgg gactctgaat  300
ggcctgagtg tgaccggcga tgctgagaac caataccaga cactgtacaa gctctacgag  360
aggtgtgagg tggtgatggg gaaccttgag attgtgctca cgggacacaa tgccgacctc  420
tccttcctgc agtggattcg agaagtgaca ggctatgtcc tcgtggccat gaatgaattc  480
tctactctac cattgcccaa cctccgcgtg gtgcgaggga cccaggtcta cgatgggaag  540
tttgccatct tcgtcatgtt gaactataac accaactcca gccacgctct gcgccagctc  600
cgcttgactc agctcaccga gattctgtca gggggtgttt atattgagaa gaacgataag  660
ctttgtcaca tggacacaat tgactggagg gacatcgtga gggaccgaga tgctgagata  720
gtggtgaagg acaatggcag aagctgtccc ccctgtcatg aggtttgcaa ggggcgatgc  780
tggggtcctg gatcagaaga ctgccagaca ttgaccaaga ccatctgtgc tcctcagtgt  840
aatggtcact gctttgggcc caaccccaac cagtgctgcc atgatgagtg tgccgggggc  900
tgctcaggcc ctcaggacac agactgcttt gcctgccggc acttcaatga cagtggagcc  960
tgtgtacctc gctgtccaca gcctcttgtc tacaacaagc taactttcca gctggaaccc  1020
aatccccaca ccaagtatca gtatggagga gtttgtgtag ccagctgtcc ccataacttt  1080
gtggtggatc aaacatcctg tgtcagggcc tgtcctcctg acaagatgga agtagataaa  1140
aatgggctca agatgtgtga gccttgtggg ggactatgtc ccaaagcctg tgagggaaca  1200
ggctctggga gccgcttcca gactgtggac tcgagcaaca ttgatggatt tgtgaactgc  1260
accaagatcc tgggcaacct ggactttctg atcaccggcc tcaatggaga cccctggcac  1320
aagatccctg ccctggaccc agagaagctc aatgtcttcc ggacagtacg ggagatcaca  1380
ggttacctga acatccagtc ctggccgccc cacatgcaca acttcagtgt tttttccaat  1440
ttgacaacca ttggaggcag aagcctctac aaccggggct tctcattgtt gatcatgaag  1500
aacttgaatg tcacatctct gggcttccga tccctgaagg aaattagtgc tgggcgtatc  1560
tatataagtg ccaataggca gctctgctac caccactctt tgaactggac caaggtgctt  1620
cgggggccta cggaagagcg actagacatc aagcataatc ggccgcgcag agactgcgtg  1680
gcagagggca aagtgtgtga cccactgtgc tcctctgggg gatgctgggg cccaggccct  1740
ggtcagtgct tgtcctgtcg aaattatagc cgaggaggtg tctgtgtgac ccactgcaac  1800
tttctgaatg gggagcctcg agaatttgcc catgaggccg aatgcttctc ctgccacccg  1860
gaatgccaac ccatgggggg cactgccaca tgcaatggct cgggctctga tacttgtgct  1920
caatgtgccc attttcgaga tgggccccac tgtgtgagca gctgccccca tggagtccta  1980
ggtgccaagg gcccaatcta caagtaccca gatgttcaga atgaatgtcg gccctgccat  2040
gagaactgca cccaggggtg taaaggacca gagcttcaag actgtttagg acaaacactg  2100
gtgctgatcg gcaaaaccca tctgacaatg gctttgacag tgatagcagg attggtagtg  2160
attttcatga tgctgggcgg cacttttctc tactggcgtg ggcgccggat tcagaataaa  2220
agggctatga ggcgatactt ggaacggggt gagagcatag agcctctgga ccccagtgag  2280
aaggctaaca aagtcttggc cagaatcttc aaagagacag agctaaggaa gcttaaagtg  2340
cttggctcgg gtgtctttgg aactgtgcac aaaggagtgt ggatccctga gggtgaatca  2400
```

-continued

```
atcaagattc cagtctgcat taaagtcatt gaggacaaga gtggacggca gagttttcaa  2460
gctgtgacag atcatatgct ggccattggc agcctggacc atgcccacat tgtaaggctg  2520
ctgggactat gcccagggtc atctctgcag cttgtcactc aatatttgcc tctgggttct  2580
ctgctggatc atgtgagaca acaccggggg gcactggggc cacagctgct gctcaactgg  2640
ggagtacaaa ttgccaaggg aatgtactac cttgaggaac atggtatggt gcatagaaac  2700
ctggctgccc gaaacgtgct actcaagtca cccagtcagg ttcaggtggc agattttggt  2760
gtggctgacc tgctgcctcc tgatgataag cagctgctat acagtgaggc caagactcca  2820
attaagtgga tggcccttga gagtatccac tttgggaaat acacacacca gagtgatgtc  2880
tggagctatg gtgtgacagt ttgggagttg atgaccttcg gggcagagcc ctatgcaggg  2940
ctacgattgg ctgaagtacc agacctgcta gagaaggggg agcggttggc acagccccag  3000
atctgcacaa ttgatgtcta catggtgatg gtcaagtgtt ggatgattga tgagaacatt  3060
cgcccaacct ttaaagaact agccaatgag ttcaccagga tggcccgaga cccaccacgg  3120
tatctggtca taaagagaga gagtgggcct ggaatagccc ctgggccaga gccccatggt  3180
ctgacaaaca agaagctaga ggaagtagag ctggagccag aactagacct agacctagac  3240
ttggaagcag aggaggacaa cctggcaacc accacactgg gctccgccct cagcctacca  3300
gttggaacac ttaatcggcc acgtgggagc cagagccttt taagtccatc atctggatac  3360
atgcccatga accagggtaa tcttgggggg tcttgccagg agtctgcagt ttctgggagc  3420
agtgaacggt gccccgtcc agtctctcta cacccaatgc cacggggatg cctggcatca  3480
gagtcatcag aggggcatgt aacaggctct gaggctgagc tccaggagaa agtgtcaatg  3540
tgtagaagcc ggagcaggag ccggagccca cggccacgcg gagatagcgc ctaccattcc  3600
cagcgccaca gtctgctgac tcctgttacc ccactctccc cacccgggtt agaggaagag  3660
gatgtcaacg gttatgtcat gccagataca cacctcaaag gtactccctc ctcccgggaa  3720
ggcacccttt cttcagtggg tctcagttct gtcctgggta ctgaagaaga agatgaagat  3780
gaggagtatg aatacatgaa ccggaggaga aggcacagtc cacctcatcc ccctaggcca  3840
agttcccttg aggagctggg ttatgagtac atggatgtgg ggtcagacct cagtgcctct  3900
ctgggcagca cacagagttg cccactccac cctgtaccca tcatgcccac tgcaggcaca  3960
actccagatg aagactatga atatatgaat cggcaacgag atggaggtgg tcctgggggt  4020
gattatgcag ccatgggggc ctgcccagca tctgagcaag ggtatgaaga gatgagagct  4080
tttcaggggc ctggacatca ggccccccat gtccattatg cccgcctaaa aactctacgt  4140
agcttagagg ctacagactc tgcctttgat aaccctgatt actggcatag caggcttttc  4200
cccaaggcta atgcccagag aacgtaactc ctgctccctg tggcactcag ggagcattta  4260
atggcagcta gtgcctttag agggtaccgt cttctcccta ttccctctct ctcccaggtc  4320
ccagcccctt ttccccagtc ccagacaatt ccattcaatc tttggaggct tttaaacatt  4380
ttgacacaaa attcttatgg tatgtagcca gctgtgcact ttcttctctt tcccaacccc  4440
aggaaaggtt ttccttattt tgtgtgcttt cccagtccca ttcctcagct tcttcacagg  4500
cactcctgga gatatgaagg attactctcc atatcccttc ctctcaggct cttgactact  4560
tggaactagg ctcttatgtg tgcctttgtt tcccatcaga ctgtcaagaa gaggaaaggg  4620
aggaaaccta gcagaggaaa gtgtaatttt ggtttatgac tcttaacccc ctagaaagac  4680
agaagcttaa aatctgtgaa gaaagaggtt aggagtagat attgattact atcataattc  4740
agcacttaac tatgagccag gcatcatact aaacttcacc tacattatct cacttagtcc  4800
tttatcatcc ttaaaacaat tctgtgacat acatattatc tcattttaca caaagggaag  4860
tcgggcatgg tggctcatgc ctgtaatctc agcactttgg gaggctgagg cagaaggatt  4920
acctgaggca aggagtttga gaccagctta gccaacatag taagaccccc atctc       4975
```

```
SEQ ID NO: 193          moltype = AA  length = 1342
FEATURE                 Location/Qualifiers
source                  1..1342
                        mol_type = protein
                        organism = Homo sapiens
SEQUENCE: 193
MRANDALQVL GLLFSLARGS EVGNSQAVCP GTLNGLSVTG DAENQYQTLY KLYERCEVVM  60
GNLEIVLTGH NADLSFLQWI REVTGYVLVA MNEFSTLPLP NLRVVRGTQV YDGKFAIFVM  120
LNYNTNSSHA LRQLRLTQLT EILSGGVYIE KNDKLCHMDT IDWRDIVRDR DAEIVVKDNG  180
RSCPPCHEVC KGRCWGPGSE DCQTLTKTIC APQCNGHCFG PNPNQCCHDE CAGGCSGPQD  240
TDCFACRHFN DSGACVPRCP QPLVYNKLTF QLEPNPHTKY QYGGVCVASC PHNFVVDQTS  300
CVRACPPDKM EVDKNGLKMC EPCGGLCPKA CEGTGSGSRF QTVDSSNIDG FVNCTKILGN  360
LDFLITGLNG DPWHKIPALD PEKLNVFRTV REITGYLNIQ SWPPHMHNFS VFSNLTTIGG  420
RSLYNRGFSL LIMKNLNVTS LGFRSLKEIS AGRIYISANR QLCYHHSLNW TKVLRGPTEE  480
RLDIKHNRPR RDCVAEGKVC DPLCSSGGCW GPGPGQCLSC RNYSRGGVCV THCNFLNGEP  540
REFAHEAECF SCHPECQPMG GTATCNGSGS DTCAQCAHFR DGPHCVSSCP HGVLGAKGPI  600
YKYPDVQNEC RPCHENCTQG CKGPELQDCL GQTLVLIGKT HLTMALTVIA GLVVIFMMLG  660
GTFLYWRGRR IQNKRAMRRY LERGESIEPL DPSEKANKVL ARIFKETELR KLKVLGSGVF  720
GTVHKGVWIP EGESIKIPVC IKVIEDKSGR QSFQAVTDHM LAIGSLDHAH IVRLLGLCPG  780
SSLQLVTQYL PLGSLLDHVR QHRGALGPQL LLNWGVQIAK GMYYLEEHGM VHRNLAARNV  840
LLKSPSQVQV ADFGVADLLP PDDKQLLYSE AKTPIKWMAL ESIHFGKYTH QSDVWSYGVT  900
VWELMTFGAE PYAGLRLAEV PDLLEKGERL AQPQICTIDV YMVMVKCWMI DENIRPTFKE  960
LANEFTRMAR DPPRYLVIKR ESGPGIAPGP EPHGLTNKKL EEVELEPELD LDLDLEAEED  1020
NLATTTLGSA LSLPVGTLNR PRGSQSLLSP SSGYMPMNQG NLGGSCQESA VSGSSERCPR  1080
PVSLHPMPRG CLASESSEGH VTGSEAELQE KVSMCRSRSR SRSPRPRGDS AYHSQRHSLL  1140
TPVTPLSPPG LEEEDVNGYV MPDTHLKGTP SSREGTLSSV GLSSVLGTEE EDEDEEYEYM  1200
NRRRRHSPPH PPRPSSLEEL GYEYMDVGSD LSASLGSTQS CPLHPVPIMP TAGTTPDEDY  1260
EYMNRQRDGG GPGGDYAAMG ACPASEQGYE EMRAFQGPGH QAPHVHYARL KTLRSLEATD  1320
SAFDNPDYWH SRLFPKANAQ RT                                          1342
```

```
SEQ ID NO: 194          moltype = DNA  length = 4541
FEATURE                 Location/Qualifiers
source                  1..4541
                        mol_type = other DNA
                        organism = synthetic construct
```

SEQUENCE: 194
ggatcctcta gggtcccagc tcgcctcgat ggagctcctc ccgccgctgc ctcagtcctt 60
cctgttgctg ctgctgttgc ctgccaagcc cgcggcgggc gaggactggc agtgcccgcg 120
cacccccctac gcggcctctc gcgactttga cgtgaagtac gtggtgccca gcttctccgc 180
cggaggcctg gtacaggcca tggtgaccta cgagggcgac agaaatgaga gtgctgtgtt 240
tgtagccata cgcaatcgcc tgcatgtgct tgggcctgac ctgaagtctg tccagagcct 300
ggccacgggc cctgctggag accctggctg ccagacgtgt gcagcctgtg gcccaggacc 360
ccacggccct cccggtgaca cagacacaaa ggtgctggtg ctggatcccg cgctgcctgc 420
gctggtcagt tgtggctcca gcctgcaggg ccgctgcttc ctgcatgacc tagagcccca 480
agggacagcc gtgcatctgg cagcgccagc ctgcctcttc tcagcccacc ataaccggcc 540
cgatgactgc cccgactgtg tggccagccc attgggcacc cgtgtaactg tggttgagca 600
aggccaggcc tcctatttct acgtggcatc ctcactggac gcagccgtgg ctggcagctt 660
cagcccacgc tcagtgtcta tcaggcgtct caaggctgac gcctcgggat tcgcaccggg 720
ctttgtggcg ttgtcagtgc tgcccaagca tcttgtctcc tacagtattg aatacgtgca 780
cagcttccac acgggagcct tcgtatactt cctgactgta cagccggcca gcgtgacaga 840
tgatcctagt gccctgcaca cacgcctggc acggcttagc gccactgagc cagagttggg 900
tgactatcgg gagctggtcc tcgactgcag atttgctcca aaacgcaggc gccgggggc 960
cccagaaggc ggacagccct accctgtgct gcaggtggcc cactccgctc cagtgggtgc 1020
ccaacttgcc actgagctga gcatcgccga gggccaggaa gtactatttg ggtctttgt 1080
gactggcaag gatggtggtc ctggcgtggg ccccaactct gtcgtctgtg ccttccccat 1140
tgacctgctg gacacactaa ttgatgaggg tgtggagcgc tgttgtgaat ccccagtcca 1200
tccaggcctc cggcgaggcc tcgacttctt ccagtcgccc agtttttgcc ccaacccgcc 1260
tggcctggaa gccctcagcc ccaacaccag ctgccgccac ttccctctgc tggtcagtag 1320
cagcttctca cgtgtggacc tattcaatgg gctgttggga ccagtacagg tcactgcatt 1380
gtatgtgaca cgccttgaca acgtcacagt ggcacacatg ggcacaatgg atgggcgtat 1440
cctgcaggtg gagctggtca ggtcactaaa ctacttgctg tatgtgtcca acttctcact 1500
gggtgacagt gggcagcccg tgcagcggga tgtcagtcgt cttggggacc acctactctt 1560
tgcctctggg gaccaggttt tccaggtacc tatccgaggc cctggctgcc gccacttcct 1620
gacctgtggg cgttgcctaa gggcatggca tttcatgggc tgtggctggt gtgggaacat 1680
gtgcggccag cagaaggagt gtcctggctc ctggcaacag gaccactgcc cacctaagct 1740
tactgagttc cacccccaca gtggacctct aaggggcagt acaaggctga ccctgtgtgg 1800
ctccaacttc taccttcacc cttctggtct ggtgcctgag ggaacccatc aggtcactgt 1860
gggccaaagt ccctgccggc cactgcccaa ggacagctca aaactcagac cagtgccccg 1920
gaaagacttt gtagaggagt ttgagtgtga actggagccc ttgggcaccc aggcagtggg 1980
gcctaccaac gtcagcctca ccgtgactaa catgccaccg ggcaagcact tccgggtaga 2040
cggcacctcc gtgctgagag gcttctcttt catggagcca gtgctgatag cagtgcaacc 2100
cctctttggc ccacgggcag gaggcacctg tctcactctt gaaggccaga gtctgtctgt 2160
aggcaccagc cgggctgtgc tggtcaatgg gactgagtgt ctgctagcac gggtcagtga 2220
ggggcagctt ttatgtgcca cacccccctgg ggccacggtg gccagtgtcc cccttagcct 2280
gcaggtgggg ggtgcccagg tacctggttc ctggaccttc cagtacagag aagaccctgt 2340
cgtgctaagc atcagcccca actgtggcta catcaactcc cacatcacca tctgtggcca 2400
gcatctaact tcagcatggc acttagtgct gtcattccat gacgggctta gggcagtgga 2460
aagcaggtgt gagaggcagc ttccagagca gcagctgtgc cgccttcctg aatatgtggt 2520
ccgagacccc cagggatggg tggcagggaa tctgagtgcc cgaggggatg gagctgctgg 2580
ctttacactg cctggctttc gcttcctacc ccccacccat ccacccagtg ccaacctagt 2640
tccactgaag cctgaggagc atgccattaa gtttgagtat attgggctgg gcgctgtggc 2700
tgactgtgtg ggtatcaacg tgaccgtggg tggtgagagc tgccagcacg agttccgggg 2760
ggacatggtt gtctgccccc tgccccccatc cctgcagctt ggccaggatg gtgccccatt 2820
gcaggtctgc gtagatggtg aatgtcatat cctgggtaga gtggtgcggc cagggccaga 2880
tggggtccca cagagcacgc tccttggtat cctgctgcct ttgctgctgc ttgtggctgc 2940
actggcgact gcactggtct tcagctactg gtggcggagg aagcagctag ttcttcctcc 3000
caacctgaat gacctggcat ccctggacca gactgctgga gccacacccc tgcctattct 3060
gtactcgggc tctgactaca gaagtggcct tgcactccct gccattgatg gtctggattc 3120
caccacttgt gtccatggag catccttctc cgatagtgaa gatgaatcct gtgtgccact 3180
gctgcggaaa gagtccatcc agctaaggga cctggactct gcgctcttgg ctgaggtcaa 3240
ggatgtgctg attccccatg agcgggtggt cacccacagt gaccgagtca ttggcaaagg 3300
ccactttgga gttgtctacc acggagaata catagaccag gcccagaatc gaatccaatg 3360
tgccatcaag tcactaagtc gcatcacaga gatgcagcag gtggaggcct tcctgcgaga 3420
ggggctgctc atgcgtggcc tgaaccaccc gaatgtgctg gctctcattg gtatcatgtt 3480
gccacctgag ggcctgcccc atgtgctgct gccctatatg tgccacggtg acctgctcca 3540
gttcatccgc tcacctcagc ggaaccccac cgtgaaggac ctcatcagct ttggcctgca 3600
ggtagcccgc ggcatggagt acctggcaga gcagaagttt gtgcacaggg acctggctgc 3660
gcggaactgc atgctggacg agtcattcac agtcaaggtg gctgactttg gtttggcccg 3720
cgacatcctg gacagggagt actatagtgt tcaacagcat cgccacgctc gcctacctgt 3780
gaagtggatg gcgctggaga gcctgcagac ctatagattt accaccaagt ctgatgtgtg 3840
gtcatttggt gtgctgctgt gggaactgct gacacggggt gccccaccat accgccacat 3900
tgaccctttt gaccttaccc acttcctggc ccagggtcgg cgcctgcccc agcctgagta 3960
ttgccctgat tctctgtacc aagtgatgca gcaatgctgg gaggcagacc cagcagtgcg 4020
acccaccttc agagtactag tgggggaggt ggagcagata gtgtctgcac tgcttgggga 4080
ccattatgtg cagctgccag caacctacat gaacttgggc cccagcacct cgcatgagat 4140
gaatgtgcgt ccagaacagc cgcagttctc acccatgcca gggaatgtac gccggccccg 4200
gccactctca gagcctcctc ggcccacttg acttagttct tgggctggac ctgcttagct 4260
gccttgagct aaccccaagg ctgcctctgg gccatgccag gccagagcag tggccctcca 4320
ccttgttcct gccctttaac tttcagaggc aataggtaaa tgggcccatt aggtccctca 4380
ctccacagag tgagccagtg agggcagtcc tgcaacatgt atttatggag tgcctgctgt 4440
ggaccctgtc ttctgggcac agtggactca gcagtgacca caccaacact gacccttgaa 4500
ccaataaagg aacaaatgac tattaaagca caaaaaaaaa a 4541

SEQ ID NO: 195 moltype = AA length = 661

-continued

```
FEATURE                 Location/Qualifiers
source                  1..661
                        mol_type = protein
                        organism = Homo sapiens
SEQUENCE: 195
MELLPPLPQS FLLLLLLPAK PAAGEDWQCP RTPYAASRDF DVKYVVPSFS AGGLVQAMVT  60
YEGDRNESAV FVAIRNRLHV LGPDLKSVQS LATGPAGDPG CQTCAACGPG PHGPPGDTDT  120
KVLVLDPALP ALVSCGSSLQ GRCFLHDLEP QGTAVHLAAP ACLFSAHHNR PDDCPDCVAS  180
PLGTRVTVVE QGQASYFYVA SSLDAAVAGS FSPRSVSIRR LKADASGFAP GFVALSVLPK  240
HLVSYSIEYV HSFHTGAFVY FLTVQPASVT DDPSALHTRL ARLSATEPEL GDYRELVLDC  300
RFAPKRRRRG APEGGQPYPV LQVAHSAPVG AQLATELSIA EGQEVLFGVF VTGKDGGPGV  360
GPNSVVCAFP IDLLDTLIDE GVERCCESPV HPGLRRGLDF FQSPSFCPNP PGLEALSPNT  420
SCRHFPLLVS SSFSRVDLFN GLLGPVQVTA LYVTRLDNVT VAHMGTMDGR ILQVELVRSL  480
NYLLYVSNFS LGDSGQPVQR DVSRLGDHLL FASGDQVFQV PIRGPGCRHF LTCGRCLRAW  540
HFMGCGWCGN MCGQQKECPG SWQQDHCPPK LTEFHPHSGP LRGSTRLTLC GSNFYLHPSG  600
LVPEGTHQVT VGQSPCRPLP KDSSKLRPVP RKDFVEEFEC ELEPLGTQAV GPTNVSLTVT  660
N                                                                 661

SEQ ID NO: 196          moltype = DNA  length = 3935
FEATURE                 Location/Qualifiers
source                  1..3935
                        mol_type = other DNA
                        organism = synthetic construct
SEQUENCE: 196
aggggcagaa gttgcgcgca ggccggcggg cgggagcgga caccgaggcc ggcgtgcagg  60
cgtgcgggtg tgcgggagcc gggctcgggg ggatcggacc gagagcgaga agcgcggcat  120
ggagctccag gcagcccgcg cctgcttcgc cctgctgtgg ggctgtgcgc tggccgcggc  180
cgcggcggcg cagggcaagg aagtggtact gctggacttt gctgcagctg gaggggagct  240
cggctggctc acacacccgt atggcaaagg gtgggacctg atgcagaaca tcatgaatga  300
catgccgatc tacatgtact ccgtgtgcaa cgtgatgtct ggcgaccagg acaactggct  360
ccgcaccaac tgggtgtacc gaggagaggc tgagcgtatc ttcattgagc tcaagtttac  420
tgtacgtgac tgcaacagct tccctggtgg cgccagctcc tgcaaggaga ctttcaacct  480
ctactatgcc gagtcggacc tggactacgg caccaacttc cagaagcgcc tgttcaccaa  540
gattgacacc attgcgcccg atgagatcac cgtcagcagc gacttcgagg cacgccacgt  600
gaagctgaac gtggaggagc gctccgtggg gccgctcacc cgcaaaggct tctacctggc  660
cttccaggat atcggtgcct gtgtggcgct gctctccgtc cgtgtctact acaagaagtg  720
ccccgagctg ctgcagggcc tggcccactt ccctgagacc atcgccggct ctgatgcacc  780
ttccctggcc actgtggccg gcacctgtgt ggaccatgcc gtggtgccac cggggggtga  840
agagccccgt atgcactgtg cagtggatgg cgagtggctg gtgcccattg ggcagtgcct  900
gtgccaggca ggctacgaga aggtggagga tgcctgccag gcctgctcgc ctggattttt  960
taagtttgag gcatctgaga gcccctgctt ggagtgccct gagcacacgc tgccatcccc  1020
tgagggtgcc acctcctgcg agtgtgagga aggcttcttc cgggcacctc aggacccagc  1080
gtcgatgcct tgcacacgac ccccctccgc cccacactac ctcacagccg tgggcatggg  1140
tgccaaggtg gagctgcgct ggacgccccc tcaggacagc gggggccgcg aggacattgt  1200
ctacagcgtc acctgcgaac agtgctggcc cgagtctggg gaatgcgggc cgtgtgaggc  1260
cagtgtgcgc tactcggagc ctcctcacgg actgacccgc accagtgtga cagtgagcga  1320
cctggagccc cacatgaact acaccttcac cgtggaggcc cgcaatggcg tctcaggcct  1380
ggtaaccagc cgcagcttcc gtactgccag tgtcagcatc aaccagacag agcccccaa  1440
ggtgaggctg gagggccgca gcaccacctc gcttagcgtc tcctggagca tccccccgcc  1500
gcagcagagc cgagtgtgga agtacgaggt cacttaccgc aagaagggag actccaacag  1560
ctacaatgtg cgccgcaccg agggtttctc cgtgaccctg gacgacctgg ccccagacac  1620
cacctacctg gtccaggtgc aggcactgac gcaggagggc caggggccg gcagcaaggt  1680
gcacgaattc cagacgctgt ccccggaggg atctggcaac ttggcggtga ttggcggcgt  1740
ggctgtcggt gtggtcctgc ttctggtgct ggcaggagtt ggcttcttta tccaccgcag  1800
gaggaagaac cagcgtgccc gccagtcccc ggaggacgtt tacttctcca agtcagaaca  1860
actgaagccc ctgaagacat acgtggaccc ccacacatat gaggacccca accaggctgt  1920
gttgaagttc actaccgaga tccatccatc ctgtgtcact cggcagaagg tgatcggagc  1980
aggagagttt ggggaggtgt acaagggcat gctgaagaca tcctcgggga agaaggaggt  2040
gccggtggcc atcaagacgc tgaaagccgg ctacacagag aagcagcgag tggacttcct  2100
cggcgaggcc ggcatcatgg gccagttcag ccaccacaac atcatccgcc tagagggcgt  2160
catctccaaa tacaagccca tgatgatcat cactgagtac atggagaatg gggccctgga  2220
caagttcctt cgggagaagg atggcgagtt cagcgtgctg cagctggtgg gcatgctgcg  2280
gggcatcgca gctggcatga agtacctggc caacatgaac tatgtgcacc gtgacctggc  2340
tgcccgcaac atcctcgtca acagcaacct ggtctgcaag gtgtctgact ttggcctgtc  2400
ccgcgtgctg gaggacgacc ccgaggccac ctacaccacc agtggcggca agatccccat  2460
ccgctggacc gccccggagg ccatttccta ccggaagttc acctctgcca gcgacgtgtg  2520
gagctttggc attgtcatgt gggaggtgat gacctatggc gagcggccct actgggagtt  2580
gtccaaccac gaggtgatga aagccatcaa tgatggcttc cggctcccca cacccatgga  2640
ctgcccctcc gccatctacc agctcatgat gcagtgctgg cagcaggagc gtgcccgccg  2700
ccccaagttc gctgacatcg tcagcatcct ggacaagctc attcgtgccc ctgactccct  2760
caagaccctg gctgactttg acccccgcgt gtctatccgg ctccccagca cgagcggctc  2820
ggagggggtg cccttccgca cggtgtccga gtggctggag tccatcaaga tgcagcagta  2880
tacggagcac ttcatggcgg ccggctacac tgccatcgag aaggtggtgc agatgaccaa  2940
cgacgacatc aagaggattg gggtgcggct gcccggccac cagaagcgca tcgcctacag  3000
cctgctggga ctcaaggacc aggtgaacac tgtggggatc cccatctgag cctcgacagg  3060
gcctggagcc ccatcggcca agaatacttg aagaaacaga gtggcctccc tgctgtgcca  3120
tgctgggcca ctggggactt tatttatttc tagttctttc ctccccctgc aacttccgct  3180
gaggggtctc ggatgacacc ctggcctgaa ctgaggagat gaccagggat gctgggctgg  3240
gccctctttc cctgcgagac gcacacagct gagcacttag caggcaccgc cacgtcccag  3300
```

-continued

```
catccctgga gcaggagccc cgccacagcc ttcggacaga catataggat attcccaagc  3360
cgaccttccc tccgccttct cccacatgag gccatctcag gagatggagg gcttggccca  3420
gcgccaagta aacagggtac ctcaagcccc atttcctcac actaagaggg cagactgtga  3480
acttgactgg gtgagaccca aagcggtccc tgtccctcta gtgccttctt tagaccctcg  3540
ggccccatcc tcatccctga ctggccaaac ccttgctttc ctgggccttt gcaagatgct  3600
tggttgtgtt gaggttttta aatatatatt ttgtactttg tggagaaaat gtgtgtgtgt  3660
ggcaggggggc cccgccaggg ctggggacag agggtgtcaa acattcgtga gctggggact  3720
cagggaccgg tgctgcagga gtgtcctgcc catgccccag tcggccccat ctctcatcct  3780
tttggataag tttctattct gtcagtgtta aagattttgt tttgttggac attttttttcg  3840
aatcttaatt tattattttt tttatattta ttgttagaaa atgacttatt tctgctctgg  3900
aataaagttg cagatgattc aaaaaaaaaa aaaaa                              3935

SEQ ID NO: 197          moltype = AA  length = 976
FEATURE                 Location/Qualifiers
source                  1..976
                        mol_type = protein
                        organism = Homo sapiens
SEQUENCE: 197
MELQAARACF ALLWGCALAA AAAAQGKEVV LLDFAAAGGE LGWLTHPYGK GWDLMQNIMN  60
DMPIYMYSVC NVMSGDQDNW LRTNWVYRGE AERIFIELKF TVRDCNSFPG GASSCKETFN  120
LYYAESDLDY GTNFQKRLFT KIDTIAPDEI TVSSDFEARH VKLNVEERSV GPLTRKGFYL  180
AFQDIGACVA LLSVRVYYKK CPELLQGLAH FPETIAGSDA PSLATVAGTC VDHAVVPPGG  240
EEPRMHCAVD GEWLVPIGQC LCQAGYEKVE DACQACSPGF FKFEASESPC LECPEHTLPS  300
PEGATSCECE EGFFRAPQDP ASMPCTRPPS APHYLTAVGM GAKVELRWTP PQDSGGREDI  360
VYSVTCEQCW PESGECGPCE ASVRYSEPPH GLTRTSVTVS DLEPHMNYTF TVEARNGVSG  420
LVTSRSFRTA SVSINQTEPP KVRLEGRSTT SLSVSWSIPP PQQSRVWKYE VTYRKKGDSN  480
SYNVRRTEGF SVTLDDLAPD TTYLVQVQAL TQEGQGAGSK VHEFQTLSPE GSGNLAVIGG  540
VAVGVVLLLV LAGVGFFIHR RRKNQRARQS PEDVYFSKSE QLKPLKTYVD PHTYEDPNQA  600
VLKFTTEIHP SCVTRQKVIG AGEFGEVYKG MLKTSSGKKE VPVAIKTLKA GYTEKQRVDF  660
LGEAGIMGQF SHHNIIRLEG VISKYKPMMI ITEYMENGAL DKFLREKDGE FSVLQLVGML  720
RGIAAGMKYL ANMNYVHRDL AARNILVNSN LVCKVSDFGL SRVLEDDPEA TYTTSGGKIP  780
IRWTAPEAIS YRKFTSASDV WSFGIVMWEV MTYGERPYWE LSNHEVMKAI NDGFRLPTPM  840
DCPSAIYQLM MQCWQQERAR RPKFADIVSI LDKLIRAPDS LKTLADFDPR VSIRLPSTSG  900
SEGVPFRTVS EWLESIKMQQ YTEHFMAAGY TAIEKVVQMT NDDIKRIGVR LPGHQKRIAY  960
SLLGLKDQVN TVGIPI                                                    976

SEQ ID NO: 198          moltype = DNA  length = 1146
FEATURE                 Location/Qualifiers
source                  1..1146
                        mol_type = other DNA
                        organism = synthetic construct
SEQUENCE: 198
cctcaatgac actcatggag gaaatgctga gagaagcatt cagatgcatg acacaaggta  60
agactgccaa aaatcttgtt cttgctctcc tcattttgtt atttgtttta tttttaggag  120
ttttgagagc aaaatgacaa cacccagaaa ttcagtaaat gggactttcc cggcagagcc  180
aatgaaaggc cctattgcta tgcaatctgg tccaaaacca ctcttcagga ggatgtcttc  240
actggtgggc cccacgcaaa gcttcttcat gagggaatct aagactttgg gggctgtcca  300
gattatgaat gggctcttcc acattgccct ggggggtctt ctgatgatcc cagcagggat  360
ctatgcaccc atctgtgtga ctgtgtggta ccctctctgg ggaggcatta tgtatattat  420
ttccggatca ctcttggcag caacggagaa aaactctagg aagtgtttgg tcaaaggaaa  480
aatgataatg aattcattga gcctctttgc tgccatttct ggaatgattc tttcaatcat  540
ggacatactt aatattaaaa tttcccattt tttaaaaatg gagagtctga attttattag  600
agctcacaca ccatatatta acatatacaa ctgtgaacca gctaatccct ctgagaaaaa  660
ctccccatct acccaatact gttacagcat acaatctctg ttcttgggca ttttgtcagt  720
gatgctgatc tttgccttct tccaggaact tgtaatagct ggcatcgttg agaatgaatg  780
gaaaagaacg tgctccagac ccaaatctaa catagttctc ctgtcagcag aagaaaaaaa  840
agaacagact attgaaataa aagaagaagt ggttgggcta actgaaacat cttcccaacc  900
aaagaatgaa gaagacattg aaattattcc aatccaagaa gaggaagaag aagaaacaga  960
gacgaacttt ccagaacctc cccaagatca ggaatcctca ccaatagaaa atgacagctc  1020
tccttaagtg atttcttctg ttttctgttt cctttttttaa acattagtgt tcatagcttc  1080
caagagacat gctgactttc atttcttgag gtactctgca catacgcacc acatctctat  1140
ctggcc                                                               1146

SEQ ID NO: 199          moltype = AA  length = 297
FEATURE                 Location/Qualifiers
source                  1..297
                        mol_type = protein
                        organism = Homo sapiens
SEQUENCE: 199
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEETETNFP EPPQDQESSP IENDSSP      297

SEQ ID NO: 200          moltype = DNA  length = 8605
FEATURE                 Location/Qualifiers
source                  1..8605
                        mol_type = other DNA
```

-continued organism = synthetic construct
SEQUENCE: 200
aattcgccaa ctgaaaaagt gggaaaggat gtctggaggc gaggcgtccc attacagagg 60
aaggagctcg ctatataagc cagccaaagt tggctgcacc ggccacagcc tgcctactgt 120
cacccgcctc tcccgcgcgc agatacacgc cccgcctcc gtgggcacaa aggcagcgct 180
gctggggaac tcgggggaac gcgcacgtgg gaaccgccgc agctccacac tccaggtact 240
tcttccaagg acctaggtct ctcgcccatc ggaaagaaaa taattctttc aagaagatca 300
gggacaactg atttgaagtc tactctgtgc ttctaaatcc ccaattctgc tgaaagtgag 360
ataccctaga gccctagagc cccagcagca cccagccaaa cccacctcca ccatgggggc 420
catgactcag ctgttggcag gtgtctttct tgctttcctt gccctcgcta ccgaaggtgg 480
ggtcctcaag aaagtcatcc ggcacaagcg acagagtggg gtgaacgcca ccctgccaga 540
agagaaccag ccagtggtgt ttaaccacgt ttacaacatc aagctgccag tgggatccca 600
gtgttcggtg gatctggagt cagccagtgg ggagaaagac ctggcaccgc cttcagagcc 660
cagcgaaagc tttcaggagc acacagtgga tggggaaaac cagattgtct tcacacatcg 720
catcaacatc cccgccggg cctgtggctg tgccgcagcc cctgatgtta aggagctgct 780
gagcagactg gaggagctgg agaacctggt gtcttccctg agggagcaat gtactgcagg 840
agcaggctgc tgtctccagc ctgccacagg ccgcttggac accaggccct tctgtagcgg 900
tcggggcaac ttcagcactg aaggatgtgg ctgtgtctgc gaacctggct ggaaaggccc 960
caactgctct gagcccgaat gtccaggcaa ctgtcacctt cgaggccggt gcattgatgg 1020
gcagtgcatc tgtgacgacg gcttcacggg cgaggactgc agccagctgg cttgccccag 1080
cgactgcaat gaccagggca agtgcgtaaa tggagtctgc atctgtttcg aaggctacgc 1140
cggggctgac tgcagccgtg aaatctgccc agtgccctgc agtgaggagc acggcacatg 1200
tgtagatggc ttgtgtgtgt gccacgatgg ctttgcaggc gatgactgca acaagcctct 1260
gtgtctcaac aattgctaca accgtggacg atgcgtggag aatgagtgcg tgtgtgatga 1320
gggtttcacg ggcgaagact gcagtgagct catctgcccc aatgactgct tcgaccgggg 1380
ccgctgcatc aatggcacct gctactgcga agaaggcttc acaggtgaag actgcgggaa 1440
acccacctgc ccacatgcct gccacaccca gggccggtgt gaggaggggc agtgtgtatg 1500
tgatgagggc tttgccggtg tggactgcag cgagaagagg tgtcctgctg actgtcacaa 1560
tcgtggccgc tgtgtagacg ggcggtgtga gtgtgatgat ggtttcactg gagctgactg 1620
tggggagctc aagtgtccca atggctgcag tggccatggc cgctgtgtca atgggcagtg 1680
tgtgtgtgat gagggctata ctggggagga ctgcagccag ctacggtgcc ccaatgactg 1740
tcacagtcgg ggccgctgtg tcgagggcaa atgtgtatgt gagcaaggct tcaagggcta 1800
tgactgcagt gacatgagct gccctaatga ctgtcaccag cacggccgct gtgtgaatgg 1860
catgtgtgtt tgtgatgacg gctacacagg ggaagactgc cgggatcgcc aatgccccag 1920
ggactgcagc aacaggggcc tctgtgtgga cggacagtgc gtctgtgagg acggcttcac 1980
cggccctgac tgtgcagaac tctcctgtcc aaatgactgc catggccagg gtcgctgtgt 2040
gaatgggcag tgcgtgtgcc atgaaggatt tatgggcaaa gactgcaagg agcaaagatg 2100
tcccagtgac tgtcatggcc agggccgctg cgtggacggc cagtgcatct gccacgaggg 2160
cttcacaggc ctggactgtg gccagcactc ctgccccagt gactgcaaca acttaggaca 2220
atgcgtctcg ggccgctgca tctgcaacga gggctacagc ggagaagact gctcagaggt 2280
gtctcctccc aaagacctcg ttgtgacaga agtgacggaa gagacggtca acctggcctg 2340
ggacaatgag atgcgggtca cagagtacct tgtcgtgtac acgcccaccc acgagggtgg 2400
tctggaaatg cagttccgtg tgcctgggga ccagacgtcc accatcatcc aggagctgga 2460
gcctggtgtg gagtacttta tccgtgtatt tgccatcctg gagaacaaga agagcattcc 2520
tgtcagcgcc agggtggcca cgtacttacc tgcacctgaa ggcctgaaat tcaagtccat 2580
caaggagaca tctgtggaag tggagtggga tcctctagac attgcttttg aaacctggga 2640
gatcatcttc cggaatatga ataaagaaga tgagggagag atcaccaaaa gcctgaggag 2700
gccagagacc tcttaccggc aaactggtct agctcctggg caagagtatg agatatctct 2760
gcacatagtg aaaaacaata cccggggccc tggcctgaag agggtgacca ccacacgctt 2820
ggatgccccc agccagatcg aggtgaaaga tgtcacagac accactgcct tgatcacctg 2880
gttcaagccc ctggctgaga tcgatggcat tgagctgacc tacggcatca aagacgtgcc 2940
aggagaccgt accaccatcg atctcacaga ggacgagaac cagtactcca tcgggaacct 3000
gaagcctgac actgagtacg aggtgtccct catctcccgc agaggtgaca tgtcaagcaa 3060
cccagccaaa gagaccttca caacaggcct cgatgctccc aggaatcttc gacgtgtttc 3120
ccagacagat aacagcatca ccctggaatg gaggaatggc aaggcagcta ttgacagtta 3180
cagaattaag tatgcccccca tctctggagg ggaccacgct gaggttgatg ttccaaagag 3240
ccaacaagcc acaaccaaaa ccacactcac aggtctgagg ccgggaactg aatatgggat 3300
tggagtttct gctgtgaagg aagacaagga gagcaatcca gcgaccatca acgcagccac 3360
agagttggac acgcccaagg accttcaggt ttctgaaact gcagagacca gcctgaccct 3420
gctctggaag acaccgttgg ccaaatttga ccgctaccgc ctcaattaca gtctccccac 3480
aggccagtgg gtgggagtgc agcttccaag aaacaccact tcctatgtcc tgagaggcct 3540
ggaaccagga caggagtaca atgtcctcct gacagccgag aaaggcagac acaagagcaa 3600
gcccgcacgt gtgaaggcat ccactgaaca agcccctgag ctggaaaacc tcaccgtgac 3660
tgaggttggc tgggatggcc tcagactcaa ctggaccgca gctgaccagg cctatgagca 3720
ctttatcatt caggtgcagg aggccaacaa ggtggaggca gctcggaacc tcaccgtgcc 3780
tggcagcctt cgggctgtgg acataccggg cctcaaggct gctacgcctt atacagtctc 3840
catctatggg gtgatccagg gctatagaac accagtgctc tctgctgagg cctccacagg 3900
ggaaactccc aatttgggag aggtcgtggt ggccgaggtg ggctgggatg ccctcaaact 3960
caactggact gctccagaag gggcctatga gtactttttc attcaggtgc aggaggctga 4020
cacagtagag gcagcccaga acctcaccgt cccaggagga ctgaggtcca cagacctgcc 4080
tgggctcaaa gcagccactc attataccat caccatccgc ggggtcactc aggacttcag 4140
cacaacccct ctctctgttg aagtcttgac agaggaggtt ccagatatgg gaaacctcac 4200
agtgaccgag gttagctggg atgctctcag actgaactgg accacgccag atggaaccta 4260
tgaccagttt actattcagg tccaggaggc tgaccaggtg gaagaggctc acaatctcac 4320
ggttcctggc agcctgcgtt ccatggaaat cccaggcctc agggctggca ctccttacac 4380
agtcaccctg cacggcgagg tcaggggcca cagcactcga ccccttgctg tagaggtcgt 4440
cacagaggat ctcccacagc tgggagattt agccgtgtct gaggttggct gggatggcct 4500
cagactcaac tggaccgcag ctgacaatgc ctatgagcac tttgtcattc aggtgcagga 4560
ggtcaacaaa gtggaggcag cccagaacct cacgttgcct ggcagcctca gggctgtgga 4620

```
catcccgggc ctcgaggctg ccacgcctta tagagtctcc atctatgggg tgatccgggg  4680
ctatagaaca ccagtactct ctgctgaggc ctccacagcc aaagaacctg aaattggaaa  4740
cttaaatgtt tctgacataa ctcccgagag cttcaatctc tcctggatgg ctaccgatgg  4800
gatcttcgag acctttacca ttgaaattat tgattccaat aggttgctgg agactgtgga  4860
atataatatc tctggtgctg aacgaactgc ccatatctca gggctacccc ctagtactga  4920
ttttattgtc tacctctctg gacttgctcc cagcatccgg accaaaacca tcagtgccac  4980
agccacgaca gaggccctgc cccttctgga aaacctaacc atttccgaca ttaatcccta  5040
cgggttcaca gtttcctgga tggcatcgga gaatgccttt gacagctttc tagtaacggt  5100
ggtggattct gggaagctgc tggacccccca ggaattcaca ctttcaggaa cccagaggaa  5160
gctggagctt agaggcctca taactggcat tggctatgag gttatggtct ctggcttcac  5220
ccaagggcat caaaccaagc ccttgagggc tgagattgtt acagaagccg aaccggaagt  5280
tgacaacctt ctggtttcag atgccaccccc agacggtttc cgtctgtcct ggacagctga  5340
tgaaggggtc ttcgacaatt ttgttctcaa aatcagagat accaaaaagc agtctgagcc  5400
actggaaata accctacttg cccccgaacg taccagggac ataacaggtc tcagagaggc  5460
tactgaatac gaaattgaac tctatggaat aagcaaagga aggcgatccc agacagtcag  5520
tgctatagca acaacagcca tgggctcccc aaaggaagtc attttctcag acatcactga  5580
aaattcggct actgtcagct ggagggcacc cacagcccaa gtggagagct tccggattac  5640
ctatgtgccc attacaggag gtacaccctc catggtaact gtggacggaa ccaagactca  5700
gaccaggctg gtgaaactca tacctggcgt ggagtacctt gtcagcatca tcgccatgaa  5760
gggctttgag gaaagtgaac ctgtctcagg gtcattcacc acagctctgg atggcccatc  5820
tggcctggtg acagccaaca tcactgactc agaagccttg gccaggtggc agccagccat  5880
tgccactgtg gacagttatg tcatctccta cacaggcgag aaagtgccag aaattacacg  5940
cacggtgtcc gggaacacag tggagtatgc tctgaccgac ctcgagcctg ccacggaata  6000
cacactgaga atctttgcag agaaagggcc ccagaagagc tcaaccatca ctgccaagtt  6060
cacaacagac ctcgattctc caagagactt gactgctact gaggttcagt cggaaactgc  6120
cctccttacc tggcgacccc cccgggcatc agtcaccggt tacctgctgg tctatgaatc  6180
agtggatggc acagtcaagg aagtcattgt gggtccagat accacctcct acagcctggc  6240
agacctgagc ccatccaccc actacacagc caagatccag gcactcaatg ggcccctgag  6300
gagcaatatg atccagacca tcttcaccac aattggactc ctgtacccct tccccaagga  6360
ctgctcccaa gcaatgctga atggagacac gacctctggc ctctacacca tttatctgaa  6420
tggtgataag gctgaggcgc tggaagtctt ctgtgacatg acctctgatg gggggtggatg  6480
gattgtgttc ctgagacgca aaaacggacg cgagaacttc taccaaaact ggaaggcata  6540
tgctgctgga tttggggacc gcagagaaga attctggctt gggctggaca acctgaacaa  6600
aatcacagcc caggggcagt acgagctccg ggtggacctg cgggaccatg ggagacagc  6660
ctttgctgtc tatgacaagt tcagcgtggg agatgccaag actcgctaca agctgaaggt  6720
ggaggggtac agtgggacag caggtgactc catggcctac cacaatggca gatccttctc  6780
cacctttgac aaggacacag attcagccat caccaactgt gctctgtcct acaaaggggc  6840
tttctggtac aggaactgtc accgtgtcaa cctgatgggg agatatgggg acaataacca  6900
cagtcagggc gttaactggt tccactggaa gggccacgaa cactcaatcc agtttgctga  6960
gatgaagctg agaccaagca acttcagaaa tcttgaaggc aggcgcaaac gggcataaat  7020
tccagggacc actgggtgag agaggaataa ggcccagagc gaggaaagga ttttaccaaa  7080
gcatcaatac aaccagccca accatcggtc cacacctggg catttggtga gagtcaaagc  7140
tgaccatgga tccctggggc caacggcaac agcatgggcc tcacctcctc tgtgatttct  7200
ttctttgcac caaagacatc agtctccaac atgtttctgt tttgttgttt gattcagcaa  7260
aaatctccca gtgacaacat cgcaatagtt ttttacttct cttaggtggc tctgggaatg  7320
ggagaggggt aggatgtaca ggggtagttt gttttagaac cagccgtatt ttacatgaag  7380
ctgtataatt aattgtcatt atttttgtta gcaaagatta aatgtgtcat tggaagccat  7440
cccttttttt acatttcata caacagaaac cagaaaagca atactgtttc cattttaagg  7500
atatgattaa tattattaat ataataatga tgatgatgat gatgaaaact aaggattttt  7560
caagagatct ttctttccaa aacatttctg gacagtacct gattgtattt tttttttaaa  7620
taaaagcaca agtacttttg agtttgttat tttgctttga attgttgagt ctgaatttca  7680
ccaaagccaa tcatttgaac aaagcgggga atgttgggat aggaaaggta agtagggata  7740
gtggtcaagt gggagggggtg gaaaggagac taaagactgg gagagaggga agcacttttt  7800
ttaaaataaag ttgaacacac ttgggaaaag cttacaggcc aggcctgtaa tcccaacact  7860
ttgggaggcc aaggtgggag gatagcttaa ccccaggagt ttgagaccag cctgagcaac  7920
atagtgagaa cttgtctcta cagaaaaaaa aaaaaaaaaa aatttaatta ggcaagcgtg  7980
gtagtgcgca cctgtcgtcc cagctactca ggaggctgag gtaggaaaat cactggagcc  8040
caggagttag aggttacagt gagctatgat cacactactg cactccagcc tgggcaacag  8100
agggagaccc tgtctctaaa taaaaaaaga aaagaaaaaa aaagcttaca acttgagatt  8160
cagcatcttg ctcagtattt ccaagactaa tagattatgg tttaaaagat gcttttatac  8220
tcatttcta atgcaactcc tagaaactct atgatatagt tgaggtaagt attgttacca  8280
cacatgggct aagatcccca gaggcagact gcctgagttc aattcttggc tccaccattc  8340
ccaagttccc taacctctct atgcctcagt ttcctcttct gtaaagtagg gacactcata  8400
cttctcattt cagaacattt ttgtgaagaa taaattatgt tatccatttg aggcccttag  8460
aatggtaccc ggtgtatatt aagtgctagt acatgttagc tatcatcatt atcactttat  8520
atgagatgga ctggggttca tagaaaccca atgacttgat tgtggctact actcaataaa  8580
taatagaatt tggatttaaa aaaaa                                        8605
```

```
SEQ ID NO: 201          moltype = AA  length = 2201
FEATURE                 Location/Qualifiers
source                  1..2201
                        mol_type = protein
                        organism = Homo sapiens
SEQUENCE: 201
MGAMTQLLAG VFLAFLALAT EGGVLKKVIR HKRQSGVNAT LPEENQPVVF NHVYNIKLPV  60
GSQCSVDLES ASGEKDLAPP SEPSESFQEH TVDGENQIVF THRINIPRRA CGCAAAPDVK  120
ELLSRLEELE NLVSSLREQC TAGAGCCLQP ATGRLDTRPF CSGRGNFSTE GCGCVCEPGW  180
KGPNCSEPEC PGNCHLRGRC IDGQCICDDG FTGEDCSQLA CPSDCNDQGK CVNGVCICFE  240
GYAGADCSRE ICPVPCSEEH GTCVDGLCVC HDGFAGDDCN KPLCLNNCYN RGRCVENECV  300
```

-continued

```
CDEGFTGEDC SELICPNDCF DRGRCINGTC YCEEGFTGED CGKPTCPHAC HTQGRCEEGQ  360
CVCDEGFAGV DCSEKRCPAD CHNRGRCVDG RCECDDGFTG ADCGELKCPN GCSGHGRCVN  420
GQCVCDEGYT GEDCSQLRCP NDCHSRGRCV EGKCVCEQGF KGYDCSDMSC PNDCHQHGRC  480
VNGMCVCDDG YTGEDCRDRQ CPRDCSNRGL CVDGQCVCED GFTGPDCAEL SCPNDCHGQG  540
RCVNGQCVCH EGFMGKDCKE QRCPSDCHGQ GRCVDGQCIC HEGFTGLDCG QHSCPSDCNN  600
LGQCVSGRCI CNEGYSGEDC SEVSPPKDLV VTEVTEETVN LAWDNEMRVT EYLVVYTPTH  660
EGGLEMQFRV PGDQTSTIIQ ELEPGVEYFI RVFAILENKK SIPVSARVAT YLPAPEGLKF  720
KSIKETSVEV EWDPLDIAFE TWEIIFRNMN KEDEGEITKS LRRPETSYRQ TGLAPGQEYE  780
ISLHIVKNNT RGPGLKRVTT TRLDAPSQIE VKDVTDTTAL ITWFKPLAEI DGIELTYGIK  840
DVPGDRTTID LTEDENQYSI GNLKPDTEYE VSLISRRGDM SSNPAKETFT TGLDAPRNLR  900
RVSQTDNSIT LEWRNGKAAI DSYRIKYAPI SGGDHAEVDV PKSQQATTKT TLTGLRPGTE  960
YGIGVSAVKE DKESNPATIN AATELDTPKD LQVSETAETS LTLLWKTPLA KFDRYRLNYS  1020
LPTGQWVGVQ LPRNTTSYVL RGLEPGQEYN VLLTAEKGRH KSKPARVKAS TEQAPELENL  1080
TVTEVGWDGL RLNWTAADQA YEHFIIQVQE ANKVEAARNL TVPGSLRAVD IPGLKAATPY  1140
TVSIYGVIQG YRTPVLSAEA STGETPNLGE VVVAEVGWDA LKLNWTAPEG AYEYFFIQVQ  1200
EADTVEAAQN LTVPGGLRST DLPGLKAATH YTITIRGVTQ DFSTTPLSVE VLTEEVPDMG  1260
NLTVTEVSWD ALRLNWTTPD GTYDQFTIQV QEADQVEEAH NLTVPGSLRS MEIPGLRAGT  1320
PYTVTLHGEV RGHSTRPLAV EVVTEDLPQL GDLAVSEVGW DGLRLNWTAA DNAYEHFVIQ  1380
VQEVNKVEAA QNLTLPGSLR AVDIPGLEAA TPYRVSIYGV IRGYRTPVLS AEASTAKEPE  1440
IGNLNVSDIT PESFNLSWMA TDGIFETFTI EIIDSNRLLE TVEYNISGAE RTAHISGLPP  1500
STDFIVYLSG LAPSIRTKTI SATATTEALP LLENLTISDI NPYGFTVSWM ASENAFDSFL  1560
VTVVDSGKLL DPQEFTLSGT QRKLELRGLI TGIGYEVMVS GFTQGHQTKP LRAEIVTEAE  1620
PEVDNLLVSD ATPDGFRLSW TADEGVFDNF VLKIRDTKKQ SEPLEITLLA PERTRDITGL  1680
REATEYEIEL YGISKGRRSQ TVSAIATTAM GSPKEVIFSD ITENSATVSW RAPTAQVESF  1740
RITYVPITGG TPSMVTVDGT KTQTRLVKLI PGVEYLVSII AMKGFEESEP VSGSFTTALD  1800
GPSGLVTANI TDSEALARWQ PAIATVDSYV ISYTGEKVPE ITRTVSGNTV EYALTDLEPA  1860
TEYTLRIFAE KGPQKSSTIT AKFTTDLDSP RDLTATEVQS ETALLTWRPP RASVTGYLLV  1920
YESVDGTVKE VIVGPDTTSY SLADLSPSTH YTAKIQALNG PLRSNMIQTI FTTIGLLYPF  1980
PKDCSQAMLN GDTTSGLYTI YLNGDKAEAL EVFCDMTSDG GGWIVFLRRK NGRENFYQNW  2040
KAYAAGFGDR REEFWLGLDN LNKITAQGQY ELRVDLRDHG ETAFAVYDKF SVGDAKTRYK  2100
LKVEGYSGTA GDSMAYHNGR SFSTFDKDTD SAITNCALSY KGAFWYRNCH RVNLMGRYGD  2160
NNHSQGVNWF HWKGHEHSIQ FAEMKLRPSN FRNLEGRRKR A                     2201

SEQ ID NO: 202         moltype = DNA  length = 2814
FEATURE                Location/Qualifiers
source                 1..2814
                       mol_type = other DNA
                       organism = synthetic construct
SEQUENCE: 202
aagaacgccc ccaaaatctg tttctaattt tacagaaatc ttttgaaact tggcacggta  60
ttcaaaagtc cgtggaaaga aaaaaacctt gtcctggctt cagcttccaa ctacaaagac  120
agacttggtc cttttcaacg gttttcacag atccagtgac ccacgctctg aagacagaat  180
tagctaactt tcaaaaacat ctggaaaaat gaagacttgg gtaaaaatcg tatttggagt  240
tgccacctct gctgtgcttg ccttattggt gatgtgcatt gtcttacgcc cttcaagagt  300
tcataactct gaagaaaata caatgagagc actcacactg aaggatattt taaatggaac  360
attttcttat aaaacatttt ttccaaactg gatttcagga caagaatatc ttcatcaatc  420
tgcagataac aatatagtac tttataatat tgaaacagga caatcatata ccattttgag  480
taatagaacc atgaaaagtg tgaatgcttc aaattacggc ttatcacctg atcggcaatt  540
tgtatatcta gaaagtgatt attcaaagct ttggagatac tcttacacag caacatatta  600
catctatgac cttagcaatg gagaatttgt aagaggaaat gagcttcctc gtccaattca  660
gtatttatgc tggtcgcctg ttgggagtaa attagcatat gtctatcaaa acaatatcta  720
tttgaaacaa agaccaggag atccaccttt tcaaataaca tttaatggaa gagaaaataa  780
aatatttaat ggaatcccag actgggttta tgaagaggaa atgcttccta caaaatatgc  840
tctctggtgg tctcctaatg gaaaattttt ggcatatgcg gaatttaatg ataaggatat  900
accagttatt gcctattcct attatggcga tgaacaatat cctagaacaa taaatattcc  960
atacccaaag gctggagcta agaatcccgt tgttcggata tttattatcg ataccactta  1020
ccctgcgtat gtaggtcccc aggaagtgcc tgttccagca atgatagcct caagtgatta  1080
ttatttcagt tggctcacgt gggttactga tgaacgagta tgtttgcagt ggctaaaaag  1140
agtccagaat gtttcggtcc tgtctatatg tgacttcagg gaagactggc agacatggga  1200
ttgtccaaag acccaggagc atatagaaga aagcagaact ggatgggctg gtggattctt  1260
tgtttcaaga ccagttttca gctatgatgc catttcgtac tacaaaatat ttagtgacaa  1320
ggatggctac aaacatattc actatatcaa agacactgtg gaaaatgcta ttcaaattac  1380
aagtggcaag tgggaggcca taaatatatt cagagtaaca caggattcac tgtttttattc  1440
tagcaatgaa tttgaagaat accctggaag aagaaacatc tacagaatta gcattggaag  1500
ctatcctcca agcaagaagt gtgttacttg ccatctaagg aaagaaaggt gccaatatta  1560
cacagcaagt ttcagcgact acgccaagta ctatgcactt gtctgctacg gcccaggcat  1620
ccccatttcc acccttcatg atggacgcac tgatcaagaa attaaaatcc tggaagaaaa  1680
caaggaattg gaaaatgctt tgaaaaatat ccagctgcct aaagaggaaa ttaagaaact  1740
tgaagtagat gaaattactt tatggtacaa gatgattctt cctcctcaat ttgacagatc  1800
aaagaagtat cccttgctaa ttcaagtgta tggtggtccc tgcagtcaga gtgtaaggtc  1860
tgtatttgct gttaattgga tatcttatct tgcaagtaag gaagggatgg tcattgcctt  1920
ggtggatggt cgaggaacag ctttccaagg tgacaaactc ctctatgcag tgtatcgaaa  1980
gctgggtgtt tatgaagttg aagaccagat tacagctgtc agaaaattca tagaaatggg  2040
tttcattgat gaaaaaagaa tagccatatg ggctggtcc tatggaggat acgtttcatc  2100
actggccctt gcatctggaa ctggtctttt caaatgtggt atagcagtgg ctccagtctc  2160
cagctgggaa tattacgcgt ctgtctacac agagagattc atgggtctcc caacaaagga  2220
tgataatctt gagcactata agaattcaac tgtgatggca agagcagaat atttcagaaa  2280
tgtagactat cttctcatcc acggaacagc agatgataat gtgcactttc aaaactcagc  2340
acagattgct aaagctctgg ttaatgcaca agtggatttc caggcaatgt ggtactctga  2400
```

```
ccagaaccac ggcttatccg gcctgtccac gaaccactta tacacccaca tgacccactt  2460
cctaaagcag tgtttctctt tgtcagacta aaaacgatgc agatgcaagc ctgtatcaga  2520
atctgaaaac cttatataaa cccctcagac agtttgctta ttttattttt tatgttgtaa  2580
aatgctagta taaacaaaca aattaatgtt gttctaaagg ctgttaaaaa aaagatgagg  2640
actcagaagt tcaagctaaa tattgtttac attttctggt actctgtgaa agaagagaaa  2700
agggagtcat gcattttgct ttggacacag tgttttatca cctgttcatt tgaagaaaaa  2760
taataaagtc agaagttcaa aaaaaaaaaa aaaaaaaaaa aaagcggccg ctcg        2814

SEQ ID NO: 203         moltype = AA  length = 760
FEATURE                Location/Qualifiers
source                 1..760
                       mol_type = protein
                       organism = Homo sapiens
SEQUENCE: 203
MKTWVKIVFG VATSAVLALL VMCIVLRPSR VHNSEENTMR ALTLKDILNG TFSYKTFFPN  60
WISGQEYLHQ SADNNIVLYN IETGQSYTIL SNRTMKSVNA SNYGLSPDRQ FVYLESDYSK  120
LWRYSYTATY YIYDLSNGEF VRGNELPRPI QYLCWSPVGS KLAYVYQNNI YLKQRPGDPP  180
FQITFNGREN KIFNGIPDWV YEEEMLPTKY ALWWSPNGKF LAYAEFNDKD IPVIAYSYYG  240
DEQYPRTINI PYPKAGAKNP VVRIFIIDTT YPAYVGPQEV PVPAMIASSD YYFSWLTWVT  300
DERVCLQWLK RVQNVSVLSI CDFREDWQTW DCPKTQEHIE ESRTGWAGGF FVSRPVFSYD  360
AISYYKIFSD KDGYKHIHYI KDTVENAIQI TSGKWEAINI FRVTQDSLFY SSNEFEEYPG  420
RRNIYRISIG SYPPSKKCVT CHLRKERCQY YTASFSDYAK YYALVCYGPG IPISTLHDGR  480
TDQEIKILEE NKELENALKN IQLPKEEIKK LEVDEITLWY KMILPPQFDR SKKYPLLIQV  540
YGGPCSQSVR SVFAVNWISY LASKEGMVIA LVDGRGTAFQ GDKLLYAVYR KLGVYEVEDQ  600
ITAVRKFIEM GFIDEKRIAI WGWSYGGYVS SLALASGTGL FKCGIAVAPV SSWEYYASVY  660
TERFMGLPTK DDNLEHYKNS TVMARAEYFR NVDYLLIHGT ADDNVHFQNS AQIAKALVNA  720
QVDFQAMWYS DQNHGLSGLS TNHLYTHMTH FLKQCFSLSD                        760

SEQ ID NO: 204         moltype = DNA  length = 1815
FEATURE                Location/Qualifiers
source                 1..1815
                       mol_type = other DNA
                       organism = synthetic construct
SEQUENCE: 204
gcagagctct gtgctccctg cagtcaggac tctgggaccg caggggggctc ccggaccctg  60
actctgcagc cgaaccggca cggtttcgtg gggacccagg cttgcaaagt gacggtcatt  120
ttctctttct ttctccctct tgagtccttc tgagatgatg gctctgggcg cagcgggagc  180
tacccgggtc tttgtcgcga tggtagcggc ggctctcggc ggccaccctc tgctgggagt  240
gagcgccacc ttgaactcgg ttctcaattc caacgctatc aagaacctgc cccccaccgct  300
gggcggcgct gcggggcacc caggctctgc agtcagcgcc gcgccgggaa tcctgtaccc  360
gggcgggaat aagtaccaga ccattgacaa ctaccagccg tacccgtgcg cagaggacga  420
ggagtgcggc actgatgagt actgcgctag tcccacccgc ggaggggacg caggcgtgca  480
aatctgtctc gcctgcagga agcgccgaaa acgctgcatg cgtcacgcta tgtgctgccc  540
cgggaattac tgcaaaaatg gaatatgtgt gtcttctgat caaaatcatt tccgaggaga  600
aattgaggaa accatcactg aaagctttgg taatgatcat agcaccttgg atgggtattc  660
cagaagaacc accttgtctt caaaaatgta tcacaccaaa ggacaagaag gttctgtttg  720
tctccggtca tcagactgtg cctcaggatt gtgttgtgct agacacttct ggtccaagat  780
ctgtaaacct gtcctgaaag aaggtcaagt gtgtaccaag cataggagaa aaggctctca  840
tggactagaa atattccagc gttgttactg tggagaaggt ctgtcttgcc ggatacagaa  900
agatcaccat caagccagta attcttctag gcttcacact tgtcagagac actaaaccag  960
ctatccaaat gcagtgaact ccttttatat aatagatgct atgaaaacct tttatgacct  1020
tcatcaactc aatcctaagg atatacaagt tctgtggttt cagttaagca ttccaataac  1080
accttccaaa aacctggagt gtaagagctt tgtttcttta tggaactccc ctgtgattgc  1140
agtaaattac tgtattgtaa attctcagtg tggcacttac ctgtaaatgc aatgaaactt  1200
ttaattattt ttctaaaggt gctgcactgc ctatttttcc tcttgttatg taaatttttg  1260
tacacattga ttgttatctt gactgacaaa tattctatat tgaactgaag taaatcattt  1320
cagcttatag ttcttaaaag cataaccctt taccccattt aattctagag tctagaacgc  1380
aaggatctct tggaatgaca aatgataggt acctaaaatg taacatgaaa atactagctt  1440
attttctgaa atgtactatc ttaatgctta aattatattt ccctttaggc tgtgatagtt  1500
tttgaaataa aatttaacat ttaatatcat gaaatgttat aagtagacat acattttggg  1560
attgtgatct tagaggtttg tgtgtgtgta cgtatgtgtg tgttctacaa gaacggaagt  1620
gtgatatgtt taaagatgat cagagaaaag acagtgtcta aatataagac aatattgatc  1680
agctctagaa taactttaaa gaaagacgtg ttctgcattg ataaactcaa atgatcatgg  1740
cagaatgaga gtgaatctta cattactact ttcaaaaata gtttccaata aattaataat  1800
acctaaaaaa aaaaa                                                   1815

SEQ ID NO: 205         moltype = AA  length = 266
FEATURE                Location/Qualifiers
source                 1..266
                       mol_type = protein
                       organism = Homo sapiens
SEQUENCE: 205
MMALGAAGAT RVFVAMVAAA LGGHPLLGVS ATLNSVLNSN AIKNLPPPLG GAAGHPGSAV  60
SAAPGILYPG GNKYQTIDNY QPYPCAEDEE CGTDEYCASP TRGGDAGVQI CLACRKRRKR  120
CMRHAMCCPG NYCKNGICVS SDQNHFRGEI EETITESFGN DHSTLDGYSR RTTLSSKMYH  180
TKGQEGSVCL RSSDCASGLC CARHFWSKIC KPVLKEGQVC TKHRRKGSHG LEIFQRCYCG  240
EGLSCRIQKD HHQASNSSRL HTCQRH                                        266

SEQ ID NO: 206         moltype = DNA  length = 523
```

-continued

```
FEATURE                 Location/Qualifiers
source                  1..523
                        mol_type = other DNA
                        organism = synthetic construct
SEQUENCE: 206
ctcctggttc aaaagcagct aaaccaaaag aagcctccag acagccctga gatcacctaa  60
aaagctgcta ccaagacagc cacgaagatc ctaccaaaat gaagcgcttc ctcttcctcc  120
tactcaccat cagcctcctg gttatggtac agatacaaac tggactctca ggacaaaacg  180
acaccagcca aaccagcagc ccctcagcat ccagcaacat aagcggaggc attttccttt  240
tcttcgtggc caatgccata atccacctct tctgcttcag ttgaggtgac acgtctcagc  300
cttagccctg tgccccctga aacagctgcc accatcactc gcaagagaat cccctccatc  360
tttgggaggg gttgatgcca gacatcacca ggttgtagaa gttgacaggc agtgccatgg  420
gggcaacagc caaaataggg gggtaatgat gtaggggcca agcagtgccc agctgggggt  480
caataaagtt acccttgtac ttgcaaaaaa aaaaaaaaaa aaa                    523

SEQ ID NO: 207          moltype = AA  length = 61
FEATURE                 Location/Qualifiers
source                  1..61
                        mol_type = protein
                        organism = Homo sapiens
SEQUENCE: 207
MKRFLFLLLT ISLLVMVQIQ TGLSGQNDTS QTSSPSASSN ISGGIFLFFV ANAIIHLFCF  60
S                                                                  61

SEQ ID NO: 208          moltype = DNA  length = 2672
FEATURE                 Location/Qualifiers
source                  1..2672
                        mol_type = other DNA
                        organism = synthetic construct
SEQUENCE: 208
cttccagaga gcaatatggc tggttcccca acatgcctca ccctcatcta tatcctttgg  60
cagctcacag ggtcagcagc ctctggaccc gtgaaagagc tggtcggttc cgttggtggg  120
gccgtgactt tcccccctgaa gtccaaagta aagcaagttg actctattgt ctggaccttc  180
aacacaaccc ctcttgtcac catacagcca gaagggggca ctatcatagt gacccaaaat  240
cgtaataggg agagagtaga cttcccagat ggaggctact ccctgaagct cagcaaactg  300
aagaagaatg actcagggat ctactatgtg gggatataca gctcatcact ccagcagccc  360
tccacccagg agtacgtgct gcatgtctac gagcacctgt caaagcctaa agtcaccatg  420
ggtctgcaga gcaataagaa tggcacctgt gtgaccaatc tgacatgctg catggaacat  480
ggggaagagg atgtgattta tacctggaag gccctggggc aagcagccaa tgagtcccat  540
aatgggtcca tcctccccat ctcctggaga tggggagaaa gtgatatgac cttcatctgc  600
gttgccagga accctgtcag cagaaacttc tcaagcccca tccttgccag gaagctctgt  660
gaaggtgctg ctgatgaccc agattcctcc atggtcctcc tgtgtctcct gttggtgccc  720
ctcctgctca gtctctttgt actggggcta tttctttggt ttctgaagag agagagacaa  780
gaagagtaca ttgaagagaa gaagagagtg gacatttgtc gggaaactcc taacatatgc  840
ccccattctg gagagaacac agagtacgac acaatccctc acactaatag aacaatccta  900
aaggaagatc cagcaaatac ggtttactcc actgtggaaa taccgaaaaa gatggaaaat  960
ccccactcac tgctcacgat gccagacaca ccaaggctat ttgcctatga gaatgttatc  1020
tagacagcag tgcactcccc taagtctctg ctcaaaaaaa aaacaattct cggcccaaag  1080
aaaacaatca gaagaattca ctgatttgac tagaaacatc aaggaagaat gaagaacgtt  1140
gactttttttc caggataaat tatctctgat gcttctttag atttaagagt tcataattcc  1200
atccactgct gagaaatctc ctcaaaccca gaaggtttaa tcacttcatc ccaaaaatgg  1260
gattgtgaat gtcagcaaac cataaaaaaa gtgcttagaa gtattcctat agaaatgtaa  1320
atgcaaggtc acacatatta atgacagcct gttgtattaa tgatggctcc aggtcagtgt  1380
ctggagtttc attccatccc agggcttgga tgtaaggatt ataccaagag tcttgctacc  1440
aggagggcaa gaagaccaaa acagacagac aagtccagca gaagcagatg cacctgacaa  1500
aaatggatgt attaattggc tctataaact atgtgcccag cactatgctg agcttacact  1560
aattggtcag acgtgctgtc tgccctcatg aaattggctc caaatgaatg aactactttc  1620
atgagcagtt gtagcaggcc tgaccacaga ttcccagagg gccaggtgtg gatccacagg  1680
acttgaaggt caaagttcac aaagatgaag aatcagggta gctgaccatg tttggcagat  1740
actataatgg agacacagaa gtgtgcatgg cccaaggaca aggacctcca gccaggcttc  1800
atttatgcac ttgtgctgca aaagaaaagt ctaggtttta aggctgtgcc agaacccatc  1860
ccaataaaga gaccgagtct gaagtcacat tgtaaatcta gtgtaggaga cttggagtca  1920
ggcagtgaga ctggtggggc acggggggca gtgggtactt gtaaaccttt aaagatggtt  1980
aattcattca atagatattt attaagaacc tatgcggccc ggcatggtgg ctcacacctg  2040
taatcccagc actttgggag gccaaggtgg gtgggtcatc tgaggtcagg agttcaagac  2100
cagcctggcc aacatggtga aaccccatct ctactaaaga tacaaaaatt tgctgagcgt  2160
ggtggtgtgc acctgtaatc ccagctactc gagaggccaa ggcatgagaa tcgcttgaac  2220
ctgggaggtg gaggttgcag tgagctgaga tggcaccact gcactccggc ctaggcaacg  2280
agagcaaaac tccaatacaa acaaacaaac aaacacctgt gctaggtcag tctggcacgt  2340
aagatgaaca tccctaccaa cacagagctc accatctctt atacttaagt gaaaaacatg  2400
gggaagggga aaggggaatg gctgcttttg atatgttccc tgacacatat cttgaatgga  2460
gacctcccta ccaagtgatg aaagtgttga aaaacttaat aacaaatgct tgttgggcaa  2520
gaatgggatt gaggattatc ttctctcaga aaggcattgt gaaggaattg agccagatct  2580
ctctccctac tgcaaaaccc tattgtagta aaaaagtctt ctttactatc ttaataaaac  2640
agatattgtg agattcaaaa aaaaaaaaaa aa                                2672

SEQ ID NO: 209          moltype = AA  length = 335
FEATURE                 Location/Qualifiers
source                  1..335
```

```
                         mol_type = protein
                         organism = Homo sapiens
SEQUENCE: 209
MAGSPTCLTL IYILWQLTGS AASGPVKELV GSVGGAVTFP LKSKVKQVDS IVWTFNTTPL  60
VTIQPEGGTI IVTQNRNRER VDFPDGGYSL KLSKLKKNDS GIYYVGIYSS SLQQPSTQEY  120
VLHVYEHLSK PKVTMGLQSN KNGTCVTNLT CCMEHGEEDV IYTWKALGQA ANESHNGSIL  180
PISWRWGESD MTFICVARNP VSRNFSSPIL ARKLCEGAAD DPDSSMVLLC LLLVPLLLSL  240
FVLGLFLWFL KRERQEEYIE EKKRVDICRE TPNICPHSGE NTEYDTIPHT NRTILKEDPA  300
NTVYSTVEIP KKMENPHSLL TMPDTPRLFA YENVI                           335

SEQ ID NO: 210          moltype = DNA  length = 3292
FEATURE                 Location/Qualifiers
source                  1..3292
                        mol_type = other DNA
                        organism = synthetic construct
SEQUENCE: 210
ccgcggtggt cccaatctct tccttcctcc atgaggtgtc tggggtcggg gccccagttc  60
ttcctggagt ccatctggag tctctcctac tttctagaga atccattggg tcttgtttac  120
aacgtggatg gggacagact gtgcagcgtg gagggaaggg gagggaggga ggtttgggaa  180
gagcctcctg tggggtcctg tcactgcccc agatgcccca acaccctgtg atacctgcac  240
ccctgccaca tctgtccctc actccaaact cagctcaagg ggatggtggc agggaagaag  300
gtgagcttgg aacccaggca gccctggggt caccacctcc agctggggtt cctcctctgt  360
aaagtggagg tataacggta cccacctcct ggggtggctg tgaggattca gagctgataa  420
ggtgaacgcc tagggcgggc cctggtgcag agagagcgct cagctcctag gctggattaa  480
ctgtccctgg ggcacagatc tcggtctggg gcctgtggaa acctcagagc cacccctgaa  540
cccccaccga gccacctttg cctcgcagtg ccatggcctc gtctccgagt tacaggaaaa  600
ggcagagaat gcccttctca ggtggccctc tgggagagac actctccttg actccaaagc  660
cacgcttggc tgcaaactgg gccagcacca caaggctggg caagcaaaca tcctaatccc  720
accaaaacca caccgacctc caccctgtga cactctgcaa caaacacacg gcctactctt  780
gtcacccggg ccggccaata agcacggaag aggcaaggcc tcagaccctg gacagacatc  840
ctccctccag aggcacccag ggcctcagcc ttctcctccc tccctggcct caatttctcc  900
acctgtgacc cagggcaggt ggatccaggg agaagaacct tctggctcca tctcaccgtg  960
ggtcctgcca gcacacacaa agatttggcc tctcaaagcc tagctctgcc agcgtccttc  1020
tgctcaagaa ctctccatga ctcccagtgg ccctaaggac aaagtcctgg catttgaggc  1080
cctcccaatg cagggccaga ctctgcctct ccagcttcct gtccccacca cacccctgct  1140
gtctcacggt ggtccgactg tttcctgctt ctgttgcttt gcttagtctg gcaccctgct  1200
ggcatgcttt ctcacccttc ttccccaatc ccaactcacc cagtctttca aagggcaggc  1260
taaataccag gcctccaggt ggcccaggat tcttctctga gctttcatgg gcctggccct  1320
gggtgctacc tgtgagtagt cccacggtgg gtacatagta ggtgcgctta ctgtttgcaa  1380
gaatgaacat gggacagttt ggggactgtc acccagctca gggagcactg atggggaagc  1440
atctcctgta tgtcccaggg ctcagtgctg tagtgtcctg accctcagaa atctcataat  1500
ggcttggtca ggaaggcatc gtgccccact ttgcaaacag ggggtgctga gaattgaggg  1560
gccttgtcca aggtctcatg gctaggagca agcagaatcg gatttgaacc cagggccacg  1620
tgacttcaga agtgccatta aagtccccat aatttggagc tgtcttcttt tttttttttct  1680
tttctttttt tttgagaccg agcctcactc tgtcacctag gccaggagtg cagtggtctg  1740
atctcagctc actgcaacct ccgcctccta ggttcaagtg attctctagc ctcagcctcc  1800
caagtagctg ggactacagg cgcacgtcat catgcccagc taacttttgt atttttagta  1860
gagatgggtt ttcaccatgt tggtcaggct ggtctcgaac tcctgacctc aagtgatccg  1920
tctgcctcgg cctctcaaag tgctgggatt ataaggcttg agccactaca ctcggcctgg  1980
agctgtgttt tgtcggtgaa ggattttcca cccatgaagg ggtcagacgt gaagtgtgtg  2040
gccctgggca gctcctctga gcccagagac gccagcccta gccgccttgc tgtgccactt  2100
tgggacttcc ctccctagcc tgagcttcag ttttcctgcc tgttaggcag ccccatgtca  2160
actgcactta gtaggccggg tttgatgccc gacaagacgt gaagtggtgg aggtgggcag  2220
gatcccagcg ctaccatctt cttgaaccag tgatctcaac acatcggatt tctgtttcct  2280
catctgcaaa atgggatcag tgagctcagg tgggtcacaa attctacagg aactacttta  2340
gccaagcccg gcccccctgaa agttcccctc ggtgggctgt tagggtgatt gttttcatct  2400
gtggggctcc tgatgcgtcc cacccaccag ccttggagag ggtgggatgg gagggtgggg  2460
tgcttgggga gacaagccta gagcctgggc ctcccacccc actgcctccc cccatcccag  2520
ggccccccac ccagtgacaa agcccgtggc acttcctcta cccggttggc aggcggcctg  2580
gcccagcccc ttctctaagg aagcgcattt cctgcctccc tgggccggcc gggctggatg  2640
agccgggagc tccctgctgc cggtcatacc acagccttca tctgcgccct ggggccagga  2700
ctgctgctgt cactgccatc cattggagcc cagcaccccc tccccgccca tccttcggac  2760
agcaactcca gcccagcccc gcgtccctgt gtccacttct cctgaccctc ggccgccacc  2820
ccagaaggct ggagcaggga cgccgtcgct ccggccgcct gctcccctcg ggtccccgtg  2880
cgagcccacg ccggccccgg tgcccgcccg cagccctgcc actggacaca ggataaggcc  2940
cagcgcacag gcccccacgt ggacagcatg gaccgcggca cgctccctct ggctgttgcc  3000
ctgctgctgg ccagctgcag cctcagcccc acaagtaggt gtccagggac ccagggtggg  3060
gagactcggc ctccggtgca cggaccaggc cccaagtatt cccggcctcc ttcctgtatc  3120
ctgagctcac gcccagcaga gccatccttg gggctctgga gggtcaccaa ccctcccagt  3180
ttgctggaac taaatggtta tgcaggactt tcagtgttga aagaaagcct cgggcaaact  3240
gggctgactc tttcacttta accctggtct ctggcgtctg ctcacccagc tg          3292

SEQ ID NO: 211          moltype = AA  length = 22
FEATURE                 Location/Qualifiers
source                  1..22
                        mol_type = protein
                        organism = Homo sapiens
SEQUENCE: 211
MDRGTLPLAV ALLLASCSLS PT                                         22
```

```
SEQ ID NO: 212          moltype = DNA  length = 1399
FEATURE                 Location/Qualifiers
source                  1..1399
                        mol_type = other DNA
                        organism = synthetic construct
SEQUENCE: 212
agtgtgaaat cttcagagaa gaatttctct ttagttcttt gcaagaaggt agagataaag  60
acactttttc aaaaatggca atggtatcag aattcctcaa gcaggcctgg tttattgaaa  120
atgaagagca ggaatatgtt caaactgtga agtcatccaa aggtggtccc ggatcagcgg  180
tgagccccta tcctaccttc aatccatcct cggatgtcgc tgccttgcat aaggccataa  240
tggttaaagg tgtggatgaa gcaaccatca ttgacattct aactaagcga aacaatgcac  300
agcgtcaaca gatcaaagca gcatatctcc aggaaacagg aaagcccctg gatgaaacac  360
ttaagaaagc ccttacaggt caccttgagg aggttgtttt agctctgcta aaaactccag  420
cgcaatttga tgctgatgaa cttcgtgctg ccatgaaggg ccttggaact gatgaagata  480
ctctaattga gattttggca tcaagaacta acaaagaaat cagagacatt aacagggtct  540
acagagagga actgaagaga gatctggcca aagacataac ctcagacaca tctggagatt  600
ttcggaacgc tttgctttct cttgctaagg gtgaccgatc tgaggacttt ggtgtgaatg  660
aagacttggc tgattcagat gccagggcct tgtatgaagc aggagaaagg agaaagggga  720
cagacgtaaa cgtgttcaat accatcctta ccaccagaag ctatccacaa cttcgcagag  780
tgtttcagaa atacaccaag tacagtaagc atgacatgaa caaagttctg gacctggagt  840
tgaaaggtga cattgagaaa tgcctcacag ctatcgtgaa gtgcgccaca agcaaaccag  900
ctttctttgc agagaagctt catcaagcca tgaaaggtgt tggaactcgc cataaggcat  960
tgatcaggat tatggtttcc cgttctgaaa ttgacatgaa tgatatcaaa gcattctatc  1020
agaagatgta tggtatctcc ctttgccaag ccatcctgga tgaaaccaaa ggagattatg  1080
agaaaatcct ggtggctctt tgtggaggaa actaaacatt cccttgatgg tctcaagcta  1140
tgatcagaag actttaatta tatattttca tcctataagc ttaaatagga aagtttcttc  1200
aacaggatta cagtgtagct acctacatgc tgaaaaatat agcctttaaa tcatttttat  1260
attataactc tgtataatag agataagtcc atttttaaa aatgttttcc ccaaaccata  1320
aaaccctata caagttgttc tagtaacaat acatgagaaa gatgtctatg tagctgaaaa  1380
taaaatgacg tcacaagac                                               1399

SEQ ID NO: 213          moltype = AA  length = 346
FEATURE                 Location/Qualifiers
source                  1..346
                        mol_type = protein
                        organism = Homo sapiens
SEQUENCE: 213
MAMVSEFLKQ AWFIENEEQE YVQTVKSSKG GPGSAVSPYP TFNPSSDVAA LHKAIMVKGV  60
DEATIIDILT KRNNAQRQQI KAAYLQETGK PLDETLKKAL TGHLEEVVLA LLKTPAQFDA  120
DELRAAMKGL GTDEDTLIEI LASRTNKEIR DINRVYREEL KRDLAKDITS DTSGDFRNAL  180
LSLAKGDRSE DFGVNEDLAD SDARALYEAG ERRKGTDVNV FNTILTTRSY PQLRRVFQKY  240
TKYSKHDMNK VLDLELKGDI EKCLTAIVKC ATSKPAFFAE KLHQAMKGVG TRHKALIRIM  300
VSRSEIDMND IKAFYQKMYG ISLCQAILDE TKGDYEKILV ALCGGN                  346

SEQ ID NO: 214          moltype = DNA  length = 3080
FEATURE                 Location/Qualifiers
source                  1..3080
                        mol_type = other DNA
                        organism = synthetic construct
SEQUENCE: 214
cactggcttc aggagctgaa taccctccca ggcacacaca ggtgggacac aaataagggt  60
tttggaacca ctattttctc atcacgacag caacttaaaa tgcctgggaa gatggtcgtg  120
atccttggag cctcaaatat actttggata atgtttgcag cttctcaagc ttttaaaatc  180
gagaccaccc cagaatctag atatcttgct cagattggtg actccgtctc attgacttgc  240
agcaccacag gctgtgagtc ccatttttc tcttggagaa cccagataga tagtccactg  300
aatgggaagg tgacgaatga ggggaccaca tctacgctga caatgaatcc tgttagtttt  360
gggaacgaac actcttacct gtgcacagca acttgtgaat ctaggaaatt ggaaaaagga  420
atccaggtgg agatctactc ttttcctaag gatccagaga ttcatttgag tggccctctg  480
gaggctggga agccgatcac agtcaagtgt tcagttgctg atgtataccc atttgacagg  540
ctggagatag acttactgaa aggagatcat ctcatgaaga gtcaggaatt tctggaggat  600
gcagacagga agtccctgga aaccaagagt ttggaagtaa cctttactcc tgtcattgag  660
gatattggaa aagttcttgt ttgccgagct aaattacaca ttgatgaaat ggattctgtg  720
cccacagtaa ggcaggctgt aaaagaattg caagtctaca tatcacccaa gaatacagtt  780
atttctgtga atccatccac aaagctgcaa gaaggtggct ctgtgaccat gacctgttcc  840
agcgagggtc taccagctcc agagattttc tggagtaaga aattagataa tgggaatcta  900
cagcaccttt ctggaaatgc aactctcacc ttaattgcta tgaggatgga agattctgga  960
atttatgtgt gtgaaggagt taatttgatt gggaaaaaca gaaaagaggt ggaattaatt  1020
gttcaagaga aaccatttac tgttgagatc tcccctggac cccggattgc tgctcagatt  1080
ggagactcag tcatgttgac atgtagtgtc atgggctgtg aatccccatc tttctcctgg  1140
agaacccaga tagacagccc tctgagcggg aaggtgagga gtgaggggac caattccacg  1200
ctgaccctga gccctgtgag ttttgagaac gaacactctt atctgtgcac agtgacttgt  1260
ggacataaga aactggaaaa gggaatccag gtggagctct actcattccc tagagatcca  1320
gaaatcgaga tgagtggtgg cctcgtgaat gggagctctg tcactgtaag ctgcaaggtt  1380
cctagcgtgt accccccttga ccggctggag attgaattac ttaaggggga gactattctg  1440
gagaatatag agtttttgga ggatacggat atgaaatctc tagagaacaa aagtttggaa  1500
atgaccttca tccctaccat tgaagatact ggaaaagctc ttgtttgtca ggctaagtta  1560
catattgatg acatggaatt cgaacccaaa caaaggcaga gtacgcaaac actttatgtc  1620
aatgttgccc ccagagatac aaccgtcttg gtcagccctt cctccatcct ggaggaaggc  1680
```

```
agttctgtga atatgacatg cttgagccag ggctttcctg ctccgaaaat cctgtggagc  1740
aggcagctcc ctaacgggga gctacagcct ctttctgaga atgcaactct caccttaatt  1800
tctacaaaaa tggaagattc tggggtttat ttatgtgaag gaattaacca ggctggaaga  1860
agcagaaagg aagtggaatt aattatccaa gttactccaa aagacataaa acttacagct  1920
tttccttctg agagtgtcaa agaaggagac actgtcatca tctcttgtac atgtggaaat  1980
gttccagaaa catggataat cctgaagaaa aaagcggaga caggagacac agtactaaaa  2040
tctatagatg gcgcctatac catccgaaag gcccagttga aggatgcggg agtatatgaa  2100
tgtgaatcta aaaacaaagt tggctcacaa ttaagaagtt taacacttga tgttcaagga  2160
agagaaaaca acaaagacta tttttctcct gagcttctcg tgctctattt tgcatcctcc  2220
ttaataatac ctgccattgg aatgataatt tactttgcaa gaaaagccaa catgaagggg  2280
tcatatagtc ttgtagaagc acagaaatca aaagtgtagc taatgcttga tatgttcaac  2340
tggagacact atttatctgt gcaaatcctt gatactgctc atcattcctt gagaaaaaca  2400
atgagctgag aggcagactt ccctgaatgt attgaacttg gaaagaaatg cccatctatg  2460
tcccttgctg tgagcaagaa gtcaaagtaa aacttgctgc ctgaagaaca gtaactgcca  2520
tcaagatgag agaactggag gagttccttg atctgtatat acaataacat aatttgtaca  2580
tatgtaaaat aaaattatgc catagcaaga ttgcttaaaa tagcaacact ctatatttag  2640
attgttaaaa taactagtgt tgcttggact attataattt aatgcatgtt aggaaaattt  2700
cacattaata tttgctgaca gctgaccttt gtcatctttc ttctatttta ttccctttca  2760
caaaatttta ttcctatata gtttattgac aataatttca ggttttgtaa agatgccggg  2820
ttttatattt ttatagacaa ataataagca aagggagcac tgggttgact ttcaggtact  2880
aaatacctca acctatggta taatggttga ctgggtttct ctgtatagta ctggcatggt  2940
acggagatgt ttcacgaagt ttgttcatca gactcctgtg caactttccc aatgtggcct  3000
aaaaatgcaa cttcttttta ttttcttttg taaatgttta ggtttttttg tatagtaaag  3060
tgataatttc tggaattaaa                                              3080

SEQ ID NO: 215          moltype = AA  length = 739
FEATURE                 Location/Qualifiers
source                  1..739
                        mol_type = protein
                        organism = Homo sapiens
SEQUENCE: 215
MPGKMVVILG ASNILWIMFA ASQAFKIETT PESRYLAQIG DSVSLTCSTT GCESPFFSWR  60
TQIDSPLNGK VTNEGTTSTL TMNPVSFGNE HSYLCTATCE SRKLEKGIQV EIYSFPKDPE  120
IHLSGPLEAG KPITVKCSVA DVYPFDRLEI DLLKGDHLMK SQEFLEDADR KSLETKSLEV  180
TFTPVIEDIG KVLVCRAKLH IDEMDSVPTV RQAVKELQVY ISPKNTVISV NPSTKLQEGG  240
SVTMTCSSEG LPAPEIFWSK KLDNGNLQHL SGNATLTLIA MRMEDSGIYV CEGVNLIGKN  300
RKEVELIVQE KPFTVEISPG PRIAAQIGDS VMLTCSVMGC ESPSFSWRTQ IDSPLSGKVR  360
SEGTNSTLTL SPVSFENEHS YLCTVTCGHK KLEKGIQVEL YSFPRDPEIE MSGGLVNGSS  420
VTVSCKVPSV YPLDRLEIEL LKGETILENI EFLEDTDMKS LENKSLEMTF IPTIEDTGKA  480
LVCQAKLHID DMEFEPKQRQ STQTLYVNVA PRDTTVLVSP SSILEEGSSV NMTCLSQGFP  540
APKILWSRQL PNGELQPLSE NATLTLISTK MEDSGVYLCE GINQAGRSRK EVELIIQVTP  600
KDIKLTAFPS ESVKEGDTVI ISCTCGNVPE TWIILKKKAE TGDTVLKSID GAYTIRKAQL  660
KDAGVYECES KNKVGSQLRS LTLDVQGREN NKDYFSPELL VLYFASSLII PAIGMIIYFA  720
RKANMKGSYS LVEAQKSKV                                               739

SEQ ID NO: 216          moltype = AA  length = 5
FEATURE                 Location/Qualifiers
REGION                  1..5
                        note = Synthetic sequence: Heavy chain CDR1
source                  1..5
                        mol_type = protein
                        organism = synthetic construct
SEQUENCE: 216
DNYMH                                                              5

SEQ ID NO: 217          moltype = AA  length = 17
FEATURE                 Location/Qualifiers
REGION                  1..17
                        note = Synthetic sequence: Heavy chain CDR2
source                  1..17
                        mol_type = protein
                        organism = synthetic construct
SEQUENCE: 217
WIDPENGDTE YAPKFRG                                                 17

SEQ ID NO: 218          moltype = AA  length = 11
FEATURE                 Location/Qualifiers
REGION                  1..11
                        note = Synthetic sequence: Heavy chain CDR3
source                  1..11
                        mol_type = protein
                        organism = synthetic construct
SEQUENCE: 218
LIYAGYLAMD Y                                                       11

SEQ ID NO: 219          moltype = AA  length = 10
FEATURE                 Location/Qualifiers
REGION                  1..10
                        note = Synthetic sequence: Light chain CDR1
```

```
source                  1..10
                        mol_type = protein
                        organism = synthetic construct
SEQUENCE: 219
SASSSVTYMH                                                                10

SEQ ID NO: 220          moltype = AA  length = 7
FEATURE                 Location/Qualifiers
REGION                  1..7
                        note = Synthetic sequence: Light chain CDR2
source                  1..7
                        mol_type = protein
                        organism = synthetic construct
SEQUENCE: 220
STSNLAS                                                                   7

SEQ ID NO: 221          moltype = AA  length = 9
FEATURE                 Location/Qualifiers
REGION                  1..9
                        note = Synthetic sequence: Light chain CDR3
source                  1..9
                        mol_type = protein
                        organism = synthetic construct
SEQUENCE: 221
QQRSTYPLT                                                                 9

SEQ ID NO: 222          moltype = AA  length = 11
FEATURE                 Location/Qualifiers
REGION                  1..11
                        note = Synthetic sequence: Light chain CDR1
source                  1..11
                        mol_type = protein
                        organism = synthetic construct
SEQUENCE: 222
KASQDVGTSV A                                                              11

SEQ ID NO: 223          moltype = AA  length = 7
FEATURE                 Location/Qualifiers
REGION                  1..7
                        note = Synthetic sequence: Light chain CDR2
source                  1..7
                        mol_type = protein
                        organism = synthetic construct
SEQUENCE: 223
WTSTRHT                                                                   7

SEQ ID NO: 224          moltype = AA  length = 8
FEATURE                 Location/Qualifiers
REGION                  1..8
                        note = Synthetic sequence: Light chain CDR3
source                  1..8
                        mol_type = protein
                        organism = synthetic construct
SEQUENCE: 224
QQYSLYRS                                                                  8

SEQ ID NO: 225          moltype = AA  length = 5
FEATURE                 Location/Qualifiers
REGION                  1..5
                        note = Synthetic sequence: Heavy chain CDR1
source                  1..5
                        mol_type = protein
                        organism = synthetic construct
SEQUENCE: 225
TYWMS                                                                     5

SEQ ID NO: 226          moltype = AA  length = 17
FEATURE                 Location/Qualifiers
REGION                  1..17
                        note = Synthetic sequence: Heavy chain CDR2
source                  1..17
                        mol_type = protein
                        organism = synthetic construct
SEQUENCE: 226
EIHPDSSTIN YAPSLKD                                                        17

SEQ ID NO: 227          moltype = AA  length = 10
FEATURE                 Location/Qualifiers
REGION                  1..10
```

```
                      note = Synthetic sequence: Heavy chain CDR3
source                1..10
                      mol_type = protein
                      organism = synthetic construct
SEQUENCE: 227
LYFGFPWFAY                                                      10

SEQ ID NO: 228        moltype = AA  length = 15
FEATURE               Location/Qualifiers
REGION                1..15
                      note = Synthetic sequence: Light chain CDR1
source                1..15
                      mol_type = protein
                      organism = synthetic construct
SEQUENCE: 228
KASQSVDYDG DSYLN                                                15

SEQ ID NO: 229        moltype = AA  length = 7
FEATURE               Location/Qualifiers
REGION                1..7
                      note = Synthetic sequence: Light chain CDR2
source                1..7
                      mol_type = protein
                      organism = synthetic construct
SEQUENCE: 229
DASNLVS                                                         7

SEQ ID NO: 230        moltype = AA  length = 9
FEATURE               Location/Qualifiers
REGION                1..9
                      note = Synthetic sequence: Light chain CDR3
source                1..9
                      mol_type = protein
                      organism = synthetic construct
SEQUENCE: 230
QQSTEDPWT                                                       9

SEQ ID NO: 231        moltype = AA  length = 5
FEATURE               Location/Qualifiers
REGION                1..5
                      note = Synthetic sequence: Heavy chain CDR1
source                1..5
                      mol_type = protein
                      organism = synthetic construct
SEQUENCE: 231
SYWMN                                                           5

SEQ ID NO: 232        moltype = AA  length = 17
FEATURE               Location/Qualifiers
REGION                1..17
                      note = Synthetic sequence: Heavy chain CDR2
source                1..17
                      mol_type = protein
                      organism = synthetic construct
SEQUENCE: 232
QIWPGDGDTN YNGKFKG                                              17

SEQ ID NO: 233        moltype = AA  length = 15
FEATURE               Location/Qualifiers
REGION                1..15
                      note = Synthetic sequence: Heavy chain CDR3
source                1..15
                      mol_type = protein
                      organism = synthetic construct
SEQUENCE: 233
RETTTVGRYY YAMDY                                                15
```